US012338248B2

(12) United States Patent
Wang et al.

(10) Patent No.: US 12,338,248 B2
(45) Date of Patent: Jun. 24, 2025

(54) AMINOPYRIMIDINE DERIVATIVES AS CYCLIN-DEPENDENT KINASE INHIBITORS

(71) Applicant: Accutar Biotechnology Inc., Cranbury, NJ (US)

(72) Inventors: Xiangzhu Wang, Branford, CT (US); Yimin Qian, Plainsboro, NJ (US); Wei He, Zionsville, IN (US); Jie Su, New York, NY (US); Ke Liu, Bellevue, WA (US); Jie Fan, New York, NY (US)

(73) Assignee: Accutar Biotechnology Inc., Cranbury, NJ (US)

( * ) Notice: Subject to any disclaimer, the term of this patent is extended or adjusted under 35 U.S.C. 154(b) by 0 days.

(21) Appl. No.: 18/780,132

(22) Filed: Jul. 22, 2024

(65) Prior Publication Data

US 2025/0084095 A1    Mar. 13, 2025

Related U.S. Application Data

(60) Provisional application No. 63/515,021, filed on Jul. 21, 2023.

(51) Int. Cl.
| | |
|---|---|
| *C07D 493/08* | (2006.01) |
| *A61K 31/506* | (2006.01) |
| *A61K 31/5377* | (2006.01) |
| *A61K 31/5383* | (2006.01) |
| *A61P 35/00* | (2006.01) |
| *C07D 498/08* | (2006.01) |
| *C07D 519/00* | (2006.01) |

(52) U.S. Cl.
CPC .......... *C07D 493/08* (2013.01); *A61K 31/506* (2013.01); *A61K 31/5377* (2013.01); *A61K 31/5383* (2013.01); *A61P 35/00* (2018.01); *C07D 498/08* (2013.01); *C07D 519/00* (2013.01)

(58) Field of Classification Search
CPC .. C07D 493/08; C07D 498/08; C07D 519/00; A61K 31/506; A61K 31/5377; A61K 31/5383; A61P 35/00
See application file for complete search history.

(56) References Cited

U.S. PATENT DOCUMENTS

| | | |
|---|---|---|
| 10,059,690 B2 | 8/2018 | Ciblat et al. |
| 10,370,371 B2 | 8/2019 | Du et al. |
| 10,766,884 B2 | 9/2020 | Chen et al. |
| 2004/0171630 A1 | 9/2004 | Kim et al. |
| 2016/0074409 A1 | 3/2016 | Rothbaum et al. |
| 2022/0064146 A1 | 3/2022 | Devita et al. |
| 2022/0073485 A1 | 3/2022 | Foley et al. |
| 2022/0177459 A1 | 6/2022 | Du et al. |
| 2023/0295130 A1 | 9/2023 | Li et al. |
| 2023/0357211 A1 | 11/2023 | Clark et al. |

FOREIGN PATENT DOCUMENTS

| | | | |
|---|---|---|---|
| WO | WO 2016/192630 A1 | 12/2016 | |
| WO | WO 2019/207463 A1 | 10/2019 | |
| WO | WO 2022/058871 A1 | 3/2022 | |
| WO | WO 2022/149057 A1 | 7/2022 | |
| WO | WO 2022/166799 A1 | 8/2022 | |
| WO | WO 2022/199662 A1 | 9/2022 | |
| WO | WO 2023/016447 A1 | 2/2023 | |
| WO | WO 2023/040998 A1 | 3/2023 | |
| WO | WO 2023/116862 A1 | 6/2023 | |
| WO | WO 2023/172957 A1 | 9/2023 | |
| WO | WO 2023/178547 A1 | 9/2023 | |
| WO | WO 2023/208172 A1 | 11/2023 | |
| WO | WO 2023/208173 A1 | 11/2023 | |
| WO | WO 2023/213271 A1 | 11/2023 | |
| WO | WO 2023/227125 A1 | 11/2023 | |
| WO | WO 2024/022487 A1 | 2/2024 | |
| WO | WO 2024/077216 A1 | 4/2024 | |
| WO | WO 2024/088323 A1 | 5/2024 | |
| WO | WO 2024/119122 A1 | 6/2024 | |
| WO | WO-2024220866 A1 * | 10/2024 | ............. A61P 35/00 |

OTHER PUBLICATIONS

Abdel-Magid, A. F. "Combination of Cyclin-Dependent Kinase 4 Inhibitors and Androgen Receptor Inhibitors as Cancer Therapy." ACS Medicinal Chemistry Letters, vol. 13, No. 9, Aug. 22, 2022, pp. 1408-1410.

PCT International Search Report and Written Opinion, PCT Application No. PCT/US2024/039034, Oct. 31, 2024, 13 pages.

* cited by examiner

*Primary Examiner* — Matthew P Coughlin
*Assistant Examiner* — Anna Grace Kuckla
(74) *Attorney, Agent, or Firm* — Miho Kaneko; Carl Morales; Goodwin Procter LLP

(57) ABSTRACT

The present disclosure relates to novel CDK inhibitors, pharmaceutical compositions containing such compounds, and their use in prevention and treatment of diseases and conditions associated with CDK.

48 Claims, 1 Drawing Sheet

Specification includes a Sequence Listing.

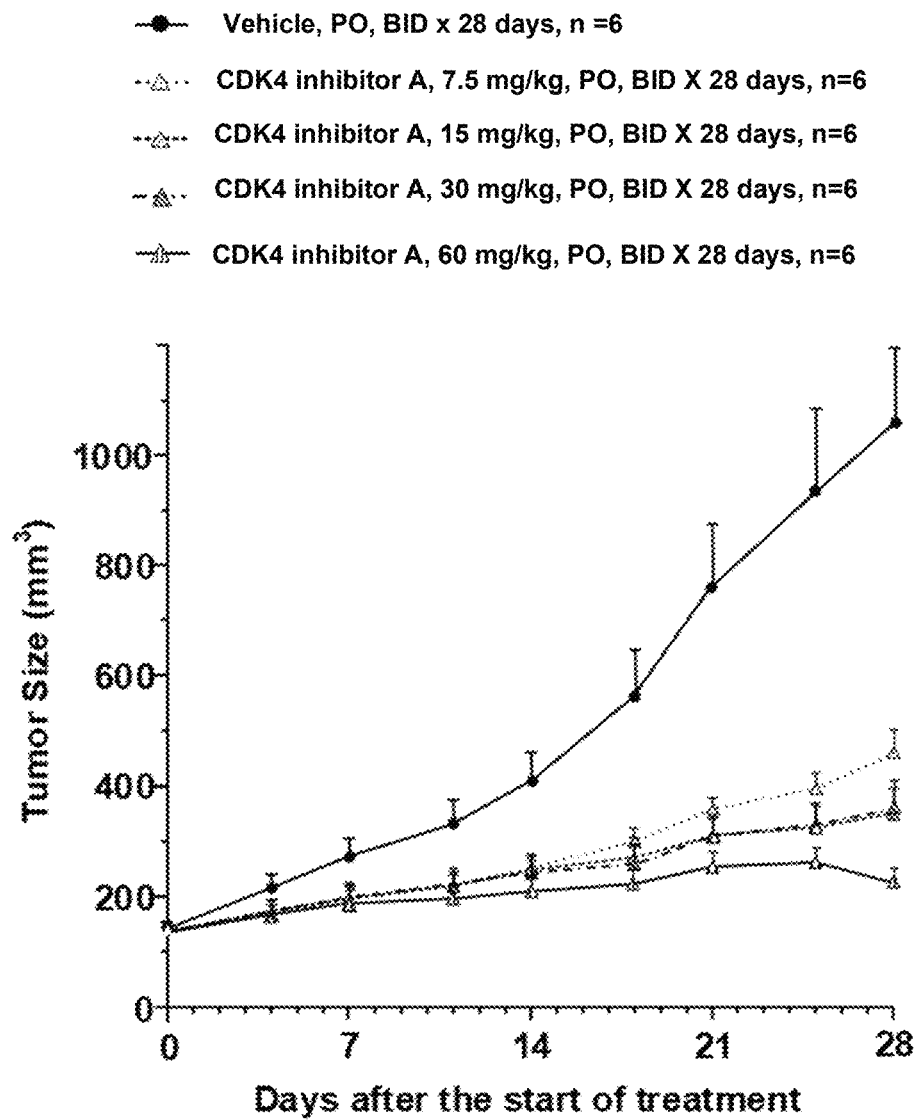

SEQUENCE LISTING

```
Sequence total quantity: 5
SEQ ID NO: 1            moltype = AA  length = 10
FEATURE                 Location/Qualifiers
source                  1..10
                        mol_type = protein
                        organism = synthetic construct
SITE                    1
                        note = Fluorescein modified residue
SEQUENCE: 1
PKTPKKAKKL                                                              10

SEQ ID NO: 2            moltype = AA  length = 14
FEATURE                 Location/Qualifiers
source                  1..14
                        mol_type = protein
                        organism = synthetic construct
SITE                    14
                        note = Amidated residue
SEQUENCE: 2
RRFRPASPLR GPPK                                                         14

SEQ ID NO: 3            moltype = AA  length = 26
FEATURE                 Location/Qualifiers
source                  1..26
                        mol_type = protein
                        organism = synthetic construct
SITE                    1
                        note = Fluorescein modified residue
SITE                    26
                        note = Amidated residue
SEQUENCE: 3
ACSYSPTSPS YSPTSPSYSP TSPSKK                                            26

SEQ ID NO: 4            moltype = DNA  length = 20
FEATURE                 Location/Qualifiers
source                  1..20
                        mol_type = other DNA
                        organism = synthetic construct
SEQUENCE: 4
atctcggtga acgatgcaat                                                   20

SEQ ID NO: 5            moltype = DNA  length = 20
FEATURE                 Location/Qualifiers
source                  1..20
                        mol_type = other DNA
                        organism = synthetic construct
SEQUENCE: 5
gaccacgttg gggtgctcga                                                   20
```

AMINOPYRIMIDINE DERIVATIVES AS CYCLIN-DEPENDENT KINASE INHIBITORS

SEQUENCE LISTING

The instant application contains a Sequence Listing which has been submitted electronically in XML file format and is hereby incorporated by reference in its entirety. Said XML copy, created on Oct. 10, 2024, is named 59270US_CRF_sequencelisting.xml and is 6,948 bytes in size.

BACKGROUND

Cyclin-Dependent Kinases (CDKs) are a family of protein kinases that participate in regulating a wide range of physiological processes. For instance, CDKs have been identified as regulators of the cell cycle, mRNA processing, and differentiation of nerve cells. The majority of known CDK complexes regulate progression through the cell cycle and are present in all eukaryotes. CDKs are also implicated in the development and proliferation of cancer cells through unregulated and abnormal expression of CDKs (Malumbres M. et al. *Nat Rev Cancer*, 2009; Vijayaraghavan, S. et al., *Target Oncology*, 2018). CDKs are mainly divided into two groups based on their cellular function: cell cycle regulators (CDK1, CDK2, CDK4, and CDK6) and gene transcription regulators (CDK7, CDK8, CDK9, CDK11, CDK 12, and CDK13). Other CDKs (CDK3, CDK5, CDK10, CDK14, CDK16, CDK18, and CDK20) were discovered more recently but their biological function is poorly understood (Chou J. et al. *Cancer Discov*, 2020).

CDK4 and CDK6 are important regulators of cell cycle progression at the G1-S checkpoint, which are controlled by D-type cyclins and INK4 endogenous CDK inhibitors, such as $p16^{INK4a}$ (CDKN2A). Dysregulation of the cyclin D-CDK4/6-INK4-retinoblastoma (Rb) pathway has been reported to be associated with development of endocrine therapy resistance. CDK4, a member of the CDK family, is a catalytic subunit of the protein kinase complex that is involved in controlling the transition from the G1-phase to the S-phase in the cell-cycle. Specifically, this process is controlled by the regulatory subunits D-type cyclins and CDK inhibitor p16 (INK4a) Mutations in the CDK4 gene as well as in the related proteins including D-type cyclins, p16 (INK4a), and Rb have been linked to tumorigenesis of a variety of cancers Zuo L. et al. *Nature Genet*, 1996; "Cyclin D-dependent kinases, INK4 inhibitors and cancer", *Biochim. Biophys. Acta*, 2002, 1602, 73-87; Ortega S. et al. *Cancer Res*, 2008).

CDK inhibitors have been shown to be useful in treating cancer. Increased activity or temporally abnormal activation of CDKs has been shown to result in the development of human tumors, and human tumor development is commonly associated with alterations in either the CDK proteins themselves or their regulators.

Inhibitors of cyclin-dependent kinases 4 and 6 (CDK4/61) combined with endocrine therapy (ET) are currently the standard of care for patients with HR4/HER2-metastatic breast cancer (MBC). The CDK4/6i palbociclib, ribociclib and abemaciclib are FDA approved in combination with endocrine therapies in both first and second line settings (Cogliati V. et al. *Life*, 2022).

But despite the initial success of CDK4/6 inhibitors in the clinic, treatment related adverse effects, especially hematologic toxicity such as neutropenia, prevented continued dosing of CDK4/6 inhibitors. Currently, both palbociclib and ribociclib are administered on a three week on/one week off schedule. Mouse genetic and other emerging data suggest that the observed hematologic toxicity is likely linked to CDK6-cyclin D3 inhibition (Sicinska et al., *Mol Cell Biol*, 2006; Cooper et al. *Nat Immunol*, 2006).

Because CDK 4 has been identified as the singular oncogenic driver in many breast cancers, a selective CDK4 inhibitor may provide improved safety profile and enhanced effectiveness.

Accordingly, there remains an unmet medical need to develop novel CDK4 selective inhibitors, which potentially lead to greater efficacy, improved toxicity profile and may overcome the resistance mechanisms observed with current CDK inhibitors (e.g., CDK4/6i).

SUMMARY

The present disclosure is directed to novel CDK inhibitors, compositions comprising the disclosed compounds, and uses thereof. In some embodiments, the compounds disclosed herein modulate the activity of CDK, including CDK4 and/or CDK6. In some embodiments, the compounds disclosed herein show high CDK4 selectivity over other kinases including CDK1, CDK2, CDK6, and CDK9. In some embodiments, the compounds disclosed herein are selective for CDK4.

In some embodiments, the present disclosure provides a compound, wherein the compound is represented by Formula I or is a pharmaceutically acceptable salt thereof:

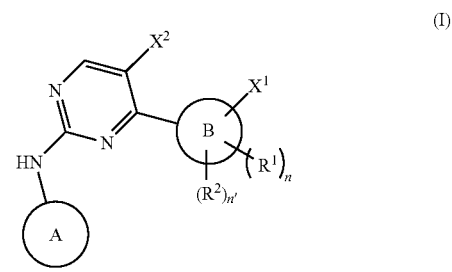

(I)

wherein:
Ring B is an 8-12 membered bicyclic heteroaryl, 9-12 membered bicyclic heterocyclic group, 10-14 membered tricyclic heteroaryl, 10-14 membered tricyclic heterocyclic group, or 10-14 membered spiro-heterocyclic group;

each $R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic baloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)O$R^{1B}$, —C(=O)N($R^{1B}$)$_2$, —NHC(=O)O$R^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

each $R^2$ is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;

$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Ring A is

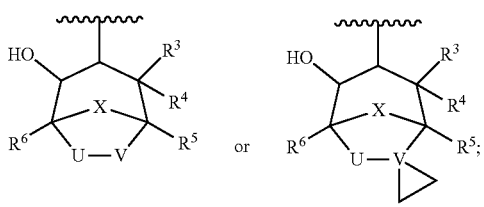

wherein:

$R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;

$R^5$ and $R^6$ are independently selected from hydrogen, deuterium, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$—$R^X$, wherein $R^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or $C(R^U)_2$, wherein $R^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

V is O, C, or $C(R^V)_2$, wherein $R^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

n is 0, 1, 2, 3, or 4; and n' is 0, 1, or 2;

with the proviso that one but not both of U and V is O.

In some embodiments, the compound of Formula I is represented by Formula IA:

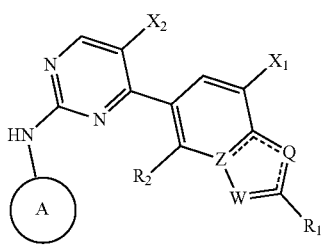

(IA)

wherein: ══ is a single bond or a double bond;

Q is N or $CR^O$, wherein $R^O$ is independently selected from hydrogen, halogen, and cyano;

Z is C;

W is selected from $C(R^{W1})_2$, O, S, N, and $NR^{W2}$, wherein $R^{W1}$ is independently selected from hydrogen, halogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$;

$R^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$; and each $R^{1D}$ is independently selected from halogen, $C_1$-$C_6$ alkyl, $C_1$-$C_6$ baloalkyl, and hydroxyl; or W and $R^1$ may be taken together with the C atom to which both are attached to form a carbocyclic ring of 5-8 atoms or a heterocyclic ring of 5-8 atoms, wherein the carbocyclic ring and heterocyclic ring is each optionally substituted with 1, 2, 3, or 4 $R^{1E}$; or W, Z, $R^2$ and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$; and each $R^{1E}$ is independently selected from $C_1$-$C_6$ alkyl, hydroxyl, and an oxo group.

In some embodiments, the compound of Formula IA is represented by Formula IA':

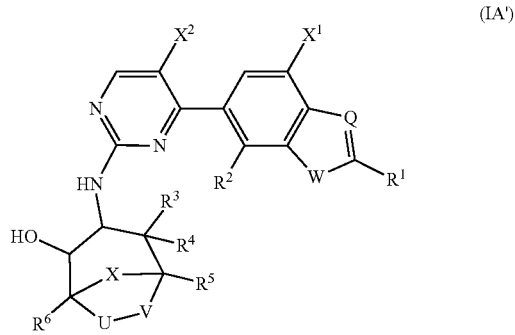

(IA')

wherein:

$R^2$ is hydrogen or $C_1$-$C_6$ alkyl;

$R^3$ and $R^4$ are independently selected from hydrogen, deuterium, halogen, and $C_1$-$C_6$ alkyl;

$R^5$ and $R^6$ are independently selected from hydrogen, $C_1$-$C_4$ alkyl, $C_3$-$C_8$ cycloalkyl, and aryl;

X is O;

$X^1$ is selected from halogen, $C_1$-$C_8$ alkyl, and $C_1$-$C_5$ haloalkyl;

$X^2$ is selected from hydrogen, halogen, $C_1$-$C_8$ alkyl, and $C_1$-$C_4$ haloalkyl;

Q is N or $CR^O$, wherein $R^O$ is independently selected from hydrogen, halogen, and cyano;

W is $NR^{W2}$, wherein $R^{W2}$ is selected from $C_1$-$C_6$ alkyl, $C_3$-$C_6$ cycloalkyl, 5-6 membered bicyclic carbocyclic group, and a 3-7 membered heterocyclic group, wherein each of the $C_1$-$C_6$ alkyl and $C_3$-$C_6$ cycloalkyl is optionally substituted with 1, 2, or 3 $R^{1D}$;

each $R^{1D}$ is independently selected from halogen, $C_1$-$C_6$ alkyl, $C_1$-$C_5$ haloalkyl, and hydroxyl;

U is O or $C(R^U)_2$, wherein $R^u$ is independently selected from hydrogen, deuterium, halogen, and $C_1$-$C_3$ alkyl, wherein the $C_1$-$C_3$ alkyl is optionally substituted with hydroxyl; and V is O or $C(R^V)_2$, wherein $R^V$ is independently selected from hydrogen, deuterium, halogen, hydroxyl, $C_1$-$C_3$ alkyl, and $C_3$-$C_6$ cycloalkyl, and wherein the $C_1$-$C_3$ alkyl is optionally substituted with hydroxyl.

In some embodiments, the compound of Formula IA' is represented by Formula IA":

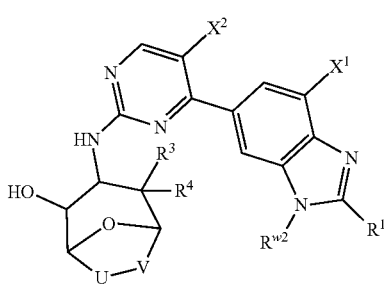

(IA")

wherein:

$R^{W2}$ is selected from $C_1$-$C_8$ alkyl, $C_3$-$C_8$ cycloalkyl, and a 4-5 membered heterocyclic group, wherein each of the $C_1$-$C_8$ alkyl and $C_3$-$C_8$ cycloalkyl is optionally substituted with 1 or 2$R^{1D}$.

In some embodiments, the compound of Formula I is represented by Formula IB:

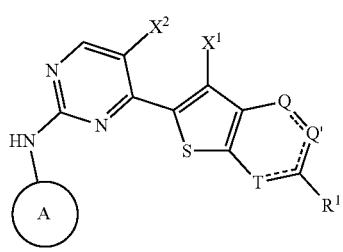

(IB)

wherein:

━━━ is a single bond or a double bond;

Q is $CR^Q$, N, or $NR^Q$, wherein $R^Q$ is selected from hydrogen, halogen, $C_1$-$C_4$ alkyl, and an oxo group;

Q' is $CR^{Q'}$, N, $NR^{Q'}$, wherein $R^{Q'}$ is selected from hydrogen, $C_1$-$C_4$ alkyl, and $C_1$-$C_4$ haloalkyl; and T is $CR^{T1}$ or $NR^{T2}$, wherein $R^{T1}$ is halogen or $R^{T2}$, and $R^{T2}$ is hydrogen or $C_1$-$C_6$ alkyl, wherein the $C_1$-$C_6$ alkyl is optionally substituted with 1, 2, or 3 groups independently selected from halogen, $C_1$-$C_6$ alkyl, and hydroxyl.

In some embodiments, the compound of Formula I is represented by Formula IC:

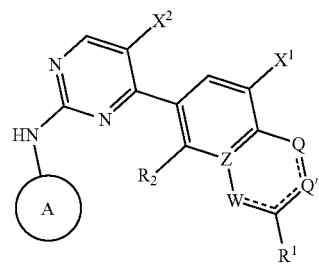

(IC)

wherein:

━━━ is a single bond or a double bond;

Q is N, O, or $CR^Q$, wherein $R^Q$ is selected from hydrogen, halogen, and an oxo group;

Q' is CH, $CH_2$, $CR^{Q'}$, N, or NR", wherein $R^{Q'}$ is halogen or R", and R" is selected from $C_1$-$C_6$ alkyl, $C_3$-$C_6$ cycloalkyl, $C_1$-$C_4$ haloalkyl, and a 3-8 membered heterocyclic group, wherein each of the $C_1$-$C_6$ alkyl and $C_3$-$C_6$ cycloalkyl are each optionally substituted with 0, 1, 2, or 3 groups independently selected from halogen, $C_1$-$C_6$ alkyl, and hydroxyl;

Z is C; and

W is $CR^{W1}$, N, or $NR^{W2}$, wherein $R^{W1}$ is selected from hydrogen, halogen, $C_1$-$C_6$ alkyl, $C_3$-$C_6$ cycloalkyl, and a 3-8 membered heterocyclic group, wherein each of the $C_1$-$C_6$ alkyl and $C_3$-$C_6$ cycloalkyl is optionally substituted with 1, 2, or 3 $R^{1D}$;

$R^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$; and each $R^{1D}$ is independently selected from halogen, $C_1$-$C_6$ alkyl, and hydroxyl; or W, Z, $R^2$ and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$, and wherein each $R^{1E}$ is independently selected from $C_1$-$C_6$ alkyl, hydroxyl, and an oxo group.

In some embodiments, the compound of Formula I is represented by Formula ID:

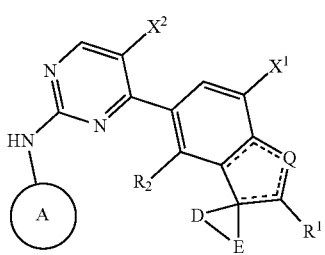

(ID)

wherein:

━━━ is a single bond or a double bond; and

Q is N or $CR^Q$, wherein $R^Q$ is independently selected from hydrogen, halogen, and cyano; and D and E together with the carbon atom to which they are both attached form a carbocyclic ring of 5-8 atoms or a heterocyclic ring of 5-8 atoms containing 1 to 2 heteroatoms selected from O, S, and N, wherein any carbon ring may be optionally substituted with halogen, $C_1$-$C_4$ alkyl, or hydroxyl.

Also disclosed herein are methods of treatment. The disclosed methods may comprise treating a subject (e.g., a human subject) in need thereof, wherein the subject has a disease or condition modulated at least in part by a cyclin-dependent kinase (CDK), such as cancer. The methods may comprise administering to the subject an effective amount of a compound disclosed herein. In some embodiments, a method for inhibiting a CDK (e.g., CDK4) in a subject is provided. In some embodiments, the disclosure provides a CDK inhibitor for use in the treatment of a solid tumor cancer. In some embodiments, the solid tumor is prostate, pancreatic, or breast cancer. In some embodiments, the cancer is selected from breast cancer, prostate cancer, bone cancer, brain cancer, colorectal cancer, lung cancer, ovarian cancer, uterine cancer, liposarcoma, liver cancer, rhabdoid cancer, sarcoma, skin cancer, kidney cancer, stomach cancer, pancreatic cancer, esophageal cancer, head and neck cancer, bladder cancer, leukemia, lymphoma, and thyroid cancer.

In some embodiments, the present disclosure provides compositions (e.g., pharmaceutical compositions) comprising one or more compounds disclosed herein (e.g., Formula I) and one or more pharmaceutically acceptable carriers, pharmaceutically acceptable vehicles, pharmaceutically acceptable excipients, or combinations thereof.

BRIEF DESCRIPTION OF THE DRAWING

FIG. 1 illustrates the dose-dependent inhibition of MCF7 tumor growth by CDK4 inhibitor A.

DETAILED DESCRIPTION

Definitions

When describing the embodiments of the present disclosure, which may include compounds and pharmaceutically acceptable salts thereof, pharmaceutical compositions containing such compounds and methods of using such compounds and compositions, the following terms, if present, have the following meanings unless otherwise indicated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member Thus, for example, a group having 1-3 articles refers to groups having 1, 2, or 3 articles. Similarly, a group having 1-5 articles refers to groups having 1, 2, 3, 4, or 5 articles, and so forth.

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.:

Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl", "cycloaliphatic", or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms. In some embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or a substituted nitrogen of a heterocyclic ring, for example N (as in 3,4-dihydro-2H-pyrrolyl), NH (as in pyrrolidinyl) or NR*(as in N-substituted pyrrolidinyl)).

The term "unsaturated", as used herein, means that a moiety has one or more units of unsaturation.

The term "alkylene" refers to a divalent alkyl group. An "alkylene chain" is a polymethylene group, i.e., $-(CH_2)_n-$, wherein n is a positive integer, for example, from 1 to 6, from 1 to 4, from 1 to 3, from 1 to 2, or from 2 to 3. A substituted alkylene chain is a polymethylene group in which one or more methylene hydrogen atoms are replaced with a substituent Suitable substituents include those described below for a substituted aliphatic group.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)—C(O)—, (alkenyl)—C(O)—, (alkynyl)-C(O)—, (aryl)-C(O)—, (cycloalkyl)-C(O)—, (heteroaryl)-C (O)—, and (heterocyclyl)-C (O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as ($C_2$-$C_6$)-alkenyl. Exemplary alkenyl groups include, but are not limited to, vinyl, allyl, butenyl, pentenyl, hexenyl, butadienyl, pentadienyl, hexadienyl, 2-ethylhexenyl, 2 propyl 2-butenyl, and 4-(2-methyl-3-butene)-pentenyl.

The term "alkyl" as used herein refers to a saturated straight or branched hydrocarbon, such as a straight or branched group of 1 to 8 carbon atoms, referred to herein as $C_{1-8}$ alkyl. Exemplary alkyl groups include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3 methyl-1-pentyl, 4-methyl-1-pentyl, 2-methyl-2-pentyl, 3-methyl-2-pentyl, 4 methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkoxy" means a straight or branched chain saturated hydrocarbon containing 1-12 carbon atoms containing a terminal "O" in the chain, e.g., —O (alkyl). Examples of alkoxy groups include, without limitation, methoxy, ethoxy, propoxy, butoxy, t-butoxy, or pentoxy groups.

The term "alkylene" as used herein refers to a divalent alkyl radical. Representative examples of $C_{1-10}$ alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)-alkynyl Exemplary alkynyl groups include, but are not limited to, ethynyl, propynyl, butynyl, pentynyl, hexynyl, methylpropynyl, 4-methyl-1-butynyl, 4-propyl-2-pentynyl, and 4 butyl 2 hexynyl.

The term "aryl" herein refers to an all carbon monocyclic or fused-ring polycyclic (i.e., rings which share adjacent pairs of carbon atoms) groups having a completely conjugated pi-electron system. An aryl group may be selected from: monocyclic carbocyclic aromatic rings, for example, phenyl; bicyclic ring systems such as 7-12 membered, e.g., 9-10 membered, bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene. For example, the aryl group may be a 6-membered carbocyclic aromatic ring fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Divalent radicals formed from substituted benzene derivatives and having the free valences at ring atoms are named as substituted phenylene radicals. Divalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. In some embodiments, a heteroaromatic ring is fused to one or more aryl, cycloaliphatic, or heterocyclyl rings, where the radical or point of attachment is on the heteroaromatic ring (or in the case of a divalent fused heteroarylene ring system, at least one radical or point of attachment is on a heteroaromatic ring). Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbozolyl, acridinyl, phenazinyl, phenothiazinyl, phenoxazinyl, tetrahydrquinolinyl, tetrahydroisoquinolinyl, and pyrido[2,3-b]-1,4-oxazin-3 (4H)-one. A heteroaryl group may be mono-, bicyclic, or tricyclic. The term "heteroaryl" may be used interchangeably with the terms "heteroaryl ring", "heteroaryl group", or "heteroaromatic", any of which terms include rings that are optionally substituted. In some embodiments, the heteroaryl is a 8-12 membered bicyclic heteroaryl or a 10-14 membered tricyclic heteroaryl.

The term "cyano" as used herein refers to CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_5$)-cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

"Haloalkyl" means an alkyl group substituted with one or more halogens. Examples of haloalkyl groups include, but are not limited to, trifluoromethyl, difluoromethyl, pentafluoroethyl, trichloromethyl, etc.

A "heterocyclyl" or "heterocyclic" group is a ring structure having from 3 to 14 atoms, for example 4 to 13 atoms, wherein one or more atoms are selected from the group consisting of N, O, and S wherein the ring N atom may be oxidized to N—O, and the ring S atom may be oxidized to SO or $SO_2$, the remainder of the ring atoms being carbon. The heterocyclyl may be a monocyclic, a bicyclic, a tricyclic, a spirocyclic, or a bridged ring system. The heterocyclic group is independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabicycloheptanyls, hexahydropyrrolizinyl 4 (1H)-oxide, tetrahydro-2H-thiopyranyl 1-oxide and tetrahydro-2H-thiopyranyl 1,1-dioxide. Specifically excluded from the scope of this term are compounds having adjacent annular O) and/or S atoms.

A "spirocycle", "spirocyclyl", or "spirocyclylene" refers to a chemical entity having two heterocyclyl or two cycloalkyl moieties as defined herein, or to a combination of one or more heterocyclyl and one or more cycloalkyl moiety, having one ring atom in common, i.e., the two rings are connected via one common ring atom. Some exemplary spirocyclic ring systems, yet non-limiting examples of spirocyclic ring systems, include

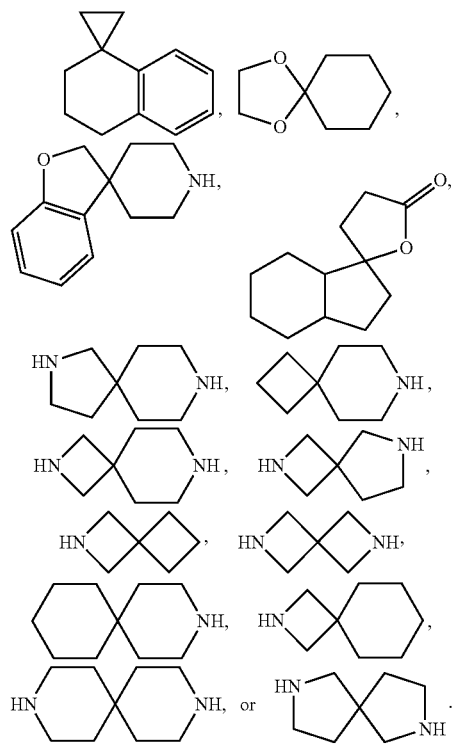

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As used herein and unless otherwise specified, the suffix "-ene" is used to describe a divalent group. Thus, any of the terms above can be modified with the suffix "-ene" to describe a divalent version of that moiety. For example, a divalent carbocycle is "carbocyclylene", a divalent aryl ring is "arylene", a divalent benzene ring is "phenylene", a divalent heterocycle is "heterocyclylene", a divalent heteroaryl ring is "heteroarylene", a divalent alkyl chain is "alkylene", a divalent alkenyl chain is "alkylene", a divalent alkynyl chain is "alkynylene", and so forth.

As described herein, compounds of the disclosure may, when specified, contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

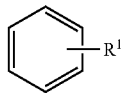

refers to at least

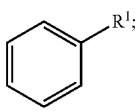

and

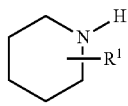

refers to at least

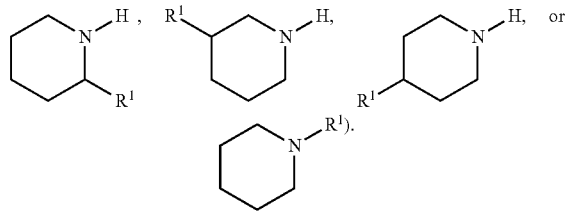

In addition, in a polycyclic ring system, substituents may, unless otherwise indicated, replace a hydrogen on any individual ring (e.g.,

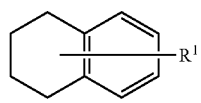

refers to at least

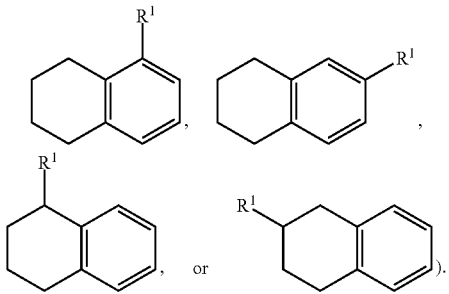

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are those that result in the formation of stable or chemically feasible compounds. The term "stable", as used herein, refers to compounds that are not substantially altered when subjected to conditions to allow for their purification, detection, and, in certain embodiments, their recovery, purification, and use for one or more of the purposes disclosed herein.

Those skilled in the art will appreciate that a bond designated as ⚌ in a small molecule structure, as used herein, refers to a bond that, in some embodiments, is a single (e.g., saturated) bond, and in some embodiments, is a double (e.g., unsaturated) bond. For example, the following structure:

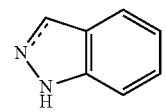

is intended to encompass both

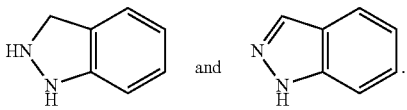 [SMILES: c1ccc2c(c1)CNN2 ; c1ccc2[nH]ncc2c1]

The term "oxo", as used herein, means an oxygen that is double bonded to a carbon atom thereby forming a carbonyl.

The terms "hydroxy" and "hydroxyl" as used herein refer to —OH.

Some of the compounds may exist with different points of attachment of hydrogen, referred to as "tautomers." For example, compounds including carbonyl —CH$_2$C(O)— groups (keto forms) may undergo tautomerism to form hydroxyl —CH═C(OH)— groups (enol forms). Both keto and enol forms, individually as well as mixtures thereof, are also intended to be included where applicable.

The compounds, tautomers, solvates, or pharmaceutically acceptable salts of the disclosure may contain an asymmetric center and may thus exist as enantiomers. For example, where the compounds possess two or more asymmetric centers, they may additionally exist as diastereoisomers. Enantiomers and diastereoisomers fall within the broader class of stereoisomers. All such possible stereoisomers as substantially pure resolved enantiomers, racemic mixtures thereof, as well as mixtures of diastereoisomers are intended to be included in this disclosure. All stereoisomers of the compounds, tautomers, solvates, and pharmaceutically acceptable salts thereof are intended to be included. Unless specifically mentioned otherwise, reference to one isomer applies to any of the possible isomers. Whenever the isomeric composition is unspecified, all possible isomers are included.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column.

"Stereoisomer" or "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration For example, the compound mixture has an (S)-enantiomeric excess of greater than 55%, 60%, 65%, 70%, 75%, 80%, 85%, 90%, 95%, 96%, 97%, 98%, 99%, 99.5%, or more. In other embodiments, the compound mixture has an (S)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5%, or more. In other embodiments, the compound mixture has an (R)-enantiomeric purity of greater than 55%, 60%, 65%, 70%, 75%, 80%, 85%, 90%, 95%, 96%, 97%, 98%, 99%, 99.5% or more. In some other embodiments, the compound mixture has an (R)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5% or more.

Individual stereoisomers of compounds of the present disclosure can be prepared synthetically from commercially available starting materials that contain asymmetric or stereogenic/chiral centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent Stereoisomers can also be obtained from stereomerically-pure intermediates, reagents, and catalysts by well-known asymmetric synthetic methods.

Thus, if one enantiomer is pharmacologically more active, less toxic, or has a preferred disposition in the body than the other enantiomer, it would be therapeutically more beneficial to administer that enantiomer preferentially.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

Additionally, as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinylpyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure.

The term "pharmaceutically acceptable composition" as used herein refers to a composition comprising at least one compound as disclosed herein formulated together with one or more pharmaceutically acceptable carriers.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer As used herein, "cancer" refers to diseases, disorders, and conditions that involve abnormal cell growth with the potential to invade or spread to other parts of the body. Exemplary cancers include, but are not limited to, breast cancer, prostate cancer, bone cancer, brain cancer, colorectal cancer, lung cancer, ovarian cancer, uterine cancer, liposarcoma, liver cancer, rhabdoid cancer, sarcoma, skin cancer, kidney cancer, stomach cancer, pancreatic cancer, esophageal cancer, head and neck cancer, bladder cancer, leukemia, lymphoma, and thyroid cancer.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds, and the like. In certain embodiments, the subject is a primate. In some embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" compound is one that is sufficiently similar to a particular compound of interest to permit a relevant comparison. In some embodiments, information about a reference compound is obtained simultaneously with information about a particular compound. In some embodiments, comparison of a particular compound of interest with a reference compound establishes identity with, similarity to, or difference of the particular compound of interest relative to the compound.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventive effect, such as by ameliorating symptoms associated with the disease, preventing or delaying the onset of the disease or condition, and/or also lessening the severity or frequency of symptoms of the disease or condition. A therapeutically effective amount is commonly administered in a dosing regimen that may comprise multiple doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat," "treating," or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

Additionally, unless otherwise stated, structures described herein are also meant to include compounds that differ only in the presence of one or more isotopically enriched atoms. For example, compounds having the present structures except for the replacement of hydrogen by deuterium (2H) or tritium (3H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein is a compound, wherein the compound is represented by Formula I or is a pharmaceutically acceptable salt thereof:

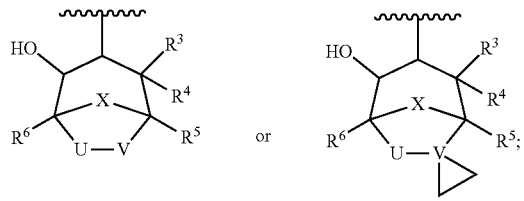

wherein:
Ring B is an 8-12 membered bicyclic heteroaryl, 9-12 membered bicyclic heterocyclic group, 10-14 membered tricyclic heteroaryl, 10-14 membered tricyclic heterocyclic group, or 10-14 membered spiro-heterocyclic group;

each $R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)OR$^{1B}$, —C(=O)N(R$^{1B}$)$_2$, —NHC(=O)OR$^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

each $R^2$ is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy. $C_1$-$C_6$ haloalkoxy, and a 3-7 membered heterocyclic group;

$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Ring A is

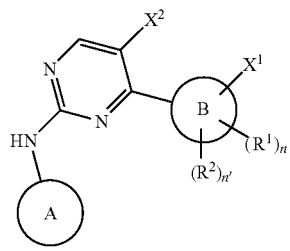

wherein:
$R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;

$R^5$ and $R^6$ are independently selected from hydrogen, deuterium, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$-RAY, wherein Ra is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or C(R$^U$)$_2$, wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

V is O, C, or C(R$^V$)$_2$, wherein R$^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

n is 0, 1, 2, 3, or 4; and n' is 0, 1, or 2;

with the proviso that one but not both of U and V is O.

In some embodiments, n is 0. In some embodiments, n is 1. In some embodiments, n is 2. In some embodiments, n is 3. In some embodiments, n is 4.

In some embodiments, n' is 0. In some embodiments, n' is 1. In some embodiments, n' is 2.

In some embodiments, the compound of Formula I is represented by Formula IA:

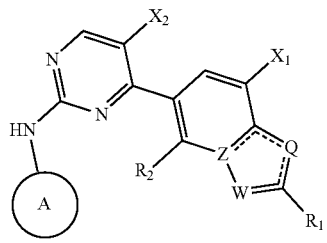

(IA)

wherein:

═══ is a single bond or is a double bond;

$R^1$ is selected from $C_1$-$C_8$ alkyl, $C_1$-$C_5$ haloalkyl, $C_3$-$C_6$ cycloalkyl, $C_3$-$C_6$ cyclic haloalkyl, $C_5$-$C_7$ bicyclic alkyl, a 4-6 membered heterocyclic group, a 6-10 membered aryl, and a 5-6 membered heteroaryl, wherein each of the $C_1$-$C_8$ alkyl, $C_3$-$C_6$ cycloalkyl, $C_3$-$C_6$ cyclic haloalkyl, $C_5$-$C_7$ bicyclic alkyl, 4-6 membered heterocyclic group, 6-8 membered aryl, and 5-6 membered heteroaryl is independently substituted with 0, 1, 2, or 3 $R^{1A}$, Q is N or $CR^O$, wherein $R^O$ is independently selected from hydrogen, halogen, and cyano;

Z is C;

W is selected from $C(R^{W1})_2$, O, S, N, and $NR^{W2}$, wherein $R^{W1}$ is independently selected from hydrogen, halogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$;

$R^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$; and each $R^{1D}$ is independently selected from halogen, $C_1$-$C_6$ alkyl, $C_1$-$C_6$ haloalkyl, and hydroxyl; or W and $R^1$ may be taken together with the C atom to which both are attached to form a carbocyclic ring of 5-8 atoms or a heterocyclic ring of 5-8 atoms, wherein the carbocyclic ring and heterocyclic ring is each optionally substituted with 1, 2, 3, or 4 $R^{1E}$; or W, Z, $R^2$ and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$; and each $R^{1E}$ is independently selected from $C_1$-$C_6$ alkyl, hydroxyl, and an oxo group.

In some embodiments, the compound of Formula IA is represented by Formula IA'-1:

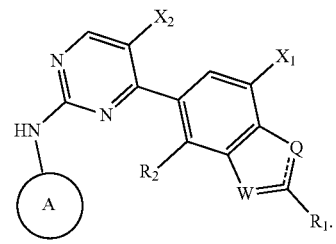

(IA'-1)

In some embodiments, the compound of Formula IA is represented by Formula IA':

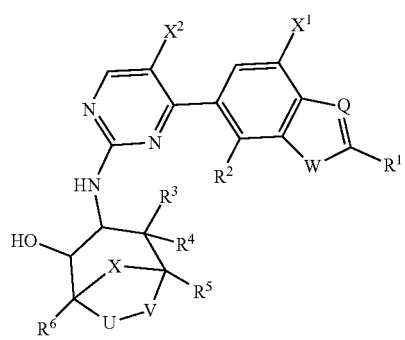

(IA')

wherein:

$R^2$ is hydrogen or $C_1$-$C_6$ alkyl;

$R^3$ and $R^4$ are independently selected from hydrogen, deuterium, halogen, and $C_1$-$C_6$ alkyl;

$R^5$ and $R^6$ are independently selected from hydrogen, $C_1$-$C_4$ alkyl, $C_3$-$C_8$ cycloalkyl, and aryl;

X is O;

$X^1$ is selected from halogen, $C_1$-$C_8$ alkyl, and $C_1$-$C_5$ haloalkyl;

$X^2$ is selected from hydrogen, halogen, $C_1$-$C_5$ alkyl, and $C_1$-$C_4$ haloalkyl;

Q is N or $CR^O$, wherein $R^O$ is independently selected from hydrogen, halogen, and cyano;

W is $NR^{W2}$, wherein $R^{w2}$ is selected from $C_1$-$C_6$ alkyl, $C_3$-$C_6$ cycloalkyl, 5-6 membered bicyclic carbocyclic group, and a 3-7 membered heterocyclic group, wherein each of the $C_1$-$C_6$ alkyl and $C_3$-$C_6$ cycloalkyl is optionally substituted with 1, 2, or 3 $R^{1D}$;

each $R^{1D}$ is independently selected from halogen, $C_1$-$C_6$ alkyl, $C_1$-$C_3$ haloalkyl, and hydroxyl;

U is O or $C(R^U)_2$, wherein $R^U$ is independently selected from hydrogen, deuterium, halogen, and $C_1$-$C_3$ alkyl, wherein the $C_1$-$C_4$ alkyl is optionally substituted with hydroxyl; and V is O or $C(R^V)_2$, wherein $R^V$ is independently selected from hydrogen, deuterium, halogen, hydroxyl, $C_1$-$C_4$ alkyl, and $C_3$-$C_6$ cycloalkyl, and wherein the $C_1$-$C_4$ alkyl is optionally substituted with hydroxyl.

In some embodiments, the compound of Formula IA' is represented by Formula IA'':

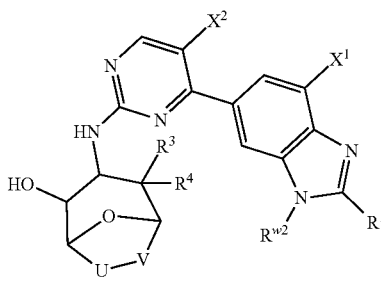

(IA'')

wherein:
- $R^1$ is selected from $C_1$-$C_8$ alkyl, $C_3$-$C_6$ cycloalkyl, $C_3$-$C_6$ cyclic haloalkyl, $C_5$-$C_7$ bicyclic alkyl, a 4-6 membered heterocyclic group, a 6 membered aryl, and a 6 membered heteroaryl, wherein each of the $C_1$-$C_8$ alkyl, $C_3$-$C_6$ cycloalkyl, $C_3$-$C_6$ cyclic haloalkyl, $C_5$-$C_7$ bicyclic alkyl, 4-6 membered heterocyclic group, 6 membered aryl, and 6 membered heteroaryl is independently substituted with 0, 1, 2, or 3 $R^{1A}$;
- each $R^{1A}$ is independently selected from halogen, hydroxyl, an oxo group, amino, $C_1$-$C_4$ alkyl, $C_3$-$C_6$ cycloalkyl, $C_1$-$C_6$ alkoxy, —C(=O)OR$^{1B}$, —C(=O)N(R$^{1B}$)$_2$, and —NHC(=O)OR$^{1B}$, each $R^{1B}$ is independently selected from hydrogen, $C_1$-$C_3$ alkyl, and $C_3$-$C_8$ cycloalkyl;
- $R^3$ and $R^4$ are independently selected from hydrogen, deuterium, halogen, hydroxyl, and $C_1$-$C_3$ alkyl;
- $X^1$ is halogen;
- $X^2$ is halogen;
- $R^{W2}$ is selected from $C_1$-$C_8$ alkyl, $C_3$-$C_5$ cycloalkyl, and a 4-5 membered heterocyclic group, wherein each of the $C_1$-$C_8$ alkyl and $C_3$-$C_8$ cycloalkyl is optionally substituted with 1 or 2$R^{1D}$.
- U is O or C(R$^U$)$_2$, wherein R$^U$ is independently selected from hydrogen, deuterium, halogen, and $C_1$-$C_2$ alkyl, wherein the $C_1$-$C_2$ alkyl is optionally substituted with hydroxyl; and
- V is O or C(R$^V$)$_2$, wherein R$^V$ is independently selected from hydrogen, deuterium, halogen, hydroxyl, and $C_1$-$C_2$ alkyl, wherein the $C_1$-$C_2$ alkyl is optionally substituted with hydroxyl;

with the proviso that one but not both of U and V is O.

In some embodiments, the compound of Formula I is represented by Formula IB:

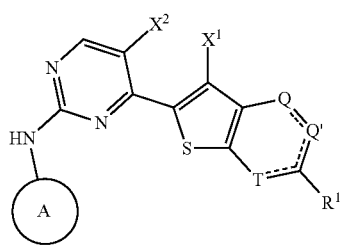

(IB)

wherein:
- ⎯⎯ is a single bond or a double bond;
- Q is CR$^O$, N, or NR$^O$, wherein R$^O$ is selected from hydrogen, halogen, $C_1$-$C_4$ alkyl, and an oxo group;
- Q' is CR$^{Q'}$, N, NR$^{Q'}$, wherein R$^{O'}$ is selected from hydrogen, $C_1$-$C_4$ alkyl, and $C_1$-$C_4$ haloalkyl; and
- T is CR$^{T1}$ or NR$^{T2}$, wherein R$^{T1}$ is halogen or R$^{T2}$, and R$^{T2}$ is hydrogen or $C_1$-$C_6$ alkyl, wherein the $C_1$-$C_6$ alkyl is optionally substituted with 1, 2, or 3 groups independently selected from halogen, $C_1$-$C_6$ alkyl, and hydroxyl.

In some embodiments, the compound of Formula I is represented by Formula IC:

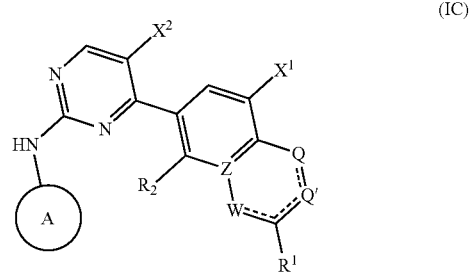

(IC)

wherein:
- ⎯⎯ is a single bond or a double bond;
- Q is N, O, or CR$^O$, wherein R$^O$ is selected from hydrogen, halogen, and an oxo group;
- Q' is CH, CH$_2$, CR$^{Q'}$, N, or NR'', wherein R'' is halogen or R''', and R''' is selected from $C_1$-$C_6$ alkyl, $C_3$-$C_6$ cycloalkyl, $C_1$-$C_4$ haloalkyl, and a 3-8 membered heterocyclic group, wherein each of the $C_1$-$C_6$ alkyl and $C_3$-$C_6$ cycloalkyl are each optionally substituted with 0, 1, 2, or 3 groups independently selected from halogen, $C_1$-$C_6$ alkyl, and hydroxyl;
- Z is C; and
- W is CR$^{W1}$, N, or NR$^{W2}$, wherein
  - R$^{W1}$ is selected from hydrogen, $C_1$-$C_6$ alkyl, $C_3$-$C_6$ cycloalkyl, and a 3-8 membered heterocyclic group, wherein each of the $C_1$-$C_6$ alkyl and $C_3$-$C_6$ cycloalkyl is optionally substituted with 1, 2, or 3 $R^{1D}$,
  - R$^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 R''); and
  - each R'' is independently selected from halogen, $C_1$-$C_6$ alkyl, and hydroxyl; or
- W, Z, $R^2$ and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 R$^{1E}$, and wherein each R$^{1E}$ is independently selected from $C_1$-$C_6$ alkyl, hydroxyl, and an oxo group.

In some embodiments, the compound of Formula I is represented by Formula ID:

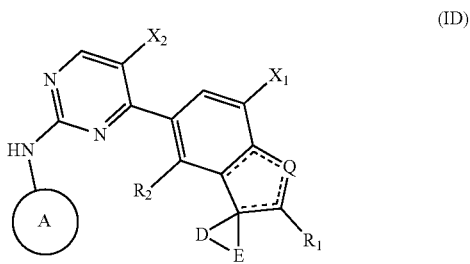

(ID)

wherein:

- ⸺ is a single bond or a double bond; and
- Q is N or CR$^O$, wherein R is independently selected from hydrogen, halogen, and cyano; and
- D and E together with the carbon atom to which they are both attached form a carbocyclic ring of 5-8 atoms or a heterocyclic ring of 5-8 atoms containing 1 to 2 heteroatoms selected from O, S, and N, wherein any carbon ring may be optionally substituted with halogen, $C_1$-$C_4$ alkyl, or hydroxyl.

In some embodiments, Ring B is selected from:

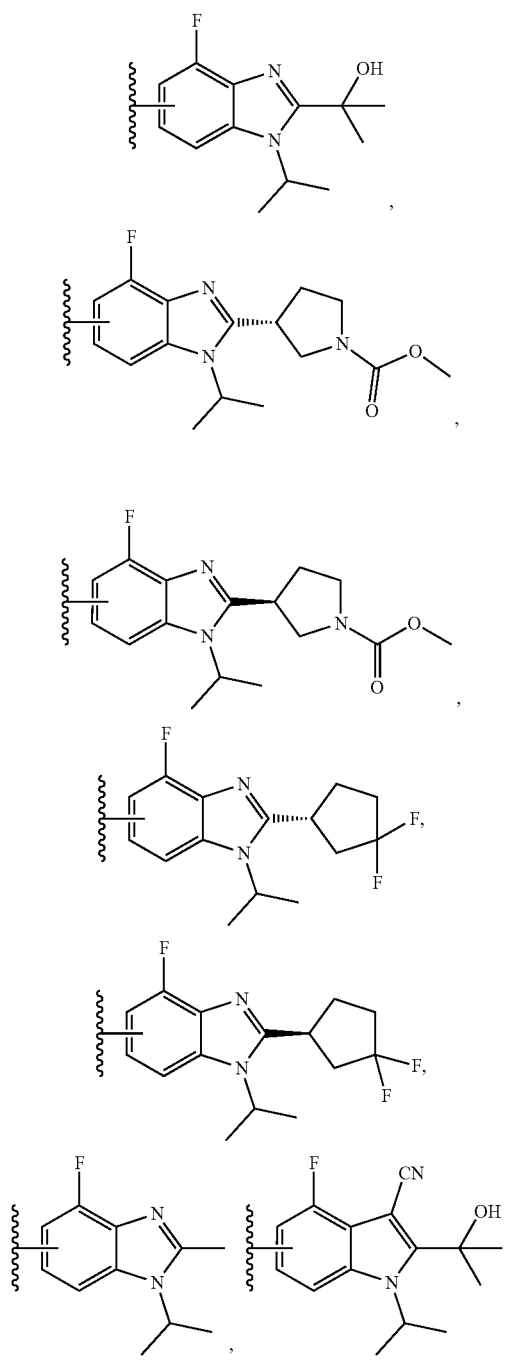

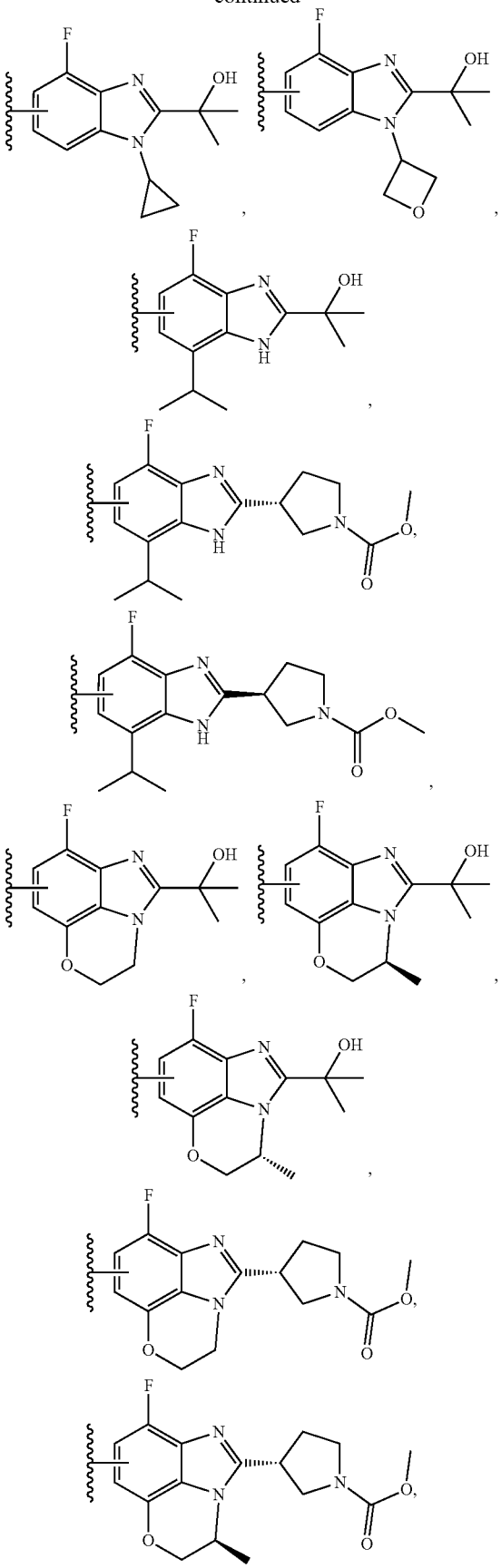

27
-continued
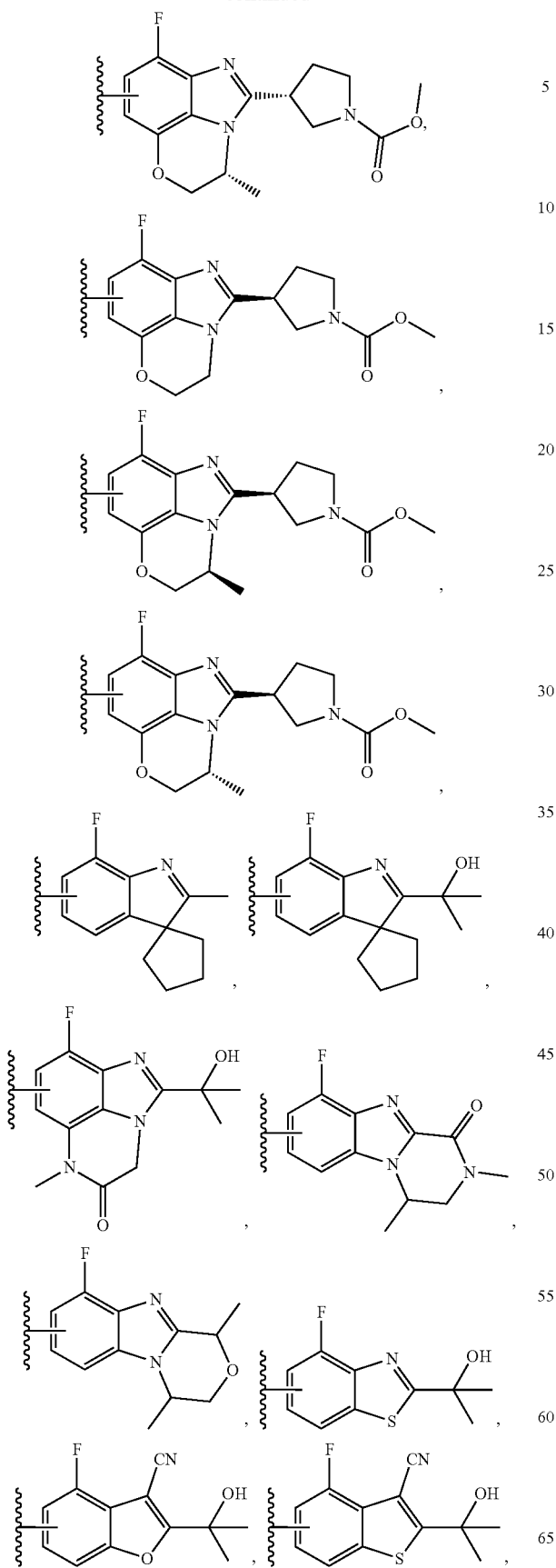
28
-continued
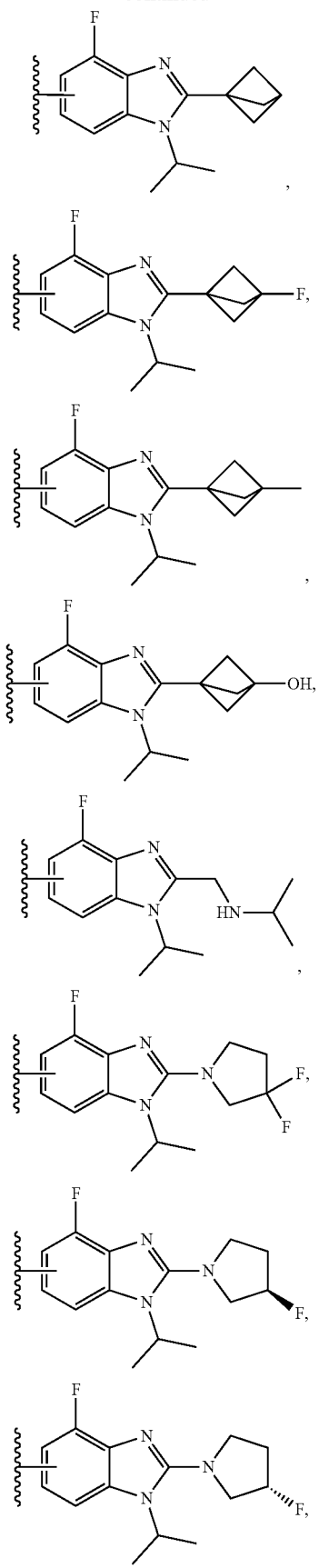

-continued
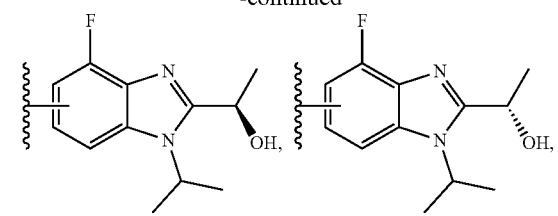
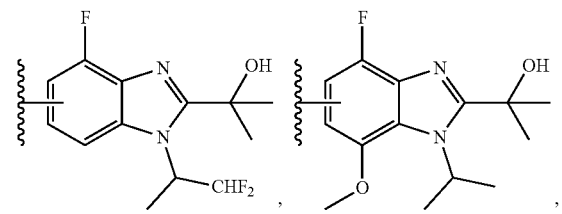
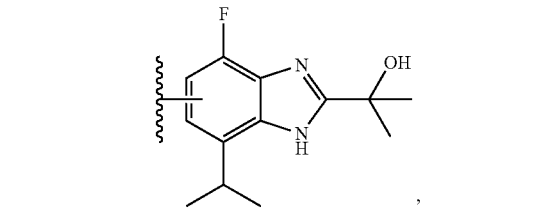
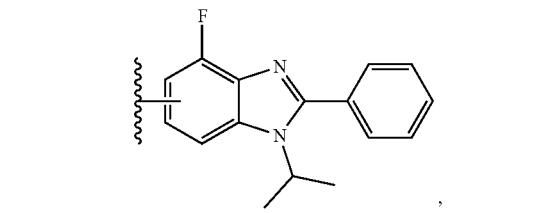
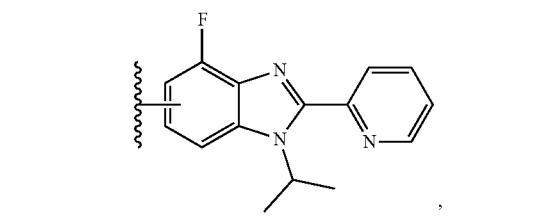
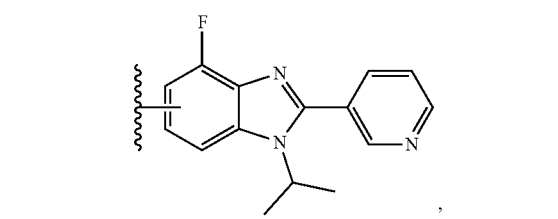
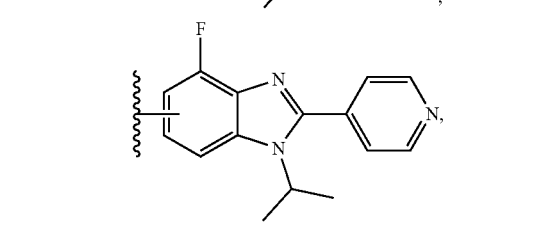
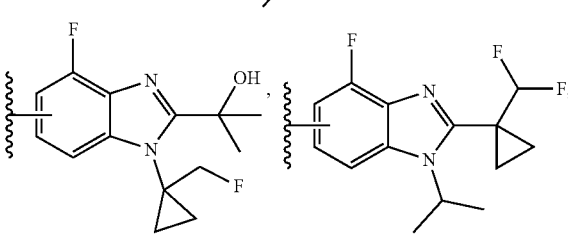
-continued
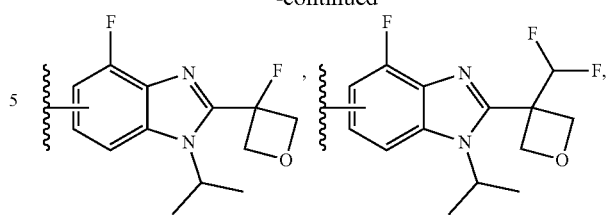
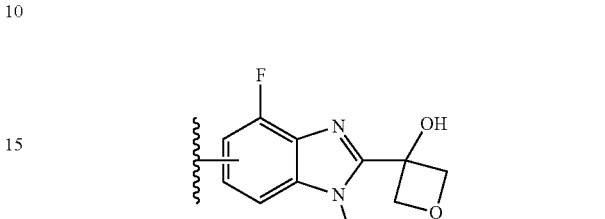
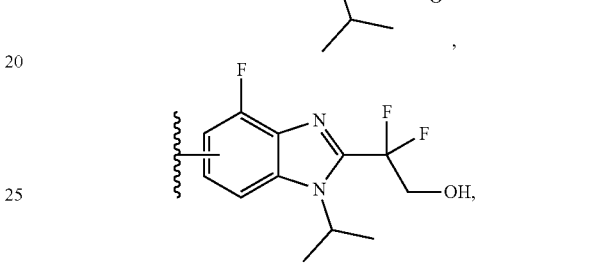
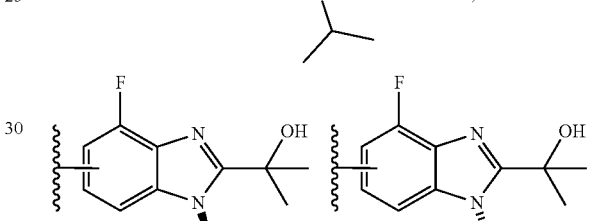
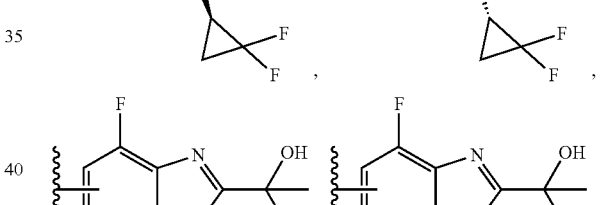
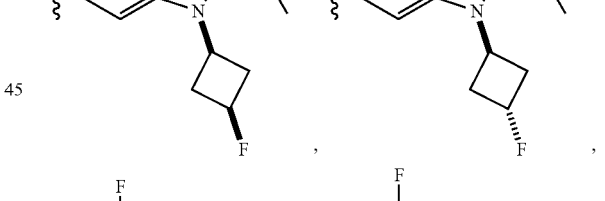
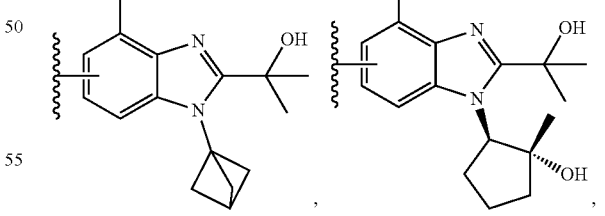
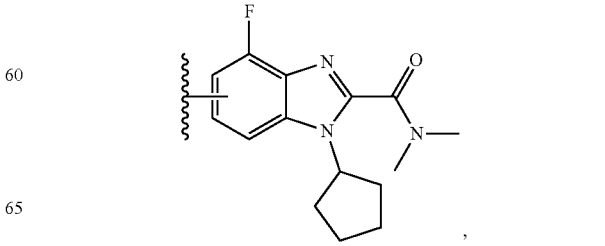

31
-continued
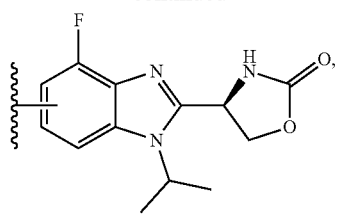
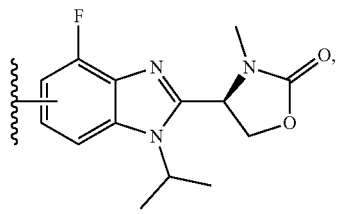
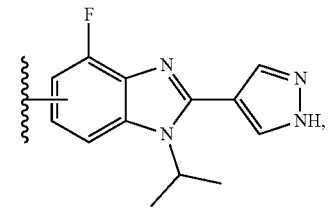
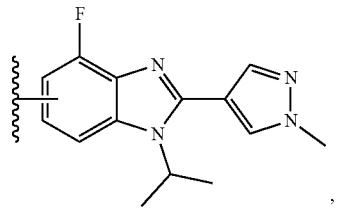
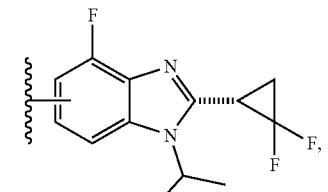
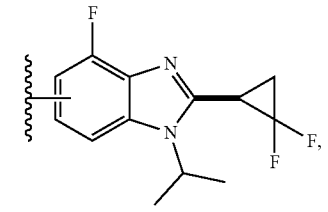
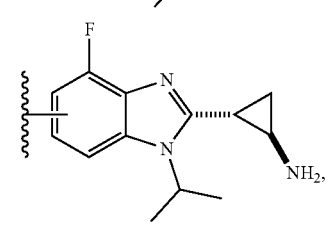
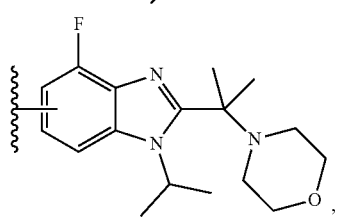
32
-continued
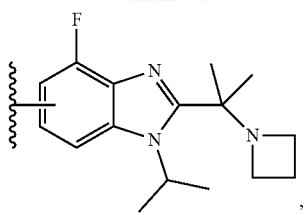
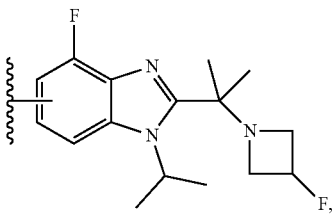
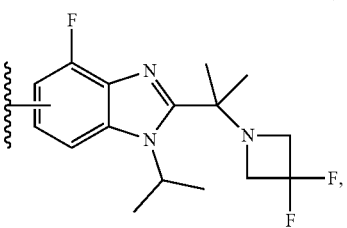
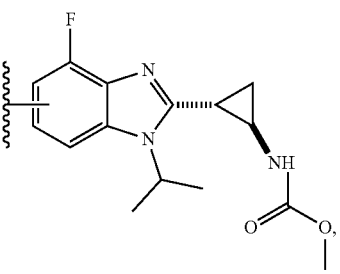
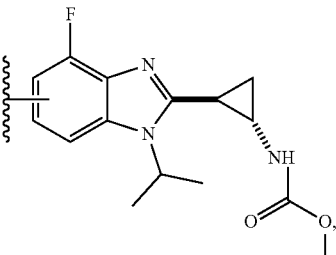
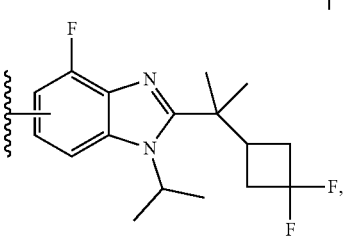
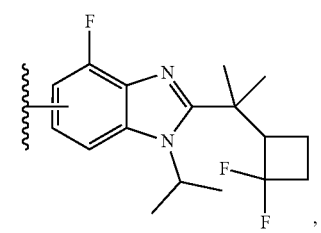

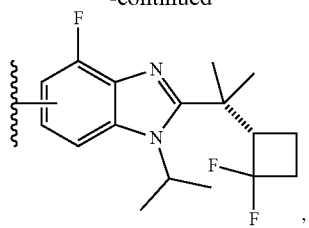,
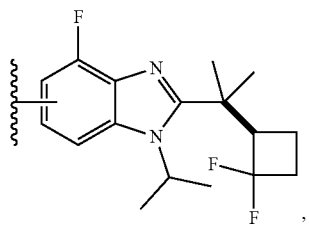,
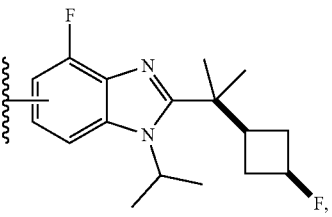,
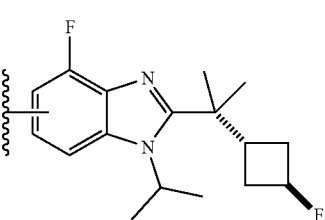,
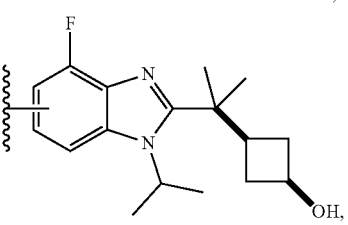,
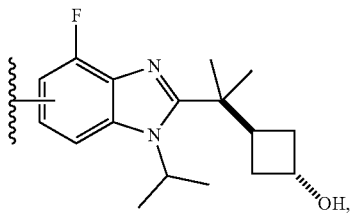,
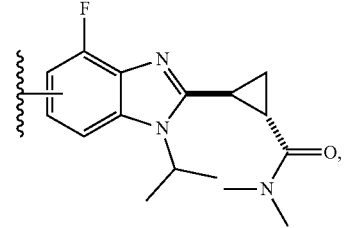,
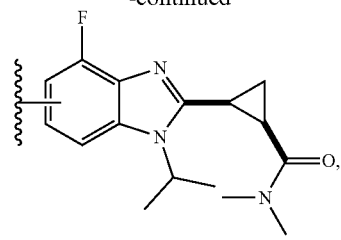,
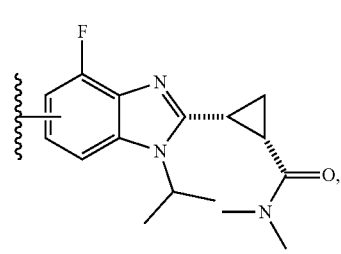,
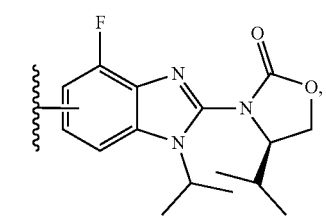,
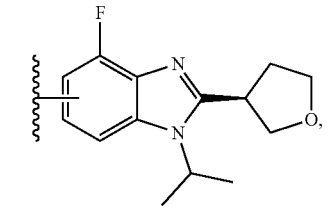,
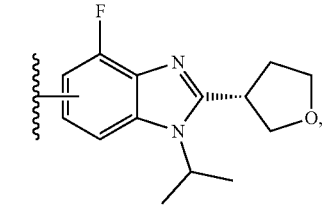,
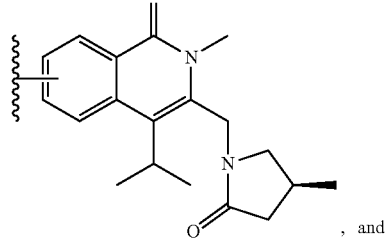, and
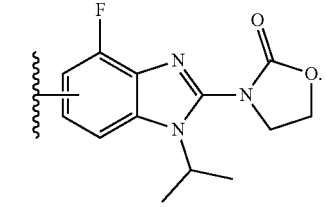.

In some embodiments, Ring B is
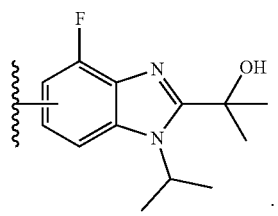
In some embodiments, Ring B is
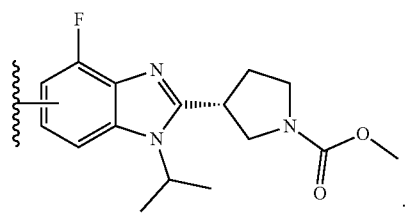
In some embodiments, Ring B is
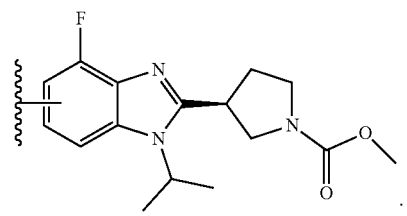
In some embodiments, Ring B is
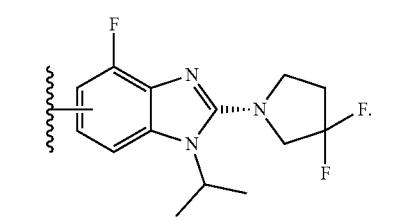
In some embodiments, Ring B is
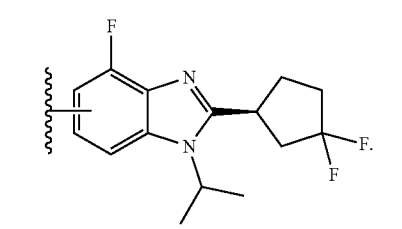
In some embodiments, Ring B is
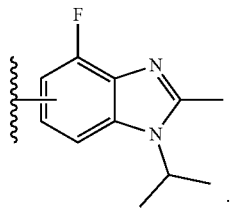
In some embodiments, Ring B is
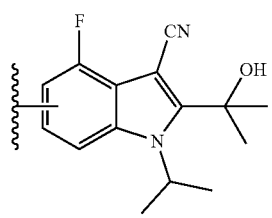
In some embodiments, Ring B is
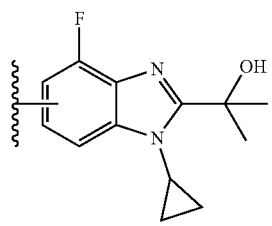
In some embodiments, Ring B is
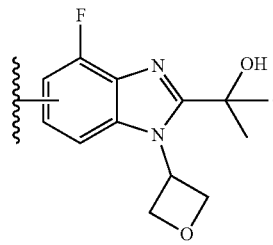
In some embodiments, Ring B is
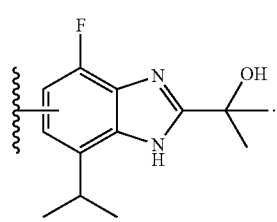

In some embodiments, Ring B is
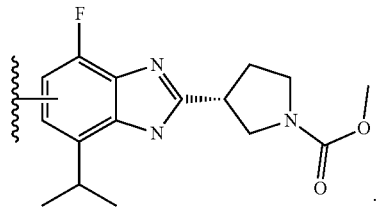
In some embodiments, Ring B is
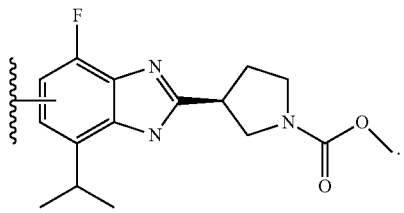
In some embodiments, Ring B is
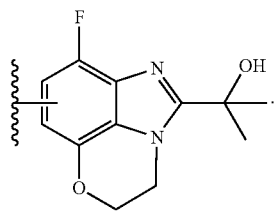
In some embodiments, Ring B is
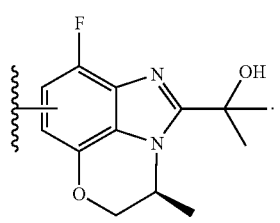
In some embodiments, Ring B is
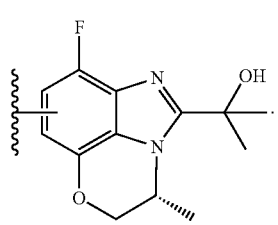
In some embodiments, Ring B is
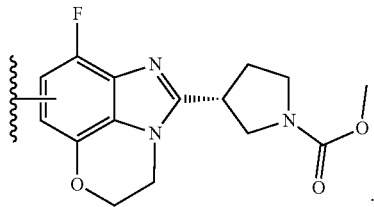
In some embodiments, Ring B is
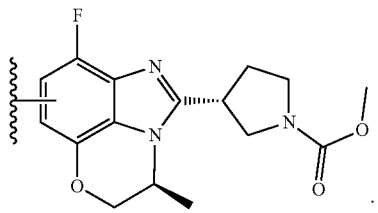
In some embodiments, Ring B is
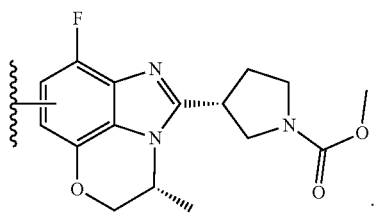
In some embodiments, Ring B is
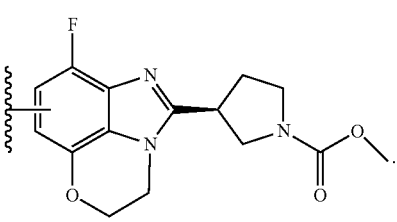
In some embodiments, Ring B is
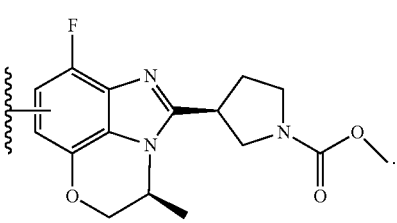

In some embodiments, Ring B is
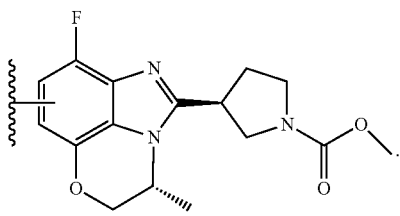
In some embodiments, Ring B is
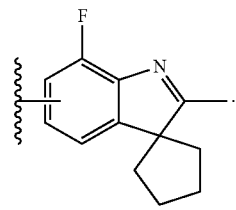
In some embodiments, Ring B is
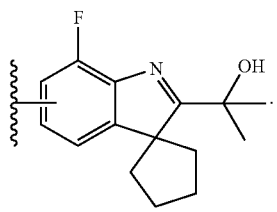
In some embodiments, Ring B is
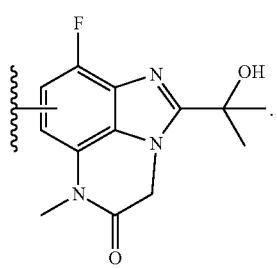
In some embodiments, Ring B is
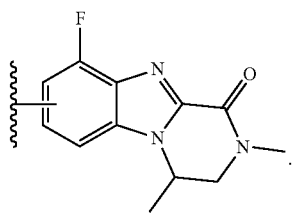
In some embodiments, Ring B is
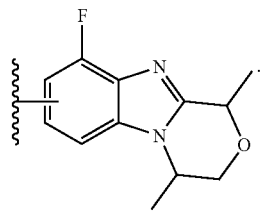
In some embodiments, Ring B is
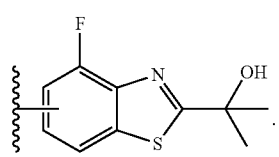
In some embodiments, Ring B is
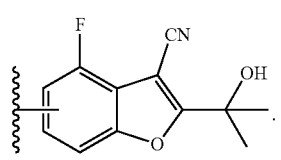
In some embodiments, Ring B is
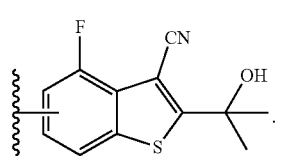
In some embodiments, Ring B is
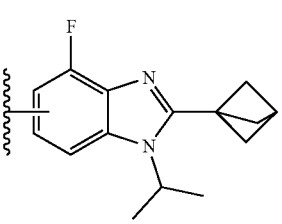
In some embodiments, Ring B is
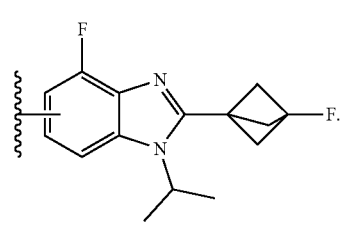

In some embodiments, Ring B is
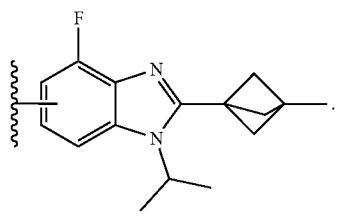
In some embodiments, Ring B is
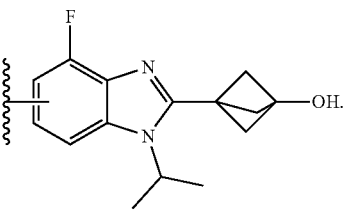
In some embodiments, Ring B is
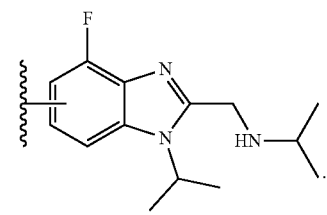
In some embodiments, Ring B is
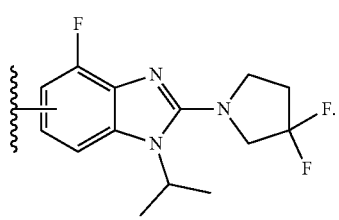
In some embodiments, Ring B is
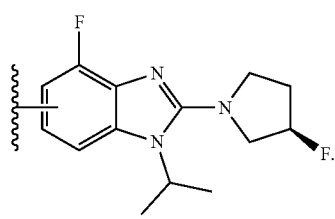
In some embodiments, Ring B is
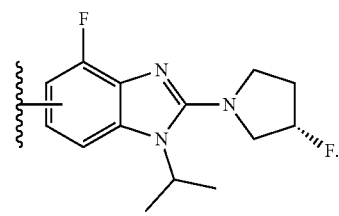
In some embodiments, Ring B is
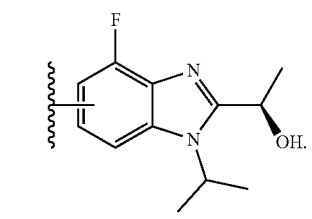
In some embodiments, Ring B is
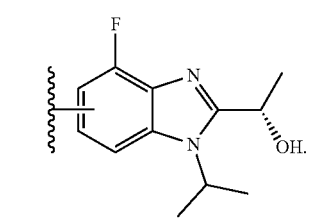
In some embodiments, Ring B is
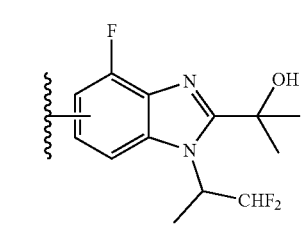
In some embodiments, Ring B is
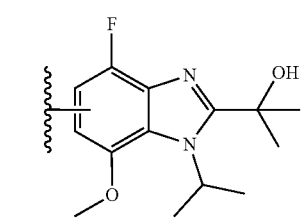

In some embodiments, Ring B is
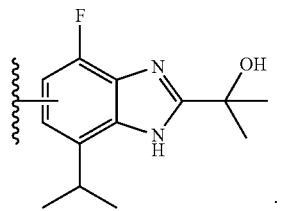
In some embodiments, Ring B is
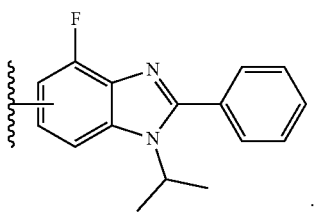
In some embodiments, Ring B is
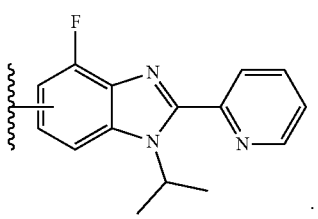
In some embodiments, Ring B is
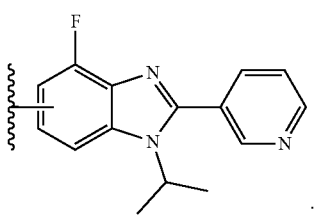
In some embodiments, Ring B is
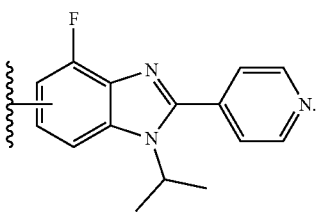
In some embodiments, Ring B is
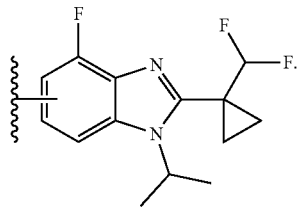
In some embodiments, Ring B is
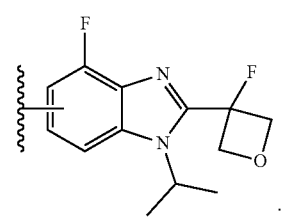
In some embodiments, Ring B is
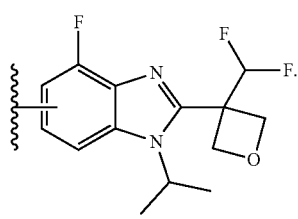
In some embodiments, Ring B is
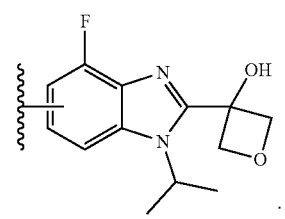
In some embodiments, Ring B is
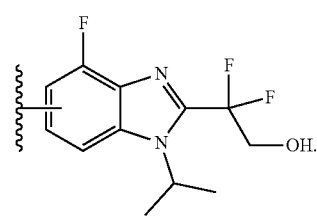

In some embodiments, Ring B is
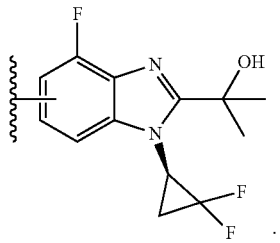
In some embodiments, Ring B is
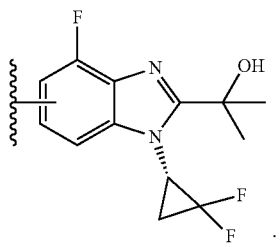
In some embodiments, Ring B is
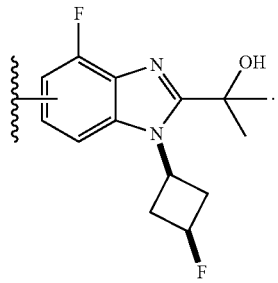
In some embodiments, Ring B is
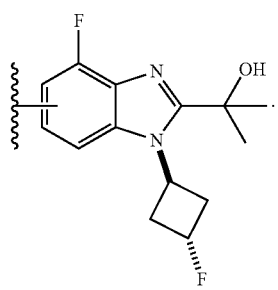
In some embodiments, Ring B is
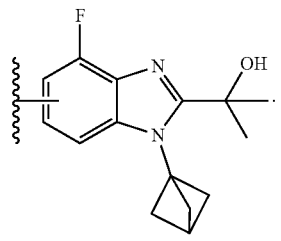
In some embodiments, Ring B is
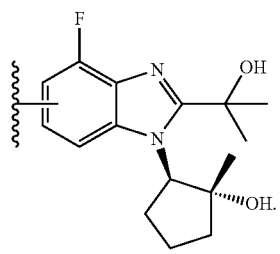
In some embodiments, Ring B is
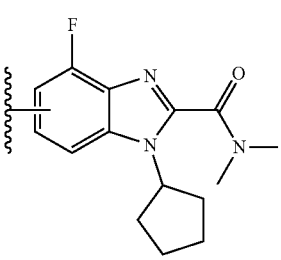
In some embodiments, Ring B is

In some embodiments, Ring B is
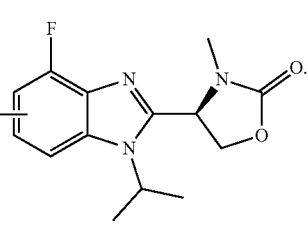

In some embodiments, Ring B is
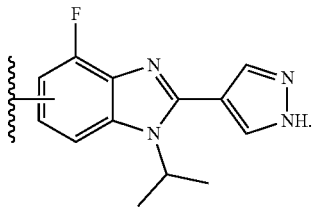
In some embodiments, Ring B is
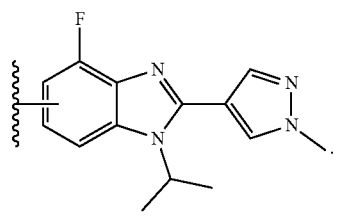
In some embodiments, Ring B is
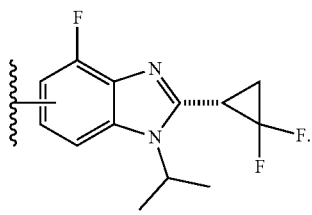
In some embodiments, Ring B is
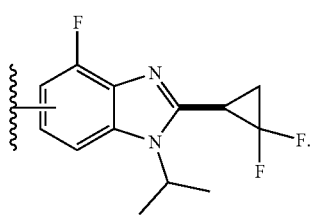
In some embodiments, Ring B is
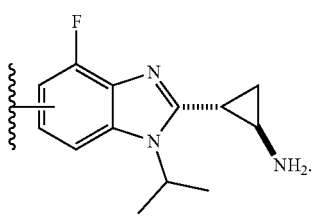
In some embodiments, Ring B is
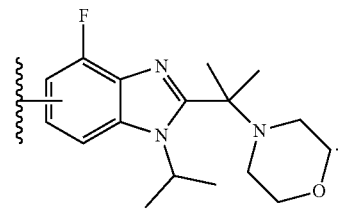
In some embodiments, Ring B is
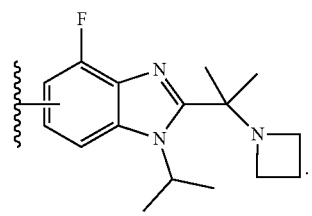
In some embodiments, Ring B is
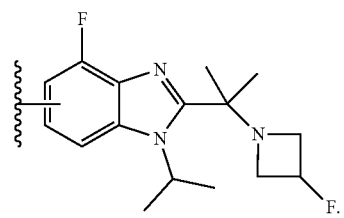
In some embodiments, Ring B is
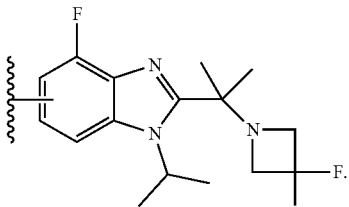
In some embodiments, Ring B is
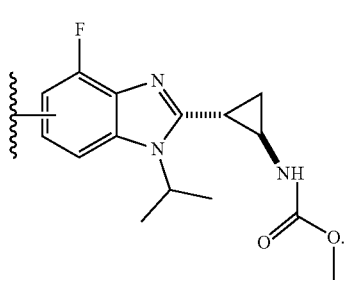

In some embodiments, Ring B is
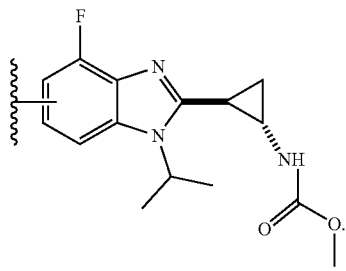
In some embodiments, Ring B is
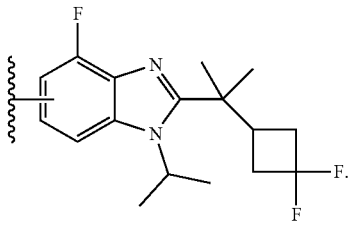
In some embodiments, Ring B is
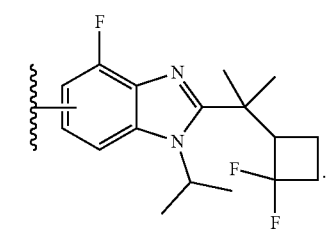
In some embodiments, Ring B is
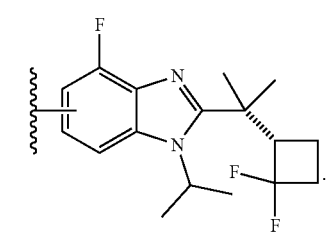
In some embodiments, Ring B is
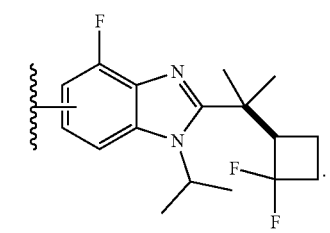
In some embodiments, Ring B is
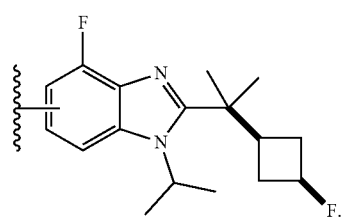
In some embodiments, Ring B is
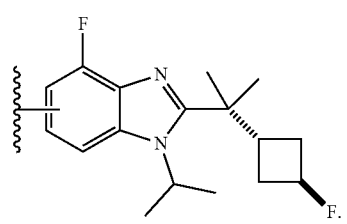
In some embodiments, Ring B is
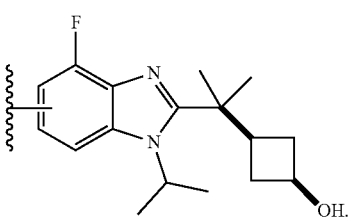
In some embodiments, Ring B is
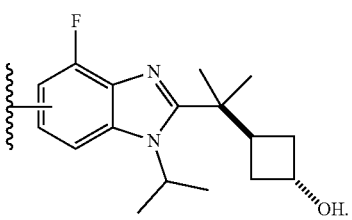
In some embodiments, Ring B is
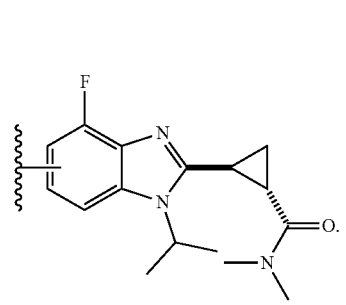

In some embodiments, Ring B is
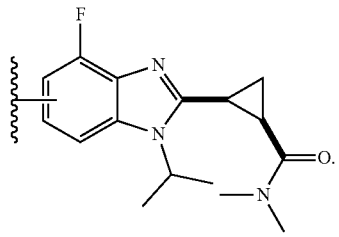
In some embodiments, Ring B is
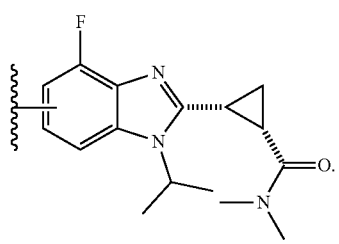
In some embodiments, Ring B is
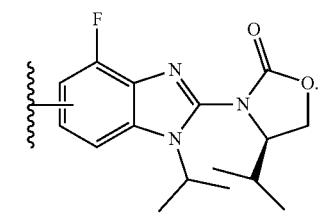
In some embodiments, Ring B is
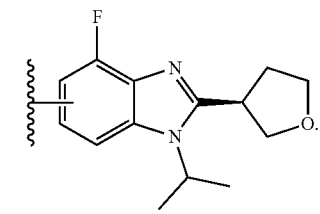
In some embodiments, Ring B is
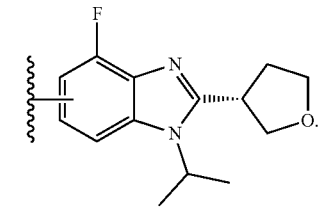
In some embodiments, Ring B is
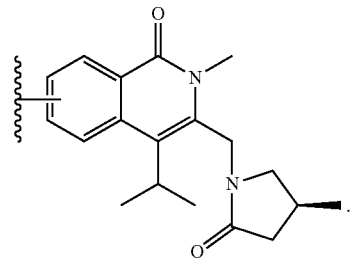
In some embodiments, Ring B is
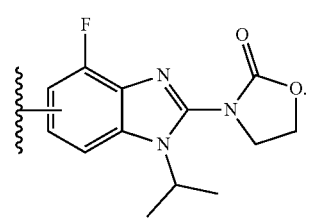
In some embodiments, Ring B is selected from:
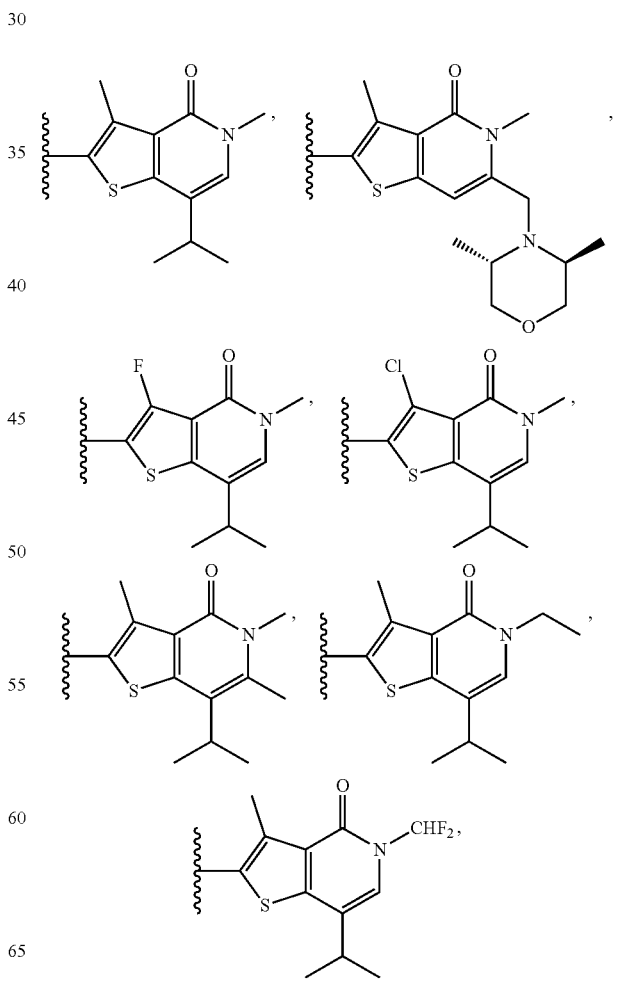

-continued
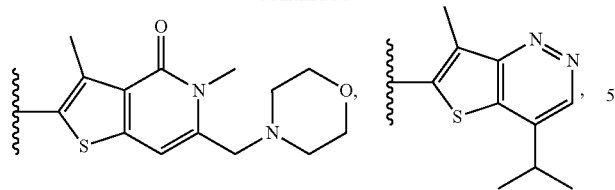 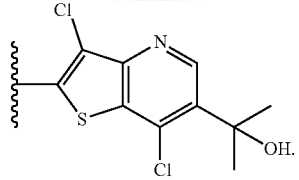
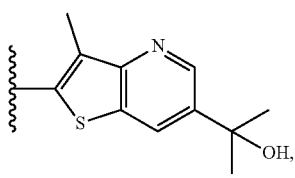
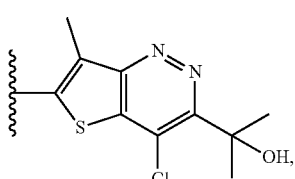
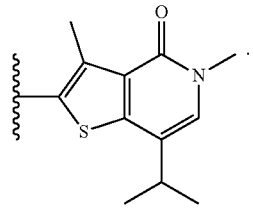 [SMILES: *c1sc2c(C(C)C)cn(C)c(=O)c2c1C]
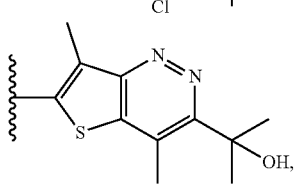
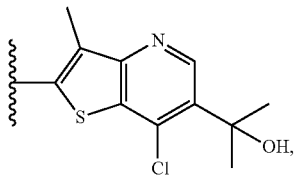
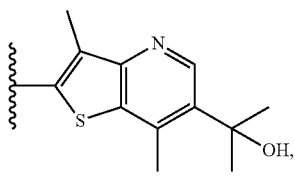
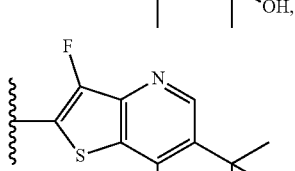
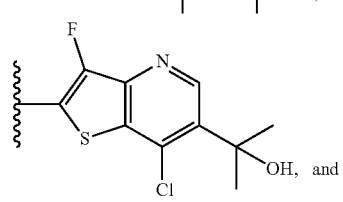 OH, and
-continued
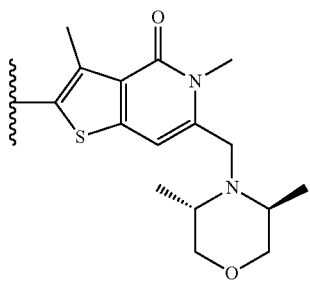
In some embodiments, Ring B is
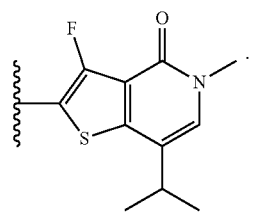 [SMILES: *c1sc2c(C(C)C)cn(C)c(=O)c2c1F]
In some embodiments, Ring B is
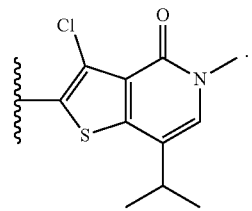 [SMILES: *c1sc2c(C(C)C)cn(C)c(=O)c2c1Cl]
In some embodiments, Ring B is In some embodiments, Ring B is
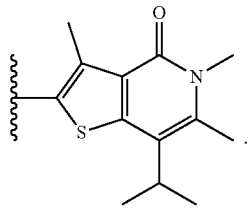 [SMILES: *c1sc2c(C(C)C)c(C)n(C)c(=O)c2c1C]
In some embodiments, Ring B is
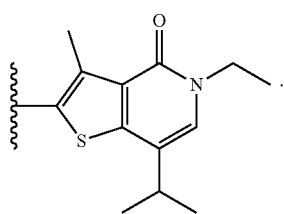 [SMILES: *c1sc2c(C(C)C)cn(CC)c(=O)c2c1C]
In some embodiments, Ring B is
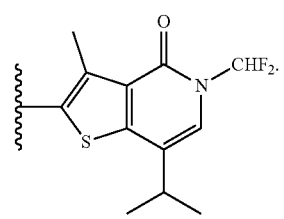 [SMILES: *c1sc2c(C(C)C)cn(C(F)F)c(=O)c2c1C]
In some embodiments, Ring B is
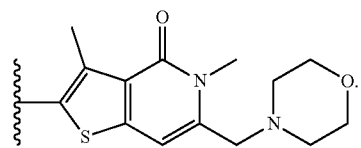 [SMILES: *c1sc2cc(CN3CCOCC3)n(C)c(=O)c2c1C]
In some embodiments, Ring B is
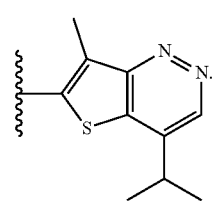 [SMILES: *c1sc2c(C(C)C)cnnc2c1C]
In some embodiments, Ring B is
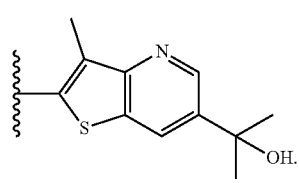 [SMILES: *c1sc2cc(C(C)(C)O)cnc2c1C]
In some embodiments, Ring B is
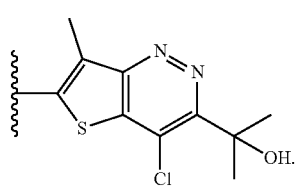 [SMILES: *c1sc2c(Cl)c(C(C)(C)O)nnc2c1C]
In some embodiments, Ring B is
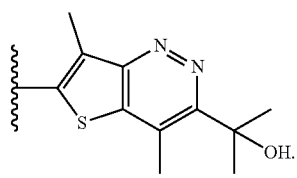 [SMILES: *c1sc2c(C)c(C(C)(C)O)nnc2c1C]
In some embodiments, Ring B is
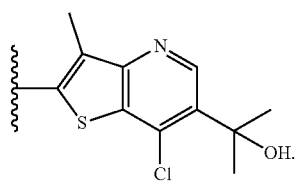 [SMILES: *c1sc2c(Cl)c(C(C)(C)O)cnc2c1C]
In some embodiments, Ring B is
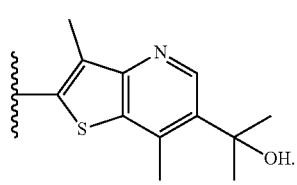 [SMILES: *c1sc2c(C)c(C(C)(C)O)cnc2c1C]
In some embodiments, Ring B is
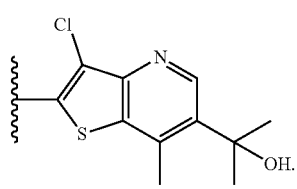
In some embodiments, Ring B is
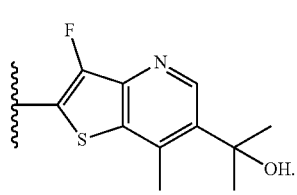 [SMILES: *c1sc2c(C)c(C(C)(C)O)cnc2c1F]

In some embodiments, Ring B is
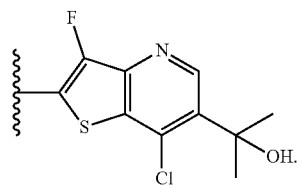 [SMILES: *c1sc2c(Cl)c(C(C)(C)O)cnc2c1F]
In some embodiments, Ring B is
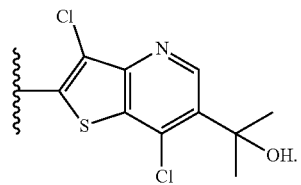
In some embodiments, Ring B is selected from:
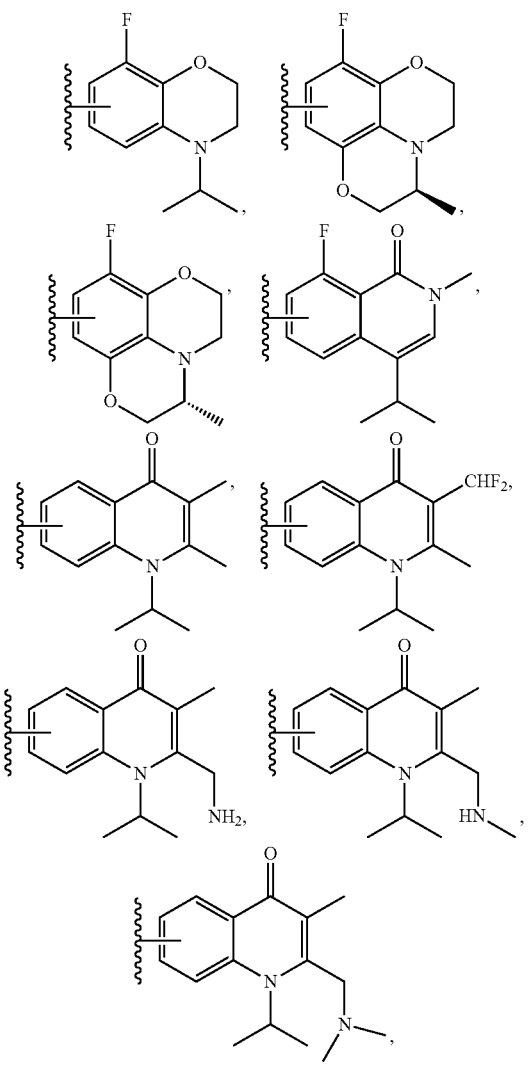
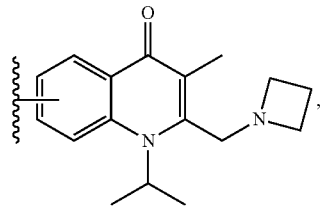
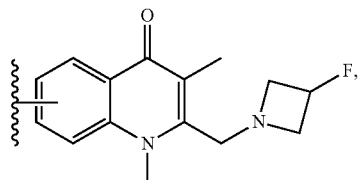
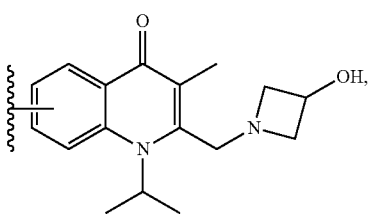
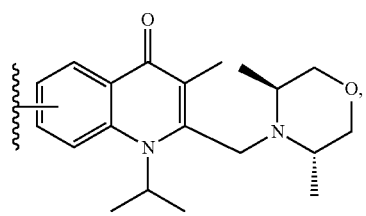
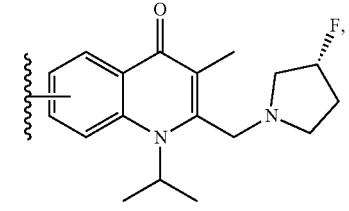
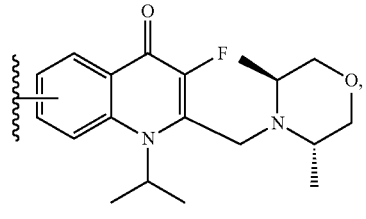
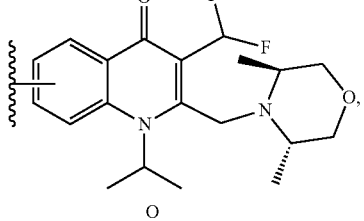
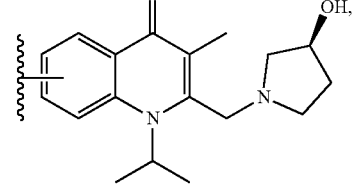

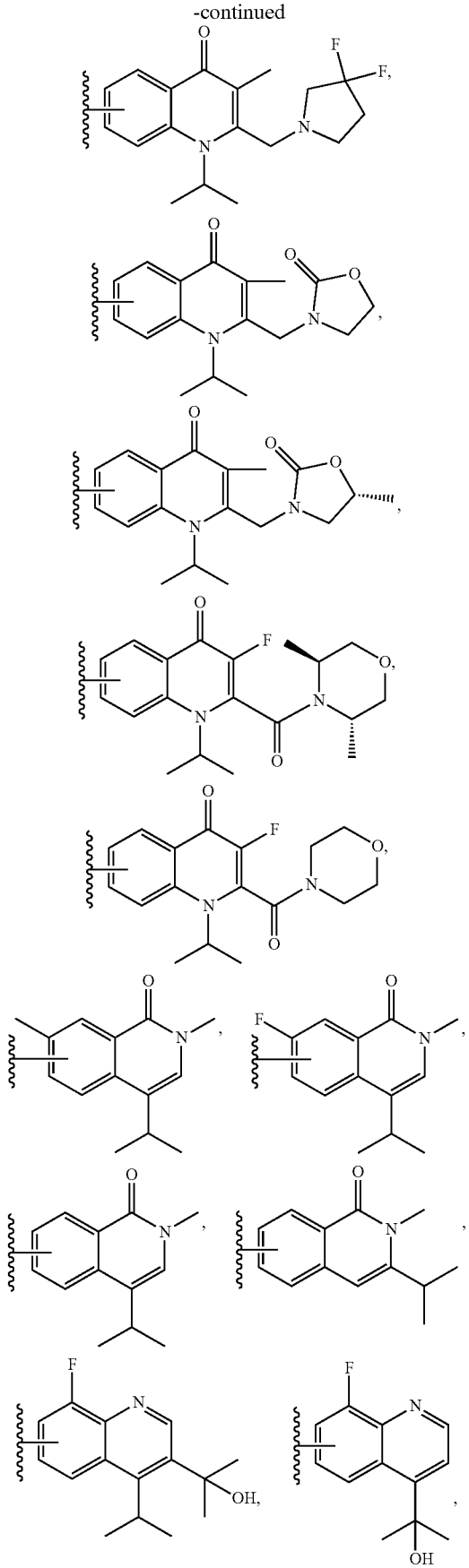
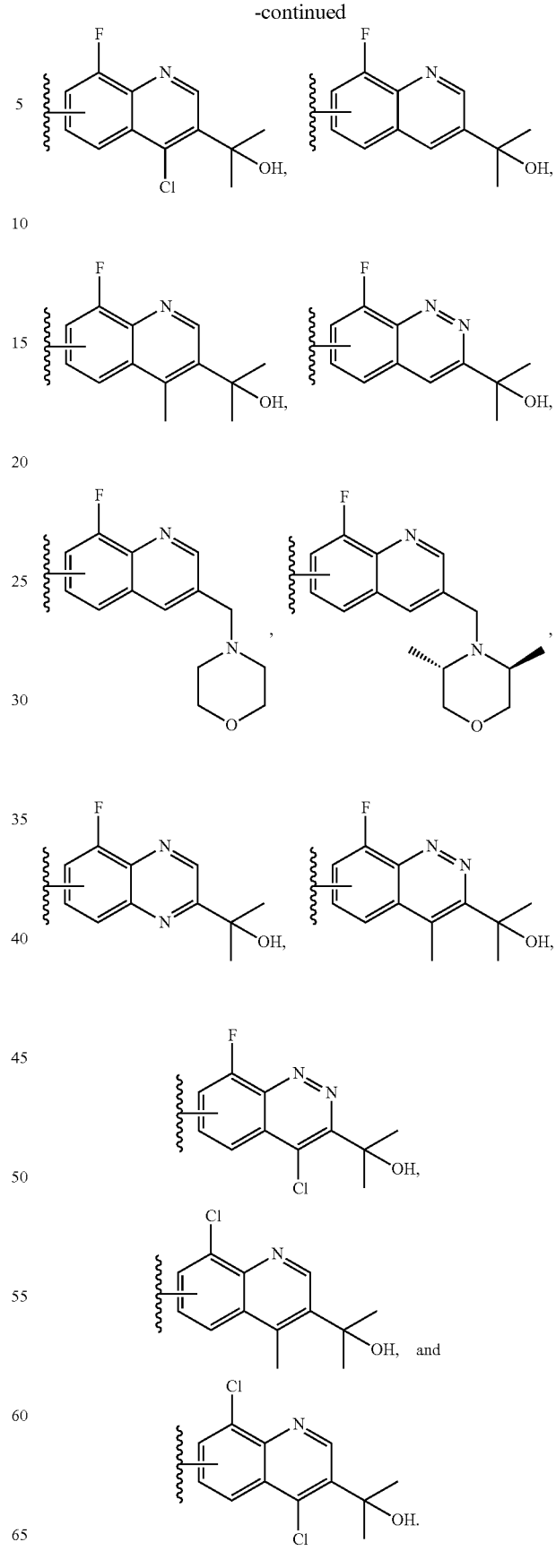

In some embodiments, Ring B is
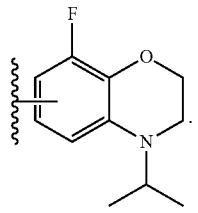
In some embodiments, Ring B is
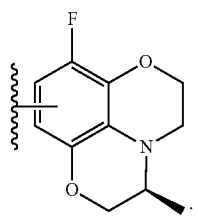
In some embodiments, Ring B is
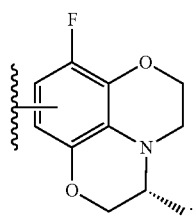
In some embodiments, Ring B is
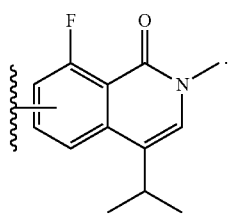
In some embodiments, Ring B is
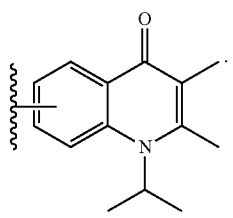
In some embodiments, Ring B is
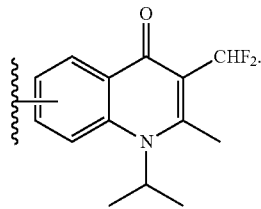
In some embodiments, Ring B is
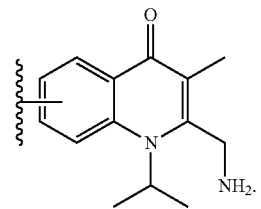
In some embodiments, Ring B is
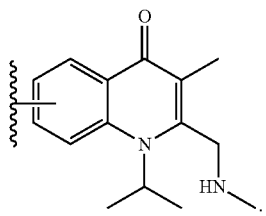
In some embodiments, Ring B is
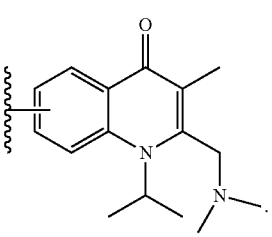
In some embodiments, Ring B is
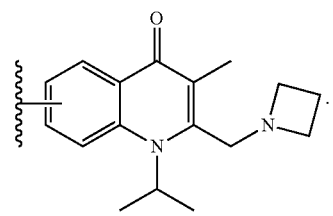

In some embodiments, Ring B is
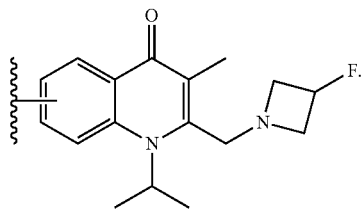
In some embodiments, Ring B is
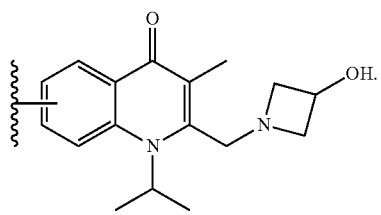
In some embodiments, Ring B is
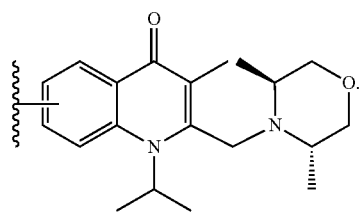
In some embodiments, Ring B is
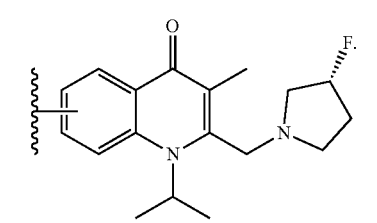
In some embodiments, Ring B is
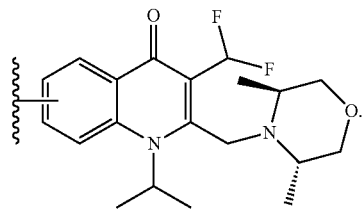
In some embodiments, Ring B is
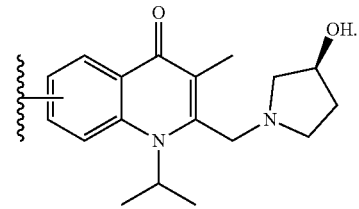
In some embodiments, Ring B is
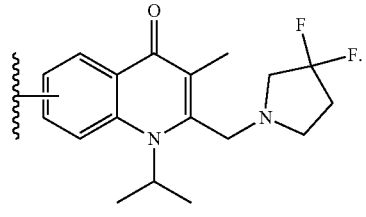
In some embodiments, Ring B is
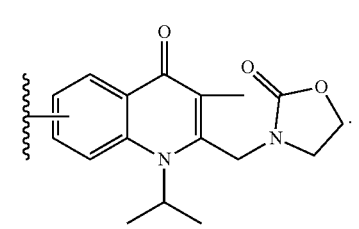
In some embodiments, Ring B is
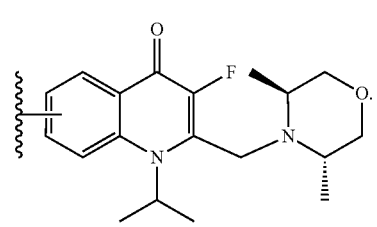
In some embodiments, Ring B is
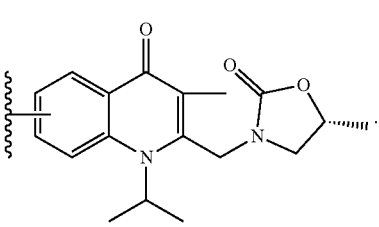

In some embodiments, Ring B is
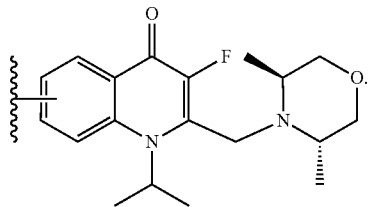
In some embodiments, Ring B is
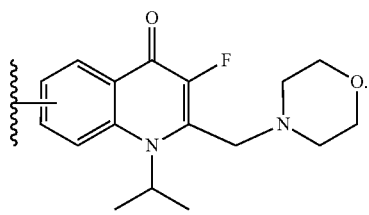
In some embodiments, Ring B is
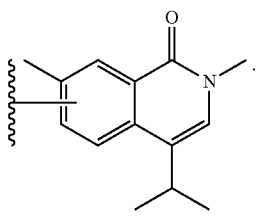
In some embodiments, Ring B is
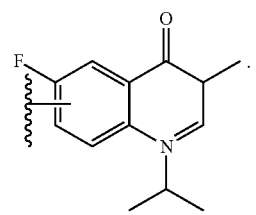
In some embodiments, Ring B is
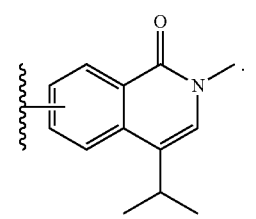
In some embodiments, Ring B is
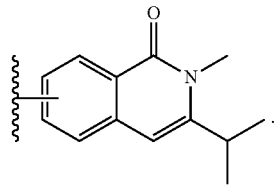
In some embodiments, Ring B is
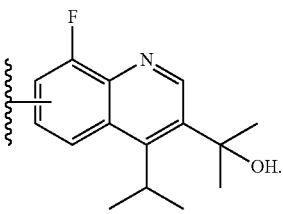
In some embodiments, Ring B is
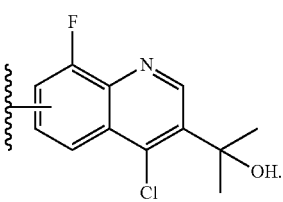
In some embodiments, Ring B is In some embodiments, Ring B is

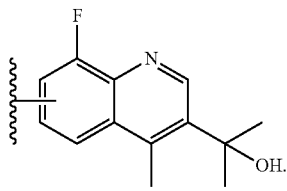

In some embodiments, Ring B is

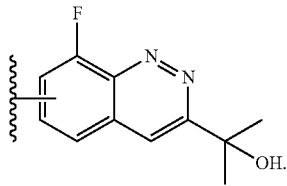

In some embodiments, Ring B is

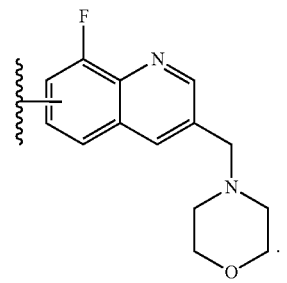

In some embodiments, Ring B is

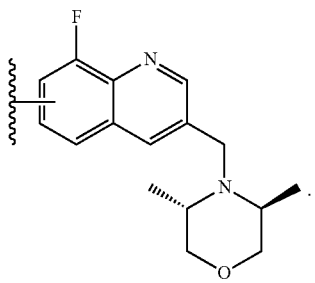

In some embodiments, Ring B is

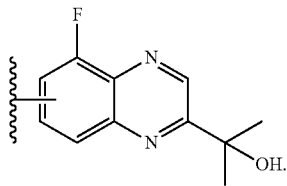

In some embodiments, Ring B is

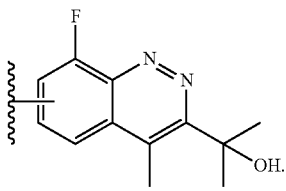

In some embodiments, Ring B is

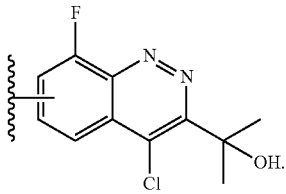

In some embodiments, Ring B is

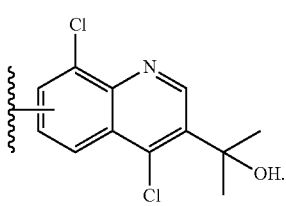

In some embodiments, Ring B is

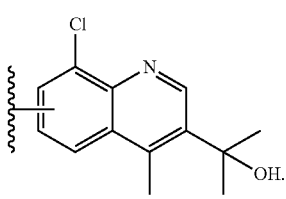

In some embodiments, W is selected from $C(R^{w1})_2$, O, S, N, and $NR^{w2}$.

In some embodiments, W is $C(R^{w1})_2$.

In some embodiments, W is $NR^{w2}$.

In some embodiments, $R^{w1}$ is independently selected from hydrogen, halogen, $C_1$-$C_3$ alkyl, $C_3$-$C_8$ cycloalkyl, 5-7 membered bicyclic heterocyclic group, and a 3-8 membered heterocyclic group, wherein each of the $C_1$-$C_3$ alkyl and $C_3$-$C_8$ cycloalkyl is optionally substituted with 1, 2, or 3 $R^{1D}$.

In some embodiments, $R^{w2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$.

In some embodiments, $R^{1D}$ is independently selected from halogen, methyl, and hydroxyl.

In some embodiments, W is selected from:
NH,

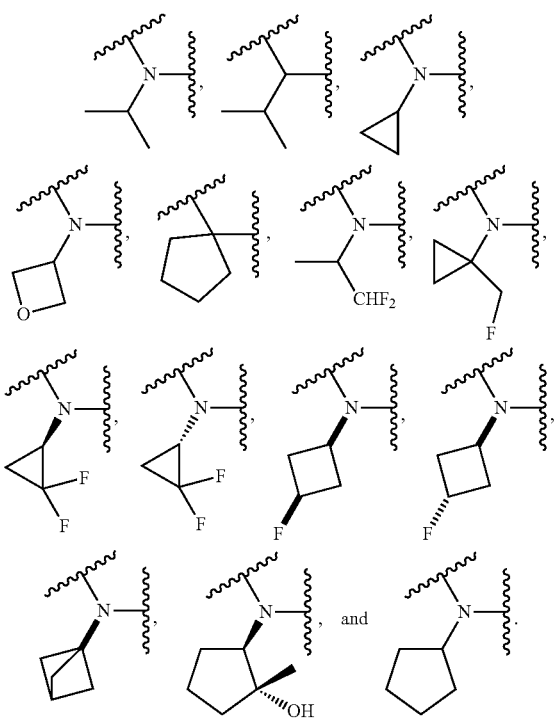

In some embodiments, W is NH. In some embodiments, W is

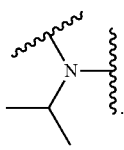 [SMILES: *N(*)C(C)C]

In some embodiments, W is

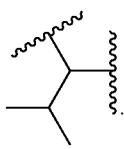 [SMILES: *C(*)C(C)C]

In some embodiments, W is

In some embodiments, W is

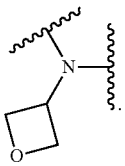 [SMILES: *N(*)C1COC1]

In some embodiments, W is

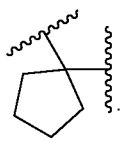

In some embodiments, W is

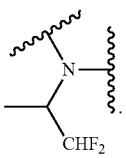

In some embodiments, W is

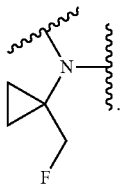

In some embodiments, W is

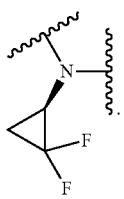

In some embodiments, W is

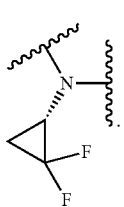

In some embodiments, W is

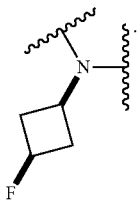

In some embodiments, W is

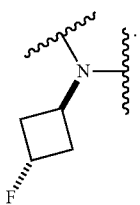

In some embodiments, W is

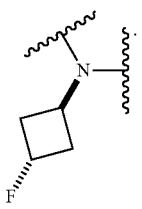

In some embodiments, W is

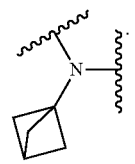

In some embodiments, W is

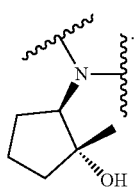 [SMILES: *N(*)[C@@H]1CCC[C@@]1(C)O]

In some embodiments, W is

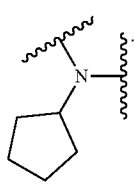 [SMILES: *N(*)C1CCCC1]

In some embodiments, W and $R^1$ are taken together with the C atom to which both are attached to form a heterocyclic ring of 6-7 atoms, wherein the ring has 1 to 3 heteroatoms independently selected from N, S, and O, and wherein the ring is optionally substituted with 1, 2, or 3 $R^{1E}$. In some embodiments, $R^{1E}$ is independently a $C_1$-$C_3$ alkyl or an oxo group. In some embodiments, the ring is

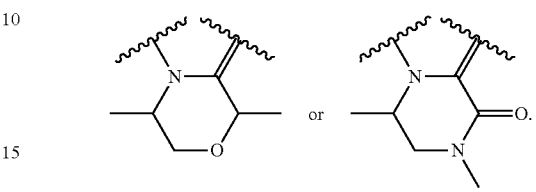

In some embodiments, W, Z, $R^2$ and the C atom to which $R^2$ is attached are taken together to form a heterocyclic ring of 6-7 atoms, wherein the heterocyclic ring is optionally substituted with 1, 2, 3, or 4 $R^{1E}$. In some embodiments, W, $R^2$ and the C atom to which $R^2$ is attached are taken together to form a ring selected from:

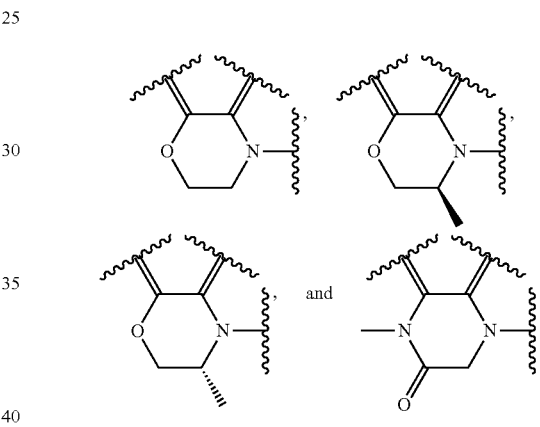

In some embodiments, $X^1$ is selected from bromine, chlorine, fluorine, $C_1$-$C_3$ alkyl, and $C_1$-$C_3$ haloalkyl. In some embodiments, $X^1$ is selected from fluorine, chlorine, —$CF_3$, and —$CHF_2$. In some embodiments, $X^1$ is fluorine. In some embodiments, $X^1$ is chlorine.

In some embodiments, $X^2$ is selected is selected from hydrogen, halogen, $C_1$-$C_3$ alkyl, and $C_1$-$C_3$ haloalkyl. In some embodiments, $X^2$ is selected from hydrogen, bromine, chlorine, fluorine, —$CH_3$, —$CF_3$, and —$CHF_2$. In some embodiments, $X^2$ is fluorine. In some embodiments, $X^2$ is chlorine.

In some embodiments, $R^1$ is selected from $C_1$-$C_8$ alkyl, $C_3$-$C_6$ cycloalkyl, $C_1$-$C_6$ haloalkyl, $C_3$-$C_6$ cyclic haloalkyl, $C_5$-$C_7$ bicyclic alkyl, $C_1$-$C_6$ aminoalkyl, $C_1$-$C_6$ alkoxy, an oxo group, a 4-6 membered heterocyclic group, 6-membered aryl and 5-6 membered heteroaryl, wherein each of the $C_1$-$C_8$ alkyl, $C_3$-$C_6$ cycloalkyl, $C_1$-$C_6$ haloalkyl, $C_3$-$C_6$ cyclic haloalkyl, $C_5$-$C_7$ bicyclic alkyl, $C_1$-$C_6$ aminoalkyl, $C_1$-$C_6$ alkoxy, 4-6 membered heterocyclic group, 6-membered aryl, and 5-6 membered heteroaryl are independently substituted with 0, 1, 2, or 3 $R^{1A}$.

In some embodiments, $R^{1A}$ is independently selected from halogen, hydroxyl, oxo, amino, $C_1$-$C_8$ alkyl, $C_3$-$C_6$ cycloalkyl, $C_1$-$C_6$ alkoxy, $C_3$-$C_6$ cyclic alkoxy, —C(=O)O$R^{1B}$, —C(=O)N($R^{1B}$)$_2$, —NHC(=O)O$R^{1B}$, and 4-6 membered heterocyclic group, wherein the 4-6 membered heterocyclic group is optionally substituted with 1, 2, or 3 $R^{1C}$.

In some embodiments, $R^{1B}$ is independently selected from hydrogen, $C_1$-$C_5$ alkyl, and $C_4$-$C_6$ cycloalkyl.

In some embodiments, $R^{1C}$ is independently selected from hydroxyl, halogen, an oxo group, $C_1$-$C_5$ alkyl, and $C_3$-$C_6$ cycloalkyl.

In some embodiments, $R^1$ is selected from:

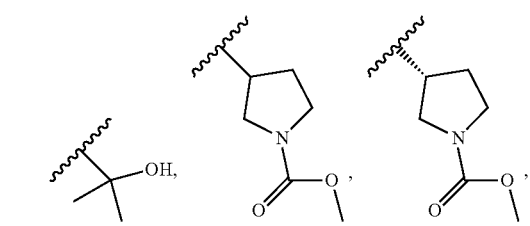
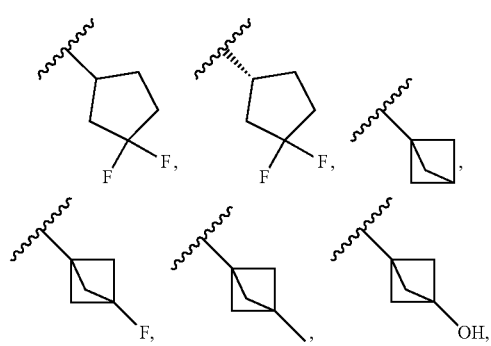
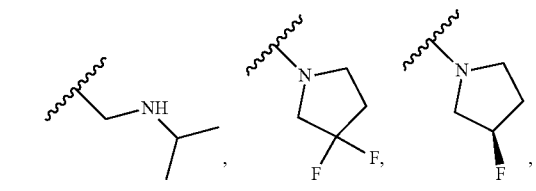
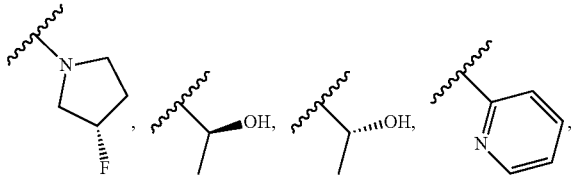
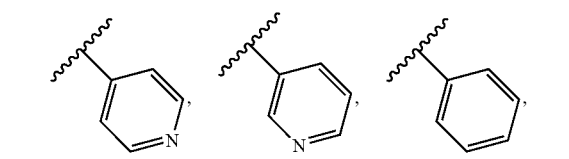
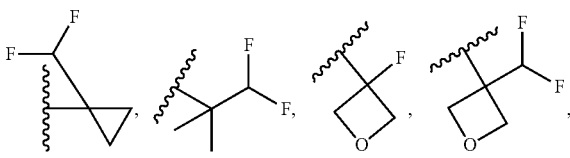
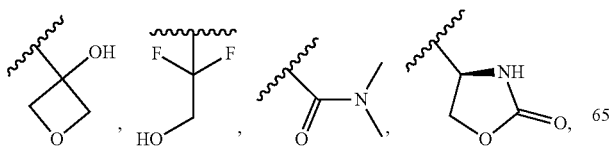

-continued

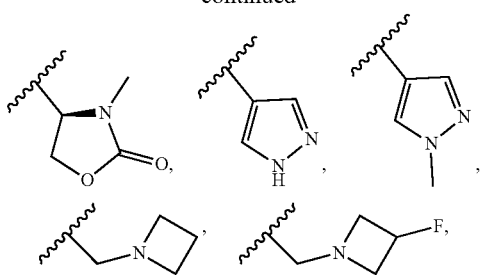
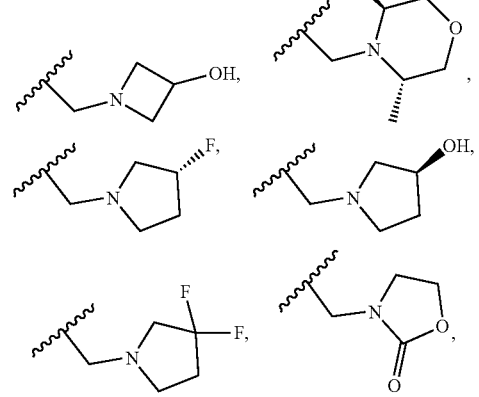
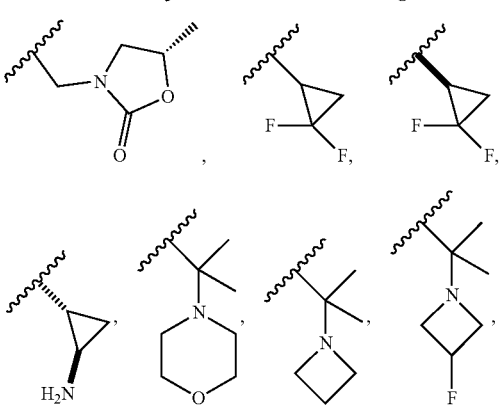
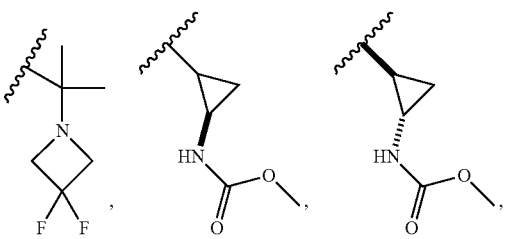
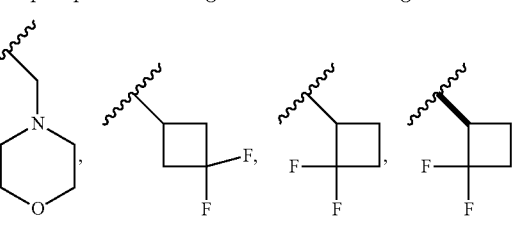
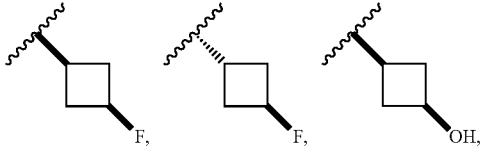

In some embodiments, R¹ is selected from:

In some embodiments, R¹ is

In some embodiments, R¹ is

In some embodiments, R¹ is

In some embodiments, R¹ is

In some embodiments, R¹ is

In some embodiments, $R^1$ is

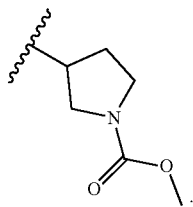 [SMILES: *C1CCN(C(=O)OC)C1]

In some embodiments, $R^1$ is

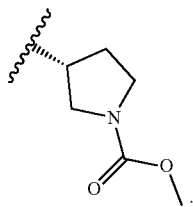

In some embodiments, $R^1$ is

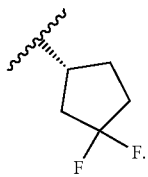 [SMILES: *[C@@H]1CCC(F)(F)C1]

In some embodiments, $R^1$ is

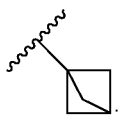

In some embodiments, $R^1$ is

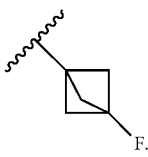 [SMILES: *C12CC(F)(C1)C2]

In some embodiments, $R^1$ is

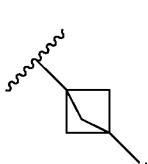 [SMILES: *C12CC(C)(C1)C2]

In some embodiments, $R^2$ is hydrogen or $C_1$-$C_8$ alkyl. In some embodiments, $R^2$ is hydrogen. In some embodiments, $R^2$ is methyl, ethyl, propyl, or isopropyl. In some embodiments, $R^2$ is methyl. In some embodiments, $R^2$ is propyl. In some embodiments, $R^2$ is isopropyl.

In some embodiments, T is $CR^{T1}$. In some embodiments, $R^{T1}$ is halogen. In some embodiments, $R^{T1}$ is $R^{T2}$. In some embodiments, $R^{T2}$ is hydrogen or $C_1$-$C_4$ alkyl. In some embodiments, $R^{T2}$ is selected from hydrogen, methyl, and isopropyl.

In some embodiments, Q' is N. In some embodiments, Q' is $NR^Q$. In some embodiments, $R^Q$ is selected from hydrogen, methyl ethyl, propyl, and $C_1$-$C_3$ haloalkyl. In some embodiments, RR is selected from hydrogen, methyl, ethyl, and —$CHF_2$. In some embodiments, $R^{Q'}$ is hydrogen. In some embodiments, $R^Q$ is methyl. In some embodiments, R.° is ethyl. In some embodiments, $R^Q$ is —$CHF_2$.

In some embodiments, $R^3$ is selected from hydrogen, deuterium, halogen (e.g., fluorine), and methyl. In some embodiments. $R^3$ is hydrogen. In some embodiments, $R^3$ is deuterium. In some embodiments, $R^3$ is fluorine. In some embodiments, $R^3$ is methyl.

In some embodiments, $R^4$ is selected from hydrogen, deuterium, halogen (e.g., fluorine), and methyl. In some embodiments, $R^4$ is hydrogen. In some embodiments, $R^4$ is deuterium. In some embodiments, $R^4$ is fluorine. In some embodiments, $R^4$ is methyl.

In some embodiments, $R^6$ is hydrogen.

In some embodiments, X is O.

In some embodiments, X is N—$S(O)_2$—$R^X$. In some embodiments, $R^X$ is selected from $C_1$-$C_5$ alkyl, $C_3$-$C_6$ cycloalkyl, a 3-6 membered heterocyclic group, 6-membered aryl, and 6-membered heteroaryl, and wherein each of the $C_3$-$C_6$ cycloalkyl, 3-7 membered heterocyclic group, 6-membered aryl, and 6-membered heteroaryl is optionally substituted with 1, 2, or 3 groups selected from halogen, hydroxyl, and cyano.

In some embodiments, X is selected from:
O,

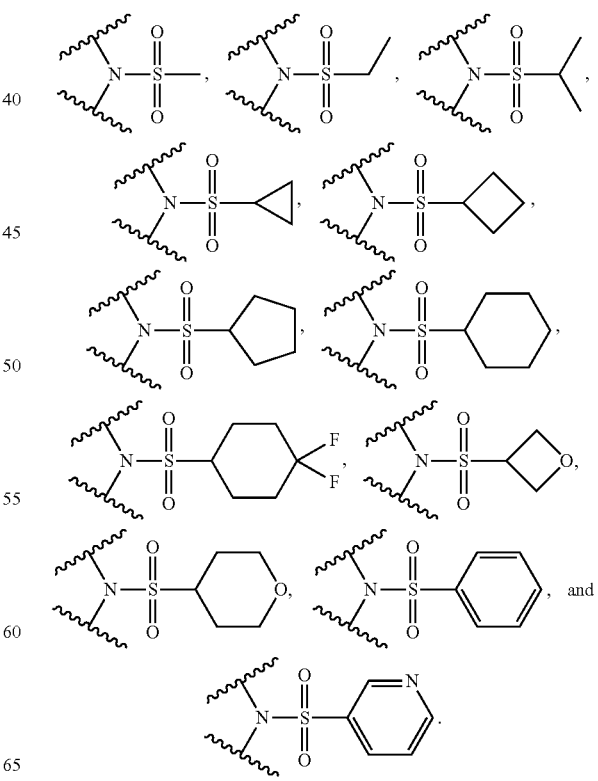

In some embodiments, X is O. In some embodiments, X is

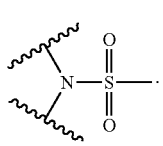

In some embodiments, X is

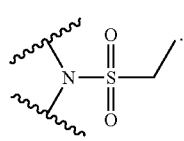

In some embodiments, X is

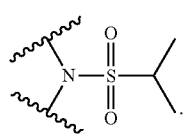 [SMILES: *N(*)S(=O)(=O)C(C)C]

In some embodiments, X is

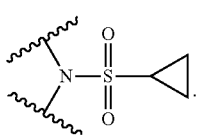 [SMILES: *N(*)S(=O)(=O)C1CC1]

In some embodiments, X is

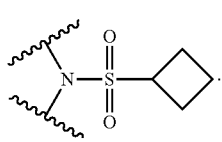 [SMILES: *N(*)S(=O)(=O)C1CCC1]

In some embodiments, X is

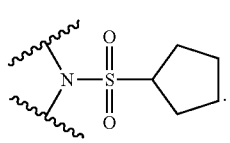

In some embodiments, X is

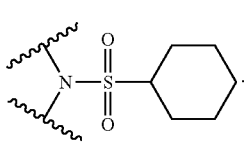

In some embodiments, X is

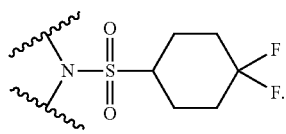 [SMILES: *N(*)S(=O)(=O)C1CCC(F)(F)CC1]

In some embodiments, X is

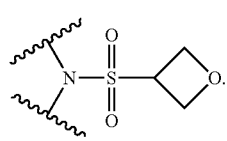 [SMILES: *N(*)S(=O)(=O)C1COC1]

In some embodiments, X is

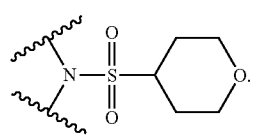

In some embodiments, X is

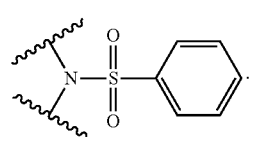 [SMILES: *N(*)S(=O)(=O)c1ccccc1]

In some embodiments, X is

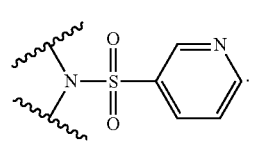

In some embodiments, U is O. In some embodiments, U is carbon.

In some embodiments, U is $C(R^1)_2$. In some embodiments, $R^U$ is independently selected from hydrogen, deuterium, fluorine, and $C_1$-$C_2$ alkyl, and wherein the $C_1$-$C_2$ alkyl is optionally substituted with hydroxyl.

In some embodiments, U is carbon.

In some embodiments, U is selected from:
O,

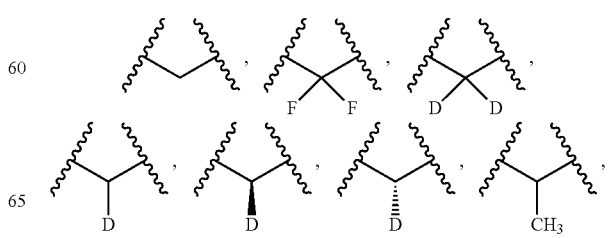

-continued

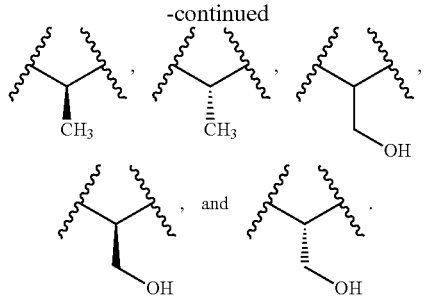

In some embodiments, V is O. In some embodiments, V is carbon.

In some embodiments, V is $C(R^V)_2$. In some embodiments, $R^V$ is independently selected from hydrogen, deuterium, fluorine, and $C_1$-$C_2$ alkyl, and wherein the $C_1$-$C_2$ alkyl is optionally substituted with hydroxyl. In some embodiments, the $C_1$-$C_2$ alkyl is substituted with hydroxyl.

In some embodiments, V is selected from:
O,

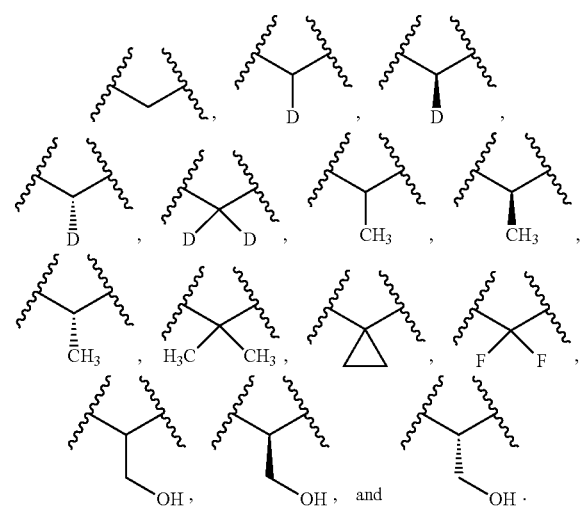

In some embodiments, one but not both of U and V is O. In some embodiments, U is O and V is carbon. In some embodiments, U is carbon and V is O.

In some embodiments, both U and V are carbon.

In some embodiments, Ring A is selected from:

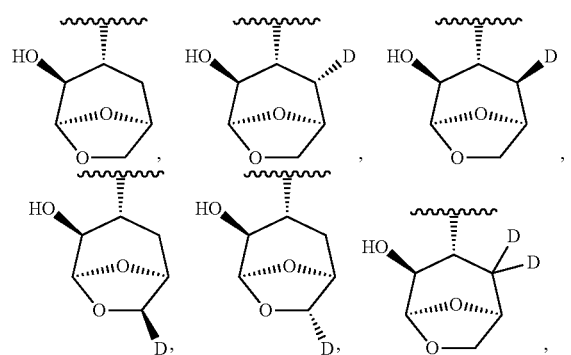

-continued

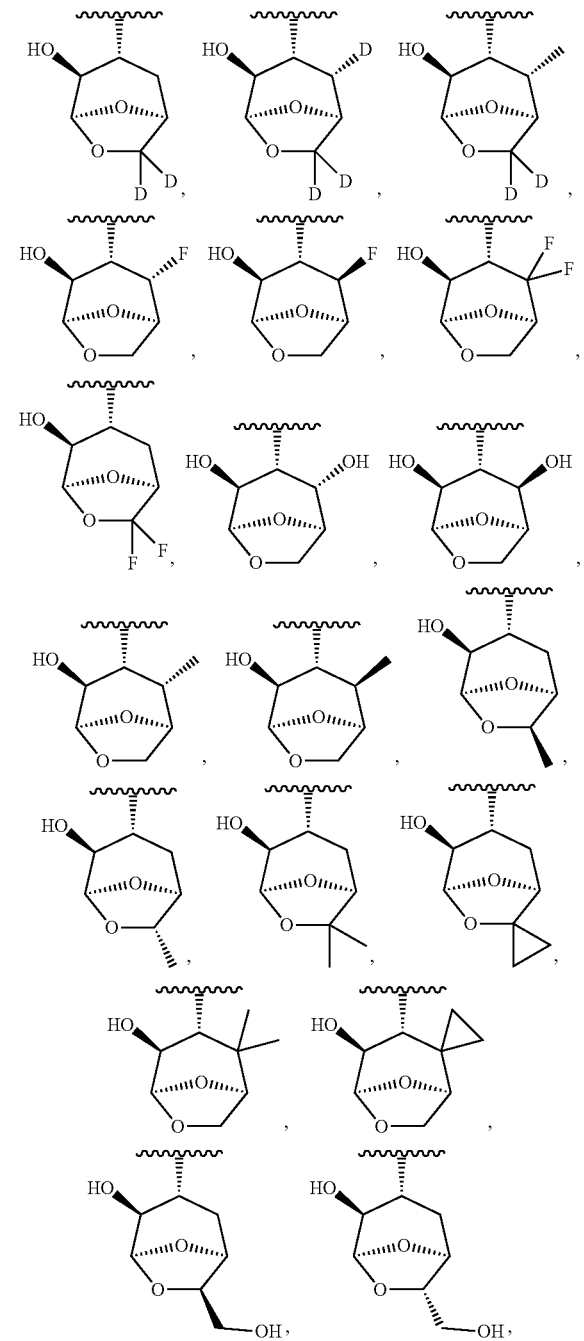

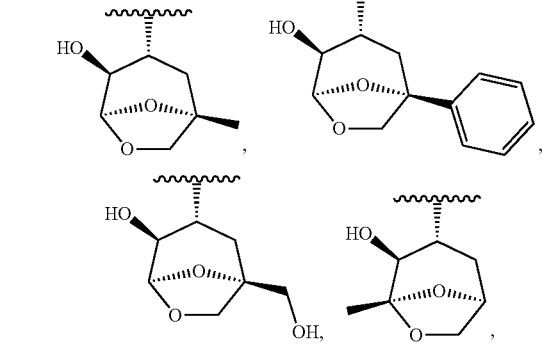

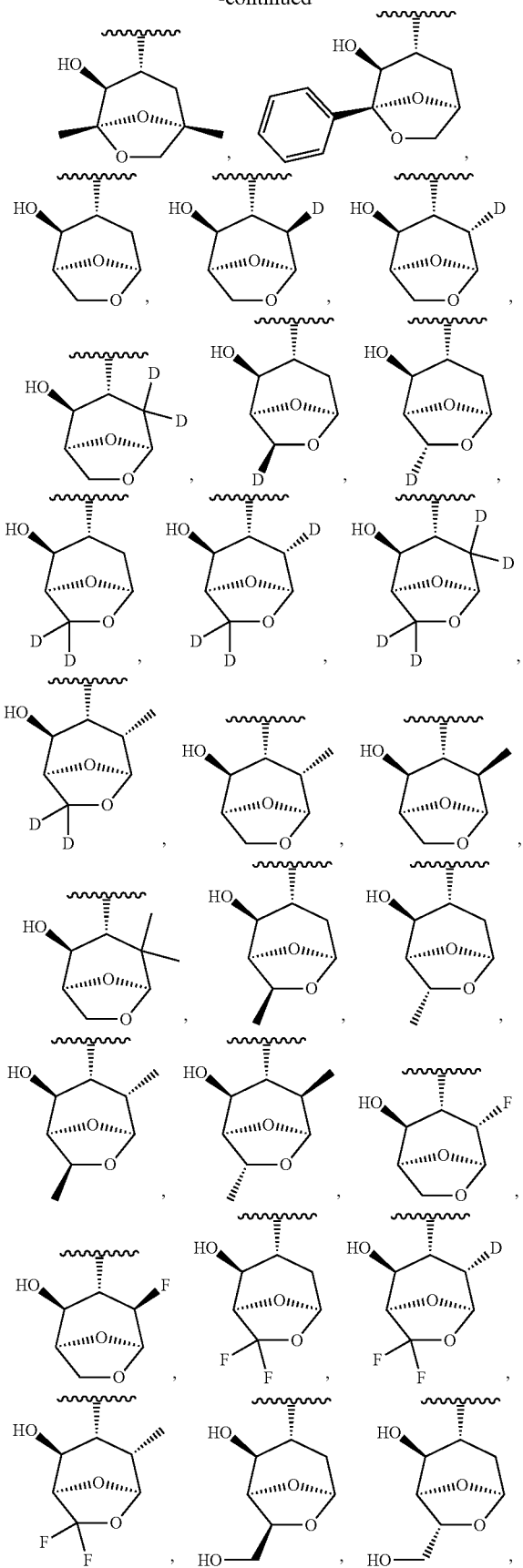
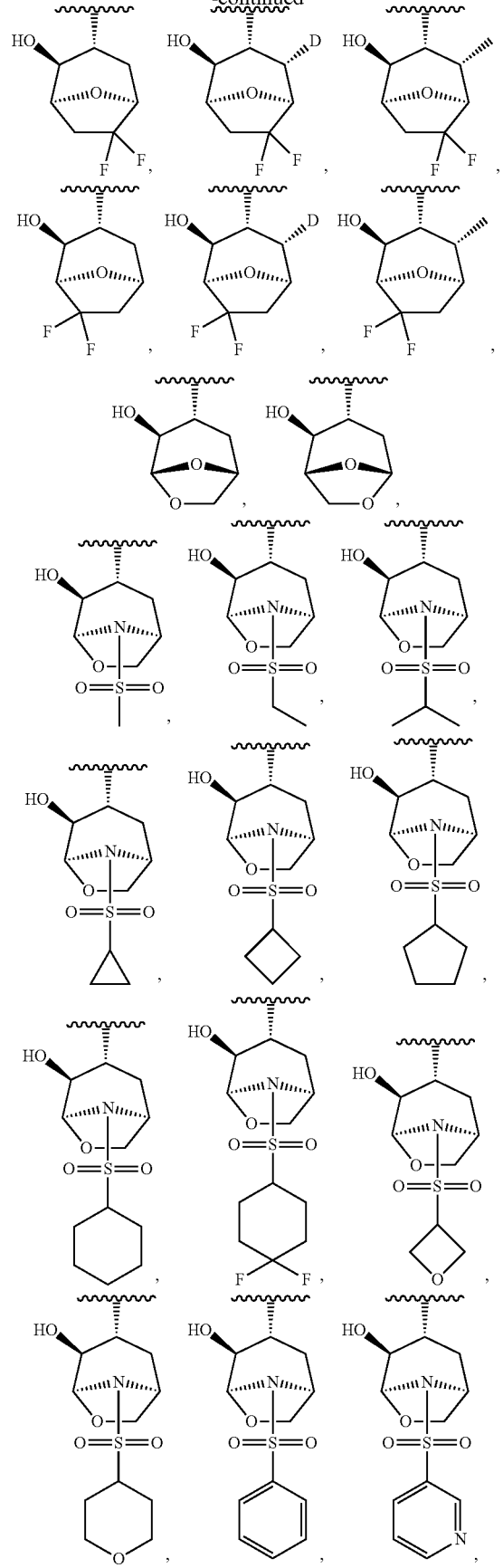

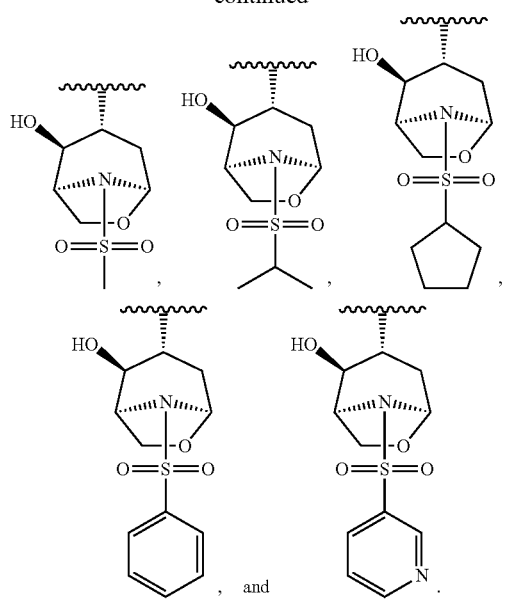
In some embodiments, Ring A is selected from: and
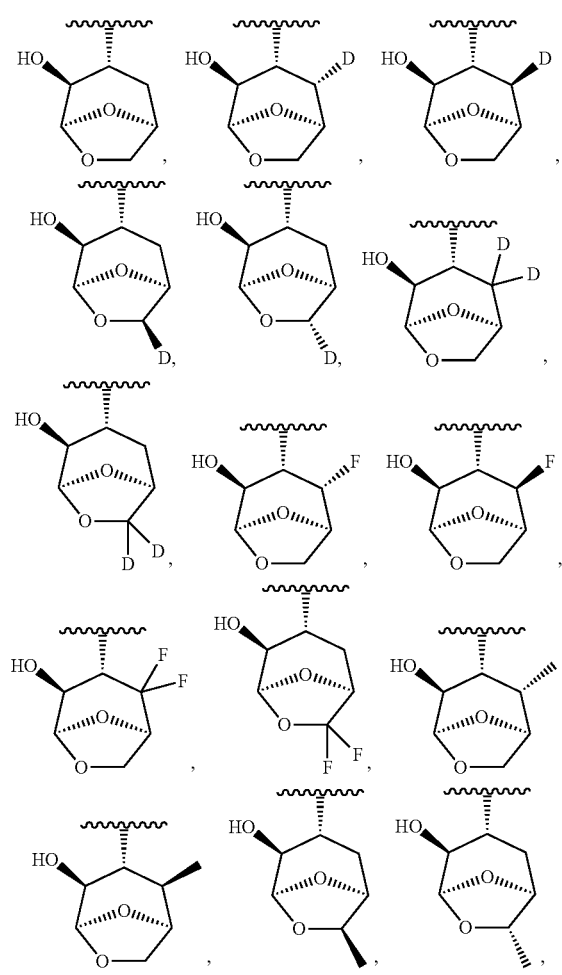
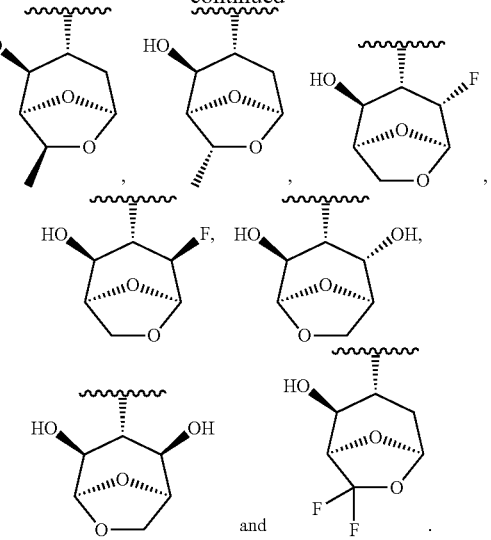
In some embodiments, Ring A is
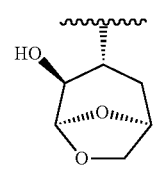
In some embodiments, Ring A is
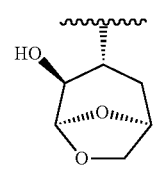
In some embodiments, Ring A is
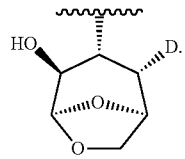
In some embodiments, Ring A is
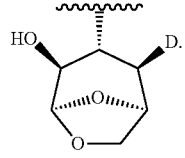
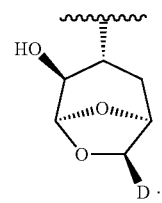

In some embodiments, Ring A is
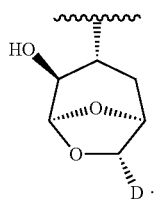
In some embodiments, Ring A is
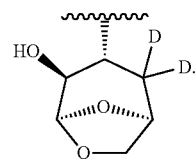
In some embodiments, Ring A is
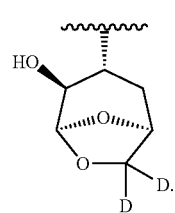
In some embodiments, Ring A is
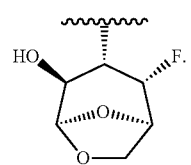
In some embodiments, Ring A is
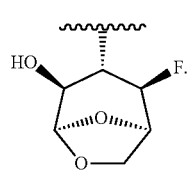
In some embodiments, Ring A is
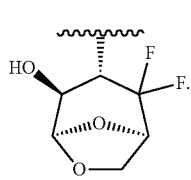
In some embodiments, Ring A is
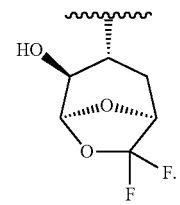
In some embodiments, Ring A is
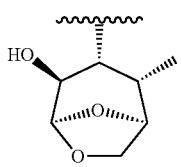
In some embodiments, Ring A is
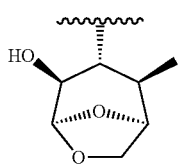
In some embodiments, Ring A is
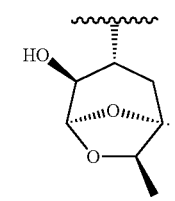
In some embodiments, Ring A is
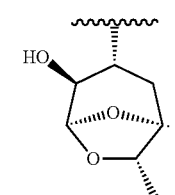
In some embodiments, Ring A is
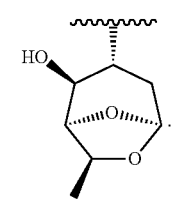

In some embodiments, Ring A is

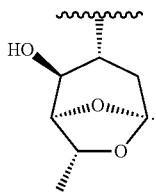

In some embodiments, Ring A is

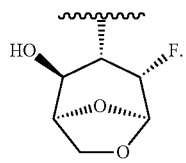

In some embodiments, Ring A is

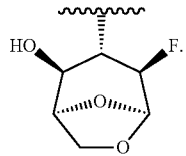

In some embodiments, Ring A is

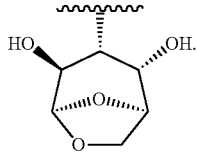 [SMILES: *[C@H]1[C@H](O)[C@@H]2OC[C@@H](O2)[C@H]1O]

In some embodiments, Ring A is

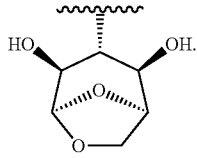 [SMILES: *[C@H]1[C@H](O)[C@@H]2OC[C@@H](O2)[C@@H]1O]

In some embodiments, Ring A is

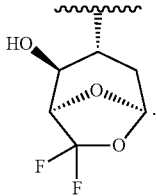

EMBODIMENTS

Additional aspects of this disclosure are set forth in the following embodiments:

Embodiment 1. A compound, wherein the compound is represented by Formula IA or is a pharmaceutically acceptable salt thereof:

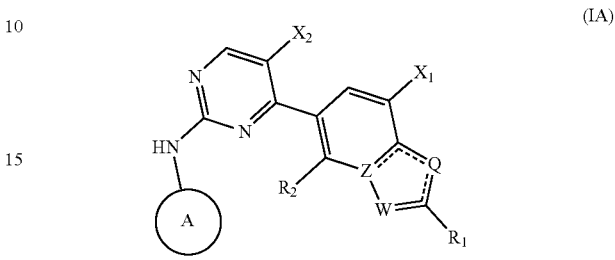

(IA)

wherein:

$\rightleftharpoons$ is a single bond or a double bond;

$R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)OR$^{1B}$, —C(=O)N(R$^{1B}$)$_2$, —NHC(=O)OR$^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

$R^2$ is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;

$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Q is N or CR$^O$, wherein R$^O$ is independently selected from hydrogen, halogen, and cyano;

Z is C;

W is selected from C(R$^{W1}$)$_2$, O, S, N, and NR$^{W2}$, wherein R$^{W1}$ is independently selected from hydrogen, halogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$;

R$^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$; and each $R^{1D}$ is independently selected from halogen, $C_1$-$C_6$ alkyl, $C_1$-$C_6$ baloalkyl, and hydroxyl; or W and $R^1$ may be taken together with the C atom to which both are attached to form a carbocyclic ring of 5-8 atoms or a heterocyclic ring of 5-8 atoms, wherein the carbocyclic ring and heterocyclic ring is each optionally substituted with 1, 2, 3, or 4 $R^{1E}$; or W, Z, $R^2$ and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$;

each $R^{1E}$ is independently selected from $C_1$-$C_6$ alkyl, hydroxyl, and an oxo group; Ring A is

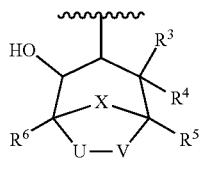 or 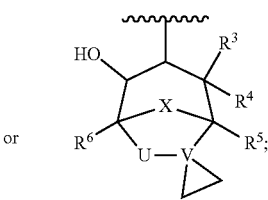;

wherein:

$R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;

$R^5$ and $R^6$ are independently selected from hydrogen, deuterium, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$—$R^X$, wherein $R^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or C($R^U$)$_2$, wherein $R^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and V is O, C, or C($R^V$)$_2$, wherein $R^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

Embodiment 2. The compound according to embodiment 1, wherein the compound of Formula IA is represented by Formula IA':

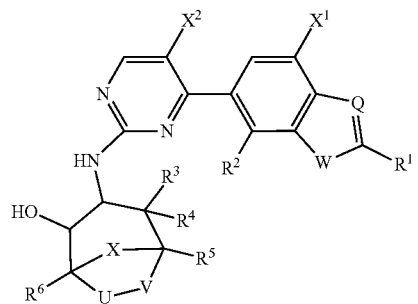

(IA')

wherein:

$R^1$ is selected from $C_1$-$C_8$ alkyl, $C_3$-$C_6$ cycloalkyl, $C_1$-$C_5$ haloalkyl, $C_3$-$C_6$ cyclic haloalkyl, $C_5$-$C_7$ bicyclic alkyl, $C_1$-$C_6$ aminoalkyl, $C_1$-$C_6$ alkoxy, an oxo group, a 4-6 membered heterocyclic group, 6-membered aryl and 5-6 membered heteroaryl, wherein each of the $C_1$-$C_5$ alkyl, $C_3$-$C_6$ cycloalkyl, $C_1$-$C_6$ haloalkyl, $C_3$-$C_6$ cyclic haloalkyl, $C_5$-$C_7$ bicyclic alkyl, $C_1$-$C_6$ aminoalkyl, $C_1$-$C_6$ alkoxy, 4-6 membered heterocyclic group, 6-membered aryl, and 5-6 membered heteroaryl are independently substituted with 0, 1, 2, or 3 $R^{1A}$;

each $R^{1A}$ is independently selected from halogen, hydroxyl, oxo, amino, $C_1$-$C_8$ alkyl, $C_3$-$C_6$ cycloalkyl, $C_1$-$C_6$ alkoxy, $C_3$-$C_6$ cyclic alkoxy, —C(=O)O$R^{1B}$, —C(=O) N($R^{1B}$)$_2$, —NHC(=O)O$R^{1B}$, and 4-6 membered heterocyclic group, wherein the 4-6 membered heterocyclic group is optionally substituted with 1, 2, or 3 $R^{1C}$;

each RIB is independently selected from hydrogen, $C_1$-$C_8$ alkyl, and $C_4$-$C_6$ cycloalkyl; and each $R^{1C}$ is independently selected from hydroxyl, halogen, an oxo group, $C_1$-$C_8$ alkyl, and $C_4$-$C_6$ cycloalkyl.

$R^2$ is selected from hydrogen, $C_1$-$C_6$ alkyl, and $C_3$-$C_8$ cycloalkyl;

$R^3$ and $R^4$ are independently selected from hydrogen, hydroxyl, deuterium, halogen, and $C_1$-$C_8$ alkyl; or $R^3$ and $R^4$ may be taken together with the carbon atom to which both are attached to form a 3-5 membered cycloalkyl;

$R^1$ and $R^e$ are independently selected from hydrogen, $C_1$-$C_4$ alkyl, $C_3$-$C_8$ cycloalkyl, and aryl;

X is O or N—S(O)$_2$—RN, wherein Ra is selected from $C_1$-$C_8$ alkyl, $C_3$-$C_6$ cycloalkyl, a 3-6 membered heterocyclic group, 6-membered aryl, and 6-membered heteroaryl, and wherein each of the $C_3$-$C_6$ cycloalkyl, 3-6 membered heterocyclic group, 6-membered aryl, and 6-membered heteroaryl is optionally substituted with 1, 2, or 3 groups selected from halogen, hydroxyl, and cyano;

$X^1$ is selected from halogen, $C_1$-$C_8$ alkyl, and $C_1$-$C_5$ haloalkyl;

$X^2$ is selected from hydrogen, halogen, $C_1$-$C_8$ alkyl, and $C_1$-$C_4$ haloalkyl;

Q is N or C$R^O$, wherein $R^O$ is hydrogen or cyano;

W is N$R^{W2}$, wherein $R^{W2}$ is selected from $C_1$-$C_6$ alkyl, $C_3$-$C_6$ cycloalkyl, 5-6 membered bicyclic carbocyclic group, and a 3-7 membered heterocyclic group, wherein each of the $C_1$-$C_6$ alkyl and $C_3$-$C_6$ cycloalkyl is optionally substituted with 1, 2, or 3 $R^{1D}$, each R"Dis independently selected from halogen, $C_1$-$C_6$ alkyl, $C_1$-$C_3$ haloalkyl, and hydroxyl; or W and $R^1$ are taken together with the C atom to which both are attached to form a heterocyclic ring of 6-7 atoms, wherein the ring has 1 to 3 heteroatoms independently selected from N, S, and O, and wherein the ring is optionally substituted with 1, 2, or 3 $R^{1E}$, wherein each $R^{1E}$ is independently a $C_1$-$C_3$ alkyl or an oxo group;

U is O or $C(R^U)_2$, wherein $R^U$ is independently selected from hydrogen, deuterium, halogen, and $C_1$-$C_3$ alkyl, wherein the $C_1$-$C_3$ alkyl is optionally substituted with hydroxyl; and V is O or $C(R^V)_2$, wherein $R^V$ is independently selected from hydrogen, deuterium, halogen, hydroxyl, $C_1$-$C_3$ alkyl, and $C_3$-$C_6$ cycloalkyl, and wherein the $C_1$-$C_3$ alkyl is optionally substituted with hydroxyl.

Embodiment 3. The compound according to embodiments 1 or 2, wherein $X^1$ and $X^2$ are independently selected from bromine, chlorine, fluorine, $C_1$-$C_8$ alkyl, and $C_1$-$C_4$ haloalkyl.

Embodiment 4. The compound according to any one of embodiments 1-3, wherein $R^2$ is hydrogen.

Embodiment 5. The compound according to any one of embodiments 1-4, wherein $R^5$ is selected from hydrogen, deuterium, and cyclopropyl, and $R^6$ is hydrogen.

Embodiment 6. The compound according to any one of embodiments 1 or 3-5, wherein W, Z. $R^2$ and the C atom to which $R^2$ is attached are taken together to form a heterocyclic ring of 6 atoms, wherein the heterocyclic ring is optionally substituted with 1, 2, or 3 $R^{1E}$.

Embodiment 7. The compound according to any one of embodiments 1 or 3-6, wherein W, $R^2$, and the C atom to which $R^2$ is attached are taken together to form a ring selected from:

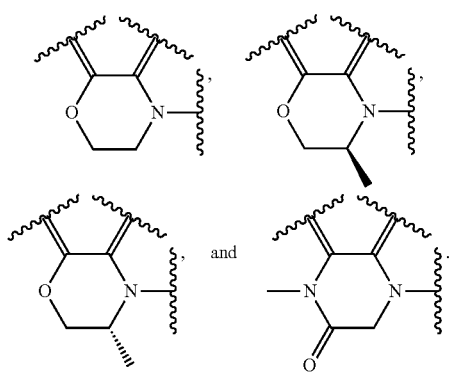

Embodiment 8. The compound according to embodiment 2, wherein W is selected from: NH,

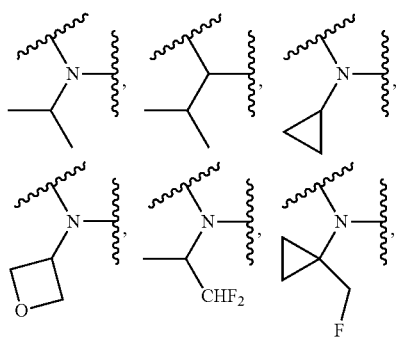

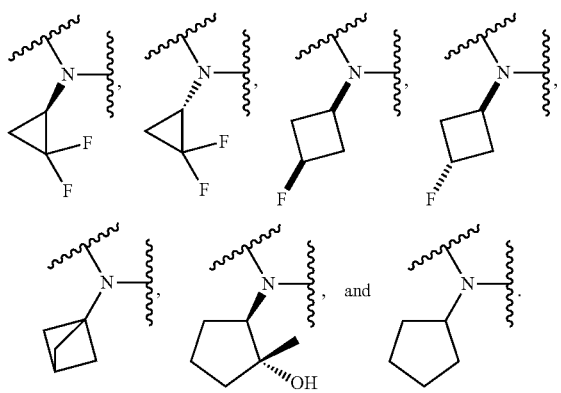

Embodiment 9. The compound according to any one of embodiments 1-8, wherein $R^1$ is selected from $C_1$-$C_3$ alkyl, $C_3$-$C_5$ cycloalkyl, $C_1$-$C_5$ haloalkyl, $C_3$-$C_6$ cyclic haloalkyl, $C_5$-$C_7$ bicyclic alkyl, $C_1$-$C_4$ aminoalkyl, $C_1$-$C_6$ alkoxy, an oxo group, a 4-6 membered heterocyclic group, 6-membered aryl and 5-6 membered heteroaryl, wherein each of the $C_1$-$C_3$ alkyl, $C_3$-$C_8$ cycloalkyl, $C_1$-$C_5$ haloalkyl, $C_3$-$C_6$ cyclic haloalkyl, $C_5$-$C_7$ bicyclic alkyl, $C_1$-$C_4$ aminoalkyl, $C_1$-$C_6$ alkoxy, 4-6 membered heterocyclic group, 6-membered aryl, and 5-6 membered heteroaryl is independently substituted with 0, 1, 2, or 3 $R^{1A}$.

Embodiment 10. The compound according to any one of embodiments 1-9, wherein $R^1$ is

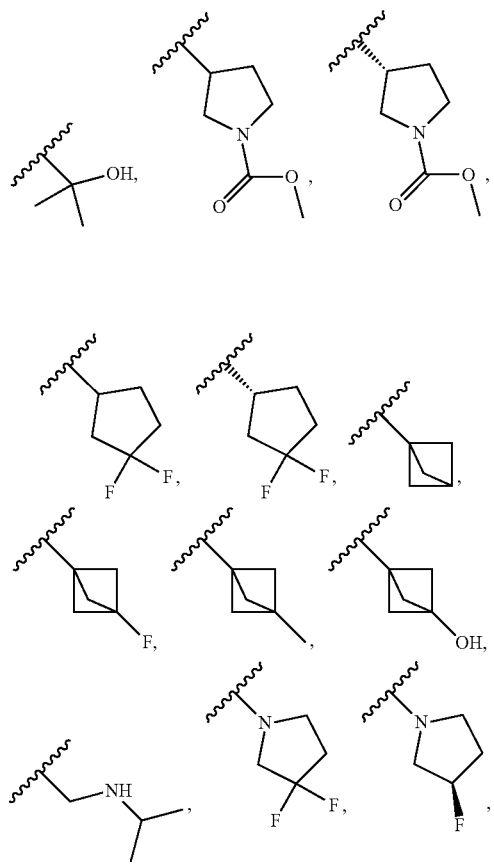

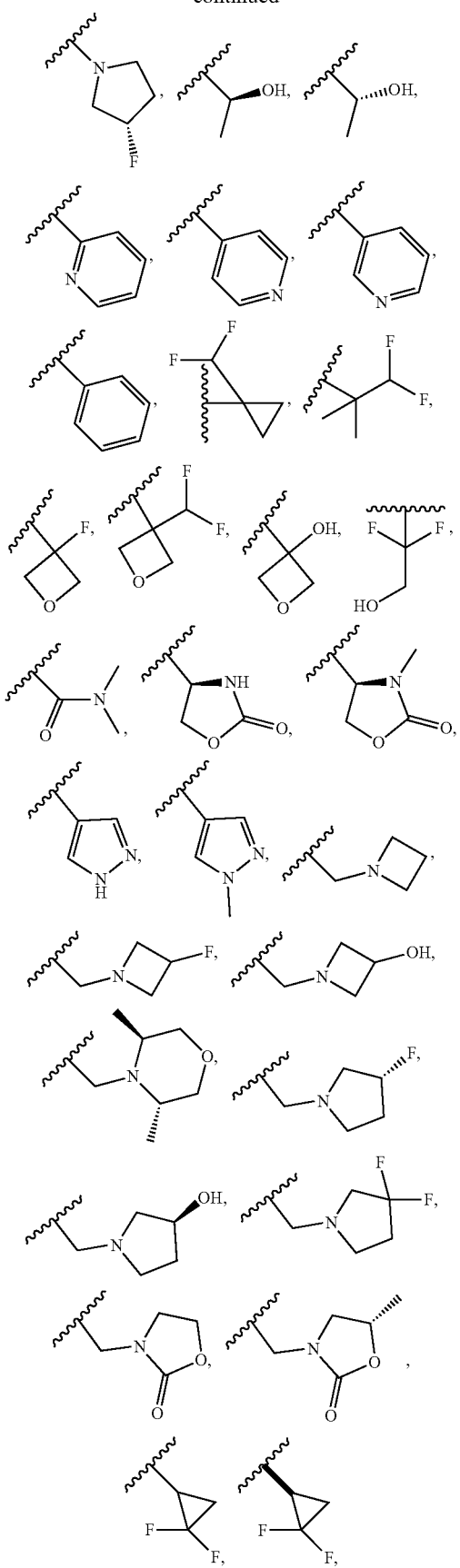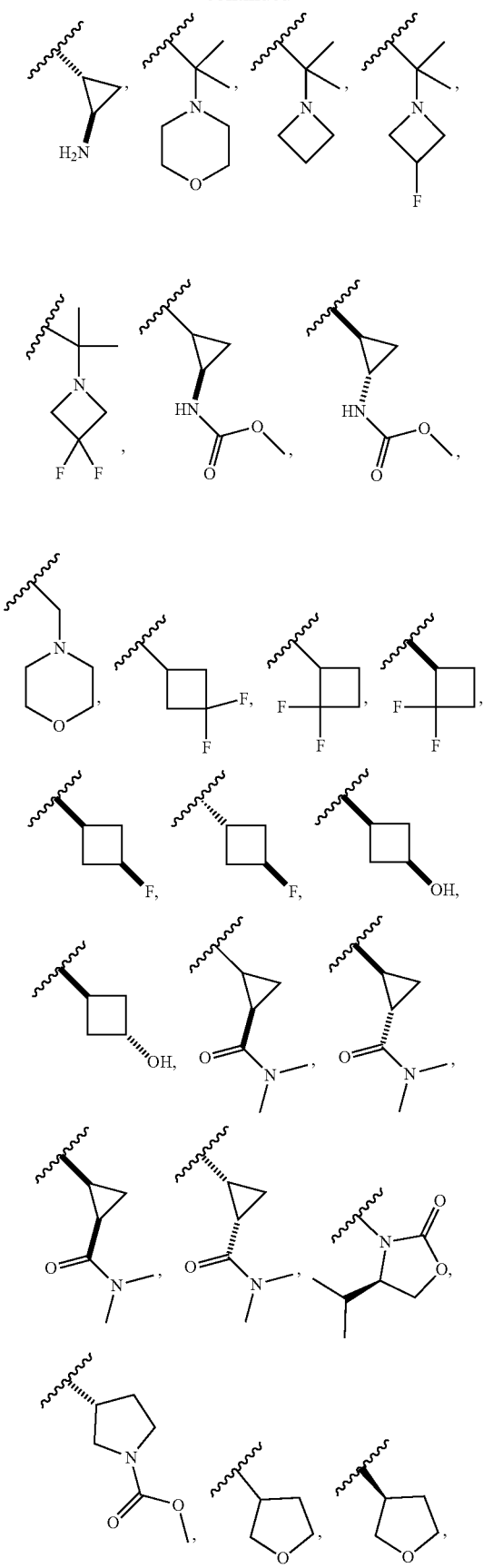

-continued

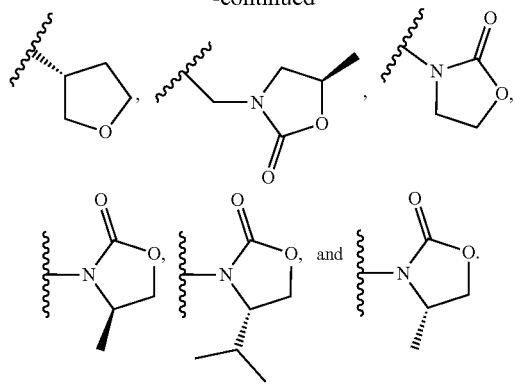

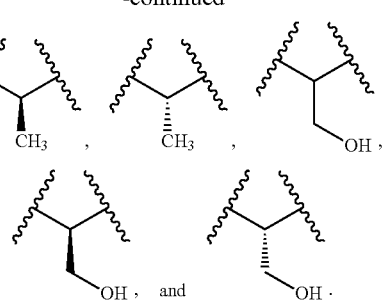

Embodiment 11. The compound according to any one of embodiments 1-10, wherein X is selected from:
O,

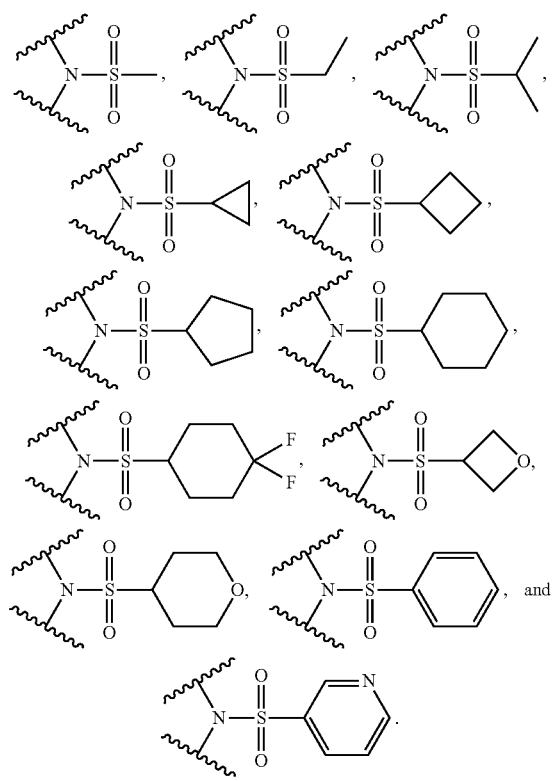

Embodiment 12. The compound according to any one of embodiments 1-11, wherein U is selected from:
O,

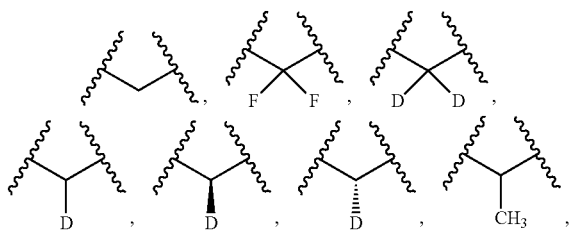

Embodiment 13. The compound according to any one of embodiments 1-12, wherein V is selected from:
O,

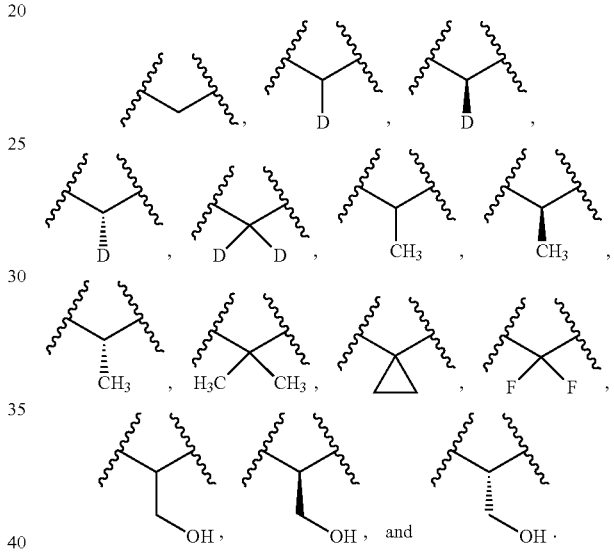

Embodiment 14. The compound according to any one of embodiments 1-13, wherein A is selected from:

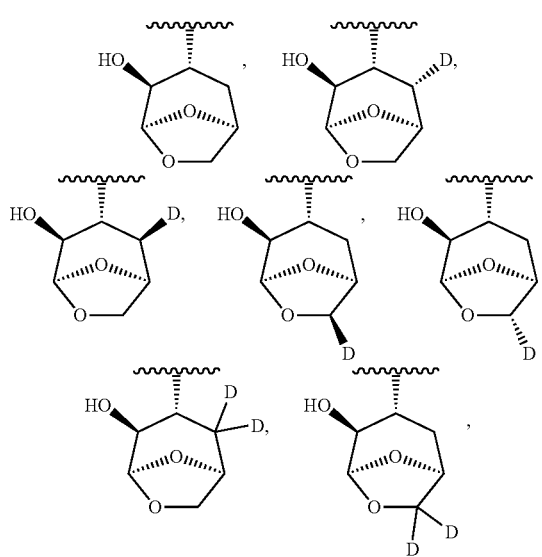

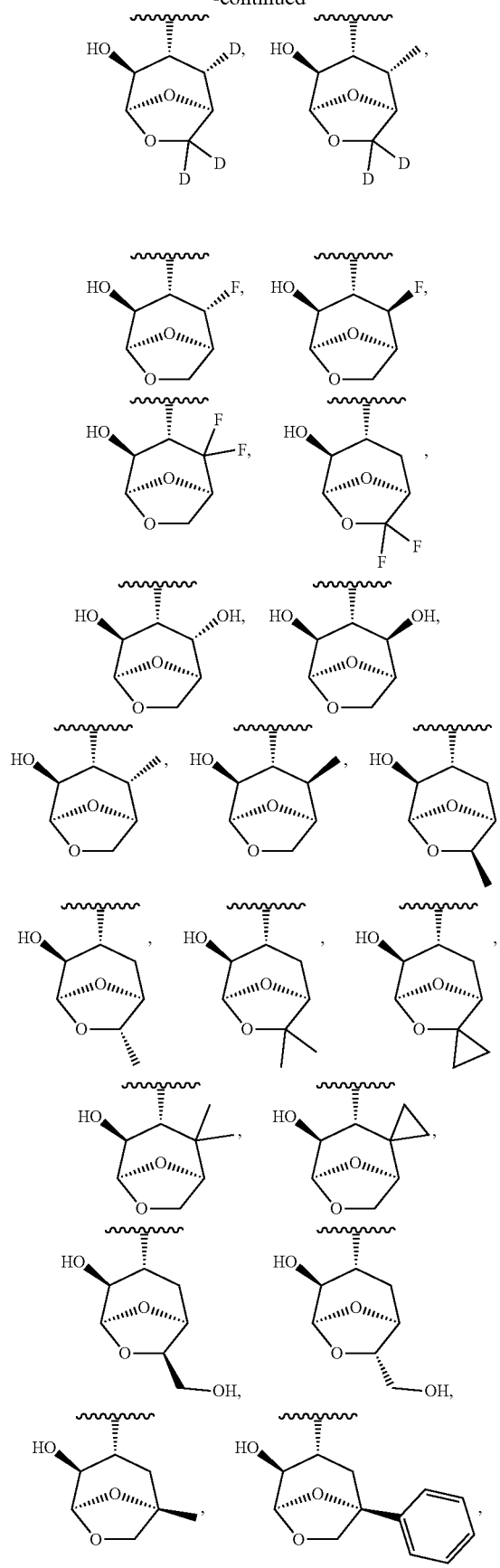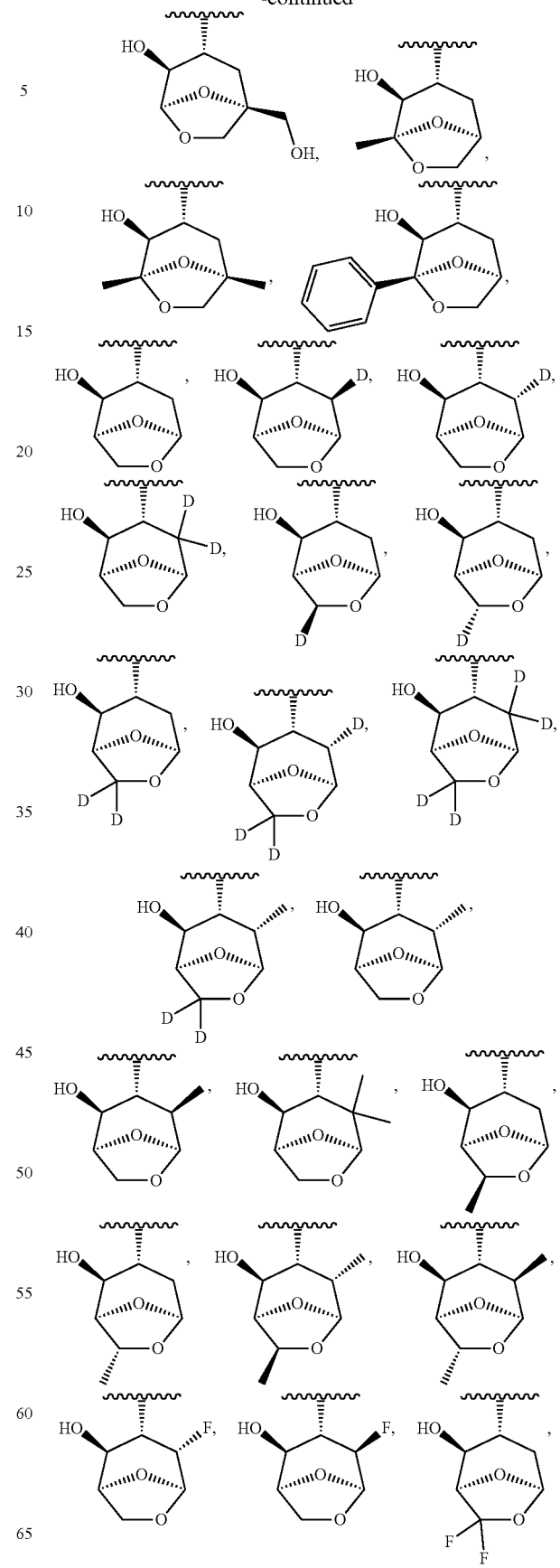

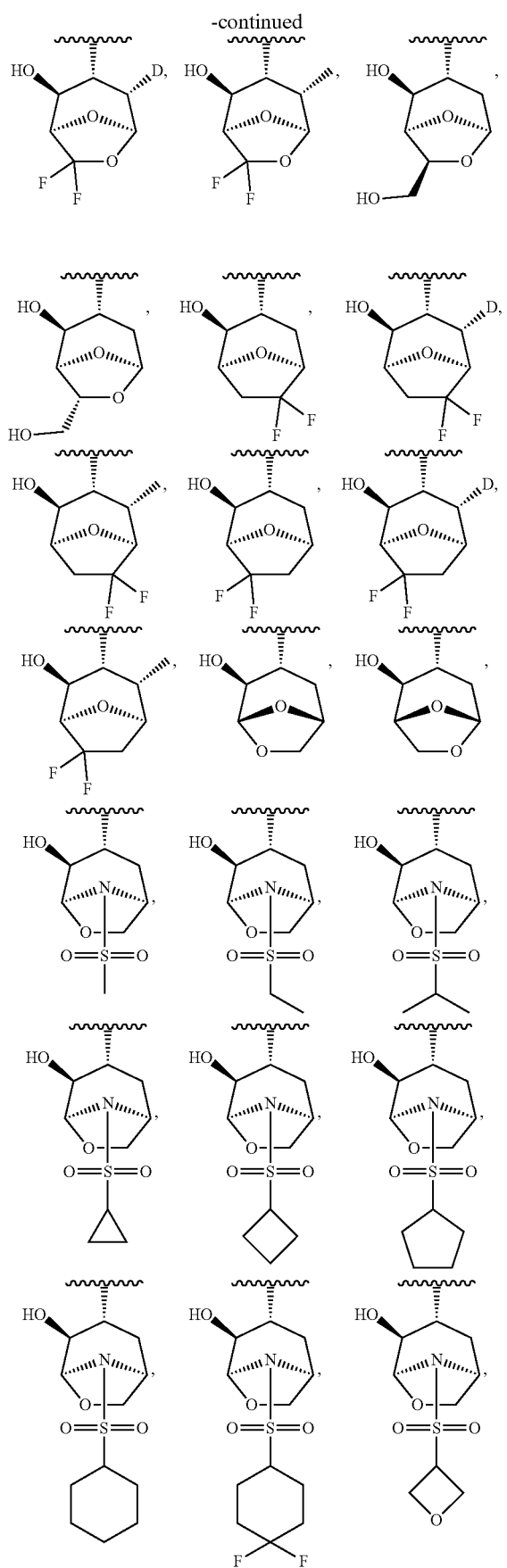
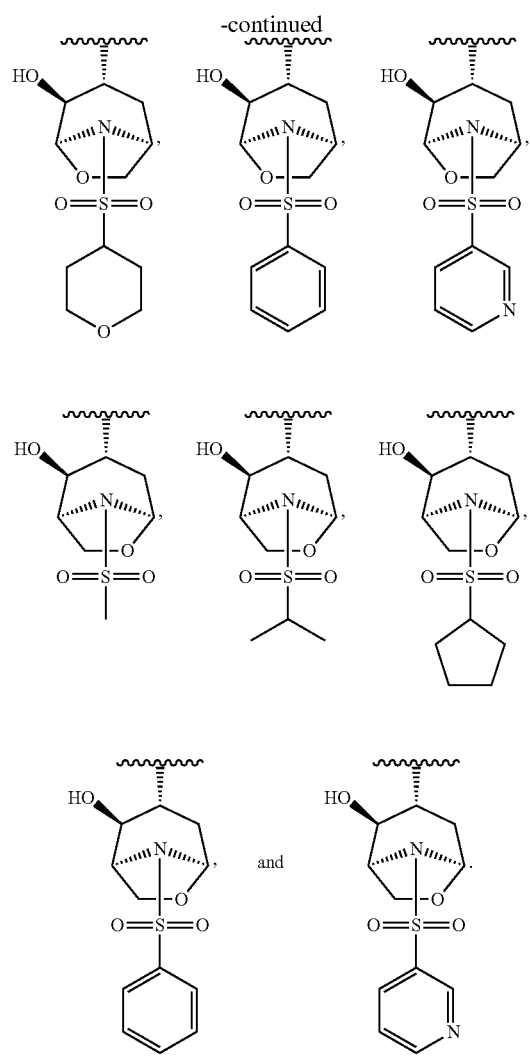
Embodiment 15. The compound according to any one of embodiments 1-14, wherein A is selected from.
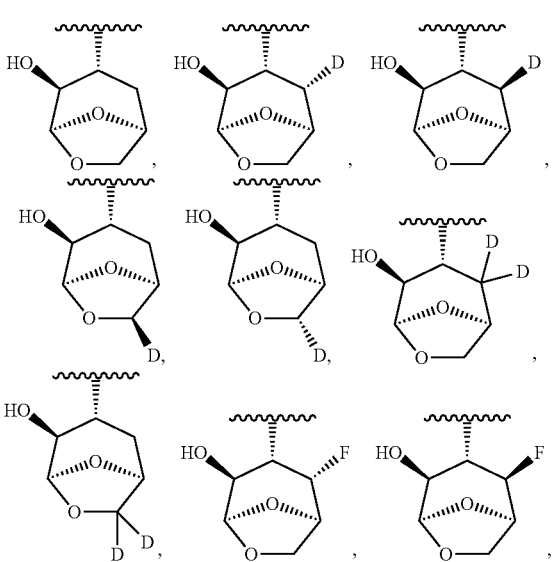

-continued

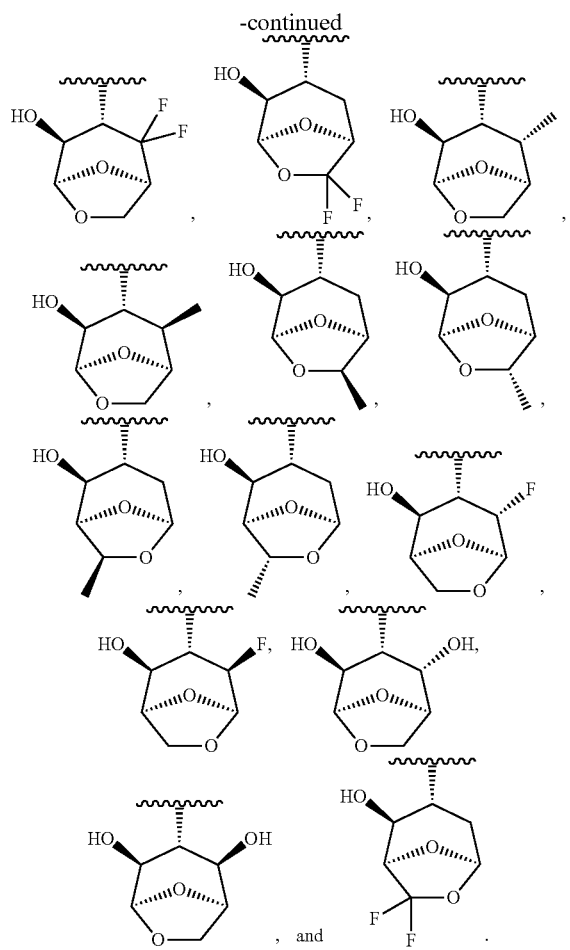

, and

Embodiment 16. The compound according to any one of embodiments 1-15, wherein the compound is selected from compounds 1-41, 44-65, 72-142, 145-187, 216-220, 221-222, 225-226, 238-249, 265-270, 272, and 296-298 (see Table 1), or a pharmaceutically acceptable salt thereof.

Embodiment 17. The compound according to any one of embodiments 1-16, wherein the compound is selected from compounds 1, 2, 13, 25, 26, 72, 136, 167-169, 172, 216, 217, 238-240, 242-246, 248, 265, 268-270, 296, and 298 (see Table 1), or a pharmaceutically acceptable salt thereof.

Embodiment 18. A pharmaceutical composition comprising a therapeutically effective amount of a compound according to any one of embodiments 1-17 and one or more pharmaceutically acceptable carriers, pharmaceutically acceptable vehicles, pharmaceutically acceptable excipients, or combinations thereof.

Embodiment 19. A method of treating a disease or condition modulated at least in part by a cyclin-dependent kinase (CDK) in a subject in need thereof, comprising administering to the subject an effective amount of at least one compound according to any one of embodiments 1-17 or a pharmaceutical composition of embodiment 18.

Embodiment 20 A method for inhibiting a CDK in a subject, comprising administering to the subject an effective amount of at least one compound according to any one of embodiments 1-17 or a pharmaceutical composition of embodiment 18.

Embodiment 21. A method for treating cancer in a subject in need thereof, comprising administering to the subject an effective amount of at least one compound according to any one of embodiments 1-17 or a pharmaceutical composition of embodiment 18.

Embodiment 22. A compound, wherein the compound is represented by Formula (IB) or is a pharmaceutically acceptable salt thereof:

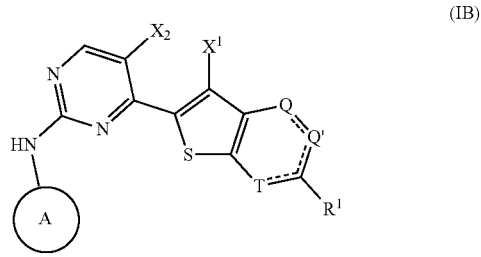

(IB)

wherein:
≡≡≡ is a single bond or a double bond;
$R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group. 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$,
each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)O$R^{1B}$, —C(=O) N($R^{1B}$)$_2$, —NHC(=O) O$R^{1B}$, and a 4-6 membered heterocyclic group, wherein the 4-6 membered heterocyclic group is optionally substituted with 1, 2, or 3 $R^{1C}$;
each $R^{1B}$ is independently selected from hydrogen, $C_1$-$C_6$ alkyl, and $C_3$-$C_6$ cycloalkyl;
each $R^{1C}$ is independently selected from hydrogen, hydroxyl, halogen, an oxo group, $C_1$-$C_6$ alkyl, and $C_3$-$C_6$ cycloalkyl;
$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;
Q is $CR^O$, N, or $NR^O$, wherein Reis selected from hydrogen, halogen, $C_1$-$C_4$ alkyl, and an oxo group;
Q' is $CR^{Q'}$, N, $NR^{O'}$, wherein $R^{O'}$ is selected from hydrogen, $C_1$-$C_4$ alkyl, and $C_1$-$C_4$ haloalkyl;
T is $CR^{T1}$ or $NR^{T2}$, wherein $R^{T1}$ is halogen or $R^{T2}$, and $R^{T2}$ is hydrogen or $C_1$-$C_6$ alkyl, wherein the $C_1$-$C_6$ alkyl is optionally substituted with 1, 2, or 3 groups independently selected from halogen, $C_1$-$C_6$ alkyl, and hydroxyl;
Ring A is

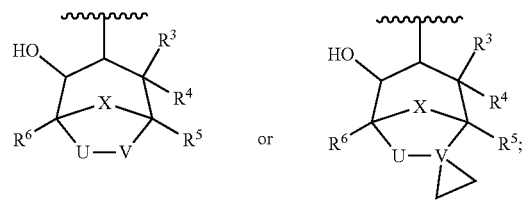

wherein:
R³ and R⁴ are independently selected from hydrogen, deuterium, halogen, hydroxyl, $C_1$-$C_6$ alkyl, and $C_3$-$C_6$ cycloalkyl; or R³ and R⁴ may be taken together with the carbon atom to which both are attached to form a 3-7 membered cycloalkyl;

R⁵ and R⁶ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$-R$^Y$, wherein R$^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or C(R$^U$)$_2$, wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and V is O, C, or C(R)$_2$, wherein R$^Y$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

Embodiment 23. The compound according to embodiment 22, wherein the compound is selected from compounds 189, 215, 223-224, 227-233, 259, 260, 266, 273, 274, 275, 276-278, and 287-290 (see Table 1), or a pharmaceutically acceptable salt thereof.

Embodiment 24. A method for treating cancer in a subject in need thereof, comprising administering to the subject an effective amount of at least one compound according to embodiment 22 or 23.

Embodiment 25. A compound, wherein the compound is represented by Formula (IC) or is a pharmaceutically acceptable salt thereof:

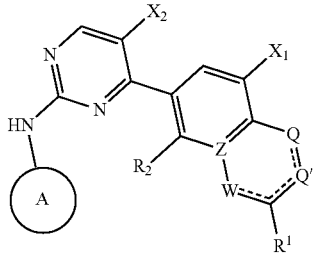

(IC)

wherein:
═══ is a single bond or a double bond,
R¹ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C^6$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_6$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(═O)OR$^{1B}$, —C(═O)N(R$^{1B}$)$_2$, —NHC(═O)OR$^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

R² is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;

X¹ and X² are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Q is N, O, or CR$^O$, wherein R$^O$ is selected from hydrogen, halogen, and an oxo group;

Q' is CH, CH$_2$, CR$^{Q'}$, N, or NR", wherein R$^O$ is halogen or R", and R" is selected from $C_1$-$C_6$ alkyl, $C_3$-$C_6$ cycloalkyl, $C_1$-$C_4$ haloalkyl, and a 3-8 membered heterocyclic group, wherein each of the $C_1$-$C_6$ alkyl and $C_3$-$C_6$ cycloalkyl are each optionally substituted with 0, 1, 2, or 3 groups independently selected from halogen, $C_1$-$C_6$ alkyl, and hydroxyl;

Z is C;

W is CR$^{W1}$, N, or NR$^{W2}$, wherein
$R^{W1}$ is selected from hydrogen, halogen, $C_1$-$C_6$ alkyl, $C_3$-$C_6$ cycloalkyl, and a 3-8 membered heterocyclic group, wherein each of the $C_1$-$C_6$ alkyl and $C_3$-$C_6$ cycloalkyl is optionally substituted with 1, 2, or 3 $R^{1D}$;

$R^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 R"); and each $R^{1D}$ is independently selected from halogen, $C_1$-$C_6$ alkyl, and hydroxyl; or W, Z, R² and the C atom to which R² is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$, and wherein each $R^{1E}$ is independently selected from $C_1$-$C_6$ alkyl, hydroxyl, and an oxo group;

Ring A is

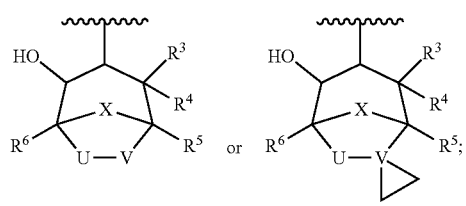

wherein:
R³ and R⁴ are independently selected from hydrogen, deuterium, halogen, hydroxyl, $C_1$-$C_6$ alkyl, and $C_3$-$C_6$ cycloalkyl; or R³ and R⁴ may be taken together with the carbon atom to which both are attached to form a 3-7 membered cycloalkyl;

R⁵ and R⁶ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$—R$^X$, wherein R$^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$cycloalkyl, 3-7 membered heterocyclic group, aryl, and heteroaryl is optionally substituted with 1, 2, or 3 groups selected from halogen, hydroxyl, and cyano;

U is O or C(R ( ), wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and V is O, C, or C(R$^V$)$_2$, wherein R$^Y$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

Embodiment 26. The compound according to embodiment 25, wherein the compound is selected from compounds 173, 188, 190-214, 234-237, 250-258, 261-264, 271, 279, 280-286, and 291-295 (see Table 1), or a pharmaceutically acceptable salt thereof.

Embodiment 27. A method for treating cancer in a subject in need thereof, comprising administering to the subject an effective amount of at least one compound according to embodiment 25 or 26.

Embodiment 28. A compound, wherein the compound is represented by Formula (ID) or is a pharmaceutically acceptable salt thereof:

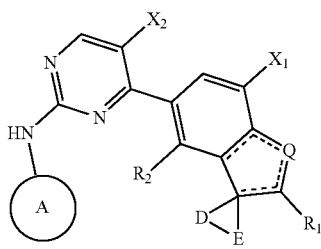

(ID)

wherein:

⸺ is a single bond or a double bond;

R¹ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_5$-$C_6$ haloalkyl, $C_3$-$C_6$ cyclic haloalkyl, $C_5$-$C_8$bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)OR$^{1B}$, —C(=O)N(R$^{1B}$)$_2$, —NHC(=O) OR"B, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

R² is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;

X¹ and X² are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Q is N or CR$^Q$, wherein R$^Q$ is independently selected from hydrogen, halogen, and cyano;

D and E together with the carbon atom to which they are both attached form a carbocyclic ring of 5-8 atoms or a heterocyclic ring of 5-8 atoms containing 1 to 2 heteroatoms selected from O, S, and N, wherein any carbon ring may be optionally substituted with halogen, $C_1$-$C_4$ alkyl, or hydroxyl;

Ring A is

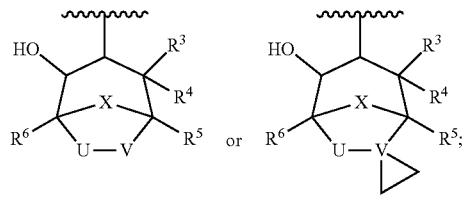

wherein:

R³ and R⁴ are independently selected from hydrogen, deuterium, halogen, hydroxyl, $C_1$-$C_6$ alkyl, and $C_3$-$C_6$ cycloalkyl; or R³ and R⁴ may be taken together with the carbon atom to which both are attached to form a 3-7 membered cycloalkyl;

R⁵ and R⁶ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$—RN, wherein RA is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or C(R$^U$)$_2$, wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and V is O, C, or C(R$^V$)$_2$, wherein R$^Y$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

Embodiment 29. The compound according to embodiment 28, wherein the compound is selected from compounds 2-3 and 143-144 (see Table 1), or a pharmaceutically acceptable salt thereof.

Embodiment 30. A method for treating cancer in a subject in need thereof, comprising administering to the subject an effective amount of at least one compound according to embodiment 28 or 29.

In some embodiments, a compound of the present disclosure is selected from Table I or a pharmaceutically acceptable salt thereof.

TABLE 1

Compounds of the present disclosure

| Cpd # | Structure | IUPAC Name |
|---|---|---|
| 1 | 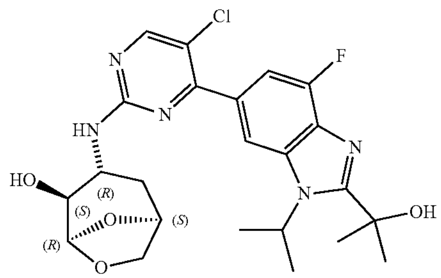 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol |
| 2 | 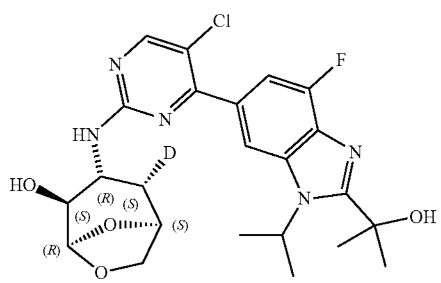 | (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-d-4-ol |
| 3 | 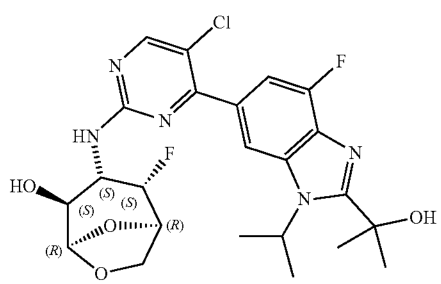 | (1R,2S,3S,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-fluoro-6,8-dioxabicyclo[3.2.1]octan-4-ol |
| 4 | 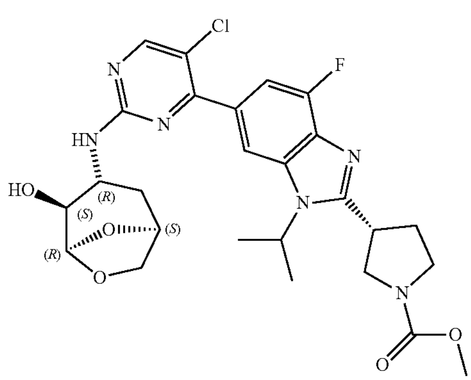 | methyl (R)-3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 5 | 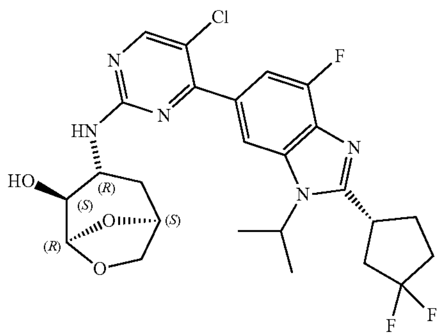 | (1S,3R,4S,5R)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-4-ol |
| 6 | 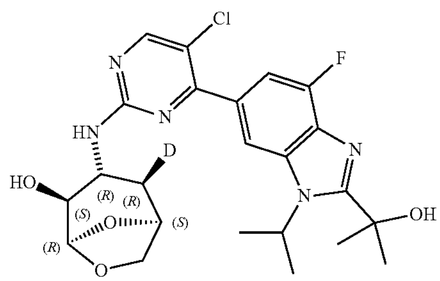 | (1S,2R,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-d-4-ol |
| 7 | 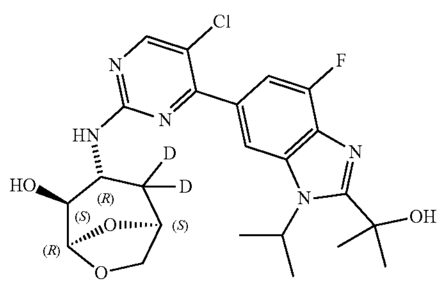 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2,2-d2-4-ol |
| 8 | 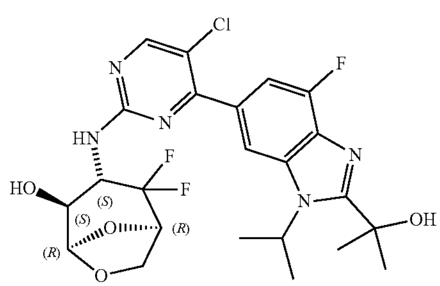 | (1R,3S,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2,2-difluoro-6,8-dioxabicyclo[3.2.1]octan-4-ol |
| 9 | 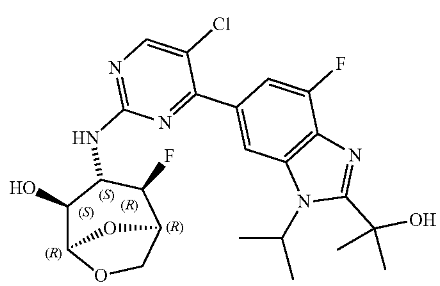 | (1R,2R,3S,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-fluoro-6,8-dioxabicyclo[3.2.1]octan-4-ol |

TABLE 1-continued

Compounds of the present disclosure

| Cpd # | Structure | IUPAC Name |
|---|---|---|
| 10 | 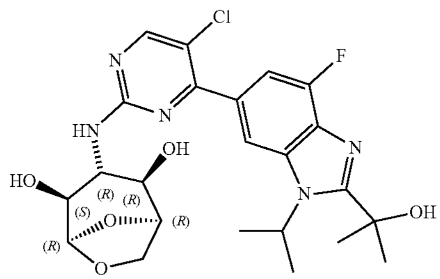 | (1R,2R,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octane-2,4-diol |
| 11 | 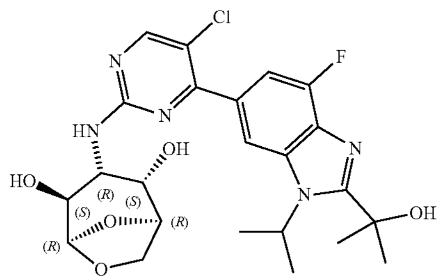 | (1R,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octane-2,4-diol |
| 12 | 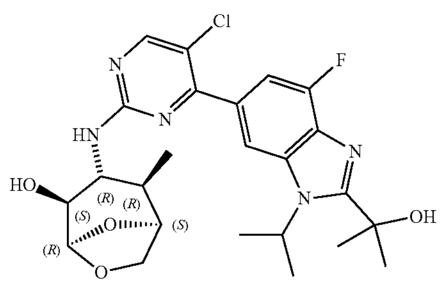 | (1S,2R,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-methyl-6,8-dioxabicyclo[3.2.1]octan-4-ol |
| 13 | 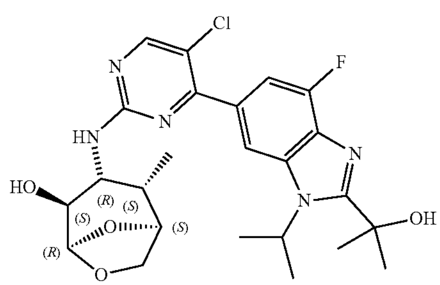 | (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-methyl-6,8-dioxabicyclo[3.2.1]octan-4-ol |
| 14 | 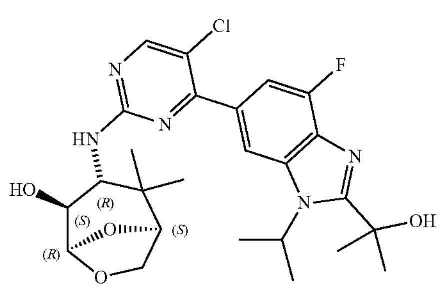 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2,2-dimethyl-6,8-dioxabicyclo[3.2.1]octan-4-ol |

TABLE 1-continued

Compounds of the present disclosure

| Cpd # | Structure | IUPAC Name |
|---|---|---|
| 15 | 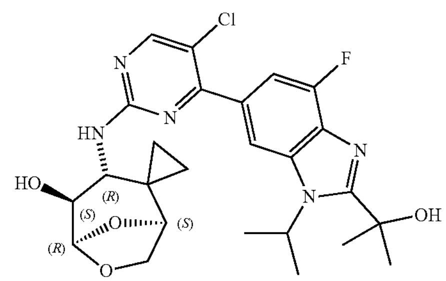 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxaspiro[bicyclo[3.2.1]octane-2,1'-cyclopropan]-4-ol |
| 16 | 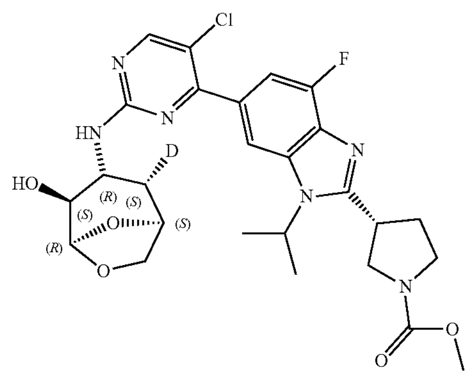 | methyl (R)-3-(6-(5-chloro-2-(((1S,2S,3R,4S,5R)-4-hydroxy-6,8-dioxabicyclo[3.2.1]octan-3-yl-2-d)amino)pyrimidin-4-yl)-4-fluoro-1-isopropyl-1H-benzo[d]imidazol-2-yl)pyrrolidine-1-carboxylate |
| 17 | 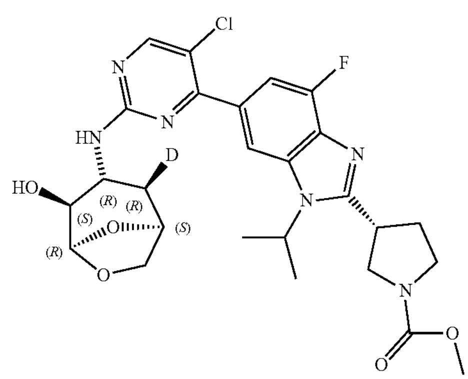 | methyl (R)-3-(6-(5-chloro-2-(((1S,2R,3R,4S,5R)-4-hydroxy-6,8-dioxabicyclo[3.2.1]octan-3-yl-2-d)amino)pyrimidin-4-yl)-4-fluoro-1-isopropyl-1H-benzo[d]imidazol-2-yl)pyrrolidine-1-carboxylate |
| 18 | 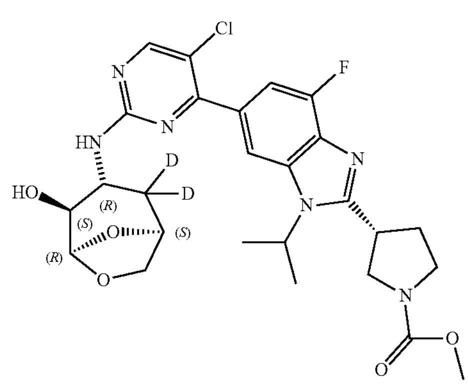 | methyl (R)-3-(6-(5-chloro-2-(((1S,3R,4S,5R)-4-hydroxy-6,8-dioxabicyclo[3.2.1]octan-3-yl-2,2-d2)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 19 | 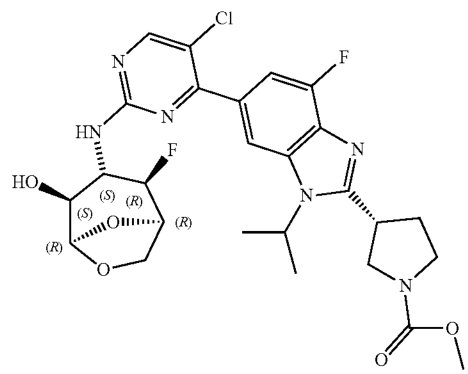 | methyl (R)-3-(6-(5-chloro-2-(((1R,2R,3S,4S,5R)-2-fluoro-4-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 20 | 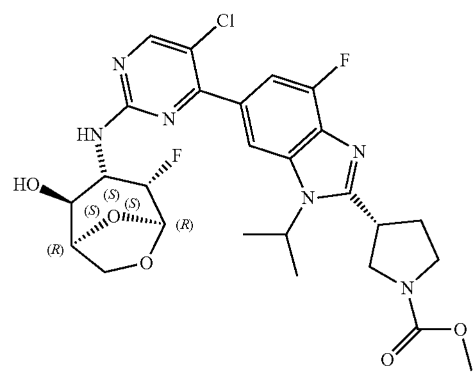 | methyl (R)-3-(6-(5-chloro-2-(((1R,2S,3S,4S,5R)-2-fluoro-4-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 21 | 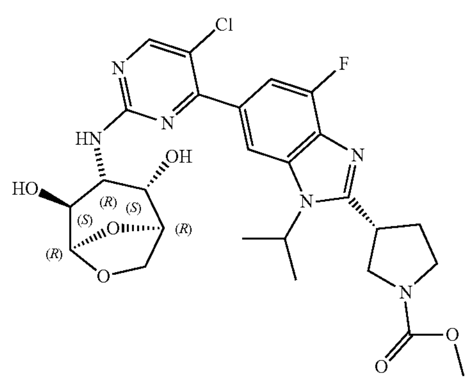 | methyl (R)-3-(6-(5-chloro-2-(((1R,2S,3R,4S,5R)-2,4-dihydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 22 | 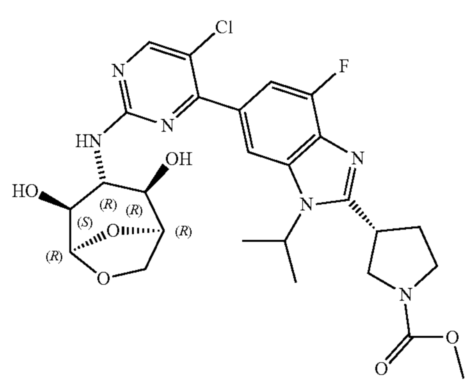 | methyl (R)-3-(6-(5-chloro-2-(((1R,2R,3R,4S,5R)-2,4-dihydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 23 | 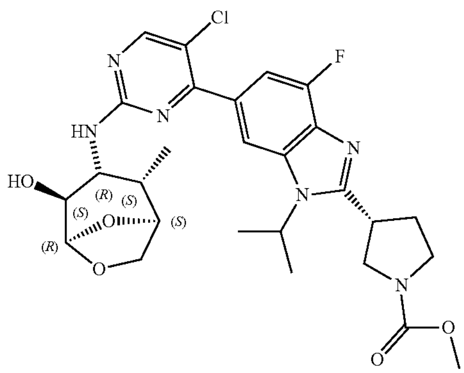 | methyl (R)-3-(6-(5-chloro-2-(((1S,2S,3R,4S,5R)-4-hydroxy-2-methyl-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 24 | 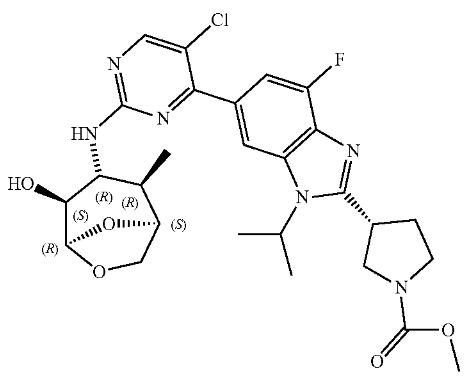 | methyl (R)-3-(6-(5-chloro-2-(((1S,2R,3R,4S,5R)-4-hydroxy-2-methyl-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 25 | 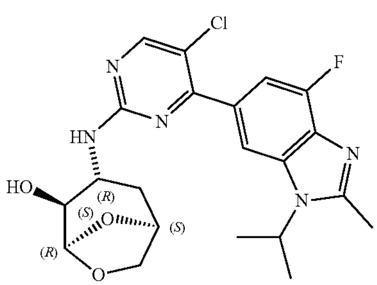 | (1S,3R,4S,5R)-3-((5-chloro-4-(4-fluoro-1-isopropyl-2-methyl-1H-benzo[d]imidazol-6-yl)pyrimidin-2-yl)amino)-6,8-dioxabicyclo[3.2.1]octan-4-ol |
| 26 | 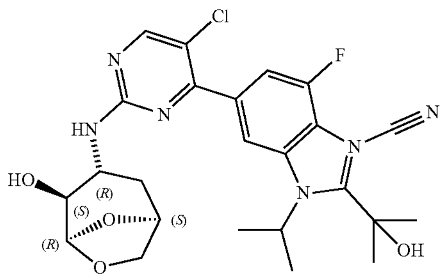 | 6-(5-chloro-2-(((1S,3R,4S,5R)-4-hydroxy-6,8-dioxabicyclo[3.2.1]octan-3-yl)amino)pyrimidin-4-yl)-4-fluoro-2-(2-hydroxypropan-2-yl)-1-isopropyl-1H-indole-3-carbonitrile |

TABLE 1-continued

Compounds of the present disclosure

| Cpd # | Structure | IUPAC Name |
|---|---|---|
| 27 | 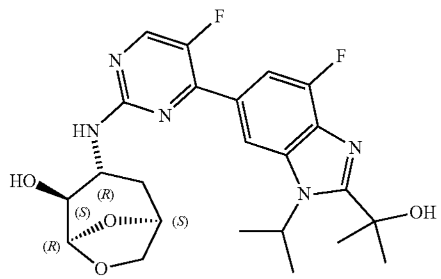 | (1S,3R,4S,5R)-3-((5-fluoro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol |
| 28 | 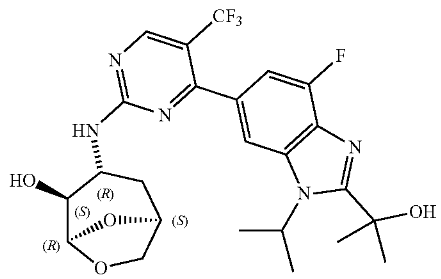 | (1S,3R,4S,5R)-3-((4-(4-fluoro-2-(2-hydroxypropan-2-yl)-1-isopropyl-1H-benzo[d]imidazol-6-yl)-5-(trifluoromethyl)pyrimidin-2-yl)amino)-6,8-dioxabicyclo[3.2.1]octan-4-ol |
| 29 | 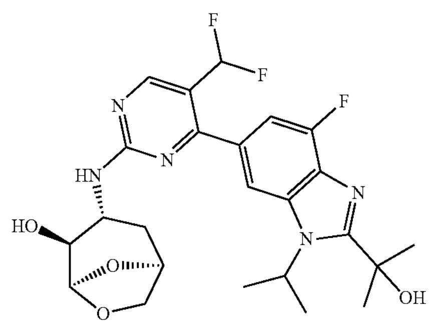 [SMILES: CC(C)n1c(C(C)(C)O)nc2c(F)cc(-c3nc(N[C@@H]4C[C@H]5CO[C@H](O5)[C@H]4O)ncc3C(F)F)cc21] | (1S,3R,4S,5R)-3-((5-(difluoromethyl)-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol |
| 30 | 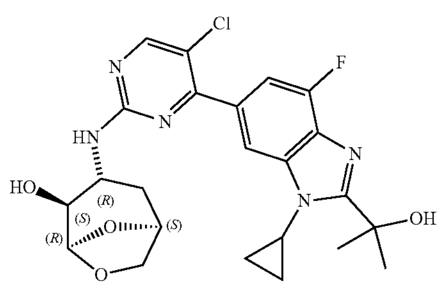 | (1S,3R,4S,5R)-3-((5-chloro-4-(1-cyclopropyl-4-fluoro-2-(2-hydroxypropan-2-yl)-1H-benzo[d]imidazol-6-yl)pyrimidin-2-yl)amino)-6,8-dioxabicyclo[3.2.1]octan-4-ol |
| 31 | 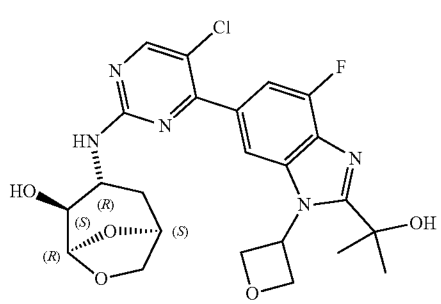 | (1S,3R,4S,5R)-3-((5-chloro-4-(4-fluoro-2-(2-hydroxypropan-2-yl)-1-(oxetan-3-yl)-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 32 | 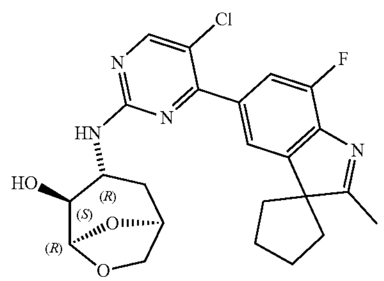 | (1S,3R,4S,5R)-3-((5-chloro-4-(7'-fluoro-2'-methylspiro[cyclopentane-1,3'-indol]-5'-yl)pyrimidin-2-yl)amino)-6,8-dioxabicyclo[3.2.1]octan-4-ol |
| 33 | 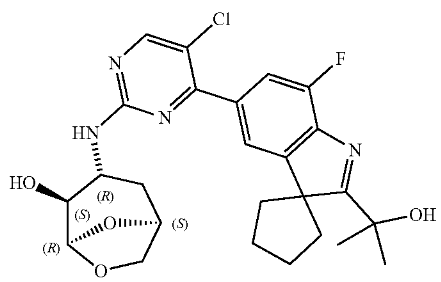 | (1S,3R,4S,5R)-3-((5-chloro-4-(7'-fluoro-2'-(2-hydroxypropan-2-yl)spiro[cyclopentane-1,3'-indol]-5'-yl)pyrimidin-2-yl)amino)-6,8-dioxabicyclo[3.2.1]octan-4-ol |
| 34 | 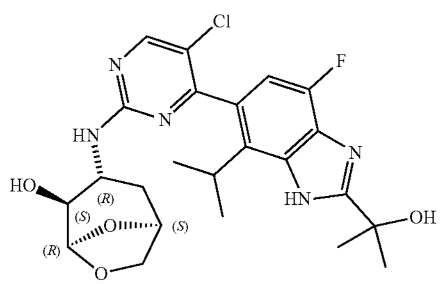 | (1S,3R,4S,5R)-3-((5-chloro-4-(4-fluoro-2-(2-hydroxypropan-2-yl)-7-isopropyl-1H-benzo[d]imidazol-6-yl)pyrimidin-2-yl)amino)-6,8-dioxabicyclo[3.2.1]octan-4-ol |
| 35 | 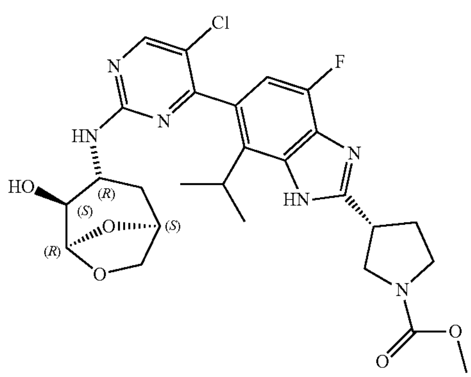 | methyl (R)-3-(6-(5-chloro-2-((((1S,3R,4S,5R)-4-hydroxy-6,8-dioxabicyclo[3.2.1]octan-3-yl)amino)pyrimidin-4-yl)-4-fluoro-7-isopropyl-1H-benzo[d]imidazol-2-yl)pyrrolidine-1-carboxylate |
| 36 | 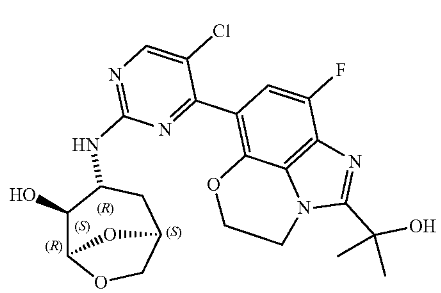 | (1S,3R,4S,5R)-3-((5-chloro-4-(8-fluoro-2-(2-hydroxypropan-2-yl)-3,4-dihydro-5-oxa-1,2a-diazaacenaphthylen-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 37 | 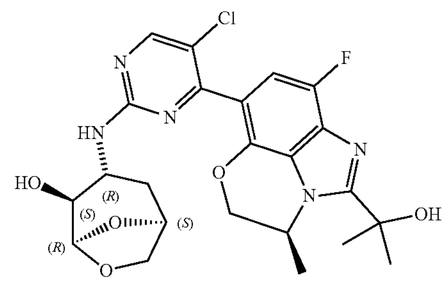 | (1S,3R,4S,5R)-3-((5-chloro-4-((S)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol |
| 38 | 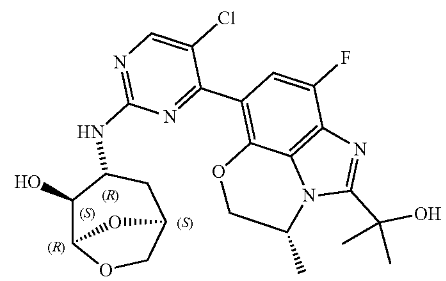 | (1S,3R,4S,5R)-3-((5-chloro-4-((R)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol |
| 39 | 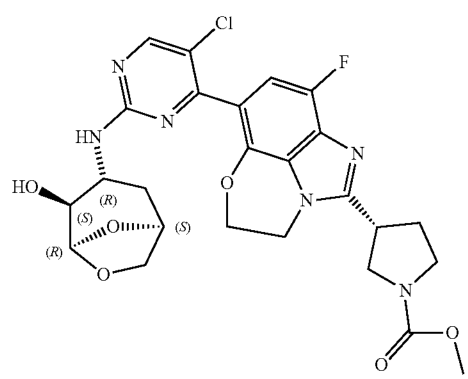 | methyl (R)-3-(6-(5-chloro-2-(((1S,3R,4S,5R)-4-hydroxy-6,8-dioxabicyclo[3.2.1]octan-3-yl)amino)pyrimidin-4-yl)-8-fluoro-3,4-dihydro-5-oxa-1,2a-diazaacenaphthylen-2-yl)pyrrolidine-1-carboxylate |
| 40 | 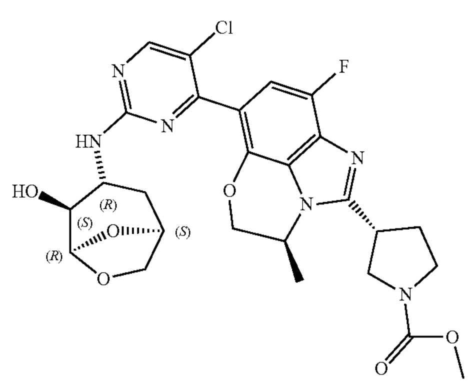 | methyl (R)-3-((S)-6-(5-chloro-2-(((1S,3R,4S,5R)-4-hydroxy-6,8-dioxabicyclo[3.2.1]octan-3-yl)amino)pyrimidin-4-yl)-8-fluoro-3-methyl-3,4-dihydro-5-oxa-1,2a-diazaacenaphthylen-2-yl)pyrrolidine-1-carboxylate |

TABLE 1-continued

Compounds of the present disclosure

| Cpd # | Structure | IUPAC Name |
|---|---|---|
| 41 | 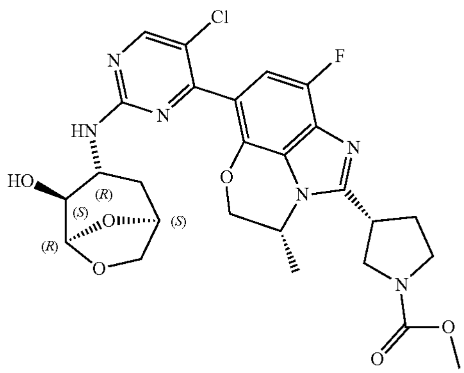 | methyl (R)-3-((R)-6-(5-chloro-2-(((1S,3R,4S,5R)-4-hydroxy-6,8-dioxabicyclo[3.2.1]octan-3-yl)amino)pyrimidin-4-yl)-8-fluoro-3-methyl-3,4-dihydro-5-oxa-1,2a-diazaacenaphthylen-2-yl)pyrrolidine-1-carboxylate |
| 42 | 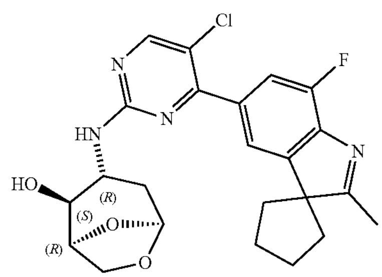 | (1S,2S,3R,5S)-3-((5-chloro-4-(7'-fluoro-2'-methylspiro[cyclopentane-1,3'-indol]-5'-yl)pyrimidin-2-yl)amino)-6,8-dioxabicyclo[3.2.1]octan-2-ol |
| 43 | 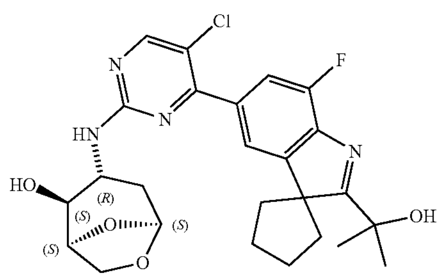 | (1S,2S,3R,5S)-3-((5-chloro-4-(7'-fluoro-2'-(2-hydroxypropan-2-yl)spiro[cyclopentane-1,3'-indol]-5'-yl)pyrimidin-2-yl)amino)-6,8-dioxabicyclo[3.2.1]octan-2-ol |
| 44 | 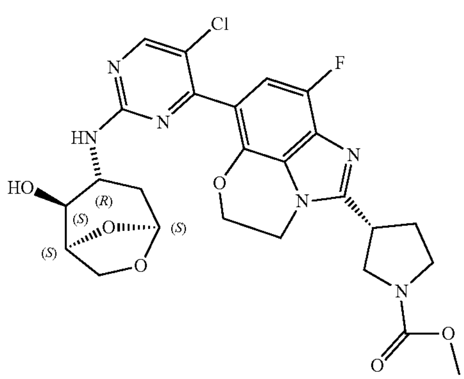 | methyl (R)-3-(6-(5-chloro-2-(((1S,2S,3R,5S)-2-hydroxy-6,8-dioxabicyclo[3.2.1]octan-3-yl)amino)pyrimidin-4-yl)-8-fluoro-3,4-dihydro-5-oxa-1,2a-diazaacenaphthylen-2-yl)pyrrolidine-1-carboxylate |

TABLE 1-continued

Compounds of the present disclosure

| Cpd # | Structure | IUPAC Name |
|---|---|---|
| 45 | 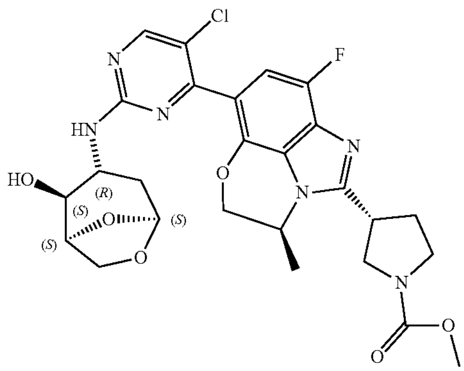 | methyl (R)-3-((S)-6-(5-chloro-2-(((1S,2S,3R,5S)-2-hydroxy-6,8-dioxabicyclo[3.2.1]octan-3-yl)amino)pyrimidin-4-yl)-8-fluoro-3-methyl-3,4-dihydro-5-oxa-1,2a-diazaacenaphthylen-2-yl)pyrrolidine-1-carboxylate |
| 46 | 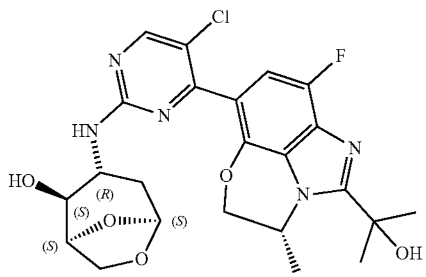 | (1S,2S,3R,5S)-3-((5-chloro-4-((R)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-2-ol |
| 47 | 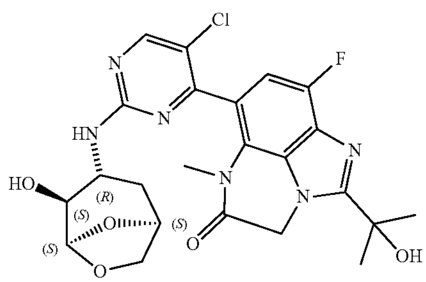 | 7-(5-chloro-2-(((1S,3R,4S,5R)-4-hydroxy-6,8-dioxabicyclo[3.2.1]octan-3-yl)amino)pyrimidin-4-yl)-9-fluoro-2-(2-hydroxypropan-2-yl)-6-methyl-4H-imidazo[1,5,4-de]quinoxalin-5(6H)-one |
| 48 | 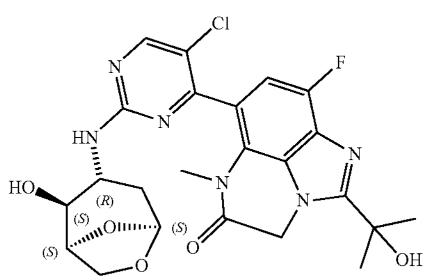 | 7-(5-chloro-2-(((1S,2S,3R,5S)-2-hydroxy-6,8-dioxabicyclo[3.2.1]octan-3-yl)amino)pyrimidin-4-yl)-9-fluoro-2-(2-hydroxypropan-2-yl)-6-methyl-4H-imidazo[1,5,4-de]quinoxalin-5(6H)-one |
| 49 | 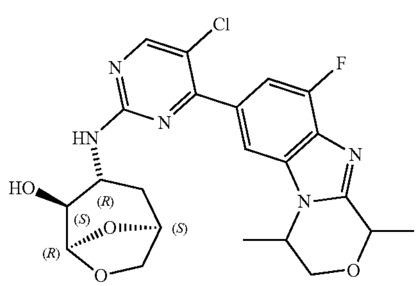 | (1S,3R,4S,5R)-3-((5-chloro-4-(9-fluoro-1,4-dimethyl-3,4-dihydro-1H-benzo[4,5]imidazo[2,1-c][1,4]oxazin-7-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 50 | 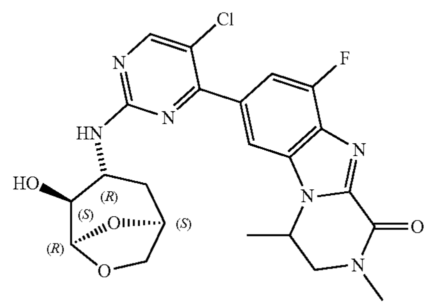 | 7-(5-chloro-2-(((1S,3R,4S,5R)-4-hydroxy-6,8-dioxabicyclo[3.2.1]octan-3-yl)amino)pyrimidin-4-yl)-9-fluoro-2,4-dimethyl-3,4-dihydrobenzo[4,5]imidazo[1,2-a]pyrazin-1(2H)-one |
| 51 | 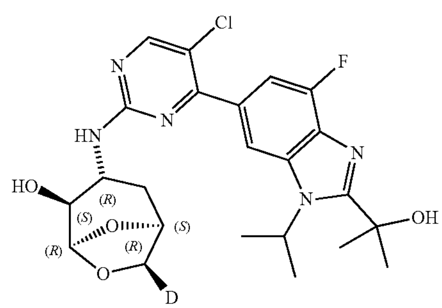 | (1S,3R,4S,5R,7R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7-d-4-ol |
| 52 | 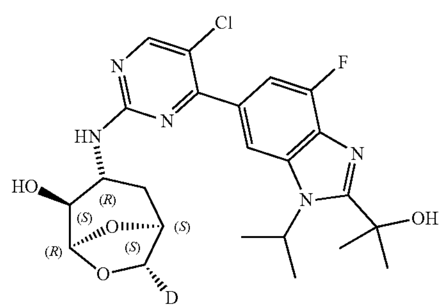 | (1S,3R,4S,5R,7S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7-d-4-ol |
| 53 | 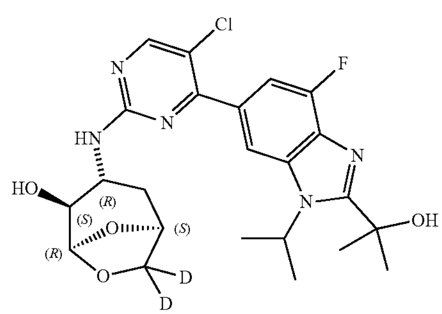 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7,7-d2-4-ol |
| 54 | 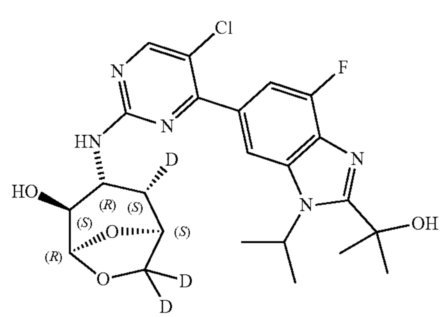 | (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2,7,7-d3-4-ol |

TABLE 1-continued

Compounds of the present disclosure

| Cpd # | Structure | IUPAC Name |
|---|---|---|
| 55 | 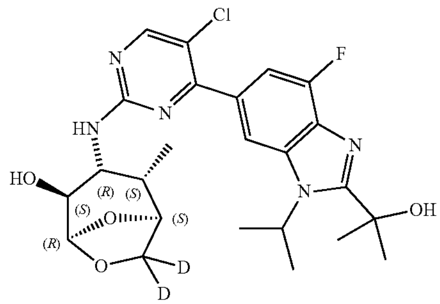 | (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-methyl-6,8-dioxabicyclo[3.2.1]octan-7,7-d2-4-ol |
| 56 | 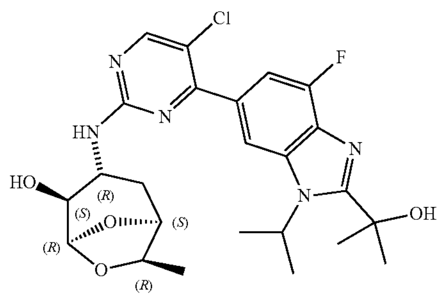 | (1S,3R,4S,5R,7R)-3-((5-chloro-4-(4-fluoro-2-(2-hydroxypropan-2-yl)-1-isopropyl-1H-benzo[d]imidazol-6-yl)pyrimidin-2-yl)amino)-7-methyl-6,8-dioxabicyclo[3.2.1]octan-4-ol |
| 57 | 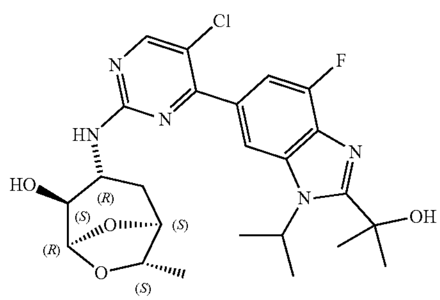 | (1S,3R,4S,5R,7S)-3-((5-chloro-4-(4-fluoro-2-(2-hydroxypropan-2-yl)-1-isopropyl-1H-benzo[d]imidazol-6-yl)pyrimidin-2-yl)amino)-7-methyl-6,8-dioxabicyclo[3.2.1]octan-4-ol |
| 58 | 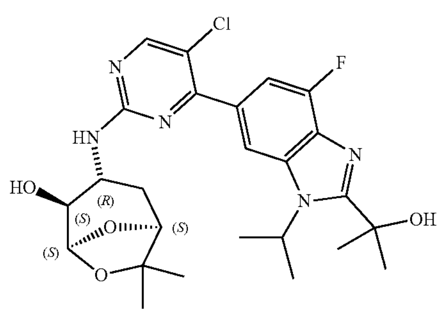 | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-7,7-dimethyl-6,8-dioxabicyclo[3.2.1]octan-4-ol |
| 59 | 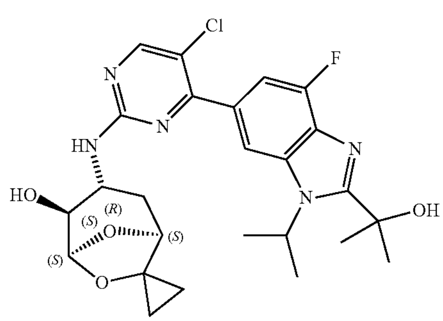 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-7,8-dioxaspiro[bicyclo[3.2.1]octane-6,1'-cyclopropan]-2-ol |

TABLE 1-continued

Compounds of the present disclosure

| Cpd # | Structure | IUPAC Name |
|---|---|---|
| 60 | 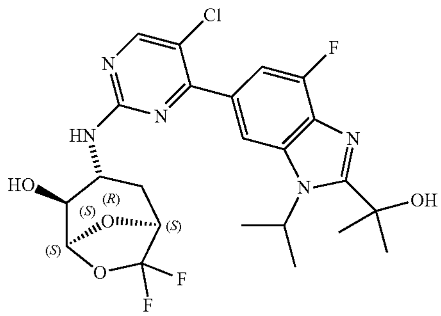 | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-6,8-dioxabicyclo[3.2.1]octan-4-ol |
| 61 | 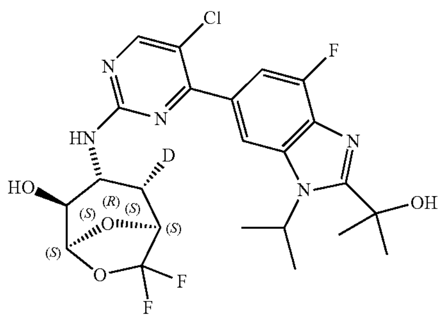 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-6,8-dioxabicyclo[3.2.1]octan-2-d-4-ol |
| 62 | 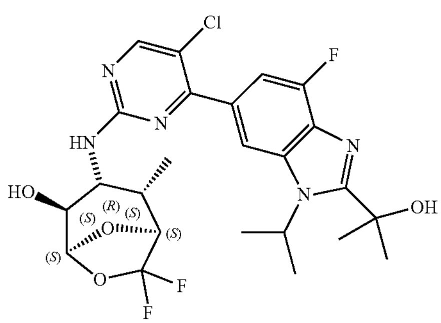 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-2-methyl-6,8-dioxabicyclo[3.2.1]octan-4-ol |
| 63 | 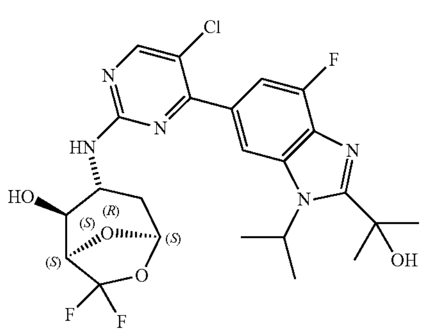 | (1R,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-6,8-dioxabicyclo[3.2.1]octan-2-ol |

TABLE 1-continued

Compounds of the present disclosure

| Cpd # | Structure | IUPAC Name |
|---|---|---|
| 64 | 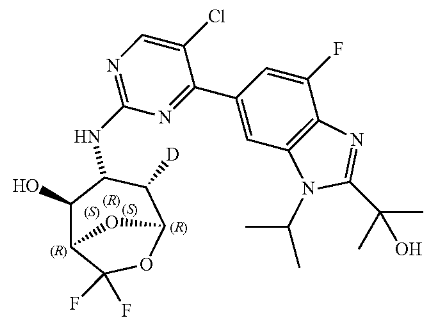 | (1R,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-6,8-dioxabicyclo[3.2.1]octan-4-d-2-ol |
| 65 | 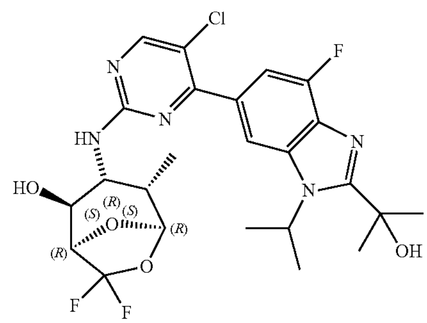 | (1R,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-7,7-difluoro-4-methyl-6,8-dioxabicyclo[3.2.1]octan-2-ol |
| 66 | 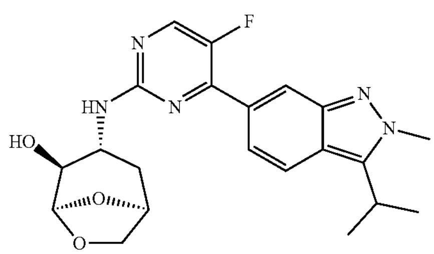 [SMILES: CC(C)c1c2ccc(-c3nc(N[C@@H]4C[C@H]5CO[C@H](O5)[C@H]4O)ncc3F)cc2nn1C] | (1S,3R,4S,5R)-3-((5-fluoro-4-(3-isopropyl-2-methyl-2H-indazol-5-yl)pyrimidin-2-yl)amino)-6,8-dioxabicyclo[3.2.1]octan-4-ol |
| 67 | 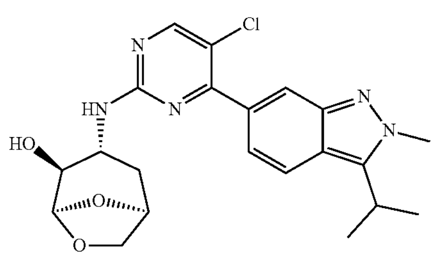 | (1S,3R,4S,5R)-3-((5-chloro-4-(3-isopropyl-2-methyl-2H-indazol-5-yl)pyrimidin-2-yl)amino)-6,8-dioxabicyclo[3.2.1]octan-4-ol |
| 68 | 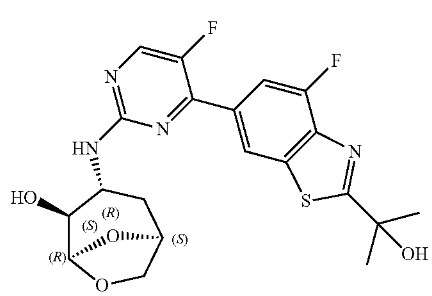 | (1S,3R,4S,5R)-3-((5-fluoro-4-(4-fluoro-2-(2-hydroxypropan-2-yl)benzo[d]thiazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 69 | 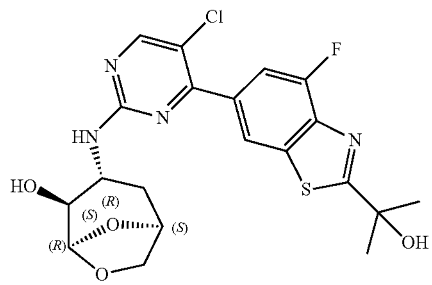 | (1S,3R,4S,5R)-3-((5-chloro-4-(4-fluoro-2-(2-hydroxypropan-2-yl)benzo[d]thiazol-6-yl)pyrimidin-2-yl)amino)-6,8-dioxabicyclo[3.2.1]octan-4-ol |
| 70 | 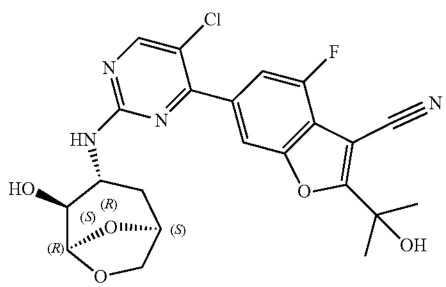 | 6-(5-chloro-2-(((1S,3R,4S,5R)-4-hydroxy-6,8-dioxabicyclo[3.2.1]octan-3-yl)amino)pyrimidin-4-yl)-4-fluoro-2-(2-hydroxypropan-2-yl)benzofuran-3-carbonitrile |
| 71 | 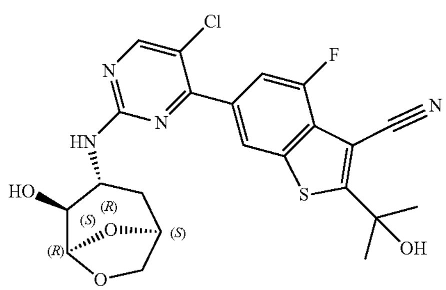 | 6-(5-chloro-2-(((1S,3R,4S,5R)-4-hydroxy-6,8-dioxabicyclo[3.2.1]octan-3-yl)amino)pyrimidin-4-yl)-4-fluoro-2-(2-hydroxypropan-2-yl)benzo[b]thiophene-3-carbonitrileoo |
| 72 | 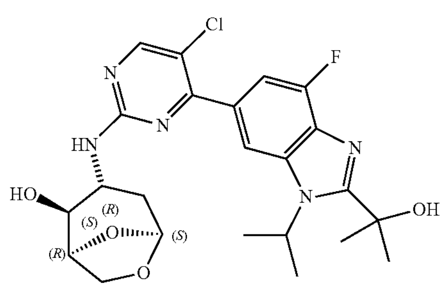 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-ol |
| 73 | 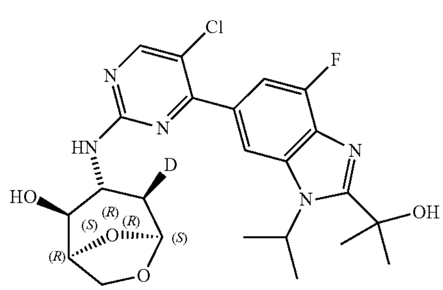 | (1S,2S,3R,4R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-d-2-ol |

TABLE 1-continued

Compounds of the present disclosure

| Cpd # | Structure | IUPAC Name |
|---|---|---|
| 74 | 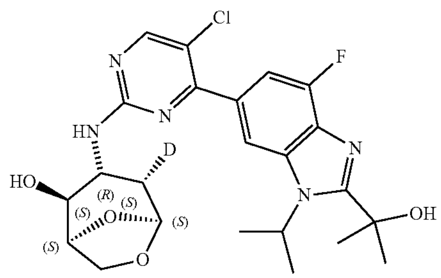 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-d-2-ol |
| 75 | 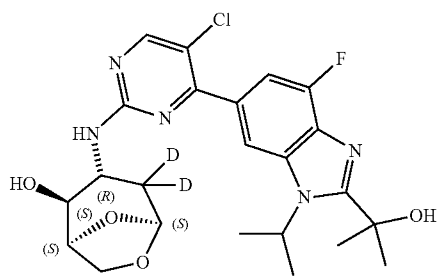 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4,4-d2-2-ol |
| 76 | 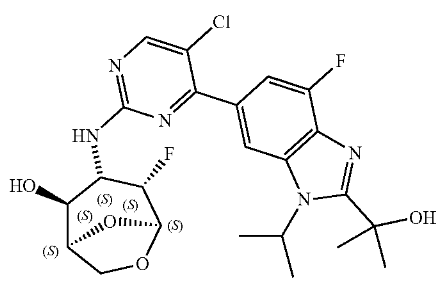 | (1S,2S,3S,4S,5S)-3-((5-chloro-4-(4-fluoro-2-(2-hydroxypropan-2-yl)-1-isopropyl-1H-benzo[d]imidazol-6-yl)pyrimidin-2-yl)amino)-4-fluoro-6,8-dioxabicyclo[3.2.1]octan-2-ol |
| 77 | 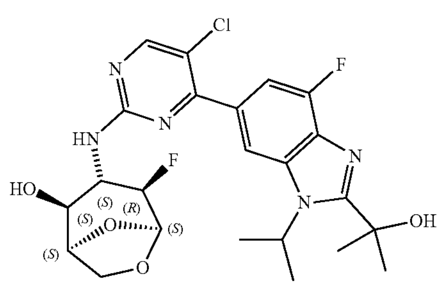 | (1S,2S,3S,4R,5S)-3-((5-chloro-4-(4-fluoro-2-(2-hydroxypropan-2-yl)-1-isopropyl-1H-benzo[d]imidazol-6-yl)pyrimidin-2-yl)amino)-4-fluoro-6,8-dioxabicyclo[3.2.1]octan-2-ol |
| 78 | 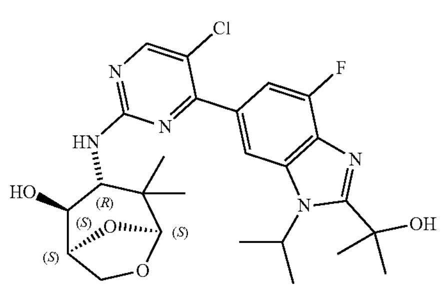 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-4,4-dimethyl-6,8-dioxabicyclo[3.2.1]octan-2-ol |

TABLE 1-continued

Compounds of the present disclosure

| Cpd # | Structure | IUPAC Name |
|---|---|---|
| 79 | 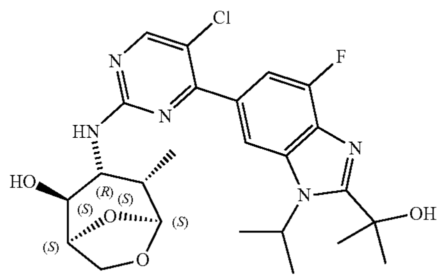 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-4-methyl-6,8-dioxabicyclo[3.2.1]octan-2-ol |
| 80 | 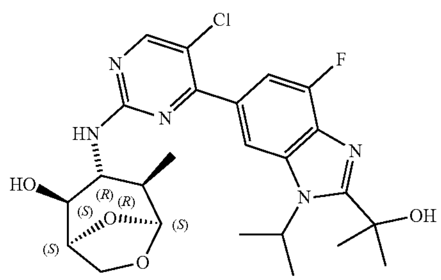 | (1S,2S,3R,4R,5S)-3-((5-chloro-4-(4-fluoro-2-(2-hydroxypropan-2-yl)-1-isopropyl-1H-benzo[d]imidazol-6-yl)pyrimidin-2-yl)amino)-4-methyl-6,8-dioxabicyclo[3.2.1]octan-2-ol |
| 81 | 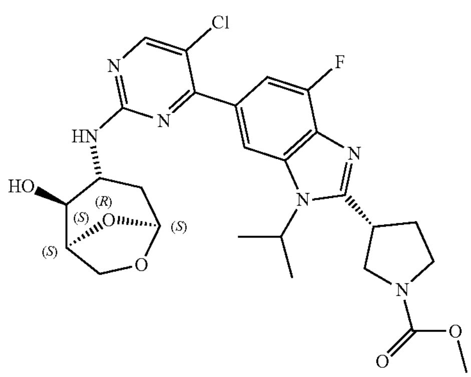 | methyl (R)-3-(6-(5-chloro-2-(((1S,2S,3R,5S)-2-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 82 | 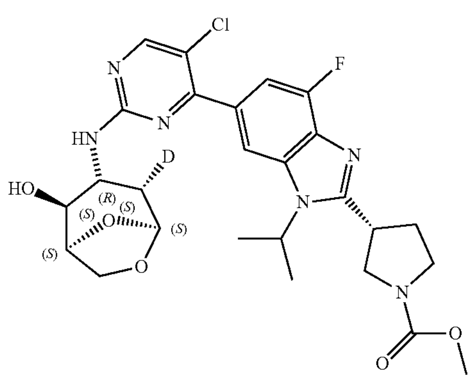 | methyl (R)-3-(6-(5-chloro-2-(((1S,2S,3R,4S,5S)-2-hydroxy-6,8-dioxabicyclo[3.2.1]octan-3-yl-4-d)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 83 | 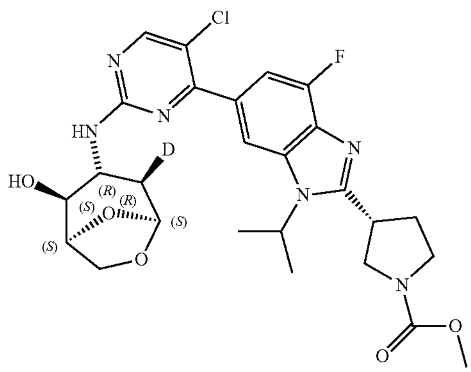 | methyl (R)-3-(6-(5-chloro-2-(((1S,2S,3R,4R,5S)-2-hydroxy-6,8-dioxabicyclo[3.2.1]octan-3-yl-4-d)amino)pyrimidin-4-yl)-4-fluoro-1-isopropyl-1H-benzo[d]imidazol-2-yl)pyrrolidine-1-carboxylate |
| 84 | 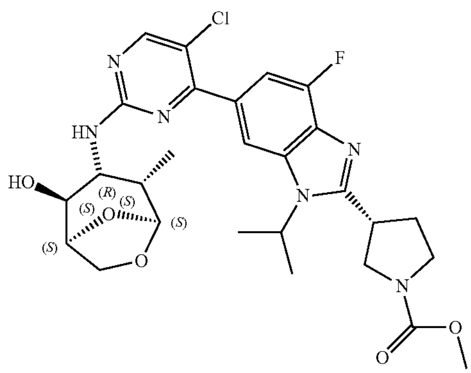 | methyl (R)-3-(6-(5-chloro-2-(((1S,2S,3R,4S,5S)-2-hydroxy-4-methyl-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 85 | 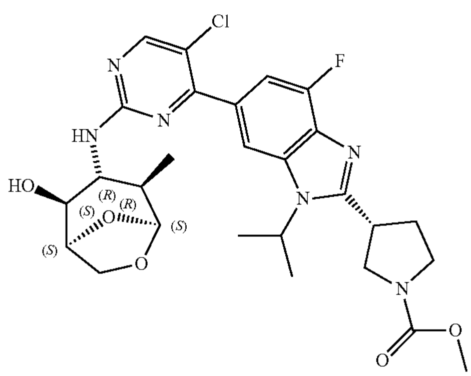 | methyl (R)-3-(6-(5-chloro-2-(((1S,2S,3R,4R,5S)-2-hydroxy-4-methyl-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 86 | 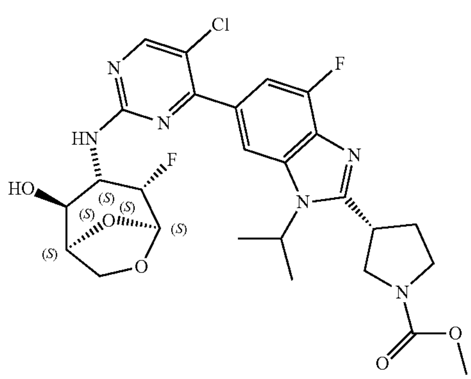 | methyl (R)-3-(6-(5-chloro-2-(((1S,2S,3S,4S,5S)-4-fluoro-2-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 87 | 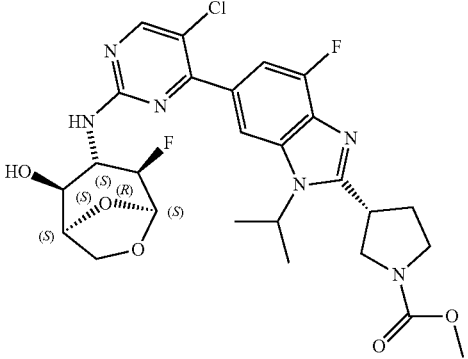 | methyl (R)-3-(6-(5-chloro-2-(((1S,2S,3S,4R,5S)-4-fluoro-2-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 88 | 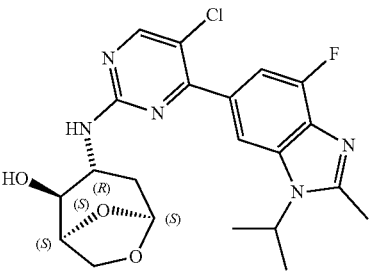 | (1S,2S,3R,5S)-3-((5-chloro-4-(4-fluoro-1-isopropyl-2-methyl-1H-benzo[d]imidazol-6-yl)pyrimidin-2-yl)amino)-6,8-dioxabicyclo[3.2.1]octan-2-ol |
| 89 | 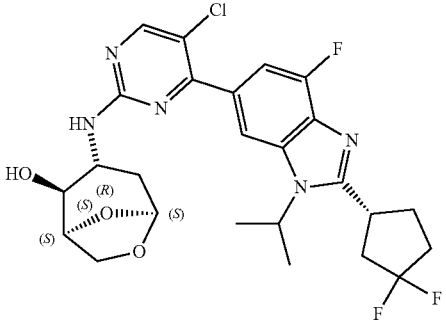 | (1S,2S,3R,5S)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-2-ol |
| 90 | 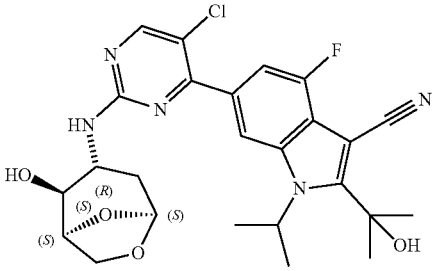 | 6-(5-chloro-2-(((1S,2S,3R,5S)-2-hydroxy-6,8-dioxabicyclo[3.2.1]octan-3-yl)amino)pyrimidin-4-yl)-4-fluoro-2-(2-hydroxypropan-2-yl)-1-isopropyl-1H-indole-3-carbonitrile |

TABLE 1-continued

Compounds of the present disclosure

| Cpd # | Structure | IUPAC Name |
| --- | --- | --- |
| 91 | 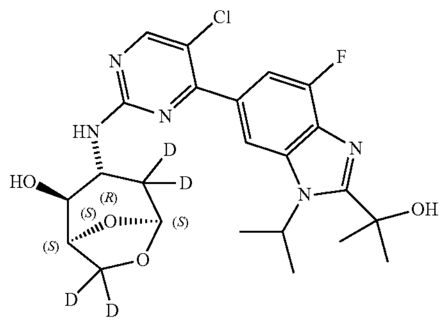 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4,4,7,7-d4-2-ol |
| 92 | 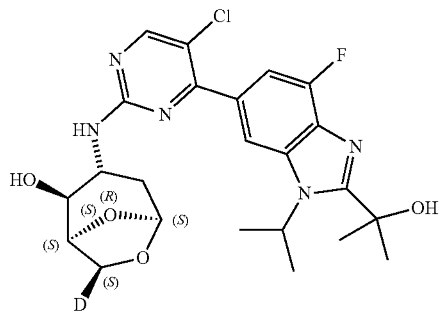 | (1S,2S,3R,5S,7S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7-d-2-ol |
| 93 | 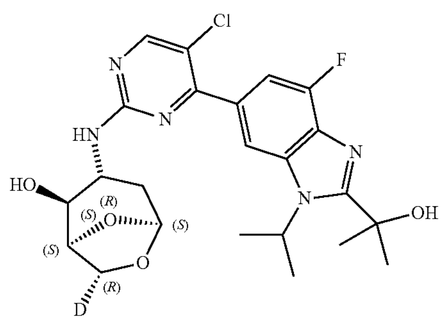 | (1S,2S,3R,5S,7R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7-d-2-ol |
| 94 | 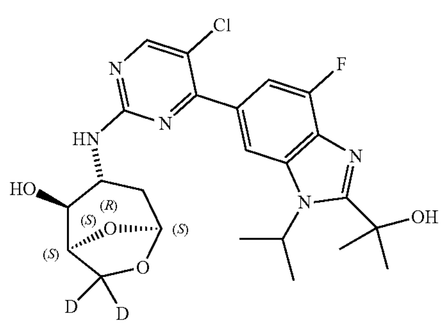 | (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-7,7-d2-2-ol |

TABLE 1-continued

Compounds of the present disclosure

| Cpd # | Structure | IUPAC Name |
|---|---|---|
| 95 | 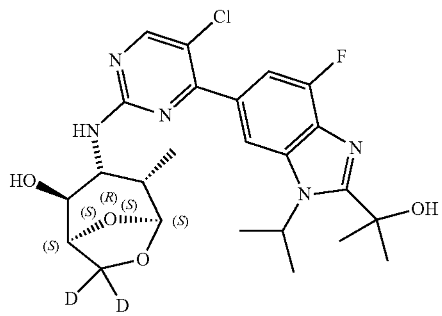 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-4-methyl-6,8-dioxabicyclo[3.2.1]octan-7,7-d2-2-ol |
| 96 | 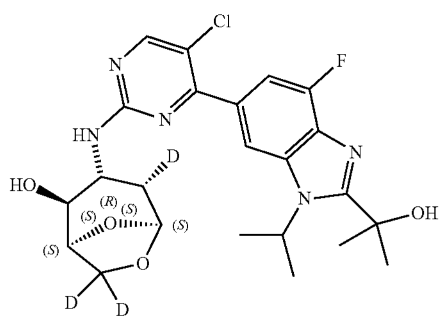 | (1S,2S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4,7,7-d3-2-ol |
| 97 | 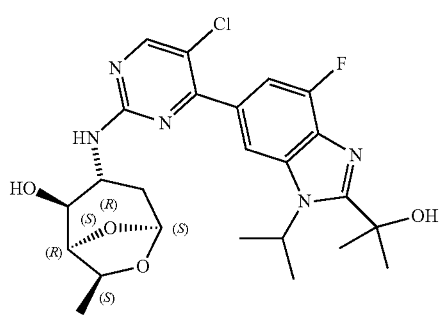 | (1R,2S,3R,5S,7S)-3-((5-chloro-4-(4-fluoro-2-(2-hydroxypropan-2-yl)-1-isopropyl-1H-benzo[d]imidazol-6-yl)pyrimidin-2-yl)amino)-7-methyl-6,8-dioxabicyclo[3.2.1]octan-2-ol |
| 98 | 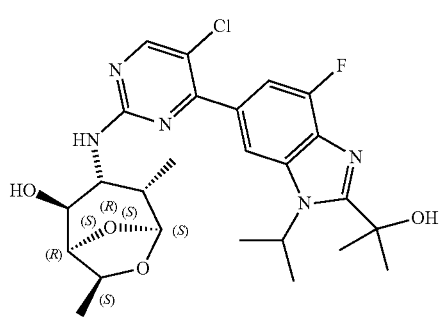 | (1R,2S,3R,4S,5S,7S)-3-((5-chloro-4-(4-fluoro-2-(2-hydroxypropan-2-yl)-1-isopropyl-1H-benzo[d]imidazol-6-yl)pyrimidin-2-yl)amino)-4,7-dimethyl-6,8-dioxabicyclo[3.2.1]octan-2-ol |

TABLE 1-continued

Compounds of the present disclosure

| Cpd # | Structure | IUPAC Name |
| --- | --- | --- |
| 99 | 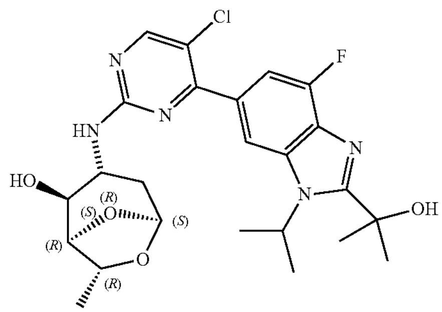 | (1R,2S,3R,5S,7R)-3-((5-chloro-4-(4-fluoro-2-(2-hydroxypropan-2-yl)-1-isopropyl-1H-benzo[d]imidazol-6-yl)pyrimidin-2-yl)amino)-7-methyl-6,8-dioxabicyclo[3.2.1]octan-2-ol |
| 100 | 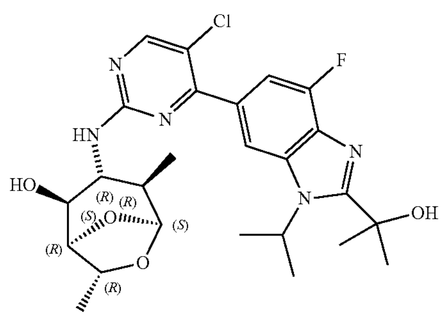 | (1R,2S,3R,4R,5S,7R)-3-((5-chloro-4-(4-fluoro-2-(2-hydroxypropan-2-yl)-1-isopropyl-1H-benzo[d]imidazol-6-yl)pyrimidin-2-yl)amino)-4,7-dimethyl-6,8-dioxabicyclo[3.2.1]octan-2-ol |
| 101 | 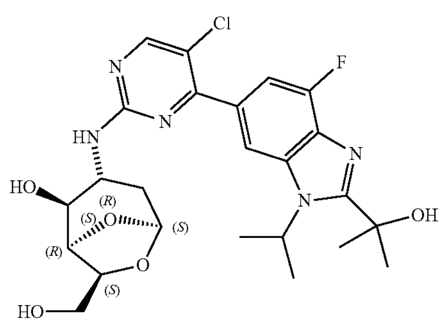 | (1R,2S,3R,5S,7S)-3-((5-chloro-4-(4-fluoro-2-(2-hydroxypropan-2-yl)-1-isopropyl-1H-benzo[d]imidazol-6-yl)pyrimidin-2-yl)amino)-7-(hydroxymethyl)-6,8-dioxabicyclo[3.2.1]octan-2-ol |
| 102 | 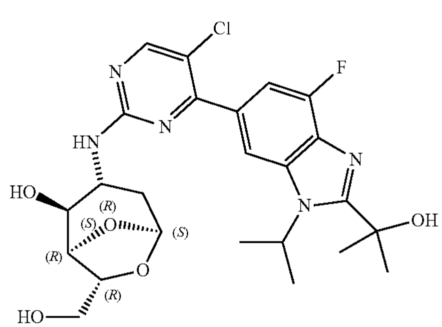 | (1R,2S,3R,5S,7R)-3-((5-chloro-4-(4-fluoro-2-(2-hydroxypropan-2-yl)-1-isopropyl-1H-benzo[d]imidazol-6-yl)pyrimidin-2-yl)amino)-7-(hydroxymethyl)-6,8-dioxabicyclo[3.2.1]octan-2-ol |

TABLE 1-continued

Compounds of the present disclosure

| Cpd # | Structure | IUPAC Name |
|---|---|---|
| 103 | 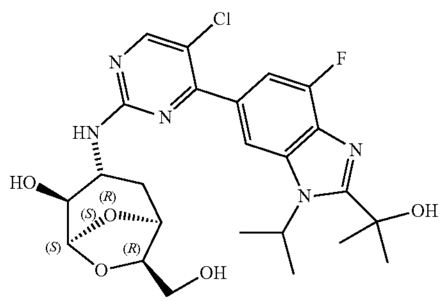 | (1S,3R,4S,5S,7R)-3-((5-chloro-4-(4-fluoro-2-(2-hydroxypropan-2-yl)-1-isopropyl-1H-benzo[d]imidazol-6-yl)pyrimidin-2-yl)amino)-7-(hydroxymethyl)-6,8-dioxabicyclo[3.2.1]octan-4-ol |
| 104 | 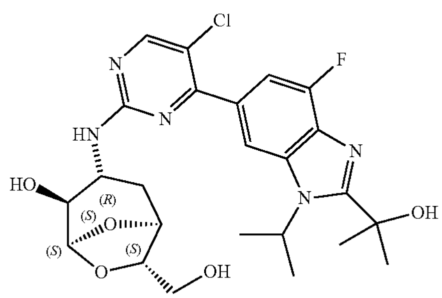 | (1S,3R,4S,5S,7S)-3-((5-chloro-4-(4-fluoro-2-(2-hydroxypropan-2-yl)-1-isopropyl-1H-benzo[d]imidazol-6-yl)pyrimidin-2-yl)amino)-7-(hydroxymethyl)-6,8-dioxabicyclo[3.2.1]octan-4-ol |
| 105 | 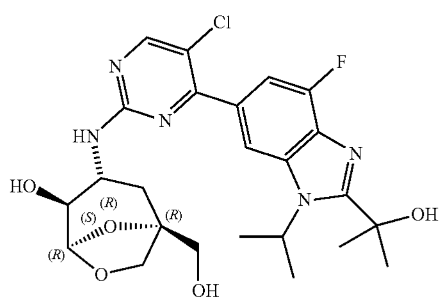 | (1R,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-1-(hydroxymethyl)-6,8-dioxabicyclo[3.2.1]octan-4-ol |
| 106 | 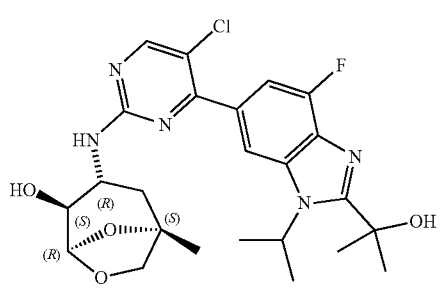 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-1-methyl-6,8-dioxabicyclo[3.2.1]octan-4-ol |
| 107 | 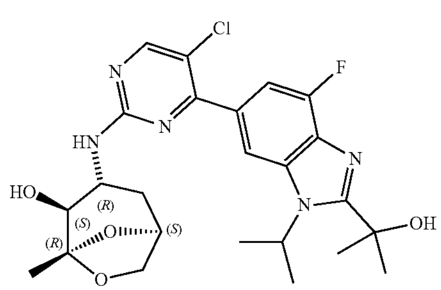 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-5-methyl-6,8-dioxabicyclo[3.2.1]octan-4-ol |

TABLE 1-continued

Compounds of the present disclosure

| Cpd # | Structure | IUPAC Name |
|---|---|---|
| 108 | 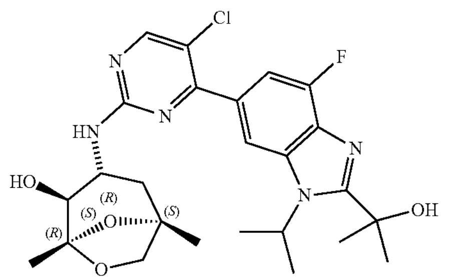 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-1,5-dimethyl-6,8-dioxabicyclo[3.2.1]octan-4-ol |
| 109 | 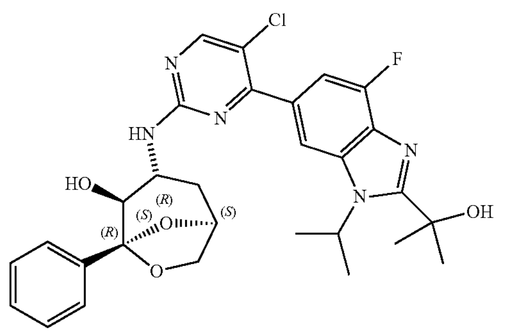 | (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-5-phenyl-6,8-dioxabicyclo[3.2.1]octan-4-ol |
| 110 | 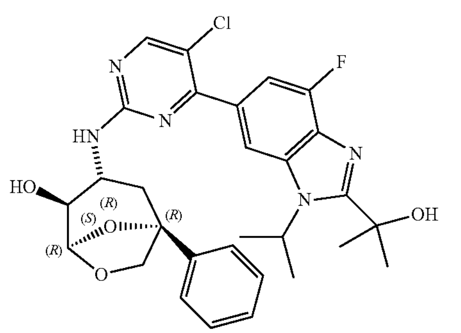 | (1S,3R,4S,5R)-3-((5-chloro-(1R,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-1-phenyl-6,8-dioxabicyclo[3.2.1]octan-4-ol |
| 111 | 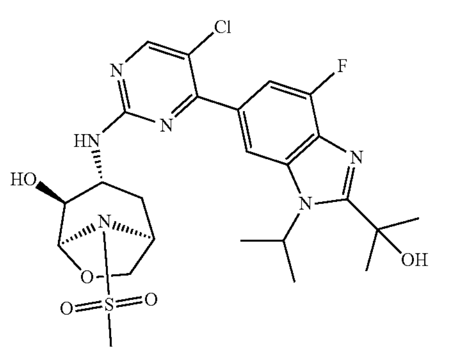 [SMILES: CC(C)n1c(C(C)(C)O)nc2c(F)cc(-c3nc(N[C@@H]4C[C@H]5CO[C@@H]([C@H]4O)N5S(C)(=O)=O)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(methylsulfonyl)-6-oxa-8-azabicyclo[3.2.1]octan-4-ol |

TABLE 1-continued

Compounds of the present disclosure

| Cpd # | Structure | IUPAC Name |
|---|---|---|
| 112 | 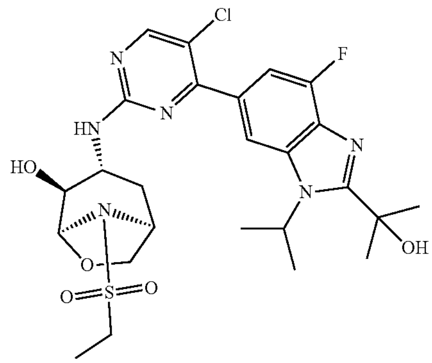 [SMILES: CCS(=O)(=O)N1[C@@H]2CO[C@H]1[C@@H](O)[C@H](Nc1ncc(Cl)c(-c3cc(F)c4nc(C(C)(C)O)n(C(C)C)c4c3)n1)C2] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(ethylsulfonyl)-6-oxa-8-azabicyclo[3.2.1]octan-4-ol |
| 113 | 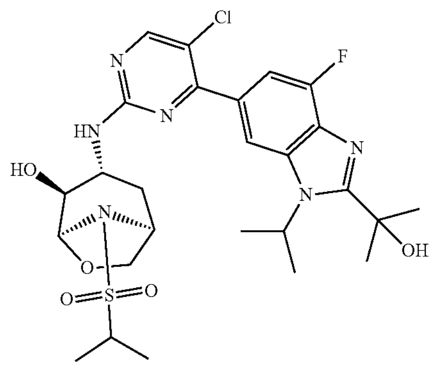 [SMILES: CC(C)n1c(C(C)(C)O)nc2c(F)cc(-c3nc(N[C@@H]4C[C@H]5CO[C@@H]([C@H]4O)N5S(=O)(=O)C(C)C)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(isopropylsulfonyl)-6-oxa-8-azabicyclo[3.2.1]octan-4-ol |
| 114 | 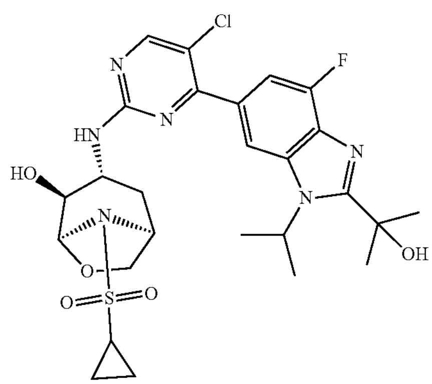 [SMILES: CC(C)n1c(C(C)(C)O)nc2c(F)cc(-c3nc(N[C@@H]4C[C@H]5CO[C@@H]([C@H]4O)N5S(=O)(=O)C4CC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(cyclopropylsulfonyl)-6-oxa-8-azabicyclo[3.2.1]octan-4-ol |
| 115 | 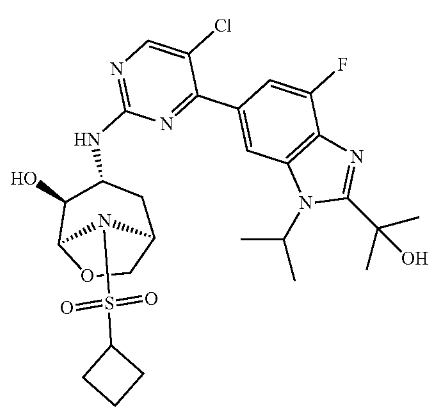 [SMILES: CC(C)n1c(C(C)(C)O)nc2c(F)cc(-c3nc(N[C@@H]4C[C@H]5CO[C@@H]([C@H]4O)N5S(=O)(=O)C4CCC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(cyclobutylsulfonyl)-6-oxa-8-azabicyclo[3.2.1]octan-4-ol |

TABLE 1-continued

Compounds of the present disclosure

| Cpd # | Structure | IUPAC Name |
|---|---|---|
| 116 | 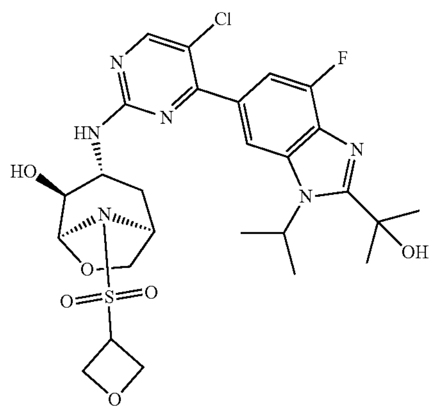 [SMILES: CC(C)n1c(C(C)(C)O)nc2c(F)cc(-c3nc(N[C@@H]4C[C@H]5CO[C@@H]([C@H]4O)N5S(=O)(=O)C4COC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(oxetan-3-ylsulfonyl)-6-oxa-8-azabicyclo[3.2.1]octan-4-ol |
| 117 | 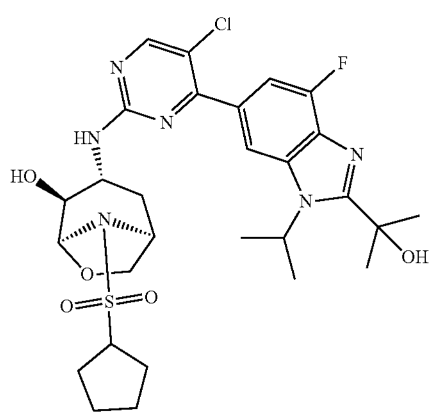 [SMILES: CC(C)n1c(C(C)(C)O)nc2c(F)cc(-c3nc(N[C@@H]4C[C@H]5CO[C@@H]([C@H]4O)N5S(=O)(=O)C4CCCC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(cyclopentylsulfonyl)-6-oxa-8-azabicyclo[3.2.1]octan-4-ol |
| 118 | 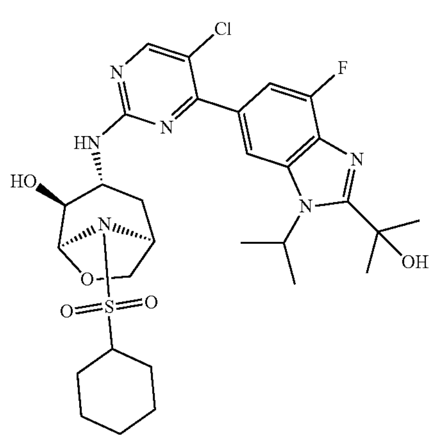 [SMILES: CC(C)n1c(C(C)(C)O)nc2c(F)cc(-c3nc(N[C@@H]4C[C@H]5CO[C@@H]([C@H]4O)N5S(=O)(=O)C4CCCCC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(cyclohexylsulfonyl)-6-oxa-8-azabicyclo[3.2.1]octan-4-ol |

TABLE 1-continued

Compounds of the present disclosure

| Cpd # | Structure | IUPAC Name |
|---|---|---|
| 119 | 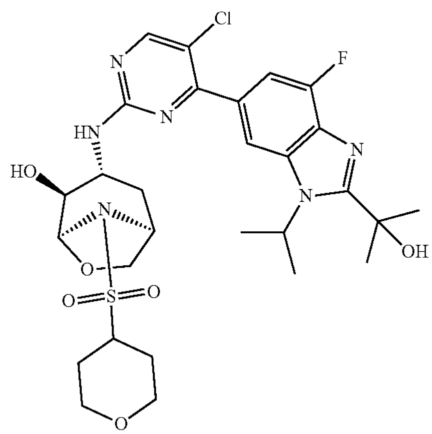 [SMILES: CC(C)n1c(C(C)(C)O)nc2c(F)cc(-c3nc(N[C@@H]4C[C@H]5CO[C@@H]([C@H]4O)N5S(=O)(=O)C4CCOCC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-((tetrahydro-2H-pyran-4-yl)sulfonyl)-6-oxa-8-azabicyclo[3.2.1]octan-4-ol |
| 120 | 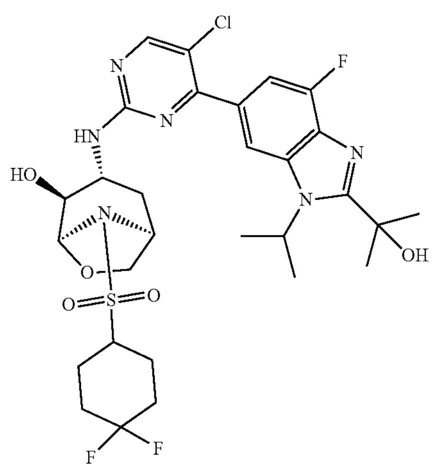 [SMILES: CC(C)n1c(C(C)(C)O)nc2c(F)cc(-c3nc(N[C@@H]4C[C@H]5CO[C@@H]([C@H]4O)N5S(=O)(=O)C4CCC(F)(F)CC4)ncc3Cl)cc21] | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-((4,4-difluorocyclohexyl)sulfonyl)-6-oxa-8-azabicyclo[3.2.1]octan-4-ol |
| 121 | 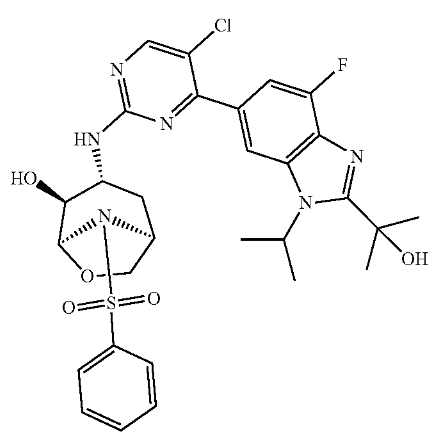 | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(phenylsulfonyl)-6-oxa-8-azabicyclo[3.2.1]octan-4-ol |

TABLE 1-continued

Compounds of the present disclosure

| Cpd # | Structure | IUPAC Name |
|---|---|---|
| 122 | 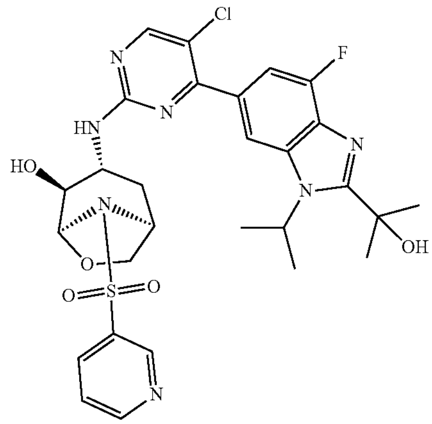 | (1S,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-8-(pyridin-3-ylsulfonyl)-6-oxa-8-azabicyclo[3.2.1]octan-4-ol |
| 123 | 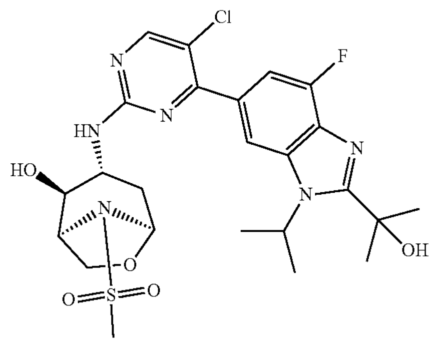 [SMILES: CC(C)n1c(C(C)(C)O)nc2c(F)cc(-c3nc(N[C@@H]4C[C@H]5OC[C@@H]([C@H]4O)N5S(C)(=O)=O)ncc3Cl)cc21] | (1S,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-8-(methylsulfonyl)-6-oxa-8-azabicyclo[3.2.1]octan-2-ol |
| 124 | 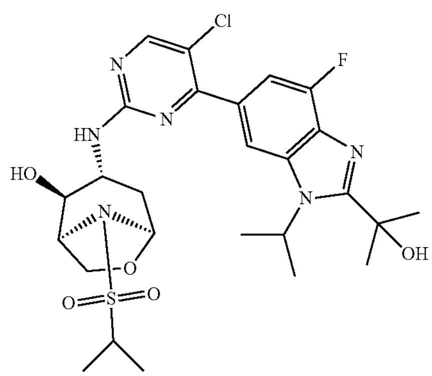 [SMILES: CC(C)n1c(C(C)(C)O)nc2c(F)cc(-c3nc(N[C@@H]4C[C@H]5OC[C@@H]([C@H]4O)N5S(=O)(=O)C(C)C)ncc3Cl)cc21] | (1S,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-8-(isopropylsulfonyl)-6-oxa-8-azabicyclo[3.2.1]octan-2-ol |
| 125 | 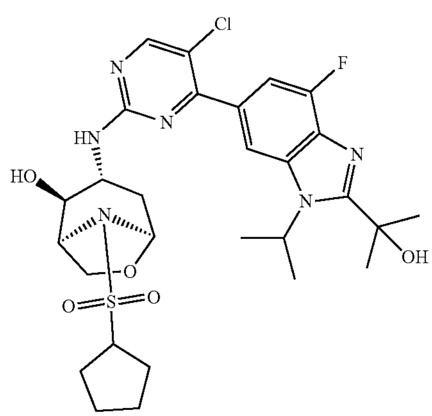 [SMILES: CC(C)n1c(C(C)(C)O)nc2c(F)cc(-c3nc(N[C@@H]4C[C@H]5OC[C@@H]([C@H]4O)N5S(=O)(=O)C4CCCC4)ncc3Cl)cc21] | (1S,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-8-(cyclopentylsulfonyl)-6-oxa-8-azabicyclo[3.2.1]octan-2-ol |

TABLE 1-continued

Compounds of the present disclosure

| Cpd # | Structure | IUPAC Name |
|---|---|---|
| 126 | 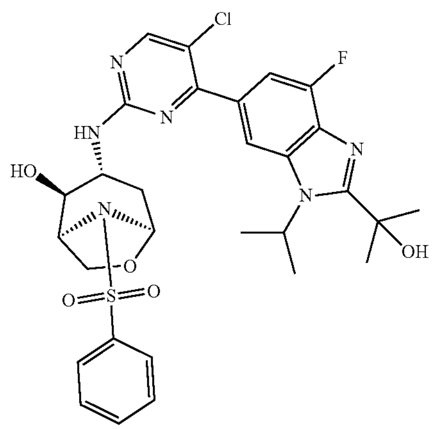 [SMILES: CC(C)n1c(C(C)(C)O)nc2c(F)cc(-c3nc(N[C@@H]4C[C@H]5OC[C@@H]([C@H]4O)N5S(=O)(=O)c4ccccc4)ncc3Cl)cc21] | (1S,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-8-(phenylsulfonyl)-6-oxa-8-azabicyclo[3.2.1]octan-2-ol |
| 127 | 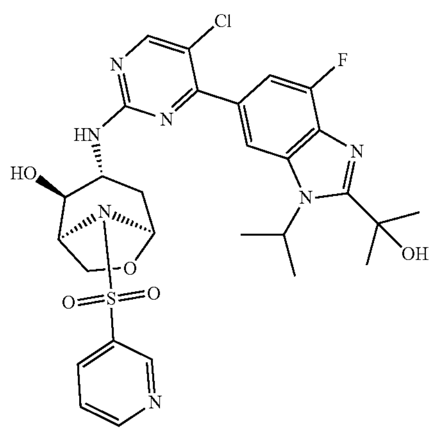 [SMILES: CC(C)n1c(C(C)(C)O)nc2c(F)cc(-c3nc(N[C@@H]4C[C@H]5OC[C@@H]([C@H]4O)N5S(=O)(=O)c4cccnc4)ncc3Cl)cc21] | (1S,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-8-(pyridin-3-ylsulfonyl)-6-oxa-8-azabicyclo[3.2.1]octan-2-ol |
| 128 | 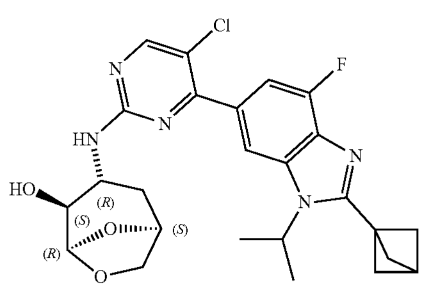 | (1S,3R,4S,5R)-3-((4-(2-(bicyclo[1.1.1]pentan-1-yl)-4-fluoro-1-isopropyl-1H-benzo[d]imidazol-6-yl)-5-chloropyrimidin-2-yl)amino)-6,8-dioxabicyclo[3.2.1]octan-4-ol |
| 129 | 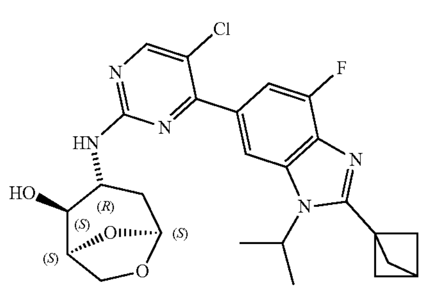 | (1S,2S,3R,5S)-3-((4-(2-(bicyclo[1.1.1]pentan-1-yl)-4-fluoro-1-isopropyl-1H-benzo[d]imidazol-6-yl)-5-chloropyrimidin-2-yl)amino)-6,8-dioxabicyclo[3.2.1]octan-2-ol |

TABLE 1-continued

Compounds of the present disclosure

| Cpd # | Structure | IUPAC Name |
|---|---|---|
| 130 | 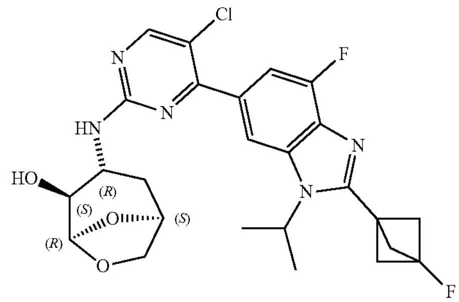 | (1S,3R,4S,5R)-3-((5-chloro-4-(4-fluoro-2-(3-fluorobicyclo[1.1.1]pentan-1-yl)-1-isopropyl-1H-benzo[d]imidazol-6-yl)pyrimidin-2-yl)amino)-6,8-dioxabicyclo[3.2.1]octan-4-ol |
| 131 | 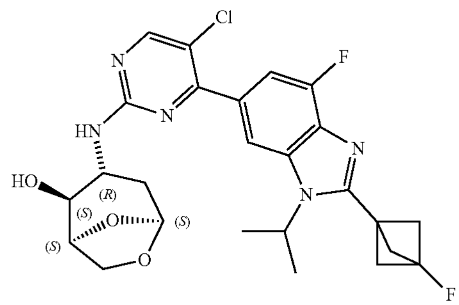 | (1S,2S,3R,5S)-3-((5-chloro-4-(4-fluoro-2-(3-fluorobicyclo[1.1.1]pentan-1-yl)-1-isopropyl-1H-benzo[d]imidazol-6-yl)pyrimidin-2-yl)amino)-6,8-dioxabicyclo[3.2.1]octan-2-ol |
| 132 | 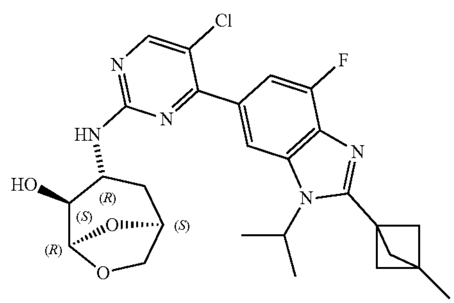 | (1S,3R,4S,5R)-3-((5-chloro-4-(4-fluoro-1-isopropyl-2-(3-methylbicyclo[1.1.1]pentan-1-yl)-1H-benzo[d]imidazol-6-yl)pyrimidin-2-yl)amino)-6,8-dioxabicyclo[3.2.1]octan-4-ol |
| 133 | 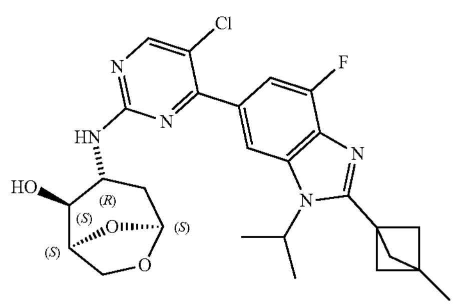 | (1S,2S,3R,5S)-3-((5-chloro-4-(4-fluoro-1-isopropyl-2-(3-methylbicyclo[1.1.1]pentan-1-yl)-1H-benzo[d]imidazol-6-yl)pyrimidin-2-yl)amino)-6,8-dioxabicyclo[3.2.1]octan-2-ol |
| 134 | 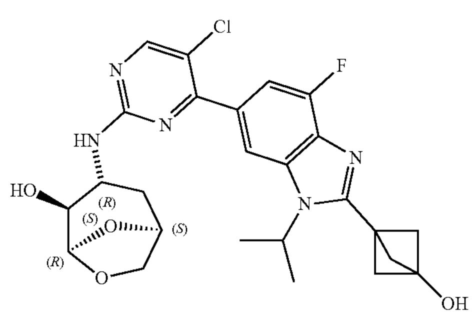 | (1S,3R,4S,5R)-3-((5-chloro-4-(4-fluoro-2-(3-hydroxybicyclo[1.1.1]pentan-1-yl)-1-isopropyl-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 135 | 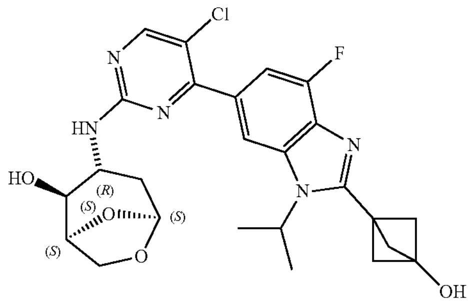 | (1S,2S,3R,5S)-3-((5-chloro-4-(4-fluoro-2-(3-hydroxybicyclo[1.1.1]pentan-1-yl)-1-isopropyl-1H-benzo[d]imidazol-6-yl)pyrimidin-2-yl)amino)-6,8-dioxabicyclo[3.2.1]octan-2-ol |
| 136 | 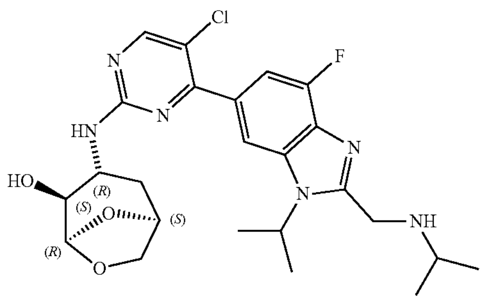 | (1S,3R,4S,5R)-3-((5-chloro-4-(4-fluoro-1-isopropyl-2-((isopropylamino)methyl)-1H-benzo[d]imidazol-6-yl)pyrimidin-2-yl)amino)-6,8-dioxabicyclo[3.2.1]octan-4-ol |
| 137 | 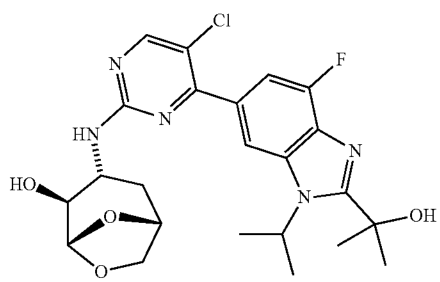 | (1R,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol |
| 138 | 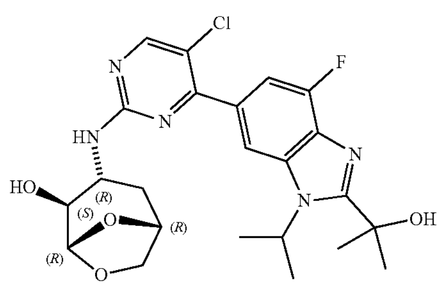 | (1R,2S,3R,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-ol |
| 139 | 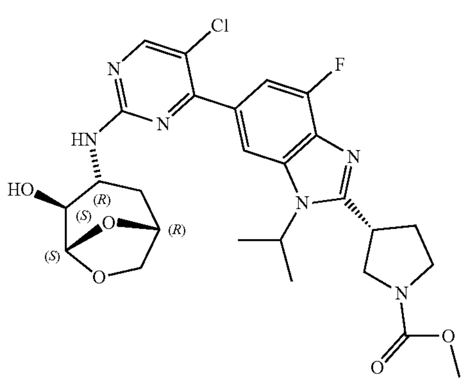 | methyl (R)-3-(6-(5-chloro-2-(((1R,3R,4S,5S)-4-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |

TABLE 1-continued

Compounds of the present disclosure

| Cpd # | Structure | IUPAC Name |
|---|---|---|
| 140 | 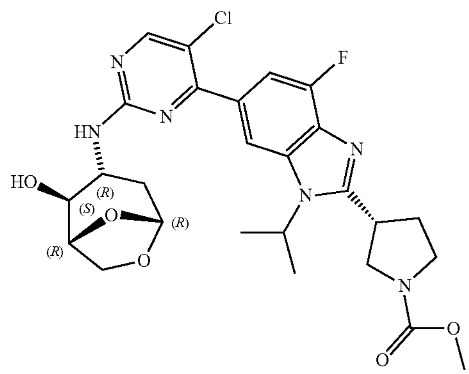 | methyl (R)-3-(6-(5-chloro-2-(((1R,2S,3R,5R)-2-hydroxy-6,8-dioxabicyclo[3.2.1]octan-3-yl)amino)pyrimidin-4-yl)-4-fluoro-1-isopropyl-1H-benzo[d]imidazol-2-yl)pyrrolidine-1-carboxylate |
| 141 | 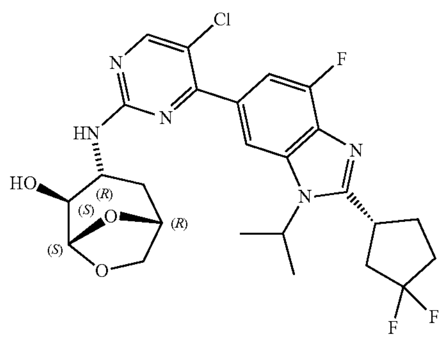 | (1R,3R,4S,5S)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-4-ol |
| 142 | 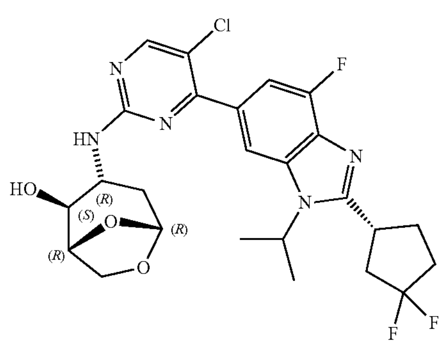 | (1R,2S,3R,5R)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-2-ol |
| 143 | 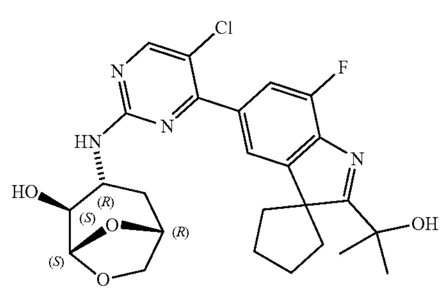 | (1R,3R,4S,5S)-3-((5-chloro-4-(7'-fluoro-2'-(2-hydroxypropan-2-yl)spiro[cyclopentane-1,3'-indol]-5'-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 144 | 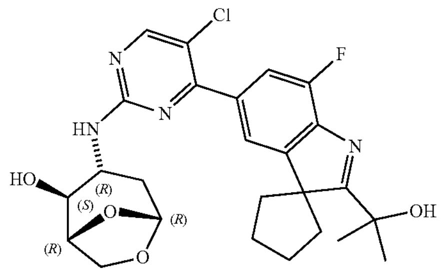 | (1R,2S,3R,5R)-3-((5-chloro-4-(7'-fluoro-2'-(2-hydroxypropan-2-yl)spiro[cyclopentane-1,3'-indol]-5'-yl)pyrimidin-2-yl)amino)-6,8-dioxabicyclo[3.2.1]octan-2-ol |
| 145 | 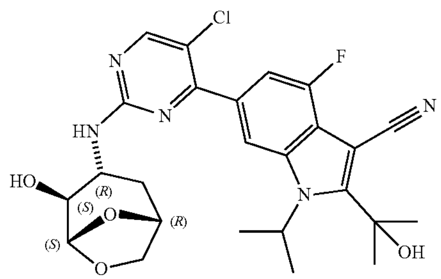 | 6-(5-chloro-2-(((1R,3R,4S,5S)-4-hydroxy-6,8-dioxabicyclo[3.2.1]octan-3-yl)amino)pyrimidin-4-yl)-4-fluoro-2-(2-hydroxypropan-2-yl)-1-isopropyl-1H-indole-3-carbonitrile |
| 146 | 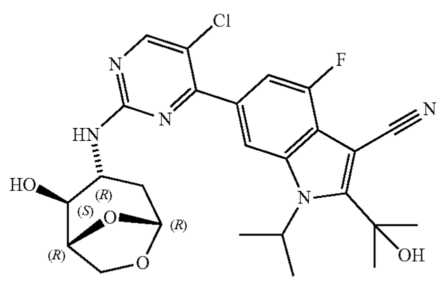 | 6-(5-chloro-2-(((1R,2S,3R,5R)-2-hydroxy-6,8-dioxabicyclo[3.2.1]octan-3-yl)amino)pyrimidin-4-yl)-4-fluoro-2-(2-hydroxypropan-2-yl)-1-isopropyl-1H-indole-3-carbonitrile |
| 147 | 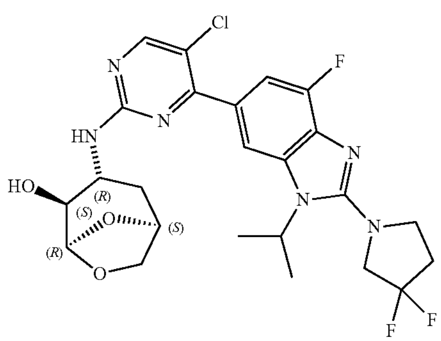 | (1S,3R,4S,5R)-3-((5-chloro-4-(2-(3,3-difluoropyrrolidin-1-yl)-4-fluoro-1-isopropyl-1H-benzo[d]imidazol-6-yl)pyrimidin-2-yl)amino)-6,8-dioxabicyclo[3.2.1]octan-4-ol |
| 148 | 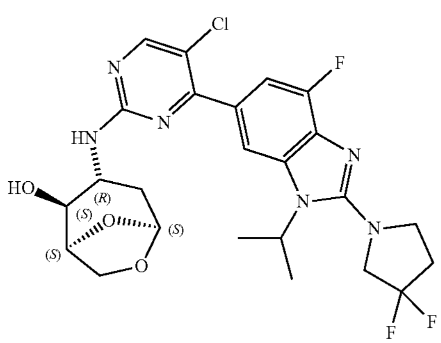 | (1S,2S,3R,5S)-3-((5-chloro-4-(2-(3,3-difluoropyrrolidin-1-yl)-4-fluoro-1-isopropyl-1H-benzo[d]imidazol-6-yl)pyrimidin-2-yl)amino)-6,8-dioxabicyclo[3.2.1]octan-2-ol |

TABLE 1-continued

Compounds of the present disclosure

| Cpd # | Structure | IUPAC Name |
|---|---|---|
| 149 | 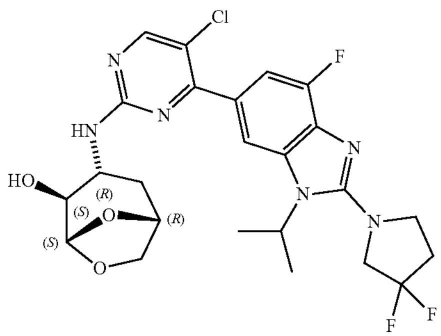 | (1R,3R,4S,5S)-3-((5-chloro-4-(2-(3,3-difluoropyrrolidin-1-yl)-4-fluoro-1-isopropyl-1H-benzo[d]imidazol-6-yl)pyrimidin-2-yl)amino)-6,8-dioxabicyclo[3.2.1]octan-4-ol |
| 150 | 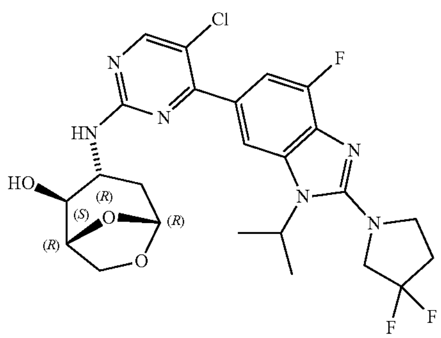 | (1R,2S,3R,5R)-3-((5-chloro-4-(2-(3,3-difluoropyrrolidin-1-yl)-4-fluoro-1-isopropyl-1H-benzo[d]imidazol-6-yl)pyrimidin-2-yl)amino)-6,8-dioxabicyclo[3.2.1]octan-2-ol |
| 151 | 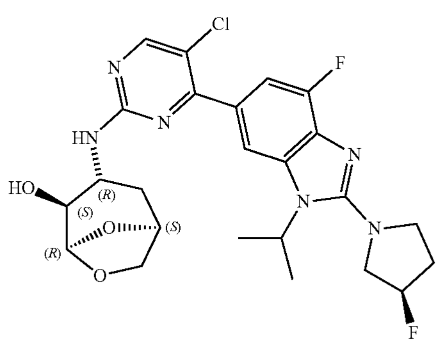 | (1S,3R,4S,5R)-3-((5-chloro-4-(4-fluoro-2-((R)-3-fluoropyrrolidin-1-yl)-1-isopropyl-1H-benzo[d]imidazol-6-yl)pyrimidin-2-yl)amino)-6,8-dioxabicyclo[3.2.1]octan-4-ol |
| 152 | 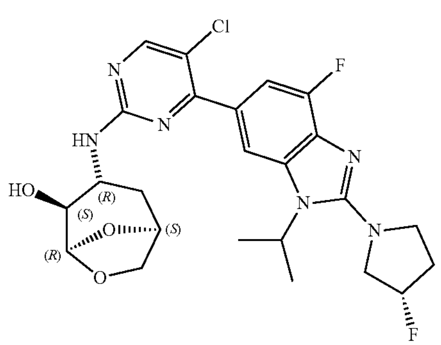 | (1S,3R,4S,5R)-3-((5-chloro-4-(4-fluoro-2-((S)-3-fluoropyrrolidin-1-yl)-1-isopropyl-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 153 | 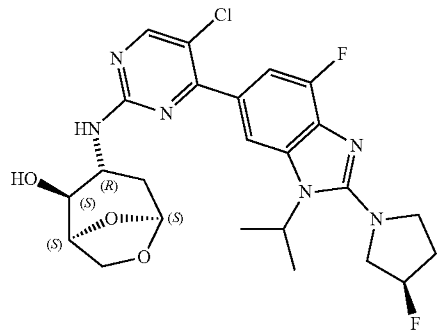 | (1S,2S,3R,5S)-3-((5-chloro-4-(4-fluoro-2-((R)-3-fluoropyrrolidin-1-yl)-1-isopropyl-1H-benzo[d]imidazol-6-yl)pyrimidin-2-yl)amino)-6,8-dioxabicyclo[3.2.1]octan-2-ol |
| 154 | 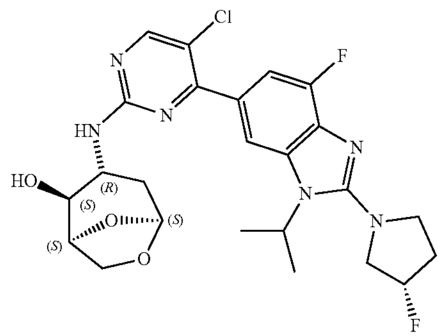 | (1S,2S,3R,5S)-3-((5-chloro-4-(4-fluoro-2-((S)-3-fluoropyrrolidin-1-yl)-1-isopropyl-1H-benzo[d]imidazol-6-yl)pyrimidin-2-yl)amino)-6,8-dioxabicyclo[3.2.1]octan-2-ol |
| 155 | 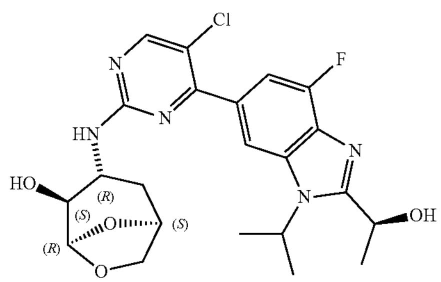 | (1S,3R,4S,5R)-3-((5-chloro-4-(4-fluoro-2-((S)-1-hydroxyethyl)-1-isopropyl-1H-benzo[d]imidazol-6-yl)pyrimidin-2-yl)amino)-6,8-dioxabicyclo[3.2.1]octan-4-ol |
| 156 | 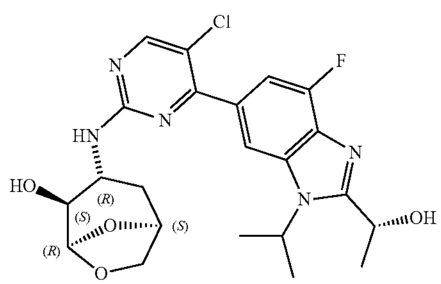 | (1S,3R,4S,5R)-3-((5-chloro-4-(4-fluoro-2-((R)-1-hydroxyethyl)-1-isopropyl-1H-benzo[d]imidazol-6-yl)pyrimidin-2-yl)amino)-6,8-dioxabicyclo[3.2.1]octan-4-ol |
| 157 | 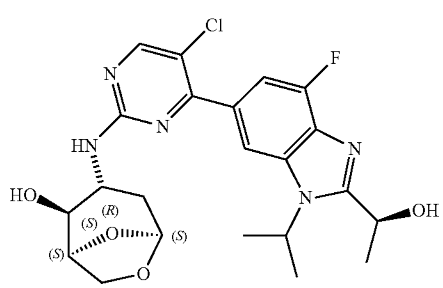 | (1S,2S,3R,5S)-3-((5-chloro-4-(4-fluoro-2-((S)-1-hydroxyethyl)-1-isopropyl-1H-benzo[d]imidazol-6-yl)pyrimidin-2-yl)amino)-6,8-dioxabicyclo[3.2.1]octan-2-ol |

TABLE 1-continued

Compounds of the present disclosure

| Cpd # | Structure | IUPAC Name |
|---|---|---|
| 158 | 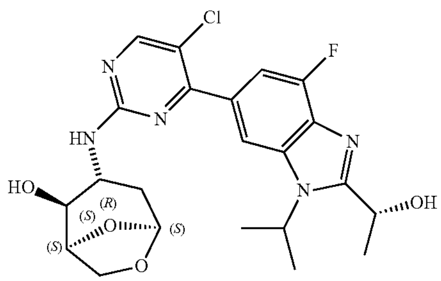 | (1S,2S,3R,5S)-3-((5-chloro-4-(4-fluoro-2-((R)-1-hydroxyethyl)-1-isopropyl-1H-benzo[d]imidazol-6-yl)pyrimidin-2-yl)amino)-6,8-dioxabicyclo[3.2.1]octan-2-ol |
| 159 | 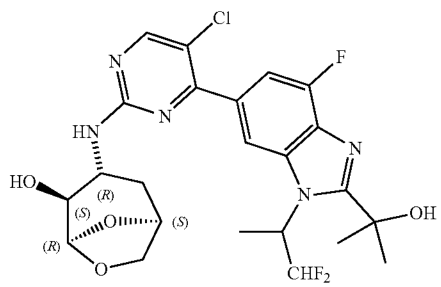 | (1S,3R,4S,5R)-3-((5-chloro-4-(1-(1,1-difluoropropan-2-yl)-4-fluoro-2-(2-hydroxypropan-2-yl)-1H-benzo[d]imidazol-6-yl)pyrimidin-2-yl)amino)-6,8-dioxabicyclo[3.2.1]octan-4-ol |
| 160 | 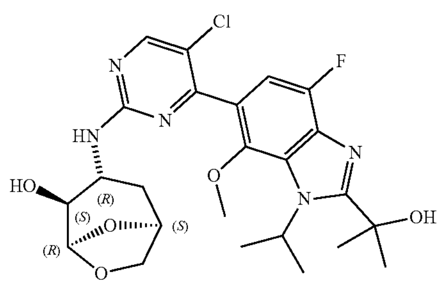 | (1S,3R,4S,5R)-3-((5-chloro-4-(4-fluoro-2-(2-hydroxypropan-2-yl)-1-isopropyl-7-methoxy-1H-benzo[d]imidazol-6-yl)pyrimidin-2-yl)amino)-6,8-dioxabicyclo[3.2.1]octan-4-ol |
| 161 | 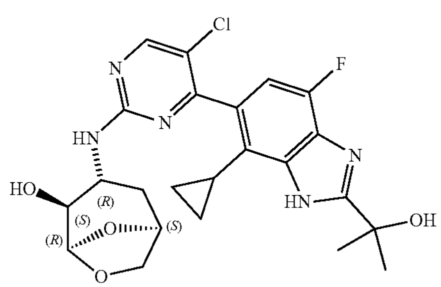 | (1S,3R,4S,5R)-3-((5-chloro-4-(7-cyclopropyl-4-fluoro-2-(2-hydroxypropan-2-yl)-1H-benzo[d]imidazol-6-yl)pyrimidin-2-yl)amino)-6,8-dioxabicyclo[3.2.1]octan-4-ol |
| 162 | 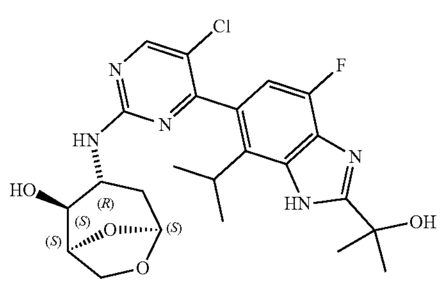 | (1S,2S,3R,5S)-3-((5-chloro-4-(4-fluoro-2-(2-hydroxypropan-2-yl)-7-isopropyl-1H-benzo[d]imidazol-6-yl)pyrimidin-2-yl)amino)-6,8-dioxabicyclo[3.2.1]octan-2-ol |

TABLE 1-continued

Compounds of the present disclosure

| Cpd # | Structure | IUPAC Name |
|---|---|---|
| 163 | 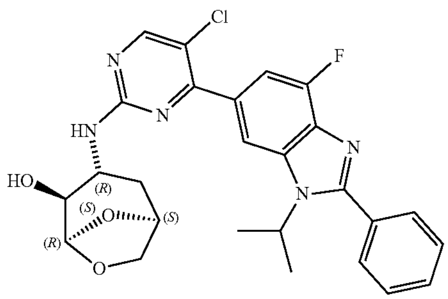 | (1S,3R,4S,5R)-3-((5-chloro-4-(4-fluoro-1-isopropyl-2-phenyl-1H-benzo[d]imidazol-6-yl)pyrimidin-2-yl)amino)-6,8-dioxabicyclo[3.2.1]octan-4-ol |
| 164 | 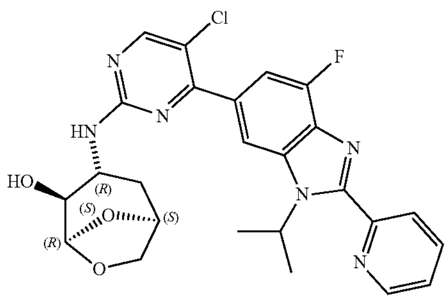 | (1S,3R,4S,5R)-3-((5-chloro-4-(4-fluoro-1-isopropyl-2-(pyridin-2-yl)-1H-benzo[d]imidazol-6-yl)pyrimidin-2-yl)amino)-6,8-dioxabicyclo[3.2.1]octan-4-ol |
| 165 | 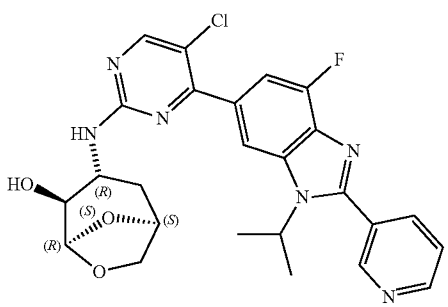 | (1S,3R,4S,5R)-3-((5-chloro-4-(4-fluoro-1-isopropyl-2-(pyridin-3-yl)-1H-benzo[d]imidazol-6-yl)pyrimidin-2-yl)amino)-6,8-dioxabicyclo[3.2.1]octan-4-ol |
| 166 | 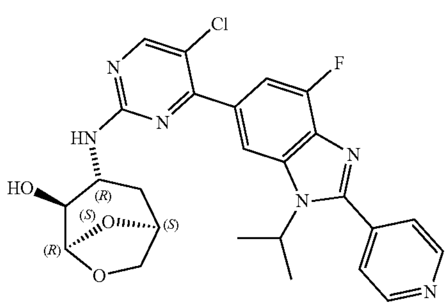 | (1S,3R,4S,5R)-3-((5-chloro-4-(4-fluoro-1-isopropyl-2-(pyridin-4-yl)-1H-benzo[d]imidazol-6-yl)pyrimidin-2-yl)amino)-6,8-dioxabicyclo[3.2.1]octan-4-ol |
| 167 | 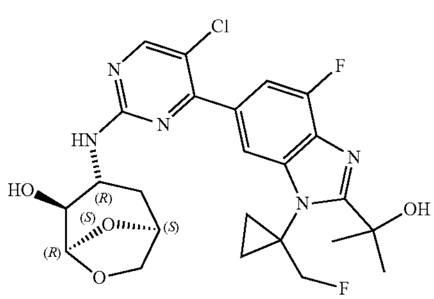 | (1S,3R,4S,5R)-3-((5-chloro-4-(4-fluoro-1-(1-(fluoromethyl)cyclopropyl)-2-(2-hydroxypropan-2-yl)-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 168 | 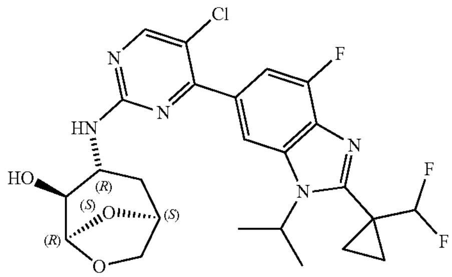 | (1S,3R,4S,5R)-3-((5-chloro-4-(2-(1-(difluoromethyl)cyclopropyl)-4-fluoro-1-isopropyl-1H-benzo[d]imidazol-6-yl)pyrimidin-2-yl)amino)-6,8-dioxabicyclo[3.2.1]octan-4-ol |
| 169 | 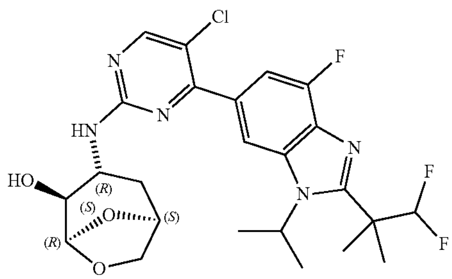 | (1S,3R,4S,5R)-3-((5-chloro-4-(2-(1,1-difluoro-2-methylpropan-2-yl)-4-fluoro-1-isopropyl-1H-benzo[d]imidazol-6-yl)pyrimidin-2-yl)amino)-6,8-dioxabicyclo[3.2.1]octan-4-ol |
| 170 | 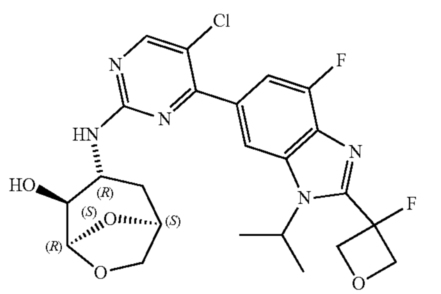 | (1S,3R,4S,5R)-3-((5-chloro-4-(4-fluoro-2-(3-fluorooxetan-3-yl)-1-isopropyl-1H-benzo[d]imidazol-6-yl)pyrimidin-2-yl)amino)-6,8-dioxabicyclo[3.2.1]octan-4-ol |
| 171 | 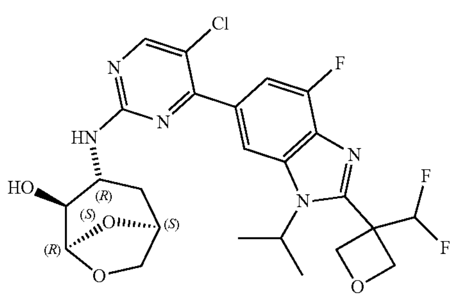 | (1S,3R,4S,5R)-3-((5-chloro-4-(2-(3-(difluoromethyl)oxetan-3-yl)-4-fluoro-1-isopropyl-1H-benzo[d]imidazol-6-yl)pyrimidin-2-yl)amino)-6,8-dioxabicyclo[3.2.1]octan-4-ol |
| 172 | 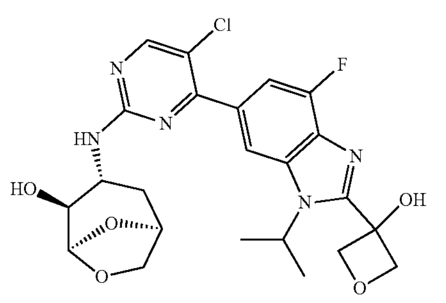 [SMILES: CC(C)n1c(C2(O)COC2)nc2c(F)cc(-c3nc(N[C@@H]4C[C@H]5CO[C@H](O5)[C@H]4O)ncc3Cl)cc21] | (1S,3R,4S,5R)-3-((5-chloro-4-(4-fluoro-2-(3-hydroxyoxetan-3-yl)-1-isopropyl-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 173 | 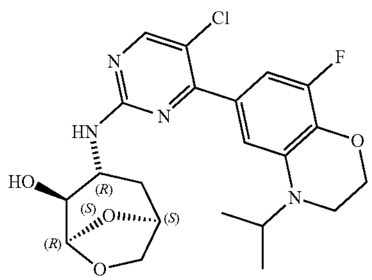 | (1S,3R,4S,5R)-3-((5-chloro-4-(8-fluoro-4-isopropyl-3,4-dihydro-2H-benzo[b][1,4]oxazin-6-yl)pyrimidin-2-yl)amino)-6,8-dioxabicyclo[3.2.1]octan-4-ol |
| 174 | 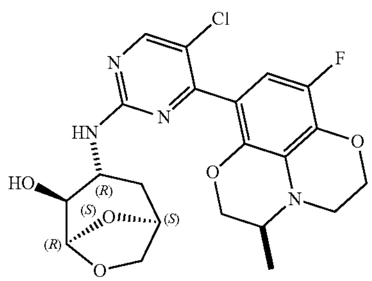 | (1S,3R,4S,5R)-3-((5-chloro-4-((S)-9-fluoro-4-methyl-2,3,4,5-tetrahydro-1,6-dioxa-3a-azaphenalen-7-yl)pyrimidin-2-yl)amino)-6,8-dioxabicyclo[3.2.1]octan-4-ol |
| 175 | 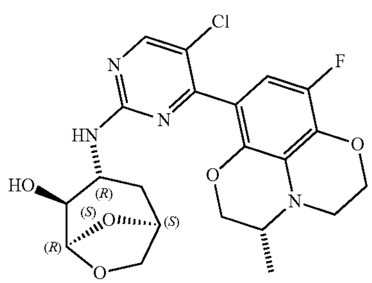 | (1S,3R,4S,5R)-3-((5-chloro-4-((R)-9-fluoro-4-methyl-2,3,4,5-tetrahydro-1,6-dioxa-3a-azaphenalen-7-yl)pyrimidin-2-yl)amino)-6,8-dioxabicyclo[3.2.1]octan-4-ol |
| 176 | 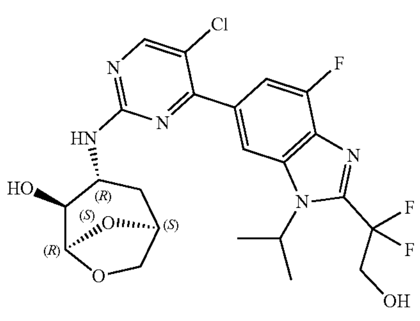 | (1S,3R,4S,5R)-3-((5-chloro-4-(2-(1,1-difluoro-2-hydroxyethyl)-4-fluoro-1-isopropyl-1H-benzo[d]imidazol-6-yl)pyrimidin-2-yl)amino)-6,8-dioxabicyclo[3.2.1]octan-4-ol |
| 177 | 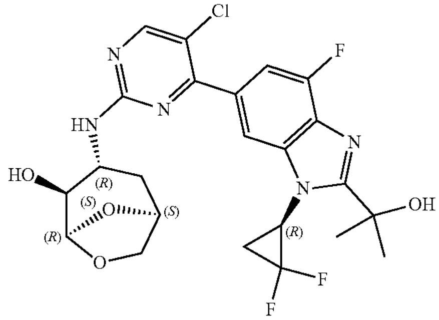 | (1S,3R,4S,5R)-3-((5-chloro-4-(1-((R)-2,2-difluorocyclopropyl)-4-fluoro-2-(2-hydroxypropan-2-yl)-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 178 | 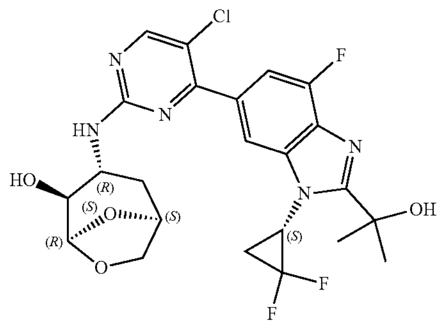 | (1S,3R,4S,5R)-3-((5-chloro-4-(1-((S)-2,2-difluorocyclopropyl)-4-fluoro-2-(2-hydroxypropan-2-yl)-1H-benzo[d]imidazol-6-yl)pyrimidin-2-yl)amino)-6,8-dioxabicyclo[3.2.1]octan-4-ol |
| 179 | 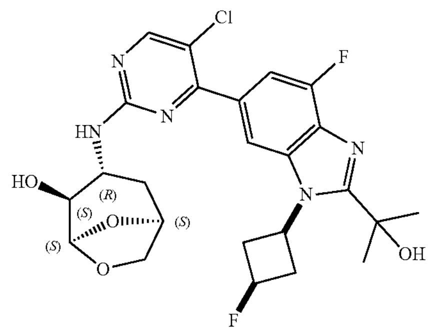 | (1S,3R,4S,5R)-3-((5-chloro-4-(4-fluoro-1-((1s,3S)-3-fluorocyclobutyl)-2-(2-hydroxypropan-2-yl)-1H-benzo[d]imidazol-6-yl)pyrimidin-2-yl)amino)-6,8-dioxabicyclo[3.2.1]octan-4-ol |
| 180 | 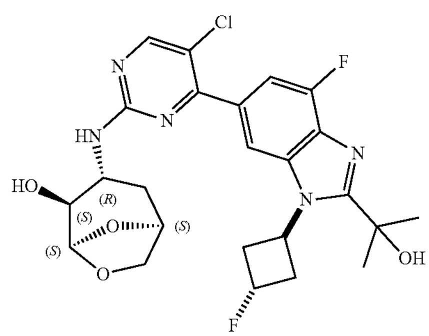 | (1S,3R,4S,5R)-3-((5-chloro-4-(4-fluoro-1-((1r,3R)-3-fluorocyclobutyl)-2-(2-hydroxypropan-2-yl)-1H-benzo[d]imidazol-6-yl)pyrimidin-2-yl)amino)-6,8-dioxabicyclo[3.2.1]octan-4-ol |
| 181 | 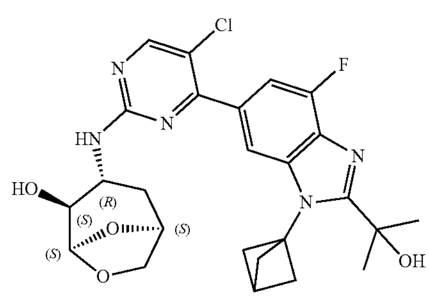 | (1S,3R,4S,5R)-3-((4-(1-(bicyclo[1.1.1]pentan-1-yl)-4-fluoro-2-(2-hydroxypropan-2-yl)-1H-benzo[d]imidazol-6-yl)-5-chloropyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 182 | 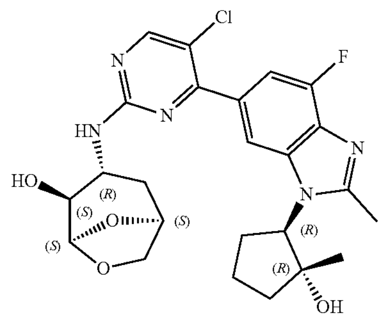 | (1S,3R,4S,5R)-3-((5-chloro-4-(4-fluoro-1-((1R,2R)-2-hydroxy-2-methylcyclopentyl)-2-methyl-1H-benzo[d]imidazol-6-yl)pyrimidin-2-yl)amino)-6,8-dioxabicyclo[3.2.1]octan-4-ol |
| 183 | 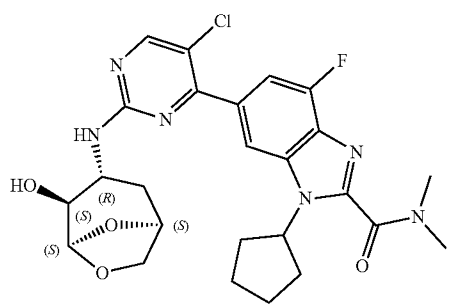 | 6-(5-chloro-2-(((1S,3R,4S,5R)-4-hydroxy-6,8-dioxabicyclo[3.2.1]octan-3-yl)amino)pyrimidin-4-yl)-1-cyclopentyl-4-fluoro-N,N-dimethyl-1H-indole-2-carboxamide |
| 184 | 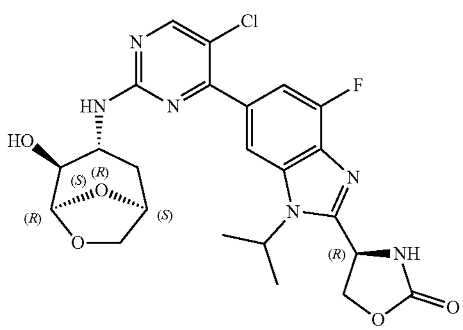 | (R)-4-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)oxazolidin-2-one |
| 185 | 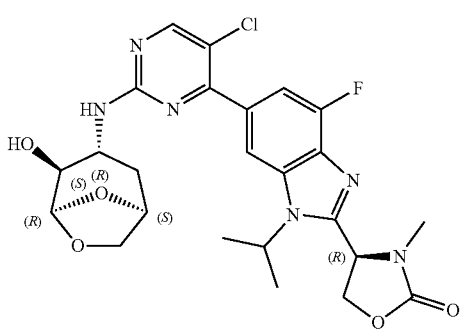 | (R)-4-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-3-methyloxazolidin-2-one |

TABLE 1-continued

Compounds of the present disclosure

| Cpd # | Structure | IUPAC Name |
|---|---|---|
| 186 | 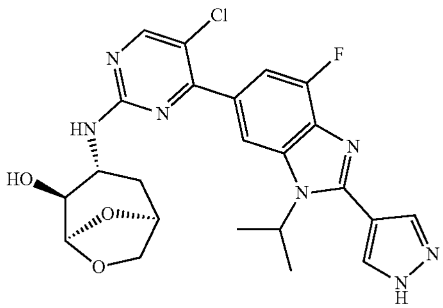 [SMILES: CC(C)n1c(-c2cn[nH]c2)nc2c(F)cc(-c3nc(N[C@@H]4C[C@H]5CO[C@H](O5)[C@H]4O)ncc3Cl)cc21] | (1S,3R,4S,5R)-3-((5-chloro-4-(4-fluoro-1-isopropyl-2-(1H-pyrazol-4-yl)-1H-benzo[d]imidazol-6-yl)pyrimidin-2-yl)amino)-6,8-dioxabicyclo[3.2.1]octan-4-ol |
| 187 | 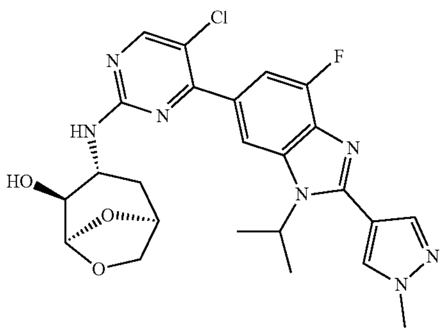 [SMILES: CC(C)n1c(-c2cnn(C)c2)nc2c(F)cc(-c3nc(N[C@@H]4C[C@H]5CO[C@H](O5)[C@H]4O)ncc3Cl)cc21] | (1S,3R,4S,5R)-3-((5-chloro-4-(4-fluoro-1-isopropyl-2-(1-methyl-1H-pyrazol-4-yl)-1H-benzo[d]imidazol-6-yl)pyrimidin-2-yl)amino)-6,8-dioxabicyclo[3.2.1]octan-4-ol |
| 188 | 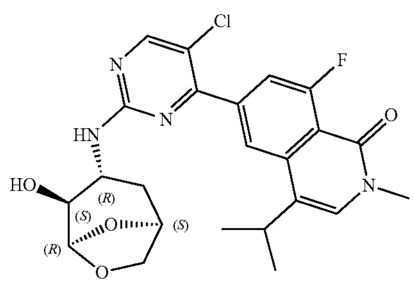 | 6-(5-chloro-2-(((1S,3R,4S,5R)-4-hydroxy-6,8-dioxabicyclo[3.2.1]octan-3-yl)amino)pyrimidin-4-yl)-8-fluoro-4-isopropyl-2-methylisoquinolin-1(2H)-one |
| 189 | 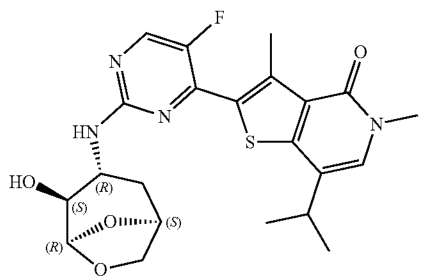 | 2-(5-fluoro-2-(((1S,3R,4S,5R)-4-hydroxy-6,8-dioxabicyclo[3.2.1]octan-3-yl)amino)pyrimidin-4-yl)-7-isopropyl-3,5-dimethylthieno[3,2-c]pyridin-4(5H)-one |
| 190 | 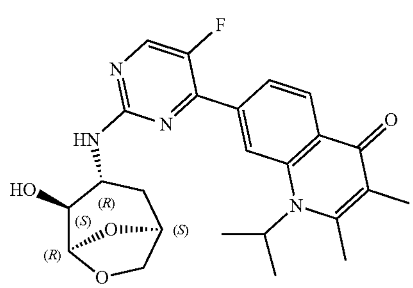 | 7-(5-fluoro-2-(((1S,3R,4S,5R)-4-hydroxy-6,8-dioxabicyclo[3.2.1]octan-3-yl)amino)pyrimidin-4-yl)-1-isopropyl-2,3-dimethylquinolin-4(1H)-one |

TABLE 1-continued

Compounds of the present disclosure

| Cpd # | Structure | IUPAC Name |
|---|---|---|
| 191 | 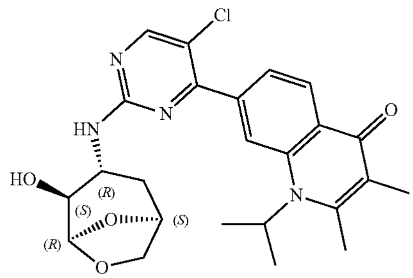 | 7-(5-chloro-2-(((1S,3R,4S,5R)-4-hydroxy-6,8-dioxabicyclo[3.2.1]octan-3-yl)amino)pyrimidin-4-yl)-1-isopropyl-2,3-dimethylquinolin-4(1H)-one |
| 192 | 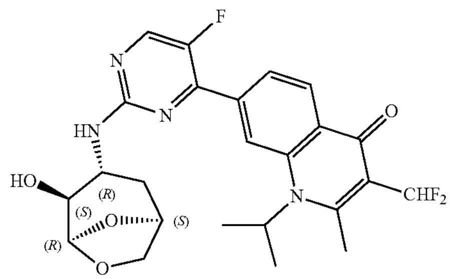 | 3-(difluoromethyl)-7-(5-fluoro-2-((((1S,3R,4S,5R)-4-hydroxy-6,8-dioxabicyclo[3.2.1]octan-3-yl)amino)pyrimidin-4-yl)-1-isopropyl-2-methylquinolin-4(1H)-one |
| 193 | 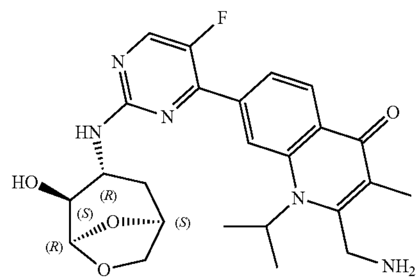 | 2-(aminomethyl)-7-(5-fluoro-2-((((1S,3R,4S,5R)-4-hydroxy-6,8-dioxabicyclo[3.2.1]octan-3-yl)amino)pyrimidin-4-yl)-1-isopropyl-3-methylquinolin-4(1H)-one |
| 194 | 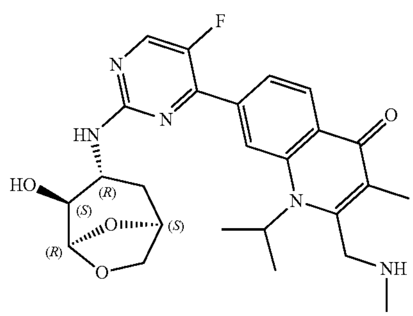 | 7-(5-fluoro-2-((((1S,3R,4S,5R)-4-hydroxy-6,8-dioxabicyclo[3.2.1]octan-3-yl)amino)pyrimidin-4-yl)-1-isopropyl-3-methyl-2-((methylamino)methyl)quinolin-4(1H)-one |
| 195 | 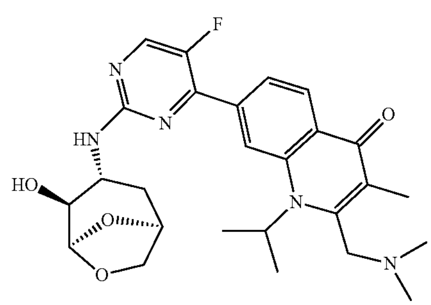 [SMILES: Cc1c(CN(C)C)n(C(C)C)c2cc(-c3nc(N[C@@H]4C[C@H]5CO[C@H](O5)[C@H]4O)ncc3F)ccc2c1=O] | 2-((dimethylamino)methyl)-7-(5-fluoro-2-((((1S,3R,4S,5R)-4-hydroxy-6,8-dioxabicyclo[3.2.1]octan-3-yl)amino)pyrimidin-4-yl)-1-isopropyl-3-methylquinolin-4(1H)-one |

TABLE 1-continued

Compounds of the present disclosure

| Cpd # | Structure | IUPAC Name |
|---|---|---|
| 196 | 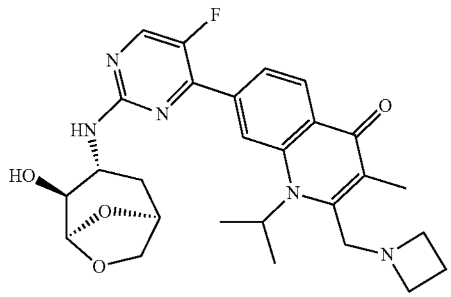 [SMILES: Cc1c(CN2CCC2)n(C(C)C)c2cc(-c3nc(N[C@@H]4C[C@H]5CO[C@H](O5)[C@H]4O)ncc3F)ccc2c1=O] | 2-(azetidin-1-ylmethyl)-7-(5-fluoro-2-(((1S,3R,4S,5R)-4-hydroxy-6,8-dioxabicyclo[3.2.1]octan-3-yl)amino)pyrimidin-4-yl)-1-isopropyl-3-methylquinolin-4(1H)-one |
| 197 | 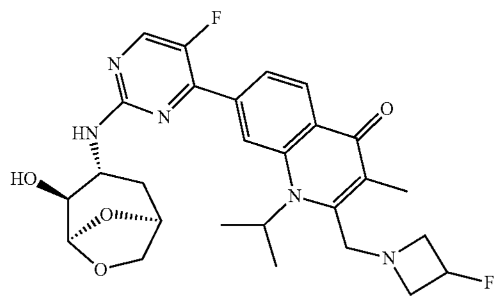 [SMILES: Cc1c(CN2CC(F)C2)n(C(C)C)c2cc(-c3nc(N[C@@H]4C[C@H]5CO[C@H](O5)[C@H]4O)ncc3F)ccc2c1=O] | 7-(5-fluoro-2-(((1S,3R,4S,5R)-4-hydroxy-6,8-dioxabicyclo[3.2.1]octan-3-yl)amino)pyrimidin-4-yl)-2-((3-fluoroazetidin-1-yl)methyl)-1-isopropyl-3-methylquinolin-4(1H)-one |
| 198 | 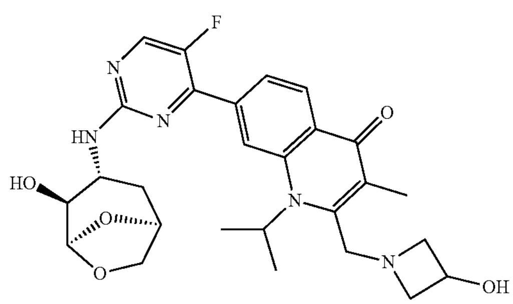 [SMILES: Cc1c(CN2CC(O)C2)n(C(C)C)c2cc(-c3nc(N[C@@H]4C[C@H]5CO[C@H](O5)[C@H]4O)ncc3F)ccc2c1=O] | 7-(5-fluoro-2-(((1S,3R,4S,5R)-4-hydroxy-6,8-dioxabicyclo[3.2.1]octan-3-yl)amino)pyrimidin-4-yl)-2-((3-hydroxyazetidin-1-yl)methyl)-1-isopropyl-3-methylquinolin-4(1H)-one |
| 199 | 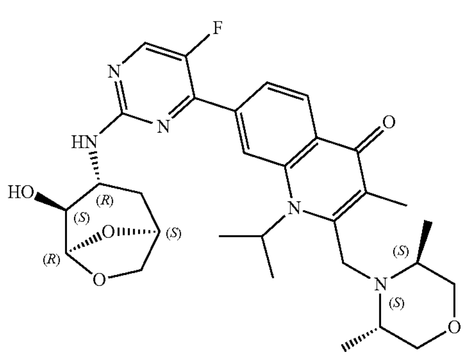 | 2-(((3S,5S)-3,5-dimethylmorpholino)methyl)-7-(5-fluoro-2-(((1S,3R,4S,5R)-4-hydroxy-6,8-dioxabicyclo[3.2.1]octan-3-yl)amino)pyrimidin-4-yl)-1-isopropyl-3-methylquinolin-4(1H)-one |

TABLE 1-continued

Compounds of the present disclosure

| Cpd # | Structure | IUPAC Name |
|---|---|---|
| 200 | 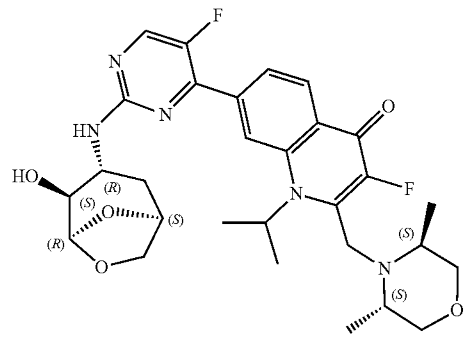 | 2-(((3S,5S)-3,5-dimethylmorpholino)methyl)-3-fluoro-7-(5-fluoro-2-(((1S,3R,4S,5R)-4-hydroxy-6,8-dioxabicyclo[3.2.1]octan-3-yl)amino)pyrimidin-4-yl)-1-isopropylquinolin-4(1H)-one |
| 201 | 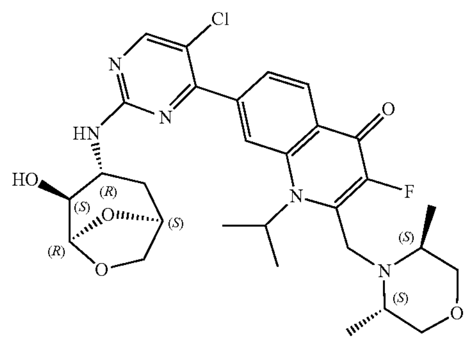 | 7-(5-chloro-2-(((1S,3R,4S,5R)-4-hydroxy-6,8-dioxabicyclo[3.2.1]octan-3-yl)amino)pyrimidin-4-yl)-2-(((3S,5S)-3,5-dimethylmorpholino)methyl)-3-fluoro-1-isopropylquinolin-4(1H)-one |
| 202 | 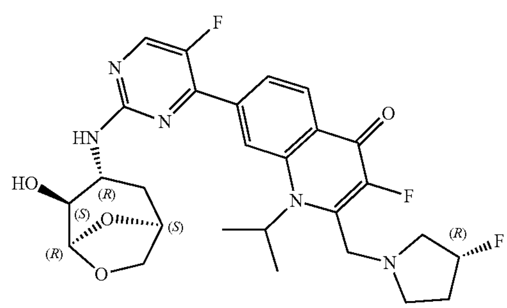 | 3-fluoro-7-(5-fluoro-2-(((1S,3R,4S,5R)-4-hydroxy-6,8-dioxabicyclo[3.2.1]octan-3-yl)amino)pyrimidin-4-yl)-2-(((R)-3-fluoropyrrolidin-1-yl)methyl)-1-isopropylquinolin-4(1H)-one |
| 203 | 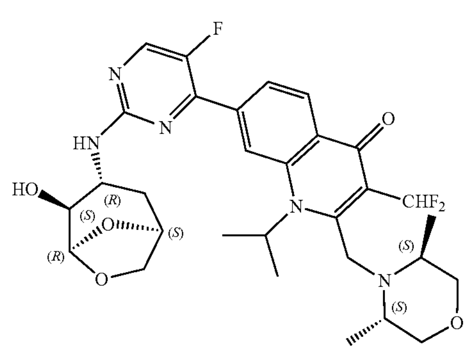 | 3-(difluoromethyl)-2-(((3S,5S)-3,5-dimethylmorpholino)methyl)-7-(5-fluoro-2-(((1S,3R,4S,5R)-4-hydroxy-6,8-dioxabicyclo[3.2.1]octan-3-yl)amino)pyrimidin-4-yl)-1-isopropylquinolin-4(1H)-one |

TABLE 1-continued

Compounds of the present disclosure

| Cpd # | Structure | IUPAC Name |
|---|---|---|
| 204 | 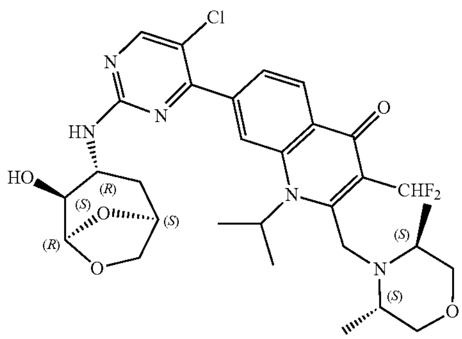 | 7-(5-chloro-2-(((1S,3R,4S,5R)-4-hydroxy-6,8-dioxabicyclo[3.2.1]octan-3-yl)amino)pyrimidin-4-yl)-3-(difluoromethyl)-2-(((3S,5S)-3,5-dimethylmorpholino)methyl)-1-isopropylquinolin-4(1H)-one |
| 205 | 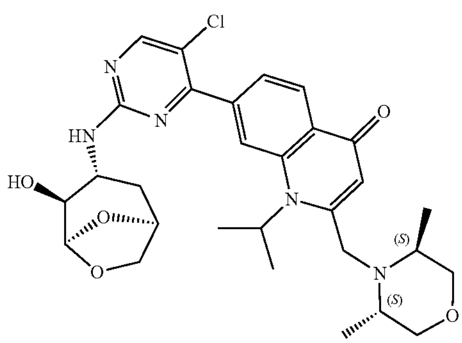 | 7-(5-chloro-2-(((1S,3R,4S,5R)-4-hydroxy-6,8-dioxabicyclo[3.2.1]octan-3-yl)amino)pyrimidin-4-yl)-2-(((3S,5S)-3,5-dimethylmorpholino)methyl)-1-isopropylquinolin-4(1H)-one |
| 206 | 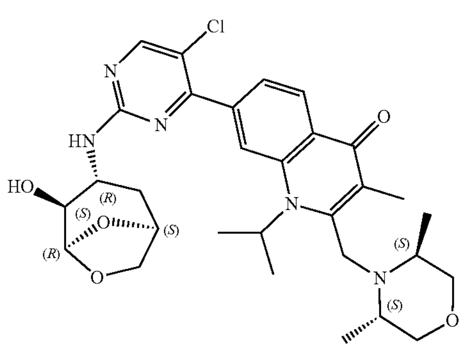 | 7-(5-chloro-2-(((1S,3R,4S,5R)-4-hydroxy-6,8-dioxabicyclo[3.2.1]octan-3-yl)amino)pyrimidin-4-yl)-2-(((3S,5S)-3,5-dimethylmorpholino)methyl)-1-isopropyl-3-methylquinolin-4(1H)-one |
| 207 | 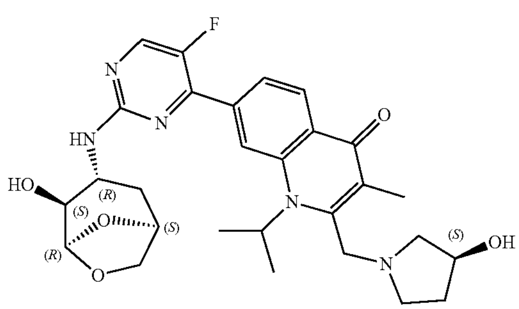 | 7-(5-fluoro-2-(((1S,3R,4S,5R)-4-hydroxy-6,8-dioxabicyclo[3.2.1]octan-3-yl)amino)pyrimidin-4-yl)-2-(((S)-3-hydroxypyrrolidin-1-yl)methyl)-1-isopropyl-3-methylquinolin-4(1H)-one |

| Cpd # | Structure | IUPAC Name |
|---|---|---|
| 208 | 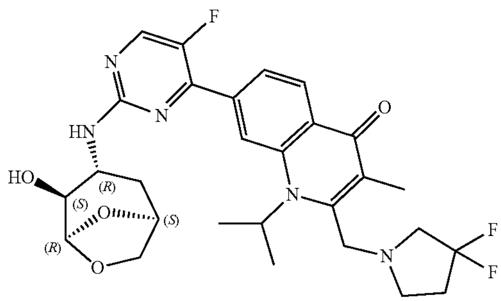 | 2-((3,3-difluoropyrrolidin-1-yl)methyl)-7-(5-fluoro-2-(((1S,3R,4S,5R)-4-hydroxy-6,8-dioxabicyclo[3.2.1]octan-3-yl)amino)pyrimidin-4-yl)-1-isopropyl-3-methylquinolin-4(1H)-one |
| 209 | 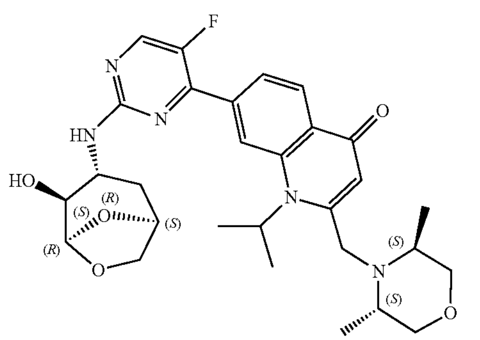 | 2-(((3S,5S)-3,5-dimethylmorpholino)methyl)-7-(5-fluoro-2-(((1S,3R,4S,5R)-4-hydroxy-6,8-dioxabicyclo[3.2.1]octan-3-yl)amino)pyrimidin-4-yl)-1-isopropylquinolin-4(1H)-one |
| 210 | 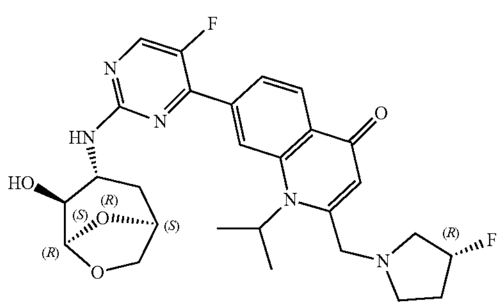 | 7-(5-fluoro-2-(((1S,3R,4S,5R)-4-hydroxy-6,8-dioxabicyclo[3.2.1]octan-3-yl)amino)pyrimidin-4-yl)-2-(((R)-3-fluoropyrrolidin-1-yl)methyl)-1-isopropylquinolin-4(1H)-one |
| 211 | 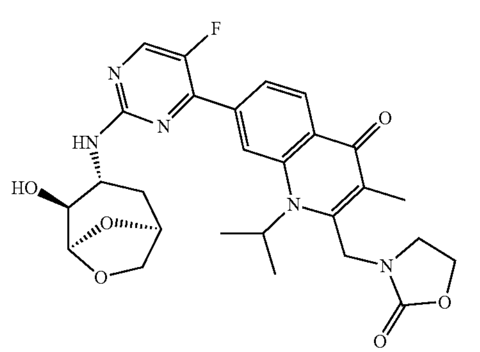 [SMILES: Cc1c(CN2CCOC2=O)n(C(C)C)c2cc(-c3nc(N[C@@H]4C[C@H]5CO[C@H](O5)[C@H]4O)ncc3F)ccc2c1=O] | 3-((7-(5-fluoro-2-(((1S,3R,4S,5R)-4-hydroxy-6,8-dioxabicyclo[3.2.1]octan-3-yl)amino)pyrimidin-4-yl)-1-isopropyl-3-methyl-4-oxo-1,4-dihydroquinolin-2-yl)methyl)oxazolidin-2-one |

TABLE 1-continued

Compounds of the present disclosure

| Cpd # | Structure | IUPAC Name |
|---|---|---|
| 212 | 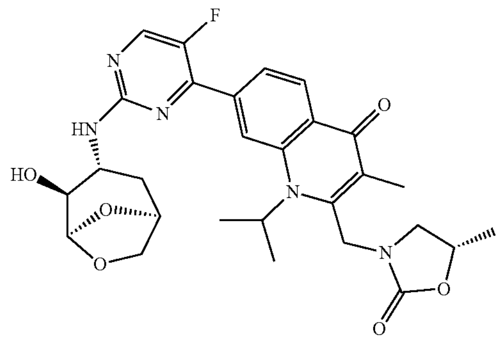 [SMILES: Cc1c(CN2C[C@H](C)OC2=O)n(C(C)C)c2cc(-c3nc(N[C@@H]4C[C@H]5CO[C@H](O5)[C@H]4O)ncc3F)ccc2c1=O] | (S)-3-((7-(5-fluoro-2-(((1S,3R,4S,5R)-4-hydroxy-6,8-dioxabicyclo[3.2.1]octan-3-yl)amino)pyrimidin-4-yl)-1-isopropyl-3-methyl-4-oxo-1,4-dihydroquinolin-2-yl)methyl)-5-methyloxazolidin-2-one |
| 213 | 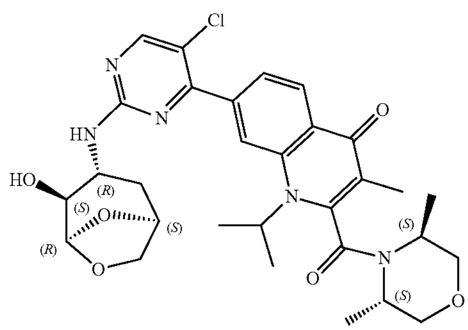 | 7-(5-chloro-2-(((1S,3R,4S,5R)-4-hydroxy-6,8-dioxabicyclo[3.2.1]octan-3-yl)amino)pyrimidin-4-yl)-2-((3S,5S)-3,5-dimethylmorpholine-4-carbonyl)-1-isopropyl-3-methylquinolin-4(1H)-one |
| 214 | 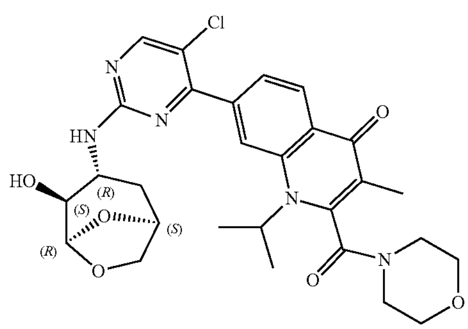 | 7-(5-chloro-2-(((1S,3R,4S,5R)-4-hydroxy-6,8-dioxabicyclo[3.2.1]octan-3-yl)amino)pyrimidin-4-yl)-1-isopropyl-3-methyl-2-(morpholine-4-carbonyl)quinolin-4(1H)-one |
| 215 | 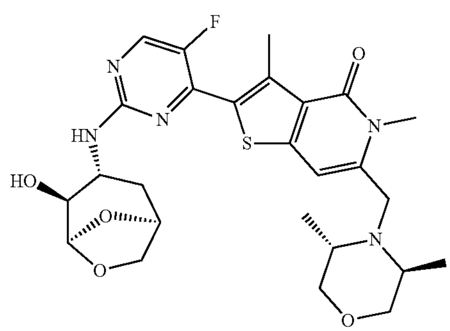 [SMILES: Cc1c(-c2nc(N[C@@H]3C[C@H]4CO[C@H](O4)[C@H]3O)ncc2F)sc2cc(CN3[C@@H](C)COC[C@@H]3C)n(C)c(=O)c12] | 6-(((3S,5S)-3,5-dimethylmorpholino)methyl)-2-(5-fluoro-2-(((1S,3R,4S,5R)-4-hydroxy-6,8-dioxabicyclo[3.2.1]octan-3-yl)amino)pyrimidin-4-yl)-3,5-dimethylthieno[3,2-c]pyridin-4(5H)-one |

TABLE 1-continued

Compounds of the present disclosure

| Cpd # | Structure | IUPAC Name |
|---|---|---|
| 216 | 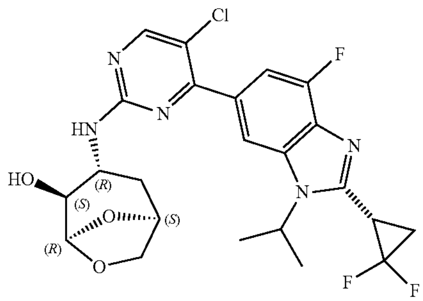 | (1S,3R,4S,5R)-3-((5-chloro-4-(2-((S)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol |
| 217 | 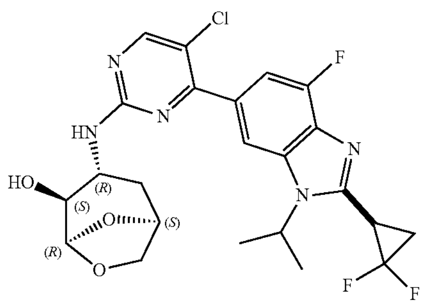 | (1S,3R,4S,5R)-3-((5-chloro-4-(2-((R)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol |
| 218 | 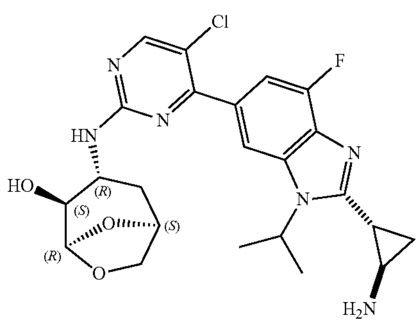 | (1S,3R,4S,5R)-3-((4-(2-((1R,2R)-2-aminocyclopropyl)-4-fluoro-1-isopropyl-1H-benzo[d]imidazol-6-yl)-5-chloropyrimidin-2-yl)amino)-6,8-dioxabicyclo[3.2.1]octan-4-ol |
| 219 | 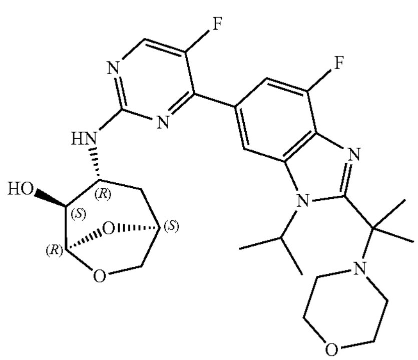 | (1S,3R,4S,5R)-3-((5-chloro-4-(4-fluoro-1-isopropyl-2-(2-morpholinopropan-2-yl)-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 220 | 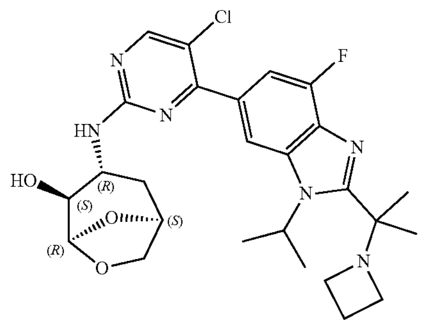 | (1S,3R,4S,5R)-3-((4-(2-(2-(azetidin-1-yl)propan-2-yl)-4-fluoro-1-isopropyl-1H-benzo[d]imidazol-6-yl)-5-chloropyrimidin-2-yl)amino)-6,8-dioxabicyclo[3.2.1]octan-4-ol |
| 221 | 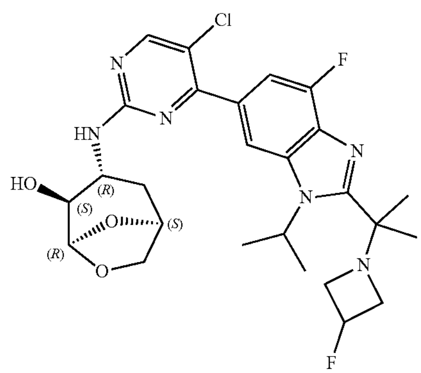 | (1S,3R,4S,5R)-3-((5-chloro-4-(4-fluoro-2-(2-(3-fluoroazetidin-1-yl)propan-2-yl)-1-isopropyl-1H-benzo[d]imidazol-6-yl)pyrimidin-2-yl)amino)-6,8-dioxabicyclo[3.2.1]octan-4-ol |
| 222 | 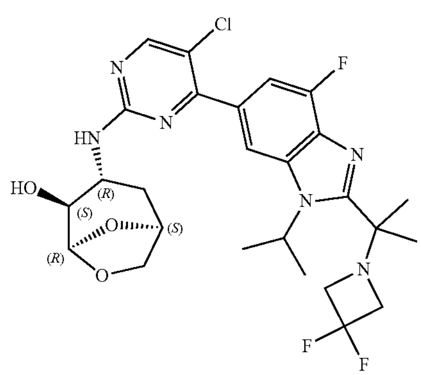 | (1S,3R,4S,5R)-3-((5-chloro-4-(2-(2-(3,3-difluoroazetidin-1-yl)propan-2-yl)-4-fluoro-1-isopropyl-1H-benzo[d]imidazol-6-yl)pyrimidin-2-yl)amino)-6,8-dioxabicyclo[3.2.1]octan-4-ol |
| 223 | 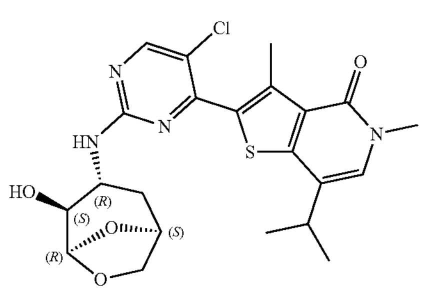 | 2-(5-chloro-2-(((1S,3R,4S,5R)-4-hydroxy-6,8-dioxabicyclo[3.2.1]octan-3-yl)amino)pyrimidin-4-yl)-7-isopropyl-3,5-dimethylthieno[3,2-c]pyridin-4(5H)-one |

TABLE 1-continued

Compounds of the present disclosure

| Cpd # | Structure | IUPAC Name |
|---|---|---|
| 224 | 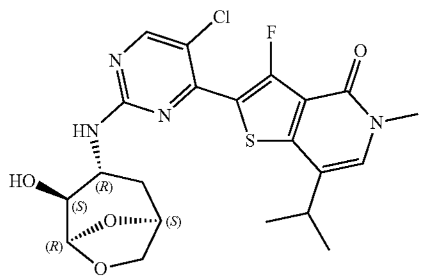 | 2-(5-chloro-2-(((1S,3R,4S,5R)-4-hydroxy-6,8-dioxabicyclo[3.2.1]octan-3-yl)amino)pyrimidin-4-yl)-3-fluoro-7-isopropyl-5-methylthieno[3,2-c]pyridin-4(5H)-one |
| 225 | 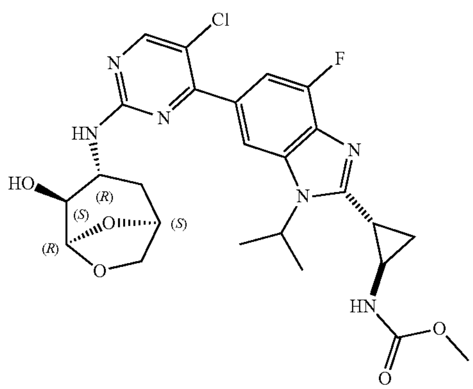 | methyl ((1R,2R)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)cyclopropyl)carbamate |
| 226 | 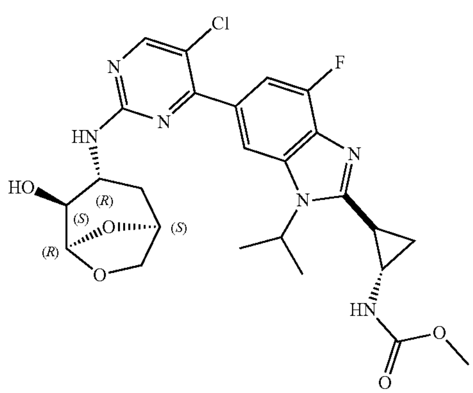 | methyl ((1S,2S)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)cyclopropyl)carbamate |
| 227 | 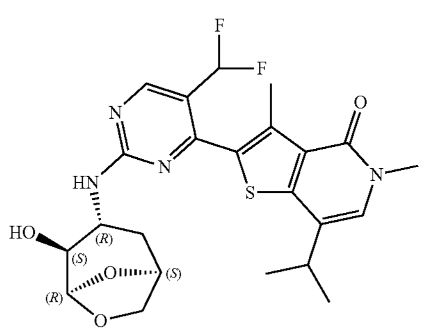 | 2-(5-(difluoromethyl)-2-(((1S,3R,4S,5R)-4-hydroxy-6,8-dioxabicyclo[3.2.1]octan-3-yl)amino)pyrimidin-4-yl)-7-isopropyl-3,5-dimethylthieno[3,2-c]pyridin-4(5H)-one |

TABLE 1-continued

Compounds of the present disclosure

| Cpd # | Structure | IUPAC Name |
|---|---|---|
| 228 | 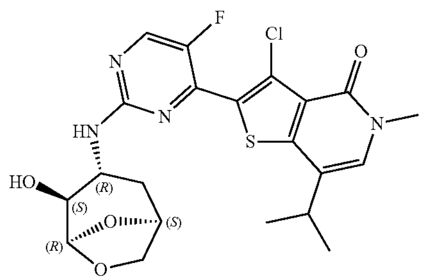 | 3-chloro-2-(5-fluoro-2-(((1S,3R,4S,5R)-4-hydroxy-6,8-dioxabicyclo[3.2.1]octan-3-yl)amino)pyrimidin-4-yl)-7-isopropyl-5-methylthieno[3,2-c]pyridin-4(5H)-one |
| 229 | 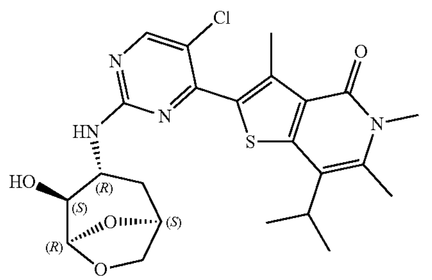 | 2-(5-chloro-2-(((1S,3R,4S,5R)-4-hydroxy-6,8-dioxabicyclo[3.2.1]octan-3-yl)amino)pyrimidin-4-yl)-7-isopropyl-3,5,6-trimethylthieno[3,2-c]pyridin-4(5H)-one |
| 230 | 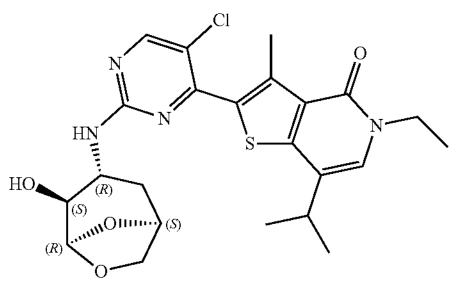 | 5-ethyl-2-(5-chloro-2-(((1S,3R,4S,5R)-4-hydroxy-6,8-dioxabicyclo[3.2.1]octan-3-yl)amino)pyrimidin-4-yl)-7-isopropyl-3-methylthieno[3,2-c]pyridin-4(5H)-one |
| 231 | 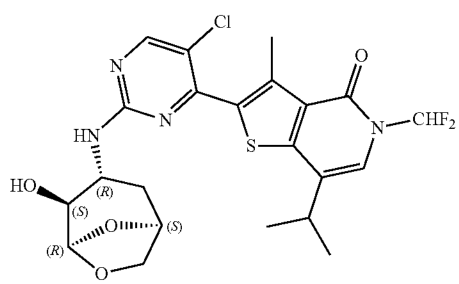 | 2-(5-chloro-2-(((1S,3R,4S,5R)-4-hydroxy-6,8-dioxabicyclo[3.2.1]octan-3-yl)amino)pyrimidin-4-yl)-5-(difluoromethyl)-7-isopropyl-3-methylthieno[3,2-c]pyridin-4(5H)-one |
| 232 | 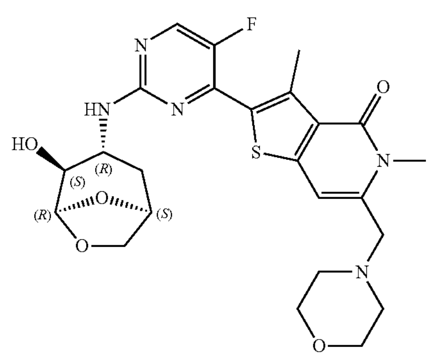 | 2-(5-fluoro-2-(((1S,3R,4S,5R)-4-hydroxy-6,8-dioxabicyclo[3.2.1]octan-3-yl)amino)pyrimidin-4-yl)-3,5-dimethyl-6-(morpholinomethyl)thieno[3,2-c]pyridin-4(5H)-one |

TABLE 1-continued

Compounds of the present disclosure

| Cpd # | Structure | IUPAC Name |
|---|---|---|
| 233 | 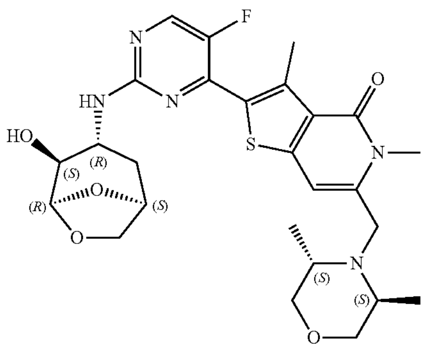 | 6-(((3S,5S)-3,5-dimethylmorpholino)methyl)-2-(5-fluoro-2-(((1S,3R,4S,5R)-4-hydroxy-6,8-dioxabicyclo[3.2.1]octan-3-yl)amino)pyrimidin-4-yl)-3,5-dimethylthieno[3,2-c]pyridin-4(5H)-one |
| 234 | 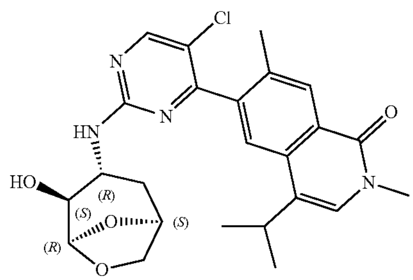 | 6-(5-chloro-2-(((1S,3R,4S,5R)-4-hydroxy-6,8-dioxabicyclo[3.2.1]octan-3-yl)amino)pyrimidin-4-yl)-4-isopropyl-2,7-dimethylisoquinolin-1(2H)-one |
| 235 | 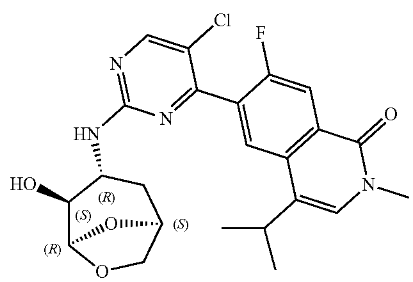 | 6-(5-chloro-2-(((1S,3R,4S,5R)-4-hydroxy-6,8-dioxabicyclo[3.2.1]octan-3-yl)amino)pyrimidin-4-yl)-7-fluoro-4-isopropyl-2-methylisoquinolin-1(2H)-one |
| 236 | 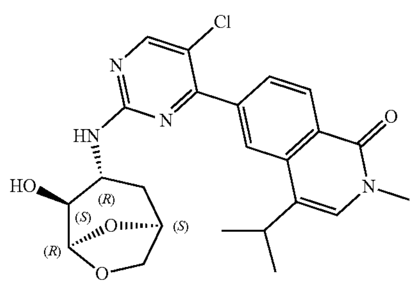 | 6-(5-chloro-2-(((1S,3R,4S,5R)-4-hydroxy-6,8-dioxabicyclo[3.2.1]octan-3-yl)amino)pyrimidin-4-yl)-4-isopropyl-2-methylisoquinolin-1(2H)-one |
| 237 | 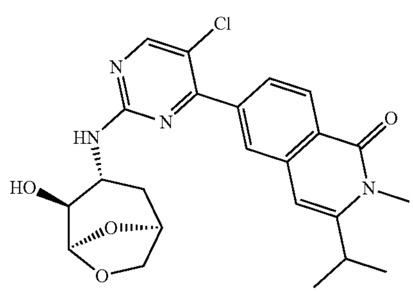 [SMILES: CC(C)c1cc2cc(-c3nc(N[C@@H]4C[C@H]5CO[C@H](O5)[C@H]4O)ncc3Cl)ccc2c(=O)n1C] | 6-(5-chloro-2-(((1S,3R,4S,5R)-4-hydroxy-6,8-dioxabicyclo[3.2.1]octan-3-yl)amino)pyrimidin-4-yl)-3-isopropyl-2-methylisoquinolin-1(2H)-one |

TABLE 1-continued

Compounds of the present disclosure

| Cpd # | Structure | IUPAC Name |
|---|---|---|
| 238 | 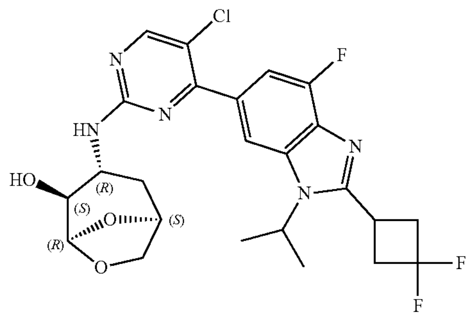 | (1S,3R,4S,5R)-3-((5-chloro-4-(2-(3,3-difluorocyclobutyl)-4-fluoro-1-isopropyl-1H-benzo[d]imidazol-6-yl)pyrimidin-2-yl)amino)-6,8-dioxabicyclo[3.2.1]octan-4-ol |
| 239 | 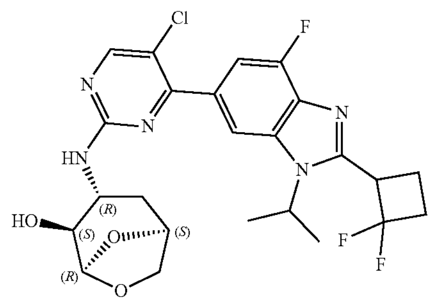 | (1S,3R,4S,5R)-3-((5-chloro-4-(2-(2,2-difluorocyclobutyl)-4-fluoro-1-isopropyl-1H-benzo[d]imidazol-6-yl)pyrimidin-2-yl)amino)-6,8-dioxabicyclo[3.2.1]octan-4-ol |
| 240 | 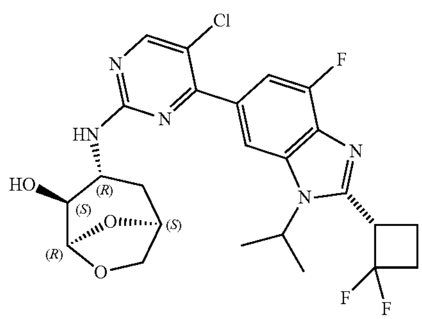 | (1S,3R,4S,5R)-3-((5-chloro-4-(2-((S)-2,2-difluorocyclobutyl)-4-fluoro-1-isopropyl-1H-benzo[d]imidazol-6-yl)pyrimidin-2-yl)amino)-6,8-dioxabicyclo[3.2.1]octan-4-ol |
| 241 | 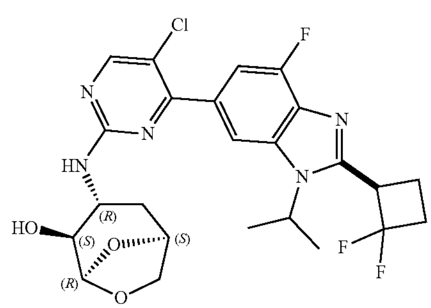 | (1S,3R,4S,5R)-3-((5-chloro-4-(2-((R)-2,2-difluorocyclobutyl)-4-fluoro-1-isopropyl-1H-benzo[d]imidazol-6-yl)pyrimidin-2-yl)amino)-6,8-dioxabicyclo[3.2.1]octan-4-ol |
| 242 | 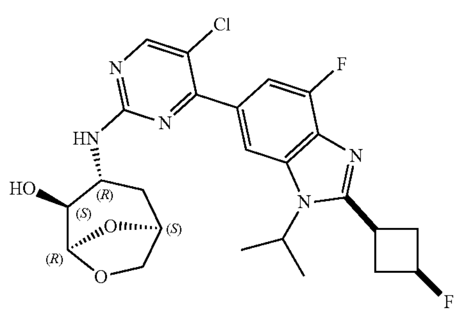 | (1S,3R,4S,5R)-3-((5-chloro-4-(4-fluoro-2-((1s,3S)-3-fluorocyclobutyl)-1-isopropyl-1H-benzo[d]imidazol-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 243 | 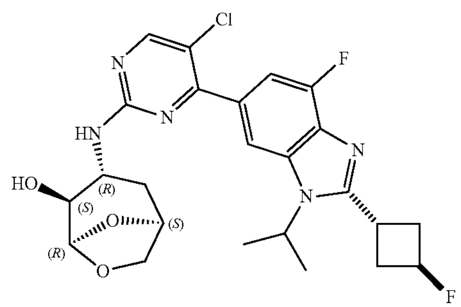 | (1S,3R,4S,5R)-3-((5-chloro-4-(4-fluoro-2-((1r,3R)-3-fluorocyclobutyl)-1-isopropyl-1H-benzo[d]imidazol-6-yl)pyrimidin-2-yl)amino)-6,8-dioxabicyclo[3.2.1]octan-4-ol |
| 244 | 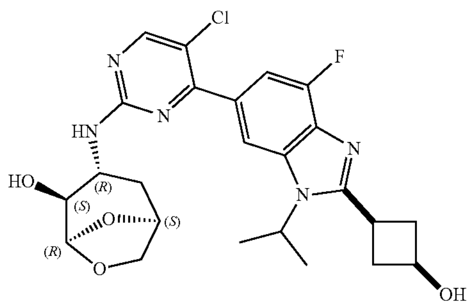 | (1S,3R,4S,5R)-3-((5-chloro-4-(4-fluoro-2-((1s,3S)-3-hydroxycyclobutyl)-1-isopropyl-1H-benzo[d]imidazol-6-yl)pyrimidin-2-yl)amino)-6,8-dioxabicyclo[3.2.1]octan-4-ol |
| 245 | 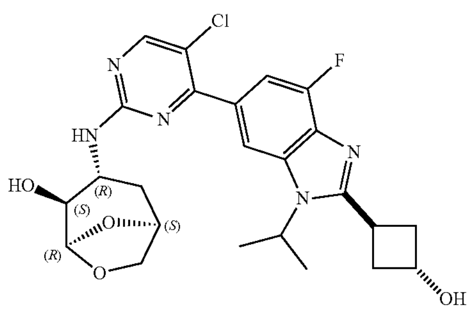 | (1S,3R,4S,5R)-3-((5-chloro-4-(4-fluoro-2-((1r,3R)-3-hydroxycyclobutyl)-1-isopropyl-1H-benzo[d]imidazol-6-yl)pyrimidin-2-yl)amino)-6,8-dioxabicyclo[3.2.1]octan-4-ol |
| 246 | 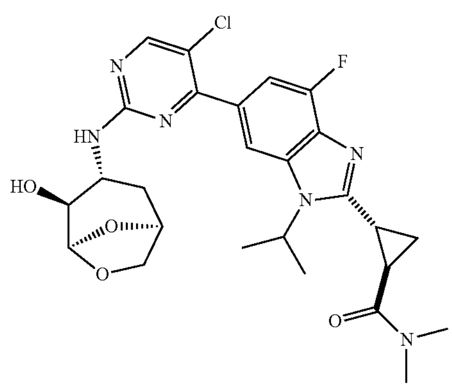 | (1R,2R)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-N,N-dimethylcyclopropane-1-carboxamide |

TABLE 1-continued

Compounds of the present disclosure

| Cpd # | Structure | IUPAC Name |
|---|---|---|
| 247 | 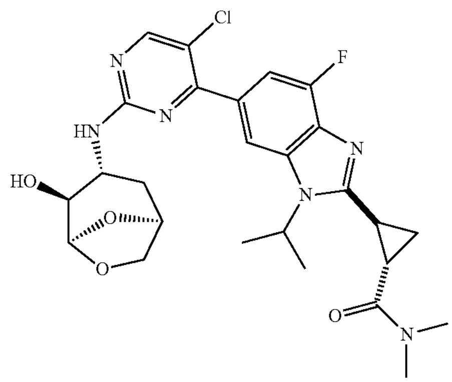 | (1S,2S)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-N,N-dimethylcyclopropane-1-carboxamide |
| 248 | 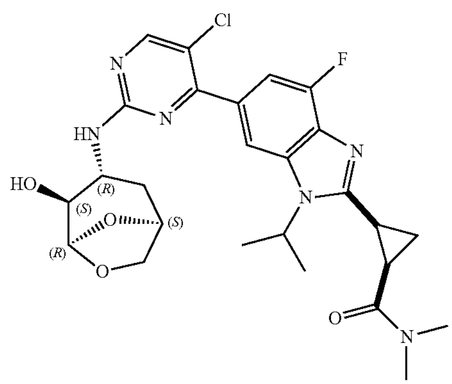 | (1R,2S)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-N,N-dimethylcyclopropane-1-carboxamide |
| 249 | 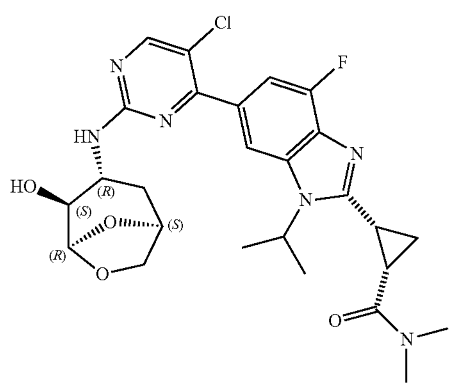 | (1S,2R)-2-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-N,N-dimethylcyclopropane-1-carboxamide |
| 250 | 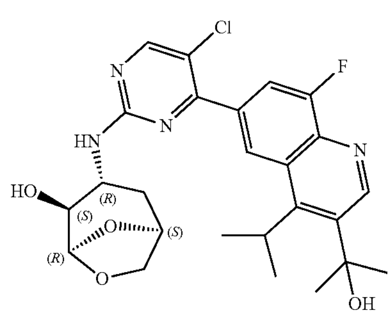 | (1S,3R,4S,5R)-3-((5-chloro-4-(8-fluoro-3-(2-hydroxypropan-2-yl)-4-isopropylquinolin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 251 | 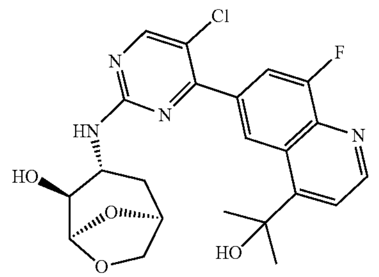 [SMILES: CC(C)(O)c1ccnc2c(F)cc(-c3nc(N[C@@H]4C[C@H]5CO[C@H](O5)[C@H]4O)ncc3Cl)cc12] | (1S,3R,4S,5R)-3-((5-chloro-4-(8-fluoro-4-(2-hydroxypropan-2-yl)quinolin-6-yl)pyrimidin-2-yl)amino)-6,8-dioxabicyclo[3.2.1]octan-4-ol |
| 252 | 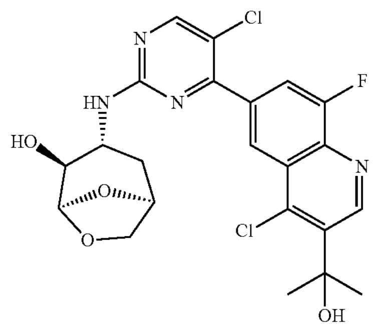 [SMILES: CC(C)(O)c1cnc2c(F)cc(-c3nc(N[C@@H]4C[C@H]5CO[C@H](O5)[C@H]4O)ncc3Cl)cc2c1Cl] | (1S,3R,4S,5R)-3-((5-chloro-4-(4-chloro-8-fluoro-3-(2-hydroxypropan-2-yl)quinolin-6-yl)pyrimidin-2-yl)amino)-6,8-dioxabicyclo[3.2.1]octan-4-ol |
| 253 | 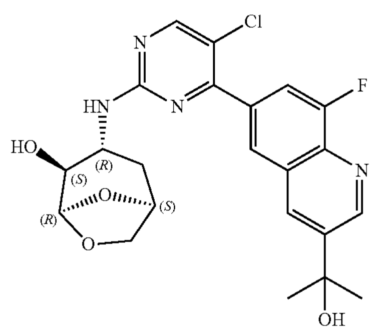 | (1S,3R,4S,5R)-3-((5-chloro-4-(8-fluoro-3-(2-hydroxypropan-2-yl)quinolin-6-yl)pyrimidin-2-yl)amino)-6,8-dioxabicyclo[3.2.1]octan-4-ol |
| 254 | 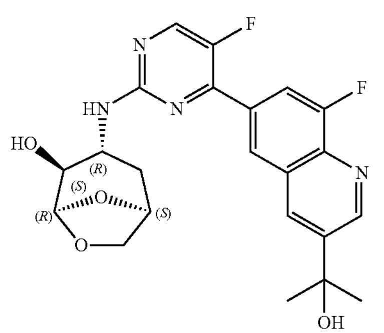 | (1S,3R,4S,5R)-3-((5-fluoro-4-(8-fluoro-3-(2-hydroxypropan-2-yl)quinolin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 255 | 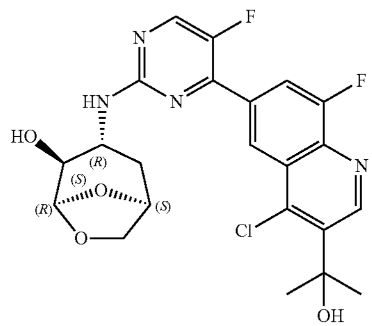 | (1S,3R,4S,5R)-3-((4-(4-chloro-8-fluoro-3-(2-hydroxypropan-2-yl)quinolin-6-yl)-5-fluoropyrimidin-2-yl)amino)-6,8-dioxabicyclo[3.2.1]octan-4-ol |
| 256 | 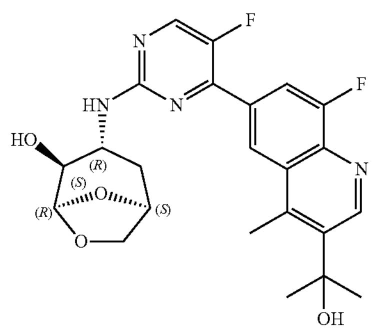 | (1S,3R,4S,5R)-3-((5-fluoro-4-(8-fluoro-3-(2-hydroxypropan-2-yl)-4-methylquinolin-6-yl)pyrimidin-2-yl)amino)-6,8-dioxabicyclo[3.2.1]octan-4-ol |
| 257 | 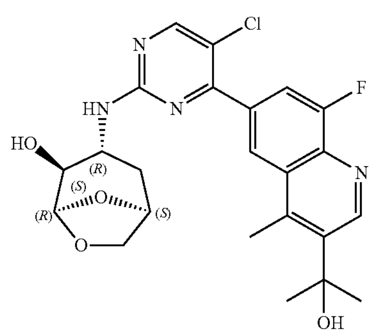 | (1S,3R,4S,5R)-3-((5-chloro-4-(8-fluoro-3-(2-hydroxypropan-2-yl)-4-methylquinolin-6-yl)pyrimidin-2-yl)amino)-6,8-dioxabicyclo[3.2.1]octan-4-ol |
| 258 | 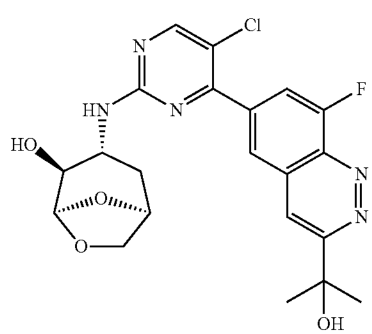 [SMILES: CC(C)(O)c1cc2cc(-c3nc(N[C@@H]4C[C@H]5CO[C@H](O5)[C@H]4O)ncc3Cl)cc(F)c2nn1] | (1S,3R,4S,5R)-3-((5-chloro-4-(8-fluoro-3-(2-hydroxypropan-2-yl)cinnolin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 259 | 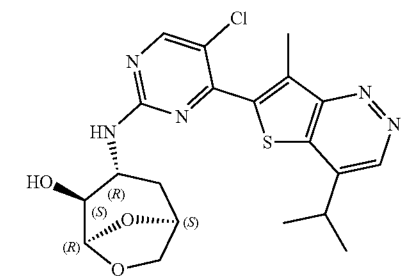 | (1S,3R,4S,5R)-3-((5-chloro-4-(4-isopropyl-7-methylthieno[3,2-c]pyridazin-6-yl)pyrimidin-2-yl)amino)-6,8-dioxabicyclo[3.2.1]octan-4-ol |
| 260 | 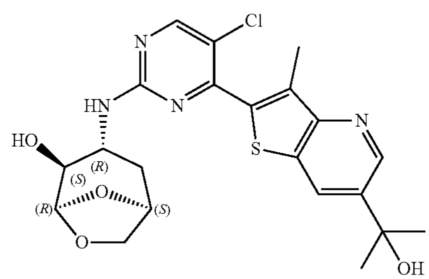 | (1S,3R,4S,5R)-3-((5-chloro-4-(6-(2-hydroxypropan-2-yl)-3-methylthieno[3,2-b]pyridin-2-yl)pyrimidin-2-yl)amino)-6,8-dioxabicyclo[3.2.1]octan-4-ol |
| 261 | 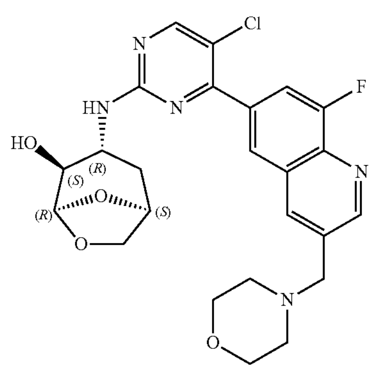 | (1S,3R,4S,5R)-3-((5-chloro-4-(8-fluoro-3-(morpholinomethyl)quinolin-6-yl)pyrimidin-2-yl)amino)-6,8-dioxabicyclo[3.2.1]octan-4-ol |
| 262 | 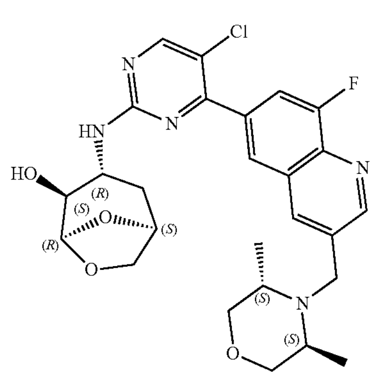 | (1S,3R,4S,5R)-3-((5-chloro-4-(3-(((3S,5S)-3,5-dimethylmorpholino)methyl)-8-fluoroquinolin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 263 | 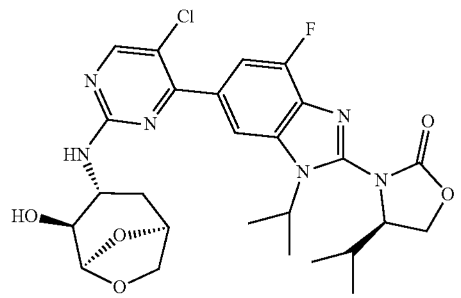 [SMILES: CC(C)[C@@H]1COC(=O)N1c1nc2c(F)cc(-c3nc(N[C@@H]4C[C@H]5CO[C@H](O5)[C@H]4O)ncc3Cl)cc2n1C(C)C] | (R)-3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-4-isopropyloxazolidin-2-one |
| 264 | 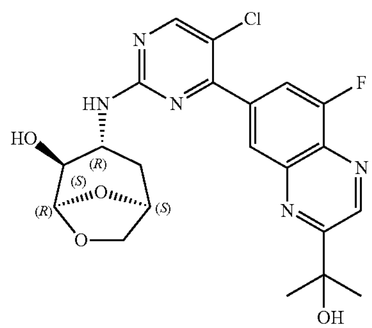 | (1S,3R,4S,5R)-3-((5-chloro-4-(8-fluoro-3-(2-hydroxypropan-2-yl)quinoxalin-6-yl)pyrimidin-2-yl)amino)-6,8-dioxabicyclo[3.2.1]octan-4-ol |
| 265 | 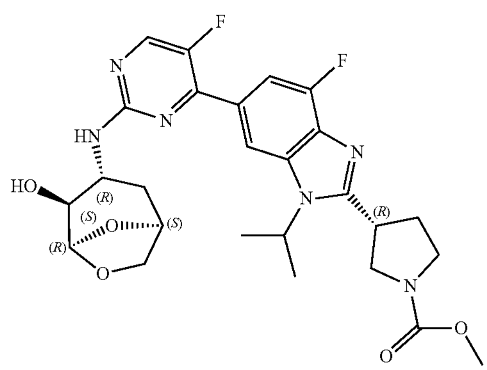 | methyl (R)-3-(4-fluoro-6-(5-fluoro-2-(((1S,3R,4S,5R)-4-hydroxy-6,8-dioxabicyclo[3.2.1]octan-3-yl)amino)pyrimidin-4-yl)-1-isopropyl-1H-benzo[d]imidazol-2-yl)pyrrolidine-1-carboxylate |
| 266 | 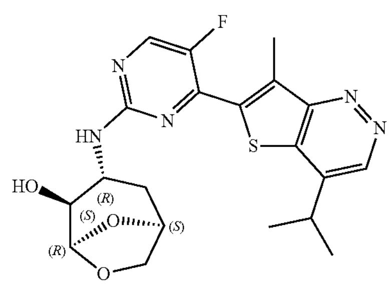 | (1S,3R,4S,5R)-3-((5-fluoro-4-(4-isopropyl-7-methylthieno[3,2-c]pyridazin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 267 | 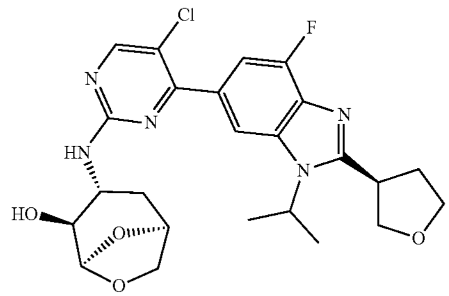 [SMILES: CC(C)n1c([C@H]2CCOC2)nc2c(F)cc(-c3nc(N[C@@H]4C[C@H]5CO[C@H](O5)[C@H]4O)ncc3Cl)cc21] | (1S,3R,4S,5R)-3-((5-chloro-4-(4-fluoro-1-isopropyl-2-((R)-tetrahydrofuran-3-yl)-1H-benzo[d]imidazol-6-yl)pyrimidin-2-yl)amino)-6,8-dioxabicyclo[3.2.1]octan-4-ol |
| 268 | 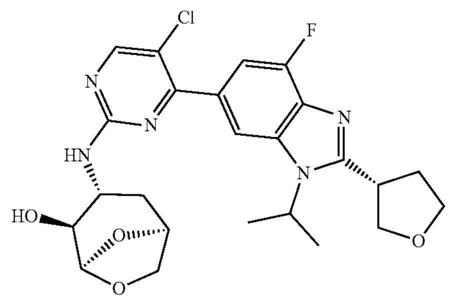 [SMILES: CC(C)n1c([C@@H]2CCOC2)nc2c(F)cc(-c3nc(N[C@@H]4C[C@H]5CO[C@H](O5)[C@H]4O)ncc3Cl)cc21] | (1S,3R,4S,5R)-3-((5-chloro-4-(4-fluoro-1-isopropyl-2-((S)-tetrahydrofuran-3-yl)-1H-benzo[d]imidazol-6-yl)pyrimidin-2-yl)amino)-6,8-dioxabicyclo[3.2.1]octan-4-ol |
| 269 | 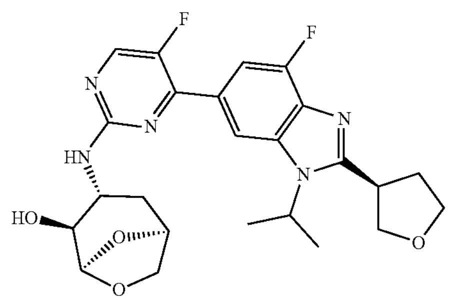 [SMILES: CC(C)n1c([C@H]2CCOC2)nc2c(F)cc(-c3nc(N[C@@H]4C[C@H]5CO[C@H](O5)[C@H]4O)ncc3F)cc21] | (1S,3R,4S,5R)-3-((5-fluoro-4-(4-fluoro-1-isopropyl-2-((R)-tetrahydrofuran-3-yl)-1H-benzo[d]imidazol-6-yl)pyrimidin-2-yl)amino)-6,8-dioxabicyclo[3.2.1]octan-4-ol |
| 270 | 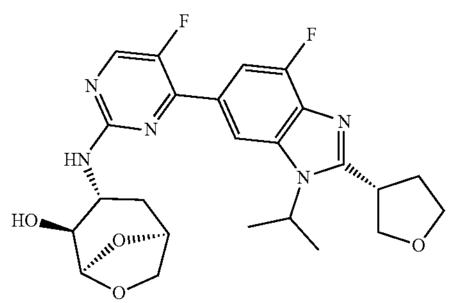 [SMILES: CC(C)n1c([C@@H]2CCOC2)nc2c(F)cc(-c3nc(N[C@@H]4C[C@H]5CO[C@H](O5)[C@H]4O)ncc3F)cc21] | (1S,3R,4S,5R)-3-((5-fluoro-4-(4-fluoro-1-isopropyl-2-((S)-tetrahydrofuran-3-yl)-1H-benzo[d]imidazol-6-yl)pyrimidin-2-yl)amino)-6,8-dioxabicyclo[3.2.1]octan-4-ol |
| 271 | 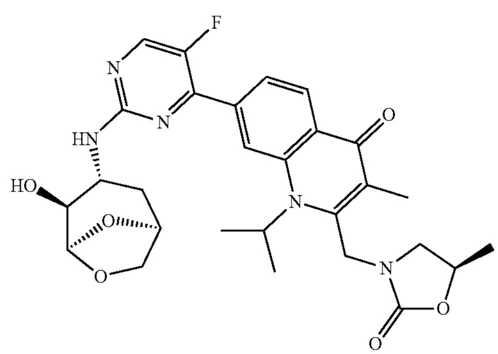 [SMILES: Cc1c(CN2C[C@@H](C)OC2=O)n(C(C)C)c2cc(-c3nc(N[C@@H]4C[C@H]5CO[C@H](O5)[C@H]4O)ncc3F)ccc2c1=O] | (R)-3-((7-(5-fluoro-2-(((1S,3R,4S,5R)-4-hydroxy-6,8-dioxabicyclo[3.2.1]octan-3-yl)amino)pyrimidin-4-yl)-1-isopropyl-3-methyl-4-oxo-1,4-dihydroquinolin-2-yl)methyl)-5-methyloxazolidin-2-one |

TABLE 1-continued

Compounds of the present disclosure

| Cpd # | Structure | IUPAC Name |
|---|---|---|
| 272 | 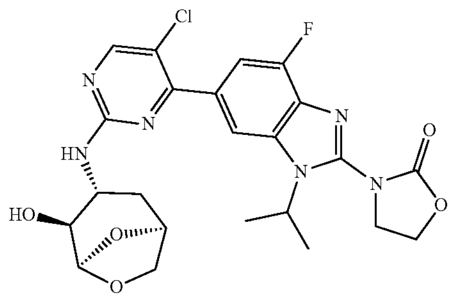 [SMILES: CC(C)n1c(N2CCOC2=O)nc2c(F)cc(-c3nc(N[C@@H]4C[C@H]5CO[C@H](O5)[C@H]4O)ncc3Cl)cc21] | 3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)oxazolidin-2-one |
| 273 | 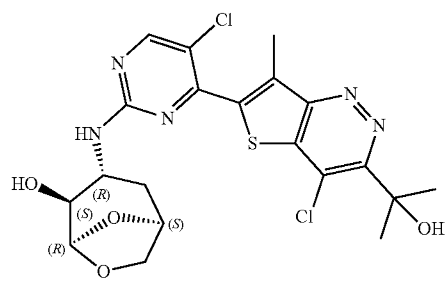 | (1S,3R,4S,5R)-3-((5-chloro-4-(4-chloro-3-(2-hydroxypropan-2-yl)-7-methylthieno[3,2-c]pyridazin-6-yl)pyrimidin-2-yl)amino)-6,8-dioxabicyclo[3.2.1]octan-4-ol |
| 274 | 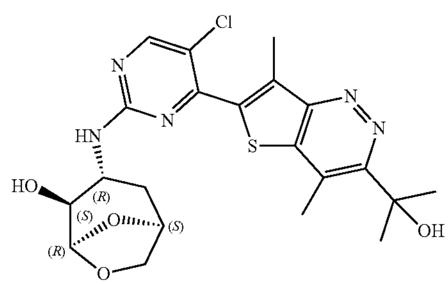 | (1S,3R,4S,5R)-3-((5-chloro-4-(3-(2-hydroxypropan-2-yl)-4,7-dimethylthieno[3,2-c]pyridazin-6-yl)pyrimidin-2-yl)amino)-6,8-dioxabicyclo[3.2.1]octan-4-ol |
| 275 | 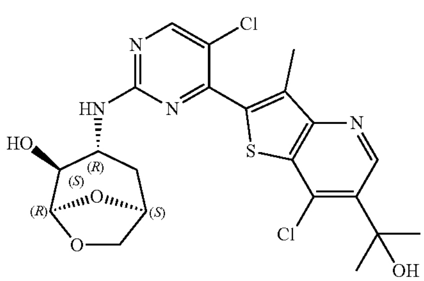 | (1S,3R,4S,5R)-3-((5-chloro-4-(7-chloro-6-(2-hydroxypropan-2-yl)-3-methylthieno[3,2-b]pyridin-2-yl)pyrimidin-2-yl)amino)-6,8-dioxabicyclo[3.2.1]octan-4-ol |
| 276 | 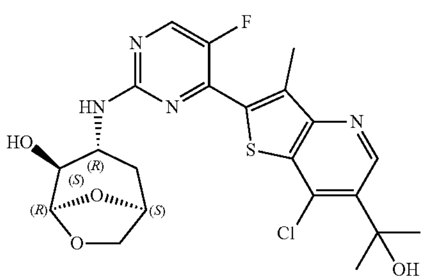 | (1S,3R,4S,5R)-3-((4-(7-chloro-6-(2-hydroxypropan-2-yl)-3-methylthieno[3,2-b]pyridin-2-yl)-5-fluoropyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 277 | 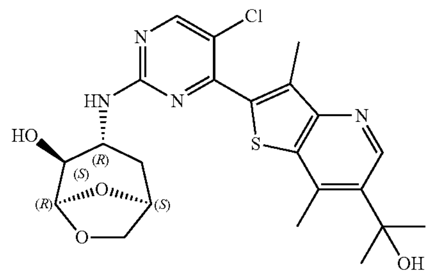 | (1S,3R,4S,5R)-3-((5-chloro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol |
| 278 | 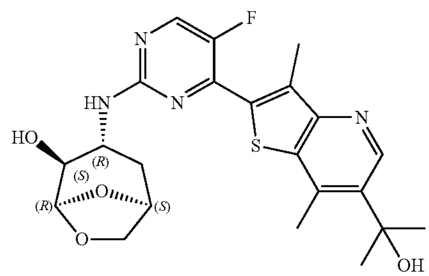 | (1S,3R,4S,5R)-3-((5-fluoro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol |
| 279 | 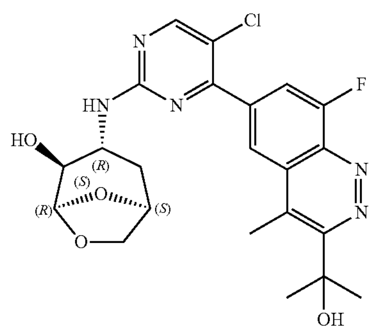 | (1S,3R,4S,5R)-3-((5-chloro-4-(8-fluoro-3-(2-hydroxypropan-2-yl)-4-methylcinnolin-6-yl)pyrimidin-2-yl)amino)-6,8-dioxabicyclo[3.2.1]octan-4-ol |
| 280 | 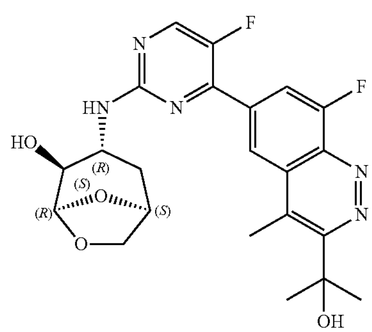 | (1S,3R,4S,5R)-3-((5-fluoro-4-(8-fluoro-3-(2-hydroxypropan-2-yl)-4-methylcinnolin-6-yl)pyrimidin-2-yl)amino)-6,8-dioxabicyclo[3.2.1]octan-4-ol |
| 281 | 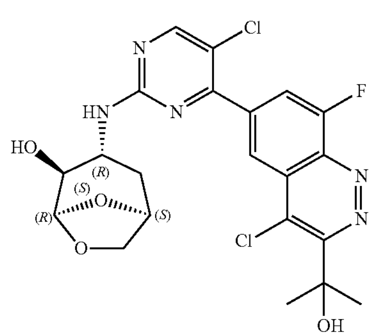 | (1S,3R,4S,5R)-3-((5-chloro-4-(4-chloro-8-fluoro-3-(2-hydroxypropan-2-yl)cinnolin-6-yl)pyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 282 | 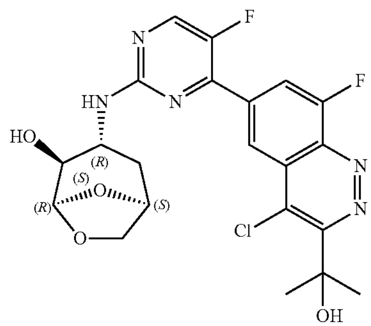 | (1S,3R,4S,5R)-3-((4-(4-chloro-8-fluoro-3-(2-hydroxypropan-2-yl)cinnolin-6-yl)-5-fluoropyrimidin-2-yl)amino)-6,8-dioxabicyclo[3.2.1]octan-4-ol |
| 283 | 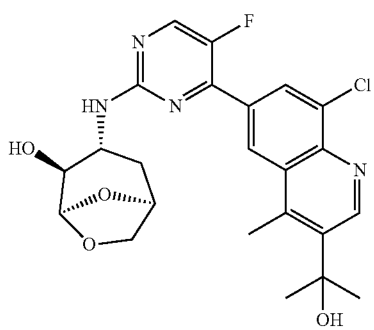 [SMILES: Cc1c(C(C)(C)O)cnc2c(Cl)cc(-c3nc(N[C@@H]4C[C@H]5CO[C@H](O5)[C@H]4O)ncc3F)cc12] | (1S,3R,4S,5R)-3-((4-(8-chloro-3-(2-hydroxypropan-2-yl)-4-methylquinolin-6-yl)-5-fluoropyrimidin-2-yl)amino)-6,8-dioxabicyclo[3.2.1]octan-4-ol |
| 284 | 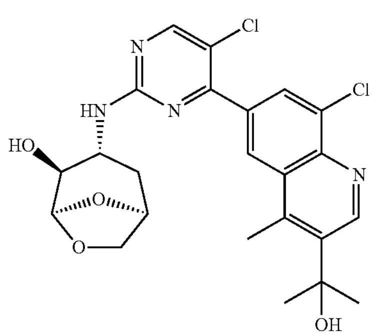 | (1S,3R,4S,5R)-3-((5-chloro-4-(8-chloro-3-(2-hydroxypropan-2-yl)-4-methylquinolin-6-yl)pyrimidin-2-yl)amino)-6,8-dioxabicyclo[3.2.1]octan-4-ol |
| 285 | 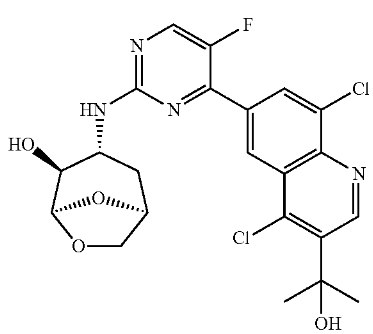 [SMILES: CC(C)(O)c1cnc2c(Cl)cc(-c3nc(N[C@@H]4C[C@H]5CO[C@H](O5)[C@H]4O)ncc3F)cc2c1Cl] | (1S,3R,4S,5R)-3-((4-(4,8-dichloro-3-(2-hydroxypropan-2-yl)quinolin-6-yl)-5-fluoropyrimidin-2-yl)amino)-6,8-dioxabicyclo[3.2.1]octan-4-ol |

TABLE 1-continued

Compounds of the present disclosure

| Cpd # | Structure | IUPAC Name |
|---|---|---|
| 286 | 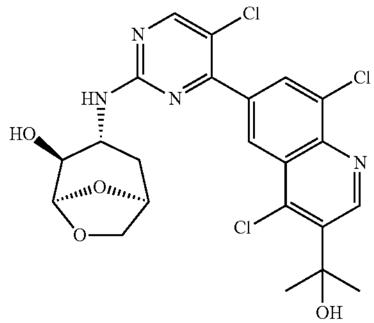 [SMILES: CC(C)(O)c1cnc2c(Cl)cc(-c3nc(N[C@@H]4C[C@H]5CO[C@H](O5)[C@H]4O)ncc3Cl)cc2c1Cl] | (1S,3R,4S,5R)-3-((5-chloro-4-(4,8-dichloro-3-(2-hydroxypropan-2-yl)quinolin-6-yl)pyrimidin-2-yl)amino)-6,8-dioxabicyclo[3.2.1]octan-4-ol |
| 287 | 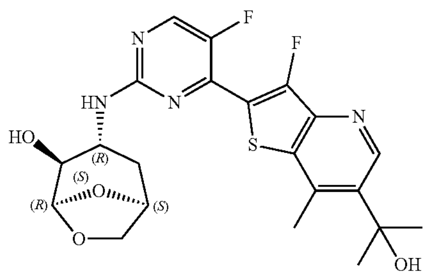 | (1S,3R,4S,5R)-3-((5-fluoro-4-(3-fluoro-6-(2-hydroxypropan-2-yl)-7-methylthieno[3,2-b]pyridin-2-yl)pyrimidin-2-yl)amino)-6,8-dioxabicyclo[3.2.1]octan-4-ol |
| 288 | 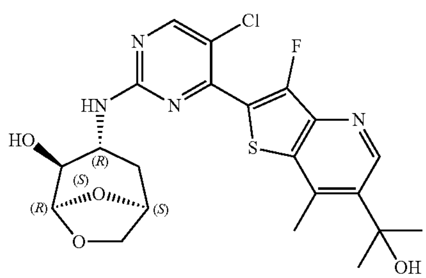 | (1S,3R,4S,5R)-3-((5-chloro-4-(3-fluoro-6-(2-hydroxypropan-2-yl)-7-methylthieno[3,2-b]pyridin-2-yl)pyrimidin-2-yl)amino)-6,8-dioxabicyclo[3.2.1]octan-4-ol |
| 289 | 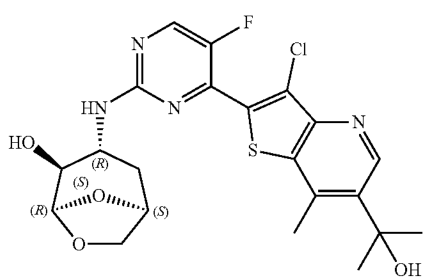 | (1S,3R,4S,5R)-3-((4-(3-chloro-6-(2-hydroxypropan-2-yl)-7-methylthieno[3,2-b]pyridin-2-yl)-5-fluoropyrimidin-2-yl)amino)-6,8-dioxabicyclo[3.2.1]octan-4-ol |
| 290 | 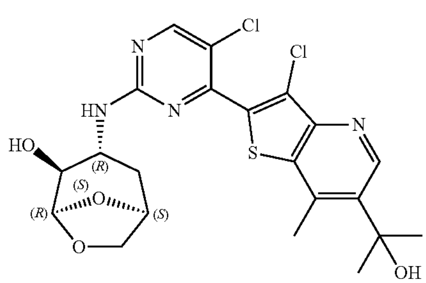 | (1S,3R,4S,5R)-3-((5-chloro-4-(3-chloro-6-(2-hydroxypropan-2-yl)-7-methylthieno[3,2-b]pyridin-2-yl)pyrimidin-2-yl)amino)-6,8-dioxabicyclo[3.2.1]octan-4-olff |

TABLE 1-continued

Compounds of the present disclosure

| Cpd # | Structure | IUPAC Name |
|---|---|---|
| 291 | 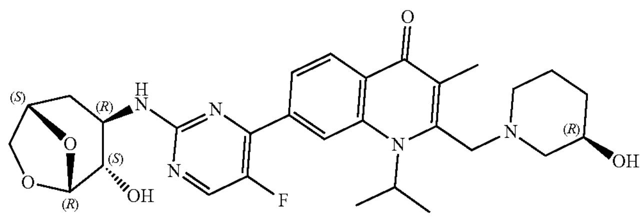 | 7-(5-fluoro-2-(((1S,3R,4S,5R)-4-hydroxy-6,8-dioxabicyclo[3.2.1]octan-3-yl)amino)pyrimidin-4-yl)-2-(((R)-3-hydroxypiperidin-1-yl)methyl)-1-isopropyl-3-methylquinolin-4(1H)-one |
| 292 | 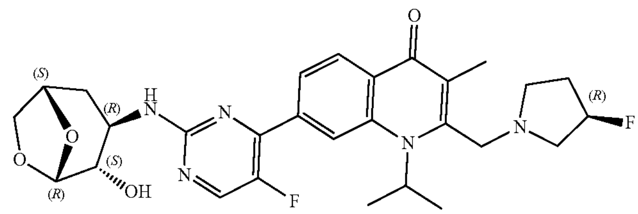 | 7-(5-fluoro-2-(((1S,3R,4S,5R)-4-hydroxy-6,8-dioxabicyclo[3.2.1]octan-3-yl)amino)pyrimidin-4-yl)-2-(((R)-3-fluoropyrrolidin-1-yl)methyl)-1-isopropyl-3-methylquinolin-4(1H)-one |
| 293 | 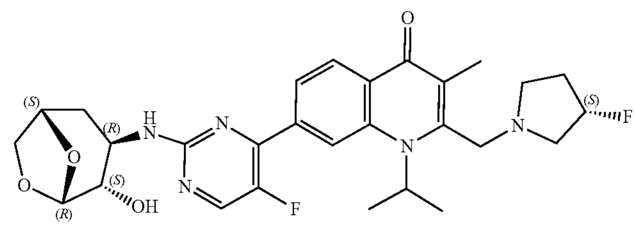 | 7-(5-fluoro-2-(((1S,3R,4S,5R)-4-hydroxy-6,8-dioxabicyclo[3.2.1]octan-3-yl)amino)pyrimidin-4-yl)-2-(((S)-3-fluoropyrrolidin-1-yl)methyl)-1-isopropyl-3-methylquinolin-4(1H)-one |
| 294 | 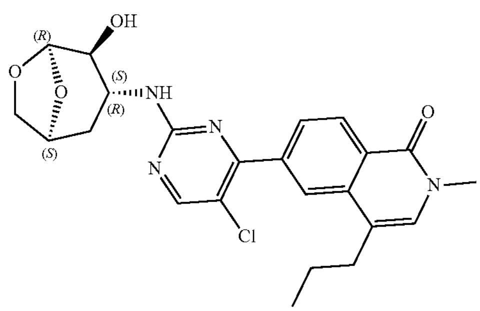 | 6-(5-chloro-2-(((1S,3R,4S,5R)-4-hydroxy-6,8-dioxabicyclo[3.2.1]octan-3-yl)amino)pyrimidin-4-yl)-2-methyl-4-propylisoquinolin-1(2H)-one |
| 295 | 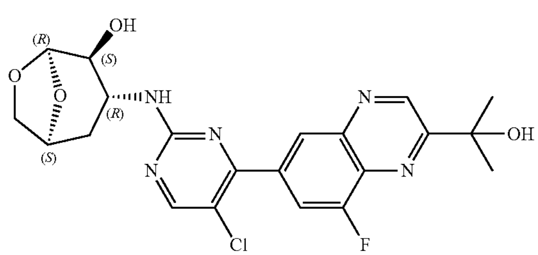 | (1S,3R,4S,5R)-3-((5-chloro-4-(8-fluoro-2-(2-hydroxypropan-2-yl)quinoxalin-6-yl)pyrimidin-2-yl)amino)-6,8-dioxabicyclo[3.2.1]octan-4-ol |
| 296 | 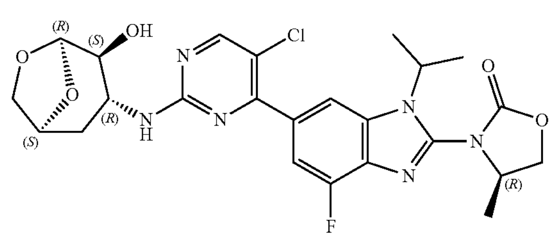 | (R)-3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-4-methyloxazolidin-2-one |

TABLE 1-continued

Compounds of the present disclosure

| Cpd # | Structure | IUPAC Name |
|---|---|---|
| 297 | 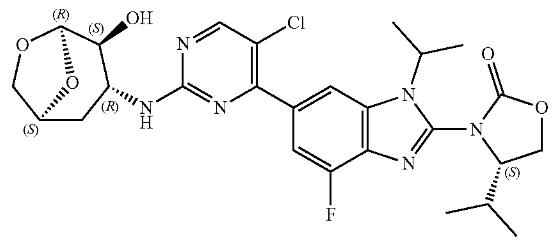 | (S)-3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-4-isopropyloxazolidin-2-one |
| 298 | 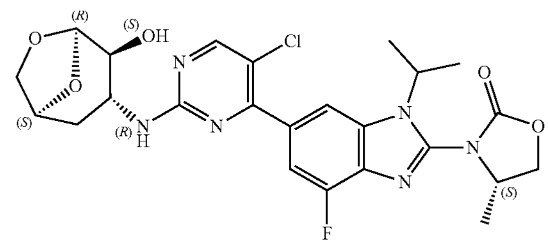 | (S)-3-(6-(5-chloro-2-(((1S,3R,4S,5R)-4-hydroxy-6,8-dioxabicyclo[3.2.1]octan-3-yl)amino)pyrimidin-4-yl)-4-fluoro-1-isopropyl-1H-benzo[d]imidazol-2-yl)-4-methyloxazolidin-2-one |

Pharmaceutical Compositions

Pharmaceutical compositions of the present disclosure comprise at least one compound of Formula I, or a tautomer, stereoisomer or a mixture of stereoisomers, or a pharmaceutically acceptable salt, or hydrate, or deuterated derivative thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Compounds of the present disclosure can be prepared and administered in a wide variety of oral, parenteral, and topical dosage forms. Thus, the compounds of the present disclosure can be administered by injection (e.g., intravenously, intramuscularly, intracutaneously, subcutaneously, intraduodenally, or intraperitoneally) In some embodiments, compounds of the present disclosure are administered orally. Also, the compounds described herein can be administered by inhalation, for example, intranasally. Additionally, the compounds of the present disclosure can be administered transdermally. It is also envisioned that multiple routes of administration (e.g., intramuscular, oral, transdermal) can be used to administer compounds of the disclosure. Accordingly, the present disclosure also provides pharmaceutical compositions comprising pharmaceutically acceptable carrier or excipient and one or more compounds of the disclosure. For preparing pharmaceutical compositions from the compounds of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is finely divided solid in a mixture with the finely divided active component. In tablets, the active component is mixed with the carrier having the necessary binding properties in suitable proportions and compacted in the shape and size desired.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I, or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from 0.1 to 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I, or tautomers, stereoisomers, pharmaceutically acceptable salts, and hydrates thereof) is generally present at a concentration of from 0.1% to 15% w/w of the composition, for example, from 0.5 to 2%.

Effective Dosages

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g., inhibiting and/or decreasing an amount of CDK in a subject).

The dosage and frequency (single or multiple doses) of compound administered can vary depending upon a variety of factors, including route of administration; size, age, sex, health, body weight, body mass index, and diet of the recipient; nature and extent of the symptoms of the disease being treated (e.g., the disease responsive treatment; and complications from any disease or treatment regimen).

Other therapeutic regimens or agents can be used in conjunction with the methods and compounds of the disclosure.

For any provided compound or test agent, the therapeutically effective amount can be initially determined from cell culture assays. Target concentrations will be those concentrations of active compound(s) that are capable of inhibiting CDK (such as CDK 4) expressed in a subject.

Therapeutically effective amounts for use in humans may be determined from animal models. For example, a dose for humans can be formulated to achieve a concentration that has been found to be effective in animals. The dosage in humans can be adjusted by monitoring biomarkers associated with cancer and adjusting the dosage upwards or downwards, as described above.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side effects.

In some embodiments, a compound of the disclosure or a pharmaceutical composition comprising the same is provided as a unit dose.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of 1 µg to 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50 (4): 219-244 (1966) and Table 2 below for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies, for example, within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In some embodiments, the present disclosure provides a pharmaceutical composition comprising a therapeutically effective amount of a compound of Formula I, or a tautomer, stereoisomer or a mixture of stereoisomers, or a pharmaceutically acceptable salt, or hydrate, or deuterated derivative thereof, and one or more of a pharmaceutically acceptable carrier, a pharmaceutically acceptable vehicle, a pharmaceutically acceptable excipient, or combinations thereof. The compounds of the disclosure can be administered alone or can be co-administered to the subject. Co-administration is meant to include simultaneous or sequential administration of the compounds individually or in combination (more than one compound). The preparations can also be combined, when desired, with other active substances (e.g., to reduce metabolic degradation).

In some embodiments, a compound as described herein can be incorporated into a pharmaceutical composition for administration by methods known to those skilled in the art and described herein for provided compounds.

Methods of Treatment

In some embodiments, a compound of Formula I, or a tautomer, stereoisomer or a mixture of stereoisomers, or a pharmaceutically acceptable salt, or hydrate, or deuterated derivative thereof, is administered to treat a disease or condition modulated at least in part by a cyclin-dependent kinase (CDK) in a subject in need thereof.

In some embodiments, the disease or condition is cancer.

In some embodiments, the cancer is a solid tumor. In some embodiments, the solid tumor is prostate, pancreatic, or breast cancer.

In some embodiments, the cancer is selected from breast cancer, prostate cancer, bone cancer, brain cancer, colorectal cancer, lung cancer, ovarian cancer, uterine cancer, liposarcoma, liver cancer, rhabdoid cancer, sarcoma, skin cancer, kidney cancer, stomach cancer, pancreatic cancer, esophageal cancer, head and neck cancer, bladder cancer, leukemia, lymphoma, and thyroid cancer. In some embodiments, the cancer is selected from breast cancer, ovarian cancer, uterine cancer, lung cancer, and prostate cancer. In some embodiments, the cancer is breast cancer. In some embodiments, the cancer is ovarian cancer. In some embodiments, the cancer is bladder cancer. In some embodiments, the cancer is uterine cancer. In some embodiments, the cancer is prostate cancer. In some embodiments, the cancer is lung cancer. In some embodiments, the cancer is esophageal cancer. In some embodiments, the cancer is head and neck cancer. In some embodiments, the cancer is colorectal cancer. In some embodiments, the cancer is kidney cancer. In some embodiments, the cancer is liver cancer. In some embodiments, the cancer is pancreatic cancer. In some embodiments, the cancer is stomach cancer. In some embodiments, the cancer is thyroid cancer. In some embodiments, the cancer is selected from colorectal cancer, liver cancer, kidney cancer, stomach cancer, pancreatic cancer, and esophageal cancer. In some embodiments, the breast cancer is advanced or metastatic breast cancer. In some embodiments, the therapeutic treatment is for the treatment of diseases and conditions associated with CDKs, such as CDK4.

In some embodiments, a compound of Formula I, or a tautomer, stereoisomer or a mixture of stereoisomers, or a pharmaceutically acceptable salt, or hydrate, or deuterated derivative thereof, is administered as a pharmaceutical composition.

In some embodiments, the disclosure provides for methods for treating a disease or condition in a subject (e g., patient) in need thereof, comprising (a) determining that the disease or condition is modulated at least in part by a cyclin-dependent kinase (CDK); and (b) administering to the subject a therapeutically effective amount of at least one compound of Formula I or a tautomer, stereoisomer or a mixture of stereoisomers, or a pharmaceutically acceptable salt, or hydrate, or deuterated derivative thereof, or a pharmaceutical composition comprising at least one compound of Formula I or a tautomer, stereoisomer or a mixture of stereoisomers, or a pharmaceutically acceptable salt, or hydrate, or deuterated derivative thereof.

In some embodiments, the disclosure provides for methods for treating a cancer in a subject (e.g., patient) in need thereof, comprising administering to the subject a therapeutically effective amount of at least one compound of Formula I or a tautomer, stereoisomer or a mixture of stereoisomers, or a pharmaceutically acceptable salt, or hydrate, or deuterated derivative thereof, or a pharmaceutical composition comprising at least one compound of Formula I or a tautomer, stereoisomer or a mixture of stereoisomers, or a pharmaceutically acceptable salt, or hydrate, or deuterated derivative thereof.

In some embodiments, the disclosure provides for methods for inhibiting CDK (e.g., CDK4) in a subject, comprising administering to the subject an effective amount of at least one compound of Formula I or a tautomer, stereoisomer or a mixture of stereoisomers, or a pharmaceutically acceptable salt, or hydrate, or deuterated derivative thereof, or a pharmaceutical composition comprising at least one compound of Formula I or a tautomer, stereoisomer or a mixture of stereoisomers, or a pharmaceutically acceptable salt, or hydrate, or deuterated derivative thereof.

In some embodiments, the cancer is selected from breast cancer, prostate cancer, bone cancer, brain cancer, colorectal cancer, lung cancer, ovarian cancer, uterine cancer, liposarcoma, liver cancer, rhabdoid cancer, sarcoma, skin cancer, kidney cancer, stomach cancer, pancreatic cancer, esophageal cancer, head and neck cancer, bladder cancer, leukemia, lymphoma and thyroid cancer. In some embodiments, the cancer is breast cancer. In some embodiments, the cancer is prostate cancer. In some embodiments, the cancer is bone cancer. In some embodiments, the cancer is brain cancer. In some embodiments, the cancer is colorectal cancer. In some embodiments, the cancer is lung cancer. In some embodiments, the cancer is ovarian cancer. In some embodiments, the cancer is uterine cancer. In some embodiments, the cancer is liposarcoma. In some embodiments, the cancer is liver cancer (e.g., hepatocellular carcinoma). In some embodiments, the cancer is rhabdoid cancer. In some embodiments, the cancer is sarcoma. In some embodiments, the cancer is skin cancer (e.g., melanoma). In some embodiments, the cancer is kidney cancer. In some embodiments, the cancer is stomach cancer. In some embodiments, the cancer is pancreatic cancer. In some embodiments, the cancer is esophageal cancer. In some embodiments, the cancer is head and neck cancer. In some embodiments, the cancer is bladder cancer (e.g., urothelial carcinoma). In some embodiments, the cancer is leukemia. In some embodiments, the cancer is lymphoma. In some embodiments, the cancer is thyroid cancer.

In some embodiments, the lung cancer is selected from non-small cell lung cancer NSCLC, small cell lung cancer (SCLC), squamous cell carcinoma, and adenocarcinoma. In some embodiments, the lung cancer is non-small cell lung cancer NSCLC. In some embodiments, the lung cancer is small cell lung cancer (SCLC). In some embodiments, the lung cancer is squamous cell carcinoma. In some embodiments the lung cancer is adenocarcinoma.

In some embodiments, the breast cancer is selected from ER-positive/HR-positive, HER2-negative breast cancer; ER-positive/HR-positive, HER2-positive breast cancer; triple negative breast cancer (TNBC), and inflammatory breast cancer. In some embodiments, the breast cancer is ER-positive/HR-positive. In some embodiments, the breast cancer is HER2-negative breast cancer. In some embodiments, the breast cancer is ER-positive/HR-positive. In some embodiments, the breast cancer is HER2-positive breast cancer. In some embodiments, the breast cancer is triple negative breast cancer (TNBC). In some embodiments, the breast cancer is inflammatory breast cancer.

In some embodiments, the breast cancer is selected from endocrine resistant breast cancer, trastuzumab or pertuzumab resistant breast cancer, breast cancer demonstrating primary or acquired resistance to CDK4/CDK6 inhibition. In some embodiments, the breast cancer is endocrine resistant breast cancer. In some embodiments, the breast cancer is trastuzumab or pertuzumab resistant breast cancer. In some embodiments, the breast cancer is breast cancer demonstrating primary or acquired resistance to CDK4/CDK6 inhibition.

In some embodiments, the breast cancer is advanced or metastatic breast cancer. In some embodiments, the breast cancer is advanced breast cancer. In some embodiments, the breast cancer is metastatic breast cancer.

In some embodiments, a compound of Formula I, or a tautomer, stereoisomer or a mixture of stereoisomers, or a pharmaceutically acceptable salt, or hydrate, or deuterated derivative thereof, is administered in combination with another therapeutic agent, e.g., chemotherapy, or used in combination with other treatments, such as radiation or surgical intervention, either as an adjuvant prior to surgery or post-operatively.

In some embodiments, a compound of Formula I, or a tautomer, stereoisomer or a mixture of stereoisomers, or a pharmaceutically acceptable salt, or hydrate, or deuterated derivative thereof, is administered with an additional anti-cancer agent. In some embodiments, the compound of Formula I and/or the pharmaceutical composition comprising the compound of Formula I, and the additional anti-cancer agent are administered concomitantly. In some embodiments, the compound of Formula I and/or the pharmaceutical composition comprising the compound of Formula I, and the additional anti-cancer agent are administered sequentially In some embodiments, the subject has been previously treated with an anti-cancer agent. In some embodiments, the anti-cancer agent is enzalutamide, apalutamide, bicalutamide, darolutamide, flutamide, abiratarone, or a combination of any of the foregoing. In some embodiments, the anti-cancer agent is enzalutamide.

In some embodiments, provided herein is a use of at least one compound of Formula I, or a tautomer, stereoisomer or a mixture of stereoisomers, or a pharmaceutically acceptable salt, or hydrate, or deuterated derivative thereof, in the preparation of a medicament. In some embodiments, the medicament is for the treatment of cancer. In some embodiments, the cancer is selected from breast cancer, prostate cancer, bone cancer, brain cancer, colorectal cancer, lung cancer, ovarian cancer, uterine cancer, liposarcoma, liver cancer, rhabdoid cancer, sarcoma, skin cancer, kidney cancer, stomach cancer, pancreatic cancer, esophageal cancer, head and neck cancer, bladder cancer, leukemia, lymphoma and thyroid cancer. In some embodiments, the cancer is breast cancer. In some embodiments, the cancer is prostate cancer. In some embodiments, the cancer is bone cancer. In some embodiments, the cancer is brain cancer. In some embodiments, the cancer is colorectal cancer. In some embodiments, the cancer is lung cancer. In some embodiments, the cancer is ovarian cancer. In some embodiments, the cancer is uterine cancer. In some embodiments, the cancer is liposarcoma. In some embodiments, the cancer is liver cancer. In some embodiments, the cancer is rhabdoid cancer. In some embodiments, the cancer is sarcoma. In some embodiments, the cancer is skin cancer. In some embodiments, the cancer is kidney cancer. In some embodiments, the cancer is stomach cancer. In some embodiments, the cancer is pancreatic cancer. In some embodiments, the cancer is esophageal cancer In some embodiments, the cancer is head and neck cancer. In some embodiments, the cancer is bladder cancer. In some embodiments, the cancer is leukemia. In some embodiments, the cancer is lymphoma. In some embodiments, the cancer is thyroid cancer.

In some embodiments, provided herein is a method of treating a disease or condition modulated at least in part by CDK4 in a subject comprising administering to the subject in need thereof at least one compound of Formula I, or a tautomer, stereoisomer or a mixture of stereoisomers, or a pharmaceutically acceptable salt, or hydrate, or deuterated derivative thereof.

In some embodiments, a compound of Formula I, or a tautomer, stereoisomer or a mixture of stereoisomers, or a pharmaceutically acceptable salt, or hydrate, or deuterated derivative thereof, may be administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula I, or a tautomer, stereoisomer or a mixture of stereoisomers, or a pharmaceutically acceptable salt, or hydrate, or deuterated derivative thereof, may be administered in combination with a hormone or hormonal analog.

In some embodiments, a compound of Formula I, or a tautomer, stereoisomer or a mixture of stereoisomers, or a pharmaceutically acceptable salt, or hydrate, or deuterated derivative thereof, may be administered in combination with a signal transduction pathway inhibitor.

In some embodiments, a compound of Formula I, or a tautomer, stereoisomer or a mixture of stereoisomers, or a pharmaceutically acceptable salt, or hydrate, or deuterated derivative thereof, may be administered in combination with an antimetabolite neoplastic agent.

In some embodiments, a compound of Formula I, or a tautomer, stereoisomer or a mixture of stereoisomers, or a pharmaceutically acceptable salt, or hydrate, or deuterated derivative thereof, may be administered in combination with a topoisomerase I inhibitor.

In some embodiments, a compound of Formula I, or a tautomer, stereoisomer or a mixture of stereoisomers, or a pharmaceutically acceptable salt, or hydrate, or deuterated derivative thereof, may be administered in combination with a topoisomerase II inhibitor.

In some embodiments, a compound of Formula I, or a tautomer, stereoisomer or a mixture of stereoisomers, or a pharmaceutically acceptable salt, or hydrate, or deuterated derivative thereof, may be administered in combination with an aromatase inhibitor.

Also provided herein is a compound of Formula I, or a pharmaceutically acceptable salt or solvate thereof, or a pharmaceutical composition thereof as defined herein for use in therapy Also provided herein is a compound of Formula I, or a pharmaceutically acceptable salt or solvate/hydrate thereof or a pharmaceutical composition thereof as defined herein for use in the treatment of cancer.

Also provided herein is a compound of Formula I, or a pharmaceutically acceptable salt or solvate thereof for use in the inhibition of CDK. In some embodiments, the CDK is CDK4.

Also provided herein is a compound of Formula I, or a pharmaceutically acceptable salt or solvate thereof or a pharmaceutical composition thereof as defined herein, for use in the treatment of a disease or condition modulated at least in part by one or more CDKs.

Also provided herein is the use of a compound of Formula I, or a pharmaceutically acceptable salt or solvate thereof, as defined herein in the manufacture of a medicament for the treatment of cancer.

Also provided herein is a use of a compound of Formula I, or a pharmaceutically acceptable salt or solvate thereof, as defined herein in the manufacture of a medicament for the inhibition of activity of one or more CDKs.

Also provided herein is the use of a compound of Formula I, or a pharmaceutically acceptable salt or solvate thereof, as defined herein, in the manufacture of a medicament for the treatment of a disease or condition modulated at least in part by CDK.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from −10° C. to 200° C. Further, except as otherwise specified, reaction times and conditions are intended to be approximate, e.g., taking place at atmospheric pressure within a temperature range of −10° C. to 200° C. over a period that can be, for example, 1 to 24 hours; reactions left to run overnight in some embodiments can average a period of 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, 3Rd Ed., 1990 New York: Plenum Press; Mundy et al., Name Reaction and Reagents in Organic Synthesis, 2"d Ed., 2005 Hoboken, NJ: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) *Protective Groups in Organic Synthesis, 3'd Ed.*, John Wiley & Sons). These groups may be removed at a convenient stage of the compound synthesis using methods that are readily apparent to those skilled in the art.

When desired, the (R)- and(S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valences apply to all compounds disclosed herein in genus or named compound for unless otherwise specified.

The following abbreviations have the definitions set forth below:

MeCN: Acetonitrile
Ac$_2$O: Acetic anhydride
AcOH: Acetic acid
aq: Aqueous
Bzpinz: 4,4,4',4',5,5,5',5'-Octamethyl-2,2'-bi-1,3,2-dioxaborolane
Bn: Benzyl
Boc: tert-Butyloxycarbonyl protecting group
Cs$_2$CO$_3$: Cesium carbonate
DCE: 1,2-Dichloroethane
DCM: Dichloromethane
DIEA: N,N-Diisopropylethylamine
DMAP: 4-Dimethylaminopyridine
DME: Dimethoxyethane
DMF: Dimethylformamide
DMSO: Dimethyl sulfoxide
DIPEA: N, N-Diisopropylethylamine
EA: Ethyl acetate
e.e.: enantiomeric excess
EtOAc: Ethyl acetate
EtOH: Ethanol
equiv: Equivalent
FA: Formic acid
KOAc: Potassium acetate
KOH: Potassium hydroxide
LDA: Lithium Diisopropylamide
LiOH: Lithium hydroxide
Mel: Methyl Iodide
MeOH: Methanol
Ms$_2$O: Methanesulfonic anhydride
MsCI: Methanesulfonyl chloride
NaBH$_4$: Sodium borohydride
NaH: Sodium hydride
NEts: Triethylamine
Pd (dppf) Cl$_2$: [1,1'-Bis(diphenylphosphino) ferrocene] dichloropalladium (II)
Pd(PPh$_3$)$_4$: Tetrakis (triphenylphosphine) palladium (0)
Pd-Ad$_2$ (n-BuP): Butyldi-1-adamantylphosphine palladium (0)
PPh$_3$: Triphenylphosphine
py: Pyridine
RT: Room temperature
sat: Saturated
SFC: Supercritical fluid chromatography
T3P: 2,4,6-Tripropyl-1,3,5,2$\lambda^5$,4$\lambda^5$,6$\lambda^5$-trioxatriphosphinane-2,4,6-trione
TEA: Triethylamine
TFA: Trfluoroacetic Acid
THF: Tetrahydrofuran
TMSCI: Trimethylsilyl chloride
TsOH: 4-Methylbenzene-1-sulfonic acid
Pd(OH)$_2$/C: Palladium hydroxide on carbon
Pd/C: Palladium on carbon Compounds described in the experimental section were prepared from commercially available starting materials. Purity of all final compounds was analyzed by HPLC with detection at 214 nm and 254 nm wavelength. All final compounds exhibited purity greater than 95%. All final compounds were characterized by LC/MS and $^1$H-NMR. Key intermediates were analyzed by 2D-$^1$H-NMR to confirm regio- and stereochemistry. The following are representative examples demonstrating how the disclosed compounds can be made. However, a person skilled in the art would understand that the compounds could be prepared by other synthesis methods.

General Synthesis Schemes

Compounds of the present disclosure can be prepared according to the following schemes. The following schemes represent the general methods that can be used in preparing these compounds. However, the synthesis of these compounds is not limited to these representative methods, as they can also be prepared by various other methods those skilled in the art in synthetic chemistry, for example, in a stepwise or modular fashion, can readily envision.

General Synthetic Scheme 1

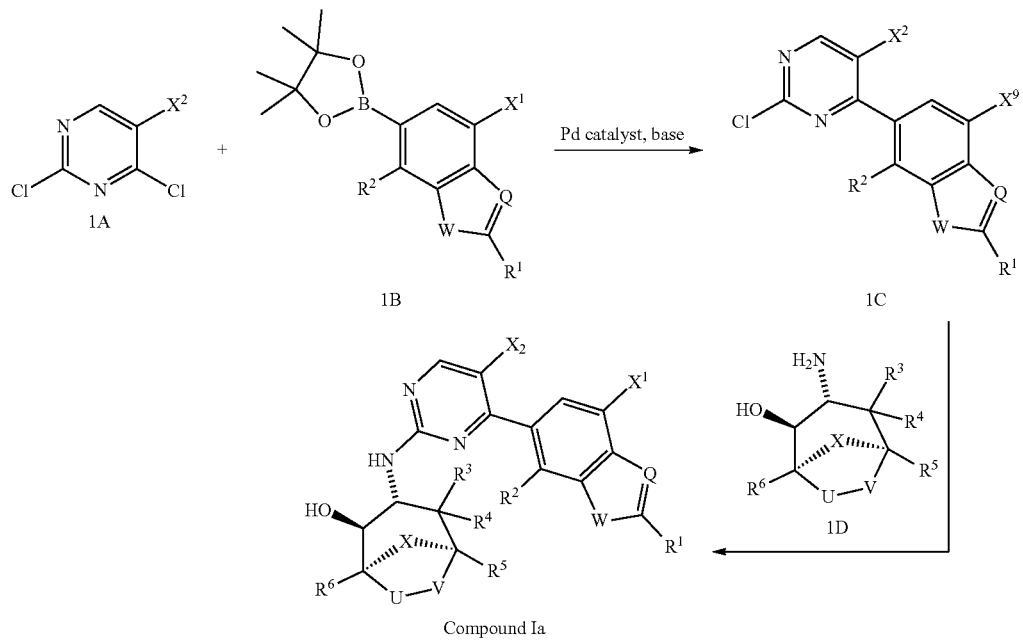

Compound Ia

In General Synthetic Scheme 1, Suzuki coupling of 5-substituted 2,4-dichloropyrimidine 1A and organoborane 1B in the presence of a suitable Pd-based catalyst such as Pd(PPh$_3$)$_4$ or Pd (dppf)$_2$Cl$_2$ and a suitable base such as K$_2$CO$_3$ or K$_3$PO$_4$ in aqueous solvents such as dioxane or DMF can be used to obtain 5-substituted-4-aryl-(or heteroaryl)-2-chloropyrimidine 1C. Subsequent displacement of the chloride in pyrimidine intermediate 1C with amine 1D can provide the target Compound Ia.

General Synthetic Scheme 2

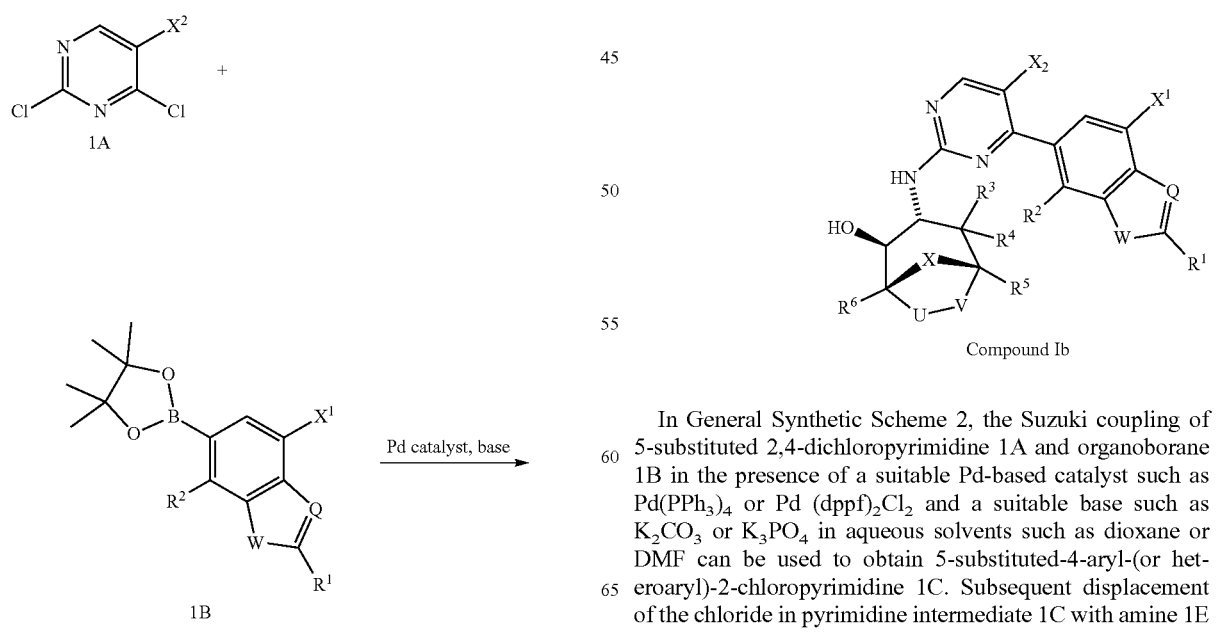

-continued

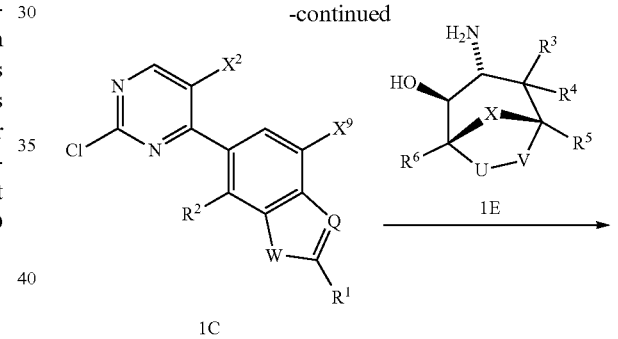

Compound Ib

In General Synthetic Scheme 2, the Suzuki coupling of 5-substituted 2,4-dichloropyrimidine 1A and organoborane 1B in the presence of a suitable Pd-based catalyst such as Pd(PPh$_3$)$_4$ or Pd (dppf)$_2$Cl$_2$ and a suitable base such as K$_2$CO$_3$ or K$_3$PO$_4$ in aqueous solvents such as dioxane or DMF can be used to obtain 5-substituted-4-aryl-(or heteroaryl)-2-chloropyrimidine 1C. Subsequent displacement of the chloride in pyrimidine intermediate 1C with amine 1E can provide the target Compound Ib.

General Synthetic Scheme 3

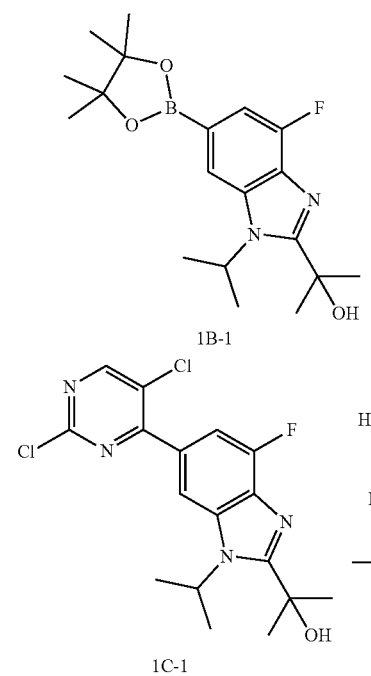

General Synthetic Scheme 4

In General Synthetic Scheme 3, a solution of the 2-(4-fluoro-1-isopropyl-6-(4,4,5,5-tetramethyl-1,3,2-dioxaborolan-2-yl)-1H-benzo[d]imidazol-2-yl) propan-2-ol (1B-1, 1 equiv.), 2,4,5-trichloropyrimidine (1A-1, 1.3 equiv.), and an inorganic base such as Na$_2$CO$_3$ (3 equiv.) or K$_2$CO$_3$ (3 equiv.) in aqueous 1,4-dioxane can be degassed and backfilled with nitrogen. Pd(PPh$_3$)$_4$ (0.1 equiv.) or Pd (dppf) Cl$_2$ (0.1 equiv.) can be added under nitrogen atmosphere. The mixture can be heated to 50° C. to 120° C. under N$_2$ until the starting material is consumed to produce the desired 2-(6-(2,5-dichloropyrimidin-4-yl)-4-fluoro-1-isopropyl-1H-benzo[d]imidazol-2-yl) propan-2-ol (1C-1). Subsequent displacement of the chloride in pyrimidine intermediate 1C-1 with amine 1D can provide the target Compound Ic.

In General Synthetic Scheme 4, Suzuki coupling reaction of methyl (R)-3-(4-fluoro-1-isopropyl-6-(4,4,5,5-tetramethyl-1,3,2-dioxaborolan-2-yl)-1H-benzo[d]imidazol-2-yl) pyrrolidine-1-carboxylate (1B-2, 1 equiv.) and 2,4,5-trichloropyrimidine (1A-1, 1.3 equiv.) can be conducted in the presence an inorganic base such as Na$_2$CO$_3$ (3 equiv.) or K$_2$CO$_3$ (3 equiv.) and a suitable Pd catalyst such as Pd(PPh$_3$)$_4$ (0.1 equiv.) or Pd (dppf) Cl$_2$ (0.1 equiv.) in aqueous 1,4-dioxane. The resulting mixture can be degassed and backfilled with nitrogen three times, and then heated under stirring to 50° C. to 120° C. under N$_2$ until the starting materials are consumed. The desired methyl (R)-3-(6-(2,5-dichloropyrimidin-4-yl)-4-fluoro-1-isopropyl-1H-benzo[d]imidazol-2-yl) pyrrolidine-1-carboxylate (1C-2) can thus be obtained. Subsequent displacement of the chloride in pyrimidine intermediate 1C-2 with amine 1D can provide the target Compound Id.

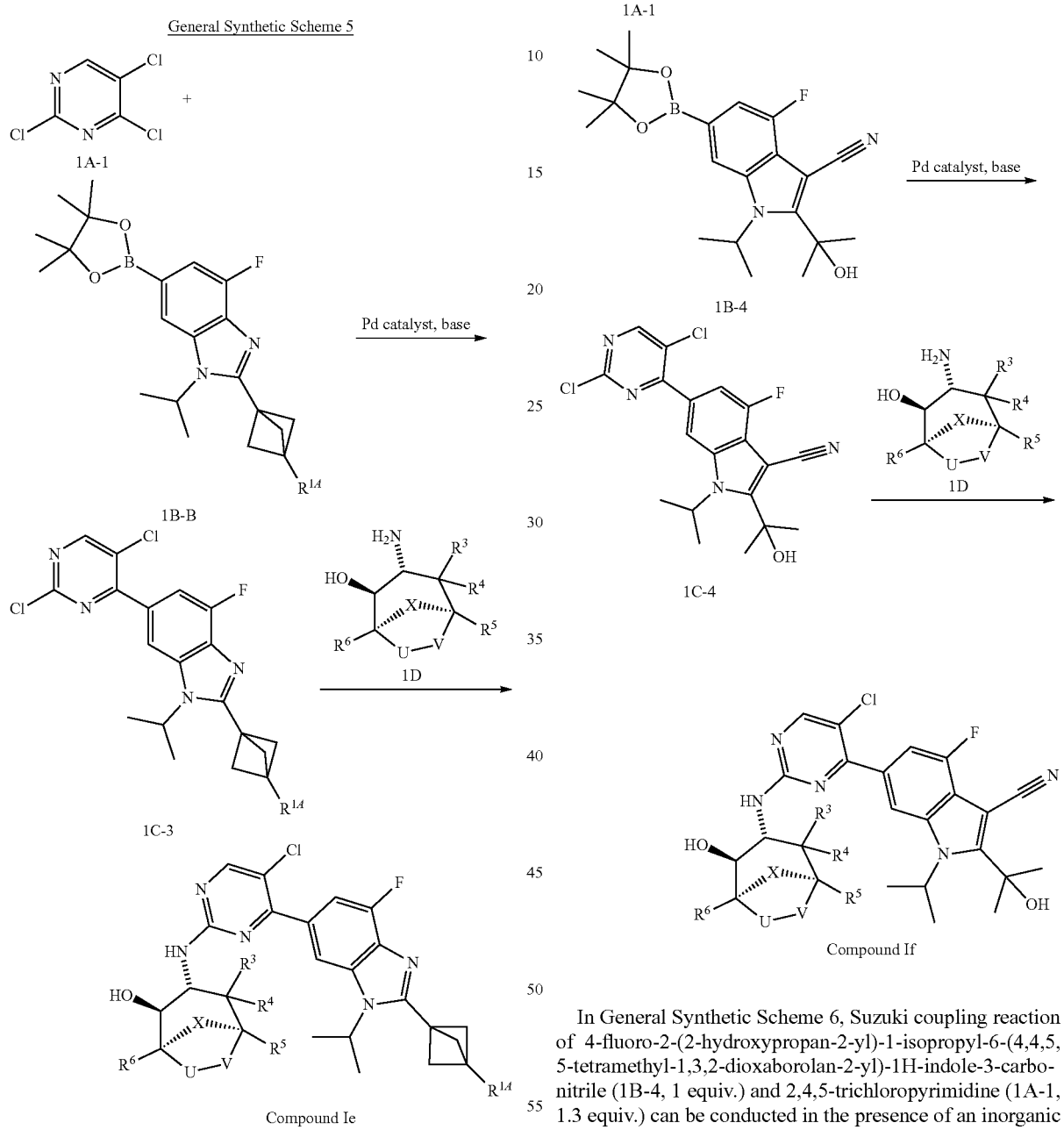

In General Synthetic Scheme 5, Suzuki coupling reaction of 2,4,5-trichloropyrimidine (1A-1, 1.3 equiv.) and organoborane (1B-3, 1.3 equiv.) in the presence of a suitable Pd-based catalyst such as Pd(PPh$_3$)$_4$ or Pd (dppf)$_2$Cl$_2$ in the presence of a base such as Na$_2$CO$_3$, K$_2$CO$_3$, or K$_3$PO$_4$ in an aqueous solvent such as dioxane, DMF can be provide 5-chloro-4-aryl-(or heteroaryl)-2-chloropyrimidine (1C-3). Subsequent displacement of the chloride in pyrimidine intermediate 1C-3 with amine 1D can provide the target Compound Ie.

In General Synthetic Scheme 6, Suzuki coupling reaction of 4-fluoro-2-(2-hydroxypropan-2-yl)-1-isopropyl-6-(4,4,5,5-tetramethyl-1,3,2-dioxaborolan-2-yl)-1H-indole-3-carbonitrile (1B-4, 1 equiv.) and 2,4,5-trichloropyrimidine (1A-1, 1.3 equiv.) can be conducted in the presence of an inorganic base such as Na$_2$CO$_3$ (3 equiv.) or K$_2$CO$_3$ (3 equiv.) and a suitable Pd catalyst such as Pd(PPh$_3$)$_4$ (0.1 equiv.) or Pd (dppf) Cl$_2$ (0.1 equiv.) in aqueous 1,4-dioxane. The resulting mixture can be degassed and backfilled with nitrogen three times, and then heated under stirring to 50° C. to 120° C. under N$_2$ until the starting materials are consumed. The desired 6-(2,5-dichloropyrimidin-4-yl)-4-fluoro-2-(2-hydroxypropan-2-yl)-1-isopropyl-1H-indole-3-carbonitrile (1C-4) can be thus obtained. Subsequent displacement of the chloride in pyrimidine intermediate 1C-4 with amine 1D can provide the target Compound If.

General Synthetic Scheme 7

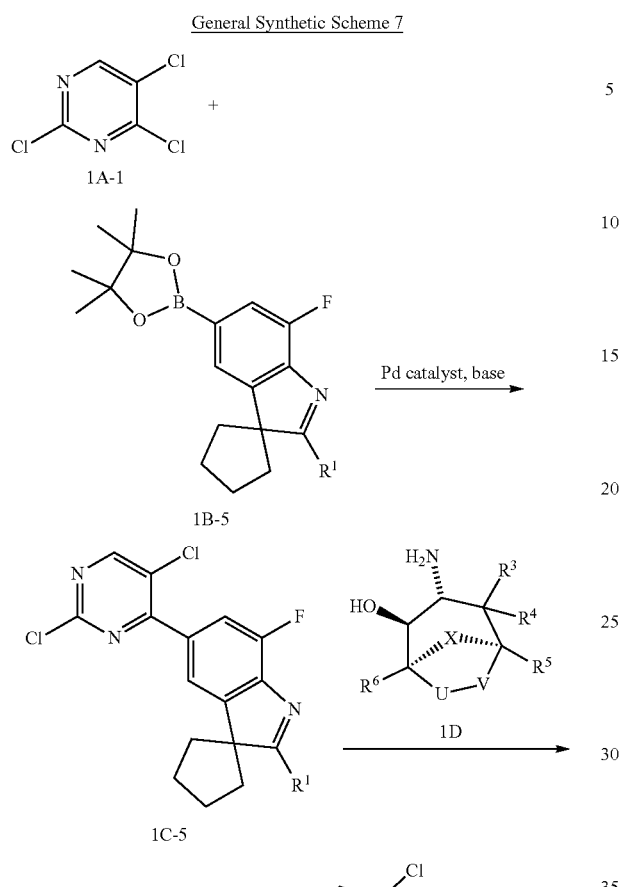

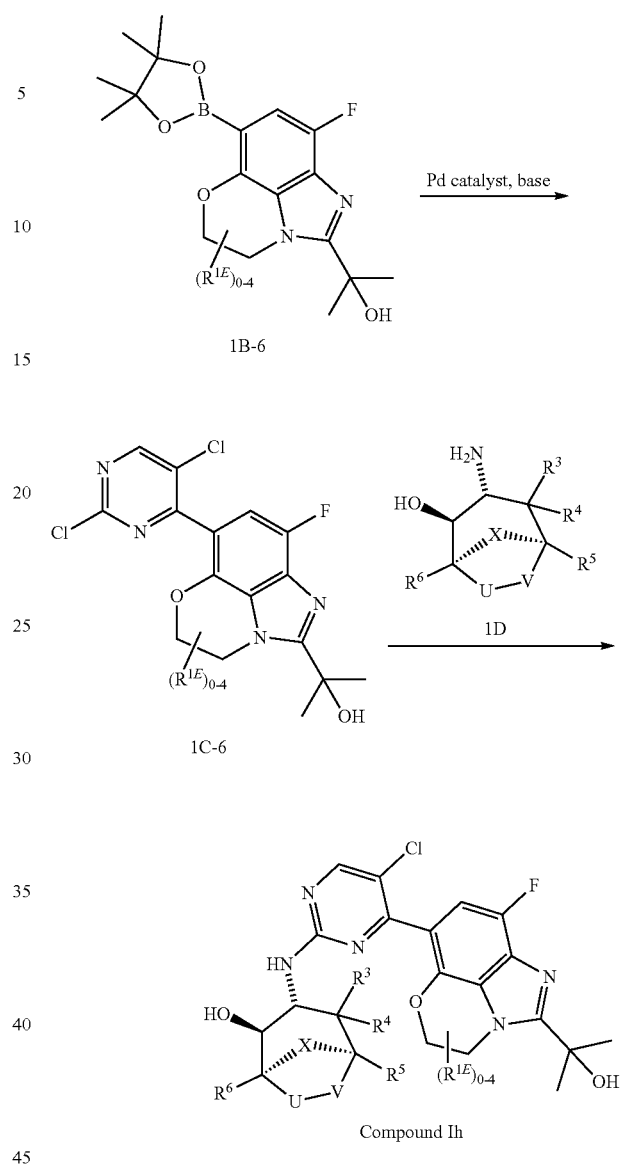

In General Synthetic Scheme 7, Suzuki coupling reaction of 2,4,5-trichloropyrimidine (1A-1, 1.3 equiv.) and organoborane (1B-5, 1.3 equiv.) can be conducted in the presence of a suitable Pd-based catalyst such as Pd(PPh$_3$)$_4$ or Pd (dppf)$_2$Cl$_2$ and a base such as Na$_2$CO$_3$, K$_2$CO$_3$, or K$_3$PO$_4$ in aqueous dioxane or DMF to provide 5-chloro-4-aryl-(or heteroaryl)-2-chloropyrimidines (1C-5). Subsequent displacement of the chloride in pyrimidine intermediate 1C-5 with amine 1D can provide the target Compound Ig.

In General Synthetic Scheme 8, Suzuki coupling reaction between 2,4,5-trichloropyrimidine (1A-1, 1.3 equiv.) and organoborane (1B-6, 1.3 equiv.) in the presence of a suitable Pd-based catalyst such as Pd(PPh$_3$)$_4$ or Pd (dppf)$_2$Cl$_2$ and a suitable base such as Na$_2$CO$_3$, K$_2$CO$_3$, or K$_3$PO$_4$ in an aqueous solvent such as dioxane or DMF can provide 5-chloro-4-aryl-(or heteroaryl)-2-chloropyrimidines (1C-6). Subsequent displacement of the chloride in pyrimidine intermediate 1C-6 with amine 1D can provide the target Compound Ih.

General Synthetic Scheme 8

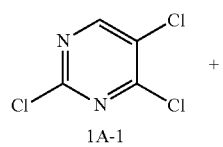

General Synthetic Scheme 9

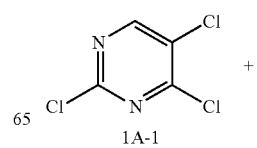

General Synthetic Scheme 10

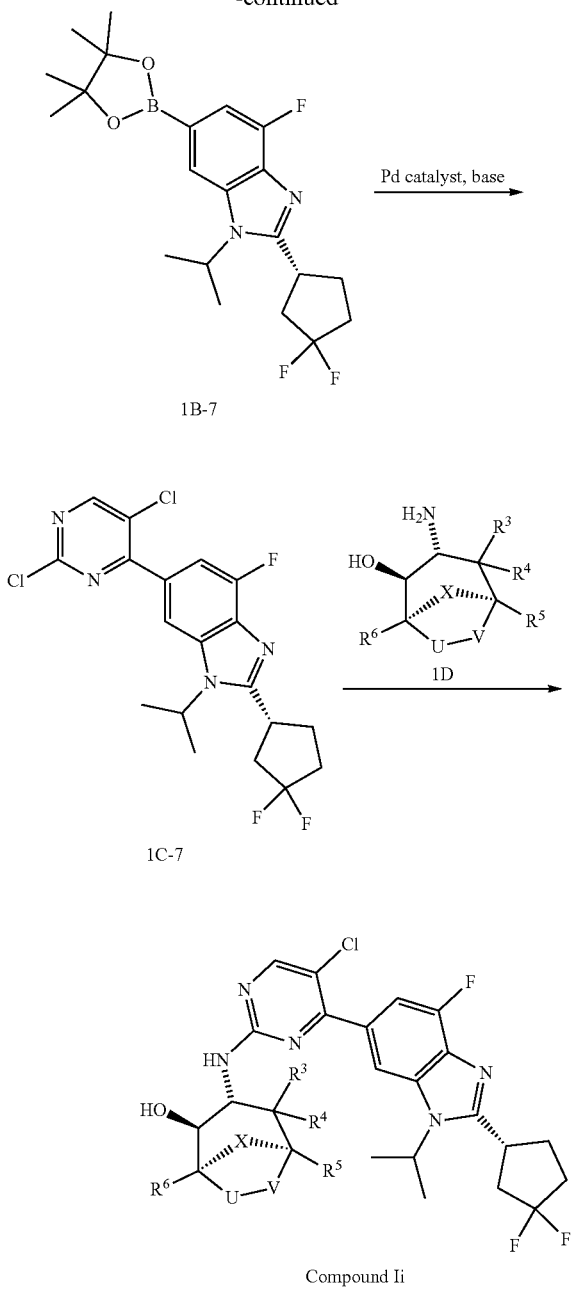

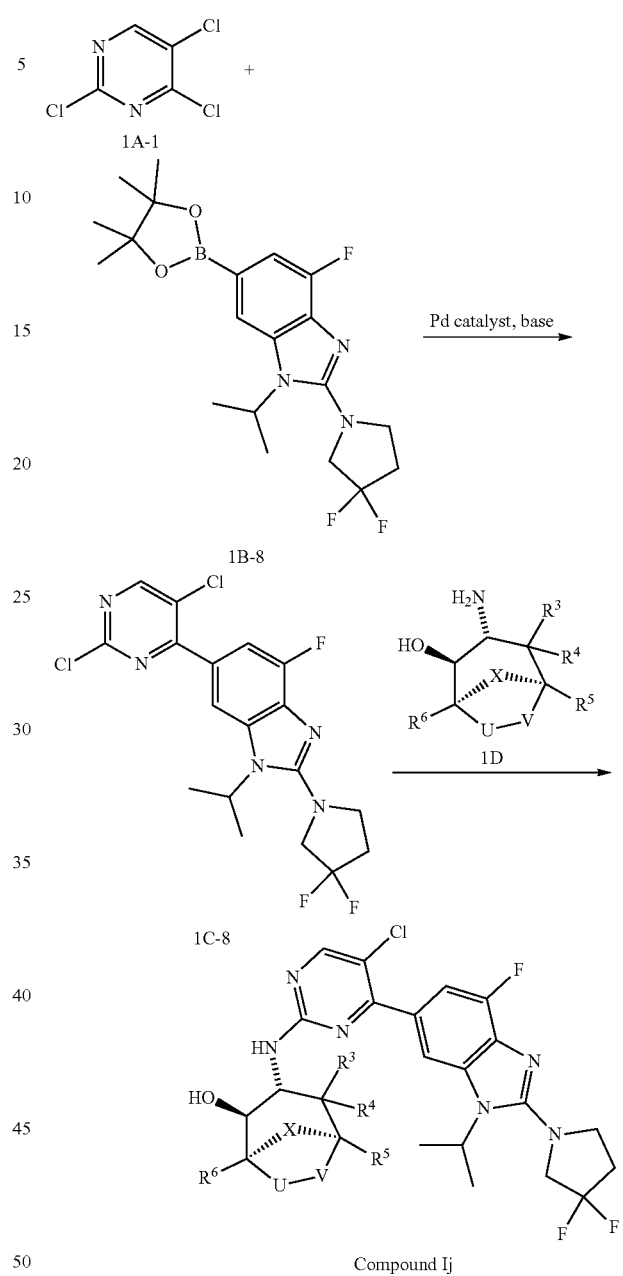

In General Synthetic Scheme 9, Suzuki coupling reaction between 2,4,5-trichloropyrimidine (1A-1, 1.3 equiv.) and (R)-2-(3,3-difluorocyclopentyl)-4-fluoro-1-isopropyl-6-(4,4,5,5-tetramethyl-1,3,2-dioxaborolan-2-yl)-1H-benzo[d]imidazole (1B-7, 1.3 equiv.) can be conducted in the presence of a suitable Pd-based catalyst such as $Pd(PPh_3)_4$ or Pd $(dppf)_2Cl_2$ and a suitable base such as $Na_2CO_3$ or $K_2CO_3$, in an aqueous solution of dioxane. The resulting mixture can be degassed and backfilled with nitrogen three times, and then heated under stirring to 50° C. to 120° C. under $N_2$ until the starting materials are consumed. The desired (R)-6-(2,5-dichloropyrimidin-4-yl)-2-(3,3-difluorocyclopentyl)-4-fluoro-1-isopropyl-1H-benzo[d]imidazole (1C-7) can be thus obtained. Subsequent displacement of the chloride in pyrimidine intermediate 1C-7 with amine 1D can provide the target Compound Ii.

In General Synthetic Scheme 10, Suzuki coupling reaction between 2,4,5-trichloropyrimidine (1A-1, 1.3 equiv.) and 2-(3,3-difluoropyrrolidin-1-yl)-4-fluoro-1-isopropyl-6-(4,4,5,5-tetramethyl-1,3,2-dioxaborolan-2-yl)-1H-benzo[d]imidazole (1B-8, 1.3 equiv.) can be conducted in the presence of a suitable Pd-based catalyst such as $Pd(PPh_3)_4$ or Pd $(dppf)_2Cl_2$ and a suitable base such as $Na_2CO_3$ or $K_2CO_3$, in an aqueous solution of dioxane. The resulting mixture can be degassed and backfilled with nitrogen three times, and then heated under stirring to 50° C. to 120° C. under $N_2$ until the starting materials are consumed. The desired 6-(2,5-dichloropyrimidin-4-yl)-2-(3,3-difluoropyrrolidin-1-yl)-4-fluoro-1-isopropyl-1H-benzo[d]imidazole (1C-8) can thus be obtained. Subsequent displacement of the chloride in pyrimidine intermediate 1C-8 with amine 1D can provide the target Compound Ij.

General Synthetic Scheme 11

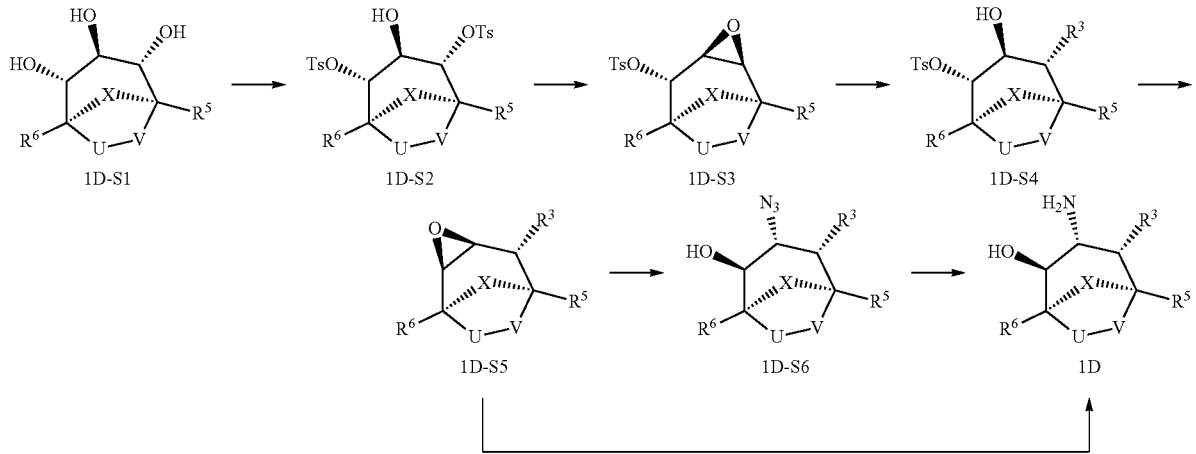

In General Synthetic Scheme 11, selective tosylation of the hydroxy groups in 1D-S1 can provide 1D-S2. Regioselective epoxidation of 1D-S2 under basic conditions can provide 1D-S3. The epoxide of 1D-S3 can be opened with reducing reagents such as $NaBH_4$ or $NaBD_4$ or organometallic reagents such as Grignard reagents or with fluorinating reagents such as DAST to provide ring-opened 1D-S4. Subsequent epoxidation thereof under basic condition can afford 1D-S5. Subjection of 1D-S5 to sodium azide can provide the desired ring-opened 1D-S6. Reduction of the azide to the corresponding amine can provide 1D. Alternatively, epoxide 1D-S5 can directly be subjected to ring-opening with $NH_4OH$ to give the 1D.

General Synthetic Scheme 12

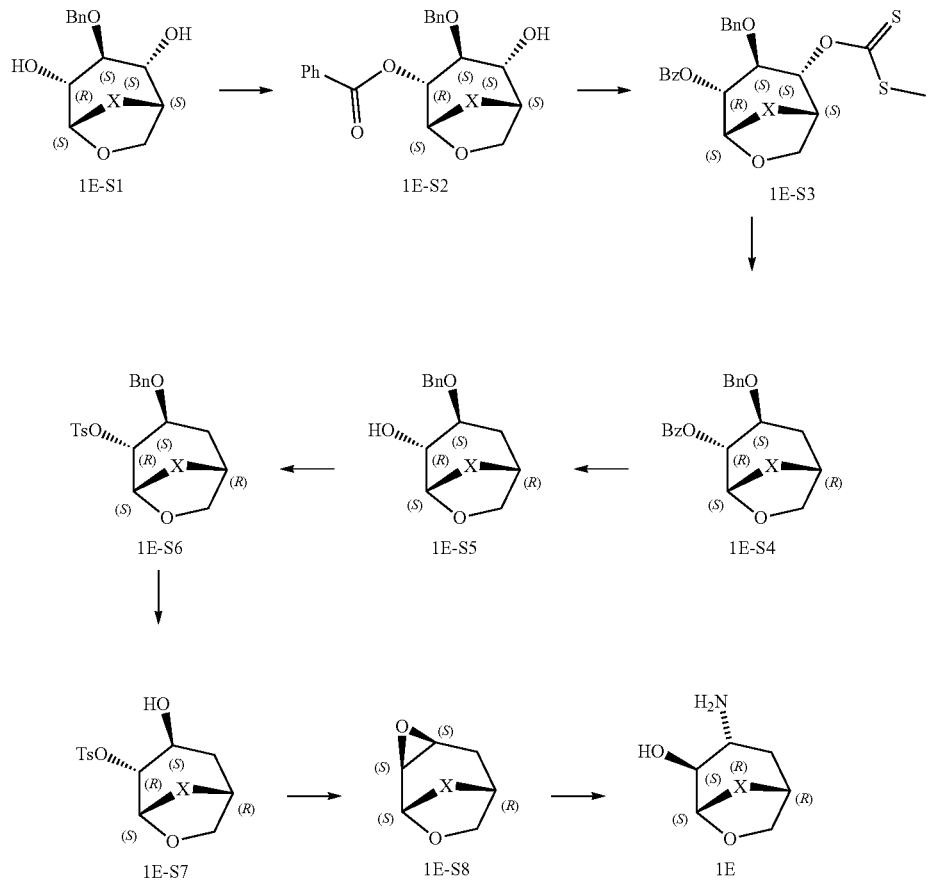

In General Synthetic Scheme 12, one of the hydroxyl groups in 1E-S1 is selectively protected with -OBz to give 1E-S2. The free hydroxyl group of 1E-S2 is then converted to thioester 1E-S3, which is reduced to yield 1E-S4. Deprotection of the -OBz group and subsequent tosylation of the newly formed hydroxy group of 1E-S5 provides 1E-S6. The debenzylation of 1E-S6 gives 1E-S7, which can lead to epoxide formation to furnish 1E-S8. The epoxide 1E-S8 can directly be subjected to ring-opening with NH₄OH to give the intermediate 1E.

General Synthetic Scheme 13

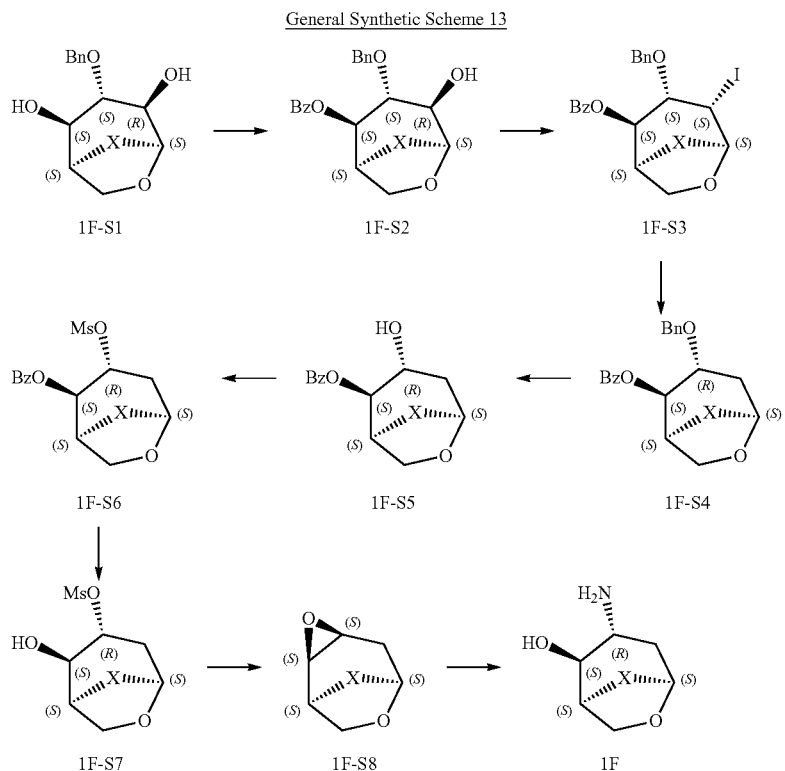

In General Synthetic Scheme 13, the hydroxyl groups in 1F-S1 are selectively protected with -OTf and OBz to give 1F-S2. The leaving group-OTf in 1F-S2 is replaced by iodide to provide 1F-S3, which is reduced to yield 1F-S4. Deprotection of the benzyl group and subsequent mesylation of the newly formed hydroxy group of 1F-S5 provides 1F-S6, which after deprotection of the benzoyl ester in 1F-S7 can lead to epoxide formation to furnish 1F-S8. The epoxide 1F-S8 can directly be subjected to ring-opening with NH₄OH to give the intermediate 1F General Synthetic Scheme 14

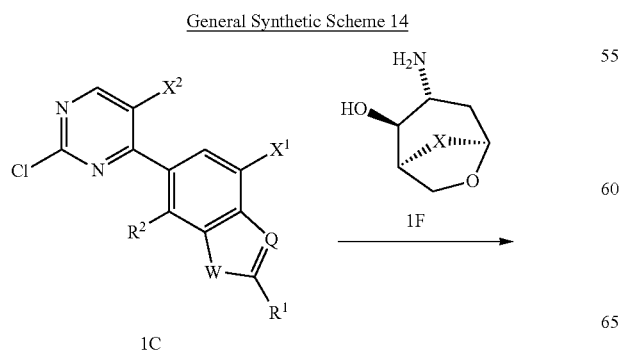

-continued

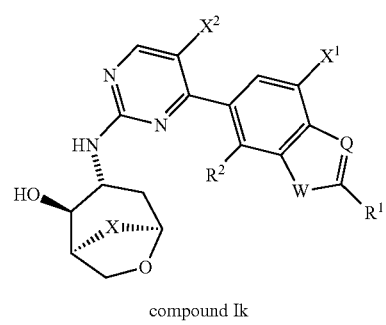

compound Ik

In General Synthetic Scheme 14, the displacement of 2-$C_1$ in the pyrimidine intermediate 1C with amine 1F provides the desired target molecules Ik.

General Synthetic Scheme 15

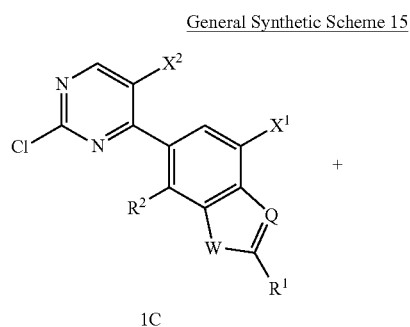

1C

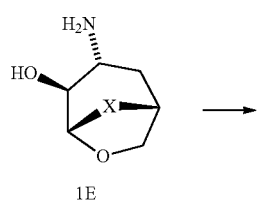

1E

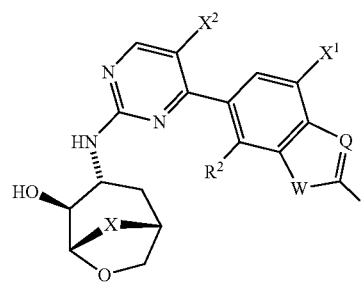

compound II

In General Synthetic Scheme 15, displacement of the chloride in pyrimidine intermediate 1C with amine 1E can provide the target Compound I.

General Synthetic Scheme 16

1A

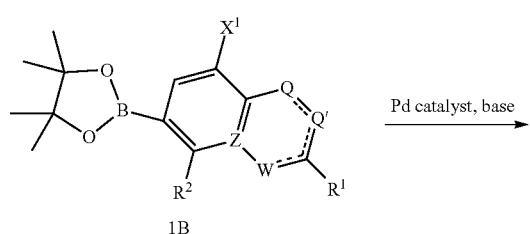

1B

Pd catalyst, base →

-continued

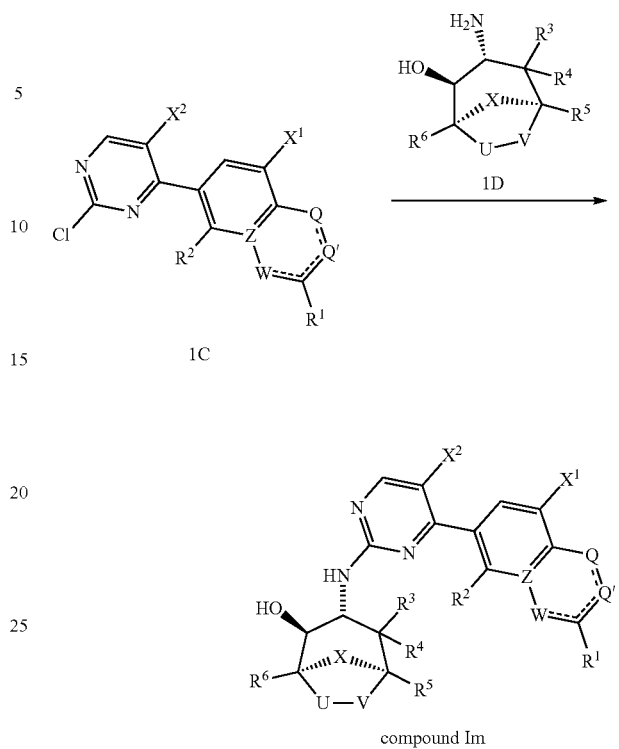

In General Synthetic Scheme 16, Suzuki coupling of 5-substituted 2,4-dichloropyrimidine 1A and organoborane 1B in the presence of a suitable Pd-based catalyst such as Pd(PPh$_3$)$_4$ or Pd (dppf)$_2$Cl$_2$ and a suitable base such as K$_2$CO$_3$ or K$_3$PO$_4$ in aqueous solvents such as dioxane or DMF can be used to obtain 5-substituted-4-aryl-(or heteroaryl)-2-chloropyrimidine 1C. Subsequent displacement of the chloride in pyrimidine intermediate 1C with amine 1D can provide the target Compound Im.

General Synthetic Scheme 17

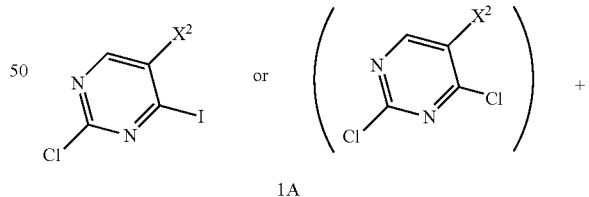

1A

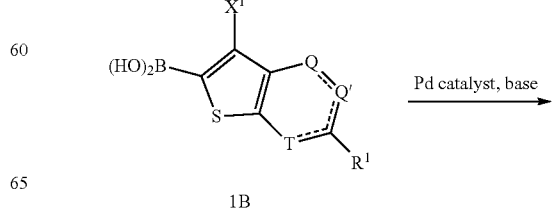

1B

Pd catalyst, base →

271
-continued

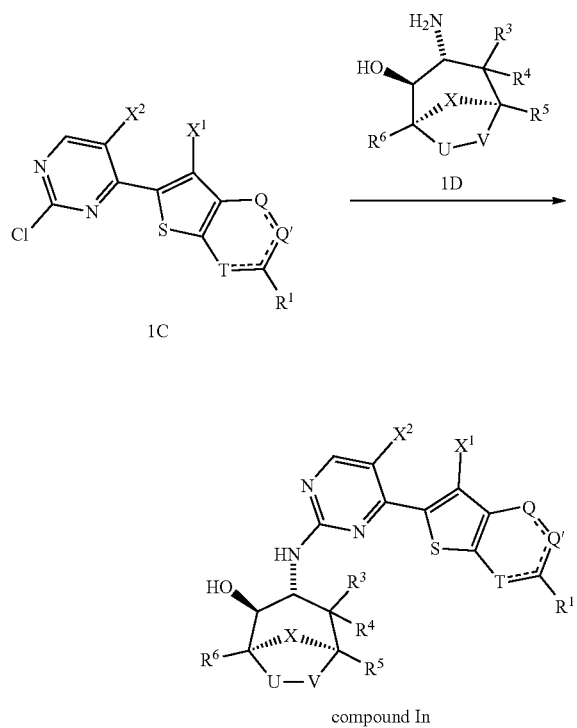

compound In

In General Synthetic Scheme 17, Suzuki coupling of 5-substituted-2-chloro-4-iodopyrimidine (or 5-substituted 2,4-dichloropyrimidine)₁A and organoborane 1B in the presence of a suitable Pd-based catalyst such as Pd(PPh₃)₄, Pd (dppf)₂Cl₂ or Pd-Ad₂ (n-BuP) and a suitable base such as K₂CO₃ or K₃PO₄ in aqueous solvents such as dioxane or DMF can be used to obtain S-substituted-4-aryl-(or heteroaryl)-2-chloropyrimidine 1C. Subsequent displacement of the chloride in pyrimidine intermediate 1C with amine 1D can provide the target Compound In.

272
-continued

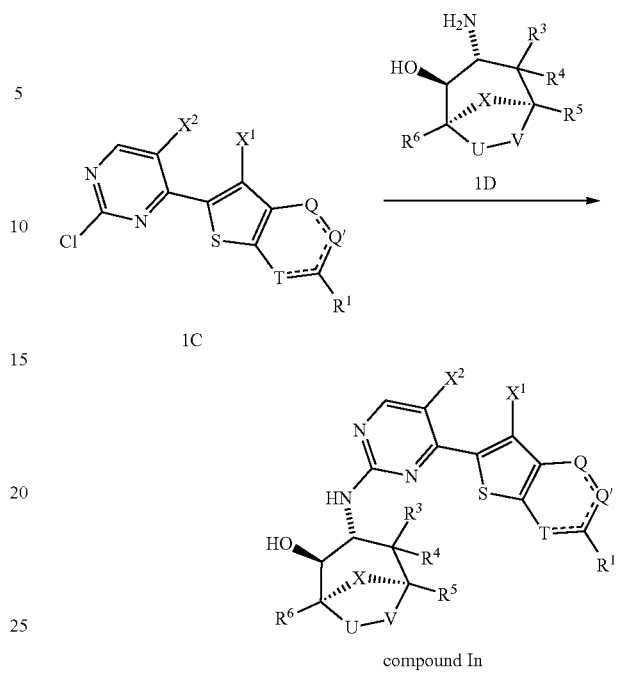

compound In

In General Synthetic Scheme 18, Suzuki coupling of 5-substituted-2-chloro-4-iodopyrimidine (or 5-substituted 2,4-dichloropyrimidine)₁A and organoborane 1B in the presence of a suitable Pd-based catalyst such as Pd(PPh₃)₄, Pd (dppf)₂Cl₂ or Pd-Ad₂ (n-BuP) and a suitable base such as K₂CO₃ or K₃PO₄ in aqueous solvents such as dioxane or DMF can be used to obtain 5-substituted-4-aryl-(or heteroaryl)-2-chloropyrimidine 1C. Subsequent displacement of the chloride in pyrimidine intermediate 1C with amine 1D can provide target Compound In.

Preparation of intermediates

Preparation of 2-(6-(2,5-dichloropyrimidin-4-yl)-4-fluoro-1-isopropyl-1H-benzo[d]imidazol-2-yl) propan-2-ol (1C-1)

General Synthetic Scheme 18

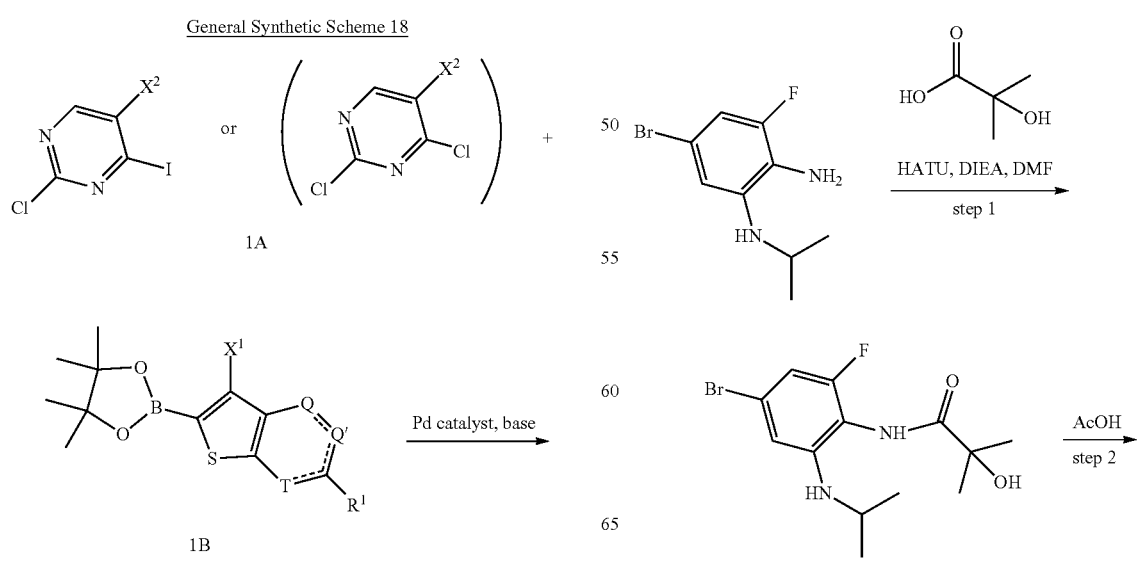

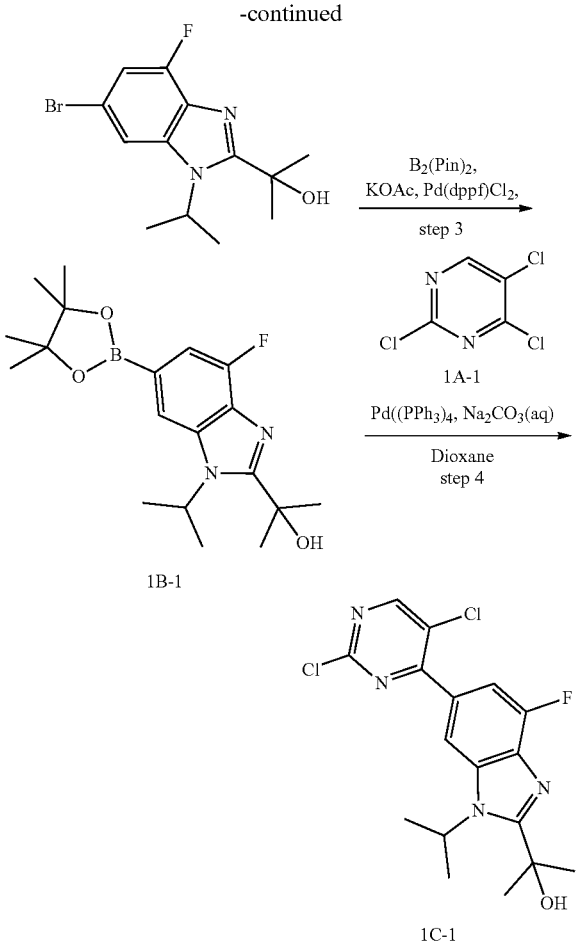

Step 1: Preparation of N-(4-bromo-2-fluoro-6-(isopropylamino)phenyl)-2-hydroxy-2-methylpropanamide To a solution of 5-bromo-3-fluoro-N[1]-isopropyl-benzene-1,2-diamine (40.5 g, 163.90 mmol, 1 equiv.) and 2-hydroxy-2-methyl-propanoic acid (17.06 g, 163.90 mmol, 1 equiv.) in DMF (500 mL) was added DIEA (42.36 g, 327.79 mmol, 57.10 mL, 2 equiv.) at 0° C., followed by addition of HATU (68.55 g, 180.29 mmol, 1.1 equiv.) in portions while the inner temperature was maintained at 0° C. After complete addition, the reaction was warmed and allowed to stir for 6 h at room temperature. The reaction mixture was quenched by addition of $H_2O$ (2000 mL), and the aqueous phase was extracted with EtOAc (1000 mL×2). The combined organic layers were washed with brine (1000 mL), dried over $Na_2SO_4$, filtered, and concentrated under reduced pressure. The resulting residue was purified by flash column chromatography (silica gel) to give N-(4-bromo-2-fluoro-6-(isopropylamino)phenyl)-2-hydroxy-2-methylpropanamide (14.7 g, 26.92% yield) as brown oil. LCMS: 332.9/334.9 [M+H]⁺.

Step 2: Preparation of 2-(6-bromo-4-fluoro-1-isopropyl-1H-benzo[d]imidazol-2-yl) propan-2-ol A solution of N-(4-bromo-2-fluoro-6-(isopropylamino) phenyl)-2-hydroxy-2-methylpropanamide (7.25 g, 21.76 mmol, 1 equiv.) in AcOH (60 mL) was allowed to stir for 8 h at 140° C. in a sealed tube. Subsequently, the reaction vessel was cooled to room temperature, and the reaction mixture was concentrated under reduced pressure. The resulting residue was dissolved in EtOAc (200 mL) and then carefully washed with saturated $Na_2CO_3$ (50 mL) and brine (50 mL) sequentially. The organic phase was dried over $Na_2SO_4$, filtered, and concentrated under reduced pressure. The residue was purified by column chromatography to give 2-(6-bromo-4-fluoro-1-isopropyl-1H-benzo[d]imidazol-2-yl) propan-2-ol (5.4 g, 39.37% yield) as off-white solid. LCMS: 314.9/316.9 [M+H]; ¹H NMR (400 MHZ, CDCl₃) δ 7.42 (s, 1H), 7.02-7.00 (d, J=8.0 Hz, 1H), 5.40-5.37 (m, 1H), 1.70 (s, 6H), 1.50 (s, 6H) ppm.

Step 3: Preparation of 2-(4-fluoro-1-isopropyl-6-(4,4,5,5-tetramethyl-1,3,2-dioxaborolan-2-yl)-1H-benzo[d]imidazol-2-yl) propan-2-ol (1B-1)

A mixture of 2-(6-bromo-4-fluoro-1-isopropyl-benzimidazol-2-yl) propan-2-ol (5.4 g, 17.13 mmol, 1 equiv.), 4,4,5,5-tetramethyl-2-(4,4,5,5-tetramethyl-1,3,2-dioxaborolan-2-yl)-1,3,2-dioxaborolane (5.22 g, 20.56 mmol, 1.2 equiv.), and KOAc (5.04 g, 51.40 mmol, 3 equiv.) in dioxane (100 mL) was degassed and backfilled with $N_2$ thrice. Then, Pd (dppf) Cl₂ (1.25 g, 1.71 mmol, 0.1 equiv.) was added under $N_2$ atmosphere, and the reaction mixture was stirred for 12 h at 100° C. under $N_2$ atmosphere. After the starting material was consumed, the reaction was allowed to cool to room temperature, and the volatiles were removed under reduced pressure. The so-obtained residue was diluted with EtOAc (100 mL) and allowed to stir for 10 min. Then, the thus-formed solid was filtered off and the filtrate was concentrated. The resulting residue was purified by column chromatography to give 2-(4-fluoro-1-isopropyl-6-(4,4,5,5-tetramethyl-1,3,2-dioxaborolan-2-yl)-1H-benzo[d]imidazol-2-yl) propan-2-ol (4.9 g, 78.95% yield) as off-white solid. LCMS: 363.1 [M+H].

Step 4: Preparation of 2-(6-(2,5-dichloropyrimidin-4-yl)-4-fluoro-1-isopropyl-1H-benzo[d]imidazol-2-yl) propan-2-ol A solution of 2-(4-fluoro-1-isopropyl-6-(4,4,5,5-tetramethyl-1,3,2-dioxaborolan-2-yl)-1H-benzo[d]imidazol-2-yl) propan-2-ol (2 g, 5.52 mmol, 1 equiv.), 2,4,5-trichloropyrimidine (1.32 g, 7.18 mmol, 1.3 equiv.), and $Na_2CO_3$ (1.76 g, 16.56 mmol, 3 equiv.) in 1,4-dioxane (30 mL) and $H_2O$ (9 mL) was degassed and backfilled with nitrogen thrice Subsequently, Pd(PPh₃)₄ (638.00 mg, 0.552 mmol, 0.1 equiv.) was added under nitrogen atmosphere, and the mixture was allowed to stir at 100° C. for 16 h under $N_2$ atmosphere until the starting material was consumed. The reaction was allowed to cool to room temperature, and volatiles were removed under reduced pressure. The so-obtained residue was diluted with EtOAc (300 mL), washed with brine (100 mL), dried over $Na_2SO_4$, and filtered. The filtrate was concentrated to give a crude product, which was purified by the column chromatography. The desired 2-(6-(2,5-dichloropyrimidin-4-yl)-4-fluoro-1-isopropyl-1H-benzo[d]imidazol-2-yl) propan-2-ol (1.73 g, 81.76% yield) was obtained as light-yellow solid. LCMS: 383.0 [M+H]⁺.

Preparation of methyl (R)-3-(6-(2,5-dichloropyrimidin-4-yl)-4-fluoro-1-isopropyl-1H-benzo[d]imidazol-2-yl) pyrrolidine-1-carboxylate (1C-2)

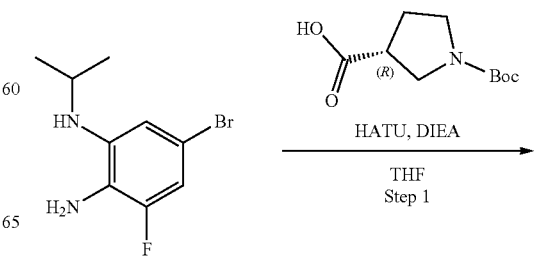

HATU, DIEA

THF
Step 1

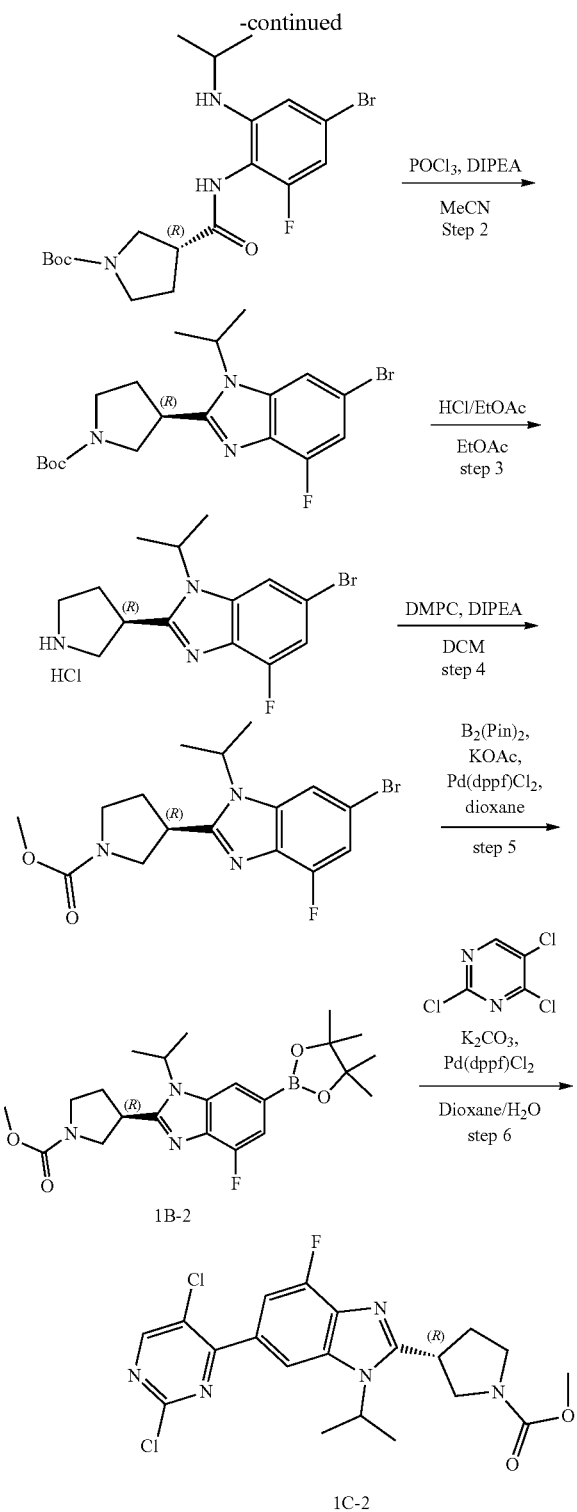

0.254 mol). The resulting mixture was allowed to stir at room temperature for 17 h. Then, volatiles were removed under reduced pressure, and the so-obtained residue was diluted with water (500 mL) and extracted with EtOAc (2×250 mL). The combined organic phases were washed with water (200 mL) and brine (200 mL) and dried over sodium sulfate. The mixture was filtered, and the filtrate was concentrated in vacuum. The resulting residue was purified by silica gel column chromatography (PE/EA=3/2) to give the desired product tert-butyl (R)-3-((4-bromo-2-fluoro-6-(isopropylamino)phenyl) carbamoyl) pyrrolidine-1-carboxylate (87 g, 85% yield) as red solid. LCMS: 442.4/444.2 [M–H]+.

Step 2: Preparation of tert-butyl (R)-3-(6-bromo-4-fluoro-1-isopropyl-1H-benzo[d]imidazol-2-yl) pyrrolidine-1-carboxylate To a solution of tert-butyl (R)-3-((4-bromo-2-fluoro-6-(isopropylamino)phenyl) carbamoyl) pyrrolidine-1-carboxylate (10.0 g, 22.50 mmol, 1.0 equiv.) in MeCN (100 mL) was added DIPEA (8.72 g, 67.5 mmol, 3.0 equiv.), followed by dropwise addition of POCl₃ (10.35 g, 67.5 mmol, 3.0 equiv.) at room temperature. The resulting solution was stirred at 40° C. for 8 h. Then, the reaction solution was allowed to cool to room temperature and carefully quenched by addition of sat. aq. NaHCO₃ (150 mL). The resulting mixture was extracted with DCM (2×150 mL). The combined organic phases were washed with sat. aq. NaHCO₃ (100 mL) and brine (100 mL), sequentially, and dried over anhydrous Na₂SO₄. The solution was filtered, and the filtrate was concentrated under reduced pressure. The residue was taken up with EtOAc (100 mL) and concentrated, the resulting brown residue tert-butyl (R)-3-(6-bromo-4-fluoro-1-isopropyl-1H-benzo[d]imidazol-2-yl) pyrrolidine-1-carboxylate (e.e. 94.1%) was used in the next step without further purification. LCMS: 426.2/428 2 [M+H].

Step 3: Preparation of (R)-6-bromo-4-fluoro-1-isopropyl-2-(pyrrolidin-3-yl)-1H-benzo[d]imidazole HCl salt To a solution of unpurified tert-butyl (R)-3-(6-bromo-4-fluoro-1-isopropyl-1H-benzo[d]imidazol-2-yl) pyrrolidine-1-carboxylate in EtOAc (30 mL) was added HCl/EA (50 mL, 4.0 M) at room temperature, and the solution was allowed to stir for 1 h. The resulting precipitation was filtered, and the filtered cake was washed with EtOAc (2×10 mL) and dried under vacuum to give (R)-6-bromo-4-fluoro-1-isopropyl-2-(pyrrolidin-3-yl)-1H-benzo[d]imidazole HCl salt (7.37 g, 90% yield for two steps) as a solid. LCMS: 326.0/328.0 [M+H]+.

Step 4: Preparation of methyl (R)-3-(6-bromo-4-fluoro-1-isopropyl-1H-benzo[d]imidazol-2-yl) pyrrolidine-1-carboxylate To a mixture of (R)-6-bromo-4-fluoro-1-isopropyl-2-(pyrrolidin-3-yl)-1H-benzo[d]imidazole HCl salt (10.34 g, 28.51 mmol, 1.0 equiv.) in DCM (100 mL) was added DIPEA (9.21 g, 71.28 mmol, 2.5 equiv.) and dimethyl dicarbonate (5.73 g, 42.77 mmol, 1.5 equiv.) at room temperature, and the resulting solution was allowed to stir for 30 min. The reaction mixture was diluted with DCM (100 mL) and washed with 7% aq. citric acid (2×100 mL). The combined organic phases were washed with brine (50 mL), dried over anhydrous Na₂SO₄, filtered, and concentrated. The resulting residue was purified by silica gel column chromatography (petroleum ether/ethyl acetate: 1/2) to afford methyl (R)-3-(6-bromo-4-fluoro-1-isopropyl-1H-benzo[d]imidazol-2-yl) pyrrolidine-1-carboxylate (5.7 g, 52% yield, e e. 93.96%) as a foam. LCMS: 384.2/386.2 [M+H].

Step 1: Preparation of tert-butyl (R)-3-((4-bromo-2-fluoro-6-(isopropylamino)phenyl) carbamoyl) pyrrolidine-1-carboxylate (R)-1-(tert-butoxycarbonyl) pyrrolidine-3-carboxylic acid (49.7 g, 0.231 mol) was added to a solution of 5-bromo-3-fluoro-N¹-isopropylbenzene-1,2-diamine (57.06 g, 0.231 mol) in THF (1000 mL) at room temperature, followed by addition of DIPEA (44.8 g, 0.346 mol) and HATU (96.57 g,

Step 5: Preparation of methyl (R)-3-(4-fluoro-1-isopropyl-6-(4,4,5,5-tetramethyl-1,3,2-dioxaborolan-2-yl)-1H-benzo[d]imidazol-2-yl) pyrrolidine-1-carboxylate (1B-2)

To a mixture of methyl (R)-3-(6-bromo-4-fluoro-1-isopropyl-1H-benzo[d]imidazol-2-yl) pyrrolidine-1-carboxylate (5.7 g, 14.83 mmol) and B2 (Pin)$_2$ (4.9 g, 19.28 mmol) in dioxane (46 mL) was added KOAc (2.912 g, 29.67 mmol) at room temperature. Then, Pd (dppf) Cl$_2$ (217 mg, 0.297 mmol) was added, and the mixture was allowed to stir at 90° C. for 2 h under nitrogen atmosphere. After cooling to room temperature, the mixture was filtered through Celite and washed with EtOAc (50 mL). The filtrate was concentrated under reduced pressure, and the residue was dissolved in EtOAc (100 mL), washed with brine (50 mL), and dried over sodium sulfate. The solution was filtered, and the filtrate was concentrated under reduced pressure to give 9.5 g of unpurified methyl (R)-3-(4-fluoro-1-isopropyl-6-(4,4,5,5-tetramethyl-1,3,2-dioxaborolan-2-yl)-1H-benzo[d]imidazol-2-yl) pyrrolidine-1-carboxylate, which was used in the next step without further purification. LCMS: 432.4 [M+H]$^+$.

Step 6: Preparation of methyl (R)-3-(6-(2,5-dichloropyrimidin-4-yl)-4-fluoro-1-isopropyl-1H-benzo[d]imidazol-2-yl) pyrrolidine-1-carboxylate To a mixture of unpurified methyl (R)-3-(4-fluoro-1-isopropyl-6-(4,4,5,5-tetramethyl-1,3,2-dioxaborolan-2-yl)-1H-benzo[d]imidazol-2-yl) pyrrolidine-1-carboxylate (9.5 g, crude, 14.83 mmol), 2,4,5-trichloropyrimidine (3.265 g, 17.8 mmol), and potassium carbonate K$_2$CO$_3$ (4.10 g, 29.67 mmol) in dioxane (51 mL) and water (15 mL), was added Pd (dppf) Cl$_2$ (217 mg, 0.297 mmol) under nitrogen atmosphere. The mixture was heated at 90° C. for 2 h under nitrogen atmosphere. After cooling to room temperature, the mixture was filtered through Celite and washed with EtOAc (200 mL). The filtrate was washed with brine (70 mL) and dried over sodium sulfate. The solid was filtered off, and the filtrate was concentrated under reduced pressure. The resulting residue was purified by silica gel column (PE/EtOAc=1/2) to give methyl (R)-3-(6-(2,5-dichloropyrimidin-4-yl)-4-fluoro-1-isopropyl-1H-benzo[d]imidazol-2-yl) pyrrolidine-1-carboxylate (3.4 g, 51% yield over 2 steps). LCMS: 452.2 [M+H]; $^1$HNMR (400 MHz, CDCl$_3$) δ 8.66 (s, 1H), 7.96 (s, 1H), 7.57 (d, J=12 Hz, 1H), 4.71-4.86 (m, 1H), 3.85-4.09 (m, 1H), 3.79-3.54 (m, 3H), 3.57 (s, 3H), 3.45-3.55 (m, 1H), 2.68-2.76 (m, 1H), 2.44-2.54 (m, 1H), 1.72 (d, J=8.0 Hz, 6H) ppm.

Preparation of (S)-6-(2,5-dichloropyrimidin-4-yl)-2-(3,3-difluorocyclopentyl)-4-fluoro-1-isopropyl-1H-benzo[d]imidazole (1C-3)

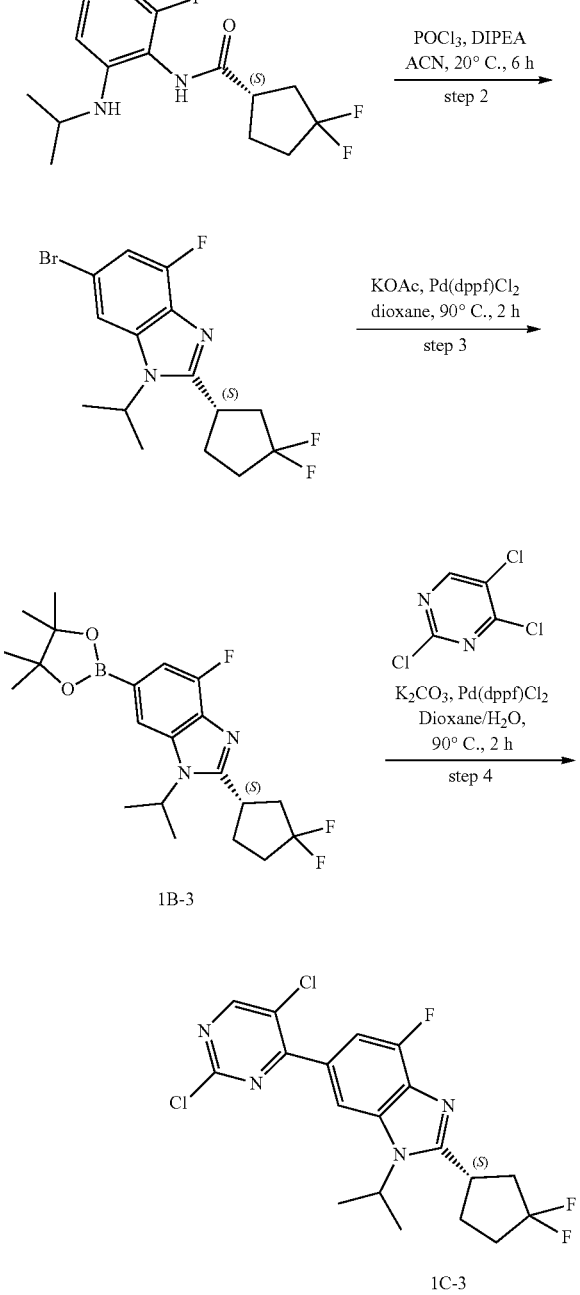

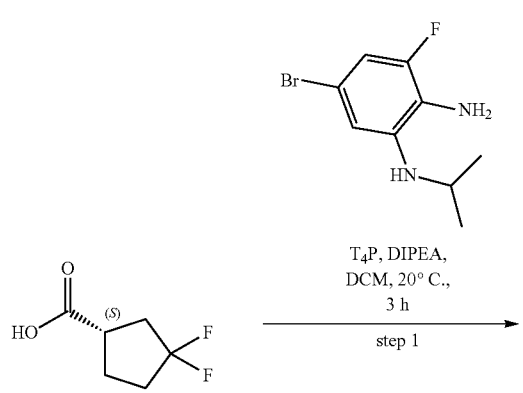

Step 1: Preparation of (S)—N-(4-bromo-2-fluoro-6-(isopropylamino)phenyl)-3,3-difluorocyclopentane-1-carboxamide To a solution of (S)-3,3-difluorocyclopentane-1-carboxylic acid (420 mg, 2.80 mmol, 1 eq) in DCM (5 mL) was added dropwise DIPEA (1.08 g, 8.39 mmol, 1.46 mL, 3 eq) and T4P (3.02 g, 8.39 mmol, 3 eq), followed by a dropwise addition of 5-bromo-3-fluoro-N$^1$-isopropyl-benzene-1,2-diamine (829.60 mg, 3.36 mmol, 1.2 eq) at 20° C., and the mixture was stirred at 20° C. for 3 hours under nitrogen atmosphere. After the completion of the reaction, the reaction mixture was quenched with H$_2$O (50 mL) and extracted with DCM (30 mL×2). The combined organic layers were washed with brine (30 mL), dried over Na$_2$SO$_4$, filtered, and the filtrate was concentrated under reduced pressure. The resulting residue was purified by column chromatography to give(S)—N-(4-bromo-2-fluoro-6-(isopropylamino)phenyl)-3,3-difluorocyclopentane-1-carboxamide (1 g, 94.2% yield) as a yellow solid. LCMS: 379.1 [M+H]$^+$.

Step 2: Preparation of(S)-6-bromo-2-(3,3-difluorocyclopentyl)-4-fluoro-1-isopropyl-1H-benzo[d]imidazole To a solution of(S)—N-(4-bromo-2-fluoro-6-(isopropylamino)phenyl)-3,3-difluorocyclopentane-1-carboxamide (300 mg, 0.79 mmol, 1 eq) in acetonitrile (10 mL), POCl$_3$ (363.91 mg, 2.37 mmol, 0.22 mL, 3 eq) and DIPEA (163.59 mg, 1.27 mmol, 0.22 mL, 1.6 eq) was added at 0° C., and the mixture was stirred at 0° C. for 1 hour, and then warmed to 20° C. and stirred for an additional 5 hours at that temperature under nitrogen atmosphere. After the completion of the reaction, the mixture was concentrated under reduced pressure. The resulting residue was carefully quenched with saturated aqueous Na$_2$CO$_3$ (20 mL) and extracted with EtOAc (30 mL×2). The combined organic layers were washed with brine (10 mL), dried over Na$_2$SO$_4$, filtered, and the filtrate was concentrated under reduced pressure. The resulting residue was purified by column chromatography to give(S)-6-bromo-2-(3,3-difluorocyclopentyl)-4-fluoro-1-isopropyl-1H-benzo[d]imidazole (210 mg, 72.0% yield) as a white solid. LCMS: 361.1 [M+H].

Step 3: Preparation of(S)-2-(3,3-difluorocyclopentyl)-4-fluoro-1-isopropyl-6-(4,4,5,5-tetramethyl-1,3,2-dioxaborolan-2-yl)-1H-benzo[d]imidazole A mixture of(S)-6-bromo-2-(3,3-difluorocyclopentyl)-4-fluoro-1-isopropyl-1H-benzo[d]imidazole (200 mg, 0.55 mmol, 1 eq), 4,4,5,5-tetramethyl-2-(4,4,5,5-tetramethyl-1,3,2-dioxaborolan-2-yl)-1,3,2-dioxaborolane (210 91 mg, 0.83 mmol, 1.5 eq), KOAc (108.68 mg, 1.11 mmol, 2 eq) and Pd (dppf) Cl$_2$ (81.03 mg, 0.11 mmol, 0.2 eq) in dioxane (3 mL) was degassed and backfilled with nitrogen for 3 times, and then stirred at 90° C. for 2 hours under nitrogen atmosphere. After the completion of the reaction, the mixture was cooled to room temperature, filtered through a short pad of Celite, rinsed with dioxane (5 mL), and the filtrate was concentrated under reduced pressure. The desired(S)-2-(3,3-difluorocyclopentyl)-4-fluoro-1-isopropyl-6-(4,4,5,5-tetramethyl-1,3,2-dioxaborolan-2-yl)-1H-benzo[d]imidazole (220 mg, crude) was obtained as a brown oil, which was used directly to next step without any purification. LCMS: 409.2 [M+H]$^+$.

Step 4: Preparation of(S)-6-(2,5-dichloropyrimidin-4-yl)-2-(3,3-difluorocyclopentyl)-4-fluoro-1-isopropyl-1H-benzo[d]imidazole A mixture of(S)-2-(3,3-difluorocyclopentyl)-4-fluoro-1-isopropyl-6-(4,4,5,5-tetramethyl-1,3,2-dioxaborolan-2-yl)-1H-benzo[d]imidazole (220 mg, 0.54 mmol, 1 eq), 2,4,5-trichloropyrimidine (148.26 mg, 0.81 mmol, 1.5 eq), Pd (dppf) Cl$_2$ (78.86 mg, 0.11 mmol, 0.2 eq) and K$_2$CO$_3$ (148.95 mg, 1.08 mmol, 2 eq) in dioxane (3 mL) and H$_2$O (0.3 mL) was degassed and backfilled with nitrogen for 3 times, and then stirred at 90° C. for 2 hours under nitrogen atmosphere. After the completion of the reaction, the mixture was cooled to room temperature, diluted with H$_2$O (5 mL) and extracted with EtOAc (15 mL×2). The combined organic layers were washed with brine (5 mL), dried over Na$_2$SO$_4$, filtered, and the filtrate was concentrated under reduced pressure. The resulting residue was purified by column chromatography to give 6-(2,5-dichloropyrimidin-4-yl)-2-[(1S)-3,3-difluorocyclopentyl]-4-fluoro-1-isopropyl-benzimidazole (180 mg, 76.8% yield) as a white solid. LCMS: 429.1 [M+H]$^+$.

Preparation of 4-fluoro-2-(2-hydroxypropan-2-yl)-1-isopropyl-6-(4,4,5,5-tetramethyl-1,3,2-dioxaborolan-2-yl)-1H-indole-3-carbonitrile (1C-4)

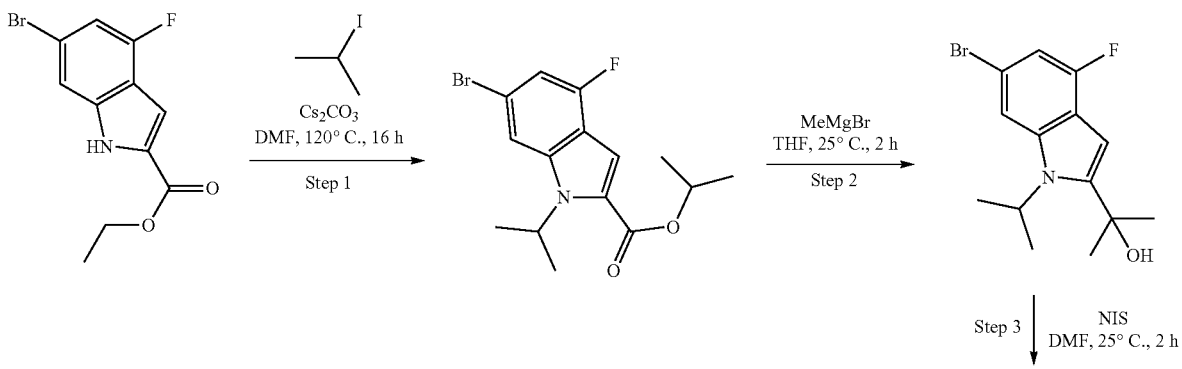

-continued

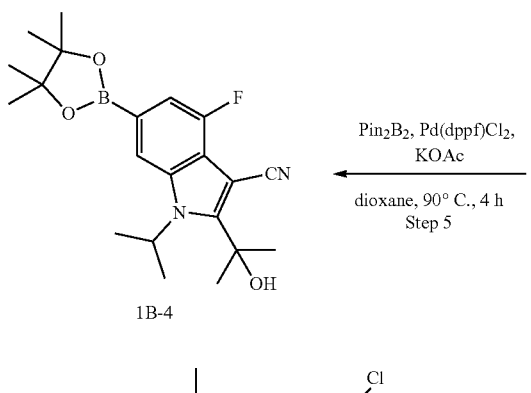 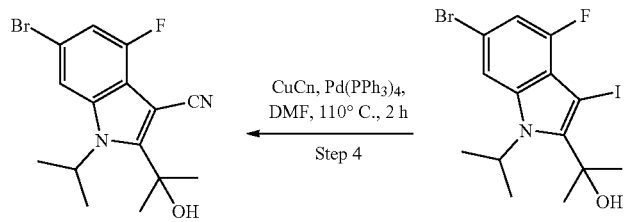

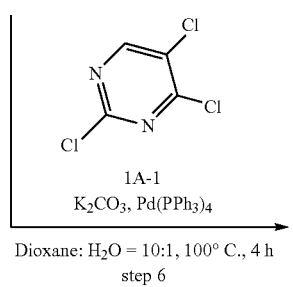 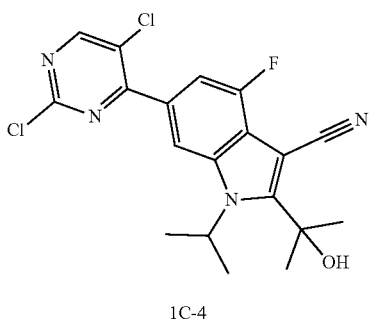

Step 1: Preparation of isopropyl 6-bromo-4-fluoro-1-isopropyl-1H-indole-2-carboxylate To a solution of ethyl 6-bromo-4-fluoro-1H-indole-2-carboxylate (1.1 g, 3.88 mmol, 1.0 eq) in DMF (3 mL) was added $Cs_2CO_3$ (3.8 g, 11.64 mmol, 3.0 eq) under $N_2$, and the mixture was stirred at 0° C. for 0.5 hour and followed by the addition of 2-iodopropane (2.0 g, 11.64 mmol, 1.2 mL, 3.0 eq). The mixture was then stirred at 120° C. for 16 hours under $N_2$. After the completion of the reaction, the mixture was cooled to room temperature, poured into aqueous $NH_4Cl$ (50 mL) and extracted with EtOAc (50 mL×3). The combined organic layer was washed with brine, dried over $Na_2SO_4$, filtered, and the filtrate was concentrated under reduced pressure. The resulting residue was purified by flash chromatography to give isopropyl 6-bromo-4-fluoro-1-isopropyl-1H-indole-2-carboxylate (1.3 g, 98% yield) as a white solid.

Step 2: Preparation of 2-(6-bromo-4-fluoro-1-isopropyl-1H-indol-2-yl) propan-2-ol To a pre-cooled solution of isopropyl 6-bromo-4-fluoro-1-isopropyl-1H-indole-2-carboxylate (1.2 g, 3.50 mmol, 1.0 eq) in THF (10 mL) was added MeMgBr (3.0 M, 7.00 mL, 6.0 eq) dropwise at 0° C. under nitrogen atmosphere. After the completion of the addition, the mixture was warmed to 25° C. and stirred at that temperature for 2 hours and subsequently poured into aqueous $NH_4Cl$ (50 mL). The aqueous solution was extracted with EtOAc (50 mL×3) and the combined organic layer was washed with brine, dried over $Na_2SO_4$ and filtered. The filtrate was concentrated under reduced pressure and the desired 2-(6-bromo-4-fluoro-1-isopropyl-indol-2-yl) propan-2-ol (980.0 mg, 89% yield) was obtained as a yellow solid, which was used without further purification. LCMS: 627.3 $[2M+H]^+$.

Step 3: Preparation of 2-(6-bromo-4-fluoro-3-iodo-1-isopropyl-1H-indol-2-yl) propan-2-ol To a solution of 2-(6-bromo-4-fluoro-1-isopropyl-indol-2-yl) propan-2-ol (230.0 mg, 0.732 mmol, 1.0 eq) in DMF (6 mL) was added dropwise NIS (247.0 mg, 1.10 mmol, 1.5 eq) at 0° C. After the completion of the addition, the mixture was warmed to 25° C. and stirred at that temperature for 2 hours. The mixture was then quenched with saturated aqueous $Na_2SO_3$ (5 mL) and extracted with ethyl acetate (10 mL×2). The combined organic layers were washed with brine 10 mL, dried over $Na_2SO_4$, filtered, and the filtrate was concentrated under reduced pressure. The desired 2-(6-bromo-4-fluoro-3-iodo-1-isopropyl-1H-indol-2-yl) propan-2-ol (250.0 mg, 77% yield) was obtained as a yellow solid. LCMS: 422.1, 424.1 $[M+H-18]^+$.

Step 4: Preparation of 6-bromo-4-fluoro-2-(2-hydroxypropan-2-yl)-1-isopropyl-1H-indole-3-carbonitrile The mixture of 2-(6-bromo-4-fluoro-3-iodo-1-isopropyl-1H-indol-2-yl) propan-2-ol (250.0 mg, 0.568 mmol, 1.0 eq) and CuCN (61.0 mg, 0.682 mmol, 1.2 eq) in DMF (8 mL) was degassed and backfilled with nitrogen for three times, and followed by the addition of $Pd(PPh_3)_4$ (131.3 mg, 0.114 mmol, 0.2 eq) under nitrogen atmosphere. The mixture was then stirred at 110° C. for 2 hours under nitrogen atmosphere. After the completion of the reaction, the mixture was cooled to room temperature, diluted with $H_2O$ (10 mL) and extracted with EtOAc (10 mL×2). The combined organic layers were washed with brine (10 mL), dried over $Na_2SO_4$, filtered, and the filtrate was concentrated under reduced pressure. The resulting residue was purified by column chromatography to afford 6-bromo-4-fluoro-2-(2-hydroxypropan-2-yl)-1-isopropyl-1H-indole-3-carbonitrile (53.0 mg, 27% yield) as a yellow solid. LCMS: 341.2 $[M+H]^+$.

Step 5: Preparation of 4-fluoro-2-(2-hydroxypropan-2-yl)-1-isopropyl-6-(4,4,5,5-tetramethyl-1,3,2-dioxaborolan-2-yl)-1H-indole-3-carbonitrile A mixture of 6-bromo-4-fluoro-2-(2-hydroxypropan-2-yl)-1-isopropyl-1H-indole-3-carbonitrile (50.0 mg, 0.147 mmol, 1.0 eq), $Pin_2B_2$ (93.6 mg, 0.369 mmol, 2.5 eq), Pd(dppf) $Cl_2$ (43.1 mg, 0.059 mmol, 0.4 eq) and KOAc (43.4 mg, 0.442 mmol, 3.0 eq) in dioxane (3 mL) was degassed and backfilled with nitrogen for three times, and then stirred at 90° C. for 4 hours under $N_2$ atmosphere. After the completion of the reaction, the mixture was cooled to room temperature and concentrated under reduced pressure. The resulting 4-fluoro-2-(1-hydroxy-1-methyl-ethyl)-1-isopropyl-6-(4, 4, 5, 5-tetramethyl-1, 3, 2-dioxaborolan-2-yl) indole-3-carbonitrile (40 mg, crude) was used for the next step reaction without further purification. LCMS: 387.4 [M+H]+.

Step 6: Preparation of 6-(2,5-dichloropyrimidin-4-yl)-4-fluoro-2-(2-hydroxypropan-2-yl)-1-isopropyl-1H-indole-3-carbonitrile To a degassed and nitrogen backfilled solution of 4-fluoro-2-(2-hydroxypropan-2-yl)-1-isopropyl-6-(4,4,5,5-tetramethyl-1,3,2-dioxaborolan-2-yl)-1H-indole-3-carbonitrile (300 mg, 0.78 mmol, 1 eq), 2,4,5-trichloropyrimidine (213.69 mg, 1.16 mmol, 1.5 eq) and K₂CO₃ (322.02 mg, 2.33 mmol, 3 eq) in dioxane (1 mL) and H₂O (0.1 mL) was added Pd(PPh₃)₄ (89.75 mg, 0.08 mmol, 0.1 eq) under nitrogen atmosphere, and the mixture was stirred at 100° C. for 4 hours under nitrogen atmosphere. After the completion of the reaction, the mixture was cooled to room temperature, diluted with water (50 mL) and extracted with EtOAc (50 mL×2). The combined organic phase was washed with brine (10 mL), dried over Na₂SO₄, filtered, and the filtrate was concentrated under reduced pressure. The resulting residue was purified by column chromatography to afford 6-(2,5-dichloropyrimidin-4-yl)-4-fluoro-2-(2-hydroxypropan-2-yl)-1-isopropyl-1H-indole-3-carbonitrile (300 mg, 92.95% yield) as a white solid. LCMS: 407.1 [M+H].

Preparation of 5'-(2,5-dichloropyrimidin-4-yl)-7'-fluoro-2'-methylspiro[cyclopentane-1,3'-indole](1C-5)

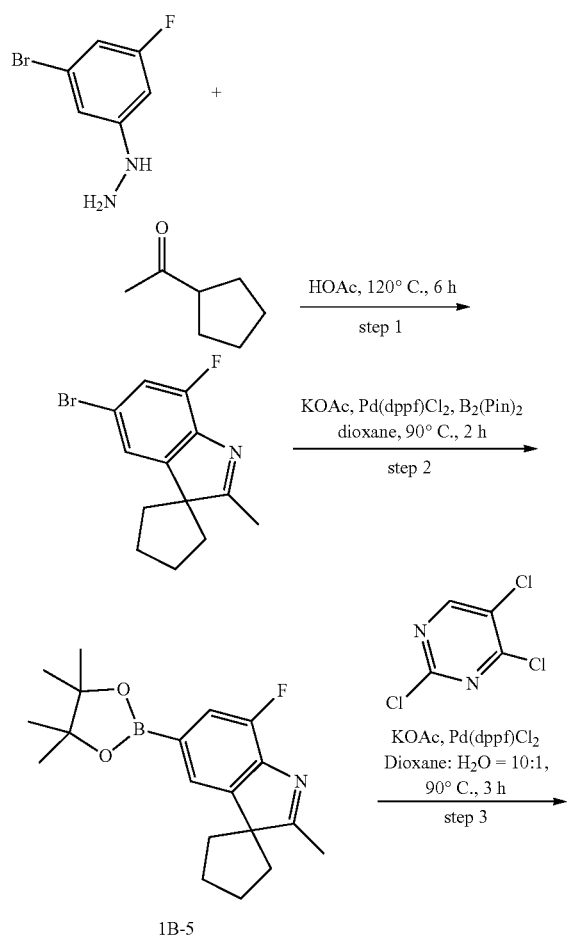

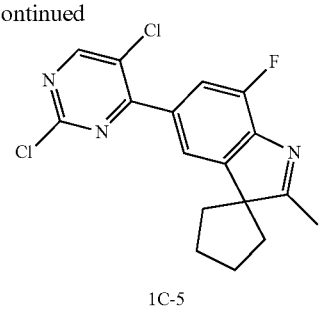

1C-5

Step 1: Preparation of 5'-bromo-7'-fluoro-2'-methylspiro[cyclopentane-1,3'-indole]

To a solution of (3-bromo-5-fluorophenyl) hydrazine (3.00 g, 12.42 mmol, 1 eq, HCl) in HOAc (30 mL) was added 1-cyclopentylethan-1-one (1.39 g, 12.42 mmol, 1 eq), and the mixture was stirred at 120° C. for 6 hours under nitrogen atmosphere. After the completion of the reaction, the mixture was cooled to room temperature, diluted with H₂O (100 mL) and the aqueous solution was extracted with EtOAc (100 mL×3). The combined organic phase was washed with brine (20 mL), dried over anhydrous Na₂SO₄, filtered, and the filtrate was concentrated in vacuo. The resulting residue was purified by column chromatography to afford 5'-bromo-7'-fluoro-2'-methylspiro[cyclopentane-1,3'-indole](1.8 g, 41.1% yield) as a brown oil. LCMS: 282.1 [M+H]+.

Step 2: Preparation of 7'-fluoro-2'-methyl-5'-(4,4,5,5-tetramethyl-1,3,2-dioxaborolan-2-yl)spiro[cyclopentane-1,3'-indole]

The mixture of 5'-bromo-7'-fluoro-2'-methylspiro[cyclopentane-1,3'-indole](900 mg, 3.19 mmol, 1 eq), 4,4,5,5-tetramethyl-2-(4,4,5,5-tetramethyl-1,3,2-dioxaborolan-2-yl)-1,3,2-dioxaborolane (1.22 g, 4.78 mmol, 1.5 eq), Pd (dppf) Cl₂ (466.80 mg, 0.64 mmol, 0.2 eq) and KOAc (626.11 mg, 6.38 mmol, 2 eq) in dioxane (10 mL) was degassed and backfilled with nitrogen for 3 times, and then stirred at 90° C. for 2 hours under nitrogen atmosphere. After the completion of the reaction, the mixture was cooled to room temperature, filtered through a short pad of celite and rinsed with dioxane (10 mL). The combined filtrate was concentrated under reduced pressure to give 7'-fluoro-2'-methyl-5'-(4,4,5,5-tetramethyl-1,3,2-dioxaborolan-2-yl)spiro[cyclopentane-1,3'-indole](1 g, crude) as a black oil, which was used into the next step without further purification. LCMS: 330.2 [M+H]+.

Step 3: Preparation of 5'-(2,5-dichloropyrimidin-4-yl)-7'-fluoro-2'-methylspiro[cyclopentane-1,3'-indole]

To a degassed and nitrogen backfilled solution of 7'-fluoro-2'-methyl-5'-(4,4,5,5-tetramethyl-1,3,2-dioxaborolan-2-yl)spiro[cyclopentane-1,3'-indole](1 g, 3.04 mmol, 1 eq) in dioxane (12 mL) and H₂O (1.2 mL) was added 2,4,5-trichloropyrimidine (668.58 mg, 3.65 mmol, 1.2 eq), Pd (dppf) Cl₂ (444.51 mg, 0.61 mmol, 0.2 eq) and KOAc (596.22 mg, 6.08 mmol, 2 eq), and the mixture was stirred at 90° C. for 3 hours under nitrogen atmosphere. After the completion of the reaction, the mixture was cooled to room temperature and concentrated under reduced pressure. The resulting residue was purified by column chromatography to afford 5'-(2,5-dichloropyrimidin-4-yl)-7'-fluoro-2'-methylspiro[cyclopentane-1,3'-indole](500 mg, 42.3% yield) as a brown solid. LCMS: 350.1 [M+H]+.

Preparation of 2-(6-(2,5-dichloropyrimidin-4-yl)-8-fluoro-3-methyl-3,4-dihydro-5-oxa-1,2a-diazaacenaphthylen-2-yl) propan-2-ol (1C-6)
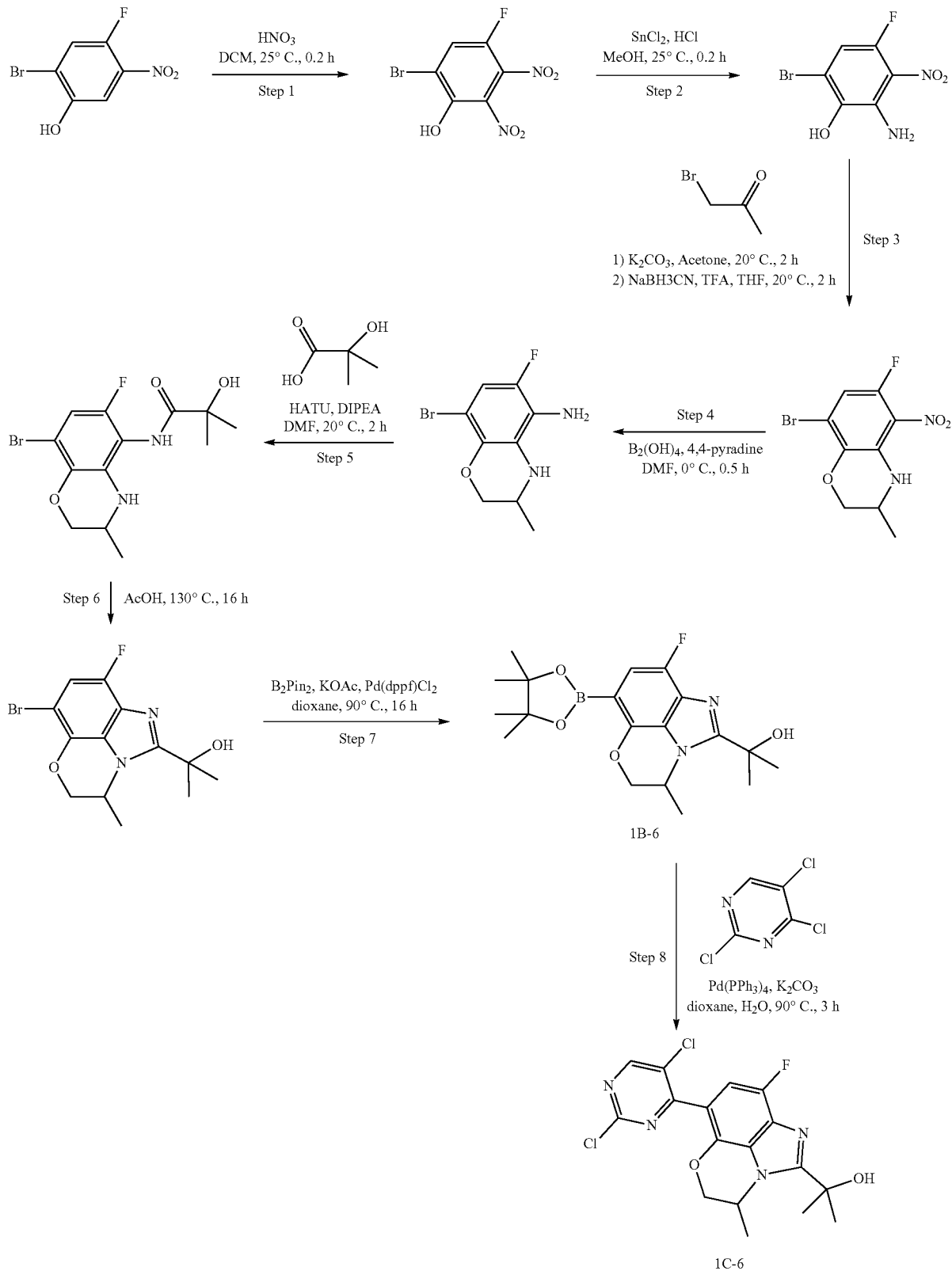

Step 1: Preparation of 6-bromo-4-fluoro-2,3-dinitrophenol

To a solution of 2-bromo-4-fluoro-5-nitro-phenol (7 g, 29.66 mmol, 1 eq) in DCM (32 mL) was slowly added a solution of HNO$_3$ (16 M, 6.07 mL, 3.27 eq) in DCM (32 mL) at 25° C., and the mixture was stirred at 25° C. for 0.2 hours after the completion of the addition. The mixture was then quenched with ice-water (100 mL) and extracted with DCM (100 mL×2). The combined organic layers were washed with brine (100 mL), dried over anhydrous Na$_2$SO$_4$, filtered and the filtrate was concentrated in vacuo. The resulting crude 6-bromo-4-fluoro-2,3-dinitrophenol (7.8 g, crude) was used into the next step without further purification. LCMS: 280.8, 282.8 [M+H].

Step 2: Preparation of 2-amino-6-bromo-4-fluoro-3-nitrophenol

To a solution of 6-bromo-4-fluoro-2,3-dinitrophenol (5.9 g, 21.00 mmol, 1 eq) in MeOH (90 mL) was added HCl (37.5 mL) and stannous chloride (11.94 g, 62.99 mmol, 1.63 mL, 3 eq) slowly at 25° C., and the mixture was stirred at that temperature for 0.2 hours under nitrogen atmosphere. After the completion of the reaction, the mixture was diluted with H$_2$O (50 mL) and extracted with EtOAc (50 mL×2). The combined organic layers were washed with brine (50 mL×2), dried over anhydrous Na$_2$SO$_4$, filtered and the filtrate was concentrated in vacuo. The resulting residue was purified by column chromatography to afford 2-amino-6-bromo-4-fluoro-3-nitrophenol (4.0 g, 75.8% yield) as a brown solid.

Step 3: Preparation of 8-bromo-6-fluoro-3-methyl-5-nitro-3,4-dihydro-2H-benzo[b][1,4]oxazine To a solution of 2-amino-6-bromo-4-fluoro-3-nitrophenol (4.6 g, 18.33 mmol, 1 eq) in acetone (90 mL) was added K$_2$CO$_3$ (3.04 g, 21.99 mmol, 1.2 eq) and 1-bromopropan-2-one (5.59 g, 40.81 mmol, 2.23 eq) at 0° C., and the mixture was then warmed to 20° C. and stirred at that temperature for 4 hours under nitrogen atmosphere. After the completion of the reaction, the mixture was diluted with H$_2$O (200 mL) and extracted with EtOAc (200 mL×3). The combined organic layers were washed with brine (200 mL×3), dried over anhydrous Na$_2$SO$_4$, filtered and the filtrate was concentrated in vacuo. The resulting residue was dissolved in THF (90 mL), followed by adding TFA (9 mL) and NaBH$_3$CN (1.73 g, 27.49 mmol, 1.5 eq) and stirred at 20° C. for 4 hours. After the completion of the reaction, the mixture was quenched with saturated aqueous NaHCO$_3$ (200 mL) and extracted with EtOAc (200 mL×2). The combined organic layers were washed with brine (200 mL×2), dried over anhydrous Na$_2$SO$_4$, filtered and the filtrate was concentrated in vacuo. The resulting residue was purified by column chromatography to afford 8-bromo-6-fluoro-3-methyl-5-nitro-3,4-dihydro-2H-benzo[b][1,4]oxazine (3.5 g, 65.61% yield). LCMS: 291.0, 293.0 [M+H]$^+$.

Step 4: Preparation of 8-bromo-6-fluoro-3-methyl-3,4-dihydro-2H-benzo[b][1,4]oxazin-5-amine To a solution of 8-bromo-6-fluoro-3-methyl-5-nitro-3,4-dihydro-2H-benzo[b][1,4]oxazine (3.4 g, 11.68 mmol, 1 eq) in DMF (35 mL) was added hypobaric acid (4.19 g, 46.72 mmol, 4 eq) and 4-(4-pyridyl)pyridine (182.44 mg, 1.17 mmol, 0.1 eq) at 0° C., and the mixture was stirred at 0° C. for 0.5 hours under nitrogen atmosphere. After the completion of the reaction, the mixture was quenched with H$_2$O (200 mL) and extracted with EtOAc (200 mL×2). The combined organic layers were washed with brine (200 mL×2), dried over anhydrous Na$_2$SO$_4$, filtered and the filtrate was concentrated in vacuo. The resulting residue was purified by column chromatography to afford 8-bromo-6-fluoro-3-methyl-3,4-dihydro-2H-benzo[b][1,4]oxazin-5-amine (1.88 g, 61.6% yield). LCMS: 261.1, 263.1 [M+H].

Step 5: Preparation of N-(8-bromo-6-fluoro-3-methyl-3,4-dihydro-2H-benzo[b][1,4]oxazin-5-yl)-2-hydroxy-2-methylpropanamide To a solution of 2-hydroxy-2-methyl-propanoic acid (765.56 mg, 7.35 mmol, 1.2 eq) in DMF (20 mL) was added HATU (3.50 g, 9.19 mmol, 1.5 eq) and DIPEA (1.58 g, 12.26 mmol, 2.13 mL, 2 eq), and the mixture was stirred at 20° C. for 0.5 hours, followed by the addition of 8-bromo-6-fluoro-3-methyl-3,4-dihydro-2H-benzo[b][1,4]oxazin-5-amine (1.6 g, 6.13 mmol, 1 eq) and stirred for an additional 2 hours under N$_2$ atmosphere. After the completion of the reaction, the mixture was quenched with H$_2$O (200 mL) and extracted with EtOAc (200 mL×2). The combined organic layers were washed with saturated aqueous brine (200 mL×2), dried over anhydrous Na$_2$SO$_4$, filtered and the filtrate was concentrated in vacuo. The resulting residue was purified by column chromatography to afford N-(8-bromo-6-fluoro-3-methyl-3,4-dihydro-2H-benzo[b][1,4]oxazin-5-yl)-2-hydroxy-2-methylpropanamide (1.2 g, 56.40% yield). LCMS: 347.1, 349.1 [M+H]$^+$.

Step 6: Preparation of 2-(6-bromo-8-fluoro-3-methyl-3,4-dihydro-5-oxa-1,2a-diazaacenaphthylen-2-yl) propan-2-ol The solution of N-(8-bromo-6-fluoro-3-methyl-3,4-dihydro-2H-benzo[b][1,4]oxazin-5-yl)-2-hydroxy-2-methyl-propanamide (400 mg, 1.15 mmol, 1 eq) in AcOH (4 mL) was stirred at 130° C. for 16 hours under nitrogen atmosphere. After the completion of the reaction, the mixture was cooled to room temperature and concentrated in vacuo. The resulting residue was purified by prep-HPLC {column: Phenomenex luna C18 150*25 mm*10 um, mobile phase: [water (FA)-ACN]; gradient: 32%-62% B over 10 min} to afford 2-(6-bromo-8-fluoro-3-methyl-3,4-dihydro-5-oxa-1,2a-diazaacenaphthylen-2-yl) propan-2-ol (150 mg, 39.5% yield). LCMS: 329.0, 331.0 [M+H]$^+$ Step 7: Preparation of 2-(8-fluoro-3-methyl-6-(4,4,5,5-tetramethyl-1,3,2-dioxaborolan-2-yl)-3,4-dihydro-5-oxa-1,2a-diazaacenaphthylen-2-yl) propan-2-ol The mixture of 2-(6-bromo-8-fluoro-3-methyl-3,4-dihydro-5-oxa-1,2a-diazaacenaphthylen-2-yl) propan-2-ol (150 mg, 0.455 mmol, 1 eq), 4,4,5,5-tetramethyl-2-(4,4,5,5-tetramethyl-1,3,2-dioxaborolan-2-yl)-1,3,2-dioxaborolane (173 58 mg, 0.683 mmol, 1.5 eq), KOAc (134.17 mg, 1.37 mmol, 3 eq) and Pd (dppf) Cl$_2$ (33.34 mg, 0.045 mmol, 0.1 eq) in dioxane (2 mL) was degassed and backfilled with nitrogen for 3 times, and then stirred at 90° C. for 16 hours under nitrogen atmosphere. After the completion of the reaction, the mixture was cooled to room temperature, filtered through a short pad of celite, rinsed with dioxane (5 mL) and the filtrate was concentrated. The resulting 2-(8-fluoro-3-methyl-6-(4,4,5,5-tetramethyl-1,3,2-dioxaborolan-2-yl)-3,4-dihydro-5-oxa-1,2a-diazaacenaphthylen-2-yl) propan-2-ol (170 mg, crude) was obtained and used into the next step without further purification. LCMS: 377.2 [M+H].

Step 8: Preparation of 2-(6-(2,5-dichloropyrimidin-4-yl)-8-fluoro-3-methyl-3,4-dihydro-5-oxa-1,2a-diazaacenaphthylen-2-yl) propan-2-ol The mixture of 2-(8-fluoro-3-methyl-6-(4,4,5,5-tetramethyl-1,3,2-dioxaborolan-2-yl)-3,4-dihydro-5-oxa-1,2a-diazaacenaphthylen-2-yl) propan-2-ol (170 mg, 0.451 mmol, 1 eq), 2,4,5-trichloropyrimidine (124.32 mg, 0 677 mmol, 1.5 eq), K$_2$CO$_3$ (187.35 mg, 1.36 mmol, 3 eq) and Pd(PPh$_3$)$_4$ (52.21 mg, 0.045 mmol, 0.1 eq) in dioxane (2 mL) and H$_2$O (0.2 mL) was degassed and backfilled with nitrogen for 3 times, and stirred at 90° C. for 3 hours under nitrogen atmosphere. After the completion of the reaction, the mixture was cooled to room temperature, filtered through a short pad of celite, rinsed with dioxane (5 mL) and the filtrate was concentrated. The resulting residue was purified by column chromatography to afford 2-(6-(2,5-dichloropyrimidin-4-yl)-8-fluoro-3-methyl-3,4-dihydro-5-oxa-1,2a-diazaacenaphthylen-2-yl) propan-2-ol (100 mg, 55.7% yield). LCMS: 397.1 [M+H]+.

Preparation of 2-(2,5-dichloropyrimidin-4-yl)-7-isopropyl-3,5-dimethylthieno[3,2-c]pyridin-4 (5H)-one (1C-7)

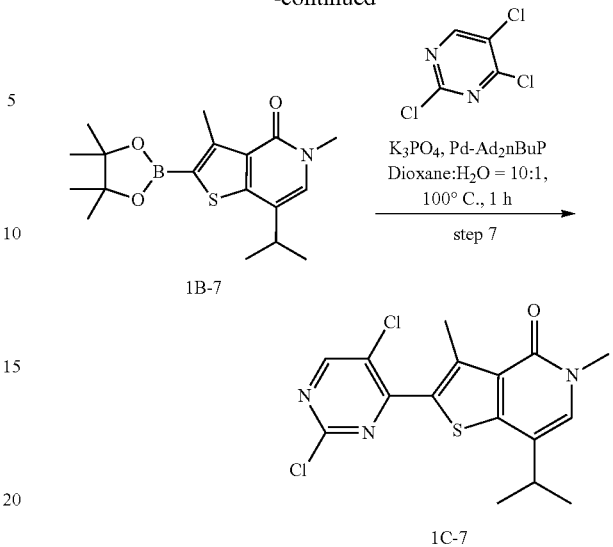

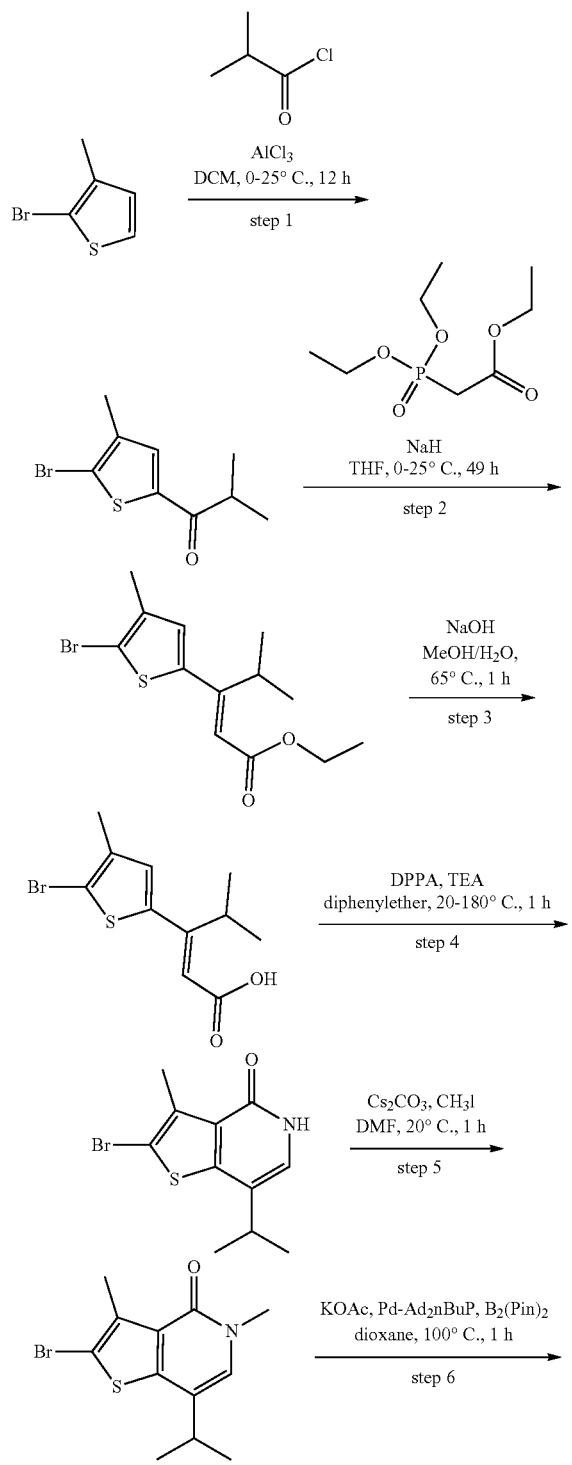

Step 1: Preparation of 1-(5-bromo-4-methylthiophen-2-yl)-2-methylpropan-1-one

To a solution of AlCl₃ (8.28 g, 62.13 mmol, 3.40 mL, 1.1 eq) in DCM (100 mL) at 0° C. was added 2-methylpropanoyl chloride (6.62 g, 62.13 mmol, 6.51 mL., 1.1 eq) dropwise, followed by the slow addition of 2-bromo-3-methyl-thiophene (10 g, 56.48 mmol, 1 eq) at 0° C. under nitrogen atmosphere, and the mixture was warmed to 25° C. and stirred for 12 hours at that temperature after the completion of the addition. The mixture was then carefully quenched with H₂O (100 mL) and extracted with dichloromethane (100 mL×3). The combined organic layers were washed with brine (30 mL), dried over anhydrous Na₂SO₄, filtered and the filtrate was concentrated in vacuo. The resulting residue was purified by column chromatography to afford 1-(5-bromo-4-methylthiophen-2-yl)-2-methylpropan-1-one (11 g, 78.8% yield) as a yellow oil. LCMS: 246.9]+, 248.9 [M+H]+.

Step 2: Preparation of ethyl (E)-3-(5-bromo-4-methylthiophen-2-yl)-4-methylpent-2-enoate To a suspension of NaH (1.21 g, 30.35 mmol, 60% purity, 1.5 eq) in THF (50 mL) at 0° C. was added ethyl 2-diethoxyphosphorylacetate (4.99 g, 22.25 mmol, 4.42 mL, 1.1 eq) dropwise at 0° C. under nitrogen atmosphere, and the mixture was stirred at 0° C. for 0.5 hour and 25° C. for an additional 0.5 hour, and then followed by the dropwise addition of a solution of 1-(5-bromo-4-methylthiophen-2-yl)-2-methylpropan-1-one (5 g, 20.23 mmol, 1 eq) in THF (15 mL). After the completion of the addition, the mixture was kept stirring at 25° C. for 48 hours under nitrogen atmosphere until the completion of the reaction. The mixture was quenched with H₂O (100 mL) and extracted with EtOAc (100 mL×3). The combined organic layers were washed with brine (20 mL), dried over anhydrous Na₂SO₄, filtered and the filtrate was concentrated in vacuo. The desired ethyl (E)-3-(5-bromo-4-methylthiophen-2-yl)-4-methylpent-2-enoate (6 g, crude) was obtained as a deep brown oil, which was used into the next step without further purification. LCMS: 317.1, 319.1 [M+H]+.

Step 3: Preparation of (E)-3-(5-bromo-4-methylthiophen-2-yl)-4-methylpent-2-enoic acid To a solution of ethyl (E)-3-(5-bromo-4-methylthiophen-2-yl)-4-methylpent-2-enoate (6 g, 18.91 mmol, 1 eq) in MeOH (40 mL) was added an aqueous NaOH [(3.78 g, 94.57 mmol, 5 eq, in H$_2$O (40 mL)]dropwise at room temperature, and the mixture was then stirred at 65° C. for 1 hour. After the completion of the reaction, the mixture was cooled to room temperature and concentrated in vacuo. The resulting residue was then dissolved in EtOAc (80 mL), acidified with 2N HCl solution (20 mL) and extracted with EtOAc (80 mL×3). The combined organic layers were washed with brine (20 mL), dried over Na$_2$SO$_4$, filtered and the filtrate was concentrated in vacuo. The desired (E)-3-(5-bromo-4-methylthiophen-2-yl)-4-methylpent-2-enoic acid (3 g, crude) was obtained as a yellow oil, which was used into the next step without further purification. LCMS: 289.0, 291.0 [M+H]$^+$.

Step 4: Preparation of 2-bromo-7-isopropyl-3-methylthieno[3,2-c]pyridin-4 (5H)-one To a solution of (E)-3-(5-bromo-4-methylthiophen-2-yl)-4-methylpent-2-enoic acid (2.6 g, 8.99 mmol, 1 eq) in phenoxybenzene (20 mL) was added dropwise TEA (2.73 g, 26.97 mmol, 3.75 mL, 3 eq) and DPPA (3.71 g, 13.49 mmol, 2.91 mL, 1.5 eq), and the mixture was stirred at 20° C. for 0.5 hour and then heated at 180° C. for 0.5 hour under nitrogen atmosphere. After the completion of the reaction, the mixture was cooled to room temperature, quenched with aqueous NaOH solution (IN, 30 mL) and stirred for an additional 30 minutes. The mixture was then extracted with EtO Ac (50 mL×3). The combined organic layers were washed with brine (50 mL), dried over Na$_2$SO$_4$, filtered and the filtrate was concentrated in vacuo. The resulting residue was purified by column chromatography to afford 2-bromo-7-isopropyl-3-methylthieno[3,2-c]pyridin-4 (5H)-one (1.2 g, 46.6% yield) as a brown oil. LCMS: 286.0, 288.0 [M+H]$^+$.

Step 5: Preparation of 2-bromo-7-isopropyl-3,5-dimethylthieno[3,2-c]pyridin-4 (5H)-one To a solution of 2-bromo-7-isopropyl-3-methylthieno[3,2-c]pyridin-4 (5H)-one (1.2 g, 4.19 mmol, 1 eq) in DMF (12 mL) was added Cs$_2$CO$_3$ (2.73 g, 8.39 mmol, 2 eq) and CH$_3$I (1.19 g, 8.39 mmol, 0.53 mL, 2 eq), and the mixture was stirred at 20° C. for 1 hour under nitrogen atmosphere. After the completion of the reaction, the mixture was quenched with H$_2$O (50 mL) and extracted with dichloromethane (50 mL×3). The combined organic layers were washed with brine (30 mL), dried over anhydrous Na$_2$SO$_4$, filtered and the filtrate was concentrated in vacuo. The resulting residue was purified by column chromatography to afford 2-bromo-7-isopropyl-3,5-dimethylthieno[3,2-c]pyridin-4 (5H)-one (1.2 g, 95.3% yield) as a brown solid. LCMS. 300 0, 302.0 [M+H]$^+$.

Step 6: Preparation of 7-isopropyl-3,5-dimethyl-2-(4,4,5,5-tetramethyl-1,3,2-dioxaborolan-2-yl) thieno[3,2-c]pyridin-4 (5H)-one A mixture of 2-bromo-7-isopropyl-3,5-dimethylthieno[3,2-c]pyridin-4 (5H)-one (300 mg, 1.0 mmol, 1 eq), [2-(2-aminophenyl)phenyl]-chloro-palladium, bis(1-adamantyl)-butyl-phosphane (66.82 mg, 0.1 mmol, 0.1 eq), 4,4,5,5-tetramethyl-2-(4,4,5,5-tetramethyl-1,3,2-dioxaborolan-2-yl)-1,3,2-dioxaborolane (380 64 mg, 1.50 mmol, 1.5 eq) and KOAc (196.14 mg, 2.00 mmol, 2 eq) in dioxane (5 mL) was degassed and back-filled with nitrogen for 3 times, and then stirred at 100° C. for 1 hour under nitrogen atmosphere. After the completion of the reaction, the mixture was cooled to room temperature, filtered through a short pad of Celite, rinsed with dioxane (5 mL) and the combined filtrate was concentrated in vacuo. The desired 7-isopropyl-3,5-dimethyl-2-(4,4,5,5-tetramethyl-1,3,2-dioxaborolan-2-yl) thieno[3,2-c]pyridin-4 (5H)-one (330 mg, crude) was obtained as a black brown oil, which was used into the next step without further purification. LCMS: 348.2 [M+H]$^+$.

Step 7: Preparation of 2-(2,5-dichloropyrimidin-4-yl)-7-isopropyl-3,5-dimethylthieno[3,2-c]pyridin-4 (5H)-one The mixture of 7-isopropyl-3,5-dimethyl-2-(4,4,5,5-tetramethyl-1,3,2-dioxaborolan-2-yl) thieno[3,2-c]pyridin-4 (5H)-one (330 mg, 0.95 mmol, 1 eq), 2,4,5-trichloropyrimidine (261.45 mg, 1.43 mmol, 1.5 eq), [2-(2-aminophenyl)phenyl]-chloro-palladium; bis(1-adamantyl)-butyl-phosphane (63.54 mg, 0.1 mmol, 0.1 eq) and K$_3$PO$_4$ (403.41 mg, 1.90 mmol, 2 eq) in dioxane (5 mL) and H$_2$O (0.5 mL) was degassed and backfilled with nitrogen for 3 times, and then stirred at 100° C. for 1 hour under N$_2$ atmosphere. After the completion of the reaction, the mixture was cooled to room temperature, filtered through a short pad of Celite, rinsed with dioxane (5 mL.) and the combined filtrate was concentrated in vacuo. The resulting residue was purified by column chromatography to afford 2-(2,5-dichloropyrimidin-4-yl)-7-isopropyl-3,5-dimethylthieno[3,2-c]pyridin-4 (5H)-one (220 mg, 62.8% yield) as a brown oil. LCMS: 368.0 [M+H].

Preparation of 2-(2-chloro-5-fluoropyrimidin-4-yl)-7-isopropyl-3,5-dimethylthieno[3,2-c]pyridine-4 (5H)-one (1C-8)

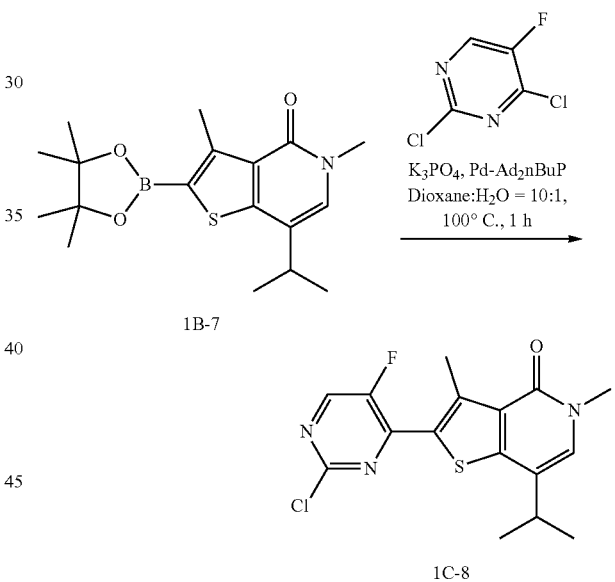

The mixture of 7-isopropyl-3,5-dimethyl-2-(4,4,5,5-tetramethyl-1,3,2-dioxaborolan-2-yl) thieno[3,2-c]pyridin-4 (5H)-one (430 mg, 1.24 mmol, 1 eq), 2,4-dichloro-5-fluoropyrimidine (310.1 mg, 1.86 mmol, 1.5 eq), K$_3$PO$_4$ (525.6 mg, 2.48 mmol, 2 eq) and [2-(2-aminophenyl)phenyl]-chloro-palladium bis(1-adamantyl)-butyl-phosphane (82.79 mg, 0.13 mmol, 0.1 eq) in dioxane (7 mL) and H$_2$O (1 mL) was degassed and back-filled with nitrogen for 3 times, and then stirred at 100° C. for 1 hour under nitrogen atmosphere. After the completion of the reaction, the mixture was cooled to room temperature, filtered through a short pad of Celite and rinsed with dioxane (10 mL). The combined filtrate was concentrated in vacuo and the resulting residue was purified by column chromatography to afford 2-(2-chloro-5-fluoropyrimidin-4-yl)-7-isopropyl-3,5-dimethylthieno[3,2-c]pyridin-4 (5H)-one (290 mg, 66.5% yield) as a yellow solid. LCMS: 352.0 [M+H]$^+$.

Preparation of 7-(2-chloro-5-fluoropyrimidin-4-yl)-2-(((3S,5S)-3,5-dimethylmorpholino)methyl)-1-isopropyl-3-methylquinolin-4(1H)-one (1C-9)
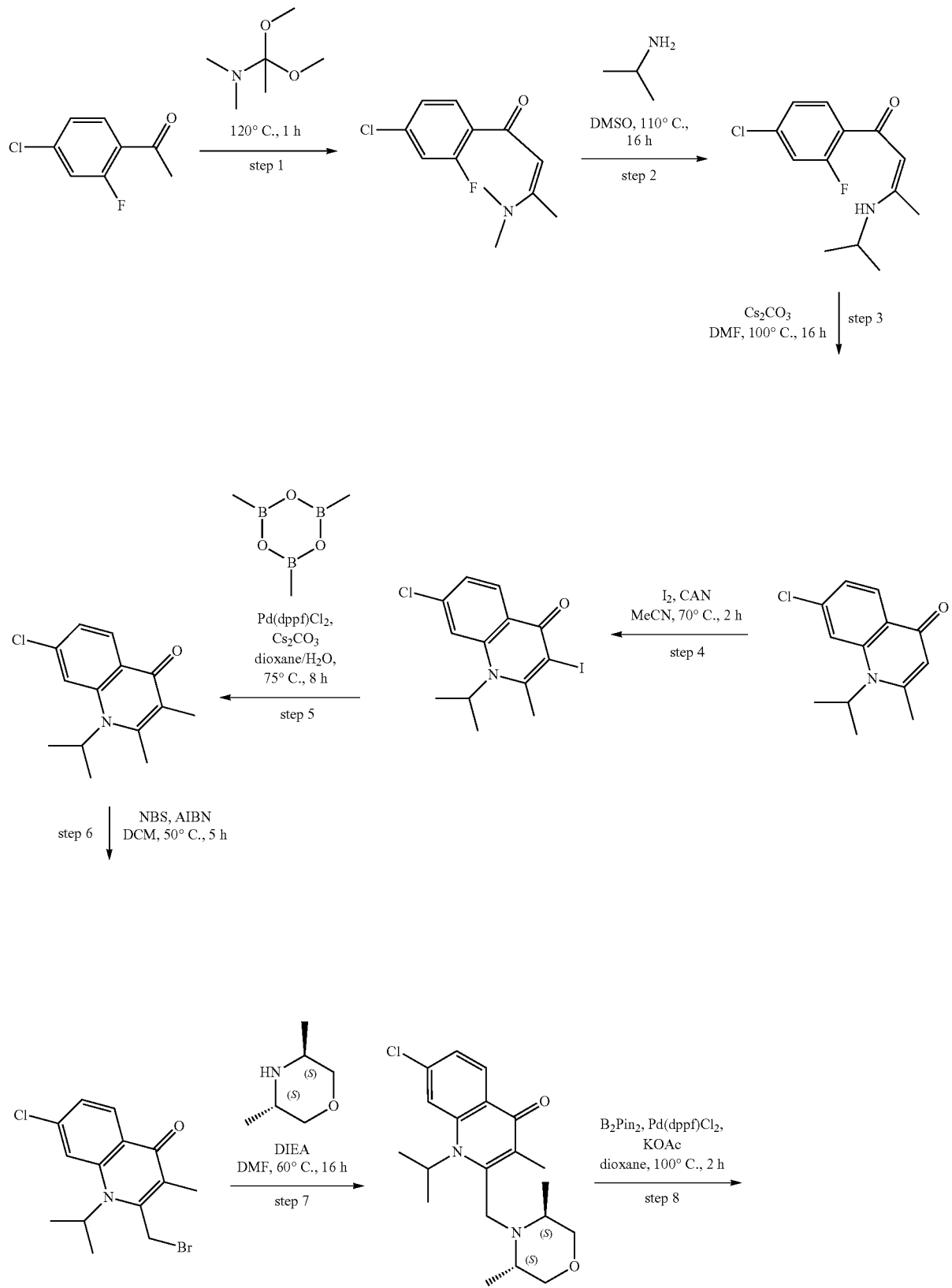

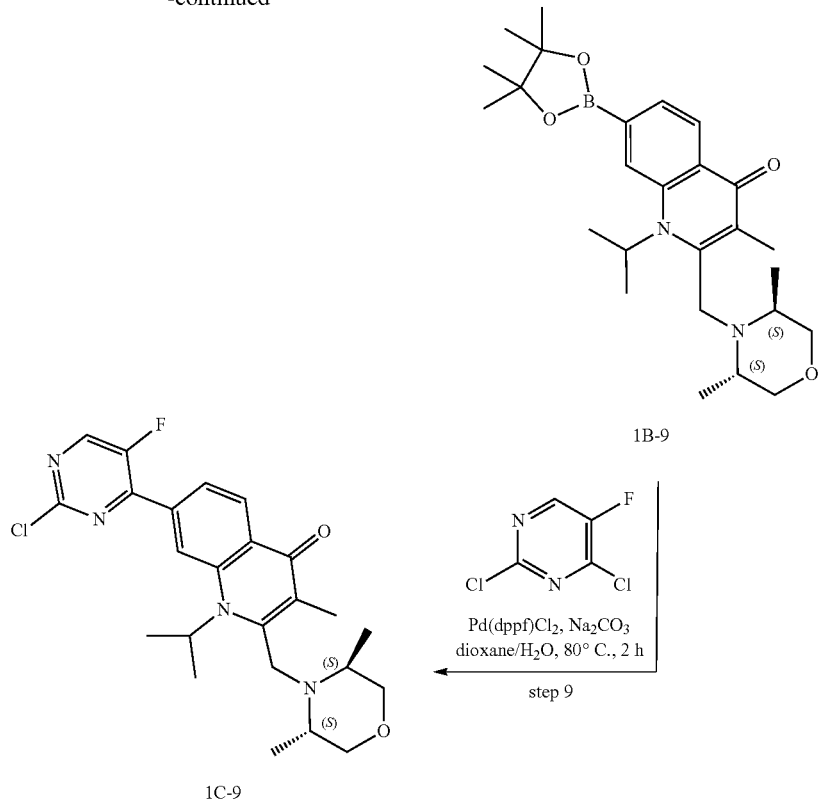

Step 1: Preparation of (Z)-1-(4-chloro-2-fluoro-phenyl)-3-(dimethylamino) but-2-en-1-one A mixture of 1-(4-chloro-2-fluoro-phenyl) ethanone (15 g, 86.9 mmol, 1 eq) and 1,1-dimethoxy-N, N-dimethyl-ethanamine (25 g, 187.7 mmol, 27.5 mL, 2.16 eq) was stirred for 1 hour at 120° C. under nitrogen atmosphere. After the completion of the reaction, the mixture was cooled to room temperature and concentrated in vacuo. The resulting residue was purified by column chromatography to afford (Z)-1-(4-chloro-2-fluoro-phenyl)-3-(dimethylamino) but-2-en-1-one (16.7 g, 79% yield) as a yellow solid. LCMS: 242.0 [M+H]$^+$.

Step 2: Preparation of (Z)-1-(4-chloro-2-fluoro-phenyl)-3-(isopropylamino) but-2-en-1-one A mixture of (Z)-1-(4-chloro-2-fluoro-phenyl)-3-(dimethylamino) but-2-en-1-one (11.05 g, 45.7 mmol, 1 eq) and propan-2-amine (3.58 g, 60.5 mmol, 5.2 mL, 1.32 eq) in DMSO (150 mL) was stirred for 16 hours at 110° C. under N$_2$ atmosphere. After the completion of the reaction, the mixture was cooled to room temperature and concentrated in vacuo. The resulting residue was purified by column chromatography to afford (Z)-1-(4-chloro-2-fluoro-phenyl)-3-(isopropylamino) but-2-en-1-one (11.05 g, 62% yield) as a yellow oil. LCMS: 256.2 [M+H]$^+$.

Step 3: Preparation of 7-chloro-1-isopropyl-2-methyl-quinolin-4-one

A mixture of (Z)-1-(4-chloro-2-fluoro-phenyl)-3-(isopropylamino) but-2-en-1-one (10.6 g, 41.45 mmol, 1 eq) and Cs$_2$CO$_3$ (27.01 g, 82.90 mmol, 2 eq) in DMF (120 mL) was stirred for 16 hours at 100° C. under nitrogen atmosphere. After the completion of the reaction, the mixture was cooled to room temperature, filtered through a short pad of celite, and the filtrate was concentrated in vacuo. The resulting residue was purified by column chromatography to afford 7-chloro-1-isopropyl-2-methyl-quinolin-4-one (8.73 g, 86% yield) as a brown solid. LCMS: 236.1 [M+H]$^+$.

Step 4: Preparation of 7-chloro-3-iodo-1-isopropyl-2-methyl-quinolin-4-one

A mixture of 7-chloro-1-isopropyl-2-methyl-quinolin-4-one (3 g, 12.73 mmol, 1 eq), I$_2$ (3.23 g, 12.73 mmol, 2.56 mL, 1 eq) and cerium ammonium nitrate (697.75 mg, 1.27 mmol, 0.1 eq) in MeCN (60 mL) was stirred for 2 hours at 70° C. under nitrogen atmosphere. After the completion of the reaction, the mixture was cooled to room temperature and concentrated in vacuo. The resulting residue was purified by column chromatography to afford 7-chloro-3-iodo-1-isopropyl-2-methyl-quinolin-4-one (2.4 g, 52% yield) as a yellow solid. LCMS: 361.8 [M+H]$^+$. Step 5: Preparation of 7-chloro-1-isopropyl-2,3-dimethyl-quinolin-4-one A mixture of 7-chloro-3-iodo-1-isopropyl-2-methyl-quinolin-4-one (2.4 g, 6.64 mmol, 1 eq), 2,4,6-trimethyl-1,3,5, 2,4,6-trioxatriborinane (3.33 g, 13.27 mmol, 3.71 mL, 2 eq), Cs$_2$CO$_3$ (4.32 g, 13.27 mmol, 2 eq) and Pd (dppf) Cl$_2$ (486 mg, 0.663 mmol, 0.1 eq) in dioxane (60 mL) and H$_2$O (6 mL) was degassed and backfilled with nitrogen for three times, and then stirred for 8 hours at 75° C. under nitrogen atmosphere After the completion of the reaction, the mixture was cooled to room temperature, filtered through a pad of the Celite, and the filtrate was concentrated in vacuo. The resulting residue was purified by column chromatography to afford 7-chloro-1-isopropyl-2,3-dimethyl-quinolin-4-one (1.2 g, 72% yield) as a yellow solid. LCMS: 250.1 [M+H]$^+$.

Step 6: Preparation of 2-(bromomethyl)-7-chloro-1-isopropyl-3-methyl-quinolin-4-one A mixture of 7-chloro-1-isopropyl-2,3-dimethyl-quinolin-4-one (1.2 g, 4.81 mmol, 1 eq), AIBN (143.6 mg, 0.874 mmol, 1.82e-1 eq) and NBS (1.03 g, 5.77 mmol, 1.2 eq) in DCM (30 mL) was stirred for 5 hours at 50° C. under nitrogen atmosphere. After the completion of the reaction, the mixture was cooled to room temperature, quenched with saturated aqueous Na$_2$SO$_3$ (50 mL) and extracted with DCM (50 mL×2). The combined organic layers were dried over anhydrous Na$_2$SO$_4$, filtered, and the filtrate was concentrated in vacuo. The resulting residue was purified by column chromatography to afford 2-(bromomethyl)-7-chloro-1-isopropyl-3-methyl-quinolin-4-one (1.25 g, 78% yield) as a yellow solid. LCMS: 328.0, 330.0 [M+H]

Step 7: Preparation of 7-chloro-2-(((3S,5S)-3,5-dimethylmorpholino)methyl)-1-isopropyl-3-methylquinolin-4 (1H)-one The mixture of 2-(bromomethyl)-7-chloro-1-isopropyl-3-methyl-quinolin-4-one (360 mg, 1.1 mmol, 1 eq), (3S,5S)-3,5-dimethylmorpholine (189.2 mg, 1.64 mmol, 1.5 eq) and DIPEA (424.7 mg, 3.29 mmol, 572.42 µL, 3 eq) in DMF (5 mL) was stirred at 60° C. for 16 hours under nitrogen atmosphere. After the completion of the reaction, the mixture was cooled to room temperature, filtered, and the filtrate was concentrated under reduced pressure. The desired 7-chloro-2-(((3S,5S)-3,5-dimethylmorpholino)methyl)-1-isopropyl-3-methylquinolin-4 (1H)-one (382 mg, crude) was obtained as a yellow oil, which was used in the next step without further purification. LCMS: 363.2 [M+H]$^+$.

Step 8: Preparation of 2-(((3S,5S)-3,5-dimethylmorpholino)methyl)-1-isopropyl-3-methyl-7-(4,4,5,5-tetramethyl-1,3,2-dioxaborolan-2-yl) quinolin-4 (1H)-one The mixture of 7-chloro-2-[[(3S,5S)-3,5-dimethylmorpholin-4-yl]methyl]-1-isopropyl-3-methyl-quinolin-4-one (382 mg, 1.05 mmol, 1 eq), Pin$_2$B$_2$ (401 mg, 1.58 mmol, 1.5 eq), KOAc (309.9 mg, 3.16 mmol, 3 eq) and Pd (dppf) Cl$_2$ (85.96 mg, 0 105 mmol, 0.1 eq) in dioxane (6 mL) was stirred at 100° C. for 2 hours under nitrogen atmosphere. After the completion of the reaction, the mixture was cooled to room temperature, filtered through a short pad of Celite, rinsed with dioxane (6 mL), and the filtrate was concentrated under reduced pressure. The desired 2-(((3S,5S)-3,5-dimethylmorpholino)methyl)-1-isopropyl-3-methyl-7-(4,4,5,5-tetramethyl-1,3,2-dioxaborolan-2-yl) quinolin-4 (1H)-one (391 mg, crude) was obtained as a yellow oil, which was used in the next step without further purification. LCMS: 455.5 [M+H]$^+$.

Step 9: Preparation of 7-(2-chloro-5-fluoropyrimidin-4-yl)-2-(((3S,5S)-3,5-dimethylmorpholino)methyl)-1-isopropyl-3-methylquinolin-4 (1H)-one To a degassed and nitrogen backfilled solution of 2-(((3S,5S)-3,5-dimethylmorpholino)methyl)-1-isopropyl-3-methyl-7-(4,4,5,5-tetramethyl-1,3,2-dioxaborolan-2-yl) quinolin-4 (1H)-one (0.5 g, 1.10 mmol, 1 eq), 2,4-dichloro-5-fluoro-pyrimidine (367.4 mg, 2.20 mmol, 2 eq) and Na$_2$CO$_3$ (583.12 mg, 5.50 mmol, 5 eq) in dioxane (10 mL) and H$_2$O (2 mL) was added Pd (dppf) Cl$_2$ (201.28 mg, 0.275 mmol, 0.25 eq) under nitrogen atmosphere, and the mixture was stirred at 80° C. for 2 hours under nitrogen atmosphere. After the completion of the reaction, the mixture was cooled to room temperature, diluted with H$_2$O (100 mL.) and extracted with DCM (100 mL×3). The combined organic phase was washed with brine, dried over sodium sulfate, filtered and the filtrate was concentrated in vacuo. The resulting residue was purified by column chromatography to afford 7-(2-chloro-5-fluoropyrimidin-4-yl)-2-(((3S,5S)-3,5-dimethylmorpholino)methyl)-1-isopropyl-3-methylquinolin-4 (1H)-one (0.5 g, 99.0% yield) as a yellow oil. LCMS: 459.2 [M+H]$^+$.

Preparation of 7-(2,5-dichloropyrimidin-4-yl)-2-(((3S, 5S)-3,5-dimethylmorpholino)methyl)-1-isopropyl-3-methylquinolin-4 (1H)-one (1C-10)

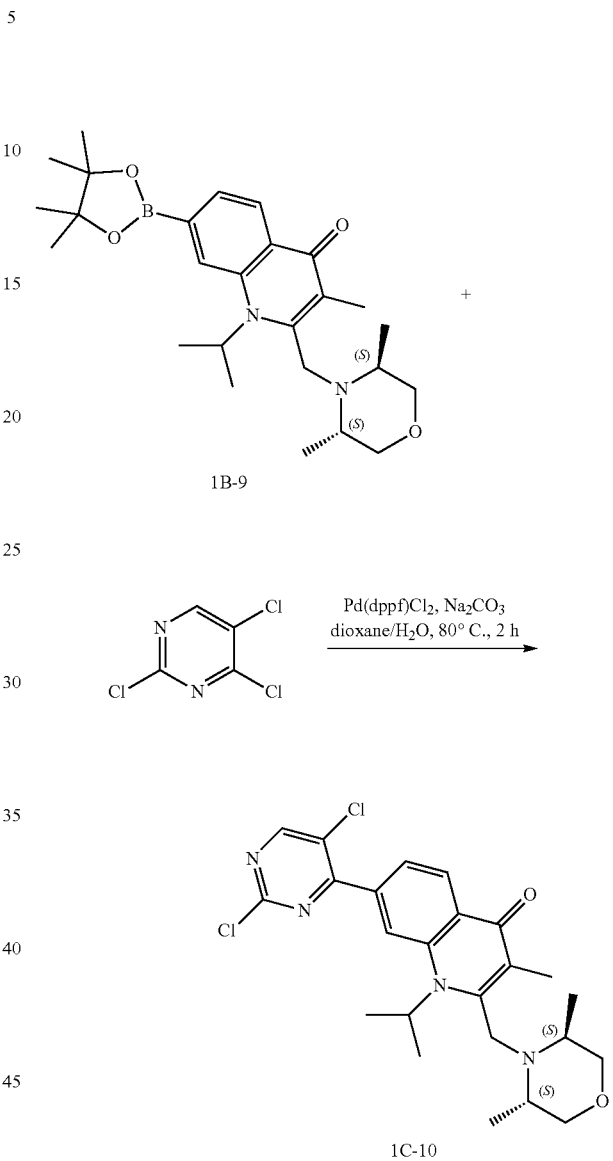

To a degassed and nitrogen backfilled solution of 2-(((3S, 5S)-3,5-dimethylmorpholino)methyl)-1-isopropyl-3-methyl-7-(4,4,5,5-tetramethyl-1,3,2-dioxaborolan-2-yl) quinolin-4 (1H)-one (0.5 g, 1.10 mmol, 1 eq), 2,4,5-trichloropyrimidine (403.65 mg, 2.20 mmol, 2 eq) and Na$_2$CO$_3$ (583.12 mg, 5.50 mmol, 5 eq) in dioxane (6 mL) and H$_2$O (1.2 mL) was added Pd (dppf) Cl$_2$ (201.28 mg, 0.275 mmol, 0.25 eq), and the mixture was stirred at 80° C. for 2 hours under nitrogen atmosphere. After the completion of the reaction, the mixture was cooled to room temperature, diluted with H$_2$O) (100 mL) and extracted with DCM (100 mL×3). The combined organic layers were washed with brine (50 mL), dried over Na$_2$SO$_4$, filtered and the filtrate was concentrated in vacuo. The resulting residue was purified by column chromatography to afford 7-(2,5-dichloro-pyrimidin-4-yl)-2-(((3S,5S)-3,5-dimethylmorpholino) methyl)-1-isopropyl-3-methylquinolin-4 (1H)-one (0.5 g, 95.5% yield) as a yellow solid. LCMS: 475.1 [M+H]$^+$ Preparation of 6-(2,5-dichloropyrimidin-4-yl)-2-(2,2-difluorocyclopropyl)-4-fluoro-1-isopropyl-1H-benzo[d]imidazole (1C-11)

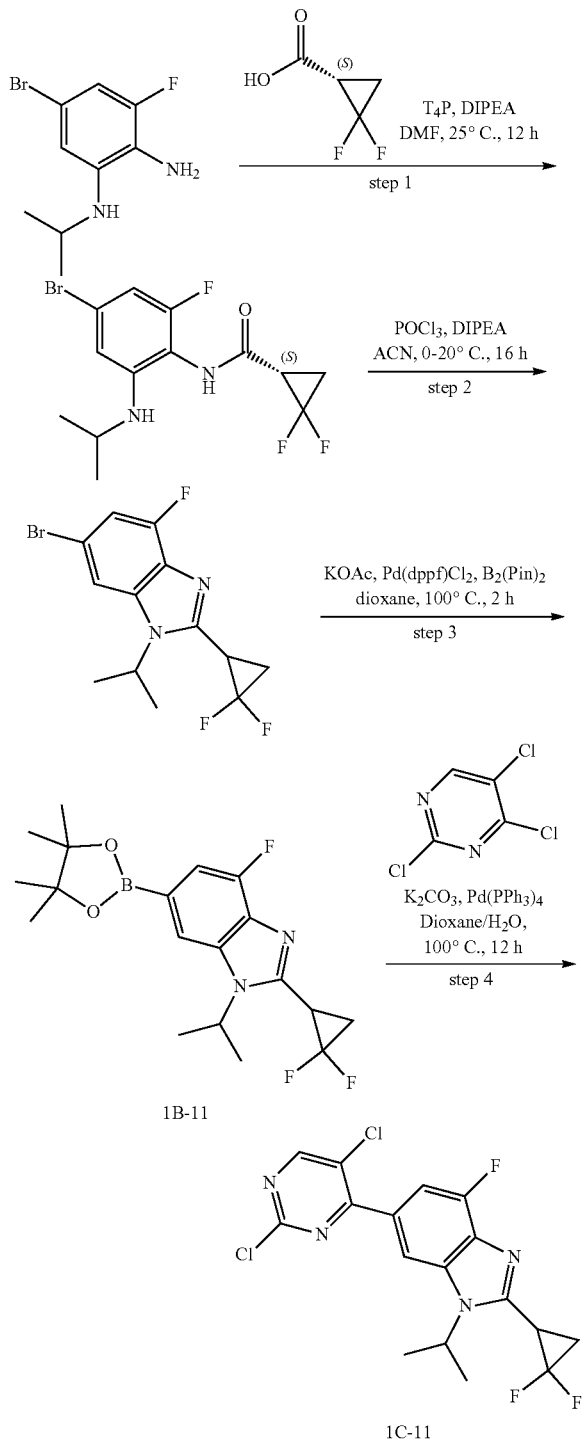

Step 1: Preparation of(S)—N-(4-bromo-2-fluoro-6-(isopropylamino)phenyl)-2,2-difluorocyclopropane-1-carboxamide To a solution of 5-bromo-3-fluoro-N$^1$-isopropylbenzene-1,2-diamine (800 mg, 3.24 mmol, 1 eq) and(S)-2,2-difluorocyclopropane-1-carboxylic acid (592.80 mg, 4.86 mmol, 1.5 eq) in DMF (6 mL) was added DIPEA (1.26 g, 9.71 mmol, 1.69 mL, 3 eq) and T4P (4.67 g, 6.47 mmol, 50% purity, 2 eq), and the mixture was stirred at 25° C. for 12 hours under nitrogen atmosphere. After the completion of the reaction, the mixture was quenched with H$_2$O (30 mL) and extracted with EtOAc (20 mL×3). The combined organic layers were washed with brine (20 mL), dried over Na$_2$SO$_4$, filtered and the filtrate was concentrated in vacuo. The resulting residue was purified by column chromatography to afford(S)—N-(4-bromo-2-fluoro-6-(isopropylamino)phenyl)-2,2-difluorocyclopropane-1-carboxamide (1 g, 87.9% yield) as a white solid. LCMS: 351.0, 353.0 [M+H]$^+$.

Step 2: Preparation of 6-bromo-2-(2,2-difluorocyclopropyl)-4-fluoro-1-isopropyl-1H-benzo[d]imidazole To a solution of(S)—N-(4-bromo-2-fluoro-6-(isopropylamino)phenyl)-2,2-difluorocyclopropane-1-carboxamide (500 mg, 1.42 mmol, 1 eq) in ACN (5 mL) was added dropwise POCl$_3$ (654.96 mg, 4.27 mmol, 0.4 mL, 3 eq) and DIPEA (552.06 mg, 4.27 mmol, 0.75 mL, 3 eq) at 0° C., and the mixture was then stirred at 20° C. for 16 hours under nitrogen atmosphere. After the completion of the reaction, the mixture was quenched with H$_2$O (30 mL) and extracted with EtOAc (30 mL×3). The combined organic layers were washed with brine (20 mL), dried over Na$_2$SO$_4$, filtered and the filtrate was concentrated in vacuo. The resulting residue was purified by column chromatography to afford 6-bromo-2-(2,2-difluorocyclopropyl)-4-fluoro-1-isopropyl-1H-benzo[d]imidazole (400 mg, 84.3% yield) as a brown solid. LCMS: 333.0, 335.0 [M+H]$^+$.

Step 3: Preparation of 2-(2,2-difluorocyclopropyl)-4-fluoro-1-isopropyl-6-(4,4,5,5-tetramethyl-1,3,2-dioxaborolan-2-yl)-1H-benzo[d]imidazole The mixture of 6-bromo-2-(2,2-difluorocyclopropyl)-4-fluoro-1-isopropyl-1H-benzo[d]imidazole (300.00 mg, 0.9 mmol, 1 eq), 4,4,5,5-tetramethyl-2-(4,4,5,5-tetramethyl-1,3,2-dioxaborolan-2-yl)-1,3,2-dioxaborolane (343.01 mg, 1.35 mmol, 1.5 eq), Pd (dppf) Cl$_2$ (65.89 mg, 0.09 mmol, 0.1 eq) and KOAc (176.76 mg, 1.80 mmol, 2 eq) in dioxane (5 mL) was degassed and backfilled with nitrogen for 3 times, and then stirred at 100° C. for 2 hours under nitrogen atmosphere. After the completion of the reaction, the mixture was cooled to room temperature, filtered through a short pad of Celite and rinsed with dioxane (5 mL). The combined filtrate was concentrated in vacuo to afford 2-(2,2-difluorocyclopropyl)-4-fluoro-1-isopropyl-6-(4,4,5,5-tetramethyl-1,3,2-dioxaborolan-2-yl)-1H-benzo[d]imidazole (320 mg, crude) as a deeply brown oil, which was used into the next step without further purification. LCMS: 381.2 [M+H]$^+$.

Step 4: Preparation of 6-(2,5-dichloropyrimidin-4-yl)-2-(2,2-difluorocyclopropyl)-4-fluoro-1-isopropyl-1H-benzo[d]imidazole The mixture of 2-(2,2-difluorocyclopropyl)-4-fluoro-1-isopropyl-6-(4,4,5,5-tetramethyl-1,3,2-dioxaborolan-2-yl)-1H-benzo[d]imidazole (320.00 mg, 0.85 mmol, 1 eq), 2,4,5-trichloropyrimidine (231.56 mg, 1.26 mmol, 1.5 eq), Pd(PPh$_3$)$_4$ (97 26 mg, 0.09 mmol, 0.1 eq) and K$_2$CO$_3$ (232.64 mg, 1.68 mmol, 2 eq) in dioxane (5 mL) and H$_2$O (0.5 mL) was degassed and backfilled with nitrogen for 3 times, and then stirred at 100° C. for 12 hours under nitrogen atmosphere. After the completion of the reaction, the mixture was cooled to room temperature, filtered through a short pad of Celite, rinsed with dioxane (5 mL) and the combined filtrate was concentrated in vacuo. The resulting residue was purified by column chromatography to afford 6-(2,5-dichloropyrimidin-4-yl)-2-(2,2-difluorocyclopropyl)-4-fluoro-1-isopropyl-1H-benzo[d]imidazole (200 mg, 59.2% yield) as a yellow oil. LCMS: 401.0 [M+H]$^+$.

Preparation of 6-(2,5-dichloropyrimidin-4-yl)-4-fluoro-2-((1r,3r)-3-fluorocyclobutyl)-1-isopropyl-1H-benzo[d]imidazole (1C-12)

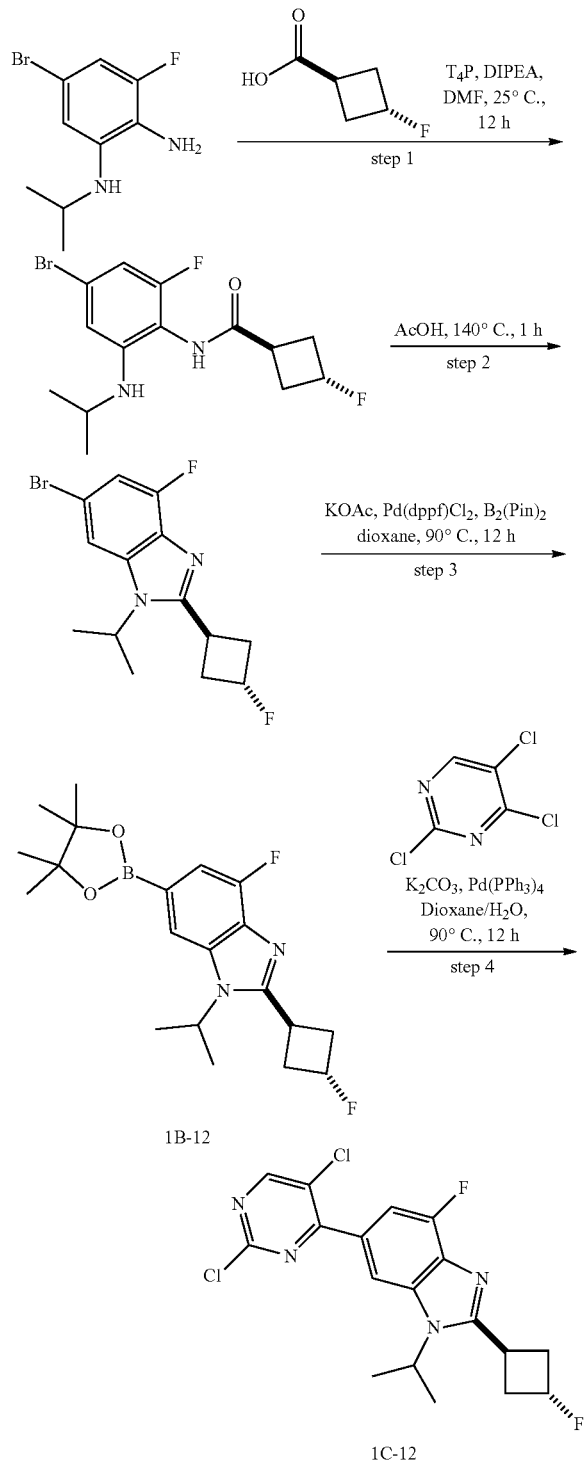

1B-12

1C-12

Step 1: Preparation of (1r,3r)-N-(4-bromo-2-fluoro-6-(isopropylamino)phenyl)-3-fluorocyclobutane-1-carboxamide A mixture of 5-bromo-3-fluoro-N¹-isopropyl-benzene-1,2-diamine (270 mg, 1.09 mmol, 1.1 eq), (1r,3r)-3-fluorocyclobutane-1-carboxylic acid (117.32 mg, 0.99 mmol, 1 eq), TAP (536.78 mg, 1.49 mmol, 1.5 eq) and DIPEA (385.13 mg, 2.98 mmol, 3 eq) in DMF (3 mL) was stirred at 25° C. for 12 hours under nitrogen atmosphere. After the completion of the reaction, the reaction mixture was diluted with water (20 mL) and extracted with EtOAc (20 mL×3). The combined organic layers were washed with brine (30 mL), dried over Na$_2$SO$_4$, filtered and the filtrate was concentrated under reduced pressure. The resulting residue was purified by column chromatography to give (1r,3r)-N-(4-bromo-2-fluoro-6-(isopropylamino)phenyl)-3-fluorocyclobutane-1-carboxamide (266 mg, 77.1% yield) as a yellow oil. LCMS: 347.1 [M+H]

Step 2: Preparation of 6-bromo-4-fluoro-2-((1r,3r)-3-fluorocyclobutyl)-1-isopropyl-1H-benzo[d]imidazole A mixture of (1r,3r)-N-(4-bromo-2-fluoro-6-(isopropylamino)phenyl)-3-fluorocyclobutane-1-carboxamide (246 mg, 0.70 mmol, 1 eq) in AcOH (3 mL) was stirred at 140° C. for 1 hour under nitrogen atmosphere. After the completion of the reaction, the mixture was cooled to room temperature and concentrated under reduced pressure. The resulting residue was purified by column chromatography to 6-bromo-4-fluoro-2-((1r,3r)-3-fluorocyclobutyl)-1-isopropyl-1H-benzo[d]imidazole (192 mg, 0.58 mmol, 82.3% yield) as a yellow oil. LCMS: 329.0 [M+H]⁺.

Step 3: Preparation of 4-fluoro-2-((1r,3r)-3-fluorocyclobutyl)-1-isopropyl-6-(4,4,5,5-tetramethyl-1,3,2-dioxaborolan-2-yl)-1H-benzo[d]imidazole A mixture of 6-bromo-4-fluoro-2-((1r,3r)-3-fluorocyclobutyl)-1-isopropyl-1H-benzo[d]imidazole (172 mg, 0.52 mmol, 1 eq), Pin$_2$B$_2$ (199.0 mg, 0.78 mmol, 1.5 eq), KOAc (153.8 mg, 1.57 mmol, 3 eq) and Pd (dppf) Cl$_2$ (38.2 mg, 0.05 mmol, 0.1 eq) in dioxane (4 mL) was degassed, backfilled with nitrogen and then stirred at 90° C. for 12 hours under nitrogen atmosphere. After the completion of the reaction, the mixture was cooled to room temperature, filtered through a short pad of Celite, rinsed with dioxane (5 mL) and the combined filtrate was concentrated under reduced pressure. The desired 4-fluoro-2-((1r,3r)-3-fluorocyclobutyl)-1-isopropyl-6-(4,4,5,5-tetramethyl-1,3,2-dioxaborolan-2-yl)-1H-benzo[d]imidazole (196 mg, crude) was obtained as a yellow oil, which was used in the next step without further purification. LCMS: 377.2 [M+H]⁺.

Step 4: Preparation of 6-(2,5-dichloropyrimidin-4-yl)-4-fluoro-2-((1r,3r)-3-fluorocyclobutyl)-1-isopropyl-1H-benzo[d]imidazole A mixture of 4-fluoro-2-((1r,3r)-3-fluorocyclobutyl)-1-isopropyl-6-(4,4,5,5-tetramethyl-1,3,2-dioxaborolan-2-yl)-1H-benzo[d]imidazole (196 mg, 0.52 mmol, 1 eq), 2,4,5-trichloropyrimidine (191.1 mg, 1.04 mmol, 2 eq), K$_2$CO$_3$ (215.9 mg, 1.56 mmol, 3 eq) and Pd(PPh$_3$)$_4$ (60.2 mg, 0.05 mmol, 0.1 eq) in dioxane (4 mL) and H$_2$O (0.4 mL) was degassed, backfilled with nitrogen and then stirred at 90° C. for 12 hours under nitrogen atmosphere. After the completion of the reaction, the mixture was cooled to room temperature, filtered through a short pad of the Celite, rinsed with dioxane (5 mL) and the combined filtrate was concentrated in vacuo. The resulting residue was purified by column chromatography to give 6-(2,5-dichloropyrimidin-4-yl)-4-fluoro-2-((1r,3r)-3-fluorocyclobutyl)-1-isopropyl-1H-benzo[d]imidazole (180 mg, 86.9% yield) as a yellow oil. LCMS: 397.1 [M+H]⁺.

Preparation of 6-(2,5-dichloropyrimidin-4-yl)-4-isopropyl-7-methylthieno[3,2-c]pyridazine (1C-13)

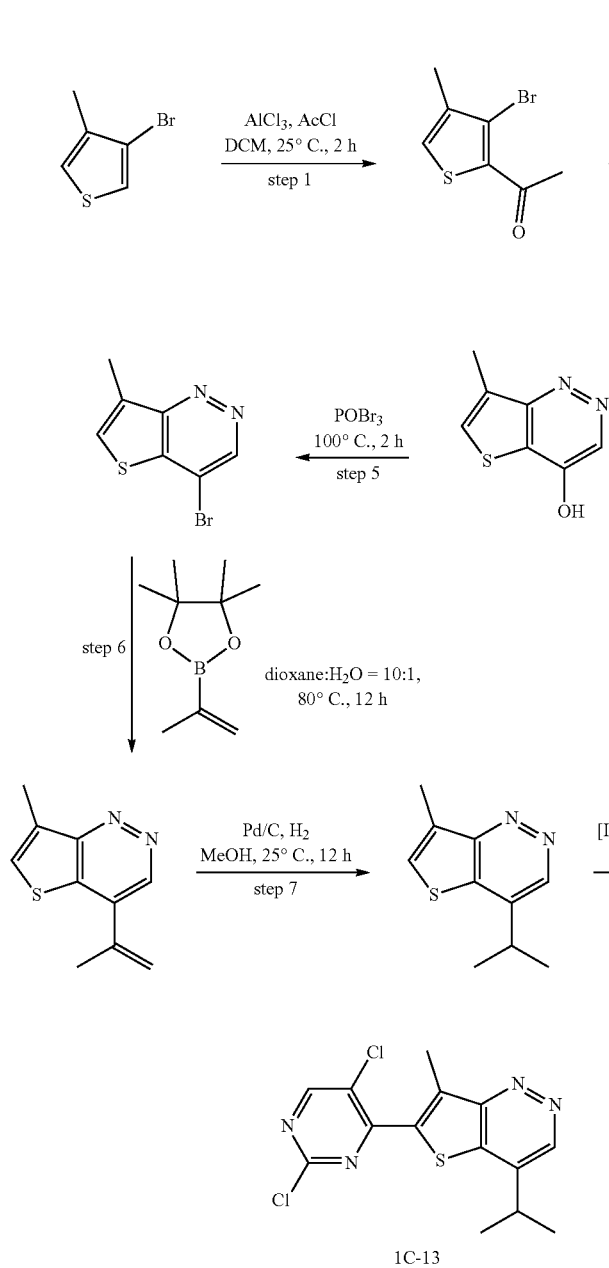
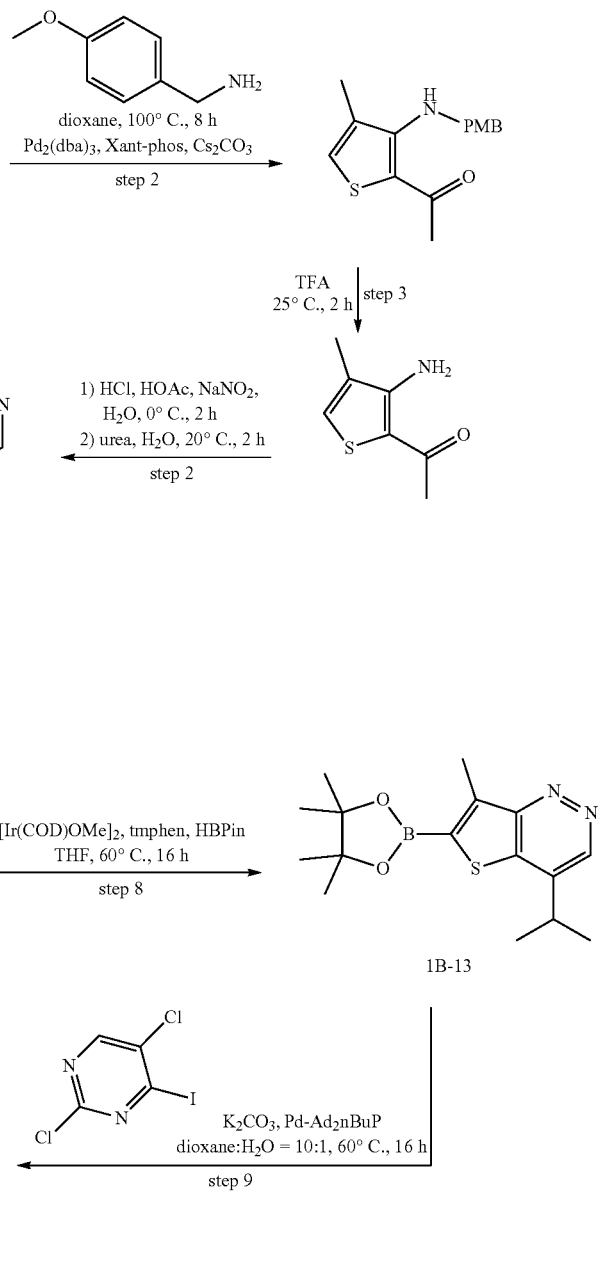

Step 1: Preparation of 1-(3-bromo-4-methylthiophen-2-yl) ethan-1-one

To a suspension of AlCl₃ (7.46 g, 55.91 mmol, 1.1 eq) and 3-bromo-4-methyl-thiophene (9 g, 50.83 mmol, 1 eq) in DCM (180 mL) was added acetyl chloride (4.39 g, 55.91 mmol, 1.1 eq) dropwise at 0° C. under nitrogen atmosphere, and the mixture was then warmed to 25° C. and stirred at that temperature for 2 hours under nitrogen atmosphere. After the completion of the reaction, the mixture was carefully quenched with water (100 mL) and extracted with DCM (100 mL×2). The combined organic layers were washed with brine (50 mL), dried over anhydrous Na₂SO₄, filtered and the filtrate was concentrated in vacuo. The resulting residue was purified by prep-HPLC {column: Phenomenex luna C18 250*80 mm*10 um; mobile phase: [water (FA)-ACN]; gradient: 45%-75% B over 20 min} to afford 1-(3-bromo-4-methylthiophen-2-yl) ethan-1-one (4.2 g, 19.17 mmol, 37.7% yield) as a yellow oil. $^1$H NMR (400 MHZ, CDCl₃-d) δ 7.30 (d, J=0.8 Hz, 1H), 2.70 (s, 3H), 2.28 (d, J=0.8 Hz, 3H) ppm.

Step 2: Preparation of 1-(3-((4-methoxybenzyl)amino)-4-methylthiophen-2-yl) ethan-1-one A mixture of 1-(3-bromo-4-methylthiophen-2-yl) ethan-1-one (2.85 g, 13.01 mmol, 1 eq), PMBNH₂ (2.86 g, 20.81 mmol, 1.6 eq), Cs₂CO₃ (8.48 g, 26.02 mmol, 2 eq), Xantphos (1.51 g, 2.60 mmol, 0.2 eq) and Pd₂(dba)₃ (1.19 g, 1.30 mmol, 0.1 eq) in dioxane (60 mL) was degassed and backfilled with nitrogen for three times, and then stirred at 100° C. for 8 hours under nitrogen atmosphere. After the completion of the reaction, the mixture was cooled to room temperature, filtered through a pad of the Celite, rinsed with dioxane (10 mL) and the combined filtrate was concentrated in vacuo. The resulting residue was purified by column chromatography to afford 1-(3-((4-methoxybenzyl)amino)-4-methylthiophen-2-yl) ethan-1-one (3.16 g, 88.2% yield) as a yellow solid. $^1$H NMR (400 MHZ, CDCl$_3$-d)δ 8.87 (br s, 1H), 7.23 (d, J=8.4 Hz, 2H), 6.97 (s, 1H), 6.88 (d, J=8.4 Hz, 2H), 4.65 (s, 2H), 3.81 (s, 3H), 2.39 (s, 3H), 2.31 (s, 3H) ppm.

Step 3: Preparation of 1-(3-amino-4-methylthiophen-2-yl) ethan-1-one

The solution of 1-(3-((4-methoxybenzyl)amino)-4-methylthiophen-2-yl) ethan-1-one (3.16 g, 11.48 mmol, 1 eq) in TFA (32 mL) was stirred at 25° C. for 2 hours, and then concentrated in vacuo. The desired 1-(3-amino-4-methylthiophen-2-yl) ethan-1-one (1.8 g, crude) was obtained as a yellow solid. LCMS: 156.0 [M+H]; $^1$H NMR (400 MHZ, CDCl$_3$-d)δ 7.01 (d, J=1.2 Hz, 1H), 6.09-5.76 (m, 2H), 2.40 (s, 3H), 2.09 (d. J=1.2 Hz, 3H) ppm.

Step 4: Preparation of 7-methylthieno[3,2-c]pyridazin-4-ol

To a solution of 1-(3-amino-4-methylthiophen-2-yl) ethan-1-one (1.8 g, 11.60 mmol, 1 eq) in AcOH (3.6 mL) was added dropwise aqueous HCl (prepared from concentrated HCl (7.2 mL) in H$_2$O (14.4 mL.)), and followed by dropwise addition of a solution of NaNO$_2$ (1.01 g, 14.61 mmol, 1.26 eq) in H$_2$O (1 mL) at 0° C. under nitrogen atmosphere, and the mixture was kept stirring at 0° C. for an additional 1 hour. Subsequently, urea (84 mg, 1.41 mmol, 0.12 eq) was added in portions at 25° C. and the mixture was kept stirring for 12 hours at 25° C. under nitrogen atmosphere. The mixture was then filtered, and the solid was collected, washed with H$_2$O (10 mL×2) and dried in vacuo. The desired 7-methylthieno[3,2-c]pyridazin-4-ol (1.9 g, 98.5% yield) was obtained as a yellow solid. LCMS: 167.1 [M+H]$^+$.

Step 5: Preparation of 4-bromo-7-methylthieno[3,2-c]pyridazine

The mixture of 7-methylthieno[3,2-c]pyridazin-4-ol (1.9 g, 11 43 mmol, 1 eq) and POBr$_3$ (22 g, 76.74 mmol, 7.80 mL, 6.71 eq) was stirred at 100° C. under nitrogen atmosphere for 12 hours. After the completion of the reaction, the mixture was cooled to room temperature, carefully quenched with cold water (50 mL) and extracted with DCM (50 mL×2). The combined organic layers were washed with brine (50 mL), dried over anhydrous Na$_2$SO$_4$, filtered and the filtrate was concentrated in vacuo. The desired 4-bromo-7-methylthieno[3,2-c]pyridazine (1.8 g, 68.7% yield) was obtained as a yellow solid. LCMS: 230.9 [M+H]$^+$.

Step 6: Preparation of 7-methyl-4-(prop-1-en-2-yl) thieno[3,2-c]pyridazine

A mixture of 4-bromo-7-methylthieno[3,2-c]pyridazine (1.6 g, 6.98 mmol, 1 eq), 2-isopropenyl-4,4,5,5-tetramethyl-1,3,2-dioxaborolane (1.54 g, 9.15 mmol, 1.31 eq), K$_3$PO$_4$ (4.45 g, 20.95 mmol, 3 eq) and Pd (dppf) Cl$_2$ (511.02 mg. 0.698 mmol, 0.1 eq) in dioxane (50 mL) and H$_2$O (5 mL) was degassed and backfilled with nitrogen for three times, and then stirred at 80° C. for 12 hours under nitrogen atmosphere. After the completion of the reaction, the mixture was cooled to room temperature, filtered through a pad of the Celite, rinsed with dioxane (15 mL.) and the combined filtrate was concentrated in vacuo. The resulting residue was purified by column chromatography to afford 7-methyl-4-(prop-1-en-2-yl) thieno[3,2-c]pyridazine (0.96 g) as a yellow solid. LCMS: 191.1 [M+H]$^+$.

Step 7: Preparation of 4-isopropyl-7-methylthieno[3,2-c]pyridazine

To a solution of 7-methyl-4-(prop-1-en-2-yl) thieno[3,2-c]pyridazine (0.96 g, 5.05 mmol, 1 eq) in MeOH (30 mL) was added Pd/C (537 mg, 0.505 mmol, 0.1 eq), and the suspension was degassed and backfilled with hydrogen for three times and then stirred under hydrogen (15 psi) at 25° C. for 12 hours. After the completion of the reaction, the mixture was filtered through a pad of the Celite, rinsed with methanol (15 mL) and the combined filtrate was concentrated in vacuo. The desired 4-isopropyl-7-methylthieno[3,2-c]pyridazine (720 mg, 74.2% yield) was obtained as a yellow oil. LCMS: 193.1 [M+H].

Step 8: Preparation of 4-isopropyl-7-methyl-6-(4,4,5,5-tetramethyl-1,3,2-dioxaborolan-2-yl) thieno[3,2-c]pyridazine A mixture of 4-isopropyl-7-methylthieno[3,2-c]pyridazine (200 mg, 1.04 mmol, 1 eq), (1Z,5Z)-cycloocta-1,5-diene;2,4-dimethyl-BLAHbicyclo[1.1.0]butane (20.68 mg, 0.0312 mmol, 0.03 eq), 3,4,7,8-tetramethyl-1,10-phenanthroline (14.75 mg, 0.0624 mmol, 0.06 eq) and 4,4,5,5-tetramethyl-1,3,2-dioxaborolane (266.23 mg, 2.08 mmol, 2 eq) in THF (6 mL) was stirred at 60° C. under nitrogen atmosphere for 16 hours. After the completion of the reaction, the mixture was cooled to room temperature, and concentrated in vacuo to afford 4-isopropyl-7-methyl-6-(4,4,5,5-tetramethyl-1,3,2-dioxaborolan-2-yl) thieno[3,2-c]pyridazine (330 mg, crude) as a brown solid. LCMS: 319.2 [M+H]$^+$.

Step 9: Preparation of 6-(2,5-dichloropyrimidin-4-yl)-4-isopropyl-7-methylthieno[3,2-c]pyridazine A mixture of 4-isopropyl-7-methyl-6-(4,4,5,5-tetramethyl-1,3,2-dioxaborolan-2-yl) thieno[3,2-c]pyridazine (30 mg, 0.127 mmol, 1 eq), 2,5-dichloro-4-iodo-pyrimidine (20 mg, 0 0727 mmol), [2-(2-aminophenyl)phenyl]-chloro-palladium;bis(1-adamantyl)-butyl-phosphane (9.00 mg, 0.0134 mmol, 0.1 eq) and K$_2$CO$_3$ (36.00 mg, 0.260 mmol, 2.05 eq) in H$_2$O (0.1 mL) and dioxane (1 mL) was stirred at 60° C. under nitrogen atmosphere for 12 hours. After the completion of the reaction, the mixture was cooled to room temperature, filtered through a short pad of the Celite, rinsed with dioxane (5 mL) and the combined filtrate was concentrated in vacuo. The resulting residue was purified by prep-TLC (PE/EtOAc=1/1, Rf=0.35) to afford 6-(2,5-dichloropyrimidin-4-yl)-4-isopropyl-7-methylthieno[3,2-c]pyridazine (8 mg, 18.5% yield) as a yellow oil. LCMS: 339.1 [M+H].

Preparation of 2-(2-(2,5-dichloropyrimidin-4-yl)-3-methylthieno[3,2-b]pyridin-6-yl) propan-2-ol (1C-14)

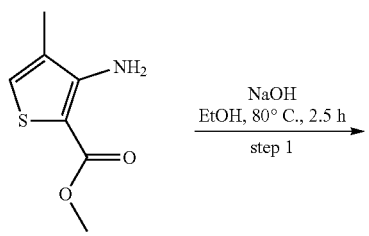

-continued

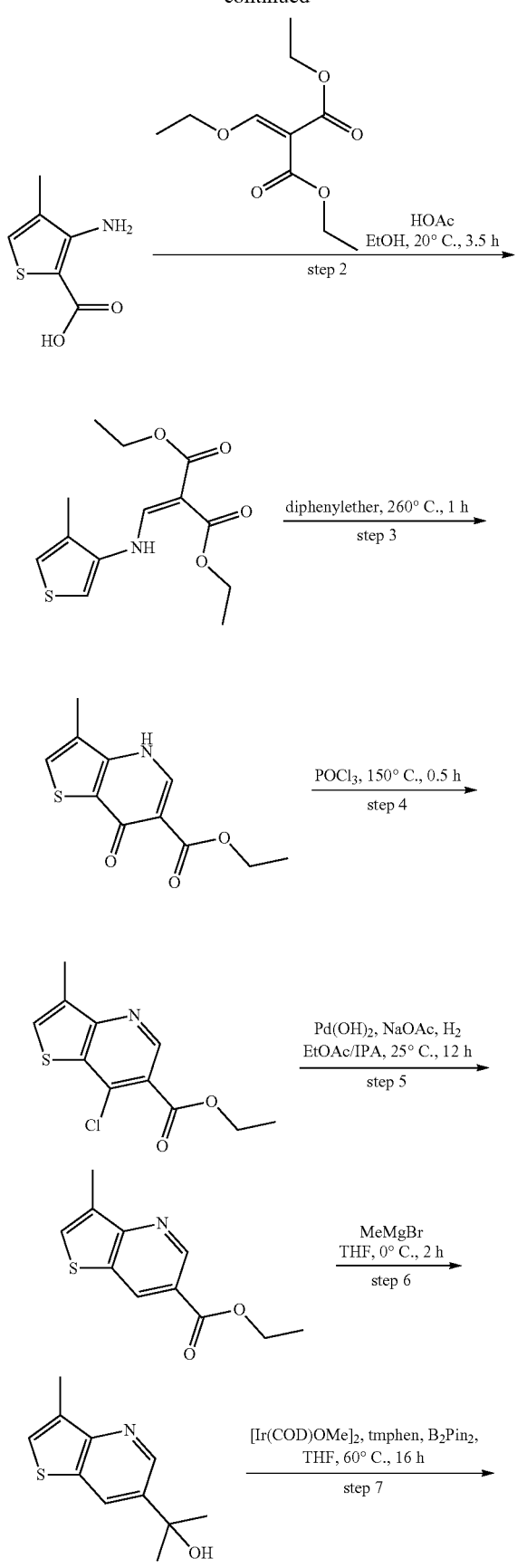

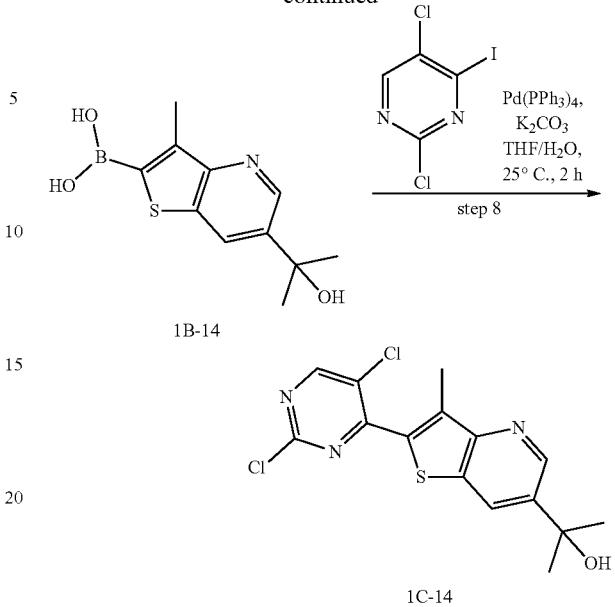

Step 1: Preparation of sodium 3-amino-4-methylthiophene-2-carboxylate

To a solution of methyl 3-amino-4-methylthiophene-2-carboxylate (5 g, 29.20 mmol, 1 eq) in EtOH (25 mL) was added aqueous NaOH (1 M, 35 mL, 1.20 eq), and the mixture was heated to 80° C. for 2.5 hours under nitrogen atmosphere. After the completion of the reaction, the mixture was cooled to room temperature and concentrated under reduced pressure to give sodium 3-amino-4-methylthiophene-2-carboxylate (5 g, 27.91 mmol, 95.56% yield) as a white solid.

Step 2: Preparation of diethyl 2-(((4-methylthiophen-3-yl)amino) methylene) malonate To a solution of sodium 3-amino-4-methylthiophene-2-carboxylate (5 g, 27.91 mmol, 1 eq) in EtOH (80 ml) was added AcOH (1.68 g, 27.91 mmol, 1.60 mL, 1 eq), and the mixture was stirred for 30 minutes and followed by the addition of diethyl 2-(ethoxymethylene) malonate (6.96 g, 32.16 mmol, 6.5 mL, 1.15 eq). The mixture was stirred at 20° C. for an additional 3 hours, and then concentrated in vacuo. The resulting residue was purified by column chromatography to afford diethyl 2-(((4-methylthiophen-3-yl) amino) methylene) malonate (6.8 g, 86.0% yield) as a yellow oil. LCMS: 284.1 [M+H]$^+$; $^1$H NMR (400 MHZ, CDCl$_3$-d)δ 10.92 (br d, J=13.2 Hz, 1H), 8.38 (d. J=13.6 Hz, 1H), 7.00-6.94 (m, 1H), 6.88 (d, J=3.3 Hz, 1H), 4.42-4.15 (m, 4H), 2.23 (d, J=0.6 Hz, 3H), 1.47-1.24 (m, 6H) ppm.

Step 3: Preparation of ethyl 3-methyl-7-oxo-4,7-dihydrothieno[3,2-b]pyridine-6-carboxylate A solution of diethyl 2-(((4-methylthiophen-3-yl)amino) methylene) malonate (6.3 g, 22.23 mmol, 1 eq) in diphenylether (70 mL) was heated and stirred at 260° C. for 1 hour under nitrogen atmosphere. After the completion of the reaction, the mixture was cooled to room temperature, diluted with petroleum ether (210 mL) and stirred for 10 minutes. The resulting precipitate was filtered, collected and dried under vacuo. The desired ethyl 3-methyl-7-oxo-4,7-dihydrothieno[3,2-b]pyridine-6-carboxylate (3.8 g, crude) was obtained as a white solid. LCMS: 238.0 [M+H]$^+$; $^1$H NMR (400 MHZ, DMSO-d$_6$) δ 12.59 (br s, 1H), 8.35 (s, 1H), 7.68 (s, 1H), 4.52-3.98 (m, 2H), 2.34 (s, 3H), 1.27 (t, J=7.0 Hz, 3H) ppm.

Step 4: Preparation of ethyl 7-chloro-3-methylthieno[3,2-b]pyridine-6-carboxylate A solution of ethyl 3-methyl-7-oxo-4, 7-dihydrothieno[3,2-b]pyridine-6-carboxylate (3.5 g. 14.75 mmol, 1 eq) in POCl₃ (20 mL) was heated and stirred at 150° C. for 0.5 hour under nitrogen atmosphere. After the completion of the reaction, the mixture was cooled to room temperature and concentrated under reduced pressure. The resulting residue was carefully quenched with saturated aqueous NaHCO₃ (100 mL) and extracted with EtOAc (50 mL×2). The combined organic layers were washed with brine (50 mL), dried over anhydrous Na₂SO₄, filtered and the filtrate was concentrated in vacuo. The desired ethyl 7-chloro-3-methylthieno[3,2-b]pyridine-6-carboxylate (3.8 g, crude) as a white solid. LCMS: 256.0 [M+H]⁺.

Step 5: Preparation of ethyl 3-methylthieno[3,2-b]pyridine-6-carboxylate

To a solution of ethyl 7-chloro-3-methylthieno[3,2-b]pyridine-6-carboxylate (3.6 g, 14.08 mmol, 1 eq) in EtOAc (100 mL) and IPA (10 mL) was added Pd(OH)₂ (1.80 g, 2.56 mmol, 20% purity, 0.18 eq) and NaOAc (7.20 g, 87.77 mmol, 6.23 eq), and the suspension was degassed, backfilled with hydrogen for 3 times and then stirred under hydrogen (50 Psi) at 25° C. for 12 hours. After the completion of the reaction, the reaction mixture was filtered through a short pad of Celite, rinsed with ethyl acetate (20 mL) and the combined filtrate was concentrated under reduced pressure. The resulting residue was purified by prep-HPLC (basic condition: column: Welch Ultimate XB-CN 250*70*10 um; mobile phase: [Hexane-EtOH]; gradient: 1%-5% B over 15 min) to afford ethyl 3-methylthieno[3,2-b]pyridine-6-carboxylate (2.85 g, 91.4% yield) as a white solid. LCMS: 222.1 [M+H]⁺.

Step 6: Preparation of 2-(3-methylthieno[3,2-b]pyridin-6-yl) propan-2-ol

To a solution of ethyl 3-methylthieno[3,2-b]pyridine-6-carboxylate (0.5 g, 2.26 mmol, 1 eq) in THF (10 mL) was added MeMgBr (3 M, 3 01 mL, 4 eq) at 0° C., and the mixture was kept stirring at that temperature for 2 hours under nitrogen atmosphere. After the completion of the reaction, the mixture was quenched with saturated aqueous NH₄Cl (50 mL) and extracted with EtO Ac (50 mL×2). The combined organic layers were washed with brine (50 mL), dried over anhydrous Na₂SO₄, filtered and the filtrate was concentrated in vacuo. The resulting residue was purified by column chromatography to afford 2-(3-methylthieno[3,2-b]pyridin-6-yl) propan-2-ol (0.44 g, 93.9% yield) as a white solid. LCMS: 208.1 [M+H]⁺.

Step 7: Preparation of (6-(2-hydroxypropan-2-yl)-3-methylthieno[3,2-b]pyridin-2-yl) boronic acid To a solution of 2-(3-methylthieno[3,2-b]pyridin-6-yl) propan-2-ol (0.15 g, 0.73 mmol, 1 eq) and 4,4,5,5-tetramethyl-1,3,2-dioxaborolane (185.21 mg, 1.45 mmol, 0.21 mL, 2 eq) in THF (3 mL) was added (1Z,5Z)-cycloocta-1,5-diene;2,4-dimethyl-bicyclo[1.1.0]butane (47.97 mg, 0.07 mmol, 0.1 eq) and 3,4,7,8-tetramethyl-1,10-phenanthroline (34.20 mg, 0.15 mmol, 0.2 eq), and the mixture was stirred at 60° C. for 12 hours under nitrogen atmosphere. After the completion of the reaction, the mixture was cooled to room temperature, filtered through a short pad of Celite, rinsed with THF (3 mL) and the combined filtrate was concentrated under reduced pressure. The desired (6-(2-hydroxypropan-2-yl)-3-methylthieno[3,2-b]pyridin-2-yl) boronic acid (0.3 g, crude) was obtained as a black oil. LCMS: 252.1 [M+H]⁺.

Step 8. Preparation of 2-(2-(2,5-dichloropyrimidin-4-yl)-3-methylthieno[3,2-b]pyridin-6-yl) propan-2-ol To a degassed and nitrogen backfilled solution of (6-(2-hydroxypropan-2-yl)-3-methylthieno[3,2-b]pyridin-2-yl) boronic acid (180 mg, 0.72 mmol, 1 eq), 2,5-dichloro-4-iodo-pyrimidine (295.55 mg, 1.08 mmol, 1.5 eq) and K₂CO₃ (297.21 mg, 2.15 mmol, 3 eq) in THF (4 mL) and H₂O (0.6 mL) was added Pd(PPh₃)₄ (47.93 mg, 0.07 mmol, 0.1 eq), and the mixture was stirred at 25° C. for 2 hours under nitrogen atmosphere. After the completion of the reaction, the reaction mixture was filtered through a short pad of Celite, rinsed with THF (4 mL) and the combined filtrate was concentrated under reduced pressure. The resulting residue was purified by column chromatography to afford 2-(2-(2,5-dichloropyrimidin-4-yl)-3-methylthieno[3,2-b]pyridin-6-yl) propan-2-ol (0.25 g, 0.7 mmol, 98.4% yield) as a yellow solid. LCMS: 354.0 [M+H]⁺.

Preparation of 2-(4-chloro-6-(2,5-dichloropyrimidin-4-yl)-8-fluoroquinolin-3-yl) propan-2-ol (1C-15)

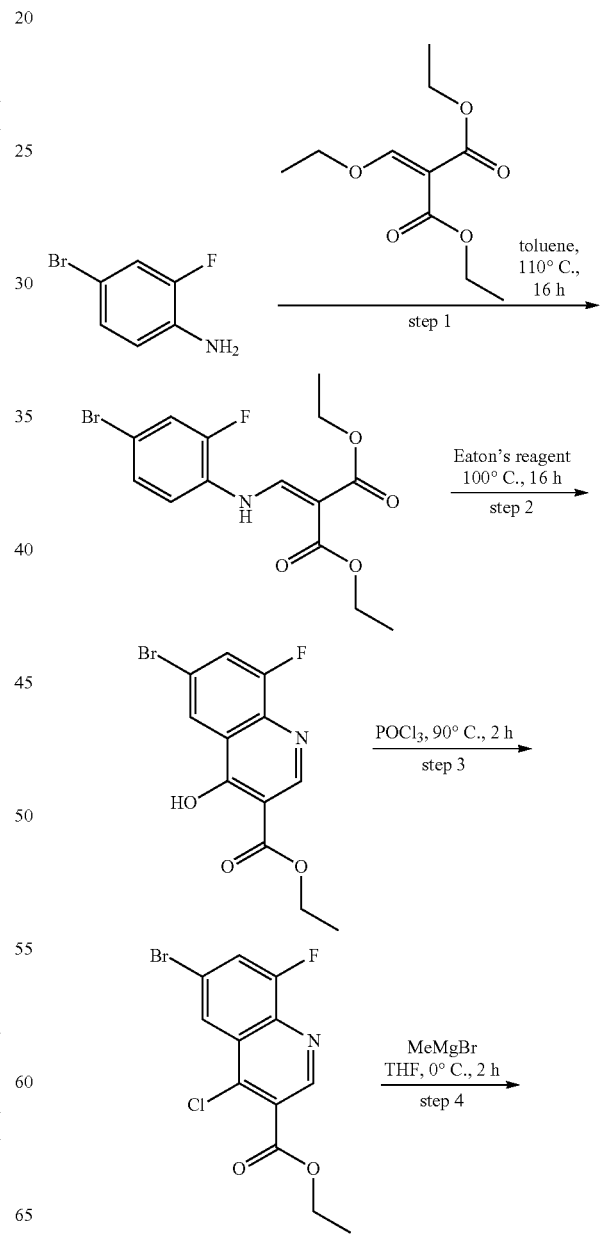

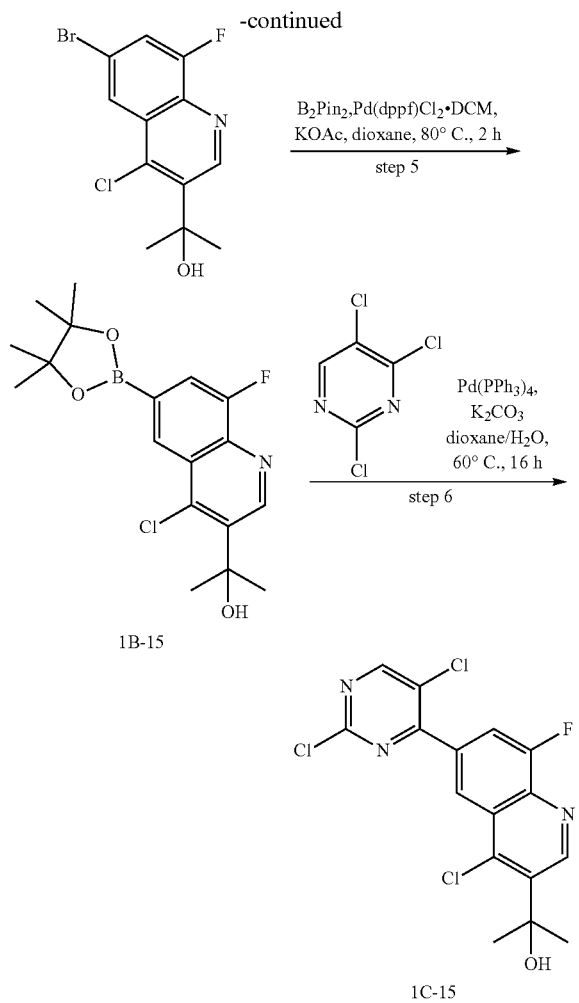

Step 1: preparation of diethyl 2-(((4-bromo-2-fluorophenyl)amino) methylene) malonate The solution of 4-bromo-2-fluoro-aniline (21.97 g, 115.62 mmol, 1 eq) and diethyl 2-(ethoxymethylene) malonate (30 g, 138.74 mmol, 28.04 mL, 1.2 eq) in toluene (100 mL) was stirred at 110° C. for 8 hours under nitrogen atmosphere. After the completion of the reaction, the mixture was cooled to room temperature, poured into H₂O (250 mL) and extracted with DCM (250 mL×3) The combined organic layers were washed with brine (100 mL), dried over anhydrous Na₂SO₄, filtered and the filtrate was concentrated in vacuo. The resulting residue was purified by column chromatography to afford diethyl 2-(((4-bromo-2-fluorophenyl)amino) methylene) malonate (30 g, 72.0% yield) as a white solid. ¹H NMR (400 MHz, DMSO-d₆) δ 10.84 (d, J=13.2 Hz, 1H), 8.43 (d, J=13.2 Hz, 1H), 7.76-7.35 (m, 3H), 4.29-3.99 (m, 4H), 1.25 (dt, J=5.2, 7.0 Hz, 6H) ppm.

Step 2: preparation of ethyl 6-bromo-8-fluoro-4-hydroxyquinoline-3-carboxylate

To a solution of diethyl 2-(((4-bromo-2-fluorophenyl) amino) methylene) malonate (15 g, 41.65 mmol, 1 eq) in toluene (100 mL) was added Eaton's reagent (54.54 g, 229.11 mmol, 36.00 mL, 5.50 eq), and the mixture was stirred at 100° C. for 12 hours under nitrogen atmosphere. After the completion of the reaction, the mixture was cooled to room temperature, quenched with ice-water (100 mL) and extracted with DCM (250 mL×2). The combined organic layers were washed with saturated aqueous NaHCO₃ (200 mL) and brine (200 mL), dried over anhydrous Na₂SO₄, filtered and the filtrate was concentrated in vacuo. The resulting residue was purified by column chromatography to afford ethyl 6-bromo-8-fluoro-4-hydroxyquinoline-3-carboxylate (3 g, 22.5% yield) as a yellow solid. LCMS: 314.0 [M+H]⁺.

Step 3: preparation of ethyl 6-bromo-4-chloro-8-fluoroquinoline-3-carboxylate

The solution of ethyl 6-bromo-8-fluoro-4-hydroxyquinoline-3-carboxylate (2.8 g, 8.91 mmol, 1 eq) in POCl₃ (30 mL) was stirred at 90° C. for 16 hours under nitrogen atmosphere. After the completion of the reaction, the mixture was cooled to room temperature, concentrated in vacuo, carefully quenched with cold H₂O (250 mL) and extracted with DCM (250 mL×3). The combined organic layers were washed with brine (100 mL), dried over anhydrous Na₂SO₄, filtered and the filtrate was concentrated under reduced pressure. The resulting residue was purified by column chromatography to afford ethyl 6-bromo-4-chloro-8-fluoroquinoline-3-carboxylate (1.5 g, 50.6% yield) as a yellow solid. LCMS: 333.9 [M+H]⁺.

Step 4: preparation of 2-(6-bromo-4-chloro-8-fluoroquinolin-3-yl) propan-2-ol

To a solution of ethyl 6-bromo-4-chloro-8-fluoroquinoline-3-carboxylate (1.2 g, 3.61 mmol, 1 eq) in THF (2 mL) was added MeMgBr (3 M, 8.40 mL, 6.98 eq) dropwised at −30° C. under nitrogen atmosphere, and the mixture was then warmed to 0° C. and stirred for 4 hours at that temperature. After the completion of the reaction, the mixture was quenched with saturated aqueous NH₄Cl (50 mL) at 0° C. and extracted with EtOAc (250 mL×2). The combined organic layers were washed with brine (100 mL), dried over anhydrous Na₂SO₄, filtered and the filtrate was concentrated in vacuo. The resulting residue was purified by column chromatography to afford 2-(6-bromo-4-chloro-8-fluoroquinolin-3-yl) propan-2-ol (0.75 g, 65.2% yield) as a yellow solid. LCMS: 320.0 [M+H]⁺.

Step 5: Preparation of 2-(4-chloro-8-fluoro-6-(4,4,5,5-tetramethyl-1,3,2-dioxaborolan-2-yl) quinolin-3-yl) propan-2-ol The mixture of 2-(6-bromo-4-chloro-8-fluoroquinolin-3-yl) propan-2-ol (700 mg, 2.20 mmol, 1 eq), 4,4,5,5-tetramethyl-2-(4,4,5,5-tetramethyl-1,3,2-dioxaborolan-2-yl)-1,3,2-dioxaborolane (1.12 g, 4.39 mmol, 2 eq), Pd (dppf) Cl₂DCM (179.44 mg, 0.22 mmol, 0.1 eq) and KOAc (646.95 mg, 6.59 mmol, 3 eq) in dioxane (10 mL) was degassed and backfilled with nitrogen for 3 times, and then stirred at 80° C. for 2 hours under nitrogen atmosphere After the completion of the reaction, the mixture was cooled to room temperature, filtered through a short pad of Celite, rinsed with dioxane (10 mL) and the combined filtrate was concentrated in vacuo. The desired 2-(4-chloro-8-fluoro-6-(4,4,5,5-tetramethyl-1,3,2-dioxaborolan-2-yl) quinolin-3-yl) propan-2-ol (700 mg crude) was obtained as a deep brown oil. LCMS: 366.1 [M+H]⁺.

Step 6. Preparation of 2-(4-chloro-6-(2,5-dichloropyrimidin-4-yl)-8-fluoroquinolin-3-yl) propan-2-ol The mixture of 2-(4-chloro-8-fluoro-6-(4,4,5,5-tetramethyl-1,3,2-dioxaborolan-2-yl) quinolin-3-yl) propan-2-ol (350 mg, 0.96 mmol, 1 eq), 2,4,5-trichloropyrimidine (263.37 mg, 1.44 mmol, 1.5 eq), Pd(PPh₃)₄ (110.62 mg, 0.096 mmol, 0.1 eq) and K₂CO₃ (396.89 mg, 2.87 mmol, 3 eq) in dioxane (5 mL) and H₂O (0.5 mL) was degassed and backfilled with nitrogen for 3 times, and then stirred at 60° C. for 16 hours under nitrogen atmosphere. After the completion of the reaction, the mixture was cooled to room temperature and concentrated in vacuo. The resulting residue was purified by prep-TlC (PE/EtOAc=2:1) to afford 2-(4-chloro-6-(2,5-dichloropyrimidin-4-yl)-8-fluoroquinolin-3-yl) propan-2-ol (350 mg, 0.91 mmol, 94.5% yield) as a light yellow oil. LCMS: 386.0 [M+H]⁺.

Preparation of 2-(4-chloro-6-(2-chloro-5-fluoropyrimidin-4-yl)-8-fluoroquinolin-3-yl) propan-2-ol (1C-16)

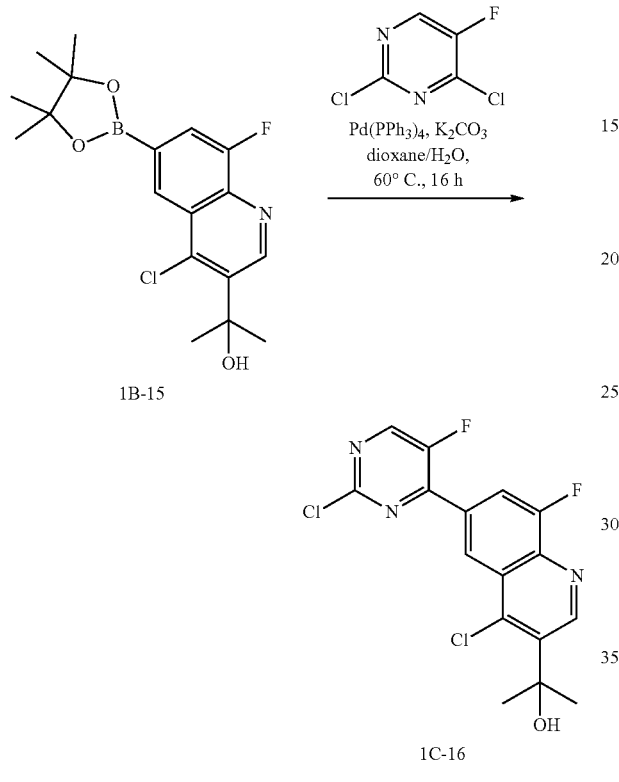

A mixture of 2-(4-chloro-8-fluoro-6-(4,4,5,5-tetramethyl-1,3,2-dioxaborolan-2-yl) quinolin-3-yl) propan-2-ol (350 mg, 0.96 mmol, 1 eq), 2,4-dichloro-5-fluoro-pyrimidine (239.74 mg, 1.44 mmol, 1.5 eq), Pd(PPh₃)₄ (110.62 mg, 0.096 mmol, 0.1 eq) and K₂CO₃ (396.90 mg, 2.87 mmol, 3 eq) in dioxane (5 mL) and H₂O (0.5 mL) was degassed and backfilled with nitrogen for 3 times, and then stirred at 60° C. for 16 hours under nitrogen atmosphere. After the completion of the reaction, the mixture was cooled to room temperature and concentrated in vacuo. The resulting residue was purified by prep-TLC (PE/EtOAc=2:1) to afford 2-(4-chloro-6-(2-chloro-5-fluoropyrimidin-4-yl)-8-fluoroquinolin-3-yl) propan-2-ol (350 mg, 98.7% yield) as a light yellow solid. LCMS: 370.0 [M+H]⁺.

Preparation of 2-(6-(2-chloro-5-fluoropyrimidin-4-yl)-8-fluoro-4-methylquinolin-3-yl) propan-2-ol (1C-17)

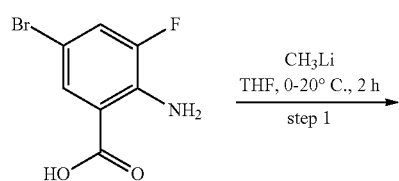

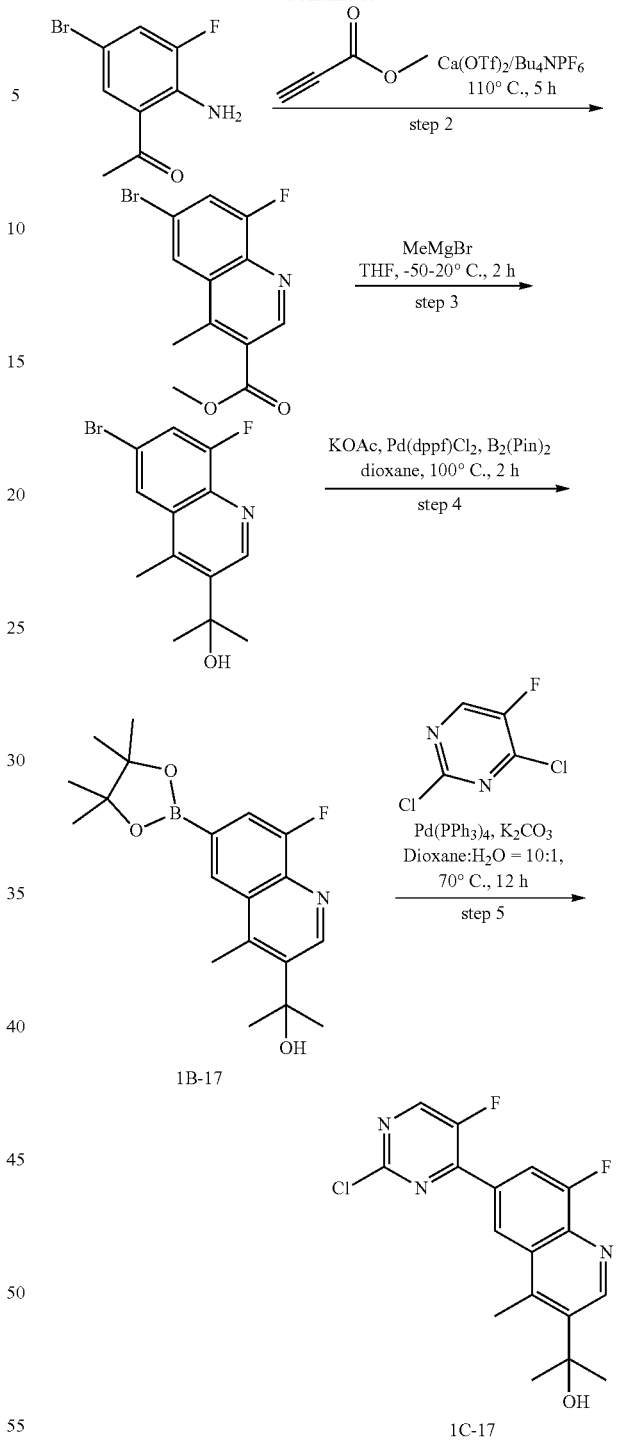

Step 1: Preparation of 1-(2-amino-5-bromo-3-fluorophenyl) ethan-1-one

To a solution of 2-amino-5-bromo-3-fluoro-benzoic acid (1 g, 4.27 mmol, 1 eq) in THF (10 mL) was added methyllithium (1.6 M, 10.68 mL, 4 eq) dropwise at 0° C., and the mixture was then warmed to 20° C. and stirred for 2 hours at that temperature under nitrogen atmosphere. After the completion of the reaction, the mixture was quenched with H₂O (60 mL) and extracted with EtOAc (60 mL.×3). The combined organic layers were washed with brine (30 mL), dried over anhydrous Na₂SO₄, filtered and the filtrate was concentrated in vacuo. The resulting residue was purified by column chromatography to afford 1-(2-amino-5-bromo-3-fluorophenyl) ethan-1-one (790 mg, 79.6% yield) as a yellow solid. LCMS: 232.0, 234.0 [M+H]⁺.

Step 2: Preparation of methyl 6-bromo-8-fluoro-4-methylquinoline-3-carboxylate

The mixture of 1-(2-amino-5-bromo-3-fluorophenyl) ethan-1-one (1.1 g, 4.74 mmol, 1 eq) and methyl prop-2-ynoate (518.10 mg. 6.16 mmol, 0.52 mL, 1.3 eq) in tetrabutylammonium hexafluorophosphate (183.66 mg, 0.48 mmol, 0.1 eq) and calcium trifluoromethanesulfonate (160.33 mg. 0.48 mmol, 0.1 eq) was stirred at 110° C. for 5 hours under nitrogen atmosphere. After the completion of the reaction, the mixture was cooled to room temperature, quenched with H₂O (50 mL) and extracted with EtOAc (50 mL×3). The combined organic layers were washed with brine (30 mL), dried over anhydrous Na₂SO₄, filtered and the filtrate was concentrated in vacuo. The resulting residue was purified by column chromatography to afford methyl 6-bromo-8-fluoro-4-methylquinoline-3-carboxylate (600 mg, 42.4% yield) as a yellow solid. LCMS: 298.0, 300.0 [M+H]⁺.

Step 3: Preparation of 2-(6-bromo-8-fluoro-4-methylquinolin-3-yl) propan-2-ol

To a solution of methyl 6-bromo-8-fluoro-4-methylquinoline-3-carboxylate (580 mg, 1.95 mmol, 1 eq) in THF (8 mL) was added MeMgBr (3 M, 1.62 mL, 2.5 eq) dropwise at −50° C., and the mixture was then stirred at 20° C. for 2 hours under nitrogen atmosphere. After the completion of the reaction, the mixture was quenched with H₂O (30 mL) and extracted with EtOAc (50 mL×3). The combined organic layers were washed with brine (30 mL), dried over anhydrous Na₂SO₄, filtered and the filtrate was concentrated in vacuo. The resulting residue was purified by column chromatography to afford 2-(6-bromo-8-fluoro-4-methylquinolin-3-yl) propan-2-ol (365 mg, 62.9% yield) as a yellow solid. LCMS: 298.0, 300.0 [M+H]⁺.

Step 4: Preparation of 2-(8-fluoro-4-methyl-6-(4,4,5,5-tetramethyl-1,3,2-dioxaborolan-2-yl) quinolin-3-yl) propan-2-ol The degassed and nitrogen backfilled mixture of 2-(6-bromo-8-fluoro-4-methylquinolin-3-yl) propan-2-ol (350 mg, 1.17 mmol, 1 eq), 4,4,5,5-tetramethyl-2-(4,4,5,5-tetramethyl-1,3,2-dioxaborolan-2-yl)-1,3,2-dioxaborolane (447.15 mg, 1.76 mmol, 1.5 eq), Pd (dppf) Cl₂ (85.90 mg, 0.12 mmol, 0.1 eq) and KOAc (230.42 mg, 2.35 mmol, 2 eq) in dioxane (5 mL) was heated and stirred at 100° C. for 2 hours under nitrogen atmosphere. After the completion of the reaction, the mixture was cooled to room temperature, filtered through a short pad of Celite, rinsed with dioxane (10 mL) and the combined filtrate was concentrated in vacuo. The desired 2-(8-fluoro-4-methyl-6-(4,4,5,5-tetramethyl-1,3,2-dioxaborolan-2-yl) quinolin-3-yl) propan-2-ol (400 mg, crude) was obtained as a black brown oil, which was used into the next step without further purification. LCMS: 346.2 [M+H]⁺.

Step 5: Preparation of 2-(6-(2-chloro-5-fluoropyrimidin-4-yl)-8-fluoro-4-methylquinolin-3-yl) propan-2-ol The mixture of 2-(8-fluoro-4-methyl-6-(4,4,5,5-tetramethyl-1,3,2-dioxaborolan-2-yl) quinolin-3-yl) propan-2-ol (100 mg, 0.3 mmol, 1 eq), 2,4-dichloro-5-fluoro-pyrimidine (72.55 mg, 0.45 mmol, 1.5 eq), Pd(PPh₃)₄ (33.47 mg, 0.03 mmol, 0.1 eq) and K₂CO₃ (80.07 mg, 0.6 mmol, 2 eq) in dioxane (1 mL) and H₂O (0.1 mL) was degassed and backfilled with nitrogen for 3 times, and then stirred at 70° C. for 12 hours under nitrogen atmosphere. After the completion of the reaction, the mixture was cooled to room temperature, filtered through a short pad of Celite, rinsed with dioxane (3 mL) and the combined filtrate was concentrated in vacuo. The resulting residue was purified by column chromatography to afford 2-(6-(2-chloro-5-fluoropyrimidin-4-yl)-8-fluoro-4-methylquinolin-3-yl) propan-2-ol (95 mg, 93.7% yield) as a yellow solid. LCMS: 350.1 [M+H]⁺.

Preparation of 2-(6-(2,5-dichloropyrimidin-4-yl)-8-fluoro-4-methylquinolin-3-yl) propan-2-ol (1C-18)

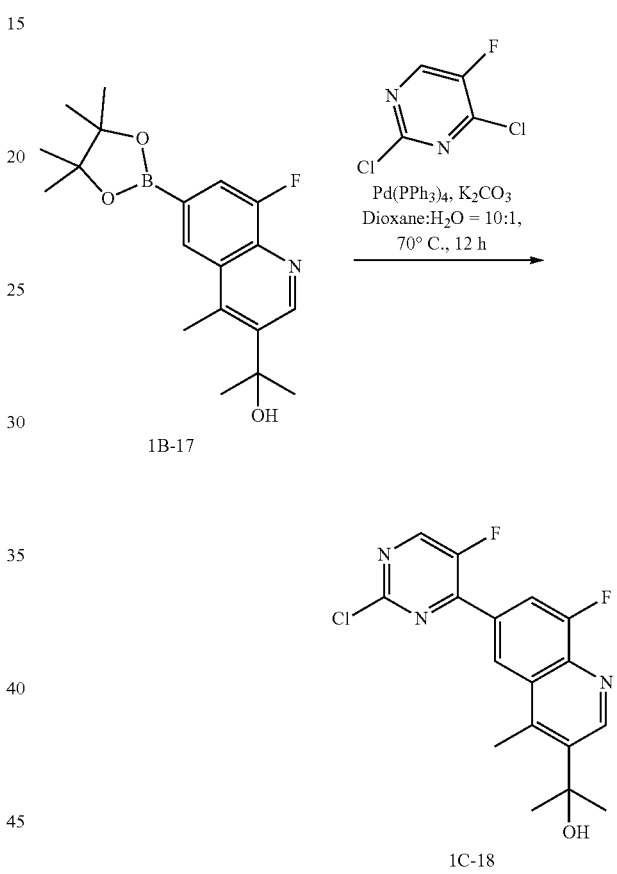

A mixture of 2-(8-fluoro-4-methyl-6-(4,4,5,5-tetramethyl-1,3,2-dioxaborolan-2-yl) quinolin-3-yl) propan-2-ol (300 mg, 0.87 mmol, 1 eq), 2,4,5-trichloropyrimidine (239.10 mg, 1.30 mmol, 1.5 eq), Pd(PPh₃)₄ (100.42 mg, 0.09 mmol, 0.1 eq) and K₂CO₃ (240.21 mg, 1.74 mmol, 2 eq) in dioxane (3 mL) and H₂O (0.3 mL) was degassed and backfilled with nitrogen for 3 times, and then stirred at 70° C. for 12 hours under nitrogen atmosphere. After the completion of the reaction, the mixture was cooled to room temperature, filtered through a short pad of Celite, rinsed with dioxane (3 mL) and the combined filtrate was concentrated in vacuo. The resulting residue was purified by column chromatography to afford 2-(6-(2,5-dichloropyrimidin-4-yl)-8-fluoro-4-methylquinolin-3-yl) propan-2-ol (290 mg, 91.1% yield) as a yellow solid. LCMS: 366.0 [M+H].

Preparation of 2-(7-chloro-2-(2,5-dichloropyrimidin-4-yl)-3-methylthieno[3,2-b]pyridine-6-yl) propan-2-ol (1C-19)

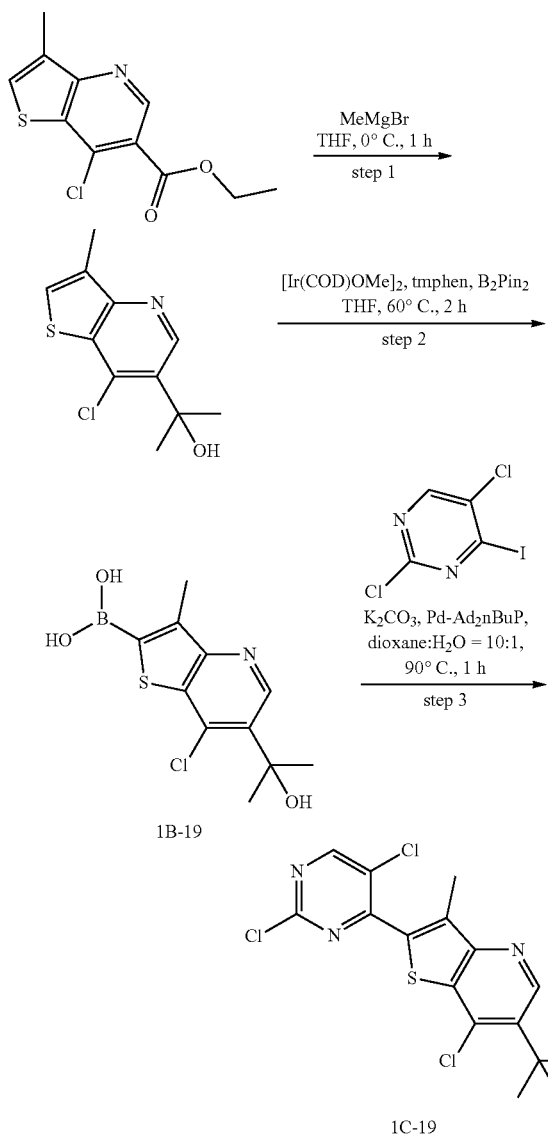

mmol, 0.06 eq) in THF (4 mL) was stirred at 20° C. for 5 minutes under nitrogen, followed by the addition of 2-(7-chloro-3-methylthieno[3,2-b]pyridin-6-yl) propan-2-ol (350 mg, 1.45 mmol, 1.0 eq) and 4,4,5,5-tetramethyl-1,3,2-dioxaborolane (371 mg, 2.90 mmol, 2.0 eq), and then kept stirring at 60° C. for 2 hours under nitrogen. After the completion of the reaction, the mixture was cooled to room temperature, filtered through a short pad of celite and rinsed with THF (4 mL). The combined filtrate was concentrated to give (7-chloro-6-(2-hydroxypropan-2-yl)-3-methylthieno[3,2-b]pyridin-2-yl) boronic acid (440 mg, crude) as a brown oil. LCMS: 286.0 [M+H].

Step 3: Preparation of 2-(7-chloro-2-(2,5-dichloropyrimidin-4-yl)-3-methylthieno[3,2-b]pyridin-6-yl) propan-2-ol To a degassed and nitrogen backfilled solution of (7-chloro-6-(2-hydroxypropan-2-yl)-3-methylthieno[3,2-b]pyridin-2-yl) boronic acid (200 mg, 0.70 mmol, 1.0 eq), 2,5-dichloro-4-iodo-pyrimidine (230 mg, 0.08 mmol, 1.2 eq) and $K_2CO_3$ (193 mg, 1.40 mmol, 2.0 eq) in dioxane (4 mL) and $H_2O$ (0.4 mL) was added [2-(2-aminophenyl)phenyl]-chloro-palladium;bis(1-adamantyl)-butyl-phosphane (46 mg, 0.07 mmol, 0.1 eq) at 20° C. under nitrogen, and the mixture was stirred at 90° C. for 1 hour under nitrogen. After the completion of the reaction, the mixture was cooled to room temperature, filtered through a short pad of celite and rinsed with dioxane (4 mL). The combined filtrate was concentrated under reduced pressure and the resulting residue was purified by column chromatography to give 2-(7-chloro-2-(2,5-dichloropyrimidin-4-yl)-3-methylthieno[3,2-b]pyridin-6-yl) propan-2-ol (130 mg, 37% yield,) as a yellow solid. LCMS: 389.9 [M+H]+.

Preparation of 2-(7-chloro-2-(2-chloro-5-fluoropyrimidin-4-yl)-3-methylthieno[3,2-b]pyridin-6-yl) propan-2-ol (1C-20)

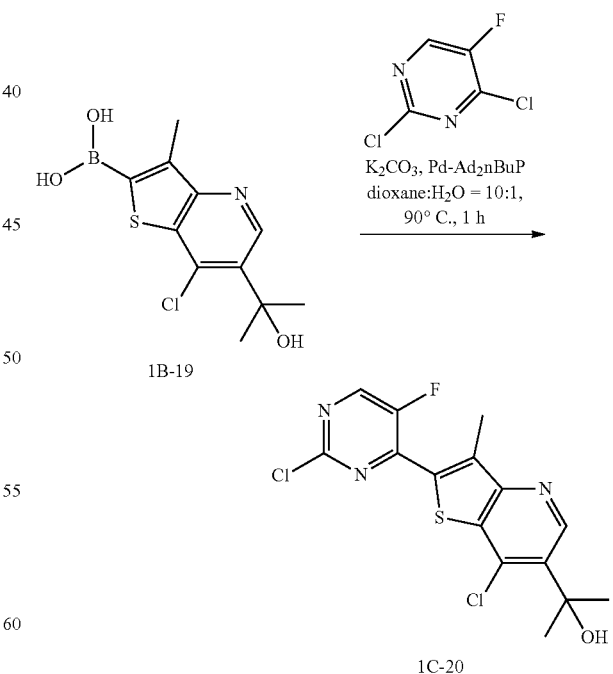

Step 1: Preparation of 2-(7-chloro-3-methylthieno[3,2-b]pyridin-6-yl) propan-2-ol To a solution of ethyl 7-chloro-3-methylthieno[3,2-b]pyridine-6-carboxylate (0.5 g, 1.96 mmol, 1.0 eq) in THF (5 mL) was added MeMgBr (3 M, 2 mL, 3.0 eq) at −40° C. under nitrogen atmosphere, and the mixture was then warmed to 0° C. and stirred at that temperature for 1 hour under nitrogen atmosphere. After the completion of the reaction, the mixture was poured into saturated aqueous $NH_4Cl$ (50 mL) and extracted with Ethyl Acetate (30 mL×3). The combined organic layers were washed with brine (50 mL), dried over $Na_2SO_4$, filtered and the filtrate was concentrated under reduced pressure. The resulting residue was purified by column chromatography to give 2-(7-chloro-3-methylthieno[3,2-b]pyridin-6-yl) propan-2-ol (0.4 g, 79% yield) as a white solid. LCMS: 242.1 [M+H]+.

Step 2: Preparation of (7-chloro-6-(2-hydroxypropan-2-yl)-3-methylthieno[3,2-b]pyridin-2-yl) boronic acid A mixture of (1Z,5Z)-cycloocta-1,5-diene; 2,4-dimethyl-BLAHbicyclo[1.1.0]butane (28 mg, 0.04 mmol, 0.03 eq) and 3,4,7,8-tetramethyl-1,10-phenanthroline (20 mg, 0.08

To a degassed and nitrogen backfilled solution of (7-chloro-6-(2-hydroxypropan-2-yl)-3-methylthieno[3,2-b]pyridin-2-yl) boronic acid (200 mg, 0.70 mmol, 1.0 eq), 2,4-dichloro-5-fluoro-pyrimidine (140 mg, 0.83 mmol, 1.2 eq) and K$_2$CO$_3$ (193 mg, 1.40 mmol, 2.0 eq) in dioxane (4 mL) and H$_2$O (0.4 mL) was added [2-(2-aminophenyl)phenyl]-chloro-palladium; bis(1-adamantyl)-butyl-phosphane (46 mg, 0.07 mmol, 0.1 eq) at 20° C. under nitrogen, and the mixture was stirred at 90° C. for 1 hour under nitrogen atmosphere. After the completion of the reaction, the mixture was cooled to room temperature, filtered through a short pad of celite and rinsed with dioxane (4 mL). The combined filtrate was concentrated under reduced pressure and the resulting residue was purified by column chromatography to give 2-(7-chloro-2-(2-chloro-5-fluoropyrimidin-4-yl)-3-methylthieno[3,2-b]pyridin-6-yl) propan-2-ol (130 mg, 40% yield) as a yellow solid. LCMS: 372.0 [M+H].

Preparation of 2-(2-(2,5-dichloropyrimidin-4-yl)-3,7-dimethylthieno[3,2-b]pyridin-6-yl) propan-2-ol (IC-21)

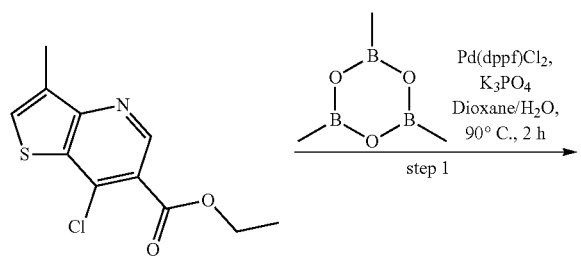

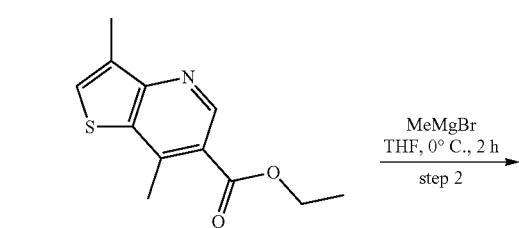

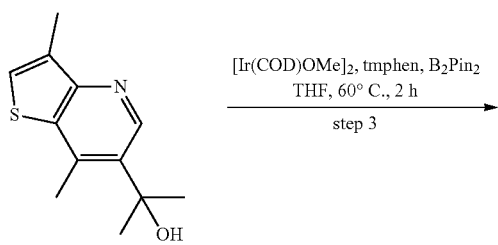

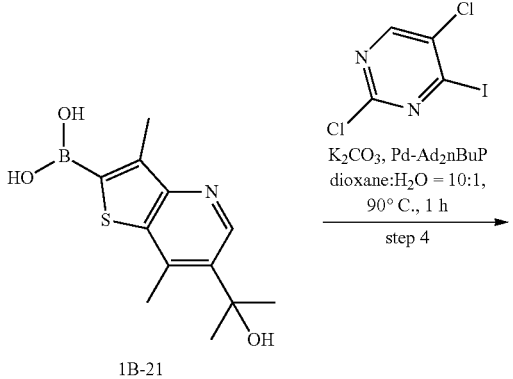

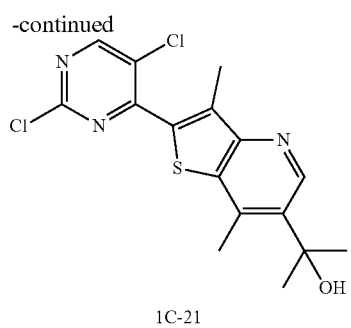

1C-21

Step 1: Preparation of ethyl 3,7-dimethylthieno[3,2-b]pyridine-6-carboxylate

To a degassed and nitrogen backfilled solution of ethyl 7-chloro-3-methylthieno[3,2-b]pyridine-6-carboxylate (0.50 g, 1.96 mmol, 1 eq), 2,4,6-trimethyl-1,3,5,2,4,6-trioxatriborinane (3.5 M, 1 mL, 1.79 eq), potassium phosphate (0.83 g, 3.91 mmol, 2 eq) in dioxane (10 mL) and water (1 mL) was added Pd (dppf) Cl$_2$ (0.14 g, 0.20 mmol, 0.1 eq) at 20° C. under nitrogen, and the mixture was stirred at 90° C. for 2 hours under nitrogen. After the completion of the reaction, the mixture was cooled to room temperature and concentrated in vacuo. The resulting residue was purified by column chromatography to give ethyl 3,7-dimethylthieno[3,2-b]pyridine-6-carboxylate (0.45 g, 1.89 mmol, 96.8% yield, 99% purity) as a white solid. LCMS: 236.1 [M+H].

Step 2: Preparation of 2-(3,7-dimethylthieno[3,2-b]pyridin-6-yl) propan-2-ol

To a solution of ethyl 3,7-dimethylthieno[3,2-b]pyridine-6-carboxylate (0.45 g, 1.91 mmol, 1 eq) in THF (5 mL) was added MeMgBr (3 M, 2 mL, 3.14 eq) at −40° C. under nitrogen atmosphere, and the mixture was warmed to 0° C. and stirred at that temperature for 2 hours under nitrogen atmosphere. After the completion of the reaction, the mixture was poured into saturated aqueous NH$_4$Cl (50 mL) and extracted with EtOAc (30 mL×3). The combined organic layers were washed with brine (50 mL), dried over Na$_2$SO$_4$, filtered and the filtrate was concentrated under reduced pressure. The resulting residue was purified by column chromatography to give 2-(3,7-dimethylthieno[3,2-b]pyridin-6-yl) propan-2-ol (0.30 g, 70.8% yield) as a white solid. LCMS: 222.1 [M+H].

Step 3. Preparation of (6-(2-hydroxypropan-2-yl)-3,7-dimethylthieno[3,2-b]pyridin-2-yl) boronic acid A mixture of (1Z,5Z)-cycloocta-1,5-diene;2,4-dimethyl-BLAHbicyclo[1.1.0]butane (40 mg, 0.06 mmol, 0.05 eq) and 3,4,7,8-tetramethyl-1,10-phenanthroline (30 mg, 0.11 mmol, 0.10 eq) in THF (4 mL) was stirred at 20° C. for 5 minutes under nitrogen, followed by the addition of 2-(3,7-dimethylthieno[3,2-b]pyridin-6-yl) propan-2-ol (250 mg, 1.13 mmol, 1.0 eq) and 4,4,5,5-tetramethyl-1,3,2-dioxaborolane (880 mg, 6.89 mmol, 6.1 eq), and then kept stirring at 60° C. for 2 hours under nitrogen. After the completion of the reaction, the mixture was cooled to room temperature, filtered through a short pad of celite and rinsed with THF (4 mL). The combined filtrate was concentrated to give (6-(2-hydroxypropan-2-yl)-3.7-dimethylthieno[3,2-b]pyridin-2-yl) boronic acid (340 mg, crude) as a brown oil, which was used into the next step without further purification. LCMS: 266.1 [M+H]$^+$.

Step 4: Preparation of 2-(2-(2,5-dichloropyrimidin-4-yl)-3,7-dimethylthieno[3,2-b]pyridin-6-yl) propan-2-ol To a degassed and nitrogen backfilled solution of (6-(2-hydroxypropan-2-yl)-3,7-dimethylthieno[3,2-b]pyridin-2- yl) boronic acid (0.15 g, 0.57 mmol, 1 eq), 2,5-dichloro-4-iodo-pyrimidine (0.19 g, 0.68 mmol, 1 21 eq) and K₂CO₃ (0.16 g, 1.13 mmol, 2 eq) in dioxane (3 mL) and H₂O (0.3 mL) was added [2-(2-aminophenyl)phenyl]-chloro-palladium; bis(1-adamantyl)-butyl-phosphane (0.04 g, 0.06 mmol, 0.1 eq) at 20° C. under nitrogen, and the mixture was stirred at 90° C. for 1 hour under nitrogen. After the completion of the reaction, the mixture was cooled to room temperature, filtered through a short pad of celite and rinsed with dioxane (4 mL). The combined filtrate was concentrated under reduced pressure and the resulting residue was purified by column chromatography to give 2-(2-(2,5-dichloropyrimidin-4-yl)-3,7-dimethylthieno[3,2-b]pyridin-6-yl) propan-2-ol (0.13 g, 54.59% yield) as a yellow solid. LCMS: 368.0 [M+H]⁺.

Preparation of 2-(2-(2-chloro-5-fluoropyrimidin-4-yl)-3,7-dimethylthieno[3,2-b]pyridin-6-yl) propan-2-ol (1C-22)

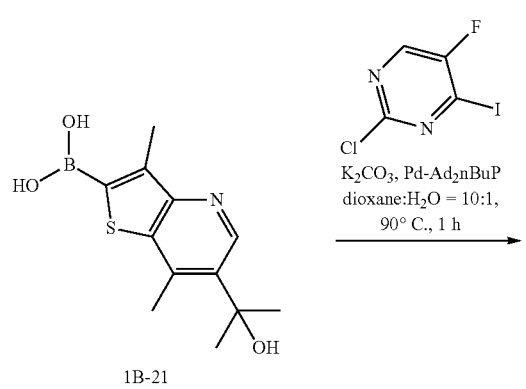

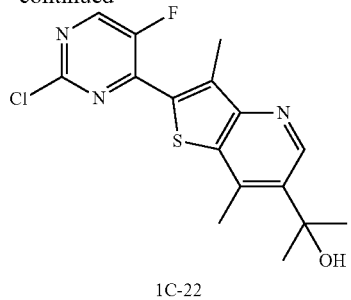

1C-22

To a degassed and nitrogen backfilled solution of (6-(2-hydroxypropan-2-yl)-3,7-dimethylthieno[3,2-b]pyridin-2-yl) boronic acid (0.15 g, 0.57 mmol, 1 eq), 2,4-dichloro-5-fluoropyrimidine (0.11 g, 0.68 mmol, 1.20 eq) and K₂CO₃ (0.16 g, 1.13 mmol, 2 eq) in dioxane (3 mL) and H₂O (0.3 mL) was added [2-(2-aminophenyl)phenyl]-chloro-palladium;bis(1-adamantyl)-butyl-phosphane (0.04 g, 0.06 mmol, 0.1 eq) at 20° C. under nitrogen, and the mixture was stirred at 90° C. for 1 hour under nitrogen. After the completion of the reaction, the mixture was cooled to room temperature, filtered through a short pad of celite and rinsed with dioxane (4 mL). The combined filtrate was concentrated under reduced pressure and the resulting residue was purified by column chromatography to give 2-(2-(2-chloro-5-fluoropyrimidin-4-yl)-3,7-dimethylthieno[3,2-b]pyridin-6-yl) propan-2-ol (0.13 g, 49.6% yield) as a yellow solid. LCMS: 352.0 [M+H].

Preparation of 2-(8-chloro-6-(2-chloro-5-fluoropyrimidin-4-yl)-4-methylquinolin-3-yl) propan-2-ol (1C-23)

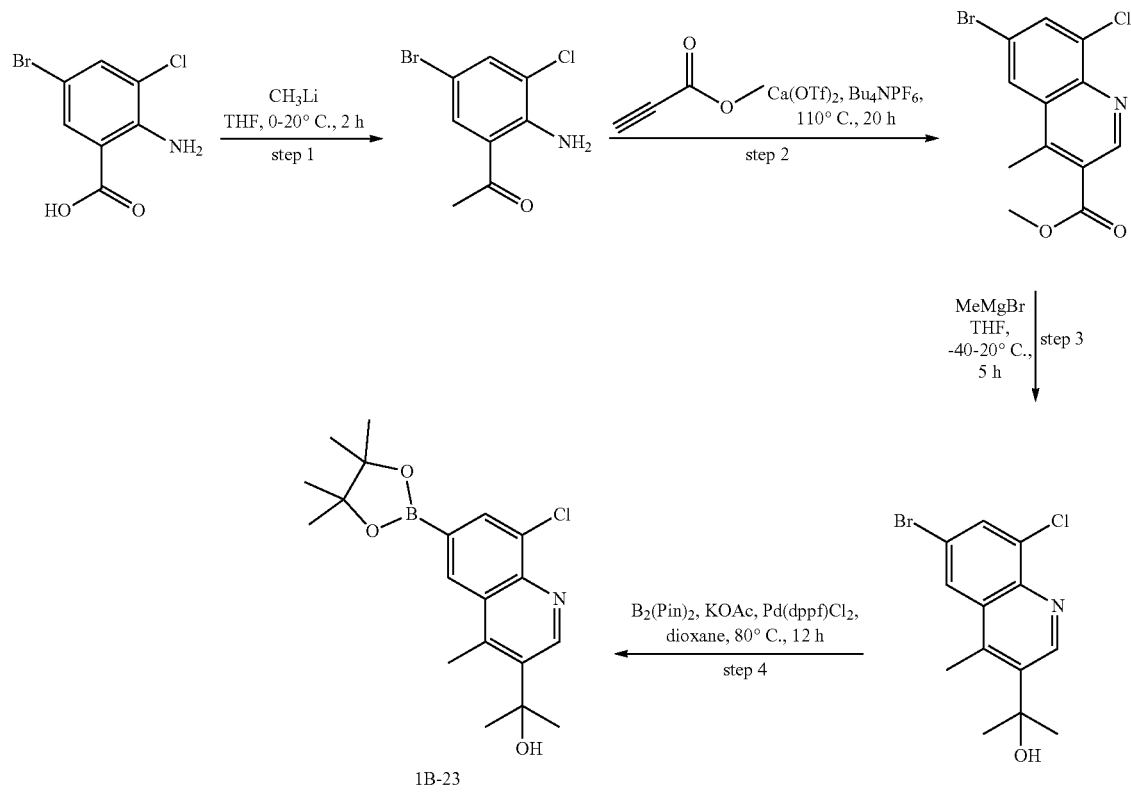

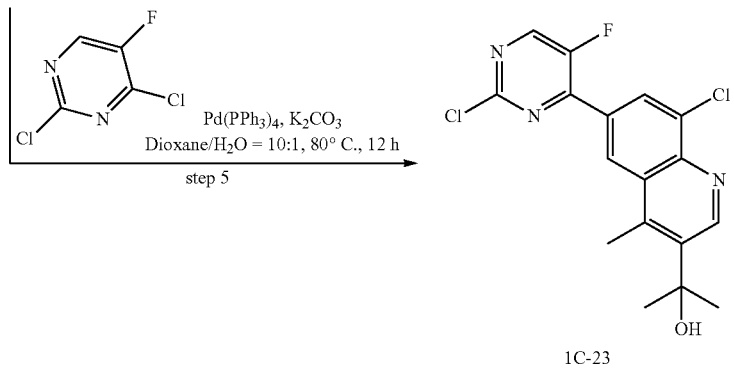

1C-23

Step 1: Preparation of 1-(2-amino-5-bromo-3-chlorophenyl) ethan-1-one

To a solution of 2-amino-5-bromo-3-chloro-benzoic acid (20 g, 79.85 mmol, 1 eq) in THF (200 mL) was added CH$_3$Li (1.6 M, 99.81 mL, 2 eq) dropwise at 0° C., and the mixture was then warmed to 20° C. and stirred for 2 hours at that temperature under nitrogen atmosphere. After the completion of the reaction, the mixture was quenched with H$_2$O (300 mL) and extracted with EtOAc (400 mL×2). The combined organic layers were washed with brine (100 mL), dried over anhydrous Na$_2$SO$_4$, filtered and the filtrate was concentrated in vacuo. The resulting residue was purified by column chromatography to afford 1-(2-amino-5-bromo-3-chlorophenyl) ethan-1-one (14.2 g, 71.5% yield) as a yellow solid. LCMS: 248.0, 250.0 [M+H]$^+$.

Step 2: Preparation of methyl 6-bromo-8-chloro-4-methylquinoline-3-carboxylate

The mixture of 1-(2-amino-5-bromo-3-chlorophenyl) ethan-1-one (9.0 g, 36.22 mmol, 1 eq) and methyl prop-2-ynoate (45.27 g, 538.46 mmol, 45.00 mL, 14.87 eq) in tetrabutylammonium hexafluorophosphate (1.40 g, 3.62 mmol, 0.1 eq) and calcium trifluoromethanesulfonate (1.22 g, 3.62 mmol, 0.1 eq) was stirred at 110° C. for 20 hours under nitrogen atmosphere. After the completion of the reaction, the mixture was cooled to room temperature, quenched with H$_2$O (100 mL) and extracted with DCM (100 mL×3). The combined organic layers were washed with brine (50 mL), dried over anhydrous Na$_2$SO$_4$, filtered and the filtrate was concentrated in vacuo. The resulting residue was purified by column chromatography to afford methyl 6-bromo-8-chloro-4-methylquinoline-3-carboxylate (5.3 g, 46.5% yield) as a light yellow solid. LCMS: 314.0, 316.0 [M+H]$^+$.

Step 3: Preparation of 2-(6-bromo-8-chloro-4-methylquinolin-3-yl) propan-2-ol

To a solution of methyl 6-bromo-8-chloro-4-methylquinoline-3-carboxylate (5.3 g, 16.85 mmol, 1 eq) in THF (106 mL) was added MeMgBr (3 M, 38 mL, 6.77 eq) at −40° C., and the mixture was then stirred at 20° C. for 5 hours under nitrogen atmosphere. After the completion of the reaction, the mixture was quenched with saturated aqueous NH$_4$Cl (100 mL) and extracted with EtOAc (100 mL×2). The combined organic layers were washed with brine (50 mL), dried over anhydrous Na$_2$SO$_4$, filtered and the filtrate was concentrated in vacuo. The resulting residue was purified by column chromatography to afford 2-(6-bromo-8-chloro-4-methylquinolin-3-yl) propan-2-ol (4.6 g, 86.7% yield) as a yellow solid. LCMS: 314.0, 316.0 [M+H]$^+$.

Step 4: Preparation of 2-(8-chloro-4-methyl-6-(4,4,5,5-tetramethyl-1,3,2-dioxaborolan-2-yl) quinolin-3-yl) propan-2-ol The degassed and nitrogen backfilled mixture of 2-(6-bromo-8-chloro-4-methylquinolin-3-yl) propan-2-ol (4.6 g, 14.62 mmol, 1 eq), 4,4,5,5-tetramethyl-2-(4,4,5,5-tetramethyl-1,3,2-dioxaborolan-2-yl)-1,3,2-dioxaborolane (4.83 g, 19.01 mmol, 1.3 eq), Pd (dppf) Cl$_2$ (1.07 g, 1.46 mmol, 0.1 eq) and KOAc (2.87 g, 29.24 mmol, 2 eq) in dioxane (92 mL) was heated and stirred at 80° C. for 12 hours under nitrogen atmosphere. After the completion of the reaction, the mixture was cooled to room temperature, filtered through a short pad of Celite, rinsed with dioxane (30 mL) and the combined filtrate was concentrated in vacuo. The resulting residue was purified by column chromatography to afford 2-(8-chloro-4-methyl-6-(4,4,5,5-tetramethyl-1,3,2-dioxaborolan-2-yl) quinolin-3-yl) propan-2-ol (5.28 g, 99.8% yield) as a yellow oil. LCMS: 362.1 [M+H]$^+$ Step 5: Preparation of 2-(8-chloro-6-(2-chloro-5-fluoropyrimidin-4-yl)-4-methylquinolin-3-yl) propan-2-ol The mixture of 2-(8-chloro-4-methyl-6-(4,4,5,5-tetramethyl-1,3,2-dioxaborolan-2-yl) quinolin-3-yl) propan-2-ol (5.28 g, 14.60 mmol, 1 eq), 2,4-dichloro-5-fluoro-pyrimidine (2.44 g, 14.60 mmol, 1 eq), Pd(PPh$_3$)$_4$ (1.69 g, 1.46 mmol, 0.1 eq) and K$_2$CO$_3$ (4.04 g, 29.20 mmol, 2 eq) in dioxane (190 mL) and H$_2$O (19 mL) was degassed and backfilled with nitrogen for 3 times, and stirred at 80° C. for 12 hours under nitrogen atmosphere. After the completion of the reaction, the mixture was cooled to room temperature, filtered through a short pad of Celite, rinsed with dioxane (30 mL) and the combined filtrate was concentrated in vacuo. The resulting residue was purified by column chromatography to afford 2-(8-chloro-6-(2-chloro-5-fluoropyrimidin-4-yl)-4-methylquinolin-3-yl) propan-2-ol (5 g, 93.5% yield) as a yellow solid. LCMS: 366.0 [M+H].

Preparation of 2-(8-chloro-6-(2,5-dichloropyrimidin-4-yl)-4-methylquinolin-3-yl) propan-2-ol (1C-24)

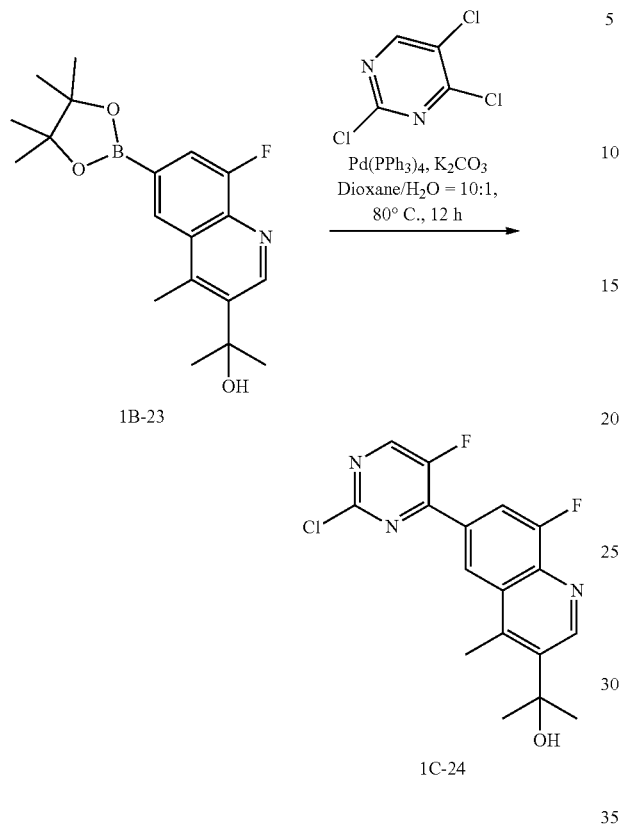

The mixture of 2-(8-chloro-4-methyl-6-(4,4,5,5-tetramethyl-1,3,2-dioxaborolan-2-yl) quinolin-3-yl) propan-2-ol (1 g, 2.76 mmol, 1 eq), 2,4,5-trichloropyrimidine (760.73 mg, 4.15 mmol, 1.5 eq), Pd(PPh$_3$)$_4$ (319.51 mg, 0.27 mmol, 0.1 eq) and K$_2$CO$_3$ (764.26 mg, 5.53 mmol, 2 eq) in dioxane (20 mL) and H$_2$O (2 mL) was degassed and backfilled with nitrogen for 3 times, and stirred at 80° C. for 12 hours under nitrogen atmosphere. After the completion of the reaction, the mixture was cooled to room temperature, filtered through a short pad of Celite, rinsed with dioxane (10 mL) and the combined filtrate was concentrated in vacuo. The resulting residue was purified by column chromatography to afford 2-(8-chloro-6-(2,5-dichloropyrimidin-4-yl)-4-methylquinolin-3-yl) propan-2-ol (1.02 g, 96.4% yield) as a yellow solid. LCMS: 382.0, 384.0 [M+H].

Preparation of 2-(4,8-dichloro-6-(2-chloro-5-fluoropyrimidin-4-yl) quinolin-3-yl) propan-2-ol (1C-25)

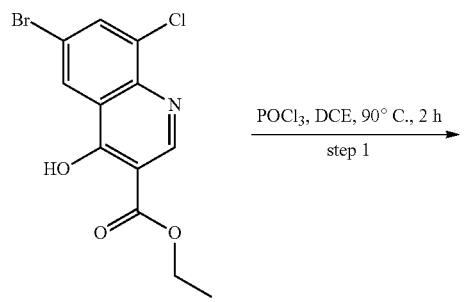

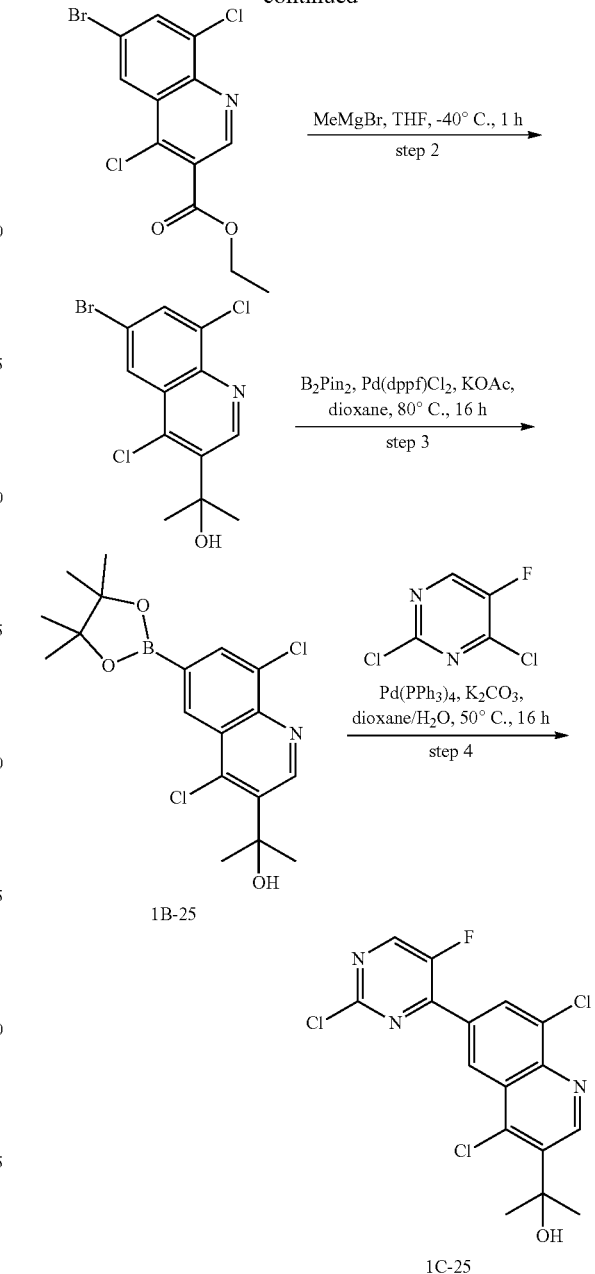

Step 1: Preparation of ethyl 6-bromo-4,8-dichloroquinoline-3-carboxylate

To a solution of ethyl 6-bromo-8-chloro-4-hydroxyquinoline-3-carboxylate (10 g, 30.3 mmol, 1 eq) in DCE (100 mL) was added POCl$_3$ (32.9 g, 214.6 mmol, 7.09 eq), and the mixture was heated to 90° C. for 2 hours under nitrogen atmosphere. After the completion of the reaction, the mixture was cooled to room temperature and concentrated under reduced pressure. The resulting residue was purified by column chromatography to give ethyl 6-bromo-4,8-dichloroquinoline-3-carboxylate (9 g, 85.2% yield) as a yellow solid. LCMS: 347.9, 349.9 [M+H]$^+$.

Step 2: Preparation of 2-(6-bromo-4,8-dichloroquinolin-3-yl) propan-2-ol

To a solution of ethyl 6-bromo-4,8-dichloroquinoline-3-carboxylate (8 g, 22.92 mmol, 1 eq) in THF (160 mL) was added MeMgBr (3 M, 45.84 mL, 6 eq) at −40° C., and the mixture was kept stirring at −40° C. for 1 hour under nitrogen atmosphere. After the completion of the reaction, the mixture was quenched with saturated aqueous NH$_4$Cl (100 ml) and extracted with EtOAc (100 mL×2). The combined organic layers were washed with brine (100 mL), dried over anhydrous Na$_2$SO$_4$, filtered and the filtrate was concentrated in vacuo. The resulting residue was purified by column chromatography to afford 2-(6-bromo-4,8-dichloro-quinolin-3-yl) propan-2-ol (5.1 g, 66.4% yield) as white solid. LCMS: 333.6, 335.6 [M+H]$^+$.

Step 3: Preparation of 2-(4,8-dichloro-6-(4,4,5,5-tetramethyl-1,3,2-dioxaborolan-2-yl) quinolin-3-yl) propan-2-ol The degassed and nitrogen backfilled mixture of 2-(6-bromo-4,8-dichloroquinolin-3-yl) propan-2-ol (5 g, 15 mmol, 1 eq), 4,4,5,5-tetramethyl-2-(4,4,5,5-tetramethyl-1,3,2-dioxaborolan-2-yl)-1,3,2-dioxaborolane (5 g, 20 mmol, 1.32 eq), Pd (dppf) Cl$_2$ (1.0 g. 1.36 mmol, 0.1 eq) and KOAc (3.0 g, 30.5 mmol, 2.05 eq) in dioxane (100 mL) was heated and stirred at 80° C. for 16 hours under nitrogen atmosphere. After the completion of the reaction, the mixture was cooled to room temperature, filtered through a short pad of Celite, rinsed with dioxane (30 mL) and the combined filtrate was concentrated in vacuo. The resulting residue was purified by column chromatography to give 2-(4,8-dichloro-6-(4,4,5,5-tetramethyl-1,3,2-dioxaborolan-2-yl) quinolin-3-yl) propan-2-ol (4.6 g, 80.6% yield) as a black solid. LCMS: 382.1 [M+H]$^+$.

Step 4: Preparation of 2-(4,8-dichloro-6-(2-chloro-5-fluoropyrimidin-4-yl) quinolin-3-yl) propan-2-ol The mixture of 2-(4,8-dichloro-6-(4,4,5,5-tetramethyl-1,3,2-dioxaborolan-2-yl) quinolin-3-yl) propan-2-ol (2.2 g, 5.76 mmol, 1 eq), 2,4-dichloro-5-fluoro-pyrimidine (1.5 g. 9.98 mmol, 1.56 eq), Pd(PPh$_3$)$_4$ (660.00 mg, 0.57 mmol, 0.1 eq) and K$_2$CO$_3$ (1.76 g, 12.7 mmol, 2.21 eq) in dioxane (40 mL) and H$_2$O (2 mL) was degassed and backfilled with nitrogen for 3 times, and stirred at 50° C. for 16 hours under nitrogen atmosphere. After the completion of the reaction, the mixture was cooled to room temperature, diluted with water (50 mL) and extracted with EtOAc (100 mL). The organic layer was washed with brine (20 mL), dried over anhydrous Na$_2$SO$_4$, filtered and the filtrate was concentrated in vacuo. The resulting residue was purified by column chromatography to afford 2-(4,8-dichloro-6-(2-chloro-5-fluoropyrimidin-4-yl) quinolin-3-yl) propan-2-ol (1.7 g, 76.3% yield) as a yellow solid. LCMS: 386.0 [M+H]$^+$.

Preparation of 2-(4,8-dichloro-6-(2,5-dichloropyrimidin-4-yl) quinoline-3-yl) propan-2-ol (1C-26)

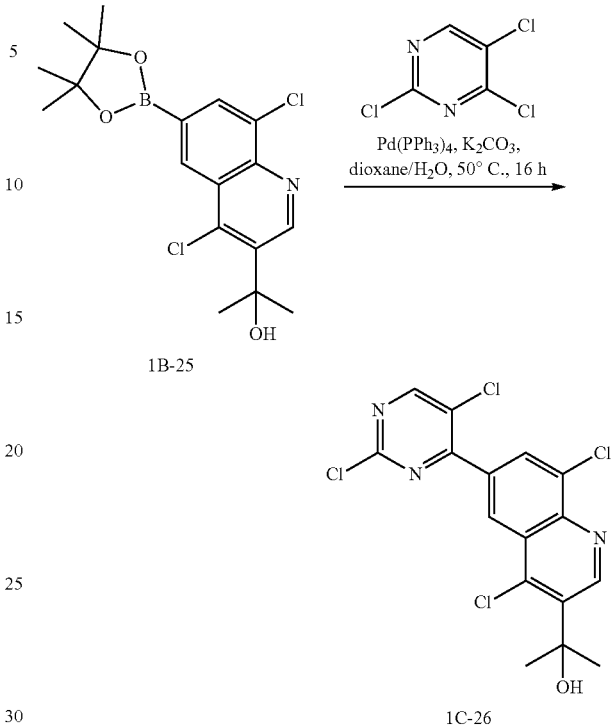

The mixture of 2-(4,8-dichloro-6-(4,4,5,5-tetramethyl-1,3,2-dioxaborolan-2-yl) quinolin-3-yl) propan-2-ol (1.1 g. 2.88 mmol, 1 eq), 2,4,5-trichloropyrimidine (0.8 g, 4.36 mmol, 1.51 eq), Pd(PPh$_3$)$_4$ (330.00 mg. 0.29 mmol, 0.1 eq) and K$_2$CO$_3$ (880.03 mg, 6.37 mmol, 2.21 eq) in dioxane (20 mL) and H$_2$O (2 mL) was degassed and backfilled with nitrogen for 3 times, and stirred at 50° C. for 16 hours under nitrogen atmosphere. After the completion of the reaction, the mixture was cooled to room temperature, diluted with water (50 mL) and extracted with EtOAc (100 mL). The organic layer was washed with brine (20 mL.), dried over anhydrous Na$_2$SO$_4$, filtered and the filtrate was concentrated in vacuo. The resulting residue was purified by column chromatography to give 2-[4,8-dichloro-6-(2,5-dichloropyrimidin-4-yl)-3-quinolyl]propan-2-ol (1 g, 2.48 mmol, 86.1% yield) as a yellow solid. LCMS: 401.9, 403.9 [M+H]$^+$.

Preparation of 2-(6-(2,5-dichloropyrimidin-4-yl)-8-fluoro-4-methylcinnolin-3-yl) propan-2-ol (1C-27)

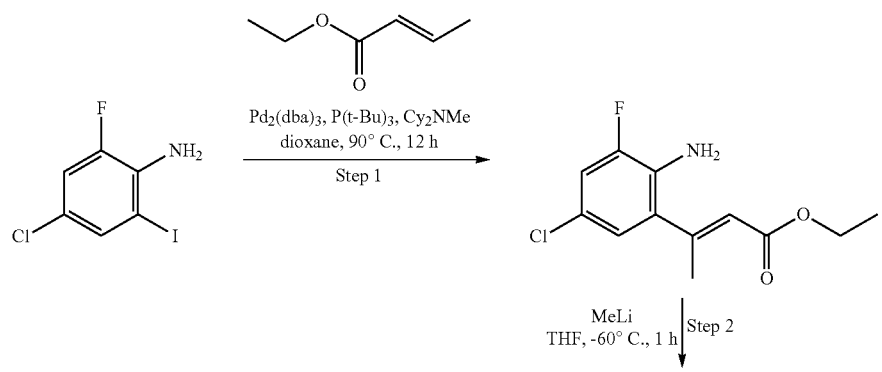

-continued

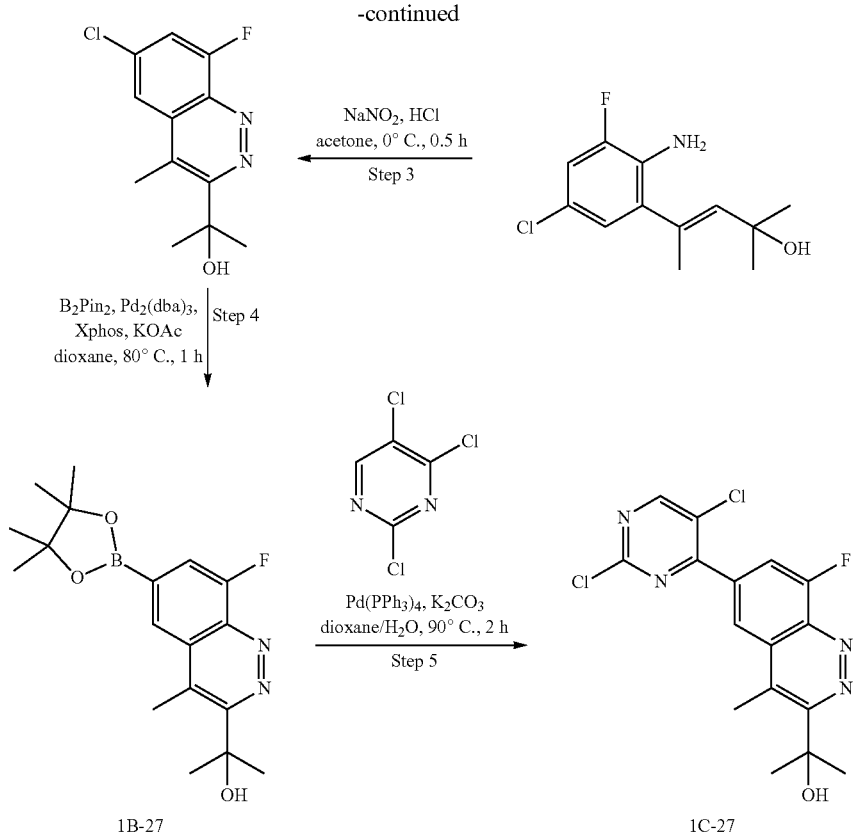

1B-27    1C-27

Step 1: Preparation of ethyl (E)-3-(2-amino-5-chloro-3-fluorophenyl) but-2-enoate A mixture of 4-chloro-2-fluoro-6-iodo-aniline (10 g, 36.84 mmol, 1 eq), ethyl (E)-but-2-enoate (6.31 g, 55.26 mmol, 6.87 mL, 1.5 eq), Pd$_2$(dba)$_3$ (3.37 g, 3.68 mmol, 0.1 eq), P (t-Bu)$_3$ (14.91 g, 7.37 mmol, 17.29 mL, 10% purity, 0.2 eq) and N-cyclohexyl-N-methyl-cyclohexanamine (8.01 g, 41.02 mmol, 8.70 mL, 1.11 eq) in dioxane (100 mL) was stirred at 90° C. for 12 hours under nitrogen atmosphere. After the completion of the reaction, the mixture was cooled to room temperature, filtered, rinsed with dioxane (20 mL) and the combined filtrate was concentrated under reduced pressure. The resulting residue was purified by prep-HPLC {column: Welch Ultimate XB-NH2 250*50*10 um; mobile phase: [Hexane-EtOH]; B %: 1%, isocratic elution mode}} to give ethyl (E)-3-(2-amino-5-chloro-3-fluorophenyl) but-2-enoate (2.653 g, 27.9% yield) as a yellow oil. LCMS: 258.1 [M+H]$^+$; $^1$H NMR (400 MHZ, CDCl$_3$-d) δ 7.45-7.40 (m, 2H), 7.27 (s, 1H), 6.83 (d. J=0.6 Hz, 1H), 5.97 (s, 1H), 4 23 (q, J=7.1 Hz, 2H), 3.89-3.74 (m, 3H), 2.46 (s, 3H), 1.32 (dt, J=0.6, 7.1 Hz, 4H) ppm.

Step 2: Preparation of (E)-4-(2-amino-5-chloro-3-fluorophenyl)-2-methylpent-3-en-2-ol To a mixture of ethyl (E)-3-(2-amino-5-chloro-3-fluorophenyl) but-2-enoate (2.6 g, 10.09 mmol, 1 eq) in THF (50 mL) was added MeLi (1.6 M, 50.45 mL, 8 eq) at −60° C., and the mixture was kept stirring at −60° C. for 1 hour under nitrogen atmosphere. After the completion of the reaction, the reaction mixture was carefully quenched with saturated aqueous NaHCO$_3$ (25 mL) at −60° C. The mixture was warmed up to room temperature, and the aqueous phase was extracted with EtOAc (50 mL×3). The combined organic layers were washed with brine, dried over anhydrous Na$_2$SO$_4$, filtered and the filtrate was concentrated under reduced pressure. The resulting residue was purified by column chromatography to give (E)-4-(2-amino-5-chloro-3-fluorophenyl)-2-methylpent-3-en-2-ol (491 mg, 19 9% yield) as a yellow oil. LCMS: 226.1 [M+H]$^+$.

Step 3: Preparation of 2-(6-chloro-8-fluoro-4-methylcinnolin-3-yl) propan-2-ol

A mixture of (E)-4-(2-amino-5-chloro-3-fluorophenyl)-2-methylpent-3-en-2-ol (491 mg, 2.01 mmol, 1 eq), NaNO$_2$ (208.51 mg, 3.02 mmol, 1.5 eq) and aqueous HCl (6 M, 10.07 mL, 30 eq) in acetone (20 mL) was stirred at 0° C. for 0.5 hours. After the completion of the reaction, the mixture was diluted with H$_2$O (30 mL) and extracted with EtOAc (30 mL×3). The combined organic layers were washed with brine, dried over anhydrous Na$_2$SO$_4$, filtered and the filtrate was concentrated under reduced pressure. The resulting residue was purified by column chromatography to give 2-(6-chloro-8-fluoro-4-methylcinnolin-3-yl) propan-2-ol (153 mg, 27.7% yield) as an yellow oil. LCMS: 255.0 [M+H]$^+$.

Step 4: Preparation of 2-(8-fluoro-4-methyl-6-(4,4,5,5-tetramethyl-1,3,2-dioxaborolan-2-yl) cinnolin-3-yl) propan-2-ol A mixture of 2-(6-chloro-8-fluoro-4-methylcinnolin-3-yl) propan-2-ol (150 mg, 0.59 mmol, 1 eq), Pin$_2$B$_2$ (224.34 mg, 0.89 mmol, 1.5 eq), Pd$_2$ (dba)$_3$ (53.93 mg, 0.059 mmol, 0.1 eq), XPhos (56.15 mg, 0.12 mmol, 0.2 eq) and KOAc (173.40 mg, 1.77 mmol, 3 eq) in dioxane (6 mL) was stirred at 80° C. for 1 hour under nitrogen atmosphere. After the completion of the reaction, the mixture was cooled to room temperature, filtered, rinsed with dioxane (5 mL) and the combined filtrate was concentrated. The desired 2-(8-fluoro-4-methyl-6-(4,4,5,5-tetramethyl-1,3,2-dioxaborolan-2-yl) cinnolin-3-yl) propan-2-ol (203 mg, crude) was obtained as a yellow oil, which was used in the next step without further purification. LCMS: 265.1 [M+H]⁺.

Step 5: Preparation of 2-(6-(2,5-dichloropyrimidin-4-yl)-8-fluoro-4-methylcinnolin-3-yl) propan-2-ol A mixture of 2-(8-fluoro-4-methyl-6-(4,4,5,5-tetramethyl-1,3,2-dioxaborolan-2-yl) cinnolin-3-yl) propan-2-ol (200 mg, 0.58 mmol, 1 eq), 2,4,5-trichloropyrimidine (158.94 mg, 0.87 mol, 1.5 eq), $K_2CO_3$ (239.52 mg, 1.73 mmol, 3 eq) and $Pd(PPh_3)_4$ (66.76 mg, 0.06 mmol, 0.1 eq) in dioxane (5 mL) and $H_2O$ (0.5 mL) was degassed and backfilled with nitrogen, and then stirred at 90° C. for 12 hours under nitrogen atmosphere. After the completion of the reaction, the mixture was cooled to room temperature, filtered through a pad of the Celite, rinsed with dioxane (5 mL) and the combined filtrate was concentrated in vacuo. The resulting residue was purified by column chromatography (PE/EA=100:0 to 0:1) to give 2-(6-(2,5-dichloropyrimidin-4-yl)-8-fluoro-4-methylcinnolin-3-yl) propan-2-ol (31 mg, 0.08 mmol, 14.6% yield) as a yellow oil. LCMS: 367.0 [M+H]⁺.

Preparation of 2-(6-(2-chloro-5-fluoropyrimidin-4-yl)-8-fluoro-4-methylcinnolin-3-yl) propan-2-ol (1C-28)

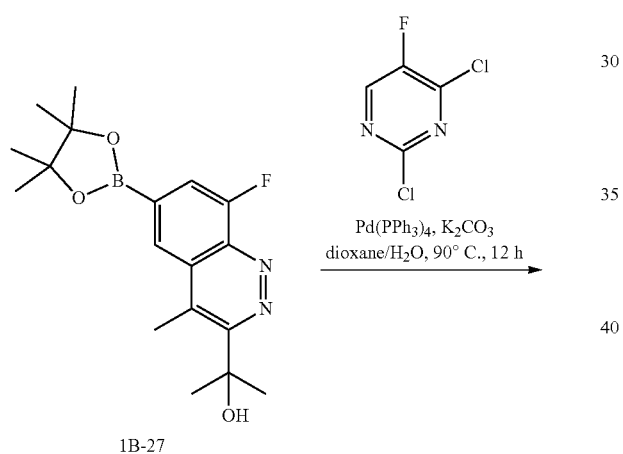

A mixture of 2-(8-fluoro-4-methyl-6-(4,4,5,5-tetramethyl-1,3,2-dioxaborolan-2-yl) cinnolin-3-yl) propan-2-ol (200 mg, 0.58 mmol, 1 eq), 2,4-dichloro-5-fluoro-pyrimidine (144.69 mg, 0.87 mmol, 1.5 eq), $K_2CO_3$ (239.53 mg, 1.73 mmol, 3 eq) and $Pd(PPh_3)_4$ (66.76 mg, 0.058 mmol, 0.1 eq) in dioxane (3 mL) and $H_2O$ (0.3 mL) was degassed and backfilled with nitrogen, and then stirred at 90° C. for 12 hours under nitrogen atmosphere. After the completion of the reaction, the mixture was cooled to room temperature, filtered through a pad of the Celite, rinsed with dioxane (5 mL) and the combined filtrate was concentrated in vacuo. The resulting residue was purified by column chromatography to give 2-(6-(2-chloro-5-fluoropyrimidin-4-yl)-8-fluoro-4-methylcinnolin-3-yl) propan-2-ol (44 mg, 21.7% yield) as a yellow oil. LCMS: 351.0 [M+H]⁺.

Preparation of (1S,3R,4S,5R)-3-amino-6,8-dioxabicyclo [3.2.1]octan-4-ol (1D-1)

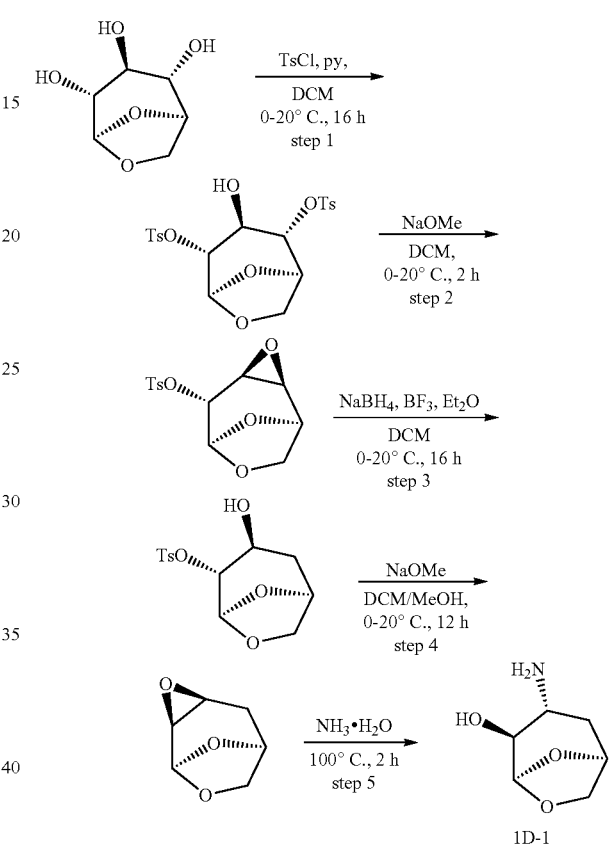

Step 1: Preparation of (1R,2S,3S,4R,5R)-3-hydroxy-6,8-dioxabicyclo[3.2.1]octane-2,4-diyl bis(4-methylbenzenesulfonate)

To a mixture of (1R,2S,3S,4R,5R)-6,8-dioxabicyclo [3.2.1]octane-2,3,4-triol (5 g, 30.84 mmol, 1 equiv.) and pyridine (5 g, 63.21 mmol, 5.10 mL, 2.05 equiv.) in anhydrous DCM (20 mL) was added TsCl (12 g, 62.94 mmol, 2.04 equiv.) at 0° C. Then, the reaction mixture was allowed to warm to 20° C. and stir for 16 h. The mixture was diluted with DCM (200 mL), washed with water (100 mL), and the organic phase was dried over anhydrous $Na_2SO_4$. The solid was filtered off and the filtrate was concentrated under reduced pressure to give a crude product that was purified by column chromatography (silica gel, Petroleum ether/Ethyl acetate=10/1 to 1/1). (1R,2S,3S,4R,5R)-3-Hydroxy-6,8-dioxabicyclo[3.2.1]octane-2,4-diyl bis(4-methylbenzenesulfonate) (10 g, 68.9% yield) was obtained as colorless oil. ¹H NMR (400 MHZ, $CDCl_3$) δ 7.66-7.83 (m, 4H), 7.31-7.40 (m, 4H), 5.24-5.33 (m, 1H), 4.57-4.65 (m, 1H), 4.51 (s, 1H), 4.36 (d, J=2.6 Hz, 1H), 4.19 (d, J=3.1 Hz, 1H), 4.00 (m, 1H), 3.93 (m, 1H), 3.63-3.70 (m, 1H), 2.98 (m, 1H), 2.43-2.50 (m, 6H) ppm.

Step 2: Preparation of (1R,2S,4S,5R,6R)-3, 7,9-trioxatricyclo[4.2.1.02.4]nonan-5-yl 4-methylbenzenesulfonate To a solution of (1R,2S,3S,4R,5R)-3-hydroxy-6,8-dioxabicyclo[3.2.1]octane-2,4-diyl bis(4-methylbenzenesulfonate) (10 g, 21.25 mmol, 1 equiv.) in DCM (80 mL) was added NaOMe (1.60 g, 29.62 mmol, 1.4 equiv.) at 0° C. Then, the reaction mixture was allowed to warm to 20° C. and stir for 2 h. The mixture was diluted with DCM (200 mL) and washed sequentially with water (2×100 mL) and brine (100 mL). The organic phase was dried over anhydrous Na$_2$SO$_4$. The solid was filtered off and the filtrate was concentrated to give the crude (1R,2S,4S,5R,6R)-3,7,9-trioxatricyclo[4.2.1.02.+]nonan-5-yl 4-methylbenzenesulfonate (6.0 g, crude) as white solid, which was used in the next step without further purification. $^1$H NMR (400 MHz, CDCl$_3$) δ 7.80-7.90 (m, 2H), 7.34-7.45 (m, 2H), 5.32 (s, 1H), 5.18 (d, J=1.2 Hz, 1H), 4.85 (m, 1H), 4.37-4.45 (m, 1H), 3.96 (m, 1H), 3.60-3.66 (m, 1H), 3.51 (m, 1H), 3.15 (m, 1H), 2.41-2.51 (m, 3H) ppm Step 3: Preparation of (1S,3S,4R,5R)-3-hydroxy-6,8-dioxabicyclo[3.2.1]octan-4-yl 4-methylbenzenesulfonate To a solution of the crude (1R,2S,4S,5R,6R)-3, 7,9-trioxatricyclo[4.2.1.02.4]nonan-5-yl 4-methylbenzenesulfonate (6 g, 20.11 mmol, 1 equiv.) in anhydrous DME (100 mL) was added BF$_3$Et$_2$O (7 g, 48.79 mmol, 6 mL, 2.5 equiv.) and NaBH$_4$ (5.5 g, 144.59 mmol, 7 equiv.) at 0° C. Then the mixture was allowed to warm to 20° C. and stir for 16 h. The mixture was poured into water (100 mL) and extracted with EtOAc (3×100 mL). The organic phase was dried over anhydrous Na$_2$SO$_4$. The solid was filtered off and the filtrate was concentrated to give the crude product, which was purified by column chromatography (SiO$_2$, PE/EA=10/1 to 2/1). (1S,3S,4R,5R)-3-Hydroxy-6,8-dioxabicyclo[3.2.1]octan-4-yl 4-methylbenzenesulfonate (2.1 g, 34.8% yield) was obtained as colorless oil. $^1$H NMR (400 MHZ, CDCl$_3$)δ 7.72-7.78 (m, 2H), 7.27-7.31 (m, 2H), 5.20 (s, 1H), 4.46 (m, 1H), 4.16 (d, J=1.2 Hz, 1H), 4.05-4.08 (m, 1H), 3.87 (m, 1H), 3.60 (m, 1H), 2.70 (br s, 1H), 2.37-2.39 (m, 3H), 2.19-2.30 (m, 1H), 1.64 (m, 1H) ppm.

Step 4: Preparation of (1R,2S,4S,6S)-3,8,9-trioxatricyclo[4.2.1.02.4]nonane

To a solution of (1S,3S,4R,5R)-3-hydroxy-6,8-dioxabicyclo[3.2.1]octan-4-yl 4-methylbenzenesulfonate (700 mg, 2.33 mmol, 1 equiv.) in anhydrous DCM (4 mL) and MeOH (4 mL) was added NaOMe (290 mg, 5.37 mmol, 2.30 equiv.) at 0° C. Then, the reaction mixture was allowed to warm to 20° C. and stir for 12 h. The mixture was diluted with DCM (100 mL) and sequentially washed with water (100 mL) and brine (100 mL). The organic phase was dried over anhydrous Na$_2$SO$_4$. The solid was filtered off and the filtrate was concentrated to give (1R,2S,4S,6S)-3,8,9-trioxatricyclo[4.2.1.02,4]nonane (295 mg, crude) as yellow oil, which was used in the next step without further purification. $^1$H NMR (400 MHZ, CDCl$_3$)δ 5.59-5.68 (m, 1H), 4.38 (m, 1H), 3.59-3.69 (m, 2H), 3.32 (m, 1H), 3.04-3.16 (m, 1H), 2.18 (m, 1H), 1.90-1.97 (m, 1H) ppm.

Step 5: Preparation of (1S,3R,4S,5R)-3-amino-6,8-dioxabicyclo[3.2.1]octan-4-ol

A mixture of (1R,2S,4S,6S)-3,8,9-trioxatricyclo[4.2.1.02.4]nonane (140 mg, 1.09 mmol, 1 equiv.) in NH$_3$H$_2$O (5 mL) was heated to 100° C. and stirred for 2 h. After cooling to room temperature, the mixture was concentrated to afford (1S,3R,4S,5R)-3-amino-6,8-dioxabicyclo[3.2.1]octan-4-ol (105 mg, crude) as yellow oil, which was used in next step without further purification. LCMS: 144.1 [M−H]

Preparation of (1S,2S,3R,4S,5R)-3-amino-6,8-dioxabicyclo[3.2.1]octan-2-d-4-ol (1D-2)

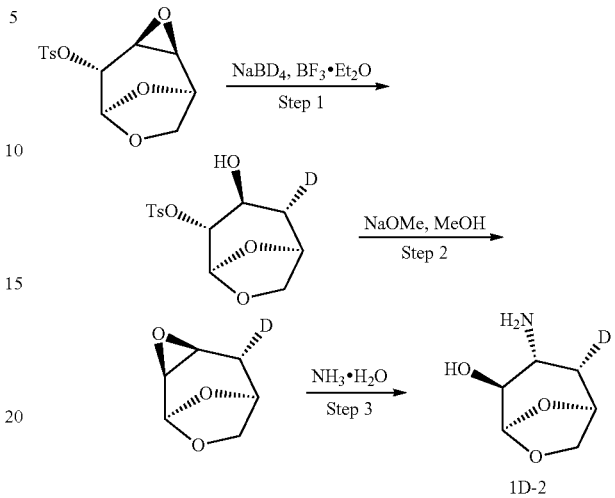

Step 1: Preparation of (1S,2S,3S,4R,5R)-3-hydroxy-6,8-dioxabicyclo[3.2.1]octan-4-yl-2-d 4-methylbenzenesulfonate To a solution of (1R,2S,4S,5R,6R)-3,7,9-trioxatricyclo[4.2.1.02.+]nonan-5-yl 4-methylbenzenesulfonate (2.3 g, 7.71 mmol, 1 equiv.) in 1,2-dimethoxyethane (50 mL) was added NaBD$_4$ (1.45 g, 38.30 mmol, 4.97 equiv.) and BF$_3$Et$_2$O (2.65 g, 18.70 mmol, 2.43 equiv.). The reaction was stirred at 20° C. for 16 h. The reaction mixture was quenched with sat. NH$_4$Cl (50 mL) and extracted with EA (100 mL). The organic phase was washed with brine (50 mL) and dried over Na$_2$SO$_4$. The solution was filtered and the filtrate was concentrated in vacuum to give a crude product, which was purified by column chromatography to give (1S,2S,3S,4R,5R)-3-hydroxy-6,8-dioxabicyclo[3.2.1] octan-4-yl-2-d 4-methylbenzenesulfonate (1 g, 43.0% yield) as white solid. $^1$H NMR (400 MHZ, CDCl$_3$)δ 7.88-7.78 (m, 2H), 7.42-7.31 (m, 2H), 5.32-5.21 (m, 1H), 4.59-4.50 (m, 1H), 4.25-4.21 (m, 1H), 4.16-4.11 (m, 1H), 3.96-3.90 (m, 1H), 3.70-3.62 (m, 1H), 2.85-2.64 (m, 1H), 2.50-2.41 (m, 3H), 1.69 (s, 1H) ppm.

Step 2: Preparation of (1R,2S,4S,5R,6S)-3,8,9-trioxatricyclo[4.2.1.02.4]nonane-5-d To a solution of (1S,2S,3S,4R,5R)-3-hydroxy-6,8-dioxabicyclo[3.2.1]octan-4-yl-2-d 4-methylbenzenesulfonate (0.5 g, 1.66 mmol, 1 equiv.) in DCM (4 mL) and MeOH (4 mL) was added NaOMe (0.2 g, 3.70 mmol, 2.23 equiv.) at 0° C. The reaction was slowly warmed to 25° C. and stirred for 16 h. Then, the reaction mixture was diluted with saturated aqueous NH$_4$Cl (50 mL) and extracted with EA (100 mL). The organic phase was washed with brine (50 mL) and dried over Na$_2$SO$_4$. The solution was filtered and the filtrate was concentrated in vacuum to give (1R,2S,4S, 5R,6S)-3,8,9-trioxatricyclo[4.2.1.02.4]nonane-5-d (0.16 g, 74.6% yield) as yellow oil. The so-obtained product was used in the next step without further purification. JH NMR (400 MHz, CDCl$_3$) δ 5.67 (d. J=3.2 Hz, 1H), 4.48-4.36 (m, 1H), 3.73-3.62 (m, 2H), 3.40-3.31 (m, 1H), 3.18-3.07 (m, 1H), 2.02-2.00 (m, 1H), 1.97-1.93 (m, 1H), 1.97-1.93 (m, 1H) ppm. Step 3: Preparation of (1S,2S,3R,4S,5R)-3-amino-6,8-dioxabicyclo[3.2.1]octan-2-d-4-ol A solution of (1R,2S,4S,5R,6S)-3,8,9-trioxatricyclo[4.2.1.02.+]nonane-5-d (0.16 g, 1.24 mmol, 1 equiv.) in NH$_3$H$_2$O (2 mL) was stirred at 100° C. for 1 h. The reaction mixture was cooled to room temperature and concentrated in vacuum give a crude product (0.1 g, 55.2% yield), which was used in the next step without further purification.

Preparation of (1S,2S,3R,4S,5R)-3-amino-2-methyl-6,8-dioxabicyclo[3.2.1]octan-4-ol (1D-3)

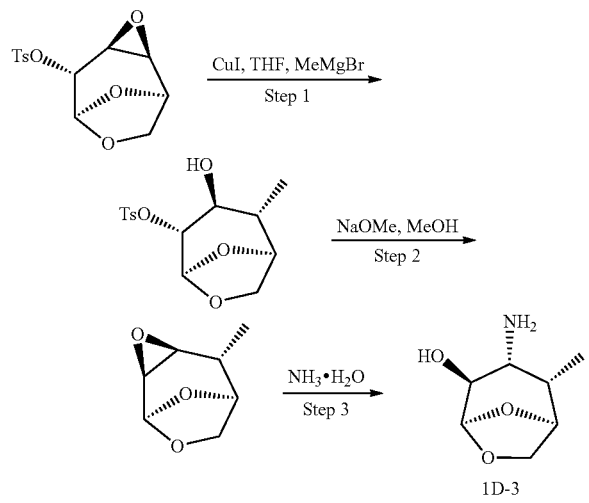

Step 1: Preparation of (1S,2S,3S,4R,5R)-3-hydroxy-2-methyl-6,8-dioxabicyclo[3.2.1]octan-4-yl 4-methylbenzenesulfonate To a solution of MeMgBr (3 M, 4.50 mL, 4 equiv.) in THF (20 mL) was added CuI (65.00 mg, 0.341 mmol, 0.1 equiv.) under N$_2$ atmosphere, followed by addition of (1R,2S,4S,5R,6R)-3,7,9-trioxatricyclo[4.2.1.02.4]nonan-5-yl 4-methylbenzenesulfonate (1 g, 3.35 mmol, 1 equiv.) at −45° C. After complete addition, the reaction mixture was stirred at 25° C. for 6 h. The mixture was then poured into water (50 mL) and extracted with EA (50 mL×3). The combined organic phases were washed with brine (50 mL) and dried over Na$_2$SO$_4$. The solution was filtered, and the filtrate was concentrated in vacuum. The resulting residue was purified by column chromatography (silica gel, petroleum ether/ethyl acetate=10/1) to give (1S,2S,3S,4R,5R)-3-hydroxy-2-methyl-6,8-dioxabicyclo[3.2.1]octan-4-yl 4-methylbenzenesulfonate (0.2 g, 18.9% yield) as yellow oil. $^1$H NMR (400 MHZ, CDCl$_3$) δ 7.75 (d, J=8.4 Hz, 2H), 7.29 (d, J=8.0 Hz, 2H), 5.19 (s, 1H), 4.23-4.18 (m, 1H), 4.14-4.10 (m, 1H), 3.99 (d, J=7.2 Hz, 1H), 3.61 (dd, J=5.2, 6.8 Hz, 1H), 3.54 (br s, 1H), 2.65 (br d, J=4.0 Hz, 1H), 2.38 (s, 3H), 1.85-1.75 (m, 1H), 1.73-1.63 (m, 1H), 1.17-1.12 (m, 3H) ppm.

Step 2: Preparation of (1R,2S,4S,5R,6S)-5-methyl-3,8,9-trioxatricyclo[4.2.1.02,4]nonane To a solution of (1S,2S,3S,4R,5R)-3-hydroxy-2-methyl-6,8-dioxabicyclo[3.2.1]octan-4-yl 4-methylbenzenesulfonate (0.2 g, 0.636 mmol, 1 equiv.) in MeOH (1 mL) and DCM (1 mL) was added NaOMe (44.68 mg, 0.827 mmol, 1.3 equiv.) at 0° C. The mixture was stirred at 25° C. for 1.5 h and then poured into water (50 mL). The aqueous phase was extracted with EA (50 mL×3). The combined organic phase was washed with brine (50 mL) and dried over Na$_2$SO$_4$. The solution was filtered, and the filtrate was concentrated in vacuum. The resulting residue was purified by prep-TLC (PE:EA=2:1) to give (1R,2S,4S,5R,6S)-5-methyl-3,8,9-trioxatricyclo[4.2.1.02,4]nonane (0.1 g, 99.51% yield, 90% purity) as white solid. $^1$H NMR (400 MHz, CDCl$_3$)δ=5.60 (d, J=3.2 Hz, 1H), 4.05 (d, J=6.0 Hz, 1H), 3.71-3.59 (m, 2H), 3.30 (t, J=3.6 Hz, 1H), 2.81 (d, J=4.0 Hz, 1H), 2.05 (m, 1H), 1.16 (d. J=7.6 Hz, 3H) ppm.

Step 3: Preparation of (1S,2S,3R,4S,5R)-3-amino-2-methyl-6,8-dioxabicyclo[3.2.1]octan-4-ol To a solution of (1R,2S,4S,5R,6S)-5-methyl-3,8,9-trioxatricyclo[4.2.1.02,4]nonane (0.1 g, 0.703 mmol, 1 equiv.) in NH$_3$H$_2$O (2 mL) was stirred at 100° C. for 12 h. The reaction mixture was cooled to room temperature and concentrated in vacuum to provide (1S,2S,3R,4S,5R)-3-amino-2-methyl-6,8-dioxabicyclo[3.2.1]octan-4-ol (0.095 g, 84.8% yield) as white solid, which was used in subsequent reactions without further purification.

Synthesis of (1R,3R,4S,5S)-3-amino-6,8-dioxabicyclo[3.2.1]octan-4-ol (1E-1)

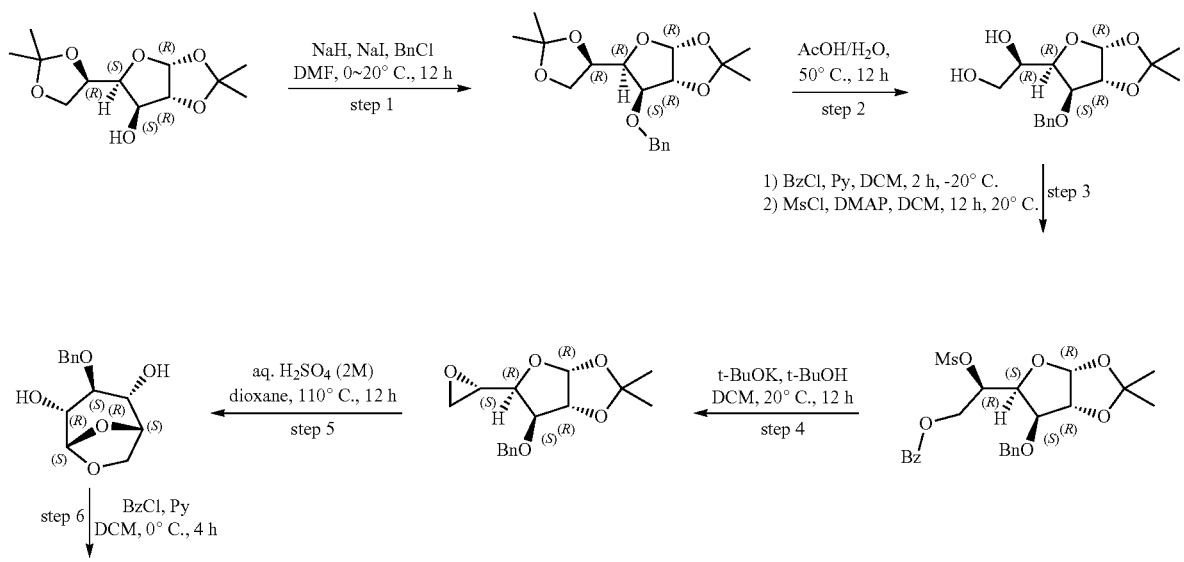

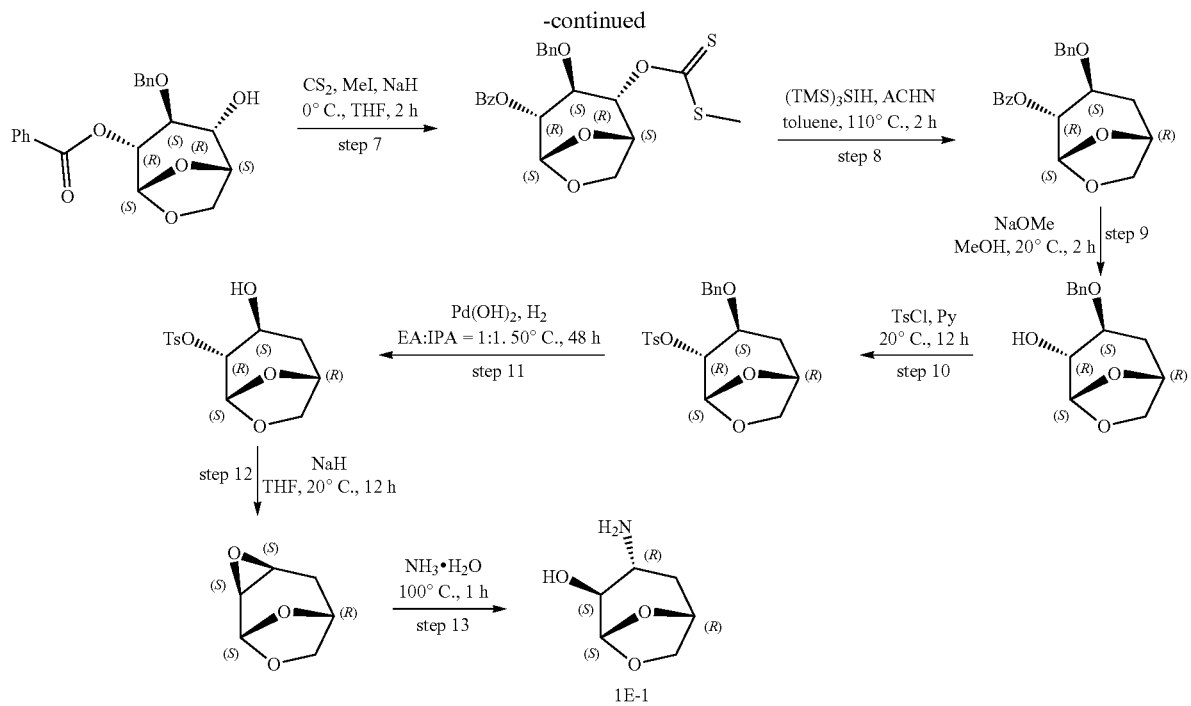

Step 1: preparation of (3aR,5R,6S,6aR)-6-(benzyloxy)-5-((R)-2,2-dimethyl-1,3-dioxolan-4-yl)-2,2-dimethyltetrahydrofuro[2,3-d][1,3]dioxole To a suspension of NaH (10 g, 250.02 mmol, 60% purity, 1.30 eq) and NaI (4.32 g, 28.81 mmol, 0.15 eq) in anhydrous DMF (150 mL) was added dropwise with a solution of (3aR,5S,6S,6aR)-5-((R)-2,2-dimethyl-1,3-dioxolan-4-yl)-2,2-dimethyltetrahydrofuro[2,3-d][1,3]dioxol-6-ol (50 g, 192.10 mmol, 1 eq) in anhydrous DMF (150 mL) at 0° C., and the mixture was stirred for 1 hour at 0° C. under nitrogen, followed by the slow addition of BnCl (29.70 g, 234.63 mmol, 27 mL, 1.22 eq) at 0° C. After the completion of the addition, the mixture was warmed to 20° C., and stirred for an additional 12 hours under nitrogen. The mixture was then quenched with saturated aqueous $NH_4Cl$ (1 L) and extracted with MTBE (500 mL×2). The combined organic layers were washed with brine (200 mL×2), dried over $Na_2SO_4$ and filtered. The filtrate was concentrated to give (3aR,5R,6S,6aR)-6-(benzyloxy)-5-((R)-2,2-dimethyl-1,3-dioxolan-4-yl)-2,2-dimethyltetrahydrofuro[2,3-d][1,3]dioxole (65 g, 96.5% yield, crude) as a yellow oil, which was directly used in next step without purification.

Step 2: preparation of (R)-1-((3aR,5R,6S,6aR)-6-(benzyloxy)-2,2-dimethyltetrahydrofuro[2,3-d][1,3]dioxol-5-yl)ethane-1,2-diol The solution of (3aR,5R,6S,6aR)-6-(benzyloxy)-5-((R)-2,2-dimethyl-1,3-dioxolan-4-yl)-2,2-dimethyltetrahydrofuro[2,3-d][1,3]dioxole (65 g, 185.50 mmol, 1 eq) in AcOH (220 mL) and Water (60 mL) was stirred for 12 hours at 50° C. After the completion of the reaction, the mixture was cooled to room temperature and concentrated under reduced pressure. The resulting residue was dissolved in EtOAc (500 mL) and sequentially washed with saturated aqueous $NaHCO_3$ (200 mL×2), water (200 mL) and brine (200 mL). The organic layer was dried over $Na_2SO_4$ and filtered The filtrate was concentrated to give (R)-1-((3aR,5R,6S,6aR)-6-(benzyloxy)-2,2-dimethyltetrahydrofuro[2,3-d][1,3]dioxol-5-yl) ethane-1,2-diol (70 g, 97.2% yield, crude) as a yellow oil, which was directly used in next step without further purification. 1H NMR ($CDCl_3$)δ 7.42-7.30 (m, 5H), 5.97-5.92 (m, 1H), 4.74 (d, J=11.6 Hz, 1H), 4.64 (d, J=4.0 Hz, 1H), 4.61-4.56 (m, 1H), 4.17-4.10 (m, 2H), 4.04 (br s, 1H), 3.86-3.79 (m, 1H), 3.75-3.67 (m, 1H), 2.75 (br s, 1H), 2.53 (br s, 1H), 1.50 (d, J=0.8 Hz, 3H), 1.37-1.32 (m, 3H) ppm.

Step 3: preparation of (R)-2-((3aR,5S,6S,6aR)-6-(benzyloxy)-2,2-dimethyltetrahydrofuro[2,3-d][1,3]dioxol-5-yl)-2-((methylsulfonyl)oxy)ethyl benzoate The solution of (R)-1-((3aR,5R,6S,6aR)-6-(benzyloxy)-2,2-dimethyltetrahydrofuro[2,3-d][1,3]dioxol-5-yl) ethane-1,2-diol (70 g, 225.56 mmol, 1 eq) and Pyridine (194.37 g, 2.46 mol, 198.33 mL, 10.89 eq) in DCM (320 mL) was cooled to −25° C. under $N_2$. To the cold solution, a solution of BzCl (32.50 g, 231.17 mmol, 26.83 mL, 1.02 eq) in DCM (40 mL) was added at −25° C. under nitrogen, followed by the addition of MsCl (51.86 g, 452.72 mmol, 35.04 mL, 2.01 eq) and DMAP (5.50 g, 45.02 mmol, 0.2 eq) at 0° C. The reaction mixture was slowly warmed to 20° C. and kept stirring for 12 hours at that temperature under nitrogen. After the completion of the reaction, the mixture was poured into ice water (500 mL) and stirred for 0.5 hour, and then extracted with DCM (500 mL). The organic layer was sequentially washed with aqueous HCl (2 N, 300 mL×2), saturated aqueous $NaHCO_3$ (300 mL) and brine (300 mL). The organic layer was dried over $Na_2SO_4$, filtered and the filtrate was concentrated. The resulting residue was purified by column chromatography to give (R)-2-((3aR,5S,6S,6aR)-6-(benzyloxy)-2,2-dimethyltetrahydrofuro[2,3-d][1,3]dioxol-5-yl)-2-((methylsulfonyl)oxy)ethyl benzoate (81 g, 72.9% yield) as a white solid. $^1H$ NMR ($CDCl_3$)δ 8.10 (dd, J=8.8, 1.2 Hz, 2H), 7.63-7.56 (m, 1H), 7.50-7.41 (m, 4H), 7.39-7.28 (m, 3H), 5.95 (d, J=3.6 Hz, 1H), 5.48-5.41 (m, 1H), 4.95 (dd, J=12.8, 2.0 Hz, 1H), 4.76-4.61 (m, 3H), 4.56-4.47 (m, 2H), 4.19-4 12 (m, 2H), 3.04-3.00 (m, 3H), 1.53 (s, 3H), 1.35 (d, J=0.8 Hz, 3H) ppm.

Step 4: preparation of (3aR,5R,6S,6aR)-6-(benzyloxy)-2,2-dimethyl-5-((S)-oxiran-2-yl)tetrahydrofuro[2,3-d][1,3]dioxole To a solution of (R)-2-((3aR,5S,6S,6aR)-6-(benzyloxy)-2,2-dimethyltetrahydrofuro[2,3-d][1,3]dioxol-5-yl)-2-((methylsulfonyl)oxy)ethyl benzoate (81 g, 164.45 mmol, 1 eq) in DCM (560 mL) and t-BuOH (160 mL) was added t-BuOK (44 g, 392.11 mmol, 2.38 eq) at 0° C. under nitrogen atmosphere, and the mixture was then warmed to 20° C. and kept stirring for 12 hours at that temperature. After the completion of the reaction, the mixture was concentrated under reduced pressure. The resulting residue was diluted with MTBE (500 mL) and water (200 mL) and then adjusted to pH=7 with aqueous HCl (IN). The precipitation was filtered off, washed with MTBE (200 mL×3) and the filtrate was extracted with MTBE (500 mL×2). The combined organic layer was washed with brine (500 mL), dried over $Na_2SO_4$, filtered, and the filtrate was concentrated. The resulting residue was purified by column chromatography to give (3aR,5R,6S,6aR)-6-(benzyloxy)-2,2-dimethyl-5-((S)-oxiran-2-yl)tetrahydrofuro[2,3-d][1,3]dioxole (40 g, 136.83 mmol, 83.20% yield) as a yellow oil. $^1$H NMR (CDCl$_3$) δ 7.39-7.31 (m, 5H), 6.02 (d, J=4.0 Hz, 1H), 4.76 (d, J=12.4 Hz, 1H), 4.66 (d, J=4.0 Hz, 1H), 4.53 (d, J=12.4 Hz, 1H), 3.99 (d, J=3.6 Hz, 1H), 3.83 (dd, J=6.4, 3.6 Hz, 1H), 3.34-3.25 (m, 1H), 2.78 (t, J=4.8 Hz, 1H), 2.56 (dd, J=4.8, 2.8 Hz, 1H), 1.47 (s, 3H), 1.34 (s, 3H) ppm.

Step 5: preparation of (1S,2R,3S,4R,5S)-3-(benzyloxy)-6,8-dioxabicyclo[3.2.1]octane-2,4-diol A solution of (3aR,5R,6S,6aR)-6-(benzyloxy)-2,2-dimethyl-5-((S)-oxiran-2-yl)tetrahydrofuro[2,3-d][1,3]dioxole (40 g, 136.83 mmol, 1 eq) in $H_2SO_4$ (2M, 80 mL, 1.17 eq) and dioxane (80 mL) was stirred for 12 hours at 110° C. under nitrogen atmosphere. After the completion of the reaction, the mixture was cooled to room temperature and concentrated under reduced pressure. The resulting crude product was diluted with EtOAc (500 mL) and water (300 mL). The organic layer was collected, and the aqueous phase was extracted with EtOAc (500 mL). The combined organic layer was washed with brine (300 mL), dried over $Na_2SO_4$, filtered and the filtrate was concentrated. The resulting residue was triturated with (EtOAc: Petrolum ether=2:1, 40 mL) to give (1S,2R,3S,4R,5S)-3-(benzyloxy)-6,8-dioxabicyclo[3.2.1]octane-2,4-diol (13 g, 37.66% yield) as a yellow solid. $^1$H NMR (CDCl$_3$) δ 7.40-7.30 (m, 5H), 5.30 (d. J=2.0 Hz, 1H), 4.99-4.71 (m, 2H), 4.43 (t, J=4.8 Hz, 1H), 4.04 (d, J=7.6 Hz, 1H), 3.91-3.84 (m, 1H), 3.73 (dd, J=7.6, 5.2 Hz, 1H), 3.69-3.63 (m, 1H), 3.40 (t, J=8.0 Hz, 1H), 2.23 (d, J=2.8 Hz, 1H), 2.02 (d, J=8.8 Hz, 1H) ppm.

Step 6: preparation of (1S,2R,3S,4R,5S)-3-(benzyloxy)-2-hydroxy-6,8-dioxabicyclo[3.2.1]octan-4-yl benzoate To a solution of (1S,2R,3S,4R,5S)-3-(benzyloxy)-6,8-dioxabicyclo[3.2.1]octane-2,4-diol (3 g, 11.89 mmol, 1 eq) and pyridine (2.94 g, 37.17 mmol, 3 mL, 3.13 eq) in DCM (25 mL) was added BzCl (1.94 g, 13.78 mmol, 1.6 mL, 1.16 eq) at 0° C., and the mixture was stirred for 4 hours at that temperature under nitrogen atmosphere. After the completion of the reaction, the mixture was quenched with MeOH (50 mL) and concentrated under reduced pressure. The resulting residue was purified by column chromatography to give (1S,2R,3S,4R,5S)-3-(benzyloxy)-2-hydroxy-6,8-dioxabicyclo[3.2.1]octan-4-yl benzoate (3.5 g, 9.82 mmol, 82.58% yield) as a white solid. $^1$H NMR (CDCl$_3$) δ 8.13-8.07 (m, 2H), 7.65-7.59 (m, 1H), 7.52-7.45 (m, 2H), 7.33-7.26 (m, 5H), 5.56 (d, J=1.6 Hz, 1H), 5.09 (dd, J=8.4, 1.6 Hz, 1H), 4.86-4.65 (m, 2H), 4.52 (t, J=4.8 Hz, 1H), 4.37-4.35 (m, 1H), 4.18 (d, J=8.0 Hz, 1H), 4.02 (dd, J=8.0, 4.0 Hz, 1H), 3.91-3.90 (m, 1H), 2.60-2.13 (m, 1H), 1.92-1.45 (m, 1H) ppm.

Step 7: preparation of (1S,2R,3S,4R,5S)-3-(benzyloxy)-2-(((methylthio) carbonothioyl)oxy)-6,8-dioxabicyclo[3.2.1]octan-4-yl benzoate To a solution of (1S,2R,3S,4R,5S)-3-(benzyloxy)-2-hydroxy-6,8-dioxabicyclo[3.2.1]octan-4-yl benzoate (3.5 g, 9.82 mmol, 1 eq) in anhydrous THF (20 mL) was added NaH (600 mg, 15.00 mmol, 60% purity, 1.53 eq) at 0° C. under nitrogen, and the mixture was stirred for 10 min, followed by the addition of CS$_2$ (1.1 g, 14.45 mmol, 1.47 eq) and then kept stirring for an additional 50 minutes. Subsequently, MeI (2.1 g, 14.80 mmol, 1.51 eq) was added at 0° C., and the mixture was kept stirring for 1 hour under nitrogen. After the completion of the reaction, the mixture was quenched with saturated aqueous NH$_4$Cl (100 mL) and extracted with EtOAc (200 mL×2). The combined organic layer was washed with brine (100 mL), dried over Na$_2$SO$_4$, filtered and the filtrate was concentrated. The resulting residue was purified by column chromatography to give (1S,2R,3S,4R,5S)-3-(benzyloxy)-2-(((methylthio) carbonothioyl)oxy)-6,8-dioxabicyclo[3.2.1]octan-4-yl benzoate (4 g, 8.96 mmol, 91.21% yield) as a yellow oil. $^1$H NMR (CDCl$_3$) δ 8.10-8.04 (m, 2H), 7.66-7.59 (m, 1H), 7.53-7.45 (m, 2H), 7 28-7.22 (m, 5H), 5.98 (dd, J=8.4, 4.4 Hz, 1H), 5.63 (d, J=1.6 Hz, 1H), 5.17 (dd, J=8.4, 1.6 Hz, 1H), 4.93 (t, J=4.8 Hz, 1H), 4.80-4.63 (m, 2H), 4.26 (t, J=8.4 Hz, 1H), 4.17-4.14 (m, 1H), 3.81 (dd, J=7.6, 5.2 Hz, 1H), 2.65-2.62 (m, 3H) ppm.

Step 8: preparation of (1R,3S,4R,5S)-3-(benzyloxy)-6,8-dioxabicyclo[3.2.1]octan-4-yl benzoate To a solution of (1S,2R,3S,4R,5S)-3-(benzyloxy)-2-(((methylthio) carbonothioyl)oxy)-6,8-dioxabicyclo[3.2.1]octan-4-yl benzoate (3 4 g, 7.61 mmol, 1 eq) and bis (trimethylsilyl) silyl-trimethyl-silane (4.03 g, 16.21 mmol, 2.13 eq) in toluene (50 mL) was added 1-[(E)-(1-cyanocyclohexyl) azo]cyclohexanecarbonitrile (380 mg, 1.56 mmol, 0.2 eq) at 20° C. under nitrogen, and the mixture was then heated and stirred at 110° C. for 2 hours under nitrogen atmosphere. After the completion of the reaction, the mixture was cooled to room temperature, diluted with water (100 mL), and extracted with EtOAc (100 mL×2). The combined organic layer was washed with brine (100 mL), dried over Na$_2$SO$_4$, filtered and the filtrate was concentrated. The resulting residue was purified by column chromatography to give (1R,3S,4R,5S)-3-(benzyloxy)-6,8-dioxabicyclo[3.2.1]octan-4-yl benzoate (1.6 g, 4.70 mmol, 61.74% yield) as a colorless oil. $^1$H NMR (CDCl$_3$) δ 8.14-8.06 (m, 2H), 7.67-7.57 (m, 1H), 7.52-7.45 (m, 2H), 7.32-7.24 (m, 5H), 5.59 (d, J=1.6 Hz, 1H), 5.10 (dd, J=8.4, 1.2 Hz, 1H), 4.71-4.56 (m, 3H), 4.13-4.03 (m, 1H), 3.86-3.77 (m, 2H), 2.22 (ddd, J=13.6, 6.8, 1.6 Hz, 1H), 2.05-1.94 (m, 1H) ppm.

Step 9: preparation of (1R,3S,4R,5S)-3-(benzyloxy)-6,8-dioxabicyclo[3.2.1]octan-4-ol To a solution of (1R,3S,4R,5S)-3-(benzyloxy)-6,8-dioxabicyclo[3.2.1]octan-4-yl benzoate (1.6 g, 4.70 mmol, 1 eq) in MeOH (10 mL) was added NaOMe (350 mg, 6.48 mmol, 1.38 eq) at 0° C., and the mixture was then warmed to 20° C. and stirred for 2 hours at that temperature under nitrogen atmosphere. After the completion of the reaction, the mixture was poured into ice water (50 mL), adjusted to pH=7 with aqueous HCl (1 N) and extracted with DCM (100 mL×2). The organic layer was washed with brine (100 mL), dried over Na$_2$SO$_4$, filtered and the filtrate was concentrated. The desired (1R,3S,4R,5S)-3-(benzyloxy)-6,8-dioxabicyclo[3.2.1]octan-4-ol (1.1 g, 4.66 mmol, 99.04% yield, crude)

was obtained as a colorless oil, which was directly used in next step without purification. LCMS: 238.3 [M+H]$^+$.

Step 10: preparation of (1R,3S,4R,5S)-3-(benzyloxy)-6,8-dioxabicyclo[3.2.1]octan-4-yl 4-methylbenzenesulfonate To a solution of (1R,3S,4R,5S)-3-(benzyloxy)-6,8-dioxabicyclo[3.2.1]octan-4-ol (1.1 g, 4.66 mmol, 1 eq) in pyridine (15 mL) was added TsCl (1 g, 5.25 mmol, 1.13 eq) at 20° C., and the mixture was stirred for 12 hours at that temperature under nitrogen atmosphere. After the completion of the reaction, the mixture was diluted with EtOAc (300 mL) and washed with water (100 mL) and brine (100 mL). The organic layer was dried over Na$_2$SO$_4$, filtered and the filtrate was concentrated. The resulting residue was purified by column chromatography to give (1R,3S,4R,5S)-3-(benzyloxy)-6,8-dioxabicyclo[3.2.1]octan-4-yl 4-methylbenzenesulfonate (1.5 g, 3.84 mmol, 82.51% yield) as a white solid. $^1$H NMR (CDCl$_3$)δ 7.77-7.69 (m, 2H), 7.23-7.18 (m, 3H), 7.16-7.12 (m, 2H), 7.07 (dd, J=7.2, 2.4 Hz, 2H), 5.42 (d, J=1.2 Hz, 1H), 4.48 (br s, 1H), 4.35-4.27 (m, 3H), 3.75 (dt, J=10.8, 7.6 Hz, 1H), 3.70-3.63 (m, 2H), 2.32-2.28 (m, 3H), 1.99 (ddd, J=13.6, 6.8, 1.6 Hz, 1H), 1.80-1.67 (m, 1H) ppm.

Step 11: preparation of (1R,3S,4R,5S)-3-hydroxy-6,8-dioxabicyclo[3.2.1]octan-4-yl 4-methylbenzenesulfonate The mixture of (1R,3S,4R,5S)-3-(benzyloxy)-6,8-dioxabicyclo[3.2.1]octan-4-yl 4-methylbenzenesulfonate (0.8 g, 2.05 mmol, 1 eq) and Pd(OH)$_2$ (287.74 mg, 2.05 mmol, 1 eq) in EtOAc (10 mL) and IPA (10 mL) was degassed and back-filled with hydrogen for 3 times, and then stirred under H$_2$ (50 Psi) for 48 hours at 50° C. After the completion of the reaction, the mixture was cooled to room temperature, filtered through a short pad of celite and rinsed with ethyl acetate (10 mL) The combined filtrate was concentrated and the resulting residue was purified by column chromatography to give (1R,3S,4R,5S)-3-hydroxy-6,8-dioxabicyclo[3.2.1]octan-4-yl 4-methylbenzenesulfonate (550 mg, 89.3% yield) as a white solid. LCMS: 323.1 [M+Na]*.

Step 12: preparation of (1S,2S,4S,6R)-3,8,9-trioxatricyclo[4.2.1.0$^{2,4}$]nonane To a solution of (1R,3S,4R,5S)-3-hydroxy-6,8-dioxabicyclo[3.2.1]octan-4-yl 4-methylbenzenesulfonate (550 mg, 1 83 mmol, 1 eq) in THF (10 mL) was added NaH (100 mg, 2.50 mmol, 60% purity, 1.37 eq) at 0° C., and the mixture was then warmed to 20° C. and stirred for 12 hours at that temperature under nitrogen atmosphere. After the completion of the reaction, the mixture was quenched with saturated aqueous NH$_4$Cl (50 mL) and extracted with EtOAc (100 mL×2). The combined organic layer was washed with brine (50 mL), dried over Na$_2$SO$_4$, filtered and the filtrate was concentrated under reduced pressure. The resulting residue was purified by prep-TLC to give (1S,2S,4S,6R)-3,8,9-trioxatricyclo[4.2.1.0$^{2,4}$]nonane (85 mg, 36.2% yield) as a yellow oil Step 13: preparation of (1R,3R,4S,5S)-3-amino-6,8-dioxabicyclo[3.2.1]octan-4-ol The solution of (1S,2S,4S,6R)-3,8,9-trioxatricyclo[4.2.1.0$^{2,4}$]nonane (80 mg, 0.624 mmol, 1 eq) in NH$_3$H$_2$O (2 mL) was stirred at 100° C. for 1 hour. After the completion of the reaction, the mixture was cooled to room temperature and concentrated under reduced pressure. The desired (1R,3R,4S,5S)-3-amino-6,8-dioxabicyclo[3.2.1]octan-4-ol (65 mg, 71.72% yield) was obtained as a yellow oil, which was used directly without purification LCMS: 146.1 [M+H]$^+$.

Preparation of (1S,2S,3R,5S)-3-amino-6,8-dioxabicyclo[3.2.1]octan-2-ol (1F-1)

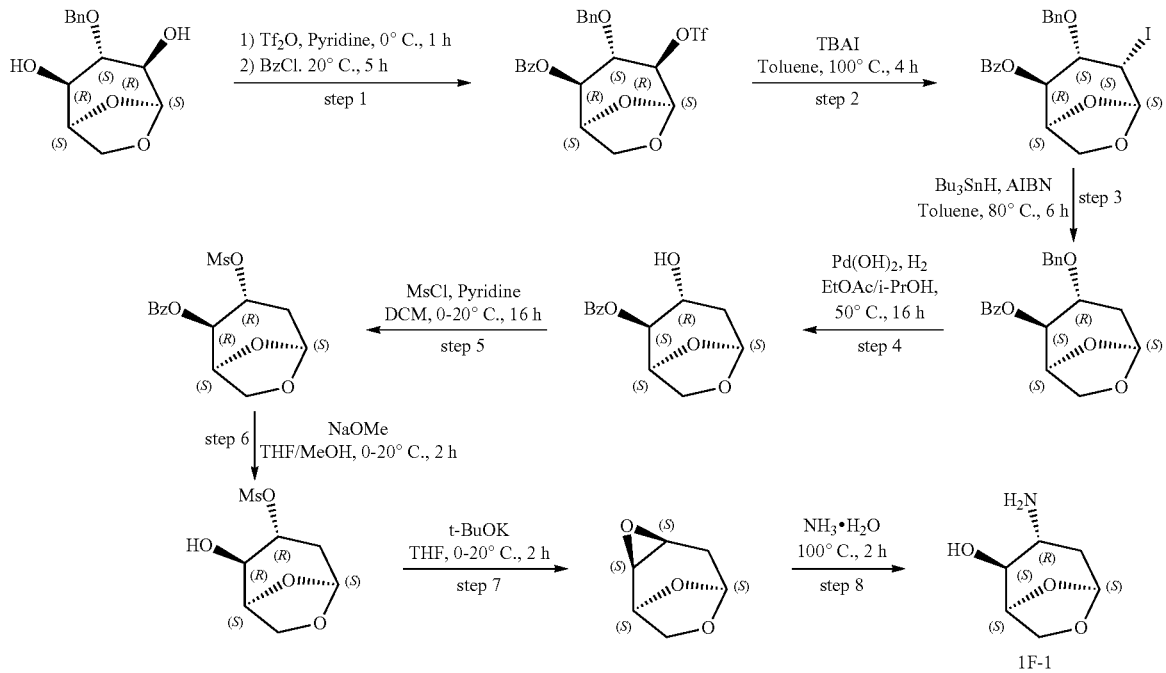

Step 1: Preparation of (1S,2R,3S,4R,5S)-3-(benzyloxy)-4-(((trifluoromethyl) sulfonyl)oxy)-6,8-dioxabicyclo[3.2.1]octan-2-yl benzoate To a solution of (1S,2R,3S,4R,5S)-3-(benzyloxy)-6,8-dioxabicyclo[3.2.1]octane-2,4-diol (3 g. 11.89 mmol, 1 eq) in pyridine (60 mL) was added dropwise Tf$_2$O (4.70 g, 16.65 mmol, 2.75 mL, 1.4 eq) at 0° C., and the mixture was stirred for 1 hour at that temperature, followed by the dropwise addition of benzoyl chloride (4.01 g, 28.54 mmol, 3.31 mL., 2.4 eq) at 0° C. under nitrogen atmosphere, and the mixture was then warmed to 20° C. and stirred for 5 hours at that temperature. After the completion of the reaction, the mixture was quenched with H$_2$O (50 mL) and extracted with EtOAc (100 mL×3). The combined organic layers were washed with brine (50 mL), dried over anhydrous Na$_2$SO$_4$, filtered and the filtrate was concentrated in vacuo. The resulting residue was purified by column chromatography to afford (1S,2R,3S,4R,5S)-3-(benzyloxy)-4-(((trifluoromethyl) sulfonyl)oxy)-6,8-dioxabicyclo[3.2.1]octan-2-yl benzoate (5.8 g, 99.8% yield) as a white solid. $^1$H NMR (400 MHZ, CDCl$_3$) δ 7.96 (d, J=7.2 Hz, 2H), 7.65-7.62 (m, 1H), 7.50-7.46 (m, 2H), 7.21 (s, 5H), 5.62 (s, 1H),.5.36-5.34 (m, 1H), 4.82-4.78 (m, 3H), 4.68 (d, J=11.2 Hz, 1H), 4.20-4.15 (m, 2H), 3.85-3.84 (m, 1H) ppm.

Step 2: Preparation of (1S,2R,3S,4S,5S)-3-(benzyloxy)-4-iodo-6,8-dioxabicyclo[3.2.1]octan-2-yl benzoate To a solution of (1S,2R,3S,4R,5S)-3-(benzyloxy)-4-(((trifluoromethyl) sulfonyl)oxy)-6,8-dioxabicyclo[3.2.1]octan-2-yl benzoate (2 g, 4.09 mmol, 1 eq) in toluene (20 mL) was added tetrabutylammonium iodide (3.02 g, 8.19 mmol, 2 eq), and the mixture was stirred at 100° C. for 4 hours under nitrogen atmosphere. After the completion of the reaction, the mixture was cooled to room temperature and concentrated in vacuo. The resulting residue was purified by column chromatography to afford (1S,2R,3S,4S,5S)-3-(benzyloxy)-4-iodo-6,8-dioxabicyclo[3.2.1]octan-2-yl benzoate (1.4 g, 73.3% yield) as a white solid. LCMS: 467.0 [M+H].

Step 3: Preparation of (1S,2S,3R,5S)-3-(benzyloxy)-6,8-dioxabicyclo[3.2.1]octan-2-yl benzoate To a solution of (1S,2R,3S,4S,5S)-3-(benzyloxy)-4-iodo-6,8-dioxabicyclo[3.2.1]octan-2-yl benzoate (1.3 g. 2.79 mmol, 1 eq) in toluene (10 mL.) was added Bu$_3$SnH (2.01 g, 6.91 mmol, 1.83 mL, 2.48 eq) and AIBN (91.57 mg, 0.56 mmol, 0.2 eq) at 0° C., and the mixture was then stirred at 80° C. for 6 hours under nitrogen atmosphere. After the completion of the reaction, the mixture was cooled to room temperature, quenched with saturated aqueous KF (50 mL) and extracted with EtOAc (100 mL×3). The combined organic layers were washed with brine (50 mL), dried over anhydrous Na$_2$SO$_4$, filtered and the filtrate was concentrated in vacuo. The resulting residue was purified by column chromatography to afford (1S,2S,3R,5S)-3-(benzyloxy)-6,8-dioxabicyclo[3.2.1]octan-2-yl benzoate (900 mg, 85.3% yield) as a colorless oil. LCMS: 341.1 [M+H]$^+$.

Step 4: Preparation of (1S,2S,3R,5S)-3-hydroxy-6,8-dioxabicyclo[3.2.1]octan-2-yl benzoate The mixture of (1S,2S,3R,5S)-3-(benzyloxy)-6,8-dioxabicyclo[3.2.1]octan-2-yl benzoate (450 mg, 1.32 mmol, 1 eq) and Pd(OH)$_2$ (1.0 g, 1.42 mmol, 20% purity, 1.08 eq) in EtOAc (20 mL) and i-PrOH (20 mL) was degassed and backfilled with hydrogen, and then stirred under hydrogen (50 psi) at 50° C. for 16 hours. After the completion of the reaction, the mixture was cooled to room temperature, filtered, rinsed with ethyl acetate (20 mL) and the combined filtrate was concentrated in vacuo. The resulting residue was purified by column chromatography to afford (1S,2S,3R, 5S)-3-hydroxy-6,8-dioxabicyclo[3.2.1]octan-2-yl benzoate (300 mg, 90.6% yield) as a colorless oil. LCMS: 251.0 [M+H]$^+$.

Step 5. Preparation of [(1S,2R,3R,5S)-3-methylsulfonyloxy-6,8-dioxabicyclo[3.2.1]octan-2-yl]benzoate To a solution of (1S,2S,3R,5S)-3-hydroxy-6,8-dioxabicyclo[3.2.1]octan-2-yl benzoate (300 mg, 1.20 mmol, 1 eq) and pyridine (474.13 mg, 5.99 mmol, 0.48 mL, 5 eq) in DCM (5 mL) was added MsCl (1.8 g, 15.71 mmol, 1.22 mL, 13.11 eq) dropwise at 0° C., and the mixture was then warm to 20° C. and stirred for 16 hours at that temperature under nitrogen atmosphere. After the completion of the reaction, the mixture was quenched with H$_2$O (50 mL) and extracted with DCM (100 mL×3). The combined organic layers were washed with brine (50 mL), dried over anhydrous Na$_2$SO$_4$, filtered and the filtrate was concentrated in vacuo. The resulting residue was purified by column chromatography to afford (1S,2R,3R,5S)-3-((methylsulfonyl)oxy)-6,8-dioxabicyclo[3.2.1]octan-2-yl benzoate (350 mg, 84.4% yield) as a colorless oil. LCMS: 329.0 [M+H]$^+$ Step 6: Preparation of (1S,2R,3R,5S)-2-hydroxy-6,8-dioxabicyclo[3.2.1]octan-3-yl methanesulfonate To a solution of (1S,2R,3R,5S)-3-((methylsulfonyl)oxy)-6,8-dioxabicyclo[3.2.1]octan-2-yl benzoate (300.00 mg, 0.91 mmol, 1 eq) in MeOH (2 mL) and THF (2 mL) was added NaOMe (5 M, 0.27 mL, 1.5 eq) at 0° C., and the mixture was warm to 20° C. and stirred for 2 hours at that temperature under nitrogen atmosphere. After the completion of the reaction, the mixture was quenched with H$_2$O (10 mL) and extracted with DCM (20 mL×3). The combined organic layers were washed with brine (50 mL), dried over anhydrous Na$_2$SO$_4$, filtered and the filtrate was concentrated in vacuo. The resulting residue was purified by prep-TLC (SiO$_2$, PE/EtOAc=3:1) to afford (1S,2R,3R,5S)-2-hydroxy-6,8-dioxabicyclo[3.2.1]octan-3-yl methanesulfonate (180 mg, 87.8% yield) as a yellow oil.

Step 7: Preparation of (1S,2S,4S,6S)-3,7,9-trioxatricyclo [4.2.1.02,4]nonane

To a solution of (1S,2R,3R,5S)-2-hydroxy-6,8-dioxabicyclo[3.2.1]octan-3-yl methanesulfonate (180 mg. 0.80 mmol, 1 eq) in THF (3 mL) was added t-BuOK (1 M, 1.6 mL, 1.99 eq) at 0° C., and the mixture was warm to 20° C. and stirred for 2 hours at that temperature under nitrogen atmosphere. After the completion of the reaction, the mixture was quenched with H$_2$O) (10 mL) and extracted with DCM (20 mL×3). The combined organic layers were washed with brine (50 mL), dried over anhydrous Na$_2$SO$_4$, filtered and the filtrate was concentrated in vacuo. The resulting residue was purified by prep-TLC (PE/EtOAc=3:1) to afford (1S, 2S,4S,6S)-3,7,9-trioxatricyclo[4.2.1.02,4]nonane (50 mg, 48.61% yield) as a yellow oil. 1H NMR (400 MHz, CDCl$_3$) δ 5.43 (d, J=3.6 Hz, 1H), 4.83 (t, J=5.0 Hz, 1H), 4.05 (d. J=6.4 Hz, 1H), 3.60-3.58 (m, 1H), 3.55-3.53 (m, 1H), 3.16-3.14 (m, 1H), 2.09-2.05 (m, 1H), 1.96-1.90 (m, 1H) ppm.

Step 8: Preparation of (1S,2S,3R,5S)-3-amino-6,8-dioxabicyclo[3.2.1]octan-2-ol

The solution of (1S,2S,4S,6S)-3,7,9-trioxatricyclo [4.2.1.02,4]nonane (40 mg, 0.31 mmol, 1 eq) in NH$_3$H$_2$O (5.32 mg, 0.31 mmol, 2 mL, 1 eq) was stirred at 100° C. for 2 hours. After the completion of the reaction, the mixture was cooled to room temperature and concentrated in vacuo. The desired (1S,2S,3R,5S)-3-amino-6,8-dioxabicyclo [3.2.1]octan-2-ol (40 mg, crude) was obtained as a yellow solid, which was used directly without further purification. LCMS: 146.1 [M+H]$^+$.

Preparation of exemplary compounds

Example 1: Synthesis of (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol (Compound 1)

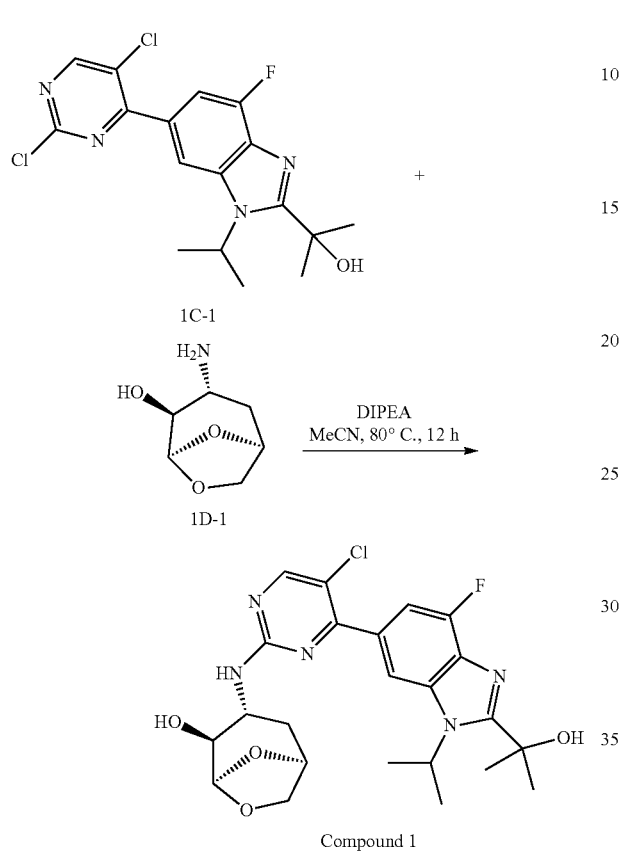

Example 2: Synthesis of (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-d-4-ol (Compound 2)

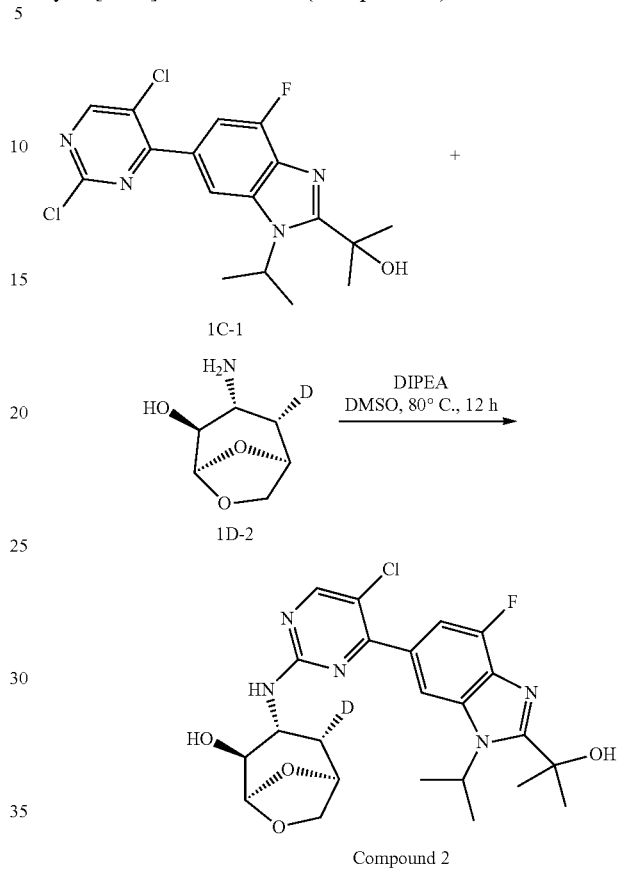

A mixture of 2-(6-(2,5-dichloropyrimidin-4-yl)-4-fluoro-1-isopropyl-1H-benzo[d]imidazol-2-yl) propan-2-ol (1C-1, 278 mg, 0.725 mmol, 1.00 eq), (1S,3R,4S,5R)-3-amino-6,8-dioxabicyclo[3.2.1]octan-4-ol (1D-1, 105 mg, 0.723 mmol, 1 eq) and DIPEA (280 mg, 2.17 mmol, 377.99 µL, 3 eq) in MeCN (3 mL) was stirred for 12 hours at 80° C. under nitrogen atmosphere. After the completion of the reaction, the mixture was cooled to room temperature and the volatiles were evaporated. The resulting residue was purified by prep-HPLC (column: Phenomenex luna C18 150*25 mm*10 um; mobile phase: [water (FA)-ACN]; gradient: 32%-52% B over 10 min), and further purified by SFC (column: DAICEL CHIRALCEL OD (250 mm*30 mm, 10 um); mobile phase: [CO$_2$-i-PrOH (0.1% NH$_3$H$_2$O)]; B %: 40%, isocratic elution mode) to afford the desired (1S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol (21.91 mg. 5.91% yield) as a white solid. LCMS: 492.3 [M+H]$^+$; $^1$H NMR (DMSO-d$_6$) δ 8.42 (br, s, 1H), 7.87-8.09 (m, 1H), 7.49-7.59 (m, 1H), 7.23-7.43 (m, 1H), 5.70-5.91 (m, 2H), 5.22 (s, 1H), 5.06 (br, s, 1H), 4.57 (br, s, 1H), 4.06-4.24 (m, 1H), 3.71-3.85 (m, 1H), 3.64 (m, 1H), 3.45-3.55 (m, 1H), 1.96-2.11 (m, 1H), 1.60-1.75 (m, 1H), 1.67 (s, 6H), 1.61 (d, J=6.8 Hz, 6H) ppm.

To a solution of 2-(6-(2,5-dichloropyrimidin-4-yl)-4-fluoro-1-isopropyl-1H-benzo[d]imidazol-2-yl) propan-2-ol (1C-1,132.48 mg, 0.328 mmol, 1 eq) and (1S,2S,3R,4S,5R)-3-amino-6,8-dioxabicyclo[3.2.1]octan-2-d-4-ol (1D-2, 80 mg, 0.493 mmol, 1.5 eq) in DMSO (1 mL) was added DIPEA (212.22 mg, 1.64 mmol, 5 eq), and the mixture was stirred at 80° C. for 2 hours under nitrogen atmosphere. After the completion of the reaction, the mixture was cooled to room temperature, poured into water (50 mL) and the aqueous phase was extracted with Ethyl Acetate (50 mL×3). The combined organic phase was washed with brine (30 mL), dried over Na$_2$SO$_4$, filtered and the filtrate was concentrated in vacuo. The resulting residue was purified by prep-HPLC (FA condition) and further purified with SFC (condition: column: DAICEL CHIRALCEL OD-H (250 mm*30 mm, 5um); mobile phase: [CO$_2$-EtOH (0.1% NH$_3$H$_2$O)];B %: 35%, isocratic elution mode) to afford (1S,2S,3R,4S,5R)-3-((5-chloro-4-(4-fluoro-2-(2-hydroxypropan-2-yl)-1-isopropyl-1/-benzo[d]imidazol-6-yl)pyrimidin-2-yl)amino)-6,8-dioxabicyclo[3.2.1]octan-2-d-4-ol (52.37 mg, 31.9% yield) as a white solid. LCMS: 493.3 [M+H]; $^1$H NMR (400 MHZ, DMSO-d$_6$) δ 8.50-8.31 (m, 1H), 8.09-7.85 (m, 1H), 7.61-7.23 (m, 2H), 5.76 (td, J=6.6, 13.2 Hz, 1H), 5.39-4.84 (m, 2H), 4.56 (br d, J=5.2 Hz, 1H), 4.22-4.03 (m, 1H), 3.88-3.68 (m, 1H), 3.64 (br t, J=6.0 Hz, 1H), 3.49 (br d, J=4.4 Hz, 1H), 2.54 (s, 1H), 2.07-1.93 (m, 1H), 1.66 (s, 6H), 1.60 (br d, J=6.8 Hz, 6H) ppm.

Example 3: Synthesis of methyl (R)-3-(6-(5-chloro-2-(((1S,3R,4S,5R)-4-hydroxy-6,8-dioxabicyclo[3.2.1]octan-3-yl)amino) pyrimidin-4-yl)-4-fluoro-1-isopropyl-1H-benzo[d]imidazol-2-yl) pyrrolidine-1-carboxylate (Compound 4)

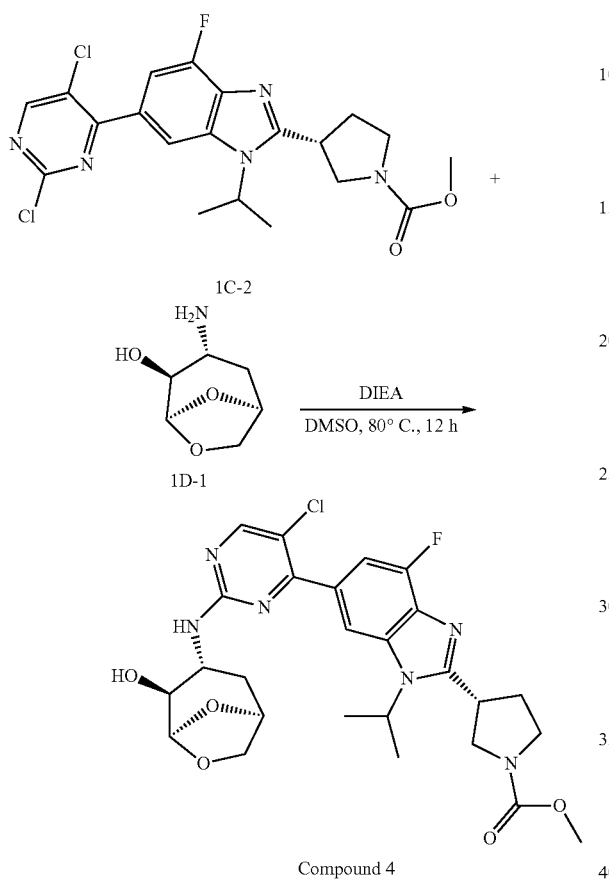

To a solution of (1S,3R,4S,5R)-3-amino-6,8-dioxabicyclo [3.2.1]octan-4-ol (1D-1, 100 mg. 0.689 mmol, 1.5 equiv.) in DMSO (2 mL) was added DIPEA (296.79 mg, 2.30 mmol, 5 equiv.) and methyl (R)-3-(6-(2,5-dichloropyrimidin-4-yl)-4-fluoro-1-isopropyl-1H-benzo[d]imidazol-2-yl) pyrrolidine-1-carboxylate (1C-2, 208 mg, 0.459 mmol, 1 equiv.). The mixture was stirred at 80° C. for 12 h under $N_2$ atmosphere. The reaction mixture was cooled to room temperature and diluted with water (2 mL). The aqueous mixture was extracted with ethyl acetate (2 mL×3). The combined organic phases were washed with brine (6 mL) and dried over $Na_2SO_4$. The solution was filtered, and the filtrate was concentrated under reduced pressure. The resulting residue was purified by prep-HPLC (column: Phenomenex luna C18 150*25 mm*10 um; mobile phase: [water (FA)-ACN]; gradient: 29%-62% B over 11 min) to afford 70 mg of product as white solid, which was further purified by prep-SFC (250 mm*30 mm, 10 um); mobile phase: [$CO_2$-EtOH (0.1% $NH_3H_2O$)]; B %: 50%, isocratic elution mode). The desired methyl (R)-3-(6-(5-chloro-2-(((1S,3R,4S,5R)-4-hydroxy-6,8-dioxabicyclo[3.2.1]octan-3-yl)amino) pyrimidin-4-yl)-4-fluoro-1-isopropyl-1H-benzo[d]imidazol-2-yl) pyrrolidine-1-carboxylate (22.52 mg, 8.64% yield) was obtained as white solid. LCMS: 561.2 [M+H]⁺; 1H NMR (400 MHZ, DMSO-$d_6$) δ 8.42 (br s, 1H), 8.07-7.88 (m, 1H), 7.62-7.31 (m, 2H), 5.22 (s, 1H), 5.02-4.92 (m, 1H), 4.56 (s, 1H), 4.15 (s, 1H), 4.00-3.88 (m, 1H), 3.86-3.80 (m, 1H), 3.71 (dd, J=7.6, 16.8 Hz, 1H), 3.63 (s, 4H), 3.60-3.53 (m, 1H), 3.53-3.41 (m, 2H), 2.40-2.31 (m, 1H), 2.29-2.13 (m, 1H), 2.08-1.94 (m, 1H), 1.85 (s, 1H), 1.72-1.66 (m, 1H), 1.61 (d, J=6.4 Hz, 6H), 1.24 (s, 1H) ppm.

Example 4: Synthesis of (1S,3R,4S,5R)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-4-ol (Compound 5)

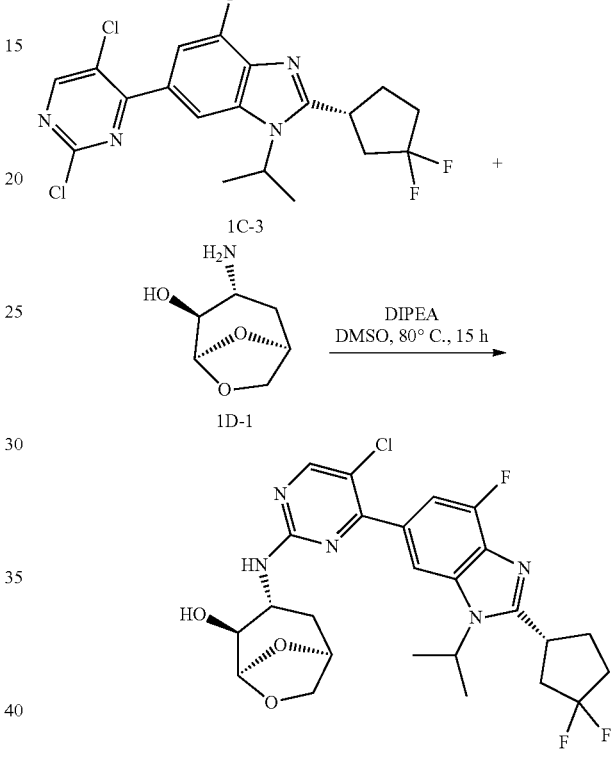

To a solution of (1S,3R,4S,5R)-3-amino-6,8-dioxabicyclo [3.2.1]octan-4-ol (1D-2, 100 mg, 0.689 mmol, 1.5 equiv.) in DMSO (2 mL) was added DIPEA (297 mg, 2.30 mmol, 5 equiv.) and (R)-6-(2,5-dichloropyrimidin-4-yl)-2-(3,3-difluorocyclopentyl)-4-fluoro-1-isopropyl-1H-benzo[d]imidazole (197 mg, 0.459 mmol, 1 equiv.). The mixture was stirred at 80° C. for 15 h under $N_2$ atmosphere. The reaction mixture was cooled to room temperature and diluted with water (2 mL). The aqueous mixture was extracted with ethyl acetate (2 mL×3). The combined organic phases were washed with brine (6 mL) and dried over $Na_2SO_4$. The solution was filtered, and the filtrate was concentrated under reduced pressure. The resulting residue was purified by prep-HPLC (column: Phenomenex luna C18 150*25 mm*10 um; mobile phase: [water (FA)-ACN]; gradient: 29%-62% B over 11 min) to afford 65 mg of product as white solid, which was further purified by prep-SFC (column: DAICEL CHIRALCEL OD (250 mm*30 mm, 10 um); mobile phase: [$CO_2$-EtOH (0.1% $NH_3H_2O$)]; B %: 35%, isocratic elution mode). The desired (1S,3R,4S,5R)-3-((5-chloro-4-(2-((R)-3,3-difluorocyclopentyl)-4-fluoro-1-isopropyl-1H-benzo[d]imidazol-6-yl)pyrimidin-2-yl)amino)-6,8-dioxabicyclo[3.2.1]octan-4-ol (21.40 mg, 8.64% yield)

was obtained as white solid. LCMS: 538.3 [M+H]$^+$; $^1$H NMR (400 MHZ, DMSO-d$_6$)δ 8.42 (s, 1H), 8.06-7.87 (m, 1H), 7.62-7.26 (m, 2H), 5.22 (s, 1H), 4.92 (td, J=6.9, 13.6 Hz, 1H), 4.57 (s, 1H), 4.23-4.08 (m, 1H), 3.92-3.85 (m, 1H), 3.82-3.70 (m, 1H), 3.64 (t, J=5.6 Hz, 1H), 3.50 (d, J=2.0 Hz, 1H), 2.81-2.60 (m, 2H), 2.40-2.27 (m, 2H), 2.23 (dd, J=6.7, 9.6 Hz, 1H), 2.11-1.94 (m, 2H), 1.85 (s, 1H), 1.72-1.64 (m, 1H), 1.64-1.56 (m, 6H) ppm.

Example 5: Synthesis of (1S,2S,3R,4S,5R)-3-((5-chloro-4-(4-fluoro-2-(2-hydroxypropan-2-yl)-1-isopropyl-1H-benzo[d]imidazol-6-yl)pyrimidin-2-yl)amino)-2-methyl-6,8-dioxabicyclo[3.2.1]octan-4-ol (Compound 13)

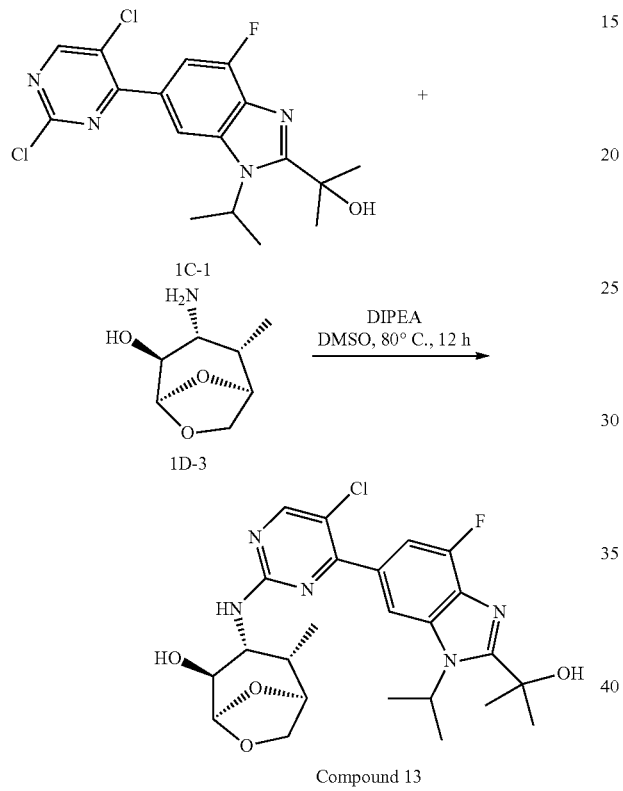

To a solution of (1S,2S,3R,4S,5R)-3-amino-2-methyl-6,8-dioxabicyclo[3.2.1]octan-4-ol (1D-3, 49 mg, 0.276 mmol, 1.5 equiv.) and 2-(6-(2,5-dichloropyrimidin-4-yl)-4-fluoro-1-isopropyl-1H-benzo[d]imidazol-2-yl) propan-2-ol (1C-1, 78 mg, 0.184 mmol, 1 equiv.) in DMSO (1.5 mL) was added DIPEA (119 mg, 0.921 mmol, 5 equiv.). The mixture was stirred at 80° C. for 12 h under N$_2$ atmosphere. The reaction mixture was cooled to room temperature and poured into aq. NH$_4$Cl (30 mL). The aqueous phase was extracted with ethyl acetate (30 mL×3). The combined organic phases were washed with brine (30 mL) and dried over Na$_2$SO$_4$. The solution was filtered, and the filtrate was concentrated under reduced pressure. The resulting residue was purified by prep-TLC (SiO$_2$, PE: EA=1:1, Rf=0.3) to give a crude product, which was further purified by SFC (condition: column: DAICEL CHIRALPAK IC (250 mm*30 mm, 10 um); mobile phase: [CO$_2$-EtOH];B %: 30%, isocratic elution mode). The desired (1S,2S,3R,4S,5R)-3-((5-chloro-4-(4-fluoro-2-(2-hydroxypropan-2-yl)-1-isopropyl-1H-benzo [d]imidazol-6-yl)amino)-2-methyl-6,8-dioxabicyclo[3.2.1]octan-4-ol (6.59 mg, 6.59% yield) was obtained as white solid. LCMS: 506.1 [M+H]$^+$; $^1$H NMR (400 MHZ, DMSO-d$_6$) δ 8.42 (s, 1H), 8.05-7.85 (m, 1H), 7.64-7.34 (m, 2H), 5.86-5.68 (m, 2H), 5.19 (s, 1H), 4.91 (d, J=6.8 Hz, 1H), 4.38 (d, J=4.8 Hz, 1H), 4.23-4.04 (m, 1H), 3.85-3.64 (m, 2H), 3.62-3.49 (m, 1H), 2.30-2.14 (m, 1H), 1.66 (s, 6H), 1.60 (d, J=6.8 Hz, 6H), 0.95 (d, J=7.2 Hz, 3H) ppm.

Example 6: Synthesis of 6-(5-chloro-2-(((1S,3R,4S,5R)-4-hydroxy-6,8-dioxabicyclo[3.2.1]octan-3-yl)amino) pyrimidin-4-yl)-4-fluoro-2-(2-hydroxypropan-2-yl)-1-isopropyl-1H-indole-3-carbonitrile (Compound 26)

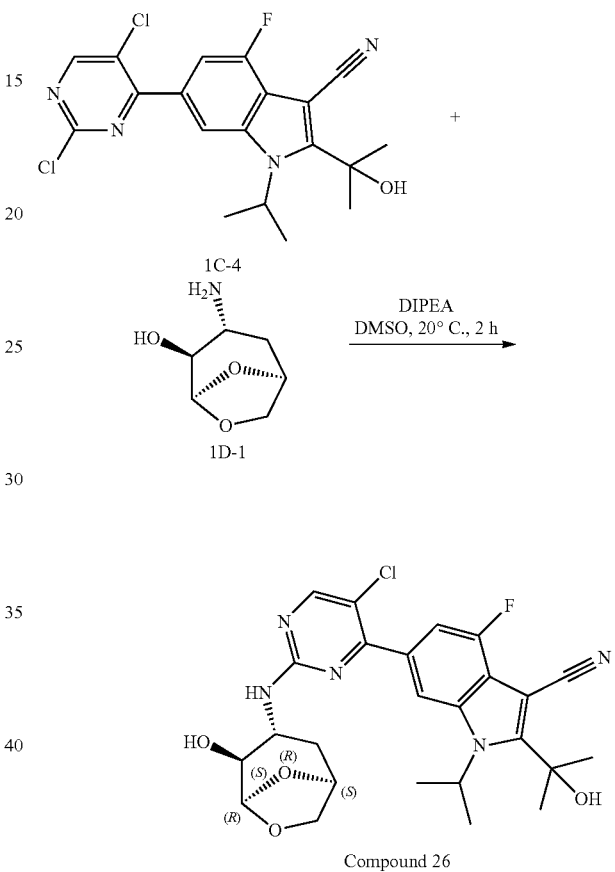

To a solution of 6-(2,5-dichloropyrimidin-4-yl)-4-fluoro-2-(2-hydroxypropan-2-yl)-1-isopropyl-1H-indole-3-carbonitrile (1C-4, 50 mg, 0.12 mmol, 1 eq) and (1S,3R,4S,5R)-3-amino-6,8-dioxabicyclo[3.2.1]octan-4-ol (1D-1, 23.17 mg, 0.16 mmol, 1.3 eq) in DMSO (1 mL) was added DIPEA (158.67 mg, 1.23 mmol, 10 eq), and the mixture was stirred at 100° C. for 12 hours under nitrogen atmosphere. After the completion of the reaction, the mixture was cooled to room temperature. The mixture was purified by prep-HPLC (column: Waters Xbridge 150×25 mm, 5 um; mobile phase: [water (NH$_4$HCO$_3$)-ACN]; gradient: 28%-48% B over 10 min) to afford 6-(5-chloro-2-(((1S,3R,4S,5R)-4-hydroxy-6,8-dioxabicyclo[3.2.1]octan-3-yl)amino) pyrimidin-4-yl)-4-fluoro-2-(2-hydroxypropan-2-yl)-1-isopropyl-1H-indole-3-carbonitrile (13.13 mg, 19.90% yield) as a white solid. LCMS: 516.2 [M+H]$^+$; $^1$H NMR (400 MHz, DMSO-d$_6$) δ 8.43 (s, 1H), 8.10-8.02 (m, 1H), 7.57-7.37 (m, 2H), 6.10 (3, 1H), 5.82-5.75 (m, 1H), 5.22 (s, 1H), 5.06-5.04 (m, 1H), 4.57 (s, 1H), 4.16-1.14 (m, 1H), 3.83-3.80 (m, 1H), 3.73-3.62 (m, 1H), 3.49-3.34 (m, 1H), 2.04-2.01 (m, 1H), 1.78-1.64 (m, 6H), 1.62 (s, 1H), 1.34-1.30 (m, 6H) ppm.

Example 7: Synthesis of (1S,3R,4S,5R)-3-((5-chloro-4-(7'-fluoro-2'-methylspiro[cyclopentane-1,3'-indol]-5'-yl)pyrimidin-2-yl)amino)-6,8-dioxabicyclo[3.2.1]octan-4-ol (Compound 32)

Example 8: Synthesis of (1S,3R,4S,5R)-3-((5-chloro-4-((S)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol (Compound 37) and (1S,3R,4S,5R)-3-((5-chloro-4-((R)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol (Compound 38)

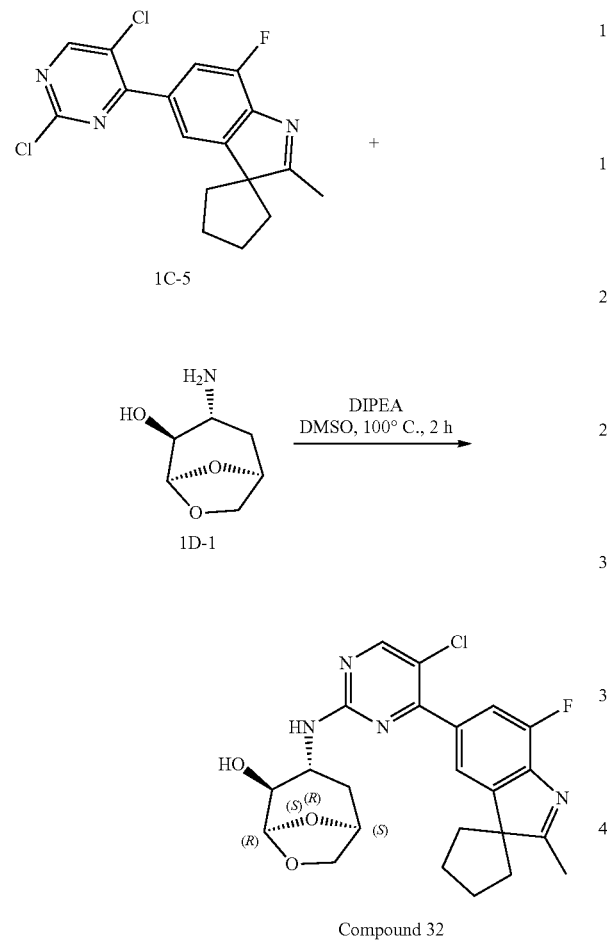

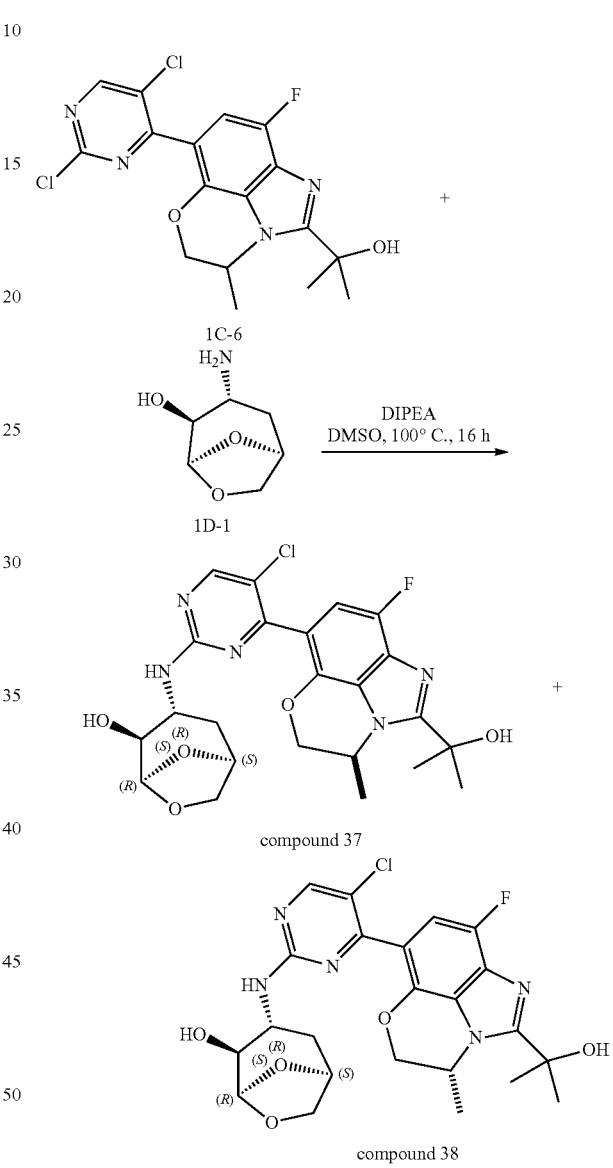

To a solution of 5'-(2,5-dichloropyrimidin-4-yl)-7'-fluoro-2'-methylspiro[cyclopentane-1,3'-indole](IC-5, 60 mg, 0.17 mmol, 1 eq) and (1S,3R,4S,5R)-3-amino-6,8-dioxabicyclo[3.2.1]octan-4-ol (1D-1, 29.84 mg, 0.21 mmol, 1.2 eq) in DMSO (1 mL) was added DIPEA (66.43 mg, 0.51 mmol, 0.09 mL, 3 eq), and the mixture was stirred at 100° C. for 2 hours under nitrogen atmosphere. After the completion of the reaction, the mixture was cooled to room temperature and the volatiles were evaporated under reduced pressure. The resulting residue was purified by prep-HPLC (column: Phenomenex luna C18 150×25 mm, 10 um; mobile phase: [water (FA)-ACN]; gradient: 36%-66% B over 10 min) to give (1S,3R,4S,5R)-3-((5-chloro-4-(7'-fluoro-2'-methylspiro[cyclopentane-1,3'-indol]-5'-yl)pyrimidin-2-yl)amino)-6,8-dioxabicyclo[3.2.1]octan-4-ol (27.6 mg, 35.0% yield) as an off-white solid. LCMS: 459.2 [M+H]; $^1$H NMR (400 MHZ, DMSO-$d_6$) δ 8.40 (s, 1H), 7.82-7.43 (m, 3H), 5.21 (s, 1H), 5.02 (d, J=6.0 Hz, 1H), 4.55 (s, 1H), 4.21-4.04 (m, 1H), 3.86-3.69 (m, 1H), 3.68-3.60 (m, 1H), 3.49-3.43 (m, 1H), 2.31 (s, 3H), 2.15-1.91 (m, 7H), 1.74 (d, J=5.6 Hz, 2H), 1.68-1.58 (m, 1H) ppm.

To a solution of 2-(6-(2,5-dichloropyrimidin-4-yl)-8-fluoro-3-methyl-3,4-dihydro-5-oxa-1,2a-diazaacenaphthylen-2-yl) propan-2-ol (1C-6, 100 mg, 0.251 mmol, 1 eq) and (1S,3R,4S,5R)-3-amino-6,8-dioxabicyclo[3.2.1]octan-4-ol (1D-1, 109.63 mg, 0.755 mmol, 3 eq) in DMSO (2 mL) was added DIPEA (97.61 mg, 0.755 mmol, 131.54 μL, 3 eq), and the mixture was stirred at 100° C. for 16 hours under nitrogen atmosphere. After the completion of the reaction, the mixture was cooled to room temperature and concentrated in vacuo. The resulting residue was purified by prep-HPLC {column: Phenomenex luna C18 150×25 mm, 10 um; mobile phase: [water (FA)-ACN]; gradient: 22%-52% B over 10 min}, and further purified by SFC (column:

DAICEL CHIRALCEL OX (250 mm×30 mm, 10 um); mobile phase: [CO₂-ACN/i-PrOH (0.1% NH₃·H₂O)]; B %: 45%, isocratic elution mode) to afford (1S,3R,4S,5R)-3-((5-chloro-4-((S)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3 2.1]octan-4-ol (20 08 mg, 15.7% yield) (Compound 37, randomly assigned absolute configuration) as an off-white solid, and (1S,3R,4S,5R)-3-((5-chloro-4-((R)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol (21.42 mg, 16.6% yield) (Compound 38, randomly assigned absolute configuration) as an off-white solid.

(1S,3R,4S,5R)-3-((5-chloro-4-((S)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol (Compound 37, randomly assigned absolute configuration) LCMS: 506.3 [M+H]⁺: $^1$H NMR (400 MHZ, DMSO-d₆) δ 8.37 (s, 1H), 7.58-7.42 (m, 1H), 7.03-6.85 (m, 1H), 5 86-5.76 (m, 1H), 5.29-5.16 (m, 2H), 5.03 (br d, J=5.6 Hz, 1H), 4.56 (br s, 1H), 4.48 (d, J=11.1 Hz, 1H), 4.29-4.17 (m, 1H), 4.16-4.01 (m, 1H), 3.85-3.68 (m, 1H), 3.63 (br s, 1H), 3.49-3.43 (m, 1H), 2.01 (br dd, J=4 4, 11 9 Hz, 1H), 1.68 (s, 3H), 1.65 (br s, 1H), 1.62 (s, 3H), 1.46 (br d, J=6.4 Hz, 3H) ppm.

(1S,3R,4S,5R)-3-((5-chloro-4-((R)-8-fluoro-2-(2-hydroxypropan-2-yl)-3-methyl-3,4-dihydro-5-oxa-1,2a-diazaacenaphthylen-6-yl)pyrimidin-2-yl)amino)-6,8-dioxabicyclo[3.2.1]octan-4-ol (Compound 38, randomly assigned absolute configuration) LCMS: 506.3 [M+H]; $^1$H NMR (400 MHZ, DMSO-d₆) δ 8.36 (s, 1H), 7.56-7.39 (m, 1H), 7.02-6.80 (m, 1H), 5.80 (s, 1H), 5.29-5.16 (m, 2H), 5.06-4.97 (m, 1H), 4.55 (br s, 1H), 4.49-4.41 (m, 1H), 4.21 (br d, J=10.0 Hz, 1H), 4.15-3.99 (m, 1H), 3.87-3.67 (m, 1H), 3.66-3.54 (m, 1H), 3.51-3.40 (m, 1H), 2.05-1.94 (m, 1H), 1.67 (s, 3H), 1.64 (br s, 1H), 1.62 (s, 3H), 1.45 (br d, J=6.4 Hz, 3H) ppm.

Example 9: Synthesis of (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-ol (Compound 72)

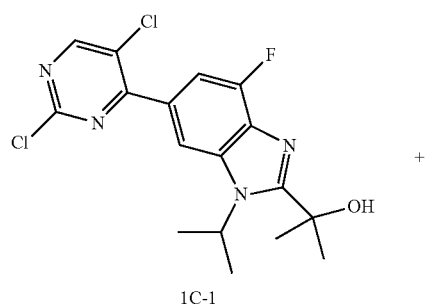

1C-1

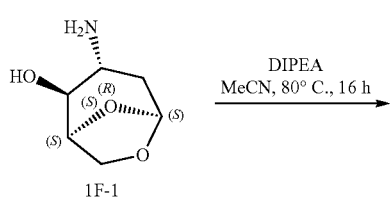

1F-1

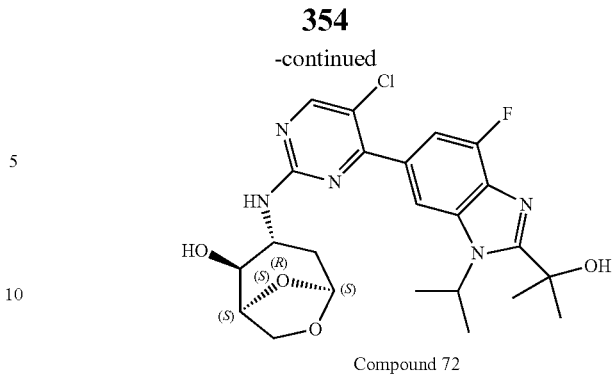

Compound 72

The mixture of 2-(6-(2,5-dichloropyrimidin-4-yl)-4-fluoro-1-isopropyl-1H-benzo[d]imidazol-2-yl) propan-2-ol (1C-1, 126.74 mg, 0.32 mmol, 1.2 eq), (1S,2S,3R,5S)-3-amino-6,8-dioxabicyclo[3.2.1]octan-2-ol (1F-1, 40.00 mg, crude, 0.26 mmol, 1 eq) and DIPEA (106.84 mg, 0.82 mmol, 0.14 mL, 3 eq) in ACN (1 mL) was stirred at 80° C. for 12 hours under nitrogen atmosphere. After the completion of the reaction, the mixture was cooled to room temperature and concentrated in vacuo. The resulting residue was purified by prep-HPLC {column: Phenomenex luna C18 150×25 mm, 10 um; mobile phase: [water (FA)-ACN]; gradient: 31%-61% B over 10 min} to give 60 mg of a white solid compound, which was further separated by SFC (column: DAICEL CHIRALPAK AD (250 mm×30 mm, 10 um); mobile phase: [CO₂-EtOH]; B %: 60%, isocratic elution mode). The desired (1S,2S,3R,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-2-ol (24.02 mg) was obtained as a white solid. LCMS: 492.2 [M+H]⁺; $^1$H NMR (400 MHZ, DMSO-d₆) δ 8.42 (d, J=3.5 Hz, 1H), 8.14-7.81 (m, 1H), 7.63-7.25 (m, 2H), 5.92-5.67 (m, 2H), 5.46 (s, 1H), 5.37-5.15 (m, 1H), 4.35 (t, J=4.5 Hz, 1H), 4.26-4.10 (m, 1H), 4.09-3.99 (m, 1H), 3.84-3.71 (m, 1H), 3.55 (t, J=6.0 Hz, 1H), 2.16-2.01 (m, 1H), 1.74-1.51 (m, 13H) ppm.

Example 10: Synthesis of (1R,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol (Compound 137)

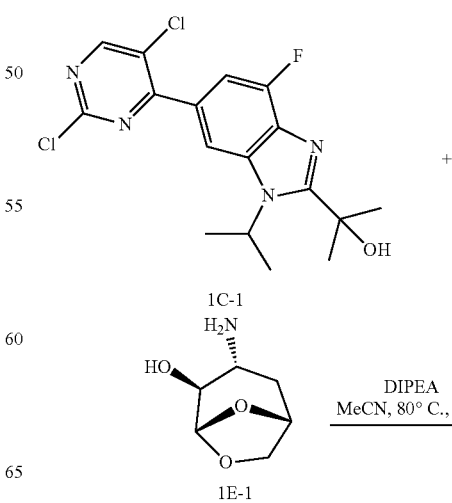

1C-1

1E-1

-continued

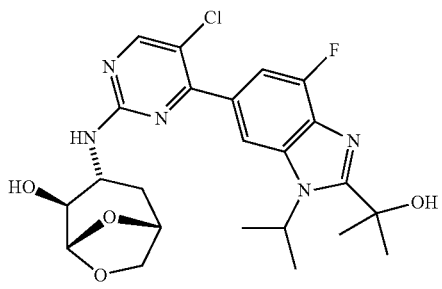

Compound 137

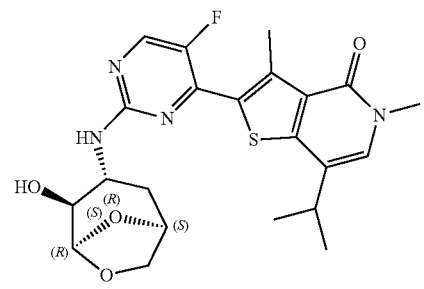

Compound 189

The mixture of (1R,3R,4S,5S)-3-amino-6,8-dioxabicyclo[3.2.1]octan-4-ol (1E-1, 65.00 mg, 0.447 mmol, 1 eq), 2-[6-(2,5-dichloropyrimidin-4-yl)-4-fluoro-1-isopropyl-benzimidazol-2-yl]propan-2-ol (IC-1, 100 mg, 0.260 mmol, 0.5 eq) and DIPEA (100 mg. 0.773 mmol, 0.134 mL, 1.73 eq) in MeCN (2 mL) was stirred for 12 hours at 85° C. under nitrogen atmosphere. After the completion of the reaction, the mixture was cooled to room temperature and concentrated under reduced pressure. The resulting residue was purified by prep-HPLC (column: Waters Xbridge C18 150× 50 mm, 10 um; mobile phase: [water (NH$_4$HCO$_3$)-ACN]; gradient: 22%-52% B over 10 min) to give (1R,3R,4S,5S)-3-((5-chloro-4-(4-fluoro-2-(2-hydroxypropan-2-yl)-1-isopropyl-1H-benzo[d]imidazol-6-yl)pyrimidin-2-yl)amino)-6,8-dioxabicyclo[3.2.1]octan-4-ol (31.36 mg, 0.062 mmol, 14.01% yield, 98.4% purity) as a white solid. LCMS: 492.3 [M+H]; $^1$H NMR (DMSO-d$_6$)δ 8.46 (s, 1H), 8.15-7.79 (m, 1H), 7.58-7.29 (m, 1H), 7.09 (br d, J=6.8 Hz, 1H), 5.97-5.67 (m, 2H), 5.36-5.17 (m, 2H), 4.62-4.49 (m, 1H), 4.00-3.92 (m, 1H), 3.82 (br s, 1H), 3.56-3.48 (m, 2H), 2.39-2.28 (m, 1H), 1.70-1.55 (m, 13H) ppm.

Example 11: Synthesis of 2-(5-fluoro-2-(((1S,3R,4S,5R)-4-hydroxy-6,8-dioxabicyclo[3.2.1]octan-3-yl)amino)pyrimidin-4-yl)-7-isopropyl-3,5-dimethylthieno[3,2-c]pyridin-4 (5H)-one (Compound 189)

To a solution of 2-(2-chloro-5-fluoropyrimidin-4-yl)-7-isopropyl-3,5-dimethylthieno[3,2-c]pyridin-4 (5H)-one (1C-8, 50 mg, 0.15 mmol, 1 eq) and (1S,3R,4S,5R)-3-amino-6,8-dioxabicyclo[3.2.1]octan-4-ol (1D-1, 30.94 mg, 0.22 mmol, 1.5 eq) in DMSO (1 mL) was added DIPEA (36.7 mg, 0.29 mmol, 2 eq), and the mixture was stirred at 90° C. for 12 hours under nitrogen atmosphere. After the completion of the reaction, the mixture was cooled to room temperature and concentrated in vacuo. The resulting residue was purified by prep-HPLC (column: Welch Xtimate C18, 150×25 mm, 5 um; mobile phase: [water (FA)-ACN]; gradient: 34%-64% B over 10 min) to afford 2-(5-fluoro-2-(((1S,3R,4S,5R)-4-hydroxy-6,8-dioxabicyclo[3.2.1]octan-3-yl)amino) pyrimidin-4-yl)-7-isopropyl-3,5-dimethylthieno[3,2-c]pyridin-4 (5H)-one (13.71 mg, 20.9% yield) as a yellow solid. LCMS: 461.1 [M+H]$^+$; $^1$H NMR (400 MHz, DMSO-d$_6$) δ 8.46 (d, J=2.8 Hz, 1H), 7.51 (s, 1H), 7.34 (d, J=8.4 Hz, 1H), 5.21 (s, 1H), 5.01 (d, J=6.0 Hz, 1H), 4.56 (s, 1H), 4.18-3.96 (m, 1H), 3.77 (d, J=6.8 Hz, 1H), 3.65 (t, J=6.0 Hz, 1H), 3.52-3.43 (m, 4H), 2.96-2.81 (m, 1H), 2.79-2.59 (m, 3H), 2.06-1.93 (m, 1H), 1.73-1.54 (m, 1H), 1.30 (d, J=6.8 Hz, 6H) ppm.

Example 12: Synthesis of 2-(((3S,5S)-3,5-dimethylmorpholino)methyl)-7-(5-fluoro-2-(((1S,3R,4S,5R)-4-hydroxy-6,8-dioxabicyclo[3.2.1]octan-3-yl)amino) pyrimidin-4-yl)-1-isopropyl-3-methylquinolin-4 (1H)-one (Compound 199)

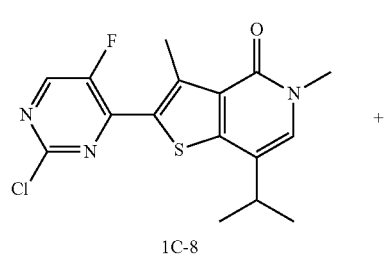

1C-8

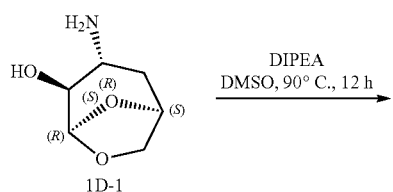

1D-1

DIPEA
DMSO, 90° C., 12 h
→

+

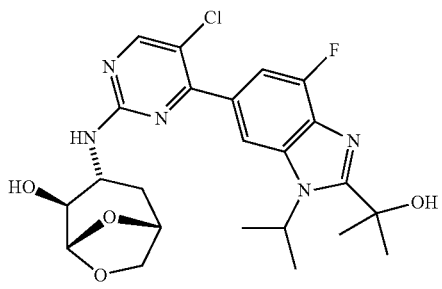

1C-9

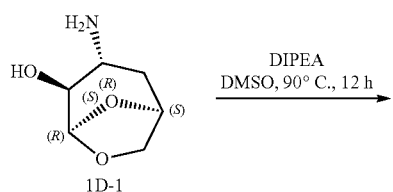

1D-1

DIPEA
DMSO, 100° C., 2 h
→

-continued

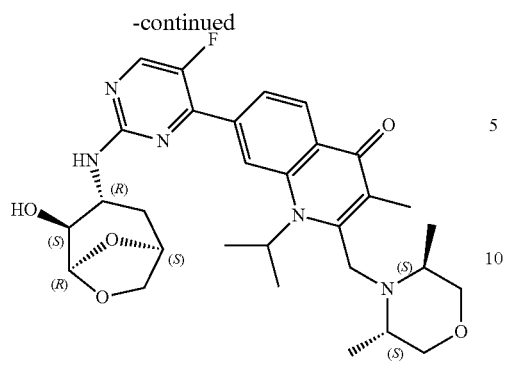

Compound 199

-continued

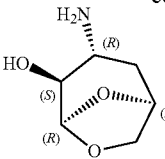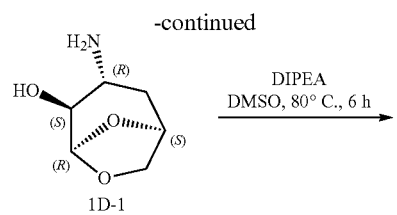

1D-1

To a solution of 7-(2-chloro-5-fluoropyrimidin-4-yl)-2-(((3S,5S)-3,5-dimethylmorpholino)methyl)-1-isopropyl-3-methylquinolin-4 (1H)-one ((1C-9, 0.08 g, 0.174 mmol, 1 eq) and (1S,3R,4S,5R)-3-amino-6,8-dioxabicyclo[3.2.1]octan-4-ol ((1D-1, 88.56 mg, 0.610 mmol, 3.5 eq) in DMSO (1.5 mL) was added DIPEA (22.53 mg, 0.174 mmol, 1 eq), and the mixture was stirred at 100° C. for 2 hours under nitrogen atmosphere. After the completion of the reaction, the mixture was cooled to room temperature, poured into $H_2O$ (10 mL) and extracted with DCM (10 mL×3). The combined organic phase was washed with brine (20 mL), dried over $Na_2SO_4$, filtered and the filtrate was concentrated in vacuo. The resulting residue was purified by prep-HPLC (FA condition; column: Phenomenex luna C18, 150×25 mm, 10 um; mobile phase: [water (FA)-ACN]; gradient: 38%-68% B over 10 min) to afford 2-(((3S,5S)-3,5-dimethylmorpholino)methyl)-7-(5-fluoro-2-(((1S,3R,4S,5R)-4-hydroxy-6,8-dioxabicyclo[3.2.1]octan-3-yl)amino) pyrimidin-4-yl)-1-isopropyl-3-methylquinolin-4 (1H)-one (41.6 mg, 41.8% yield) as a yellow solid. LCMS: 568.3 [M+H]$^+$; $^1$H NMR (400 MHZ, DMSO-$d_6$) § 8.62 (s, 1H), 8.50 (d, J=3.6 Hz, 1H), 8.32 (d, J=8.4 Hz, 1H), 7.88 (d, J=8.4 Hz, 1H), 7.34 (d, J=8.4 Hz, 1H), 5.57 (td, J=7.2, 14.0 Hz, 1H), 5.22 (d, J=1.2 Hz, 1H), 5.04 (d, J=5.6 Hz, 1H), 4.57 (s, 1H), 4.18 (d, J=15.2 Hz, 2H), 3.93-3.75 (m, 2H), 3.71-3.56 (m, 3H), 3.51 (dd, J=4.4, 8.7 Hz, 1H), 3.30-3.25 (m, 2H), 2.80 (d, J=2.4 Hz, 2H), 2.23 (s, 3H), 2.10-1.97 (m. 1H), 1.79 (d, J=6.8 Hz, 3H), 1.70 (d, J=7.2 Hz, 4H), 1.01 (d, J=6.4 Hz, 6H) ppm.

Example 13: Synthesis of 7-(5-chloro-2-(((1S,3R,4S,5R)-4-hydroxy-6,8-dioxabicyclo[3.2.1]octan-3-yl)amino) pyrimidin-4-yl)-2-(((3S,5S)-3,5-dimethylmorpholino) methyl)-1-isopropyl-3-methylquinolin-4 (1H)-one (Compound 206)

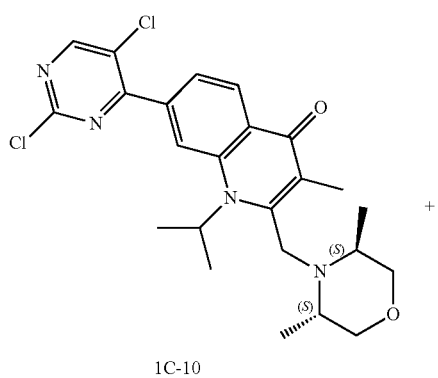

1C-10

+

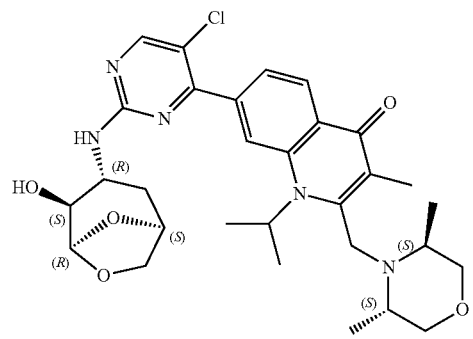

Compound 206

To a solution of 7-(2,5-dichloropyrimidin-4-yl)-2-(((3S,5S)-3,5-dimethylmorpholino)methyl)-1-isopropyl-3-methylquinolin-4 (1H)-one ((1C-10, 0.08 g, 0.168 mmol, 1 eq) and (1S,3R,4S,5R)-3-amino-6,8-dioxabicyclo[3.2.1]octan-4-ol ((1D-1, 85.49 mg, 0.588 mmol, 3.5 eq) in DMSO (1.5 mL) was added DIPEA (21.75 mg, 0.168 mmol, 0.029 mL, 1 eq), and the mixture was stirred at 80° C. for 6 hours under nitrogen atmosphere. After the completion of the reaction, the mixture was cooled to room temperature, diluted with $H_2O$ (10 mL) and extracted with DCM (20 mL×3). The combined organic layers were washed with brine (20 mL), dried over $Na_2SO_4$, filtered and the filtrate was concentrated in vacuo. The resulting residue was purified by prep-HPLC (FA condition; column: Phenomenex luna C18, 150×25 mm, 10 um; mobile phase: [water (FA)-ACN]; gradient: 40%-70% B over 10 min) to afford 7-(5-chloro-2-(((1S,3R,4S,5R)-4-hydroxy-6,8-dioxabicyclo[3.2.1]octan-3-yl)amino) pyrimidin-4-yl)-2-(((3S,5S)-3,5-dimethylmorpholino) methyl)-1-isopropyl-3-methylquinolin-4 (1H)-one (38.88 mg, 38.8% yield) as an off-white solid. LCMS: 584.3 [M+H]'; $^1$H NMR (400 MHZ, DMSO-$d_6$) δ 8.57-8.40 (m, 1H), 8.37-8.20 (m, 2H), 7.86-7.48 (m, 2H), 5.62-5.50 (m, 1H), 5.21 (s, 1H), 5.05 (d. J=4.4 Hz, 1H), 4.56 (s, 1H), 4.26-4.11 (m, 2H), 3.85 (d, J=15.2 Hz, 1H), 3.69 (s, 1H), 3.60 (dd, J=2.4, 10.6 Hz, 3H), 3.54-3.44 (m, 1H), 3.27 (dd, J=5.6, 10.8 Hz, 2H), 2.79 (s, 2H), 2.23 (s, 3H), 2.08-1.94 (m, 1H), 1.81-1.72 (m, 3H), 1.71-1.61 (m, 4H), 1.00 (d, J=6.4 Hz, 6H) ppm.

Example 14: Synthesis of (1S,3R,4S,5R)-3-((5-chloro-4-(2-((S)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (Compound 216) and (1S,3R,4S,5R)-3-((5-chloro-4-(2-((R)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (Compound 217)

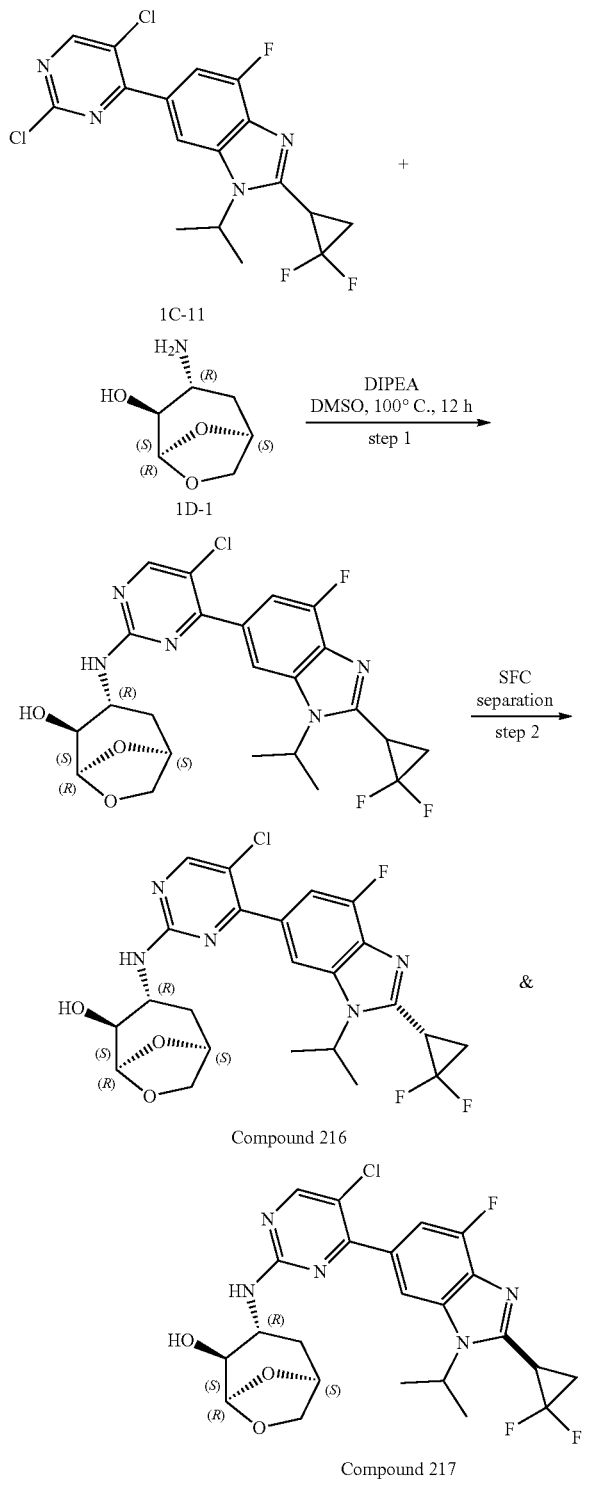

Step 1: Preparation of (1S,3R,4S,5R)-3-((5-chloro-4-(2-(2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol To a solution of 6-(2,5-dichloropyrimidin-4-yl)-2-(2,2-difluorocyclopropyl)-4-fluoro-1-isopropyl-1H-benzo[d]imidazole (1C-11, 90.00 mg, 0.23 mmol, 1 eq) and (1S,3R,4S,5R)-3-amino-6,8-dioxabicyclo[3.2.1]octan-4-ol (1D-1, 65.12 mg, 0.45 mmol, 2 eq) in DMSO (1.5 mL) was added DIPEA (57.98 mg, 0.45 mmol, 0.08 mL, 2 eq), and the mixture was stirred at 100° C. for 12 hours under nitrogen atmosphere. After the completion of the reaction, the mixture was cooled to room temperature and concentrated in vacuo. The resulting residue was purified by prep-HPLC (column: Phenomenex luna C18 150*25 mm*10 um; mobile phase: [water (FA)-ACN]; gradient: 36%-66% B over 10 min) to afford (1S,3R,4S,5R)-3-((5-chloro-4-(2-(2,2-difluorocyclopropyl)-4-fluoro-1-isopropyl-1 H-benzo[d]imidazol-6-yl)pyrimidin-2-yl)amino)-6,8-dioxabicyclo[3.2.1]octan-4-ol (45 mg, 0.088 mmol, 39.3% yield) as a white solid. LCMS: $10.3 [M+H]^+$.

Step 2: (1S,3R,4S,5R)-3-((5-chloro-4-(2-((S)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol and (1S,3R,4S,5R)-3-((S-chloro-4-(2-((R)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol The racemic (1S,3R,4S,4R)-3-((S-chloro-4-(2-(2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol was further separated by SFC (column: DAICEL CHIRALPAK AD (250 mm×30 mm, 10 um); mobile phase: [$CO_2$-ACN/EtOH (0.1% $NH_3 \cdot H_2O$)]; B %: 65%, isocratic elution mode) to afford (1S,3R,4S,5R)-3-((5-chloro-4-(2-((S)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (20.14 mg, 43.70% yield) (Compound 216, configuration randomly assigned) as a white solid and (1S,3R,4S,5R)-3-((5-chloro-4-(2-((R)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (19.89 mg, 43.15% yield) (Compound 217, configuration randomly assigned) as an off-white solid.

(1S,3R,4S,5R)-3-((5-chloro-4-(2-((S)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (Compound 216, configuration randomly assigned) LCMS: 510.2 $[M+H]^+$; $^1$H NMR (400 MHZ, DMSO-$d_6$) δ 8.42 (s, 1H), 8.13-7.83 (m, 1H), 7.62-7.27 (m, 2H), 5.21 (s, 1H), 5.15-5.02 (m, 1H), 4.97 (td, J=6.8, 13.6 Hz, 1H), 4.55 (s, 1H), 4.22-4.07 (m, 1H), 3.86-3.68 (m, 1H), 3.67-3.56 (m, 2H), 3.54-3.43 (m, 1H), 2.45-2.39 (m, 1H), 2.32-2.21 (m, 1H), 2.08-1.96 (m, 1H), 1.67-1.51 (m, 7H) ppm.

(1S,3R,4S,5R)-3-((5-chloro-4-(2-((R)-2,2-difluorocyclopropyl)-4-fluoro-1-isopropyl-1H-benzo[d]imidazol-6-yl)pyrimidin-2-yl)amino)-6,8-dioxabicyclo[3.2.1]octan-4-ol (Compound 217, configuration randomly assigned) LCMS: 510.2 $[M+H]^+$; $^1$H NMR (400 MHZ, DMSO-$d_6$) δ 8.42 (s, 1H), 8.17-7.78 (m, 1H), 7.65-7.19 (m, 2H), 5.21 (s, 1H), 5.14-5.02 (m, 1H), 4.98 (td, J=7.2, 13.8 Hz, 1H), 4.56 (s, 1H), 4.21-4.06 (m, 1H), 3.84-3.70 (m, 1H), 3.68-3.57 (m, 2H), 3.49 (d, J=1.6 Hz, 1H), 2.48-2.39 (m, 1H), 2.36-2.22 (m, 1H), 2.12-1.91 (m, 1H), 1.66-1.58 (m, 7H) ppm.

Example 15: Synthesis of 2-(5-chloro-2-(((1S,3R,4S,5R)-4-hydroxy-6,8-dioxabicyclo[3.2.1]octan-3-yl)amino)pyrimidin-4-yl)-7-isopropyl-3,5-dimethylthieno[3,2-c]pyridin-4 (5H)-one (Compound 223)

Example 16: Synthesis of (1S,3R,4S,5R)-3-((5-chloro-4-(4-fluoro-2-((1r,3R)-3-fluorocyclobutyl)-1-isopropyl-1H-benzo[d]imidazol-6-yl)pyrimidin-2-yl)amino)-6,8-dioxabicyclo[3.2.1]octan-4-ol (Compound 243)

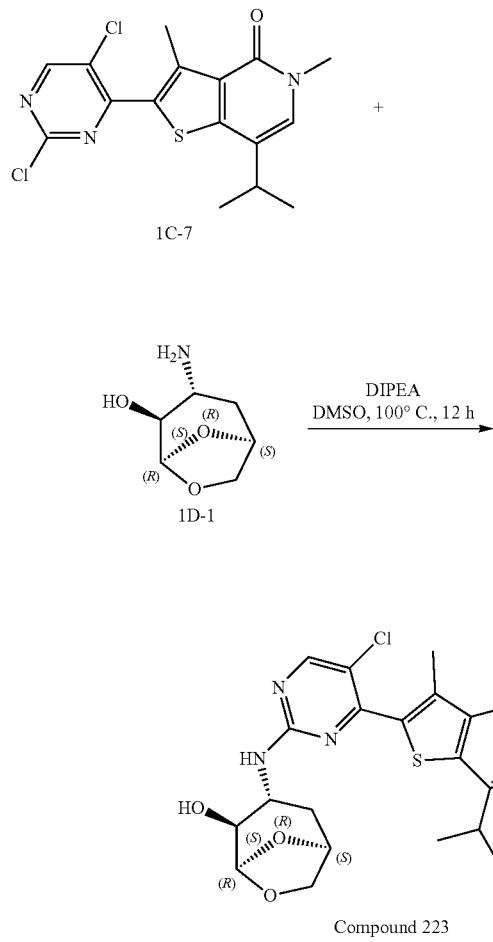

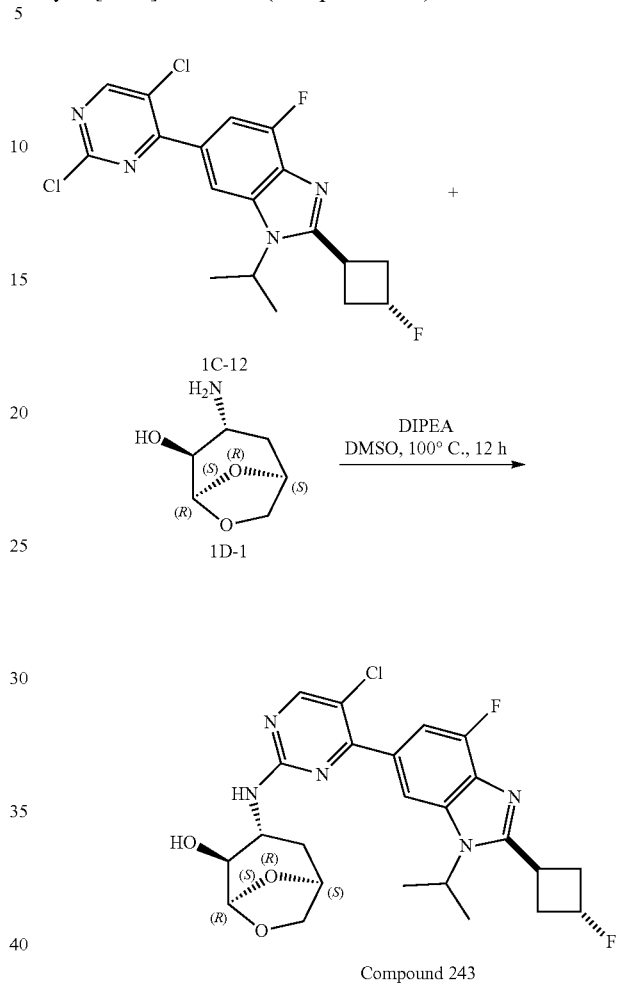

To a solution of 2-(2,5-dichloropyrimidin-4-yl)-7-isopropyl-3,5-dimethylthieno[3,2-c]pyridin-4 (5H)-one (IC-7, 60 mg, 0.17 mmol, 1 eq) and (1S,3R,4S,5R)-3-amino-6,8-dioxabicyclo[3.2.1]octan-4-ol (1D-1, 47.30 mg, 0.33 mmol, 2 eq) in DMSO (1 mL) was added DIPEA (63.17 mg, 0.49 mmol, 0.09 mL, 3 eq), and the mixture was stirred at 100° C. for 12 hours under nitrogen atmosphere. After the completion of the reaction, the mixture was cooled to room temperature and concentrated in vacuo. The resulting residue was purified by prep-HPLC (column: Phenomenex $C_{18}$, 150 mm×30 mm, 5 um; mobile phase: [water (FA)-ACN]; gradient: 40%-60% B over 10 min) to afford 2-(5-chloro-2-(((1S,3R,4S,5R)-4-hydroxy-6,8-dioxabicyclo[3.2.1]octan-3-yl)amino) pyrimidin-4-yl)-7-isopropyl-3,5-dimethylthieno[3,2-c]pyridin-4 (5H)-one (30.96 mg, 39.3% yield) as a white solid. LCMS: 477.1 [M+H]$^+$; $^1$H NMR (400 MHz, DMSO-$d_6$) δ 8.45 (s, 1H), 7.61 (d, J=8.8 Hz, 1H), 7.49 (s, 1H), 5.20 (s, 1H), 5.04 (d, J=6.0 Hz, 1H), 4.55 (s, 1H), 4.20-3.98 (m, 1H), 3.86-3.67 (m, 1H), 3.63 (t, J=5.2 Hz, 1H), 3.52-3.42 (m, 4H), 2.93-2.76 (m, 1H), 2.59-2.50 (m, 3H), 2.02-1.91 (m, 1H), 1.71-1.55 (m, 1H), 1.29 (d, J=6.8 Hz, 6H) ppm.

A mixture of 6-(2,5-dichloropyrimidin-4-yl)-4-fluoro-2-((1r,3r)-3-fluorocyclobutyl)-1-isopropyl-1H-benzo[d]imidazole (1C-12, 40 mg, 0.1 mmol, 1 eq), (1S,3R,4S,5R)-3-amino-6,8-dioxabicyclo[3.2.1]octan-4-ol (1D-1, 21.92 mg, 0.15 mmol, 1.5 eq) and DIPEA (39.03 mg, 0.3 mmol, 3 eq) in DMSO (1 mL) was stirred at 100° C. for 12 hours under nitrogen atmosphere. After the completion of the reaction, the mixture was cooled to room temperature and the volatiles were evaporated under reduced pressure. The resulting residue was purified by prep-HPLC {column: Welch Xtimate C18 150×25 mm, 5 um; mobile phase: [water (FA)-ACN]; gradient: 32%-62% B over 10 min} to afford (1S,3R,4S,5R)-3-((5-chloro-4-(4-fluoro-2-((1r,3R)-3-fluorocyclobutyl)-1-isopropyl-1H-benzo[d]imidazol-6-yl)pyrimidin-2-yl)amino)-6,8-dioxabicyclo[3.2.1]octan-4-ol (32.95 mg, 64.3% yield) as an off-white solid. LCMS: 506.1 [M+H]; $^1$H NMR (400 MHZ, DMSO-$d_6$) δ 8.47-8.36 (m, 1H), 8.03-7.84 (m, 1H), 7.61-7.28 (m, 2H), 5.42-5.19 (m, 2H), 5.08-5.01 (m, 1H), 4.73-4.63 (m, 1H), 4.59-4.53 (m, 1H), 4.20-4.08 (m, 1H), 4.05-3.96 (m, 1H), 3.85-3.68 (m, 1H), 3.67-3.61 (m, 1H), 3.54-3.44 (m, 1H), 2.92-2.80 (m, 1H), 2.80-2.64 (m, 2H), 2.10-1.94 (m, 1H), 1.67 (br t, J=11.9 Hz, 1H), 1.57 (br d, J=6.6 Hz, 6H) ppm.

Example 17: Synthesis of (1S,3R,4S,5R)-3-((5-chloro-4-(4-chloro-8-fluoro-3-(2-hydroxypropan-2-yl) quinolin-6-yl)pyrimidin-2-yl)amino)-6,8-dioxabicyclo[3.2.1]octan-4-ol (Compound 252)

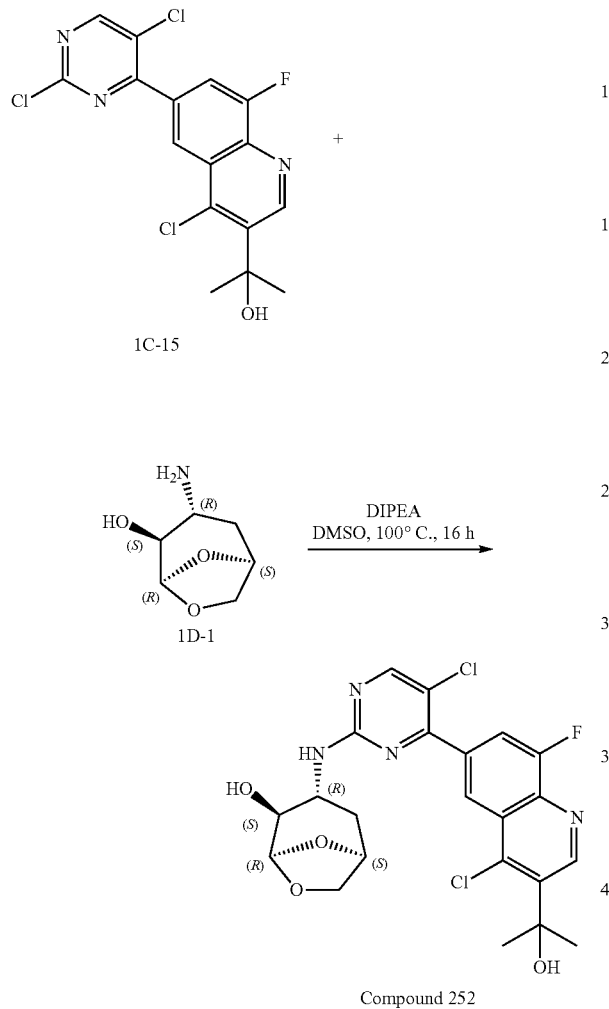

Compound 252

A mixture of 2-(4-chloro-6-(2,5-dichloropyrimidin-4-yl)-8-fluoroquinolin-3-yl) propan-2-ol (1C-15, 230 mg, 0.59 mmol, 1 eq), (1S,3R,4S,5R)-3-amino-6,8-dioxabicyclo[3.2.1]octan-4-ol (1D-1, 172.70 mg, 1.19 mmol, 2 eq) and DIPEA (230.65 mg, 1.78 mmol, 3 eq) in DMSO (5 mL) was stirred at 100° C. for 16 hours under nitrogen atmosphere. After the completion of the reaction, the mixture was cooled to room temperature and concentrated in vacuo. The resulting residue was purified by prep-HPLC {column: Phenomenex luna C18, 150×25 mm, 10 um; mobile phase: [water (FA)-ACN]; gradient: 31%-61% B over 10 min} to give (1S,3R,4S,5R)-3-((5-chloro-4-(4-chloro-8-fluoro-3-(2-hydroxypropan-2-yl) quinolin-6-yl)pyrimidin-2-yl)amino)-6,8-dioxabicyclo[3.2.1]octan-4-ol (76.74 mg, 25.7% yield) as a light yellow solid. LCMS: 495.1 [M+H]; $^1$H NMR (400 MHZ, DMSO-d$_6$) δ 9.42 (s, 1H), 8.76-8.45 (m, 2H), 7.94 (s, 1H), 7.59 (s, 1H), 5.88-5.79 (m, 1H), 5.29-5.18 (m, 1H), 5.12-5.00 (m, 1H), 4.66-4.51 (m, 1H), 4.25-4.08 (m, 1H), 3.88-3.72 (m, 1H), 3.70-3.60 (m, 1H), 3.55-3.44 (m, 1H), 2.13-1.92 (m, 1H), 1.74 (s, 6H), 1.71-1.61 (m, 1H) ppm.

Example 18: Synthesis of (1S,3R,4S,5R)-3-((4-(4-chloro-8-fluoro-3-(2-hydroxypropan-2-yl) quinolin-6-yl)-5-fluoropyrimidin-2-yl)amino)-6,8-dioxabicyclo[3.2.1]octan-4-ol (Compound 255)

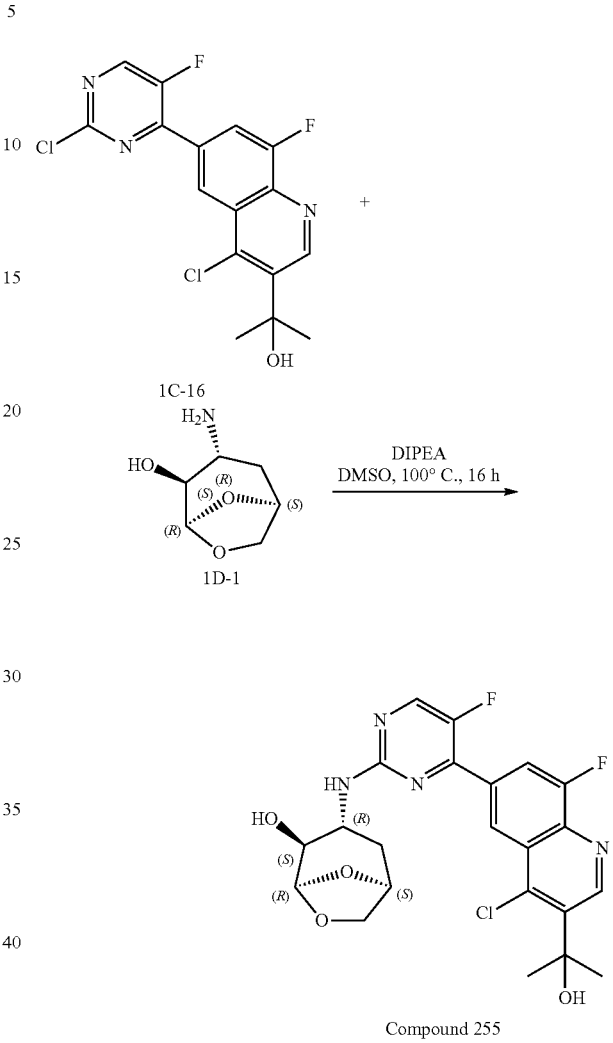

Compound 255

A mixture of 2-(4-chloro-6-(2-chloro-5-fluoropyrimidin-4-yl)-8-fluoroquinolin-3-yl) propan-2-ol (1C-16, 230 mg, 0.62 mmol, 1 eq), (1S,3R,4S,5R)-3-amino-6,8-dioxabicyclo[3.2.1]octan-4-ol (1D-1, 180.38 mg, 1.24 mmol, 2 eq) and DIPEA (240.90 mg, 1.86 mmol, 3 eq) in DMSO (5 mL) was stirred at 100° C. for 16 hours under nitrogen atmosphere. After the completion of the reaction, the mixture was cooled to room temperature and concentrated in vacuo. The resulting residue was purified by prep-HPLC {column: Phenomenex Luna C18, 150×25 mm, 10 um; mobile phase: [water (FA)-ACN]; gradient: 29%-59% B over 10 min} to give (1S,3R,4S,5R)-3-((4-(4-chloro-8-fluoro-3-(2-hydroxypropan-2-yl) quinolin-6-yl)-5-fluoropyrimidin-2-yl)amino)-6,8-dioxabicyclo[3.2.1]octan-4-ol (100.05 mg, 32.9% yield) as a yellow solid. LCMS: 479.1 [M+H], $^1$H NMR (400 MHz, DMSO-d$_6$) δ 9.49-9.40 (m, 1H), 9.00-8.74 (m, 1H), 8.52 (d, J=6.8 Hz, 1H), 8.31-8.10 (m, 1H), 7.50-7.38 (m, 1H), 5.83 (s, 1H), 5.24 (s, 1H), 5.06 (d, J=6.0 Hz, 1H), 4.66-4.53 (m, 1H), 4.26-4.09 (m, 1H), 3.89-3.80 (m, 1H), 3.75-3.65 (m, 1H), 3.56-3.49 (m, 1H), 2.14-1.99 (m, 1H), 1.75 (s, 6H), 1.71-1.63 (m, 1H) ppm.

Example 19: Synthesis of (1S,3R,4S,5R)-3-((5-fluoro-4-(8-fluoro-3-(2-hydroxypropan-2-yl)-4-methylquinolin-6-yl)pyrimidin-2-yl)amino)-6,8-dioxabicyclo[3.2.1]octan-4-ol (Compound 256)

Example 20: Synthesis of (1S,3R,4S,5R)-3-((5-chloro-4-(8-fluoro-3-(2-hydroxypropan-2-yl)-4-methylquinolin-6-yl)pyrimidin-2-yl)amino)-6,8-dioxabicyclo[3.2.1]octan-4-ol (Compound 257)

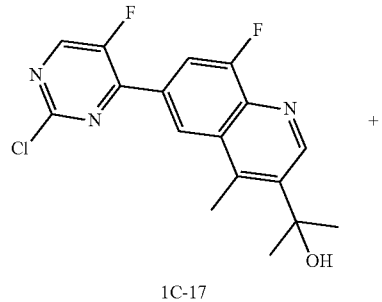

1C-17

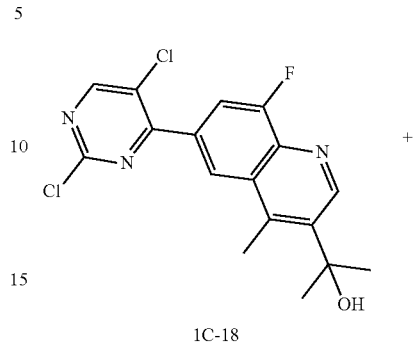

1C-18

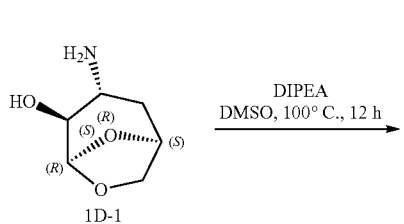

1D-1

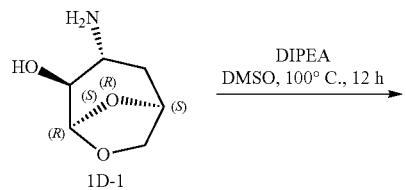

1D-1

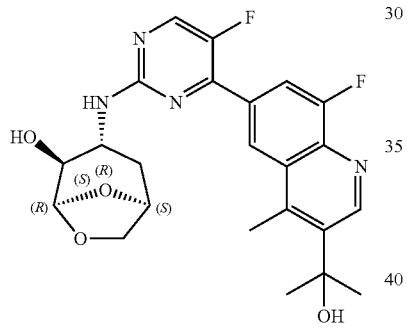

Compound 256

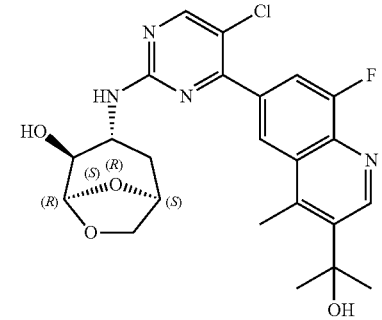

Compound 257

The solution of 2-(6-(2-chloro-5-fluoropyrimidin-4-yl)-8-fluoro-4-methylquinolin-3-yl) propan-2-ol (1C-17, 50 mg, 0.15 mmol, 1 eq), (1S,3R,4S,5R)-3-amino-6,8-dioxabicyclo[3.2.1]octan-4-ol (1D-1, 41.50 mg, 0.29 mmol, 2 eq) and DIPEA (36.95 mg, 0.29 mmol, 0.05 mL, 2 eq) in DMSO (1 mL) was stirred at 100° C. for 12 hours under nitrogen atmosphere. After the completion of the reaction, the mixture was cooled to room temperature and concentrated in vacuo. The resulting residue was purified by prep-HPLC (column: Welch Xtimate C18, 150×25 mm, 5 um; mobile phase: [water (FA)-ACN]; gradient: 22%-52% B over 10 min) to afford (1S,3R,4S,5R)-3-((5-fluoro-4-(8-fluoro-3-(2-hydroxypropan-2-yl)-4-methylquinolin-6-yl)pyrimidin-2-yl)amino)-6,8-dioxabicyclo[3.2.1]octan-4-ol (27.22 mg, 41.2% yield) as a light yellow solid. LCMS: 459.2 [M+H]$^+$; $^1$H NMR (400 MHZ, DMSO-d$_6$) δ 9.12 (s, (H), 8.75-8.62 (m, 1H), 8.51 (d, J=4.0 Hz, 1H), 8.07 (d, J=10.0 Hz, 1H), 7.38 (d, J=8.4 Hz, 1H), 5.43 (s, 1H), 5.24 (s, 1H), 5.05 (d, J=6.0 Hz, 1H), 4.59 (s, 1H), 4.23-4.06 (m, 1H), 3.84 (d, J=7.2 Hz, 1H), 3.74-3.63 (m, 1H), 3.53 (d. J=1.6 Hz, 1H), 2.99 (s, 3H), 2.23-1.91 (m, 1H), 1.68 (s, 6H), 1.67-1.60 (m, 1H) ppm.

To a solution of 2-(6-(2,5-dichloropyrimidin-4-yl)-8-fluoro-4-methylquinolin-3-yl) propan-2-ol (1C-18, 50 mg, 0.14 mmol, 1 eq) and (1S,3R,4S,5R)-3-amino-6,8-dioxabicyclo[3.2.1]octan-4-ol (1D-1, 39.64 mg, 0.28 mmol, 2 eq) in DMSO (1 mL) was added DIPEA (35.29 mg, 0.28 mmol, 0.05 mL, 2 eq), and the mixture was stirred at 100° C. for 12 hours under nitrogen atmosphere. After the completion of the reaction, the mixture was cooled to room temperature and concentrated in vacuo. The resulting residue was purified by prep-HPLC (column: Welch Xtimate C18, 150×25 mm, 5 um; mobile phase: [water (FA)-ACN]; gradient: 22%-52% B over 10 min) to afford (1S,3R,4S,5R)-3-((5-chloro-4-(8-fluoro-3-(2-hydroxypropan-2-yl)-4-methylquinolin-6-yl)pyrimidin-2-yl)amino)-6,8-dioxabicyclo[3.2.1]octan-4-ol (24.45 mg, 36.8% yield) as an off-white solid. LCMS: 475.2 [M+H]; $^1$H NMR (400 MHZ, DMSO-d$_6$) δ 9.12 (s, 1H), 8.59-8.33 (m, 2H), 8.02-7.77 (m, 1H), 7.72-7.53 (m, 1H), 5.42 (s, 1H), 5.22 (s, 1H), 5.06 (d, J=6.0 Hz, 1H), 4.57 (s, 1H), 4.23-4.09 (m, 1H), 3.86-3.72 (m, 1H), 3.65 (t, J=6.0 Hz, 1H), 3.50 (d, J=1.2 Hz, 1H), 2.96 (s, 3H), 2.12-1.93 (m, 1H), 1.68 (s, 6H), 1.67-1.60 (m, 1H) ppm.

Example 21: Synthesis of (1S,3R,4S,5R)-3-((5-chloro-4-(4-isopropyl-7-methylthieno[3,2-c]pyridazine-6-yl)pyrimidin-2-yl)amino)-6,8-dioxabicyclo[3.2.1]octan-4-ol (Compound 259)

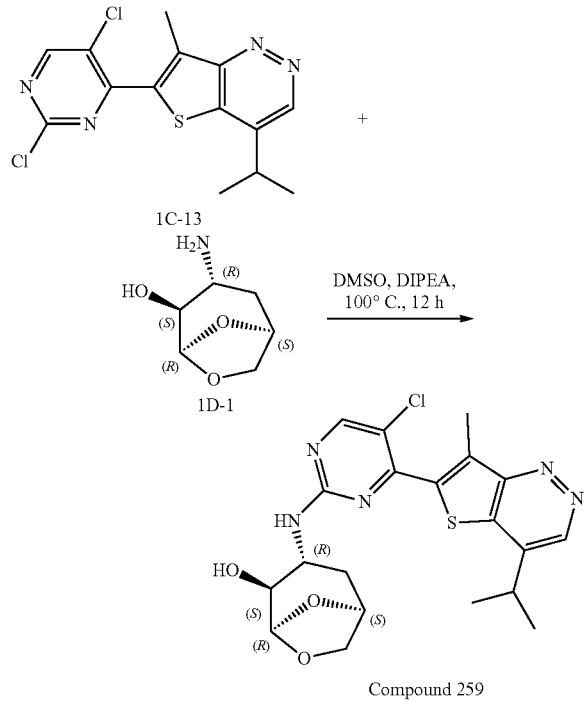

A mixture of 6-(2,5-dichloropyrimidin-4-yl)-4-isopropyl-7-methylthieno[3,2-c]pyridazine (1C-13, 8 mg, 0.023 mmol, 1 eq), (1S,3R,4S,5R)-3-amino-6,8-dioxabicyclo[3.2.1]octan-4-ol (1D-1, 8.00 mg, 0.055 mmol, 2.34 eq) and DIPEA (18.29 mg, 0.141 mmol, 6 eq) in DMSO (1 mL) was stirred at 100° C. for 12 hours under nitrogen atmosphere. After the completion of the reaction, the mixture was cooled to room temperature and the volatiles were evaporated under reduced pressure. The resulting residue was purified by prep-HPLC {column: Welch Xtimate C18, 150×25 mm, 5 um; mobile phase: [water (FA)-ACN]; gradient: 24%-54% B over 10 min} to afford (1S,3R,4S,5R)-3-((5-chloro-4-(4-isopropyl-7-methylthieno[3,2-c]pyridazin-6-yl)pyrimidin-2-yl)amino)-6,8-dioxabicyclo[3.2.1]octan-4-ol (3.85 mg, 20.5% yield) as a white solid. LCMS: 448.1 [M+H]; $^1$H NMR (400 MHZ, DMSO-$d_6$) δ 9.23 (s, 1H), 8.56 (s, 1H), 7.76 (d, J=8.8 Hz, 1H), 5.21 (s, 1H), 5.07 (d, J=6.0 Hz, 1H), 4.56 (br s, 1H), 4.17-4.08 (m, 1H), 3.84-3.78 (m, 1H), 3.66-3.58 (m, 1H), 3.49-3.46 (m, 1H), 3.28-3.22 (m, 1H), 2.56 (s, 3H), 2.02-1.97 (m, 1H), 1.67-1.62 (m, 1H), 1.42 (d, J=7.2 Hz, 6H) ppm.

Example 22: Synthesis of (1S,3R,4S,5R)-3-((5-chloro-4-(6-(2-hydroxypropan-2-yl)-3-methylthieno[3,2-b]pyridin-2-yl)pyrimidin-2-yl)amino)-6, 8-dioxabicyclo[3.2.1]octan-4-ol (Compound 260)

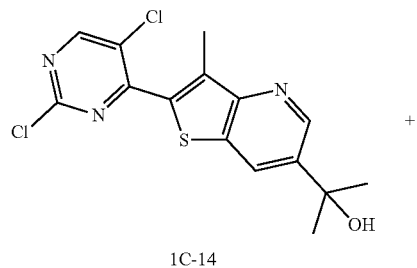

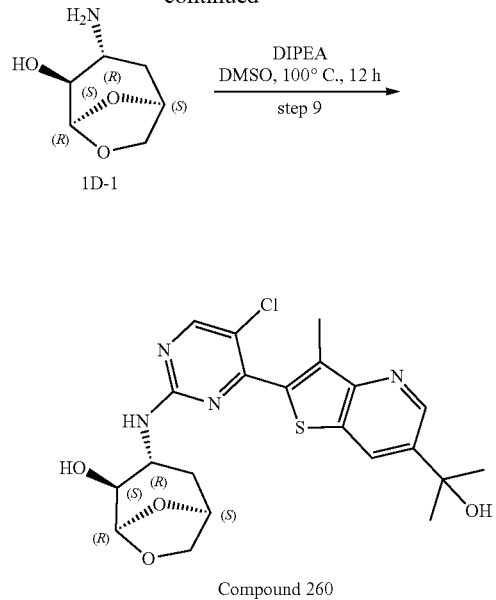

To a solution of 2-(2-(2,5-dichloropyrimidin-4-yl)-3-methylthieno[3,2-b]pyridin-6-yl) propan-2-ol (1C-14, 80 mg, 0.23 mmol, 1 eq) and (1S,3R,4S,5R)-3-amino-6,8-dioxabicyclo[3.2.1]octan-4-ol (1D-1, 65.56 mg, 0.45 mmol, 2 eq) in DMSO (1 mL) was added DIPEA (87.56 mg, 0.68 mmol, 0.12 mL, 3 eq), and the mixture was stirred at 100° C. for 12 hours under nitrogen atmosphere. After the completion of the reaction, the mixture was cooled to room temperature and the volatiles were evaporated under reduced pressure. The resulting residue was purified by prep-HPLC (FA condition: column: Welch Xtimate C18, 150×25 mm, 5 um, mobile phase: [water (FA)-ACN]; gradient: 22%-52% B over 10 min) to afford (1S,3R,4S,5R)-3-((5-chloro-4-(6-(2-hydroxypropan-2-yl)-3-methylthieno[3,2-b]pyridin-2-yl) pyrimidin-2-yl)amino)-6,8-dioxabicyclo[3.2.1]octan-4-ol (50 mg, 47.6% yield) as a white solid. LCMS: 463.1 [M+H]$^+$; $^1$H NMR (400 MHZ, DMSO-$d_6$) δ 8.89 (s, 1H), 8.52 (br d, J=1.7 Hz, 2H), 7.77-7.62 (m, 1H), 5.39 (br s, 1H), 5.21 (s, 1H), 5.08 (br d, J=5.0 Hz, 1H), 4.56 (br s, 1H), 4.24-4.00 (m, 1H), 3.86-3.68 (m, 1H), 3.63 (br d, J=0.9 Hz, 1H), 3.49 (br d, J=1.7 Hz, 1H), 2.41 (br s, 3H), 2.09-1.93 (m, 1H), 1.71-1.61 (m, 1H), 1.55 (s, 6H) ppm.

Example 23: Synthesis of (1S,3R,4S,5R)-3-((5-chloro-4-(7-chloro-6-(2-hydroxypropan-2-yl)-3-methylthieno[3,2-b]pyridin-2-yl)pyrimidin-2-yl)amino)-6,8-dioxabicyclo[3.2.1]octan-4-ol (Compound 275)

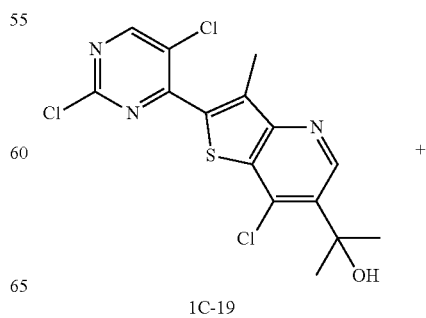

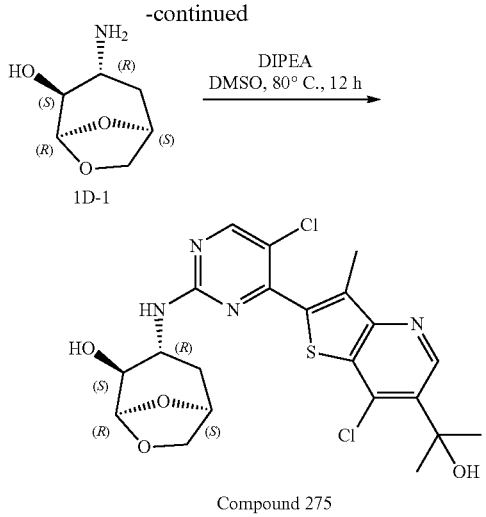

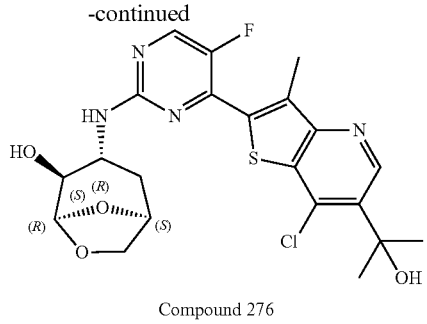

Compound 276

A mixture of 2-(7-chloro-2-(2-chloro-5-fluoropyrimidin-4-yl)-3-methylthieno[3,2-b]pyridin-6-yl) propan-2-ol (1C-20, 50 mg, 0.13 mmol, 1.0 eq), (1S,3R,4S,5R)-3-amino-6,8-dioxabicyclo[3.2.1]octan-4-ol (1D-1, 39 mg, 0.26 mmol, 2.0 eq) and DIPEA (34 mg, 0.26 mmol, 2.0 eq) in DMSO (1 mL) was stirred at 80° C. for 12 hours under nitrogen atmosphere. After the completion of the reaction, the mixture was cooled to room temperature and diluted with acetonitrile (1 mL). The resulting solution was purified by prep-HPLC (column: Phenomenex luna C18, 150×25 mm, 10 um; mobile phase: [water (FA)-ACN]; gradient: 38%-48% B over 10 min) to give (1S,3R,4S,5R)-3-((4-(7-chloro-6-(2-hydroxypropan-2-yl)-3-methylthieno[3,2-b]pyridin-2-yl)-5-fluoropyrimidin-2-yl)amino)-6,8-dioxabicyclo[3.2.1] octan-4-ol (8.86 mg, 0.02 mmol, 13.7% yield, 100% purity) as a white solid. LCMS: 481.1 [M+H]; $^1$H NMR (400 MHZ, DMSO-d$_6$) δ 9.11 (s, 1H), 8.55 (d, J=2.9 Hz, 1H), 7.46 (d, J=8.4 Hz, 1H), 5.70 (s, 1H), 5.22 (s, 1H), 5.05 (d, J=5.9 Hz, 1H), 4.57 (br s, 1H), 4.17-4.03 (m, 1H), 3.80 (d, J=7.3 Hz, 1H), 3.69-3.62 (m, 1H), 3.53-3.48 (m, 1H), 2.61 (br d, J=1.4 Hz, 3H), 2.13-1.95 (m, 1H), 1.69 (s, 6H), 1.67-1.58 (m, 1H) ppm.

Compound 275

A mixture of 2-(7-chloro-2-(2,5-dichloropyrimidin-4-yl)-3-methylthieno[3,2-b]pyridin-6-yl) propan-2-ol (1C-19, 50 mg, 0.01 mmol, 1.0 eq), (1S,3R,4S,5R)-3-amino-6,8-dioxabicyclo[3.2.1]octan-4-ol (1D-1, 28 mg, 0.02 mmol, 1.5 eq) and DIPEA (33 mg, 0.25 mmol, 2.0 eq) in DMSO (1 mL) was stirred at 80° C. for 12 hours under nitrogen atmosphere. After the completion of the reaction, the mixture was cooled to room temperature and diluted with acetonitrile (1 mL). The resulting solution was purified by prep-HPLC (column: Phenomenex luna C18, 150×25 mm, 10 um; mobile phase: [water (FA)-ACN]; gradient: 32%-62% B over 10 min) to give (1S,3R,4S,5R)-3-((5-chloro-4-(7-chloro-6-(2-hydroxypropan-2-yl)-3-methylthieno[3,2-b]pyridin-2-yl)pyrimidin-2-yl)amino)-6,8-dioxabicyclo[3.2.1]octan-4-ol (22.95 mg, 35.8% yield) as a white solid. LCMS: 497.0 [M+H]$^+$; $^1$H NMR (400 MHZ, DMSO-d$_6$) δ 9.11 (s, 1H), 8.52 (br s, 1H), 7.71 (d, J=8.6 Hz, 1H), 5.70 (s, 1H), 5.21 (s, 1H), 5.07 (d, J=5.9 Hz, 1H), 4.56 (br s, 1H), 4.23-4.00 (m, 1H), 3.86-3.67 (m, 1H), 3.63 (br s, 1H), 3.49 (br d, J=2.6 Hz, 1H), 2.42 (br s, 3H), 2.05-1.93 (m, 1H), 1.69 (s, 6H), 1.67-1.58 (m, 1H) ppm.

Example 24: Synthesis of (1S,3R,4S,5R)-3-((4-(7-chloro-6-(2-hydroxypropan-2-yl)-3-methylthieno[3,2-b]pyridin-2-yl)-5-fluoropyrimidin-2-yl)amino)-6,8-dioxabicyclo[3.2.1]octan-4-ol (Compound 276)

Example 25: Synthesis of (1S,3R,4S,5R)-3-((5-chloro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol (Compound 277)

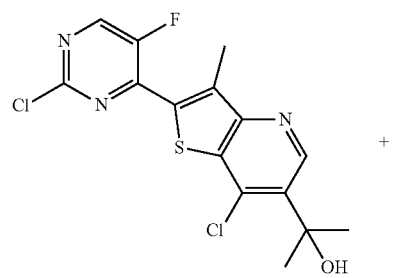

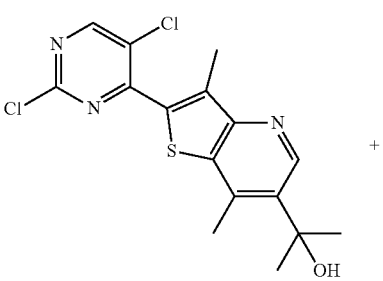

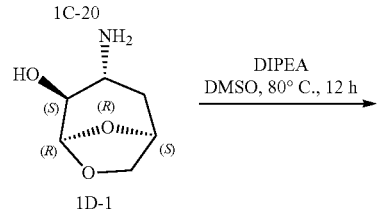

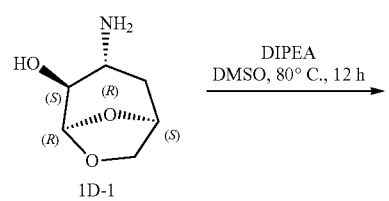

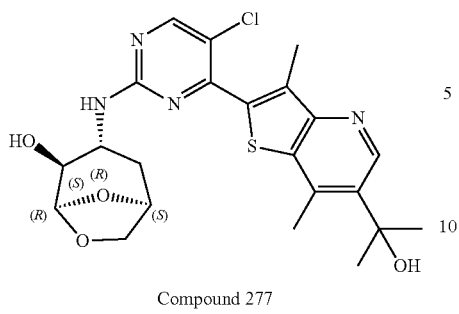

Compound 277

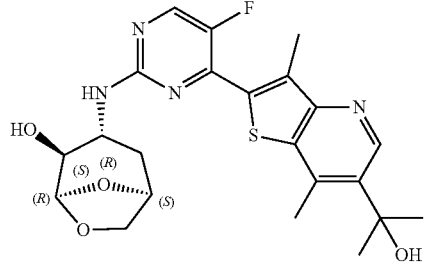

Compound 278

A mixture of 2-(2-(2,5-dichloropyrimidin-4-yl)-3,7-dimethylthieno[3,2-b]pyridin-6-yl) propan-2-ol (1C-21, 0.05 g, 0.14 mmol, 1 eq), (1S,3R,4S,5R)-3-amino-6,8-dioxabicyclo[3.2.1]octan-4-ol (1D-1, 0.03 g, 0.21 mmol, 1.52 eq) and DIPEA (0.04 g, 0.27 mmol, 47.29 µL, 2 eq) in DMSO (1 mL) was stirred at 80° C. for 12 hours under nitrogen atmosphere. After the completion of the reaction, the mixture was cooled to room temperature, and diluted with acetonitrile (1 mL). The resulting solution was purified by prep-HPLC (column: Phenomenex luna C18, 150×25 mm, 10 um; mobile phase: [water (FA)-ACN]; gradient: 23%-53% B over 10 min) and lyophilization to give (1S,3R,4S,5R)-3-((5-chloro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol (35.25 mg, 54.2% yield) as a white solid. LCMS: 477.1 [M+H]$^+$; $^1$H NMR (400 MHZ, DMSO-d$_6$) δ 8.79 (s, 1H), 8.50 (br s, 1H), 7.67 (br d, J=8.4 Hz, 1H), 5.31 (s, 1H), 5.21 (s, 1H), 5.07 (d, J=5.8 Hz, 1H), 4.56 (br s, 1H), 4.20-4.01 (m, 1H), 3.84-3.67 (m, 1H), 3.66-3.57 (m, 1H), 3.48 (br d, J=1.1 Hz, 1H), 2.79 (s, 3H), 2.47-2.37 (m, 3H), 2.05-1.94 (m, 1H), 1.71-1.65 (m, 1H), 1.63 (s, 6H) ppm.

Example 26: Synthesis of (1S,3R,4S,5R)-3-((5-fluoro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol (Compound 278)

A mixture of 2-(2-(2-chloro-5-fluoropyrimidin-4-yl)-3,7-dimethylthieno[3,2-b]pyridin-6-yl) propan-2-ol (1C-22, 0.05 g, 0.14 mmol, 1 eq), (1S,3R,4S,5R)-3-amino-6,8-dioxabicyclo[3.2.1]octan-4-ol (1D-1, 0.04 g. 0.28 mmol, 1.99 eq) and DIEA (0.37 g, 0.28 mmol, 49.51 µL, 2 eq) in DMSO (1 mL) was stirred at 80° C. for 12 hours under nitrogen atmosphere. After the completion of the reaction, the mixture was cooled to room temperature and diluted with acetonitrile (1 mL). The resulting solution was purified by prep-HPLC (column: Phenomenex luna C18, 150×25 mm, 10 um; mobile phase: [water (FA)-ACN]; gradient: 18%-48% B over 10 min) to give (1S,3R,4S,5R)-3-((5-fluoro-4-(6-(2-hydroxypropan-2-yl)-3,7-dimethylthieno[3,2-b]pyridin-2-yl)pyrimidin-2-yl)amino)-6,8-dioxabicyclo[3.2.1]octan-4-ol (36.04 mg, 54.5% yield) as a white solid. LCMS: 461.1 [M+H]$^+$; $^1$H NMR (400 MHZ, DMSO-d$_6$)δ 8.81 (s, 1H), 8.52 (d, J=2.9 Hz, 1H), 7.40 (d, J=8.6 Hz, 1H), 5.32 (s, 1H), 5.22 (s, 1H), 5.04 (d, J=5.9 Hz, 1H), 4.57 (br s, 1H), 4.17-4.05 (m, 1H), 3.80 (d, J=7.3 Hz, 1H), 3.66 (br t, J=5.7 Hz, 1H), 3.54-3.47 (m, 1H), 2.80 (s, 3H), 2.60 (br s, 3H), 2.11-1.98 (m, 1H), 1.68 (br s, 1H), 1.63 (s, 6H) ppm.

Example 27: Synthesis of (1S,3R,4S,5R)-3-((5-chloro-4-(8-fluoro-3-(2-hydroxypropan-2-yl)-4-methylcinnolin-6-yl)pyrimidin-2-yl)amino)-6,8-dioxabicyclo[3.2.1]octan-4-ol (Compound 279)

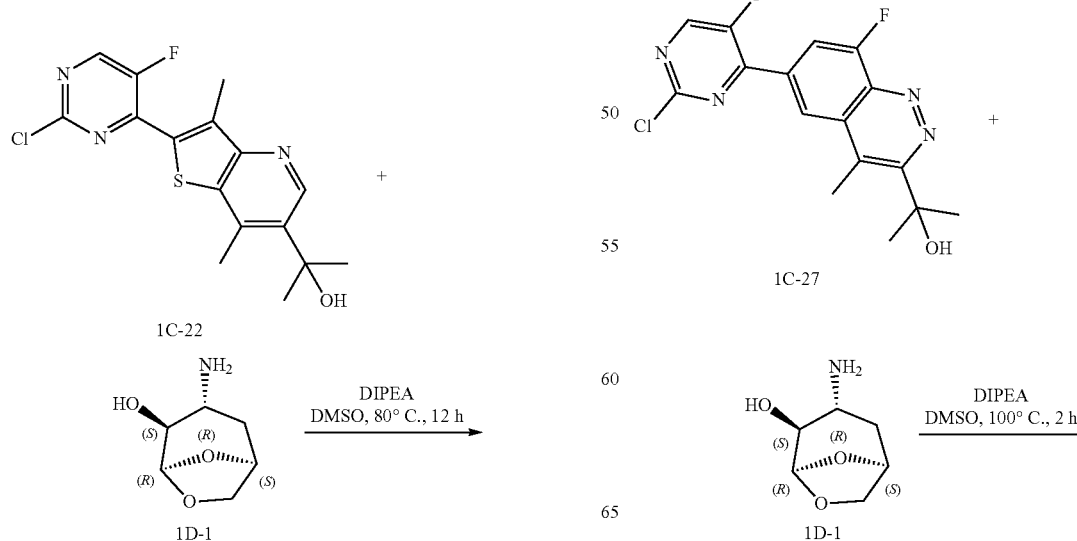

-continued

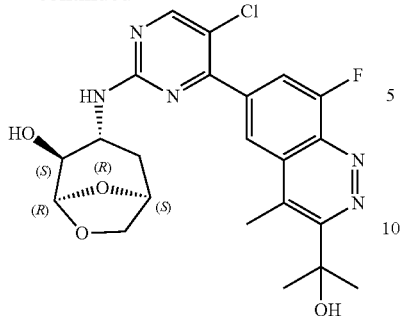

Compound 279

-continued

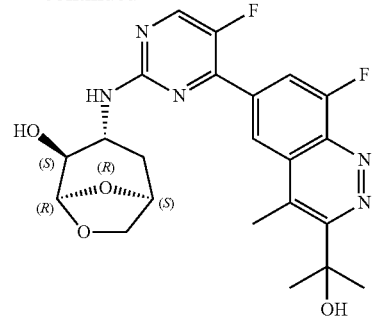

Compound 280

A mixture of 2-(6-(2,5-dichloropyrimidin-4-yl)-8-fluoro-4-methylcinnolin-3-yl) propan-2-ol (1C-27, 33 mg, 0.089 mmol, 1 eq), (1S,3R,4S,5R)-3-amino-6,8-dioxabicyclo[3.2.1]octan-4-ol (1D-1, 19.57 mg, 0.134 mmol, 1.5 eq) and DIPEA (34.84 mg, 0.269 mmol, 3 eq) in DMSO (3 mL) was stirred at 100° C. for 2 hours under nitrogen atmosphere. After the completion of the reaction, the mixture was cooled to room temperature and purified by prep-HPLC {column: Waters Xbridge C18, 150×25 mm, 5 um; mobile phase: [water (FA)-ACN]; gradient: 20%-50% B over 10 min} to afford (1S,3R,4S,5R)-3-((5-chloro-4-(8-fluoro-3-(2-hydroxypropan-2-yl)-4-methylcinnolin-6-yl)pyrimidin-2-yl)amino)-6,8-dioxabicyclo[3.2.1]octan-4-ol (13.72 mg, 31.8% yield) as a yellow solid. LCMS: 476.2 [M+H]$^+$; $^1$H NMR (400 MHz, DMSO-d$_6$) δ 8.60-8.35 (m, 2H), 8.10-7.91 (m, 1H), 7.77-7.59 (m, 1H), 5.62-5.51 (m, 1H), 5.22 (s, 1H), 5.05 (d, J=6.1 Hz, 1H), 4.57 (br s, 1H), 4.24-4.08 (m, 1H), 3.88-3.70 (m, 1H), 3.64 (br t, J=5.8 Hz, 1H), 3.53-3.45 (m, 1H), 3.03 (s, 3H), 2.12-1.95 (m, 1H), 1.78 (s, 6H), 1.71-1.64 (m, 1H) ppm.

Example 28: Synthesis of (1S,3R,4S,5R)-3-((5-fluoro-4-(8-fluoro-3-(2-hydroxypropan-2-yl)-4-methylcinnolin-6-yl)pyrimidin-2-yl)amino)-6,8-dioxabicyclo[3.2.1]octan-4-ol (Compound 280)

A mixture of 2-(6-(2-chloro-5-fluoropyrimidin-4-yl)-8-fluoro-4-methylcinnolin-3-yl) propan-2-ol (1C-28, 44 mg, 0.12 mmol, 1 eq), (1S,3R,4S,5R)-3-amino-6,8-dioxabicyclo[3.2.1]octan-4-ol (1D-1, 54.63 mg, 0.38 mmol, 3 eq) and DIPEA (48.64 mg, 0.38 mmol, 3 eq) in DMSO (2 mL) was stirred at 100° C. for 12 hours under nitrogen atmosphere. After the completion of the reaction, the mixture was cooled to room temperature and purified by prep-HPLC {column: Waters Xbridge C18, 150×25 mm, 5 um; mobile phase: [water (FA)-ACN]; gradient: 22%-52% B over 10 min} to afford (1S,3R,4S,5R)-3-((5-fluoro-4-(8-fluoro-3-(2-hydroxypropan-2-yl)-4-methylcinnolin-6-yl)pyrimidin-2-yl)amino)-6,8-dioxabicyclo[3.2.1]octan-4-ol (3.61 mg, 5.8% yield) as a yellow solid. LCMS: 460.2 [M+H]; 1H NMR (400 MHz, DMSO-d$_6$) δ 8.75-8.61 (m, 1H), 8.57 (d, J=3.6 Hz, 1H), 8.25-8.12 (m, 1H), 7.47 (br d, J=8.5 Hz, 1H), 5.63-5.55 (m, 1H), 5.24 (s, 1H), 5.05 (d, J=6.1 Hz, 1H), 4.59 (br s, 1H), 4.24-4.09 (m, 1H), 3.90-3.79 (m, 1H), 3.74-3.64 (m, 1H), 3.59-3.45 (m, 1H), 3.06 (s, 3H), 2.11-2.00 (m, 1H), 1.78 (s, 6H), 1.72-1.65 (m, 1H) ppm.

Example 29: Synthesis of (1S,3R,4S,5R)-3-((4-(8-chloro-3-(2-hydroxypropan-2-yl)-4-methylquinolin-6-yl)-5-fluoropyrimidin-2-yl)amino)-6,8-dioxabicyclo[3.2.1]octan-4-ol (Compound 283)

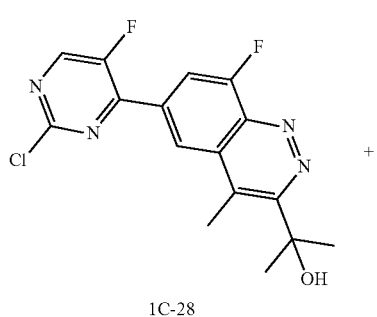

1C-28

+

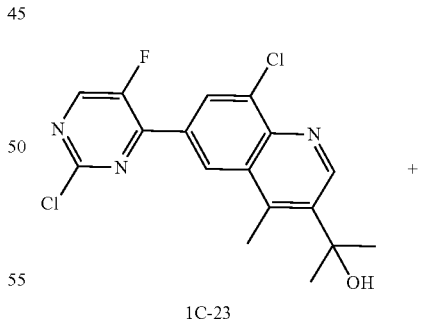

1C-23

+

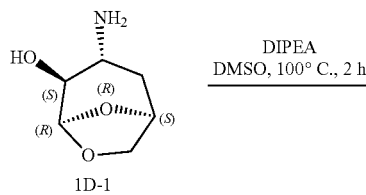

1D-1

DIPEA
DMSO, 100° C., 2 h →

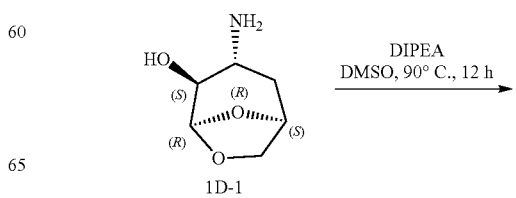

1D-1

DIPEA
DMSO, 90° C., 12 h →

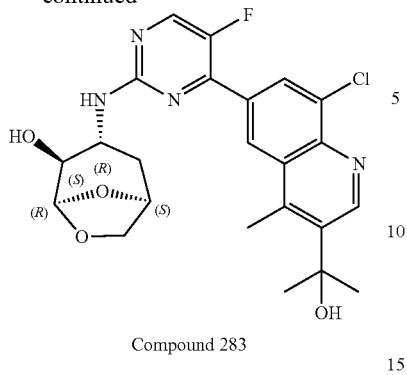

Compound 283

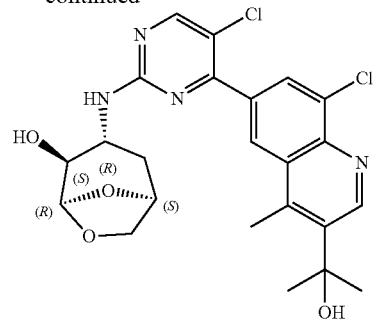

Compound 284

To a solution of 2-(8-chloro-6-(2-chloro-5-fluoropyrimidin-4-yl)-4-methylquinolin-3-yl) propan-2-ol (1C-23, 2.5 g, 6.83 mmol, 1 eq) and (1S,3R,4S,5R)-3-amino-6,8-dioxabicyclo[3.2.1]octan-4-ol (1D-1, 1.09 g, 7.51 mmol, 1.1 eq) in DMSO (25 mL) was added DIPEA (1.76 g, 13.65 mmol, 2.38 mL, 2 eq), and the mixture was stirred at 90° C. for 12 hours under nitrogen atmosphere. After the completion of the reaction, the mixture was cooled to room temperature, diluted with $H_2O$ (100 mL) and extracted with EtOAc (200 mL×3). The combined organic phase was washed with brine (60 mL), dried over $Na_2SO_4$, filtered, and the filtrate was concentrated under reduced pressure. The resulting residue was purified by prep-HPLC {column: Welch Ultimate XB-SIOH, 250×70 mm, 10 um; mobile phase: [Hexane-EtOH]; gradient: 1%-40% B over 15 min} to afford (1S,3R,4S,5R)-3-((4-(8-chloro-3-(2-hydroxypropan-2-yl)-4-methylquinolin-6-yl)-5-fluoropyrimidin-2-yl)amino)-6,8-dioxabicyclo[3.2.1]octan-4-ol (1.317 g, 40.2% yield) as an off-white solid. LCMS: 475.2 [M+H]+; ¹H NMR (400 MHZ, DMSO-d₆) & 9.18 (s, 1H), 8.90-8.76 (m, 1H), 8.52 (d, J=3.8 Hz, 1H), 8.49-8.42 (m, 1H), 7.41 (br d, J=8.0 Hz, 1H), 5.43 (s, 1H), 5.24 (s, 1H), 5.06 (d, J=6.0 Hz, 1H), 4.63-4.53 (m, 1H), 4.24-4.07 (m, 1H), 3.94-3.80 (m, 1H), 3.78-3.63 (m, 1H), 3.60-3.47 (m, 1H), 3.00 (s, 3H), 2.18-2.00 (m, 1H), 1.69 (m, 7H) ppm.

Example 30: Synthesis of (1S,3R,4S,5R)-3-((5-chloro-4-(8-chloro-3-(2-hydroxypropan-2-yl)-4-methylquinolin-6-yl)pyrimidin-2-yl)amino)-6,8-dioxabicyclo[3.2.1]octan-4-ol (Compound 284)

To a solution of 2-(8-chloro-6-(2,5-dichloropyrimidin-4-yl)-4-methylquinolin-3-yl) propan-2-ol (1C-24, 1 g, 2.61 mmol, 1 eq) and (1S,3R,4S,5R)-3-amino-6,8-dioxabicyclo [3.2.1]octan-4-ol (1D-1, 455.19 mg, 3.14 mmol, 1.2 eq) in DMSO (10 mL) was added DIPEA (675.48 mg, 5.23 mmol, 0.91 mL, 2 eq), and the mixture was stirred at 90° C. for 12 hours under nitrogen atmosphere. After the completion of the reaction, the mixture was cooled to room temperature, diluted with $H_2O$ (100 mL) and extracted with Ethyl Acetate (200 mL×3). The combined organic layers were washed with brine (60 mL), dried over $Na_2SO_4$, filtered, and the filtrate was concentrated under reduced pressure. The resulting residue was purified by prep-HPLC {column: Welch Ultimate XB-SiOH, 250×70 mm, 10 um; mobile phase: [Hexane-EtOH]; gradient: 1%-40% B over 15 min} to give (1S,3R,4S,5R)-3-((5-chloro-4-(8-chloro-3-(2-hydroxypropan-2-yl)-4-methylquinolin-6-yl)pyrimidin-2-yl)amino)-6, 8-dioxabicyclo[3.2.1]octan-4-ol (980.39 mg, 72.7% yield) as a light pink solid. LCMS: 491.1 [M+H]; ¹H NMR (400 MHZ, DMSO-d₆) δ 9.17 (s, 1H), 8.75-8.54 (m, 1H), 8.48 (br s, 1H), 8.35-8.14 (m, 1H), 7.74-7.53 (m, 1H), 5.42 (s, 1H), 5.22 (s, 1H), 5.06 (br d, J=5.8 Hz, 1H), 4.57 (br s, 1H), 4.25-4.06 (m, 1H), 3.89-3.71 (m, 1H), 3.65 (br t, J=5.7 Hz, 1H), 3.59-3.44 (m, 1H), 2.98 (s, 3H), 2.14-1.95 (m, 1H), 1.68 (m, 7H) ppm.

Example 31: Synthesis of (1S,3R,4S,5R)-3-((4-(4,8-dichloro-3-(2-hydroxypropan-2-yl) quinolin-6-yl)-5-fluoropyrimidin-2-yl)amino)-6,8-dioxabicyclo[3.2.1]octan-4-ol (Compound 285)

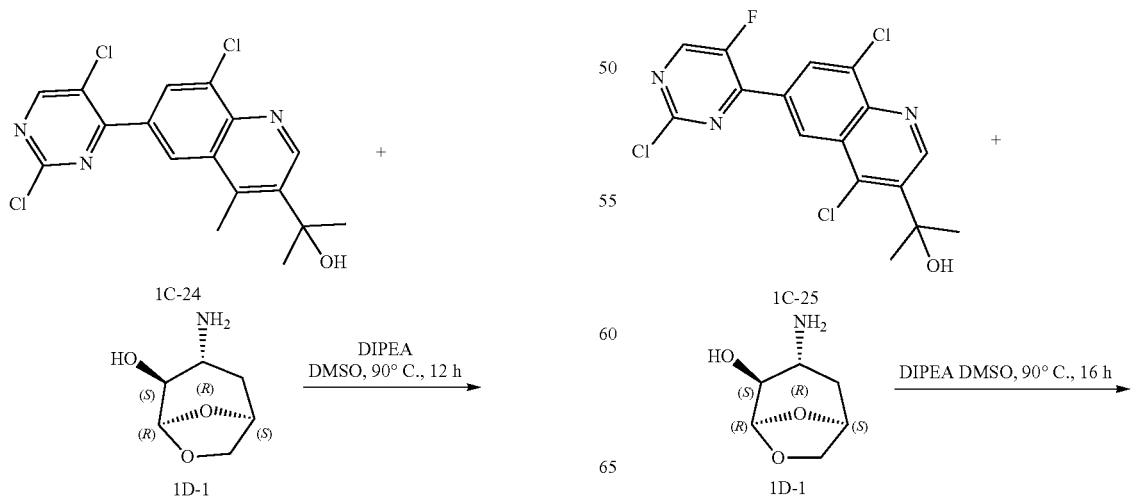

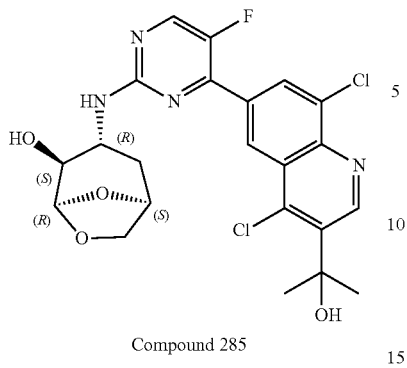

Compound 285

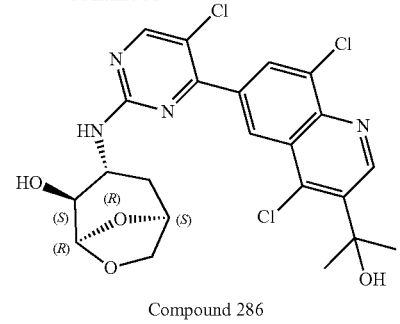

Compound 286

To a solution of 2-(4,8-dichloro-6-(2-chloro-5-fluoropyrimidin-4-yl) quinolin-3-yl) propan-2-ol (IC-25, 1.5 g, 3.88 mmol, 1 eq) and (1S,3R,4S,5R)-3-amino-6,8-dioxabicyclo[3.2.1]octan-4-ol (1D-1, 0.8 g, 5.51 mmol, 1.42 eq) in DMSO (30 mL) was added DIPEA (1.00 g, 7.76 mmol, 2 eq), and the mixture was heated to 90° C. for 16 hours under nitrogen atmosphere. After the completion of the reaction, the mixture was cooled to room temperature, diluted with water (150 ml . . . ) and extracted with EtOAc (200 mL). The organic phase was washed with brine (50 mL), dried over anhydrous $Na_2SO_4$, filtered and the filtrate was concentrated in vacuo. The resulting residue was purified by flash silica gel chromatography (Welch Ultimate XB-NH2 250×50 mm, 10 um; mobile phase: [Hexane-EtOH (0.1% $NH_3 \cdot H_2O$)]; gradient: 30%-70% B over 15 min) to give (1S,3R,4S,5R)-3-((4-(4,8-dichloro-3-(2-hydroxypropan-2-yl) quinolin-6-yl)-5-fluoropyrimidin-2-yl)amino)-6,8-dioxabicyclo[3.2.1]octan-4-ol (0.815 g, 42.4% yield) as a yellow solid. LCMS: 495.1 [M+H]; $^1$H NMR (400 MHZ, DMSO-$d_6$)δ=9.48 (s, 1H), 8.99 (br dd, J=2.7, 4.4 Hz, 1H), 8.69-8.45 (m, 2H), 7.46 (br d, J=7.6 Hz, 1H), 5.82 (s, 1H), 5.24 (s, 1H), 5.06 (d, J=6.0 Hz, 1H), 4.59 (br s, 1H), 4.27-4.04 (m, 1H), 3.85 (br d, J=6.4 Hz, 1H), 3.76-3.63 (m, 1H), 3.53 (dt, J=1.2, 3.2 Hz, 1H), 2.18-1.99 (m, 1H), 1.74 (s, 6H), 1.66 (br s, 1H) ppm.

Example 32: Synthesis of (1S,3R,4S,5R)-3-((5-chloro-4-(4,8-dichloro-3-(2-hydroxypropan-2-yl) quinolin-6-yl)pyrimidin-2-yl)amino)-6,8-dioxabicyclo[3.2.1]octan-4-ol (Compound 286)

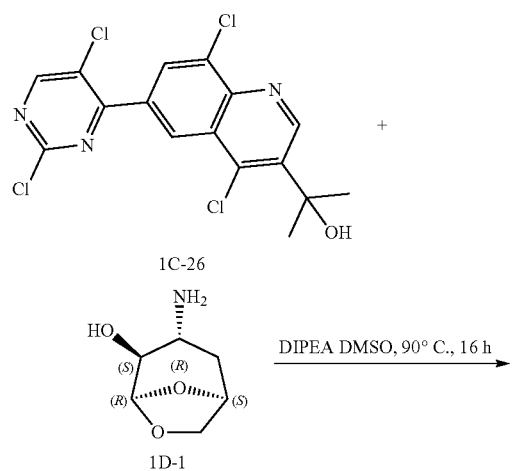

To a solution of 2-(4,8-dichloro-6-(2,5-dichloropyrimidin-4-yl) quinolin-3-yl) propan-2-ol (1C-26, 800 mg, 1.98 mmol, 1 eq) and (1S,3R,4S,5R)-3-amino-6,8-dioxabicyclo[3.2.1]octan-4-ol (1D-1, 400.00 mg, 2.76 mmol, 1.39 eq) in DMSO (12 mL) was added DIPEA (593.60 mg, 4.59 mmol, 2.31 eq), and the mixture was heated to 90° C. for 16 hours under nitrogen atmosphere. After the completion of the reaction, the mixture was cooled to room temperature, diluted with water (150 mL) and extracted with EtOAc (200 mL). The organic phase was washed with brine (50 mL), dried over anhydrous $Na_2SO_4$, filtered and the filtrate was concentrated in vacuo. The resulting residue was purified by flash silica gel chromatography (column: Welch Ultimate XB-SiOH, 250×70 mm, 10 um; mobile phase: [Hexane-EtOH (0.1% $NH_3 \cdot H_2O$)]; gradient: 1%-40% B over 15 min) to give (1S,3R,4S,5R)-3-((5-chloro-4-(4,8-dichloro-3-(2-hydroxypropan-2-yl) quinolin-6-yl)pyrimidin-2-yl)amino)-6,8-dioxabicyclo[3.2.1]octan-4-ol (0.933 g. 91.8% yield) as a yellow solid. LCMS: 513.1 [M+H]$^+$; $^1$H NMR (400 MHZ, DMSO-$d_6$) δ 9.47 (s, 1H), 8.94-8.65 (m, 1H), 8.50 (s, 1H), 8.45-8.23 (m, 1H), 7.82-7.51 (m, 1H), 5.81 (s, 1H), 5.22 (s, 1H), 5.06 (br d, J=6.0 Hz, 1H), 4.57 (s, 1H), 4.24-4.07 (m, 1H), 3.80 (d, J=1.6 Hz, 1H), 3.66 (d, J=4.8 Hz, 1H), 3.57-3.44 (m, 1H), 2.16-1.94 (m, 1H), 1.74 (s, 6H), 1.70-1.56 (m, 1H) ppm.

Compounds 23, 25, 27, 29, 33, 49, 66, 136, 151, 163, 167, 168, 169, 170, 172, 173, 174, 175, 176, 179, 180, 181, 182, 183, 184, 185, 186, 187, 188, 190, 191, 192, 193, 194, 195, 196, 197, 198, 200, 201, 202, 204, 205, 207, 208, 209, 210, 211, 212, 213, 214, 215, 219, 222, 227, 231, 232, 236, 237, 238, 239, 240, 241, 242, 246, 247, 248, 249, 250, 251, 253, 254, 261, 262, 263, 264, 265, 266, 267, 268, 269, 270, 271, and 272 were prepared using similar methods as described in Examples 1-32, and the corresponding $^1$H NMR and mass spectrometry data are listed below.

| Cpd # | LCMS and $^1$H NMR Data |
|---|---|
| 23 | LCMS: 574.2 [M + H]$^+$;<br>$^1$H NMR (400 MHz, DMSO-$d_6$ δ 8.42 (s, 1H), 8.07-7.87 (m, 1H), 7.40-7.33 (m, 2H), 5.32 (t, J = 4.6 Hz, 1H), 5.19 (s, 1H), 5.13-5.02 (m, 1H), 4.98-4.93 (m, 1H), 4.90 (d, J = 6.6 Hz, 1H), 4.38 (br d, J = 4.6 Hz, 1H), 4.18-4.05 (m, 1H), 4.00-3.88 (m, 1H), 3.84-3.79 (m, 2H), 3.74 (s, 1H), 3.71-3.66 (m, 2H), 3.62 (s, 3H), 2.26-2.22 (m, 1H), 2.03-1.98 (m, 2H), 1.61 (br d, J = 6.8 Hz, 6H), 1.48-1.43 (m, 2H), 0.95 (d, J = 7.3 Hz, 3H) ppm. |
| 25 | LCMS: 448.1 [M + H]$^+$;<br>$^1$H NMR (400 MHz, DMSO-$d_6$ δ 8.41 (s, 1H), 8.05-7.82 (m, 1H), 7.59-7.28 (m, 2H), 5.21 (d, J = 1.2 Hz, 1H), 5.11-4.98 (m, 1H), 4.81 (td, J = 6.8, J = 13.2 Hz, 1H), 4.56 (s, 1H), 4.21-4.07 (m, 1H), 3.85-3.69 (m, 1H), 3.64 (t, J = 6.4 Hz, 1H), 3.48 (s, 1H), 2.62 (s, 3H), 2.00 |

| Cpd # | LCMS and ¹H NMR Data |
|---|---|
| | (td, J = 2.4, J = 9.6 Hz, 1H), 1.64 (d, J = 11.6 Hz, 1H), 1.58 (d, J = 6.8 Hz, 6H) ppm. |
| 27 | LCMS: 476.3 [M + H]$^+$;<br>¹H NMR (400 MHz, DMSO-d$_6$ δ 8.44-8.43 (m, 1H), 8.20 (s, 1H), 7.64-7.61 (m, 1H), 7.28-7.26 (m, 1H), 5.85 (m, 1H), 5.81-5.75 (m, 1H), 5.23 (s, 1H), 5.05(s, 1H), 4.58 (s, 1H), 4.16-4.13 (m, 1H), 3.83-3.81 (m, 1H), 3.68 (s, 1H), 3.53-3.51 (m, 1H), 2.07-2.01 (m, 1H), 3.53-3.51 (m, 1H), 1.67 (s, 7H), 1.64-1.62 (m, 6H) ppm. |
| 29 | LCMS: 508.3 [M + H]$^+$;<br>¹H NMR (400 MHz, DMSO-d$_6$ δ = 8.61 (d, J = 11.2 Hz, 1H), 7.85 (dd, J = 8.4, J = 16.4 Hz, 1H), 7.79-7.61 (m, 1H), 7.33-7.14 (m, 1H), 7.12-6.67 (m, 1H), 5.83 (d, J = 11.6 Hz, 1H), 5.76 (dd, J = 6.8, J = 13.6 Hz, 1H), 5.22 (s, 1H), 5.07 (t, J = 5.4 Hz, 1H), 4.56 (s, 1H), 4.34-4.17 (m, 1H), 3.88-3.70 (m, 1H), 3.64 (d, J = 5.2 Hz, 1H), 3.50 (td, J = 8.0, J = 15.6 Hz, 1H), 2.11-1.93 (m, 1H), 1.66 (s, 7H), 1.63-1.55 (m, 6H) ppm. |
| 33 | LCMS: 503.1 [M + H]$^+$;<br>¹H NMR (400 MHz, DMSO-d$_6$ δ = 8.40 (br s, 1H), 7.77-7.59 (m, 1H), 7.59-7.41 (m, 2H), 5.29 (s, 1H), 5.21 (s, 1H), 5.03 (d, J = 5.9 Hz, 1H), 4.55 (br s, 1H), 4.25-4.02 (m, 1H), 3.85-3.69 (m, 1H), 3.67-3.59 (m, 1H), 3.55-3.41 (m, 1H), 2.77 (br d, J = 5.0 Hz, 2H), 2.15-1.99 (m, 4H), 1.99 (br s, 1H), 1.71-1.63 (m, 1H), 1.63-1.57 (m, 2H), 1.55 (s, 6H) ppm. |
| 49 | LCMS: 476.1 [M + H]$^+$;<br>¹H NMR (400 MHz, DMSO-d$_6$ δ = 8.42 (br s, 1H), 8.02-7.76 (m, 1H), 7.60-7.39 (m, 2H), 5.21 (s, 1H), 5.06-4.99(m, 2H), 4.68 (br s, 1 H), 4.56 (br s, 1 H), 4.20-4.04 (m, 3 H), 3.80-3.73 (m, 1H), 3.68-3.60 (m, 1H), 3.49 (br d, J = 3.0 Hz, 1H), 2.07-1.92 (m, 1H), 1.68-1.60 (m, 4H), 1.49 (br d, J = 6.50 Hz, 3 H) ppm. |
| 66 | LCMS: 414.1 [M + H]$^+$;<br>¹H NMR (400 MHz, DMSO-d$_6$ δ = 8.55 (s, 1H), 8.37 (d, J = 4.2 Hz, 1H), 7.85 (d, J = 8.4 Hz, 1H), 7.62 (m, J = 9.2 Hz, 1H), 7.17 (d, J = 8.0 Hz, 1H), 5.23 (s, 1H), 5.04 (d, J = 6.0 Hz, 1H), 4.57 (s, 1H), 4.18-4.09 (m, 4H), 3.82 (d, J = 7.2 Hz, 1H), 3.67 (t, J = 5.6 Hz, 1H), 3.58 (td, J = 7.2, J = 14.0 Hz, 1H), 3.54-3.48 (m, 1H), 2.12-2.01 (m, 1H), 1.70-1.61 (m, 1H), 1.48 (dd, J = 7.2 Hz, 6H) ppm. |
| 136 | LCMS: 505.2 [M + H]$^+$;<br>¹H NMR (400 MHz, DMSO-d$_6$ δ = 8.49-8.34 (m, 1H), 8.20 (s, 1H), 8.11-7.85 (m, 1H), 7.69-7.17 (m, 2H), 5.22 (s, 1H), 5.15-4.95 (m, 2H), 4.62-4.51 (m, 1H), 4.21-4.02 (m, 3H), 3.82-3.70 (m, 1H), 3.64 (br t, J = 5.7 Hz, 1H), 3.49 (br d, J = 2.6 Hz, 1H), 2.81-2.71 (m, 1H), 2.12-1.93 (m, 1H), 1.73-1.50 (m, 7H), 1.04 (d, J = 6.2 Hz, 6H) ppm. |
| 151 | LCMS: 521.1 [M + H]$^+$;<br>¹H NMR (400 MHz, DMSO-d$_6$ δ = 8.42 (s, 1H), 7.94-7.68 (m, 1H), 7.51-7.25 (m, 2H), 5.55-5.27 (m, 2H), 5.12-4.87 (m, 1H), 4.76 (td, J = 6.7, 13.5 Hz, 1H), 4.51 (br s, 1H), 4.14 (br d, J = 5.4 Hz, 1H), 4.06-3.90 (m, 1H), 3.90-3.79 (m, 2H), 3.75 (br d, J = 4.4 Hz, 1H), 3.73-3.64 (m, 1H), 3.64-3.58 (m, 1H), 3.53 (t, J = 5.7 Hz, 1H), 2.36 (td, J = 4.6, 14.4 Hz, 1H), 2.28-2.06 (m, 2H), 1.65 (d, J = 6.9 Hz, 3H), 1.55 (br d, J = 14.8 Hz, 1H), 1.50 (br d, J = 6.8 Hz, 3H) ppm. |
| 163 | LCMS: 510.3 [M + H]$^+$;<br>¹H NMR (400 MHz, DMSO-d$_6$ δ = 8.44 (s, 1H), 8.20-7.97 (m, 1H), 7.74-7.69 (m, 2H), 7.64-7.60 (m, 3H), 7.59-7.53 (m, 1H), 7.50-7.35 (m, 1H), 5.22 (s, 1H), 5.05 (d, J = 6.4 Hz, 1H), 4.83-4.72 (m, 1H), 4.56 (s, 1H), 4.23-4.11 (m, 1H), 3.87-3.70 (m, 1H), 3.64 (t, J = 5.6 Hz, 1H), 3.57-3.45 (m, 1H), 2.11-1.94 (m, 1H), 1.73-1.66 (m, 1H), 1.62 (d, J = 6.4 Hz, 6H) ppm. |
| 167 | LCMS: 522.3 [M + H]$^+$;<br>¹H NMR (400 MHz, DMSO-d$_6$ δ = 8.41 (s, 1H), 8.10-7.82 (m, 1H), 7.64-7.28 (m, 2H), 5.71-5.50 (m, 1H), 5.37-5.14 (m, 2H), 5.05 (s, 1H), 4.56 (s, 1H), 4.39-4.20 (m, 1H), 4.19-4.04 (m, 1H), 3.85-3.71 (m, 1H), 3.69-3.58 (m, 1H), 3.55-3.47 (m, 1H), 2.14-1.92 (m, 1H), 1.79-1.73 (m, 3H), 1.71-1.61 (m, 5H), 1.54 (dd, J = 3.6, 7.2 Hz, 1H), 1.42-1.33 (m, 2H) ppm. |
| 168 | LCMS: 522.3 [M + H]$^+$;<br>¹H NMR (400 MHz, DMSO-d$_6$ δ = 8.43 (s, 1H), 8.07-7.96 (m, 1H), 7.62-7.35 (m, 2H), 5.99 (t, J = 55.2 Hz, 1H), 5.22 (s, 1H), 5.14-5.04 (m, 2H), 4.56 (br s, 1H), 4.19-4.11 (m, 1H), 3.82-3.70 (m, 1H), 3.65-3.63 (m, 1H), 3.50 (br s, 1H), 2.03-1.98 (m, 1H), 1.70-1.67 (m, 1H), 1.62 (br d, J = 6.8 Hz, 6H), 1.44-1.41 (m, 2H), 1.38-1.33 (m, 2H) ppm. |
| 169 | LCMS: 526.3 [M + H]$^+$;<br>¹H NMR (400 MHz, DMSO-d$_6$ δ = 8.42 (s, 1H), 8.11-7.89 (m, 1H), 7.67-7.25 (m, 2H), 6.84-6.42 (m, 1H), 5.27-5.12 (m, 2H), 5.04 (d, J = 6.0 Hz, 1H), 4.56 (s, 1H), 4.23-4.06 (m, 1H), 3.90-3.68 (m, 1H), 3.64 (d, J = 5.6 Hz, 1H), 3.55-3.42 (m, 1H), 2.11-1.89 (m, 1H), 1.69 (s, 1H), 1.62 ( d, J = 6.8 Hz, 6H), 1.58 (s, 6H) ppm. |
| 170 | LCMS: 508.1 [M + H]$^+$;<br>¹H NMR (400 MHz, DMSO-d$_6$ δ = 8.44 (br s, 1H), 8.16-7.96 (m, 1H), 7.66-7.39 (m, 2H), 5.44-5.30 (m, 2H), 5.24-5.16 (m, 2H), 5.12 (d, J = 8.3 Hz, 1H), 5.04 (d, J = 6.0 Hz, 1H), 4.59-4.43 (m, 2H), 4.23-4.08 (m, 1H), 3.86-3.58 (m, 1H), 3.55-3.42 (m, 1H), 2.11-1.92 (m, 1H), 1.73-1.58 (m, 7H) ppm. |
| 172 | LCMS: 506.2 [M + H]$^+$;<br>¹H NMR (400 MHz, DMSO-d$_6$ δ = 8.50-8.39 (m, 1H), 8.11-7.88 (m, 1H), 7.63-7.34 (m, 2H), 7.07 (s, 1H), 5.27-5.19 (m, 3H), 5.04 (br d, J = 6.0 Hz, 1H), 4.83 (d, J = 6.7 Hz, 2H), 4.70-4.59 (m, 1H), 4.56 (br s, 1H), 4.24-4.08 (m, 1H), 3.87-3.68 (m, 1H), 3.67-3.58 (m, 1H), 3.56-3.43 (m, 1H), 2.09-1.94 (m, 1H), 1.58 (br d, J = 6.8 Hz, 7H) ppm. |
| 173 | LCMS: 506.2 [M + H]$^+$;<br>¹H NMR (400 MHz, DMSO-d$_6$ δ = 8.33 (s, 1H), 7.43 (d, J = 8.6 Hz, 1H), 7.18-6.81 (m, 2H), 5.20 (d, J = 1.2 Hz, 1H), 5.02 (d, J = 6.0 Hz, 1H), 4.55 (s, 1H), 4.27 (t, J = 4.0 Hz, 2H), 4.17-4.01 (m, 2H), 3.82-3.69 (m, 1H), 3.67-3.58 (m, 1H), 3.48 (s, 1H), 3.30-3.25 (m, 2H), 2.04-1.92 (m, 1H), 1.71-1.58 (m, 1H), 1.15 (d, J = 6.4 Hz, 6H) ppm. |
| 174 | LCMS: 465.2 [M + H]$^+$;<br>¹H NMR (400 MHz, DMSO-d$_6$ δ = 8.35-8.18 (m, 1H), 7.48-7.32 (m, 1H), 6.53-6.32 (m, 1H), 5.22 (dd, J = 4.0, 5.8 Hz, 1H), 5.04-4.97 (m, 1H), 4.59-4.50 (m, 1H), 4.41-4.29 (m, 2H), 4.17-3.94 (m, 3H), 3.83-3.66 (m, 1H), 3.64-3.53 (m, 1H), 3.46-3.38 (m, 2H), 3.26-3.07 (m, 2H), 3.26-3.07 (m, 2H), 1.96 (dd, J = 6.1, 12.5 Hz, 1H), 1.69-1.56 (m, 1H), 1.12 (d, J = 6.4 Hz, 3H) ppm. |
| 175 | LCMS: 465.2 [M + H]$^+$;<br>¹H NMR (400 MHz, DMSO-d$_6$ δ = 8.28 (s, 1H), 7.45-7.32 (m, 1H), 6.51 (s, 1H), 5.19 (s, 1H), 5.06-4.98 (m, 1H), 4.60-4.50 (m, 1H), 4.43-4.31 (m, 2H), 4.19-3.94 (m, 3H), 3.82-3.66 (m, 1H), 3.65-3.53 (m, 1H), 3.48-3.39 (m, 2H), 3.24-3.02 (m, 2H), 2.00-1.94 (m, 1H), 1.69-1.55 (m, 1H), 1.16-1.08 (m, 3H) ppm. |
| 176 | LCMS: 465.2 [M + H]$^+$;<br>¹H NMR (400 MHz, DMSO-d$_6$ δ = 8.49-8.38 (m, 1H), 8.20-8.00 (m, 1H), 7.66-7.39 (m, 2H), 5.87 (t, J = 6.6 Hz, 1H), 5.25-5.12 (m, 2H), 5.04 (d, J = 6.1 Hz, 1H), 4.61-4.53 (m, 1H), 4.34-4.08 (m, 3H), 3.85-3.67 (m, 1H), 3.64 (br d, J = 5.5 Hz, 1H), 3.55-3.43 (m, 1H), 3.23 (br s, 1H), 2.09-1.95 (m, 1H), 1.65 (br d, J = 6.6 Hz, 6H) ppm. |
| 179 | LCMS: 522.3 [M + H]$^+$;<br>¹H NMR (400 MHz, DMSO-d$_6$ δ = 8.43 ( s, 1H), 8.28-8.09 (m, 1H), 7.66-7.32 (m, 2H), 5.91 (s, 1H), 5.86-5.74 (m, 1H), 5.21 (s, 1H), 5.03 (d, J = 6.0 Hz, 1H), 4.55 ( s, 1H), 4.19-4.04 (m, 1H), 3.85-3.70 (m, 1H), 3.64 ( t, J = 6.0 Hz, 1H), 3.56-3.42 (m, 1H), 3.24-3.09 (m, 2H), 3.07-2.95 (m, 2H), 2.17-1.90 (m, 1H), 1.64 (s, 6H), 1.33-1.18 (m, 1H), 0.90-0.67 (m, 1H) ppm. |
| 180 | LCMS: 522.3 [M + H]$^+$;<br>¹H NMR (400 MHz, DMSO-d$_6$ δ = 8.42 ( s, 1H), 8.16-7.89 (m, 1H), 7.63-7.27 (m, 2H), 6.65-6.45 (m, 1H), 5.94 (s, 1H), 5.76-5.43 (m, 1H), 5.21 (s, 1H), 5.14-4.98 (m, 1H), 4.56 ( s, 1H), 4.29-4.02 (m, 1H), 3.87-3.68 (m, 1H), 3.67-3.58 (m, 1H), 3.55-3.42 (m, 1H), 3.26-3.13 (m, 1H), 2.82-2.63 (m, 2H), 1.99 ( dd, J = 5.7, 12.8 Hz, 1H), 1.65 (s, 7H), 1.37 (s, 1H) ppm. |

| Cpd # | LCMS and ¹H NMR Data |
|---|---|
| 181 | LCMS: 516.3 [M + H]⁺;<br>¹H NMR (400 MHz, DMSO-d₆ δ = 8.41 (s, 1H), 8.26-8.05 (m, 1H), 7.67-7.44 (m, 1H), 7.67-7.44 (m, 2H), 5.65 (s, 1H), 5.21 (d, J = 1.2 Hz, 1H), 5.04 (d, J = 6.0 Hz, 1H), 4.56 (s, 1H), 4.21-4.07 (m, 1H), 3.83-3.71 (m, 1H), 3.65 (t, J = 6.0 Hz, 1H), 3.54-3.43 (m, 1H), 2.69 (s, 6H), 2.63 (s, 1H), 2.06-1.96 (m, 1H), 1.74-1.66 (m, 1H), 1.65 (s, 6H) ppm. |
| 182 | LCMS: 504.3 [M + H]⁺;<br>¹H NMR (400 MHz, DMSO-d₆ δ = 8.45-8.35 (m, 1H), 7.79 (d, J = 3.4 Hz, 1H), 7.58-7.22 (m, 2H), 5.21 (s, 1H), 5.03 (d, J = 6.2 Hz, 2H), 4.78-4.67 (m, 1H), 4.56 (s, 1H), 4.20-4.06 (m, 1H), 3.85-3.69 (m, 1H), 3.64 (t, J = 5.6 Hz, 1H), 3.48 (d, J = 2.8 Hz, 1H), 2.67 (s, 3H), 2.45 (s, 1H), 2.38-2.26 (m, 1H), 2.09-1.76 (m, 5H), 1.72-1.60 (m, 1H), 0.90 (s, 3H) ppm. |
| 183 | LCMS: 530.3 [M + H]⁺;<br>¹H NMR (400 MHz, DMSO-d₆ δ = 8.41 ( s, 1H), 7.93-7.79 (m, 1H), 7.61-7.44 (m, 1H), 7.42-7.13 (m, 1H), 6.71 (s, 1H), 5.21 (s, 1H), 5.04 (d, J = 6.0 Hz, 1H), 4.85 ( t, J = 9.2 Hz, 1H), 4.56 ( s, 1H), 4.23-4.02 (m, 1H), 3.88-3.68 (m, 1H), 3.64 ( t, J = 6.0 Hz, 1H), 3.50 ( s, 1H), 3.05 ( d, J = 9.2 Hz, 6H), 2.12 ( s, 4H), 2.04-1.86 (m, 3H), 1.77-1.60 (m, 1H) ppm. |
| 184 | LCMS: 519.2 [M + H]⁺;<br>¹H NMR (400 MHz, DMSO-d₆ δ = 8.55-8.30 (m, 2H), 8.15-7.84 (m, 1H), 7.64-7.29 (m, 2H), 5.48 (dd, J = 3.6, 7.6 Hz, 1H), 5.21 (s, 1H), 5.04 (d, J = 6.0 Hz, 1H), 4.90-4.78 (m, 1H), 4.76-4.69 (m, 1H), 4.65 (dd, J = 4.4, 8.4 Hz, 1H), 4.56 (s, 1H), 4.26-4.04 (m, 1H), 3.86-3.69 (m, 1H), 3.67-3.58 (m, 1H), 3.54-3.40 (m, 1H), 2.08-1.87 (m, 1H), 1.69-1.46 (m, 7H) ppm. |
| 185 | LCMS: 533.2 [M + H]⁺;<br>¹H NMR (400 MHz, DMSO-d₆ δ = 8.42 (s, 1H), 8.13-7.87 (m, 1H), 7.62-7.27 (m, 2H), 5.60-5.44 (m, 1H), 5.21 (s, 1H), 5.03 (d, J = 6.0 Hz, 1H), 4.95-4.81 (m, 1H), 4.68 (t, J = 8.4 Hz, 1H), 4.55 (s, 1H), 4.38 (dd, J = 4.4, 8.4 Hz, 1H), 4.21-4.06 (m, 1H), 3.86-3.69 (m, 1H), 3.67-3.59 (m, 1H), 3.51-3.45 (m, 1H), 2.78 (s, 3H), 2.04-1.95 (m, 1H), 1.65-1.52 (m, 7H) ppm. |
| 186 | LCMS: 500.2 [M + H]⁺;<br>¹H NMR (400 MHz, DMSO-d₆ δ = 14.09-12.74 (m, 1H), 8.42 (br s, 1H), 8.28-7.98 (m, 2H), 7.66-7.28 (m, 2H), 5.22 (s, 1H), 5.07-4.98 (m, 1H), 4.56 (br s, 1H), 4.25-4.09 (m, 1H), 3.86-3.70 (m, 1H), 3.64 (br t, J = 5.7 Hz, 1H), 3.51-3.36 (m, 3H), 2.11-1.93 (m, 1H), 1.68-1.54 (m, 7H) ppm. |
| 187 | LCMS: 514.3 [M + H]⁺;<br>¹H NMR (400 MHz, DMSO-d₆ δ = 8.42 (s, 1H), 8.39 (s, 1H), 8.12-7.92 (m, 2H), 7.60-7.31 (m, 2H), 5.21 (d, J = 0.8 Hz, 1H), 5.09-4.96 (m, 2H), 4.56 (s, 1H), 4.23-4.09 (m, 1H), 3.97 (s, 3H), 3.85-3.69 (m, 1H), 3.64 (t, J = 5.6 Hz, 1H), 3.55-3.45 (m, 1H), 2.06-1.94 (m, 1H), 1.73-1.67 (m, 1H), 1.64 (d, J = 6.6 Hz, 6H) ppm. |
| 188 | LCMS: 475.2 [M + H]⁺;<br>¹H NMR (400 MHz, DMSO-d₆ δ = 8.51-8.44 (m, 1H), 8.08-7.84 (m, 1H), 7.68-7.45 (m, 2H), 7.44-7.34 (m, 1H), 5.21 (s, 1H), 5.04 (d, J = 6.0 Hz, 1H), 4.56 (br s, 1H), 4.21-4.02 (m, 1H), 3.85-3.59 (m, 2H), 3.50 (s, 4H), 2.07-1.94 (m, 1H), 1.71-1.60 (m, 1H), 1.27 (br d, J = 6.6 Hz, 6H) ppm. |
| 190 | LCMS: 455.2 [M + H]⁺;<br>¹H NMR (400 MHz, DMSO-d₆ δ = 8.58-8.44 (m, 2H), 8.31 (d, J = 8.5 Hz, 1H), 7.86 (br d, J = 8.3 Hz, 1H), 7.37-7.29 (m, 1H), 5.22 (d, J = 1.1 Hz, 1H), 5.14 (td, J = 7.3, 14.3 Hz, 1H), 5.04 (d, J = 5.8 Hz, 1H), 4.57 (br s, 1H), 4.26-4.11 (m, 1H), 3.80 (d, J = 7.3 Hz, 1H), 3.70-3.58 (m, 1H), 3.50 (dd, J = 6.8, 8.3 Hz, 1H), 2.56 (s, 3H), 2.09 (s, 3H), 2.06-2.00 (m, 1H), 1.73-1.64 (m, 7H) ppm. |
| 191 | LCMS: 471.2 [M + H]⁺;<br>¹H NMR (400 MHz, DMSO-d₆ δ = 8.41 (s, 1H), 8.29 (d, J = 8.4 Hz, 1H), 8.26-8.10 (m, 1H), 7.86-7.64 (m, 1H), 7.63-7.55 (m, 1H), 5.25-5.18 (m, 1H), 5.18-5.09 (m, 1H), 5.09-4.98 (m, 1H), 4.62-4.50 (m, 1H), 4.24-4.10 (m, 1H), 3.83-3.58 (m, 2H), 3.48 (dd, J = 1.6, 5.5 Hz, 1H), 2.60-2.51 (m, 4H), 2.09 (s, 3H), 2.04-1.90 (m, 1H), 1.66 (d, J = 6.0 Hz, 6H) ppm. |
| 192 | LCMS: 491.1 [M + H]⁺;<br>¹H NMR (400 MHz, DMSO-d₆ δ = 8.69-8.56 (m, 1H), 8.52 (d, J = 3.6 Hz, 1H), 8.36 (d, J = 8.4 Hz, 1H), 8.00 (br d, J = 8.4 Hz, 1H), 7.47 (s, 2H), 5.30-5.16 (m, 2H), 5.04 (d, J = 5.8 Hz, 1H), 4.63-4.51 (m, 1H), 4.10 (s, 1H), 3.80 (d, J = 7.1 Hz, 1H), 3.72-3.58 (m, 1H), 3.58-3.43 (m, 1H), 2.74 (s, 3H), 2.11-1.95 (m, 1H), 1.84-1.59 (m, 7H) ppm. |
| 193 | LCMS: 470.1 [M + H]⁺;<br>¹H NMR (400 MHz, DMSO-d₆ δ = 8.65-8.53 (m, 1H), 8.52-8.48 (m, 1H), 8.32 (d, J = 8.4 Hz, 1H), 8.29-8.26 (m, 1H), 7.91-7.83 (m, 1H), 7.40-7.29 (m, 1H), 5.56-5.43 (m, 1H), 5.22 (s, 1H), 5.17-4.91 (m, 1H), 4.61-4.54 (m, 1H), 4.24-4.13 (m, 1H), 3.98-3.86 (m, 2H), 3.80 (br d, J = 6.8 Hz, 1H), 3.65 (br t, J = 5.9 Hz, 1H), 3.51 (br s, 2H), 2.16 (s, 3H), 2.07-1.99 (m, 1H), 1.76-1.67 (m, 7H) ppm. |
| 194 | LCMS: 484.2 [M + H]⁺;<br>¹H NMR (400 MHz, DMSO-d₆ δ = 8.65-8.53 (m, 1H), 8.52-8.48 (m, 1H), 8.32 (d, J = 8.4 Hz, 1H), 8.29-8.26 (m, 1H), 7.91-7.83 (m, 1H), 7.40-7.29 (m, 1H), 5.56-5.43 (m, 1H), 5.22 (s, 1H), 5.17-4.91 (m, 1H), 4.61-4.54 (m, 1H), 4.24-4.13 (m, 1H), 3.95-3.84 (m, 2H), 3.80 (br d, J = 6.8 Hz, 1H), 3.65 (br t, J = 5.9 Hz, 1H), 3.51 (br s, 2H), 2.16 (s, 3H), 2.07-1.99 (m, 1H), 1.76-1.67 (m, 7H) ppm. |
| 195 | LCMS: 498.2 [M + H]⁺;<br>¹H NMR (400 MHz, DMSO-d₆ δ = 8.62 (s, 1H), 8.49 (d, J = 3.6 Hz, 1H), 8.34 (d, J = 8.4 Hz, 1H), 7.88 (d, J = 8.4 Hz, 1H), 7.33 (d, J = 8.4 Hz, 1H), 5.54 (quin, J = 7.2 Hz, 1H), 5.22 (s, 1H), 5.03 (d, J = 5.6 Hz, 1H), 4.57 (s, 1H), 4.25-4.12 (m, 1H), 3.80 (d, J = 7.2 Hz, 1H), 3.70 (s, 2H), 3.65 (t, J = 5.6 Hz, 1H), 3.50 (dd, J = 6.4, 8.4 Hz, 1H), 2.29 (s, 6H), 2.18 (s, 3H), 2.10-1.98 (m, 1H), 1.71-1.66 (m, 7H) ppm. |
| 196 | LCMS: 501.4 [M + H]⁺;<br>¹H NMR (400 MHz, DMSO-d₆ δ = 8.67-8.48 (m, 2H), 8.33 (d, J = 8.4 Hz, 1H), 7.88 (br d, J = 8.1 Hz, 1H), 7.34 (d, J = 8.6 Hz, 1H), 5.60-5.42 (m, 1H), 5.23 (s, 1H), 5.04 (d, J = 5.8 Hz, 1H), 4.62-4.54 (m, 1H), 4.27-4.11 (m, 1H), 3.93-3.77 (m, 3H), 3.66 (br t, J = 5.9 Hz, 1H), 3.51 (dd, J = 6.2, 8.3 Hz, 1H), 3.32-3.25 (m, 4H), 2.23 (s, 3H), 2.10-1.96 (m, 1H), 1.77-1.65 (m, 7H) ppm. |
| 197 | LCMS: 528.4 [M + H]⁺;<br>¹H NMR (400 MHz, DMSO-d₆ δ = 8.68-8.54 (m, 1H), 8.33 (d, J = 8.4 Hz, 1H), 7.88 (d, J = 8.6 Hz, 1H), 7.35 (d, J = 8.8 Hz, 1H), 5.52-5.39 (m, 1H), 5.30-5.25 (m, 1H), 5.23 (d, J = 0.8 Hz, 1H), 5.15-5.09 (m, 1H), 5.04 (s, 1H), 4.58 (s, 1H), 4.29-4.11 (m, 1H), 4.00 (s, 2H), 3.81 (d, J = 7.2 Hz, 1H), 3.74-3.62 (m, 3H), 3.50 (d, J = 8.8 Hz, 1H), 3.43-3.36 (m, 2H), 2.23 (s, 3H), 2.09-1.99 (m, 1H), 1.72-1.66 (m, 7H) ppm. |
| 198 | LCMS: 526.2 [M + H]⁺;<br>¹H NMR (400 MHz, DMSO-d₆ δ = 8.62-8.56 (m, 1H), 8.49 (d, J = 3.6 Hz, 1H), 8.33 (d, J = 8.4 Hz, 1H), 7.87 (d, J = 8.8 Hz, 1H), 7.35-7.30 (m, 1H), 5.55-5.45 (m, 1H), 5.39-5.33 (m, 1H), 5.23-5.19 (m, 1H), 5.02 (d, J = 6.0 Hz, 1H), 4.60-4.52 (m, 1H), 4.25-4.11 (m, 2H), 3.93-3.86 (m, 2H), 3.84-3.76 (m, 1H), 3.70-3.62 (m, 1H), 3.58 (t, J = 6.8 Hz, 2H), 3.53-3.46 (m, 1H), 3.04-2.96 (m, 2H), 2.23 (s, 3H), 2.09-1.99 (m, 1H), 1.71-1.64 (m, 7H) ppm. |
| 200 | LCMS: 572.2 [M + H]⁺;<br>¹H NMR (400 MHz, DMSO-d₆ δ = 8.67 (br s, 1H), 8.51 (d, J = 3.5 Hz, 1H), 8.41 (d, J = 8.6 Hz, 1H), 7.95 (br d, J = 8.7 Hz, 1H), 7.36 (br d, J = 8.7 Hz, 1H), 5.69-5.56 (m, 1H), 5.23 (s, 1H), 5.04 (d, J = 5.6 Hz, 1H), 4.57 (br s, 1H), 4.26-4.09 (m, 2H), 3.99-3.88 (m, 1H), 3.80 (d, J = 7.1 Hz, 1H), 3.68-3.56 (m, 3H), 3.54-3.47 (m, 1H), 3.30-3.23 (m, 2H), 2.80 (br d, J = 1.6 Hz, 2H), 2.07-1.99 (m, 1H), 1.80 (br d, J = 6.7 Hz, 1H), 1.74 (br d, J = 7.2 Hz, 3H), 1.69 (br s, 1H), 1.05 (d, J = 6.2 Hz, 6H) ppm. |
| 201 | LCMS: 588.2 [M + H]⁺;<br>¹H NMR (400 MHz, DMSO-d₆ δ = 8.47 (br s, 1H), 8.42-8.24 (m, 2H), 7.84-7.64 (m, 1H), 7.61 (br d, J = |

| Cpd # | LCMS and ¹H NMR Data |
|---|---|
|  | 8.6 Hz, 1H), 5.68-5.54 (m, 1H), 5.21 (s, 1H), 5.04 (br d, J = 5.9 Hz, 1H), 4.55 (br s, 1H), 4.24-4.09 (m, 2H), 4.01-3.88 (m, 1H), 3.84-3.67 (m, 1H), 3.65-3.56 (m, 3H), 3.52-3.46 (m, 1H), 3.31-3.25 (m, 2H), 2.80 (br d, J = 2.4 Hz, 2H), 2.06-1.94 (m, 1H), 1.77 (br s, 3H), 1.71 (br d, J = 7.1 Hz, 3H), 1.69-1.63 (m, 1H), 1.05 (d, J = 6.4 Hz, 6H) ppm. |
| 202 | LCMS: 546.2 [M + H]⁺; ¹H NMR (400 MHz, DMSO-d₆ δ = 8.68 (br d, J = 4.0 Hz, 1H), 8.51 (d, J = 3.7 Hz, 1H), 8.43 (d, J = 8.6 Hz, 1H), 7.96 (br d, J = 8.2 Hz, 1H), 7.36 (br d, J = 8.7 Hz, 1H), 5.45-5.35 (m, 1H), 5.31-5.13 (m, 2H), 5.03 (br d, J = 5.6 Hz, 1H), 4.57 (br s, 1H), 4.30-4.09 (m, 1H), 4.00 (br d, J = 4.9 Hz, 2H), 3.80 (d, J = 7.1 Hz, 1H), 3.65 (br t, J = 6.1 Hz, 1H), 3.52-3.47 (m, 1H), 2.99-2.88 (m, 2H), 2.79-2.65 (m, 1H), 2.46-2.41 (m, 1H), 2.25-2.13 (m, 1H), 2.07-2.00 (m, 1H), 1.98-1.85 (m, 1H), 1.74 (br d, J = 7.0 Hz, 6H), 1.70-1.65 (m, 1H) ppm. |
| 204 | LCMS: 620.5 [M + H]⁺; ¹H NMR (400 MHz, DMSO-d₆ δ = 8.53-8.35 (m, 2H), 8.34-8.28 (m, 2H), 7.96-7.68 (m, 1H), 7.64-7.60 (m, 1H), 7.53-7.33 (m, 1H), 5.41-5.25 (m, 1H), 5.21 (s, 1H), 5.08-5.00 (m, 1H), 4.59-4.50 (m, 1H), 4.34-4.12 (m, 2H), 4.11-4.00 (m, 1H), 3.85-3.67 (m, 1H), 3.67-3.58 (m, 3H), 3.52-3.46 (m, 1H), 2.99-2.88 (m, 2H), 2.54 (s, 1H), 2.03-1.97 (m, 1H), 1.85 (d, J = 6.4 Hz, 3H), 1.80-1.50 (m, 5H), 1.02-0.83 (m, 6H) ppm. |
| 205 | LCMS: 570.3 [M + H]⁺; ¹H NMR (400 MHz, DMSO-d₆ δ = 8.51-8.43 (m, 1H), 8.36-8.19 (m, 2H), 7.83-7.54 (m, 2H), 6.32 (s, 1H), 5.67-5.51 (m, 1H), 5.20 (s, 1H), 5.05 (br d, J = 5.5 Hz, 1H), 4.55 (br s, 1H), 4.31-4.09 (m, 1H), 3.83-3.67 (m, 1H), 3.65-3.56 (m, 3H), 3.49 (br d, J = 8.4 Hz, 1H), 3.43 (br d, J = 14.4 Hz, 1H), 3.30-3.22 (m, 2H), 2.75 (br d, J = 2.1 Hz, 2H), 2.07-1.94 (m, 1H), 1.79-1.71 (m, 3H), 1.67 (br d, J = 7.0 Hz, 3H), 1.64 (br d, J = 5.7 Hz, 1H), 1.03 (br d, J = 6.2 Hz, 6H) ppm. |
| 207 | LCMS: 540.2 [M + H]⁺; ¹H NMR (400 MHz, DMSO-d₆ δ = 8.72-8.55 (m, 1H), 8.49 (d, J = 3.8 Hz, 1H), 8.34 (d, J = 8.4 Hz, 1H), 7.88 (br d, J = 8.4 Hz, 1H), 7.33 (d, J = 8.5 Hz, 1H), 5.51 (td, J = 7.2, 14.3 Hz, 1H), 5.22 (d, J = 1.1 Hz, 1H), 5.06-4.99 (m, 1H), 4.70 (br d, J = 3.5 Hz, 1H), 4.57 (br s, 1H), 4.27-4.13 (m, 2H), 3.95-3.85 (m, 2H), 3.80 (d, J = 7.1 Hz, 1H), 3.65 (br t, J = 5.8 Hz, 1H), 3.53-3.47 (m, 1H), 2.85-2.77 (m, 1H), 2.77-2.69 (m, 1H), 2.57-2.54 (m, 1H), 2.46-2.43 (m, 1H), 2.19 (s, 3H), 2.08-1.97 (m, 2H), 1.71-1.64 (m, 7H), 1.61-1.54 (m, 1H) ppm. |
| 208 | LCMS: 560.2 [M + H]⁺; ¹H NMR (400 MHz, DMSO-d₆ δ = 8.72-8.56 (m, 1H), 8.51-8.47 (m, 1H), 8.34 (d, J = 8.4 Hz, 1H), 7.89 (br d, J = 8.3 Hz, 1H), 7.33 (d, J = 8.6 Hz, 1H), 5.45-5.36 (m, 1H), 5.22 (d, J = 1.1 Hz, 1H), 5.03 (d, J = 5.8 Hz, 1H), 4.57 (br s, 1H), 4.28-4.10 (m, 1H), 4.01 (s, 2H), 3.80 (d, J = 7.3 Hz, 1H), 3.65 (br t, J = 6.3 Hz, 1H), 3.53-3.47 (m, 1H), 3.10-3.01 (m, 2H), 2.85 (br t, J = 6.9 Hz, 2H), 2.28-2.18 (m, 5H), 2.08-2.00 (m, 1H), 1.71 (br d, J = 7.0 Hz, 7H) ppm. |
| 209 | LCMS: 554.4 [M + H]⁺; ¹H NMR (400 MHz, DMSO-d₆ δ = 8.67-8.55 (m, 1H), 8.53-8.47 (m, 1H), 8.30 (d, J = 8.3 Hz, 1H), 7.92 (br d, J = 8.4 Hz, 1H), 7.36 (br d, J = 8.4 Hz, 1H), 6.32 (s, 1H), 5.68-5.52 (m, 1H), 5.22 (s, 1H), 5.05 (d, J = 5.7 Hz, 1H), 4.57 (br s, 1H), 4.31-4.11 (m, 2H), 3.80 (br d, J = 7.2 Hz, 1H), 3.68-3.58 (m, 3H), 3.53-3.48 (m, 1H), 3.43 (br d, J = 14.1 Hz, 1H), 3.31-3.25 (m, 2H), 2.81-2.70 (m, 2H), 2.09-1.97 (m, 1H), 1.76 (br d, J = 6.6 Hz, 3H), 1.70 (br d, J = 7.2 Hz, 3H), 1.68-1.60 (m, 1H), 1.04 (d, J = 6.2 Hz, 6H) ppm. |
| 210 | LCMS: 528.3 [M + H]⁺; ¹H NMR (400 MHz, DMSO-d₆ δ = 8.70-8.54 (m, 1H), 8.50 (d, J = 3.7 Hz, 1H), 8.31 (d, J = 8.4 Hz, 1H), 7.92 (br d, J = 8.6 Hz, 1H), 7.36 (br d, J = 8.4 Hz, 1H), 6.22 (s, 1H), 5.41-5.32 (m, 1H), 5.31-5.12 (m, 2H), 5.04 (br d, J = 5.6 Hz, 1H), 4.57 (br s, 1H), 4.29-4.09 (m, 1H), 3.85-3.74 (m, 3H), 3.65 (br t, J = 6.1 Hz, 1H), 3.53-3.46 |
|  | (m, 1H), 2.94-2.82 (m, 2H), 2.75-2.61 (m, 1H), 2.42-2.36 (m, 1H), 2.26-2.09 (m, 1H), 2.07-1.9 (m, 1H), 1.96-1.83 (m, 1H), 1.71 (br d, J = 6.8 Hz, 6H), 1.67-1.61 (m, 1H) ppm. |
| 211 | LCMS: 540.2 [M + H]⁺; ¹H NMR (400 MHz, DMSO-d₆ δ = 8.72-8.54 (m, 1H), 8.50 (d, J = 3.8 Hz, 1H), 8.35 (d, J = 8.4 Hz, 1H), 7.91 (br d, J = 8.3 Hz, 1H), 7.34 (d, J = 8.6 Hz, 1H), 5.22 (d, J = 1.0 Hz, 1H), 5.11-4.92 (m, 2H), 4.73 (s, 2H), 4.57 (br s, 1H), 4.28 (t, J = 7.9 Hz, 2H), 4.24-4.11 (m, 1H), 3.79 (br d, J = 7.3 Hz, 1H), 3.65 (br t, J = 5.9 Hz, 1H), 3.54-3.45 (m, 3H), 2.19 (s, 3H), 2.02 (br dd, J = 5.9, 12.8 Hz, 1H), 1.74-1.68 (m, 7H) ppm. |
| 212 | LCMS: 544.2 [M + H]⁺; ¹H NMR (400 MHz, DMSO-d₆ δ = 8.70-8.51 (m, 1H), 8.50 (d, J = 3.8 Hz, 1H), 8.35 (d, J = 8.4 Hz, 1H), 7.91 (br d, J = 8.4 Hz, 1H), 7.34 (d, J = 8.9 Hz, 1H), 5.22 (d, J = 1.1 Hz, 1H), 5.09-4.96 (m, 2H), 4.80-4.61 (m, 3H), 4.60-4.54 (m, 1H), 4.27-4.12 (m, 1H), 3.79 (br d, J = 7.1 Hz, 1H), 3.65 (br t, J = 5.8 Hz, 1H), 3.58 (t, J = 8.3 Hz, 1H), 3.53-3.47 (m, 1H), 3.15-3.07 (m, 1H), 2.23-2.16 (m, 3H), 2.06-1.98 (m, 1H), 1.75-1.65 (m, 7H), 1.33-1.26 (m, 3H) ppm. |
| 213 | LCMS: 598.2 [M + H]⁺; ¹H NMR (400 MHz, DMSO-d₆ δ = 8.42 (s, 1H), 8.35 (d, J = 8.4 Hz, 1H), 8.26 (s, 1H), 7.26 (d, J = 8.4 Hz, 1H), 7.27 (d, J = 8.4 Hz, 1H), 5.22 (s, 1H), 5.08 (quin, J = 7.2 Hz, 1H), 4.80-4.61 (m, 1H), 4.58-4.51 (m, 1H), 4.23-4.12 (m, 1H), 3.85-3.76 (m, 1H), 3.68-3.60 (m, 1H), 3.53 (d, J = 9.2 Hz, 1H), 3.02 (s, 9H), 2.10-2.02 (m, 5H), 1.76-1.68 (m, 9H) ppm. |
| 214 | LCMS: 570.4 [M + H]⁺; ¹H NMR (400 MHz, DMSO-d₆ δ = 8.41 (s, 1H), 8.38 (d, J = 8.4 Hz, 1H), 8.27 (s, 1H), 7.75 (dd, J = 1.2, 8.4 Hz, 1H), 7.16-6.94 (m, 1H), 5.23 (s, 1H), 4.67 (td, J = 7.2, 14.0 Hz, 1H), 4.55 (s, 1H), 4.19 (s, 1H), 3.82-3.75 (m, 4H), 3.75-3.52 (m, 6H), 3.41-3.37 (m, 2H), 2.09 (dd, J = 5.6, 12.8 Hz, 1H), 1.98 (s, 3H), 1.85-1.70 (m, 7H) ppm. |
| 215 | LCMS: 546.2 [M + H]⁺; ¹H NMR (400 MHz, DMSO-d₆ δ = 8.44 (d, J = 2.8 Hz, 1H), 7.31 (d, J = 8.4 Hz, 1H), 7.09 (s, 1H), 5.21 (s, 1H), 4.56 (s, 1H), 4.06 (d, J = 14.5 Hz, 2H), 3.77 (d, J = 6.8 Hz, 1H), 3.65 (s, 3H), 3.60 (dd, J = 2.4, 10.8 Hz, 2H), 3.48 (d, J = 8.4 Hz, 1H), 3.42 (d, J = 14.9 Hz, 2H), 2.79-2.65 (m, 5H), 2.04-1.98 (m, 1H), 1.66-1.59 (m, 1H), 1.28-1.21 (m, 3H), 1.01 (d, J = 6.4 Hz, 6H) ppm. |
| 219 | LCMS: 561.2 [M + H]⁺; ¹H NMR (400 MHz, DMSO-d₆ δ = 8.41 (br s, 1H), 8.09-7.85 (m, 1H), 7.54 (br d, J = 3.4 Hz, 2H), 6.19-600 (m, 1H), 5.21 (s, 1H), 5.05 (d, J = 6.0 Hz, 1H), 4.56 (br s, 1H), 4.24-4.07 (m, 1H), 3.84-3.69 (m, 1H), 3.68-3.55 (m, 5H), 3.54-3.43 (m, 1H), 2.54-2.41 (m, 4H), 2.08-1.91 (m, 1H), 1.71-1.57 (m, 7H), 1.53 (s, 6H) ppm. |
| 222 | LCMS: 567.1 [M + H]⁺; ¹H NMR (400 MHz, DMSO-d₆ δ = 8.53-8.31 (m, 1H), 8.13-7.82 (m, 1H), 7.66-7.21 (m, 2H), 6.15-5.95 (m, 1H), 5.21 (d, J = 1.1 Hz, 1H), 5.04 (d, J = 6.0 Hz, 1H), 4.55 (br s, 1H), 4.20-4.08 (m, 1H), 3.77-3.58 (m, 6H), 3.53-3.46 (m, 1H), 2.07-1.92 (m, 1H), 1.69 (br s, 1H), 1.61 (br d, J = 6.8 Hz, 6H), 1.54 (s, 6H) ppm. |
| 227 | LCMS: 493.2 [M + H]⁺; ¹H NMR (400 MHz, DMSO-d₆ δ = 8.64 (d, J = 14.0 Hz, 1H), 7.95 (d, J = 8.4 Hz, 1H), 7.50 (d, J = 6.4 Hz, 1H), 7.01-6.54 (m, 1H), 5.21 (s, 1H), 5.07 (d, J = 5.6 Hz, 1H), 4.56 (s, 1H), 4.32-4.08 (m, 1H), 3.85-3.58 (m, 2H), 3.55-3.41 (m, 4H), 3.32 (s, 3H), 2.85 (qd, J = 6.8, 13.2 Hz, 1H), 1.97 (dd, J = 6.0, 12.4 Hz, 1H), 1.72-1.59 (m, 1H), 1.29 (d, J = 6.8 Hz, 6H) ppm. |
| 231 | LCMS: 513.1 [M + H]⁺; ¹H NMR (400 MHz, DMSO-d₆ δ = 8.53-8.44 (m, 1H), 8.14-7.79 (m, 1H), 7.67 (d, J = 8.4 Hz, 1H), 7.41 (s, 1H), 5.20 (s, 1H), 5.05 (d, J = 6.0 Hz, 1H), 4.55 (s, 1H), 4.19-3.99 (m, 1H), 3.84-3.68 (m, 1H), 3.66-3.58 (m, 1H), 3.50-3.44 (m, 1H), 3.00-2.91 (m, 1H), 2.59 (s, 3H), 2.04-1.91 (m, 1H), 1.70-1.56 (m, 1H), 1.32 (d, J = 6.8 Hz, 6H) ppm. |

| Cpd # | LCMS and $^1$H NMR Data |
|---|---|
| 232 | LCMS: 518.3 [M + H]$^+$;<br>$^1$H NMR (400 MHz, DMSO-d$_6$ δ = 8.44 (d, J = 2.9 Hz, 1H), 7.32 (d, J = 8.4 Hz, 1H), 6.97-6.88 (m, 1H), 5.21 (s, 1H), 4.64-4.51 (m, 1H), 4.14-3.99 (m, 1H), 3.83-3.70 (m, 1H), 3.64-3.55 (m, 9H), 3.52 (s, 2H), 2.76-2.63 (m, 4H), 2.45 (br s, 3H), 2.09-1.94 (m, 1H), 1.69-1.57 (m, 1H) ppm. |
| 236 | LCMS: 457.1 [M + H]$^+$;<br>$^1$H NMR (400 MHz, DMSO-d$_6$ δ = 8.50-8.43 (m, 1H), 8.42-8.35 (m, 1H), 8.02 (d, J = 1.6 Hz, 1H), 7.96-7.71 (m, 1H), 7.53 (d, J = 3.2 Hz, 1H), 7.42-7.23 (m, 4H), 5.29-5.15 (m, 1H), 5.09-4.99 (m, 1H), 4.61-4.53 (m, 1H), 4.21 (s, 1H), 3.84-3.77 (m, 1H), 3.66-3.60 (m, 1H), 3.55 (s, 3H), 3.51-3.45 (m, 1H), 2.09-1.94 (m, 2H), 1.72-1.60 (m, 1H), 1.29 (d, J = 6.8 Hz, 6H) ppm. |
| 237 | LCMS: 457.1 [M + H]$^+$;<br>$^1$H NMR (400 MHz, DMSO-d$_6$ δ = 8.51-8.41 (m, 1H), 8.31 (d, J = 9.6 Hz, 1H), 8.03-7.89 (m, 1H), 7.79-7.49 (m, 2H), 6.73-6.58 (m, 1H), 5.24 (s, 1H), 4.96 (s, 1H), 4.60-4.50 (m, 1H), 4.20 (d, J = 3.2 Hz, 1H), 3.87-3.69 (m, 1H), 3.60 (s, 3H), 3.52-3.40 (m, 1H), 2.06-1.94 (m, 1H), 1.69-1.58 (m, 1H), 1.29 (d, J = 6.8 Hz, 6H), 1.26-1.18 (m, 2H) ppm. |
| 238 | LCMS: 524.1 [M + H]$^+$;<br>$^1$H NMR (400 MHz, DMSO-d$_6$ δ = 8.41 (br s, 1H), 8.06-7.81 (m, 1H), 7.62-7.29 (m, 2H), 5.21 (s, 1H), 5.04 (d, J = 6.0 Hz, 1H), 4.83-4.70 (m, 1H), 4.56 (br s, 1H), 4.22-4.08 (m, 1H), 3.93-3.70 (m, 2H), 3.67-3.59 (m, 1H), 3.55-3.44 (m, 1H), 3.42-3.35 (m, 1H), 3.21-3.07 (m, 4H), 2.14-1.91 (m, 1H), 1.57 (br d, J = 6.8 Hz, 6H) ppm. |
| 239 | LCMS: 524.1 [M + H]$^+$;<br>$^1$H NMR (400 MHz, DMSO-d$_6$ δ = 8.42 (s, 1H), 8.10-7.86 (m, 1H), 7.57-7.34 (m, 2H), 5.21 (d, J = 1.2 Hz, 1H), 4.77 (td, J = 6.8, 13.6 Hz, 2H), 4.56 (s, 1H), 4.22-4.06 (m, 1H), 3.88-3.69 (m, 1H), 3.63 (t, J = 6.0 Hz, 1H), 3.48 (d, J = 4.4 Hz, 1H), 2.84-2.65 (m, 3H), 2.64-2.58 (m, 1H), 2.29-2.22 (m, 1H), 2.08-1.96 (m, 1H), 1.70-1.65 (m, 1H), 1.63 (d, J = 6.8 Hz, 3H), 1.58 (d, J = 6.4 Hz, 3H) ppm. |
| 240 | LCMS: 524.1 [M + H]$^+$;<br>$^1$H NMR (400 MHz, DMSO-d$_6$ δ = 8.42 (s, 1H), 8.12-7.88 (m, 1H), 7.57-7.34 (m, 2H), 5.21 (s, 1H), 4.82-4.71 (m, H), 4.56 (s, 1H), 4.21-4.10 (m, 1H), 3.84-3.70 (m, 1H), 3.63 (t, J = 5.6 Hz, 1H), 3.51-3.48 (m, 1H), 2.84-2.65 (m, 3H), 2.65-2.57 (m, 1H), 2.29-2.23 (m, 1H), 2.04-1.96 (m, 1H), 1.69 (d, J = 2.4 Hz, 1H), 1.63 (d, J = 6.4 Hz, 3H), 1.58 (d, J = 6.8 Hz, 3H) ppm. |
| 241 | LCMS: 524.1 [M + H]$^+$;<br>$^1$H NMR (400 MHz, DMSO-d$_6$ δ =8.49-8.35 (m, 1H), 8.12-7.89 (m, 1H), 7.60-7.29 (m, 2H), 5.21 (s, 1H), 5.04 (d, J = 6.0 Hz, 1H), 4.84-4.71 (m, 2H), 4.56 (s, 1H), 4.21-4.06 (m, 1H), 3.85-3.70 (m, 1H), 3.67-3.60 (m, 1H), 3.54-3.45 (m, 1H), 2.81-2.69 (m, 2H), 2.65-2.58 (m, 1H), 2.31-2.23 (m, 1H), 2.07-1.95 (m, 1H), 1.66 (s, 1H), 1.63 (d, J = 6.8 Hz, 3H), 1.59 (d, J = 6.4 Hz, 3H) ppm. |
| 242 | LCMS: 506.1 [M + H]$^+$;<br>$^1$H NMR (400 MHz, DMSO-d$_6$ δ =8.48-8.34 (m, 1H), 8.05-7.82 (m, 1H), 7.58-7.32 (m, 2H), 5.28-5.07 (m, 2H), 5.05 (br d, J = 6.0 Hz, 1H), 4.78-4.69 (m, 1H), 4.56 (br s, 1H), 4.22-4.09 (m, 1H), 3.85-3.68 (m, 1H), 3.68-3.61 (m, 1H), 3.53-3.40 (m, 2H), 2.93-2.85 (m, 2H), 2.69-2.52 (m, 3H), 2.11-1.92 (m, 1H), 1.57 (br d, J = 6.8 Hz, 6H) ppm. |
| 246 | LCMS: 545.2 [M + H]$^+$;<br>$^1$H NMR (400 MHz, DMSO-d$_6$ δ = 8.41 ( s, 1H), 8.07-7.79 (m, 1H), 7.65-7.24 (m, 2H), 5.21 (s, 1H), 5.11-4.91 (m, 2H), 4.56 ( s, 1H), 4.25-4.07 (m, 1H), 3.89-3.69 (m, 1H), 3.64 (t, J = 6.0 Hz, 1H), 3.49 (d, J = 2.4 Hz, 1H), 3.16 (s, 3H), 2.90 (s, 3H), 2.73-2.57 (m, 2H), 2.13-1.90 (m, 1H), 1.65-1.54 ( m, 7H), 1.53-1.38 (m, 1H) ppm. |
| 247 | LCMS: 545.2 [M + H]$^+$;<br>$^1$H NMR (400 MHz, DMSO-d$_6$ δ = 8.41 ( s, 1H), 8.10-7.76 (m, 1H), 7.62-7.19 (m, 2H), 5.21 (s, 1H), 5.10-4.94 (m, 2H), 4.56 ( s, 1H), 4.24-4.06 (m, 1H), 3.89-3.69 (m, 1H), 3.66-3.58 (m, 1H), 3.49 ( s, 1H), 3.16 (s, 3H), 2.90 (s, 3H), 2.90 (s, 3H), 2.74-2.56 (m, 2H), 2.14-1.90 (m, 1H), 1.66-1.55 (m, 7H), 1.54-1.37 (m, 1H) ppm. |
| 248 | LCMS: 545.2 [M + H]$^+$;<br>$^1$H NMR (400 MHz, DMSO-d$_6$ δ = 8.49-8.27 (m, 1H), 8.06-7.73 (m, 1H), 7.61-7.18 (m, 2H), 5.21 (s, 1H), 5.12-4.83 (m, 2H), 4.55 (s, 1H), 4.28-4.02 (m, 1H), 3.89-3.67 (m, 1H), 3.63 (t, J = 5.8 Hz, 1H), 3.49 ( s, 1H), 3.21 (s, 3H), 2.69 (s, 3H), 2.64-2.53 ( m, 2H), 2.10-1.92 (m, 1H), 1.84 ( d, J = 3.9 Hz, 1H), 1.71-1.53 (m, 4H), 1.51-1.38 (m, 4H) ppm. |
| 249 | LCMS: 545.3 [M + H]$^+$;<br>$^1$H NMR (400 MHz, DMSO-d$_6$ δ = 8.50-8.27 (m, 1H), 8.03-7.73 (m, 1H), 7.59-7.26 (m, 2H), 5.21 (s, 1H), 5.14-4.87 (m, 2H), 4.55 (s, 1H), 4.28-4.03 (m, 1H), 3.89-3.68 (m, 1H), 3.63 (t, J = 5.7 Hz, 1H), 3.49 ( d, J = 1.1 Hz, 1H), 3.21 (s, 3H), 2.69 (s, 3H), 2.64-2.54 (m, 2H), 2.12-1.92 (m, 1H), 1.88-1.77 (m, 1H), 1.71-1.56 (m, 4H), 1.52-1.36 (m, 4H) ppm. |
| 250 | LCMS: 503.1 [M + H]$^+$;<br>$^1$H NMR (400 MHz, DMSO-d$_6$ δ = 9.13 (s, 1H), 8.75-8.55 (m, 1H), 8.53-8.39 (m, 1H), 8.01-7.73 (m, 1H), 7.60 ( d, J = 7.6 Hz, 1H), 5.49 (s, 1H), 5.22 (s, 1H), 5.04 (d, J = 6.0 Hz, 1H), 4.64 (td, J = 7.2, 14.7 Hz, 1H), 4.56 ( s, 1H), 4.23-4.08 (m, 1H), 3.86-3.69 (m, 1H), 3.64 ( d, J = 4.8 Hz, 1H), 3.55-3.44 (m, 1H), 2.14-1.93 (m, 1H), 1.70 (s, 6H), 1.68-1.663 (m, 1H), 1.56 ( d, J = 7.2 Hz, 6H) ppm. |
| 251 | LCMS: 461.3 [M + H]$^+$;<br>$^1$H NMR (400 MHz, DMSO-d$_6$ δ = 9.28-9.11 (m, 1H), 8.96 (d, J = 4.6 Hz, 1H), 8.48 (br s, 1H), 8.01-7.78 (m, 1H), 7.74-7.54 (m, 2H), 5.69 (s, 1H), 5.05 (br d, J = 4.0 Hz, 1H), 4.57 (br s, 1H), 4.22-4.10 (m, 1H), 3.86-3.70 (m, 1H), 3.64 (br s, 1H), 3.56-3.44 (m, 1H), 2.17-1.93 (m, 1H), 1.75-1.63 (m, 7H) ppm. |
| 253 | LCMS: 506.3 [M + H]$^+$;<br>$^1$H NMR (400 MHz, DMSO-d$_6$ δ = 9.20 (d, J = 2.0 Hz, 1H), 8.58-8.55 (m, 1H), 8.52 (d, J = 3.6 Hz, 1H), 8.50-8.45 (m, 1H), 8.14-8.05 (m, 1H), 7.40-7.33 (m, 1H), 5.49 (s, 1H), 5.24 (s, 1H), 5.04 (d, J = 6.0 Hz, 1H), 4.61-4.55 (m, 1H), 4.22-4.10 (m, 1H), 3.91-3.80 (m, 1H), 3.73-3.63 (m, 1H), 3.51 (t, J = 6.8 Hz, 1H), 2.12-1.99 (m, 1H), 1.70-1.64 (m, 1H), 1.59 (s, 6H) ppm. |
| 254 | LCMS: 445.2 [M + H]$^+$;<br>$^1$H NMR (400 MHz, DMSO-d$_6$ δ = 8.40 (s, 1H), 7.77-7.59 (m, 1H), 7.59-7.41 (m, 2H), 5.29 (s, 1H), 5.21 (s, 1H), 5.03 (d, J = 6.0 Hz, 1H), 4.55 (s, 1H), 4.25-4.02 (m, 1H), 3.85-3.69 (m, 1H), 3.67-3.59 (m, 1H), 3.55-3.41 (m, 1H), 2.77 (d, J = 5.0 Hz, 2H), 2.15-1.99 (m, 4H), 1.99 (s, 1H), 1.71-1.63 (m, 1H), 1.63-1.57 (m, 2H), 1.55 (s, 6H) ppm. |
| 261 | LCMS: 502.2 [M + H]$^+$;<br>$^1$H NMR (400 MHz, DMSO-d$_6$ δ = 9.01 (br s, 2H), 8.36-8.17 (m, 1H), 8.05-7.78 (m, 1H), 7.64 (br d, J = 1.1 Hz, 1H), 5.22 (s, 1H), 5.06 (br d, J = 5.6 Hz, 1H), 4.56 (br s, 1H), 4.20-4.10 (m, 1H), 3.88-3.67 (m, 3H), 3.66-3.44 (m, 6H), 2.50-2.36 (m, 4H), 2.01 (br d, J = 2.3 Hz, 1H), 1.72-1.59 (m, 1H) ppm. |
| 262 | LCMS: 530.3 [M + H]$^+$;<br>$^1$H NMR (400 MHz, DMSO-d$_6$ δ = 9.03 (br s, 1H), 8.62-8.48 (m, 1H), 8.45 (s, 1H), 8.29 (s, 1H), 7.90 (br d, J = 12.0 Hz, 1H), 7.32 (br d, J = 8.3 Hz, 1H), 5.23 (d, J = 1.1 Hz, 1H), 4.56 (br s, 1H), 4.20-4.13 (m, 1H), 3.81 (d, J = 7.1 Hz, 1H), 3.79-3.60 (m, 4H), 3.58-3.47 (m, 2H), 3.45-3.33 (m, 3H), 3.10-2.90 (m, 2H), 2.10-2.03 (m, 1H), 1.77-1.68 (m, 1H), 1.12 (br s, 6H) ppm. |
| 263 | LCMS: 561.1 [M + H]$^+$;<br>$^1$H NMR (400 MHz, DMSO-d$_6$ δ = 8.43 (s, 1H), 8.14-7.94 (m, 1H), 7.61-7.38 (m, 2H), 5.21 (s, 1H), 5.04 (d, J = 6.0 Hz, 1H), 4.82 (td, J = 6.8, J = 14.0 Hz, 1H), 4.74-4.63 (m, 2H), 4.56 (s, 1H), 4.43-4.37 (m, 1H), 4.21-4.08 (m, 1H), 3.83-3.69 (m, 1H), 3.63 (s, 1H), 3.50 (d, J = 4.0 Hz, 1H), 2.07-1.96 (m, 2H), 1.67 (d, J = 6.8 Hz, 4H), 1.55 (d, J = 6.4 Hz, 3H), 0.86 (d, J = 6.8 Hz, 3H), 0.80 (d, J = 7.2 Hz, 3H) ppm. |

| Cpd # | LCMS and ¹H NMR Data |
|---|---|
| 264 | LCMS: 462.1 [M + H]⁺;<br>¹H NMR (400 MHz, DMSO-d₆ δ = 9.38 (s, 1H), 8.50 (br s, 1H), 8.39-8.23 (m, 1H), 8.11-7.92 (m, 1H), 7.66 (br s, 1H), 5.78 (s, 1H), 5.22 (s, 1H), 5.06 (d, J = 6.2 Hz, 1H), 4.56 (br s, 1H), 4.23-4.10 (m, 1H), 3.85-3.72 (m, 1H), 3.68-3.60 (m, 1H), 3.50-3.46 (m, 1H), 2.06-1.96 (m, 1H), 1.66 (br s, 1H), 1.60 (s, 6H) ppm. |
| 265 | LCMS: 545.2 [M + H]⁺;<br>¹H NMR (400 MHz, DMSO-d₆ δ = 8.43(d, J = 4.0 Hz, 1H), 8.18 (d, J = 2.3 Hz, 1H), 7.69-7.57 (m, 1H), 7.28 (d, J = 8.4 Hz, 1H), 5.05 (d, J = 5.9 Hz, 1H), 4.97 (td, J = 6.9, 13.8 Hz, 1H), 4.64-4.51 (m, 1H), 4.23-4.04 (m, 1H), 4.02-3.88 (m, 1H), 3.87-3.76 (m, 2H), 3.75-3.65 (m, 2H), 3.62 (s, 3H), 3.59-3.49 (m, 2H), 3.48-3.39 (m, 1H), 2.42-2.29 (m, 1H), 2.29-2.12 (m, 1H), 2.10-1.98 (m, 1H), 1.74-1.66 (m, 1H), 1.62 (dd, J = 2.6, 6.7 Hz, 6H) ppm. |
| 266 | LCMS: 432.1 [M + H]⁺;<br>¹H NMR (400 MHz, DMSO-d₆ δ = 9.24 (s, 1H), 8.60 (d, J = 2.4 Hz, 1H), 7.53 (d, J = 8.8 Hz, 1H), 5.23 (s, 1H), 5.05 (d, J = 5.6 Hz, 1H), 4.58 (br s, 1H), 4.14-4.10 (m, 1H), 3.82-3.80 (m, 1H), 3.68-3.65 (m, 1H), 3.53-3.49 (m, 1H), 3.30-3.25 (m, 1H), 2.75 (br s, 3H), 2.10-2.02(m, 1H), 1.69-1.62 (m, 1H), 1.43 (d, J = 6.8 Hz, 6H) ppm. |
| 267 | LCMS: 504.1 [M + H]⁺;<br>¹H NMR (400 MHz, DMSO-d₆ δ = 8.41 (br s, 1H), 8.06-7.86 (m, 1H), 7.61-7.31 (m, 2H), 5.21 (s, 1H), 5.10-4.99 (m, 1H), 4.97-4.88 (m, 1H), 4.56 (br d, J = 1.6 Hz, 1H), 4.20-4.11 (m, 2H), 4.02-3.96 (m, 1H), 3.95-3.84 (m, 3H), 3.81-3.68 (m, 1H), 3.66-3.60 (m, 1H), 3.51-3.47 (m, 1H), 2.40-2.35 (m, 1H), 2.31-2.23 (m, 1H), 2.04-1.98 (m, 1H), 1.71-1.64 (m, 1H), 1.59 (br d, J = 6.4 Hz, 6H) ppm. |
| 268 | LCMS: 504.2 [M + H]⁺;<br>¹H NMR (400 MHz, DMSO-d₆ δ = 8.46-8.36 (m, 1H), 8.06-7.84 (m, 1H), 7.61-7.27 (m, 2H), 5.21 (d, J = 1.2 Hz, 1H), 5.10-5.00 (m, 1H), 4.98-4.87 (m, 1H), 4.60-4.51 (m, 1H), 4.23-4.06 (m, 2H), 4.01-3.96 (m, 1H), 3.95 (s, 3H), 3.83-3.68 (m, 1H), 3.68-3.59 (m, 1H), 3.54-3.44 (m, 1H), 2.40 (br d, J = 4.8 Hz, 1H), 2.33-2.26 (m, 1H), 2.04-1.97 (m, 1H), 1.66 (br s, 1H), 1.60 (br d, J = 6.8 Hz, 6H) ppm. |
| 269 | LCMS: 488.2 [M + H]⁺;<br>¹H NMR (400 MHz, DMSO-d₆ δ = 8.43 (d, J = 4.0 Hz, 1H), 8.28-8.10 (m, 1H), 7.63 (br d, J = 11.6 Hz, 1H), 7.27 (d, J = 8.4 Hz, 1H), 5.23 (s, 1H), 5.10-5.00 (m, 1H), 4.99-4.89 (m, 1H), 4.57 (br d, J = 2.0 Hz, 1H), 4.21-4.07 (m, 2H), 4.02-3.96 (m, 1H), 3.96-3.84 (m, 3H), 3.81 (d, J = 7.6 Hz, 1H), 3.67 br t, J = 5.2 Hz, 1H), 3.56-3.48 (m, 1H), 2.42-2.35 (m, 1H), 2.32-2.24 (m, 1H), 2.11-2.00 (m, 1H), 1.73-1.66 (m, 1H), 1.62 (d, J = 6.8 Hz, 6H) ppm. |
| 270 | LCMS: 488.1 [M + H]⁺;<br>¹H NMR (400 MHz, DMSO-d₆ δ = 8.43 (d, J = 4.0 Hz, 1H), 8.24-8.11 (m, 1H), 7.68-7.58 (m, 1H), 7.27 (d, J = 8.4 Hz, 1H), 5.23 (s, 1H), 5.05 (d, J = 6.0 Hz, 1H), 4.95 (td, J = 6.8, 13.8 Hz, 1H), 4.58 (br d, J = 1.2 Hz, 1H), 4.20-4.10 (m, 2H), 4.01-3.96 (m, 1H), 3.95-3.84 (m, 3H), 3.81 (d, J = 7.6 Hz, 1H), 3.71-3.64 (m, 1H), 3.52 (dt, J = 3.2, 5.8 Hz, 1H), 2.43-2.35 (m, 1H), 2.33-2.25 (m, 1H), 2.09-2.25 (m, 1H), 2.09-1.99 (m, 1H), 1.68 (br s, 1H), 1.62 (dd, J = 3.2, 6.8 Hz, 6H) ppm. |
| 271 | LCMS: 554.2 [M + H]⁺;<br>¹H NMR (400 MHz, DMSO-d₆ δ = 8.68-8.52 (m, 1H), 8.50 (d, J = 3.8 Hz, 1H), 8.35 (d, J = 8.4 Hz, 1H), 7.91 (br d, J = 8.4 Hz, 1H), 7.34 (d, J = 8.6 Hz, 1H), 5.22 (d, J = 1.0 Hz, 1H), 5.08-5.00 (m, 2H), 4.75-4.55 (m, 4H), 4.29-4.10 (m, 1H), 3.79 (br d, J = 7.1 Hz, 1H), 3.65 (br t, J = 5.9 Hz, 1H), 3.58 (t, J = 8.3 Hz, 1H), 3.50 (br dd, J = 5.5, 8.3 Hz, 1H), 3.14-3.09 (m, 1H), 2.19 (s, 3H), 2.02 (br dd, J = 5.7, 12.4 Hz, 1H), 1.74-1.65 (m, 7H), 1.29 (d, J = 6.1 Hz, 3H) ppm. |
| 272 | LCMS: 519.1 [M + H]⁺;<br>¹H NMR (400 MHz, DMSO-d₆ δ = 8.48-8.38 (m, 1H), 8.11-7.91 (m, 1H), 7.66-7.33 (m, 2H), 5.21 (s, 1H), 5.04 (d, J = 6.0 Hz, 1H), 4.86-4.71 (m, 1H), 4.63 (t, J = 7.6 Hz, 2H), 4.56 (br s, 1H), 4.30-4.19 (m, 2H), 4.19-4.07 (m, 1H), 3.88-3.68 (m, 1H), 3.67-3.59 (m, 1H), 2.09-1.95 (m, 1H), 1.76-1.50 (m, 8H) ppm. |

Example 33: Phospho-Rb Expression Inhibition in MCF7 Cells Quantified by in Cell Western MCF7 cells were obtained from American Type Culture Collection (ATCC, HTB-22). MCF7 cells were plated in 96-well plates (VWR#10062-900, or Corning #3904) in 90 μL culture medium at a density of 20,000 cells/well in the DMEM growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 μL compound medium was added to each well in the cell plates. After administration of the compound, the cells were then incubated at 37° C. for 24 h. Upon completion, the cells were washed with PBS briefly. 150 μL/well of 4% formaldehyde was added and the plates were incubated at room temperature for 20 min. The cells were washed with PBS briefly, and permeabilized with 150 μL/well of ice cold 100% methanol for 10 min. The cells were washed with PBS briefly and blocked with 100 μL/well LI-COR blocking buffer for 1 h at room temperature with gentle shaking. The cells were incubated overnight at 4° C. with 50 μL primary antibody rabbit anti-Phospho-Rb (Ser807/811) (1:500, Cell Signaling, #8516) and anti-Rb (1:200, Santa Cruz, sc-73598) diluted in Intercept Blocking Buffer (LI-COR, #927-60001) containing 0.1% Tween 20. The next day, the cells were washed with 200 μL PBS containing 0.1% Tween 20, 5×5 mins at room temperature with gentle shaking, and incubated with 50 μL secondary antibody, IRDye® 800CW Goat anti-Rabbit IgG (1:1000, LI-COR, #926-32211) and IRDye® 680RD Goat anti-Mouse IgG (1:1000, LI-COR, #926-68070), in LI-COR blocking buffer with 0.2% Tween 20 for 1 h at room temperature with gentle shaking. The cells were washed with 200 μL PBS containing 0.1% Tween 20, 5×5 min at room temperature with gentle shaking. The cells were washed with PBS for 5 mins. 100 μL fresh PBS was added to each well and the plates were imaged on a LI-COR Odyssey CLX plate reader.

The p-Rb inhibition result of a compound disclosed herein and a reference compound is listed in Table 3. As shown in Table 3, compound 1 demonstrated higher potency in p-Rb inhibition than the reference compound. The reference compound is PF-07220060 (CAS #2380321-51-5).

TABLE 3

Inhibition of Cellular CDK4 Kinase Activity by Exemplary Compounds against MCF7 and 22RV1 Cells

| Cpd # | 1 | Reference Cpd |
|---|---|---|
| MCF7, pRb (Ser807/811), IC50 (uM) | 0.0404 | 0.0652 |
| 22RVI, GI50 (uM) | 0.144 | 0.153 |

Example 34: Cell Growth Inhibition of 22RV1 Cells

For cell growth assay, 22RV1 (ATCC, CRL-2505) cells were seeded in 96-well plates at 1000 cells/well in 90 µl of RPMI1640 growth medium containing 20% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 5 days. Upon completion, the plates were equilibrated at room temperature for approximately 10 min. 100 µl of CellTiter-Glo® Reagent (Promega) was added to each well. The plates were then incubated at room temperature for 10 min and luminescence was recorded by EnSpire plate reader (PerkinElmer).

The 22RV1 cell growth inhibition assay result of representative compound and the reference is listed in Table 3. Compound 1 showed slightly higher potency than the reference compound. The reference compound is PF-07220060 (CAS #2380321-51-5).

Example 35: CDK Protein Kinase Inhibition by the ADP-Glo Assay

This ADP-Glo assay measures ADP formed from a kinase reaction and indirectly quantifies the phosphorylation of peptide substrates by the CDK/cyclin protein complexes. The typical assays were carried out in Nanosyn by combining kinase/cyclin complexes, substrates, compounds, and cofactors (ATP and Mg2+) in a well of a 384-well microtiter plate (Corning 3824) and incubating at 22° C. (Table 4). At the end of the incubation, the reaction is quenched, and conversion is detected by luminescence using the Promega ADP-Glo™ Kinase Assay kit (catalog #V9102). Briefly, 5 µL of 1× enzyme and substrate buffer (or control), 50 ηL of 100× compound, and 0.5 µL of 10 mM ATP were sequentially added to a well of a 384-well plate. The assay plate was incubated at 22° C. according to assay conditions shown in Table 4.

The Final assay buffer mixture contains: 100 mM HEPES, pH 7.5, 0.1% BSA, 0.01% Triton X-100, 1 mM DTT, 5 mM $MgCl_2$, 10 µM Sodium Orthovanadate, 10 µM Beta-Glycerophosphate, 1000 µM Ultra Pure ATP (provided in the Promega ADP-Glo™ Kinase Assay kit), and 1% DMSO (from compound).

Upon completion, 5 µL of the ADP Glo reagent was added to each well and the plate was further incubated at room temperature for 45 min. 10 µL of the Kinase Detection Reagent was subsequently added to each well. After 10 min of incubation, the plate was read and analyzed on the BioTek Synergy microplate reader using BioTek Gen5 software.

CDK kinase inhibition assay conditions and the results of the representative compound and the reference compound are listed in Tables 4, 5, and 6. The reference compound is PF-07220060 (CAS #2380321-51-5). As shown in Tables 5 and 6, compound 1 is more potent than the reference compound. Compound 1 also displayed much better selectivity for CDK4 over CDK1, CDK2, CDK6 and CDK9 than the reference compound.

TABLE 5

Inhibition of Biochemical Kinase Activity by Exemplary Compounds against Representative Recombinant CDK Kinases

| Cpd # | 1 | Reference Cpd |
|---|---|---|
| CDK1-CYCLIN B, IC50 (uM) | 26.2 | 8.59 |
| CDK2-CYCLIN E, IC50 (uM) | >30 | >30 |
| CDK4-CYCLIN D1, IC50 (uM) | 0.00315 | 0.00437 |
| CDK6-CYCLIN D3, IC50 (uM) | 0.0638 | 0.0765 |
| CDK9-CYCLIN T1, IC50 (uM) | 4.88 | 1.88 |

TABLE 6

Selectivity of Exemplary Compounds against Representative Recombinant CDK Kinases

| Cpd # | 1 | Reference Cpd |
|---|---|---|
| CDK4 vs CDK1 | 8,317 | 1,966 |
| CDK4 vs CDK2 | >9,524 | >6,865 |
| CDK4 vs CDK6 | 20 | 18 |
| CDK4 vs CDK9 | 1,549 | 430 |

TABLE 4

CDK Assay Conditionslla

| Kinase | Vendor Catalog | Substrate | SEQ ID NO: | Kinase Conc (nM) | Substrate Conc (nM) | Incubation Time (h) |
|---|---|---|---|---|---|---|
| CDK1-CYCLIN B | Millipore 14-450 | FAM-PKTPKKAKKL-OH | 1 | 0.6 | 2.5 | 4 |
| CDK2-CYCLIN E1 | Millipore 14-475 | FAM-PKTPKKAKKL-OH | 1 | 8 | 10 | 4 |
| CDK4-CYCLIN D1 | ThermoFisher PV4400 | Ac-RRFRPASPLRGPPK-NH2 | 2 | 5 | 5 | 17 |
| CDK6-CYCLIN D3 | Carna 04-107 | Ac-RRFRPASPLRGPPK-NH2 | 2 | 8 | 5 | 17 |
| CDK9-CYCLIN T1 | Carna 04-110 | FAM-ACSYSPTSPSYSPTSPSYSPTSPSKK-NH2 | 3 | 6 | 5 | 17 |

Example 36: Human Hepatocyte Stability Assay

Human hepatocyte stability assay was performed at Pharmaron. Human hepatocytes from mixed genders were purchased from BioIVT (Product #X008001). Compounds and positive control were incubated with human hepatocytes. Verapmil was used as a positive control. The incubation was carried out with the test compound and positive control final concentration as 1 µM, in duplicate, over a total incubation period of 120 min. Samples were taken at 0, 15, 30, 60, 90 and 120 min and the reactions were stopped by the addition of acetonitrile with internal standard (100 nM alprazolam, 200 nM caffeine, and 100 nM tolbutamide). Samples were centrifuged for 45 min at 3,220 g. An aliquot of 100 µL of the supernatant was diluted by 100 µL ultra-pure water, and the mixture was used for LC/MS/MS analysis. The percent of parent remaining, intrinsic clearance ($CL_{int}$) and $t_{1/2}$ were calculated. The result is listed in Table 7. The reference compound is PF-07220060 (CAS #2380321-51-5).

As shown in Table 7, the result of the Verapamil validated the assay. Compound 1 demonstrated significantly higher stability than the reference compounds when incubated with human hepatocytes, which indicated compound 1 will have much lower clearance than the reference compound in humans.

TABLE 7

Human Hepatocyte Stability of Exemplary Compounds.

| Cpd | $t_{1/2}$ (min) | In vitro $CL_{int}$ (µL/min/$10^6$ cell) | Scaled-up $CL_{int}$ (mL/min/kg) | Predicted Hepatic $CL_H$ (mL/min/kg) | Hepatic Extraction Ratio (ER) |
|---|---|---|---|---|---|
| Verapamil | 15.5 | 89.6 | 277.9 | 19.2 | 0.92 |
| 1 | 555.7 | 2.5 | 6.4 | 4.9 | 0.23 |
| Reference Compound | 123.4 | 11.3 | 28.6 | 12.0 | 0.58 |

Example 37: Inhibition of Cellular Rb Phosphorylation in MCF7, SW1573-CDK6 KO and SW1573-CDK4 KO Cells and Inhibition of Growth in 22R$^V$1 Cells Generation of SW1573 cells with CDK4 or CDK6 knockout Parental SW1573 cells were obtained from the American Type Culture Collection (ATCC). CDK4 or CDK6 gene in SW1990 cells was knocked out using the CRISPR-Cas9 technology. First, gRNA complex of CDK4 or CDK6 was prepared with Alt-R CRISPR-Cas9 tracrRNA and crRNA CDK4 (5'-ATCTCGGTGAACGATGCAAT-3' (SEQ ID NO: 4)) or CDK6 (5'-GACCACGTTGGGGTGCTCGA-3' (SEQ ID NO: 5)) (IDT-Integrated DNA Technologies), and then ribonucleoprotein (RNP) complex of CDK4 or CDK6 was prepared with respective gRNA complex and Alt-R S.p. Cas9 Nuclease V3 (IDT-Integrated DNA Technologies). Next, 5×104/10 µL SW1573 cells were electroporated with the CDK4 or CDK6 RNP complex and Alt-R Cas9 Electroporation Enhancer using Neon Transfection System (Thermo Fisher). Cells were then plated in a 96-well plate to select single clones for validation of CDK4 or CDK6 knockout by western blot analysis.

Phospho-Rb expression inhibition quantified by in cell Western

MCF7 cells were obtained from American Type Culture Collection (ATCC, HTB-22). SW1573-CDK6 KO and SW1573-CDK4 KO cells were generated by the CRISPR-Cas9 technology. All cells were plated in 96-well plates (VWRW10062-900, or Corning #3904) in 90 µL culture medium at a density of 20,000 cells/well in the respective growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 24 hours. Upon completion, the cells were washed with PBS briefly. 150 µL/well of 4% formaldehyde was added and the plates were incubated at room temperature for 20 mins. The cells were washed with PBS briefly, and permeabilized with 150 µL/well of ice cold 100% methanol for 10 mins. The cells were washed with PBS briefly and blocked with 100 µL/well LI-COR blocking buffer for 1 hr at room temperature with gentle shaking. The cells were incubated overnight at 4° C. with 50 µL primary antibody rabbit anti-Phospho-Rb (Ser807/811) (1:500, Cell Signaling, #8516) and anti-Rb (1:200, Santa Cruz, sc-73598) diluted in Intercept Blocking Buffer (LI-COR, #927-60001) containing 0.1% Tween 20. The next day, the cells were washed with 200 µL PBS containing 0.1% Tween 20, 5×5 mins at room temperature with gentle shaking, and incubated with 50 µL secondary antibody, IRDye® 800CW Goat anti-Rabbit IgG (1:1000, LI-COR, #926-32211) and IRDye® 680RD Goat anti-Mouse IgG (1:1000, LI-COR, #926-68070), in LI-COR blocking buffer with 0.2% Tween 20 for 1 hr at room temperature with gentle shaking. The cells were washed with 200 µL PBS containing 0.1% Tween 20, 5×5 mins at room temperature with gentle shaking. The cells were washed with PBS for 5 mins. 100 µL fresh PBS was added to each well and the plates were imaged on a LI-COR Odyssey CLX plate reader.

Cell growth inhibition of 22RV1 cells

22RV1 cells were obtained from American Type Culture Collection (ATCC, CRL-2505). 22RV1 cells were seeded in 96-well plates at 1000 cells/well in 90 µL of RPMI1640 growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 5 days. Upon completion, the plates were equilibrated at room temperature for approximately 10 minutes. 100 µL of CellTiter-Glo® Reagent (Promega) was added to each well. The plates were then incubated at room temperature for 10 minutes and luminescence was recorded by EnSpire plate reader (PerkinElmer).

The results of inhibition of cellular Rb phosphorylation in MCF7, SW1573-CDK6 KO and SW1573-CDK4 KO cells and inhibition of growth in 22RV1 cells by exemplary compounds are summarized in Table 8.

TABLE 8

Inhibition of cellular Rb phosphorylation in MCF7, SW1573-CDK6 KO and SW1573-CDK4 KO cells and inhibition of growth in 22RV1 cells by Exemplary Compounds.

| Cpd # | MCF7 pRb IC$_{50}$ (nM) (A ≤40 nM; B >40 nM and ≤150 nM; C >150 nM and ≤1000 nM, D, >1000 nM) | 22RV1 Cell Growh GI$_{50}$, (nM) (A ≤120 nM; B >120 nM and ≤450 nM; C >450 nM and ≤3000 nM, D, >3000 nM) | SW1573 CDK6 KO pRb IC50 (nM) (A ≤40 nM; B >40 nM and ≤150 nM; C >150 nM and ≤1000 nM, D >1000 nM) | SW1573 CDK4 KO pRb IC50 (nM) (A ≤40 nM; B >40 nM and ≤150 nM; C >150 nM and ≤1000 nM, D >1000 nM) |
|---|---|---|---|---|
| 1 | B | A | A | D |
| 2 | A | A | | |
| 4 | B | B | | |
| 5 | C | B | | |
| 13 | B | B | | |
| 23 | B | B | | |
| 25 | B | B | A | D |
| 26 | B | A | | |
| 27 | B | B | | |
| 29 | C | C | | |
| 32 | A | A | | |
| 33 | B | B | | |
| 37 | B | B | | |
| 38 | A | B | | |
| 49 | B | B | | |
| 66 | B | B | B | D |
| 72 | B | B | | |
| 136 | A | A | | |
| 137 | C | D | | |
| 151 | B | B | | |
| 163 | B | B | | |
| 167 | B | A | | |
| 168 | B | A | | |
| 169 | B | A | | |
| 170 | B | C | | |
| 172 | B | B | | |
| 173 | B | B | | |
| 174 | B | B | | |
| 175 | B | B | | |
| 176 | C | C | | |
| 179 | B | B | | |
| 180 | D | C | | |
| 181 | C | B | | |
| 182 | C | B | | |
| 183 | D | D | | |
| 184 | C | B | | |
| 185 | C | C | | |
| 186 | C | B | | |
| 187 | C | B | | |
| 188 | C | B | | |
| 189 | A | A | | |
| 190 | B | B | | |
| 191 | B | C | C | D |
| 192 | C | B | | |
| 193 | C | B | | |
| 194 | B | B | B | D |
| 195 | B | B | A | D |
| 196 | B | B | B | D |
| 197 | B | B | B | D |
| 198 | C | C | | |
| 199 | A | A | A | C |
| 200 | B | B | | |
| 201 | B | B | B | D |
| 202 | C | C | B | D |
| 204 | B | B | B | D |
| 205 | B | B | B | D |
| 206 | A | A | A | C |
| 207 | B | A | | |
| 208 | A | A | | |
| 209 | B | B | | |
| 210 | C | C | | |
| 211 | D | D | | |
| 212 | C | D | | |
| 213 | D | D | | |
| 214 | D | D | | |

TABLE 8-continued

Inhibition of cellular Rb phosphorylation in MCF7, SW1573-CDK6 KO and SW1573-CDK4 KO cells and inhibition of growth in 22RV1 cells by Exemplary Compounds.

| Cpd # | MCF7 pRb IC$_{50}$ (nM) (A ≤40 nM; B >40 nM and ≤150 nM; C >150 nM and ≤1000 nM, D, >1000 nM) | 22RV1 Cell Growh GI$_{50}$, (nM) (A ≤120 nM; B >120 nM and ≤450 nM; C >450 nM and ≤3000 nM, D, >3000 nM) | SW1573 CDK6 KO pRb IC50 (nM) (A ≤40 nM; B >40 nM and ≤150 nM; C >150 nM and ≤1000 nM, D >1000 nM) | SW1573 CDK4 KO pRb IC50 (nM) (A ≤40 nM; B >40 nM and ≤150 nM; C >150 nM and ≤1000 nM, D >1000 nM) |
|---|---|---|---|---|
| 215 | B | C | | |
| 216 | A | A | A | C |
| 217 | B | B | A | C |
| 219 | B | B | | |
| 222 | C | C | | |
| 223 | A | A | A | B |
| 227 | A | A | A | C |
| 230 | A | B | A | C |
| 231 | B | C | | |
| 232 | C | C | | |
| 236 | C | C | | |
| 237 | B | C | | |
| 238 | A | B | B | C |
| 239 | A | A | A | C |
| 240 | A | A | A | C |
| 241 | B | C | | |
| 242 | A | B | | |
| 243 | B | B | B | D |
| 244 | B | B | | |
| 245 | B | B | | |
| 246 | B | B | | |
| 247 | C | C | | |
| 248 | B | C | C | D |
| 249 | D | D | | |
| 250 | A | A | | |
| 251 | B | A | | |
| 252 | A | A | A | C |
| 253 | C | B | | |
| 254 | C | B | | |
| 255 | A | A | A | D |
| 256 | A | A | A | D |
| 257 | A | A | A | C |
| 258 | D | D | | |
| 259 | A | A | A | C |
| 260 | B | B | | |
| 261 | C | C | | |
| 262 | C | C | | |
| 263 | C | D | | |
| 264 | C | C | | |
| 265 | B | B | B | D |
| 266 | A | A | | |
| 267 | B | B | | |
| 268 | A | A | B | D |
| 269 | B | B | C | D |
| 270 | B | B | B | D |
| 271 | C | D | | |
| 272 | B | C | | |
| 275 | B | C | B | D |
| 276 | A | B | A | C |
| 277 | A | B | A | D |
| 278 | A | A | | |
| 279 | C | A | | |
| 280 | C | A | | |
| 283 | A | A | | |
| 284 | A | A | | |
| 285 | A | A | | |
| 286 | A | A | | |
| 291 | C | B | | |
| 292 | B | B | | |
| 293 | A | A | A | C |
| 294 | C | C | | |
| 295 | C | D | | |
| 296 | C | C | | |
| 297 | C | C | | |
| 298 | C | C | B | D |

Example 38: In Vivo Demonstration of Activity for Compounds of Formula I

Anti-tumor efficacy study in the MCF7 human breast cancer xenograft model

A 0.36 mg 17β-estradiol sustained-release tablet (Innovative Research of America, 0.36 mg/pellet/60-day release, Cat. No.: SE-121) was inoculated into the left back of each BALB/c nude mouse 3 days before cell inoculation. Subsequently, $1 \times 10^6$ MCF7 cells in 0.1 mL of phosphate-buffered saline mixed with 0.1 mL matrigel (total 0.2-mL) was inoculated subcutaneously at the right flank of each mouse for tumor development. Treatment was started on day 10 after tumor cell inoculation when the average tumor size reached approximately 141 mm$^3$. The animals were assigned into groups using an Excel-based randomization software performing stratified randomization based upon their tumor volumes. Each group consisted of 6 tumor-bearing mice. A compound of Formula I from Table 8 (hereinafter "CDK4 inhibitor A") was freshly formulated in 10% dimethyl sulfoxide (DMSO)/30% polyethylene glycol 400 (PEG400)/60% aqueous solution containing 20% 2-hydroxypropyl-β-cyclodextrin (HP β-CD) (pH=5) and dosed twice daily. Tumor volume was determined twice weekly. As can be seen from FIG. 1, a significant decrease in tumor volume was observed for CDK4 inhibitor A of the present disclosure during the study when compared to the vehicle following dosing.

Equivalents and Incorporation by Reference

While aspects of the present disclosure have been particularly shown and described with reference to certain embodiments and various alternate embodiments, it will be understood by persons skilled in the relevant art that various changes in form and details can be made therein without departing from the spirit and scope of the present disclosure.

All references, issued patents, and patent applications cited within the body of the instant specification are hereby incorporated by reference in their entirety, for all purposes. In particular, U.S. Provisional Patent Application No. 63/497,015, filed Apr. 19, 2023, U.S. Provisional Patent Application No. 63/515,021, filed Jul. 21, 2023, and International Patent Application No. PCT/US2024/025495, filed Apr. 19, 2024, are hereby incorporated by reference in their entirety.

---

What is claimed is:

1. A compound, wherein the compound is represented by Formula IA or is a pharmaceutically acceptable salt thereof:

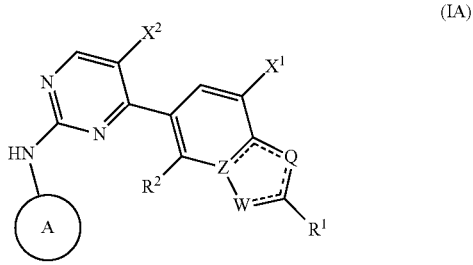

(IA)

wherein:
- ⚌ is a single bond or a double bond;
- $R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;
- each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)$OR^{1B}$, —C(=O)$N(R^{1B})_2$, —NHC(=O)$OR^{1B}$, and a 4-6 membered heterocyclic group, wherein the 4-6 membered heterocyclic group is optionally substituted with 1, 2, or 3 $R^{1C}$;
- each $R^{1B}$ is independently selected from hydrogen, $C_1$-$C_6$ alkyl, and $C_3$-$C_6$ cycloalkyl;
- each $R^{1C}$ is independently selected from hydrogen, hydroxyl, halogen, an oxo group, $C_1$-$C_6$ alkyl, and $C_3$-$C_6$ cycloalkyl;
- $R^2$ is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;
- $X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;
- Q is N or $CR^Q$, wherein $R^Q$ is independently selected from hydrogen, halogen, and cyano;
- Z is C;
- W is selected from $C(R^{W1})_2$, O, S, N, and $NR^{W2}$; wherein $R^{W1}$ is independently selected from hydrogen, halogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$;
- $R^{W2}$ is selected from hydrogen, $C_1$-$C_6$ alkyl, $C_3$-$C_6$ cycloalkyl, 5-8 membered bicyclic carbocyclic group, 5-8 membered bicyclic heterocyclic group, and a 3-8 membered heterocyclic group, wherein each of the $C_1$-$C_6$ alkyl and $C_3$-$C_6$ cycloalkyl is optionally substituted with 1, 2, or 3 $R^{1D}$; and
- each $R^{1D}$ is independently selected from halogen, $C_1$-$C_6$ alkyl, $C_1$-$C_6$ haloalkyl, and hydroxyl; or
- W and $R^1$ may be taken together with the C atom to which both are attached to form a carbocyclic ring of 5-8 atoms or a heterocyclic ring of 5-8 atoms, wherein the carbocyclic ring and heterocyclic ring is each optionally substituted with 1, 2, 3, or 4 $R^{1E}$; or
- W, Z, $R^2$, and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$;
- each $R^{1E}$ is independently selected from $C_1$-$C_6$ alkyl, hydroxyl, and an oxo group;
- Ring A is

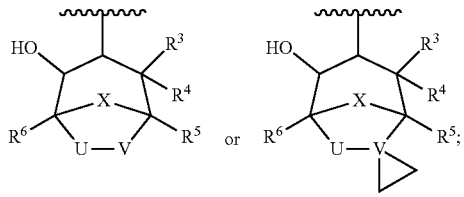

wherein:
- $R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;
- $R^5$ and $R^6$ are independently selected from hydrogen, deuterium, $C_1$-$C_6$ alkyl, $C_3$-$C_6$ cycloalkyl, and aryl, wherein the $C_1$-$C_6$ alkyl is optionally substituted with hydroxyl;
- X is O or N—S(O)$_2$—$R^X$, wherein $R^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;
- U is O or $C(R^U)_2$, wherein $R^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and
- V is O, C, or $C(R^V)_2$, wherein $R^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

2. The compound according to claim 1, wherein the compound of Formula IA is represented by Formula IA':

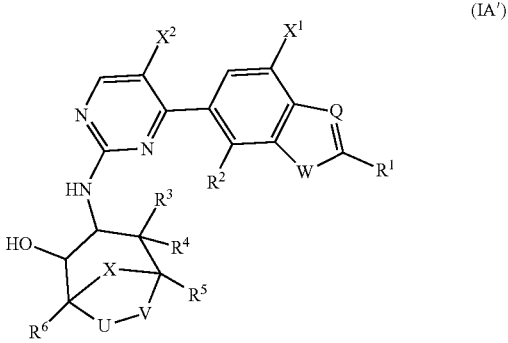

(IA')

wherein:
R$^1$ is selected from C$_1$-C$_8$ alkyl, C$_3$-C$_6$ cycloalkyl, C$_1$-C$_5$ haloalkyl, C$_3$-C$_6$ cyclic haloalkyl, C$_5$-C$_7$ bicyclic alkyl, C$_1$-C$_6$ aminoalkyl, C$_1$-C$_6$ alkoxy, an oxo group, a 4-6 membered heterocyclic group, 6-membered aryl, and 5-6 membered heteroaryl, wherein each of the C$_1$-C$_5$ alkyl, C$_3$-C$_6$ cycloalkyl, C$_1$-C$_5$ haloalkyl, C$_3$-C$_6$ cyclic haloalkyl, C$_5$-C$_7$ bicyclic alkyl, C$_1$-C$_6$ aminoalkyl, C$_1$-C$_6$ alkoxy, 4-6 membered heterocyclic group, 6-membered aryl, and 5-6 membered heteroaryl are independently substituted with 0, 1, 2, or 3 R$^{1A}$;
each R$^{1A}$ is independently selected from halogen, hydroxyl, oxo, amino, C$_1$-C$_8$ alkyl, C$_3$-C$_6$ cycloalkyl, C$_1$-C$_6$ alkoxy, C$_3$-C$_6$ cyclic alkoxy, —C(=O)OR$^{1B}$, —C(=O)N(R$^{1B}$)$_2$, —NHC(=O)OR$^{1B}$, and 4-6 membered heterocyclic group, wherein the 4-6 membered heterocyclic group is optionally substituted with 1, 2, or 3 R$^{1C}$;
each R$^{1B}$ is independently selected from hydrogen, C$_1$-C$_8$ alkyl, and C$_4$-C$_6$ cycloalkyl; and
each R$^{1C}$ is independently selected from hydroxyl, halogen, an oxo group, C$_1$-C$_8$ alkyl, and C$_4$-C$_6$ cycloalkyl;
R$^2$ is selected from hydrogen, C$_1$-C$_6$ alkyl, and C$_3$-C$_8$ cycloalkyl;
R$^3$ and R$^4$ are independently selected from hydrogen, hydroxyl, deuterium, halogen, and C$_1$-C$_3$ alkyl; or R$^3$ and R$^4$ may be taken together with the carbon atom to which both are attached to form a 3-5 membered cycloalkyl;
R$^5$ and R$^6$ are independently selected from hydrogen, C$_1$-C$_4$ alkyl, C$_3$-C$_8$ cycloalkyl, and aryl;
X is O or N—S(O)$_2$—R$^X$, wherein R$^X$ is selected from C$_1$-C$_8$ alkyl, C$_3$-C$_6$ cycloalkyl, a 3-6 membered heterocyclic group, 6-membered aryl, and 6-membered heteroaryl, and wherein each of the C$_3$-C$_6$ cycloalkyl, 3-6 membered heterocyclic group, 6-membered aryl, and 6-membered heteroaryl is optionally substituted with 1, 2, or 3 groups selected from halogen, hydroxyl, and cyano;
X$^1$ is selected from halogen, C$_1$-C$_8$ alkyl, and C$_1$-C$_5$ haloalkyl;
X$^2$ is selected from hydrogen, halogen, C$_1$-C$_8$ alkyl, and C$_1$-C$_4$ haloalkyl;
Q is N or CR$^Q$, wherein R$^Q$ is hydrogen or cyano;
W is NR$^{W2}$, wherein R$^{W2}$ is selected from C$_1$-C$_6$ alkyl, C$_3$-C$_6$ cycloalkyl, 5-6 membered bicyclic carbocyclic group, and a 3-7 membered heterocyclic group, wherein each of the C$_1$-C$_6$ alkyl and C$_3$-C$_6$ cycloalkyl is optionally substituted with 1, 2, or 3 R$^{1D}$, wherein R$^{1D}$ is independently selected from halogen, C$_1$-C$_6$ alkyl, C$_1$-C$_3$ haloalkyl, and hydroxyl; or W and R$^1$ are taken together with the C atom to which both are attached to form a heterocyclic ring of 6-7 atoms, wherein the ring has 1 to 3 heteroatoms independently selected from N, S, and O, and wherein the ring is optionally substituted with 1, 2, or 3 R$^{1E}$, wherein each R$^{1E}$ is independently a C$_1$-C$_3$ alkyl or an oxo group;
U is O or C(R$^U$)$_2$, wherein R$^U$ is independently selected from hydrogen, deuterium, halogen, and C$_1$-C$_3$ alkyl, wherein the C$_1$-C$_3$ alkyl is optionally substituted with hydroxyl; and
V is O or C(R$^V$)$_2$, wherein R$^V$ is independently selected from hydrogen, deuterium, halogen, hydroxyl, C$_1$-C$_3$ alkyl, and C$_3$-C$_6$ cycloalkyl, and wherein the C$_1$-C$_3$ alkyl is optionally substituted with hydroxyl.

3. The compound according to claim 2, wherein X$^1$ and X$^2$ are independently selected from bromine, chlorine, fluorine, C$_1$-C$_3$ alkyl, and C$_1$-C$_3$ haloalkyl.

4. The compound according to claim 2, wherein R$^2$ is hydrogen.

5. The compound according to claim 2, wherein R$^5$ is selected from hydrogen, deuterium, and cyclopropyl, and R$^6$ is hydrogen.

6. The compound according to claim 1, wherein W, Z, R$^2$, and the C atom to which R$^2$ is attached are taken together to form a heterocyclic ring of 6 atoms, wherein the heterocyclic ring is optionally substituted with 1, 2, or 3 R$^{1E}$.

7. The compound according to claim 6, wherein W, R$^2$, and the C atom to which R$^2$ is attached are taken together to form a ring selected from:

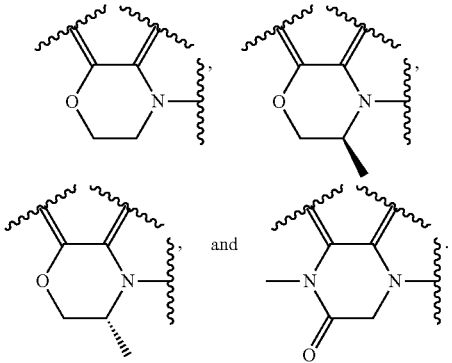

8. The compound according to claim 2, wherein W is selected from:
NH,

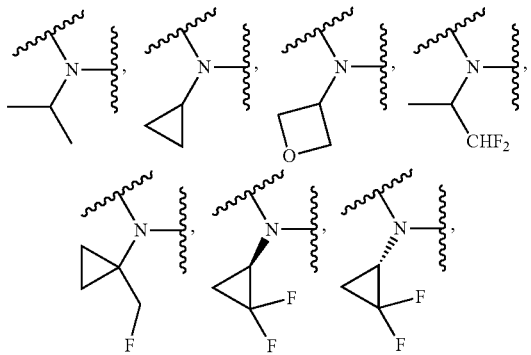

-continued

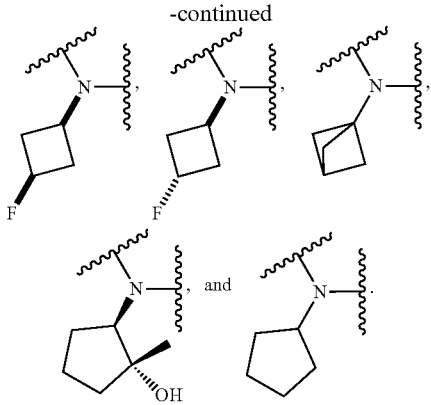

9. The compound according to claim 2, wherein $R^1$ is selected from $C_1$-$C_3$ alkyl, $C_3$-$C_8$ cycloalkyl, $C_1$-$C_5$ haloalkyl, $C_3$-$C_6$ cyclic haloalkyl, $C_5$-$C_7$ bicyclic alkyl, $C_1$-$C_4$ aminoalkyl, $C_1$-$C_6$ alkoxy, an oxo group, a 4-6 membered heterocyclic group, 6-membered aryl and 5-6 membered heteroaryl, wherein each of the $C_1$-$C_3$ alkyl, $C_3$-$C_5$ cycloalkyl, $C_1$-$C_5$ haloalkyl, $C_3$-$C_6$ cyclic haloalkyl, $C_5$-$C_7$ bicyclic alkyl, $C_1$-$C_4$ aminoalkyl, $C_1$-$C_6$ alkoxy, 4-6 membered heterocyclic group, 6-membered aryl, and 5-6 membered heteroaryl is independently substituted with 0, 1, 2, or 3 $R^{14}$.

10. The compound according to claim 9, wherein $R^1$ is selected from:

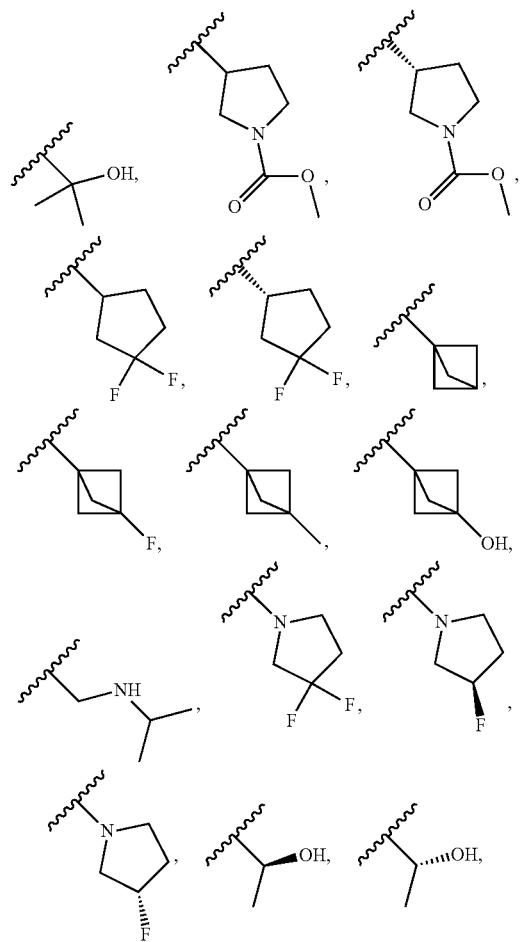

-continued

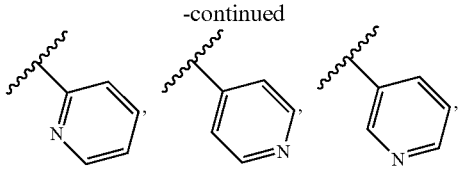

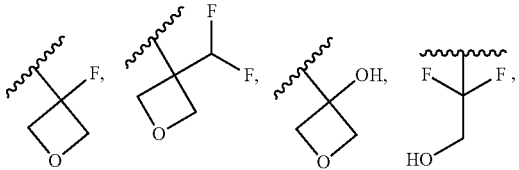

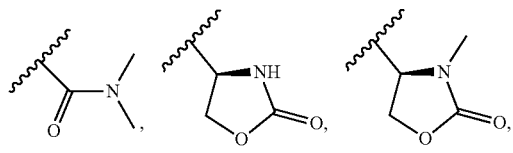

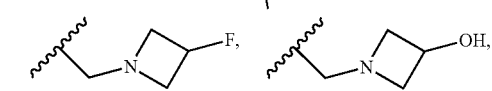

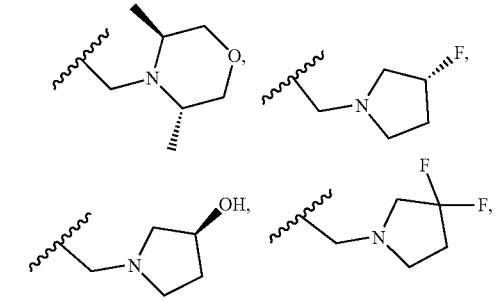

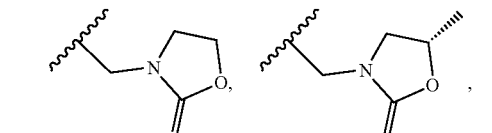

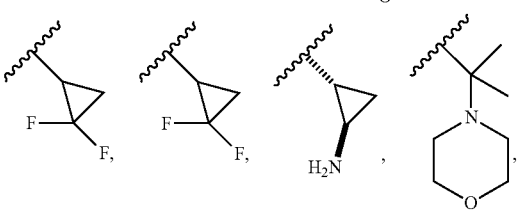

405
-continued
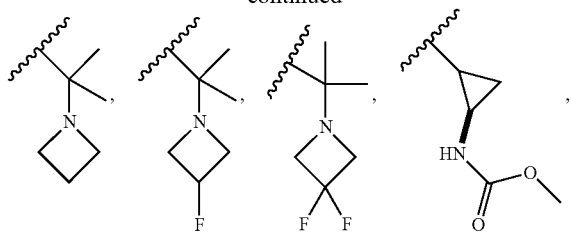
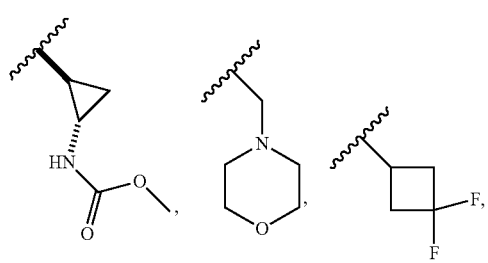
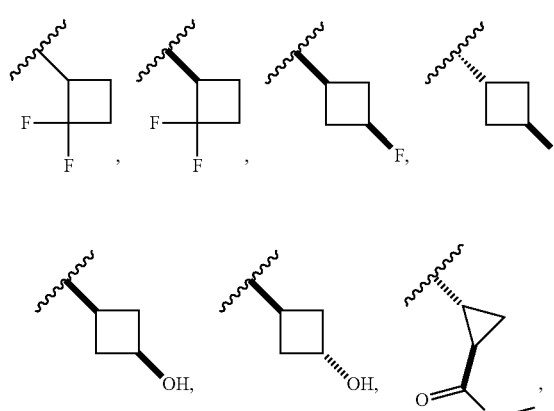
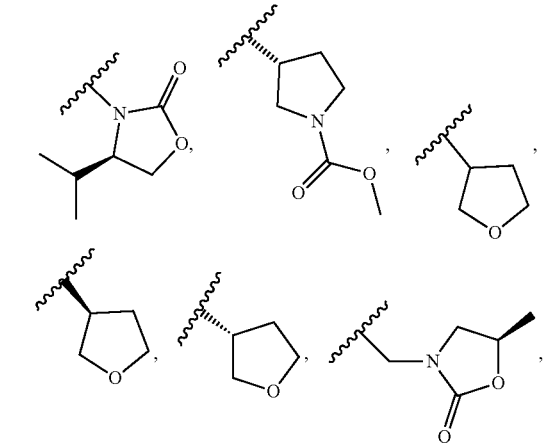
406
-continued
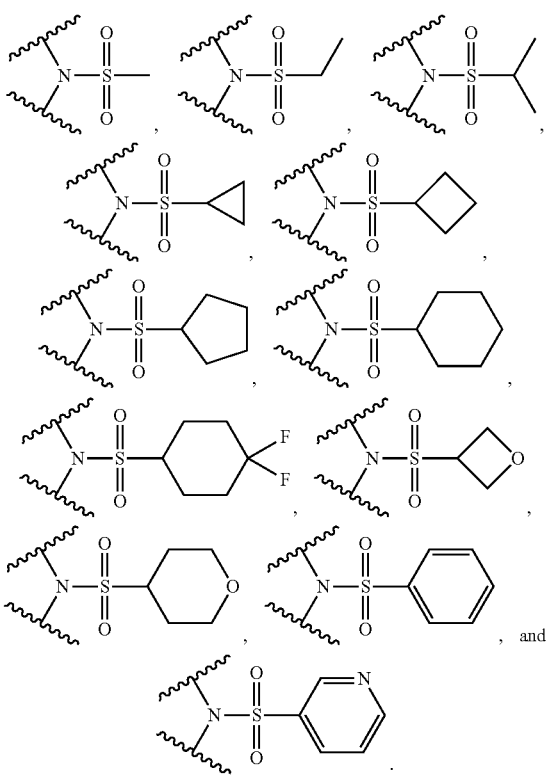
11. The compound according to claim 2, wherein X is selected from:
O,
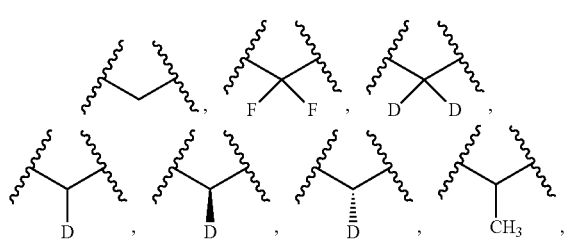
12. The compound according to claim 2, wherein U is selected from:
O, -continued
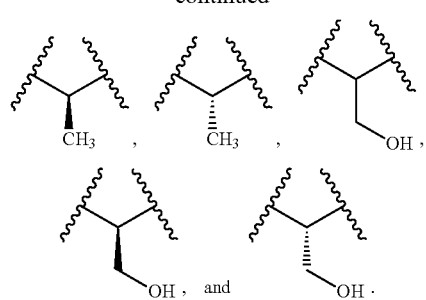
13. The compound according to claim 2, wherein V is selected from:
O,
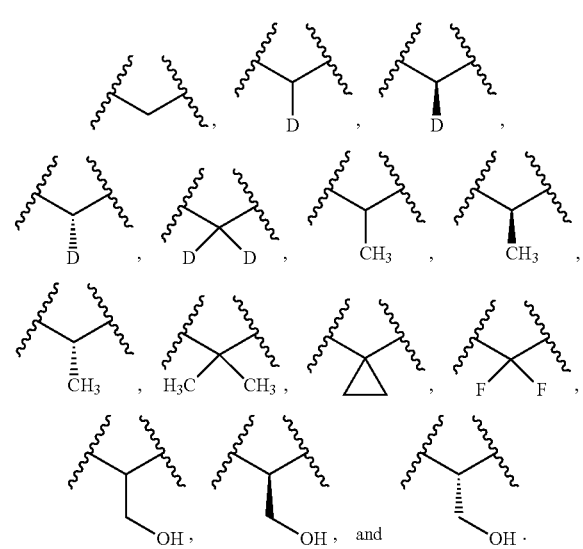
14. The compound according to claim 1, wherein Ring A is selected from:
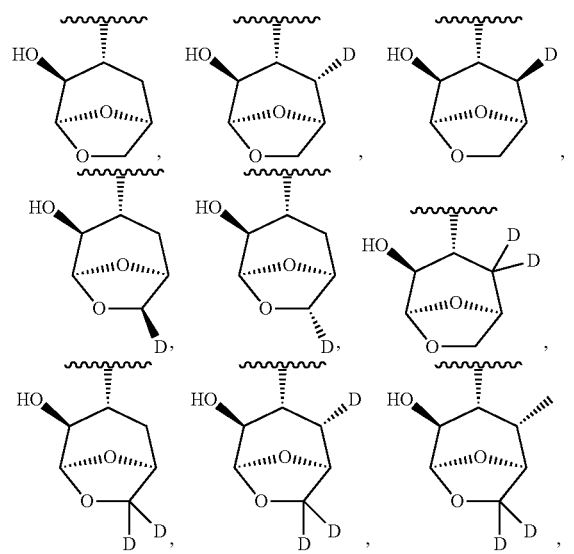
-continued
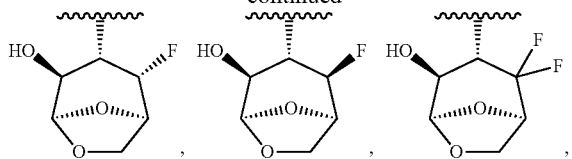
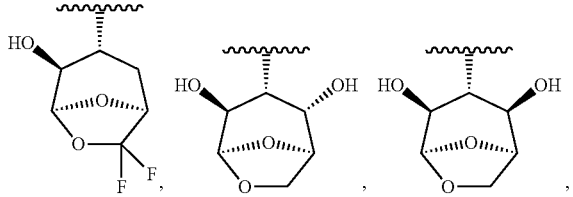
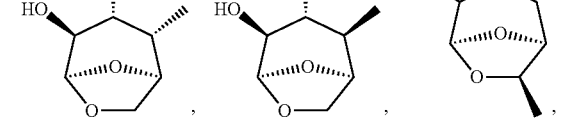
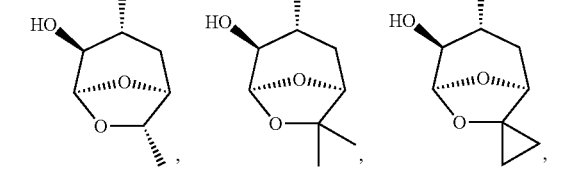
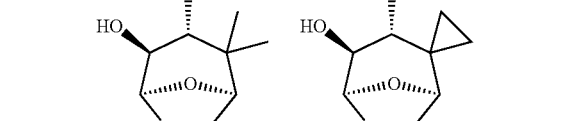
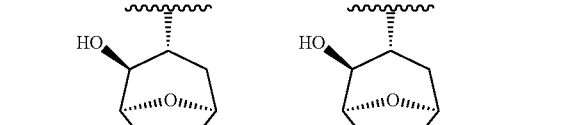

409
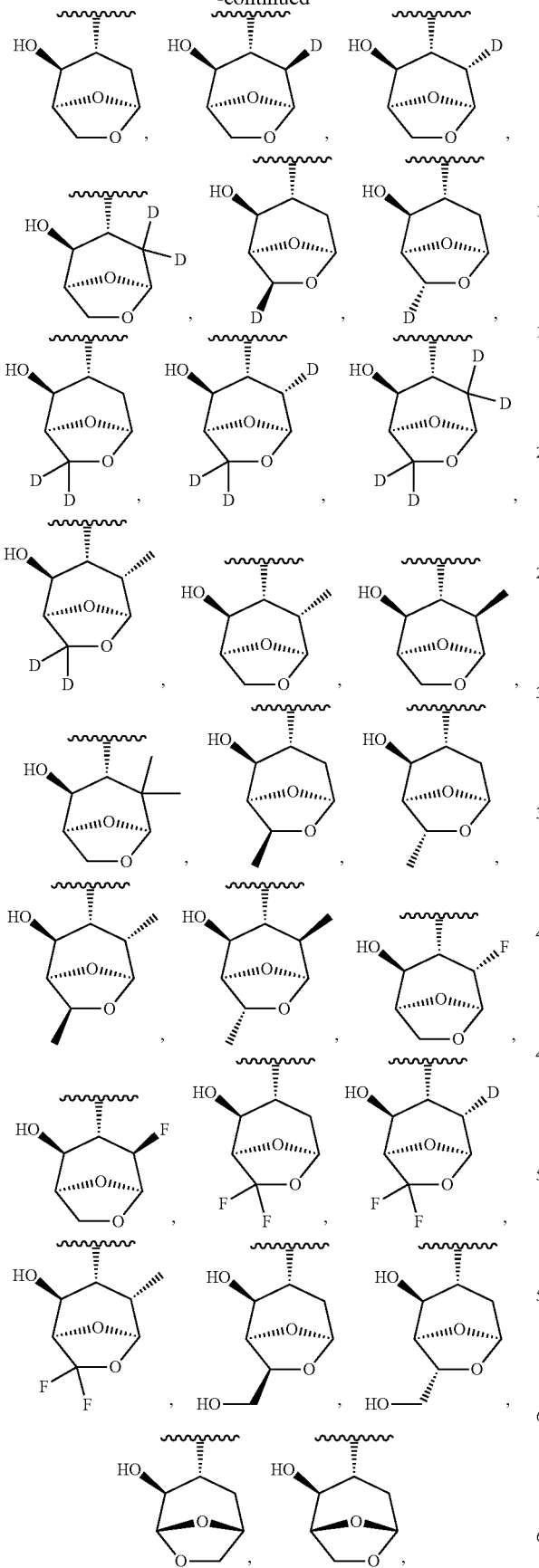
410
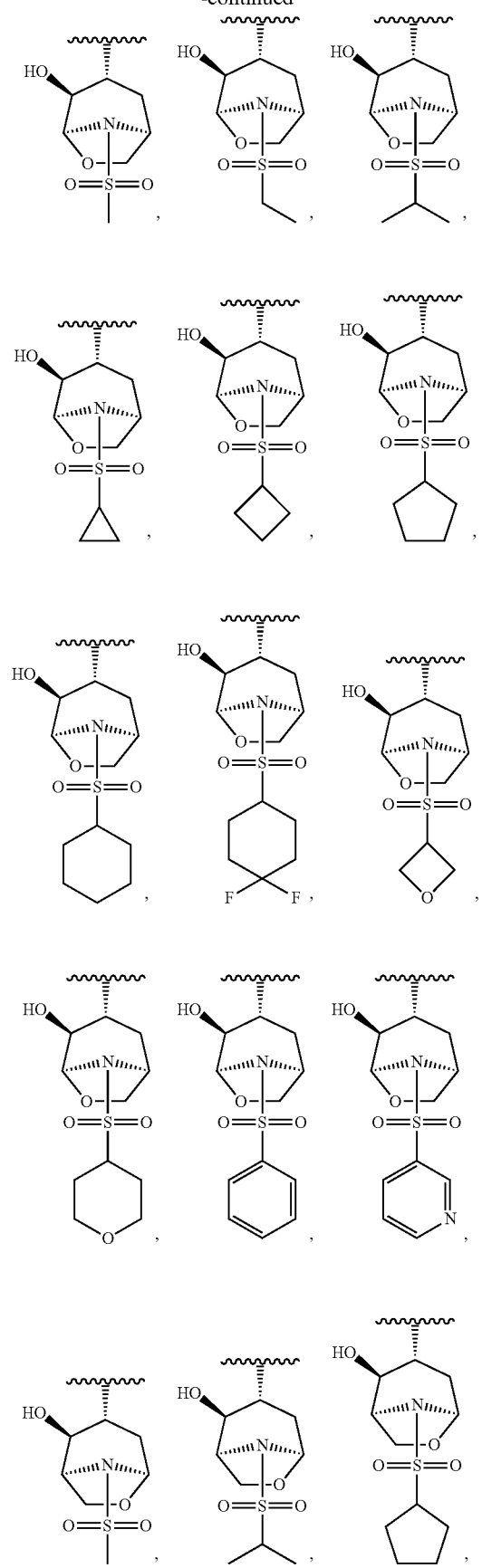

411
-continued
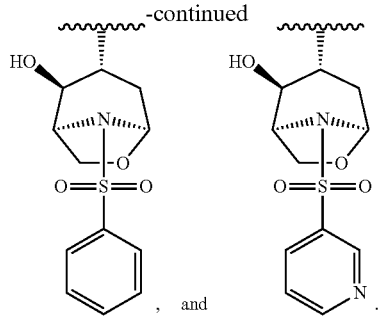
, and .
15. The compound according to claim 14, wherein Ring A is selected from:
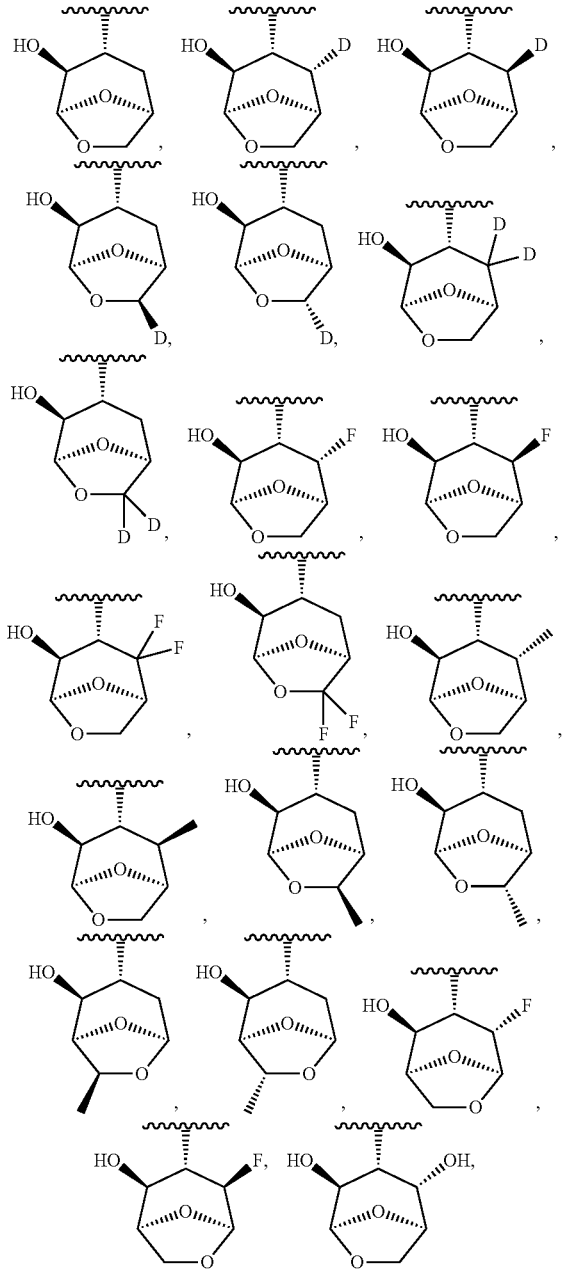
412
-continued
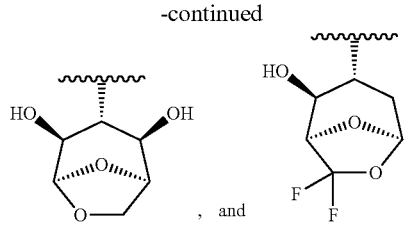
, and .
16. The compound according to claim 1, wherein the compound is selected from:
1
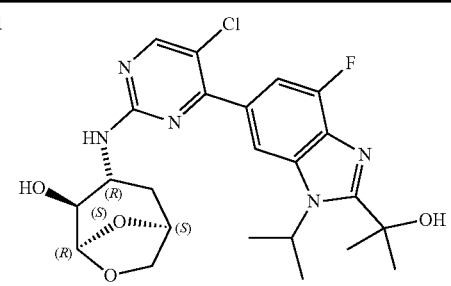
2
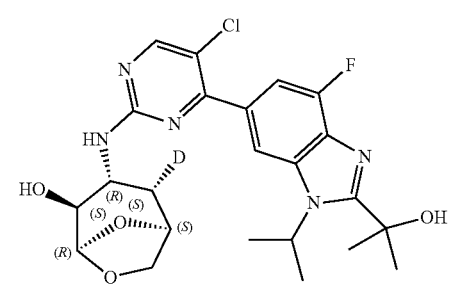
3
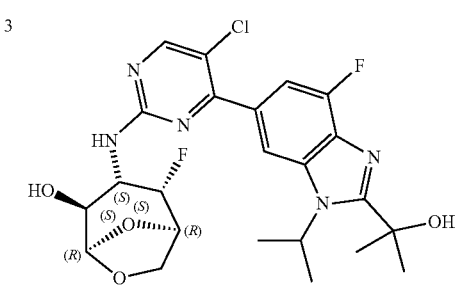
4
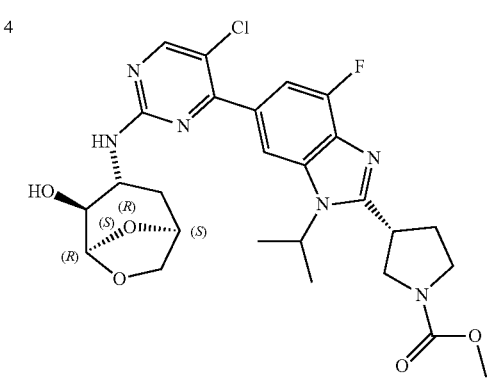

| 5 | 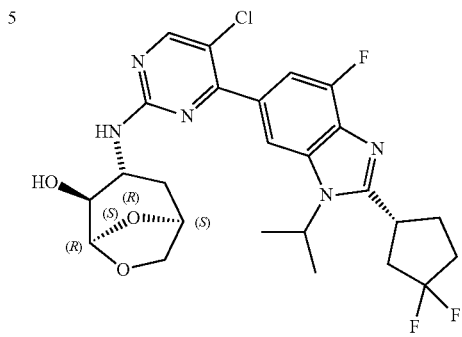 |
| --- | --- |
| 6 | 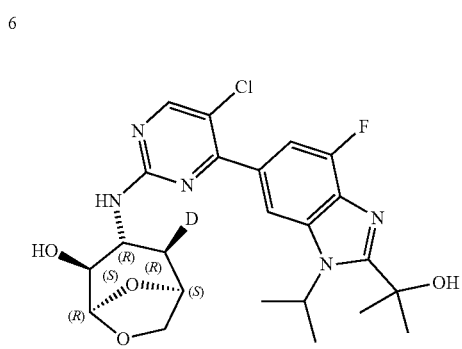 |
| 7 | 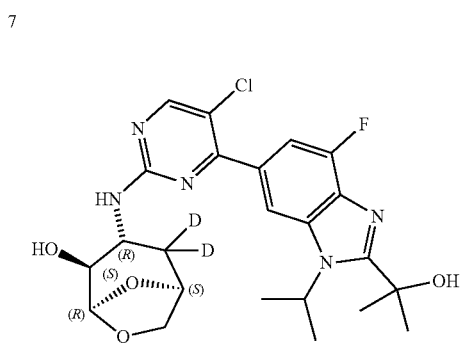 |
| 8 | 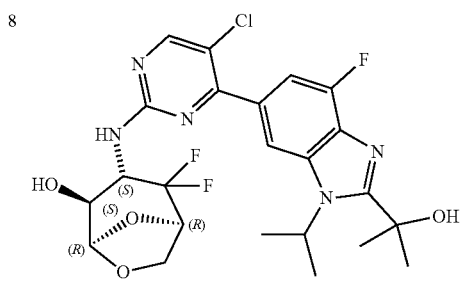 |
| 9 | 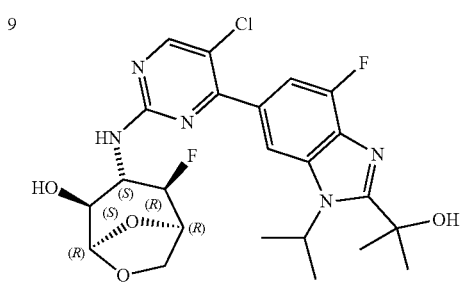 |
| 10 | 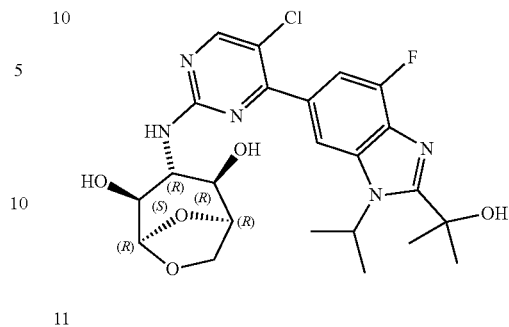 |
| --- | --- |
| 11 | 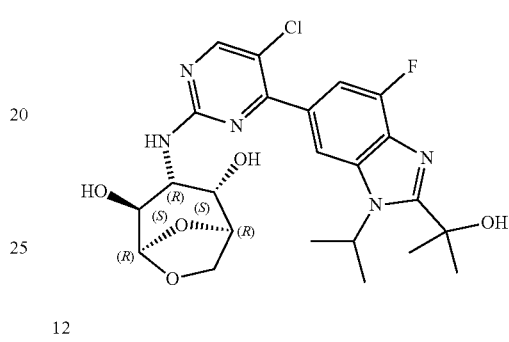 |
| 12 | 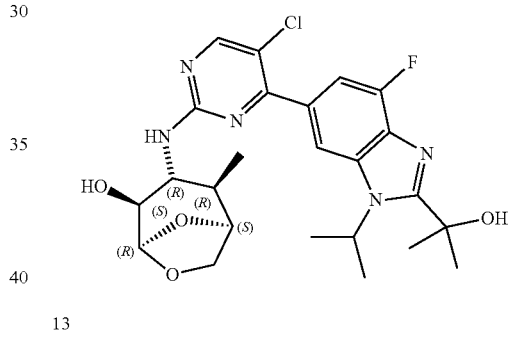 |
| 13 | 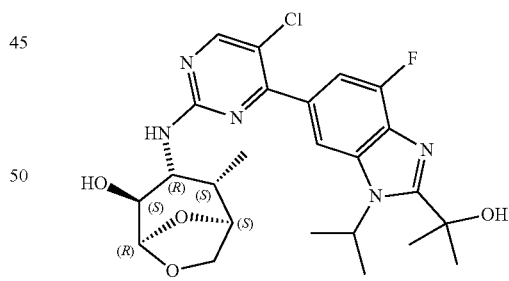 |
| 14 | 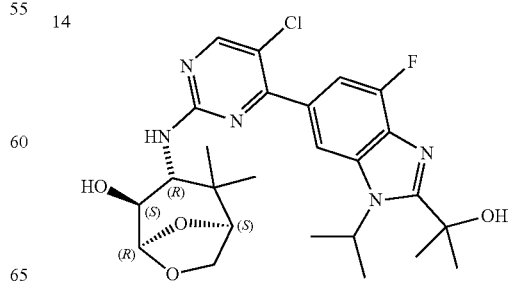 |

-continued
15 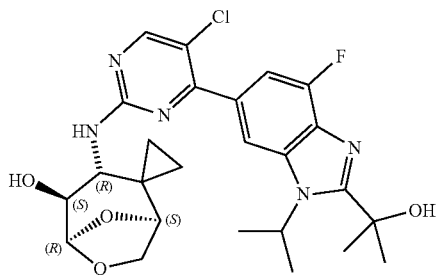
16 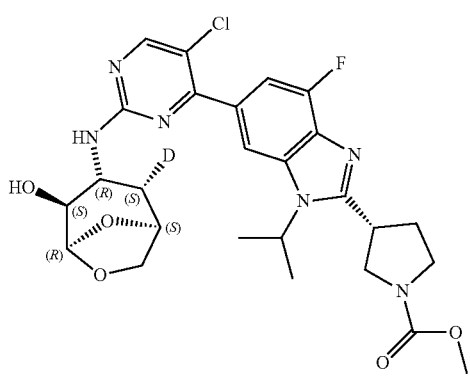
17 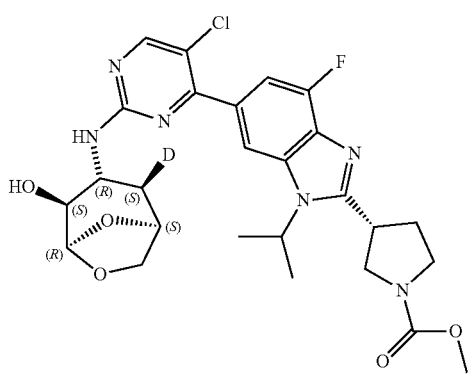
18 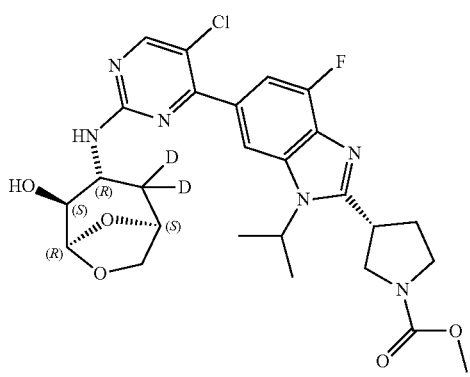
-continued
19 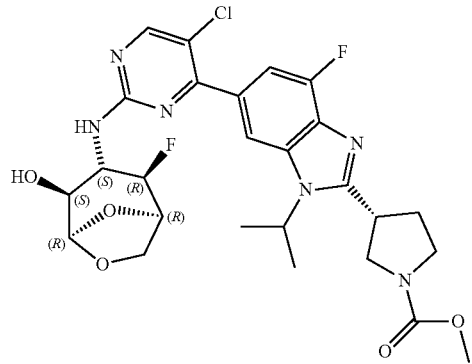
20 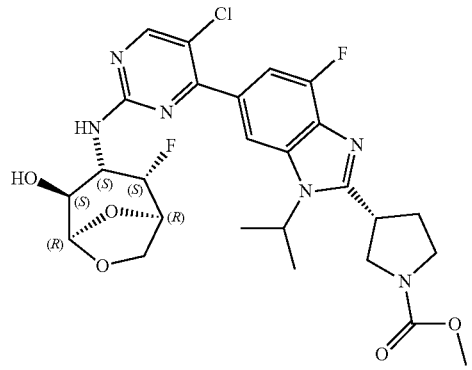
21 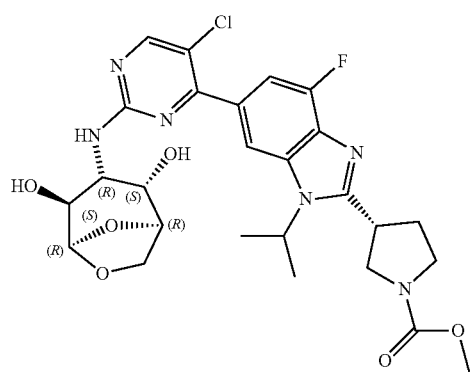
22 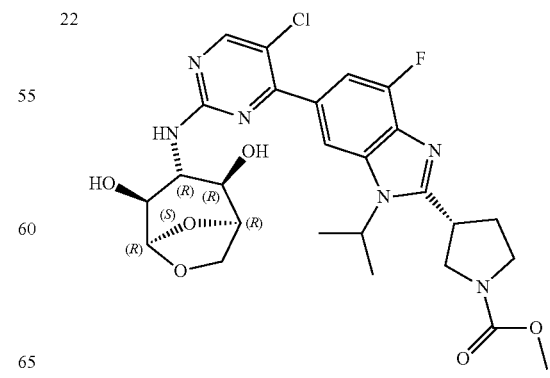

| 417 -continued | 418 -continued |
|---|---|
| 23 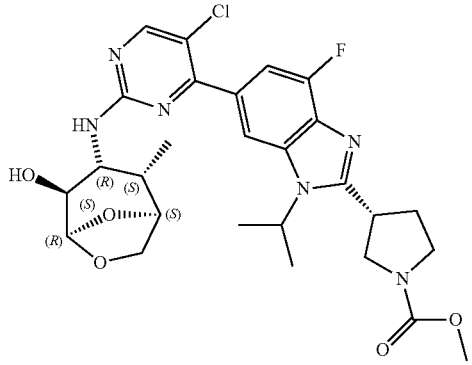 | 28 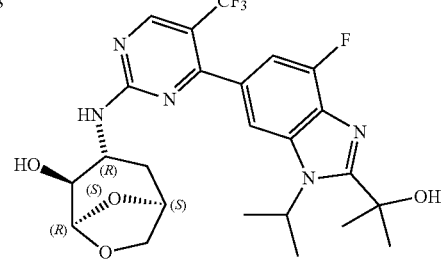 |
| 24 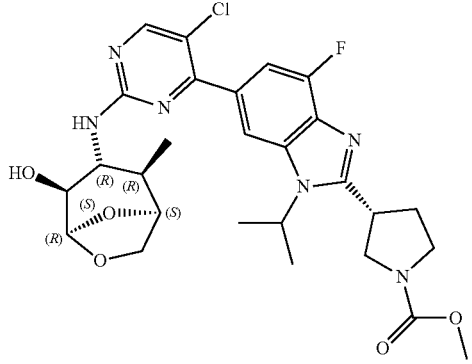 | 29 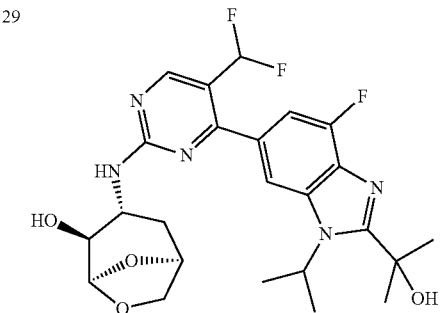 |
| 25 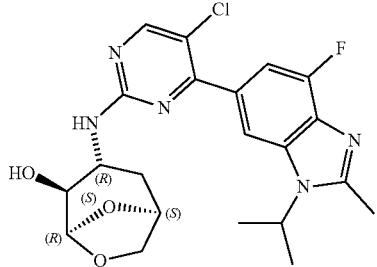 | 30 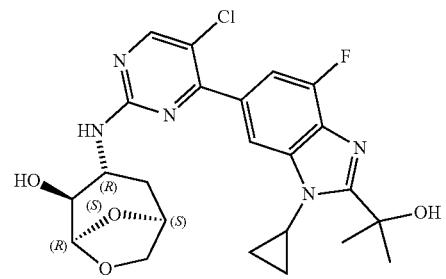 |
| 26 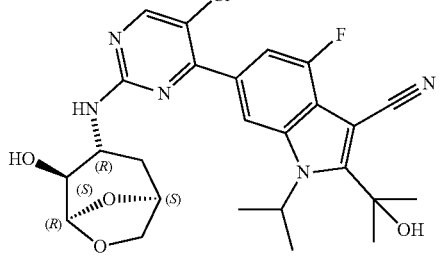 | 31 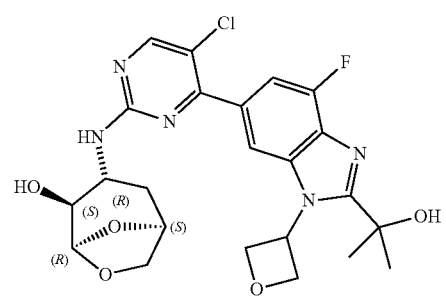 |
| 27 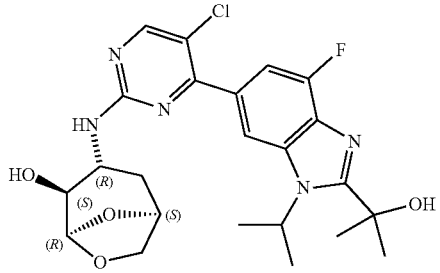 | 34 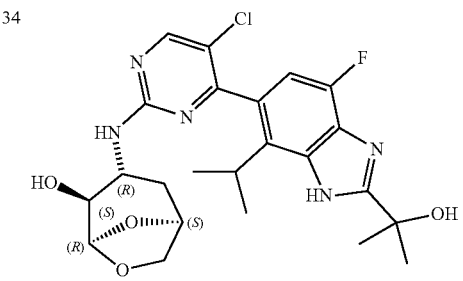 |

-continued
| | |
|---|---|
| 35 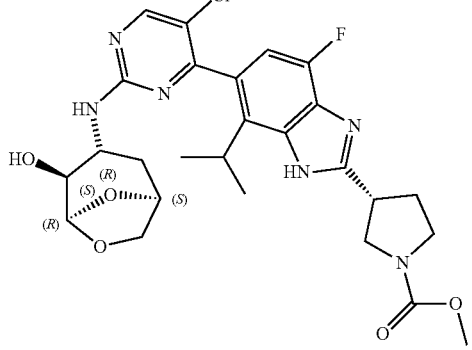 | 40 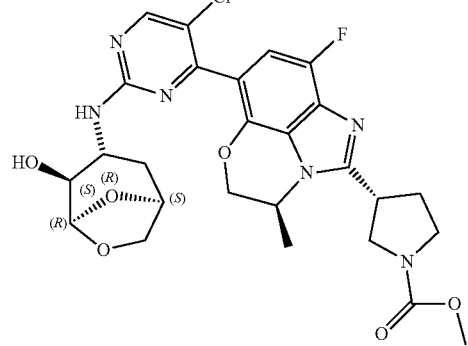 |
| 36 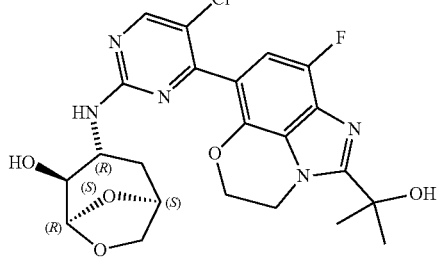 | 41 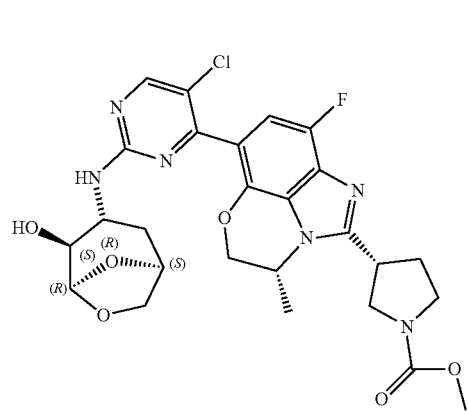 |
| 37 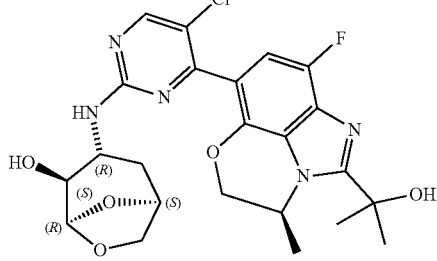 | 44 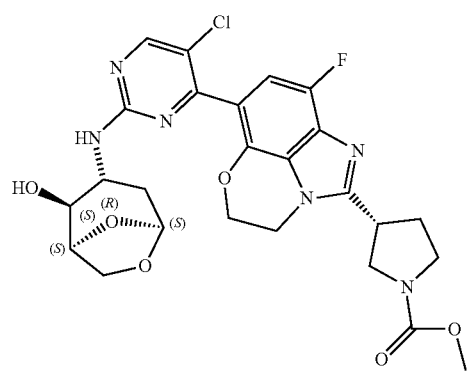 |
| 38 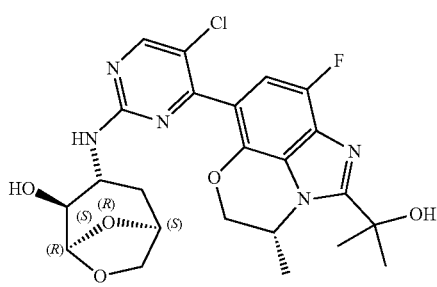 | 45 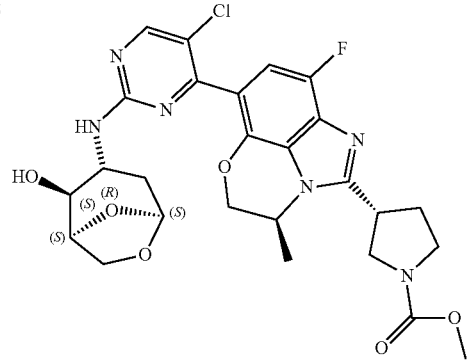 |
| 39 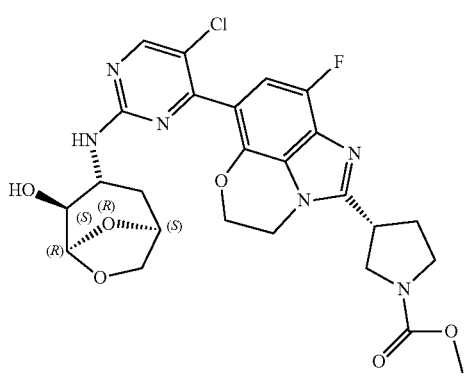 | |

-continued
46
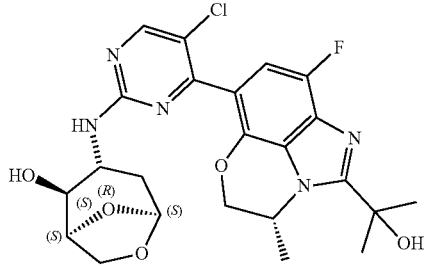
47
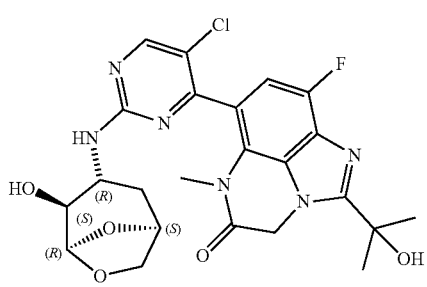
48
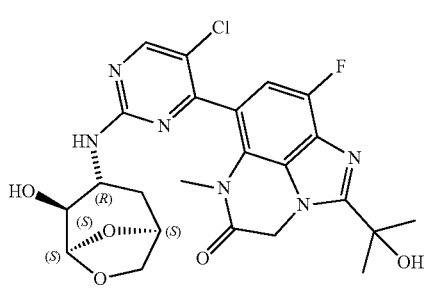
49
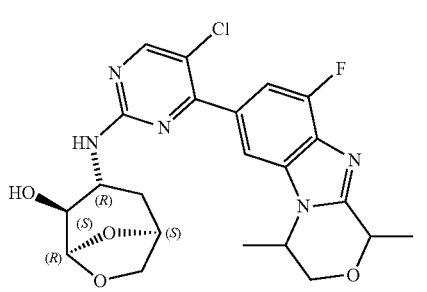
50
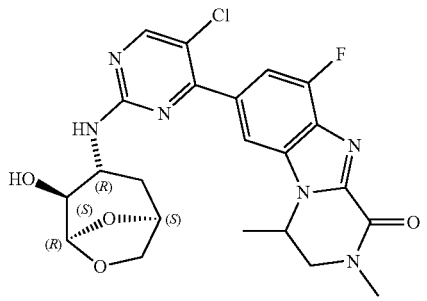
-continued
51
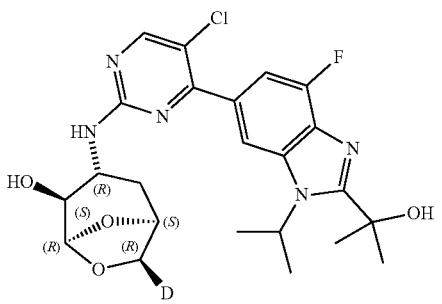
52
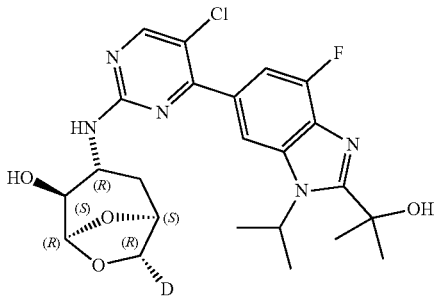
53
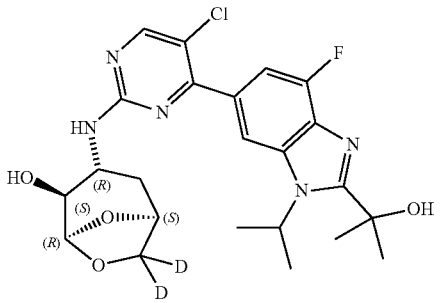
54
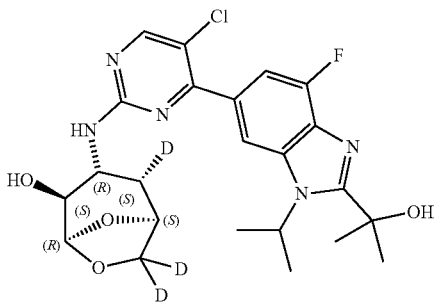
55
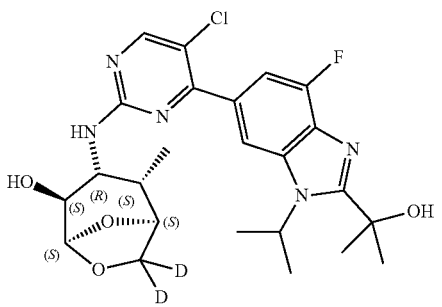

| 423 -continued | 424 -continued |
|---|---|
| 56 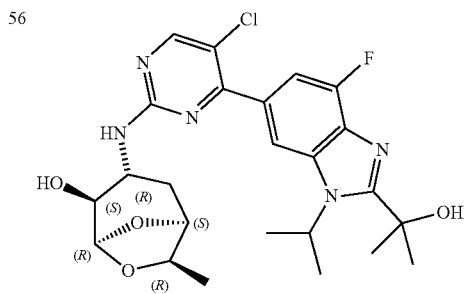 | 61 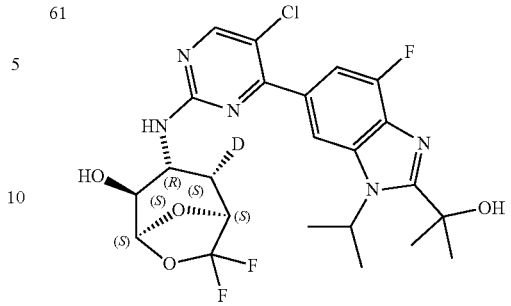 |
| 57 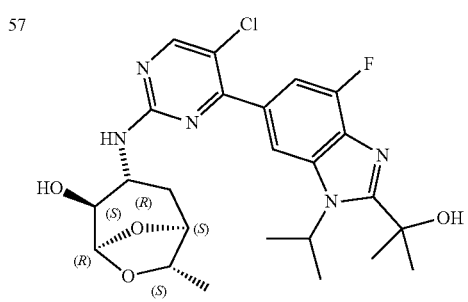 | 62 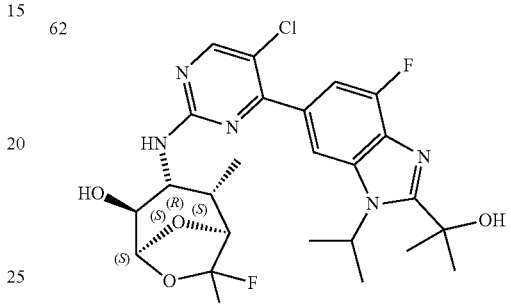 |
| 58 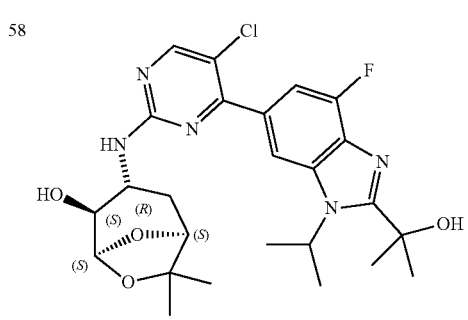 | 63 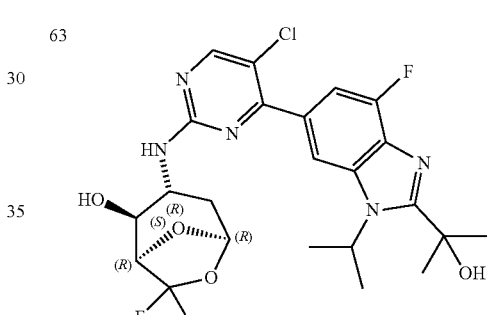 |
| 59 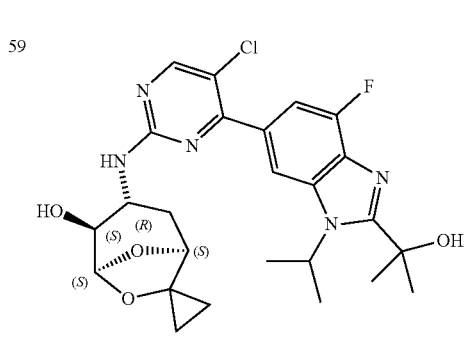 | 64 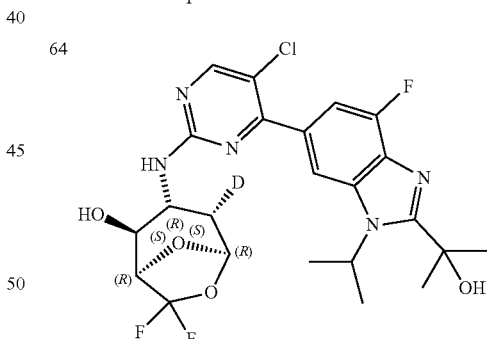 |
| 60 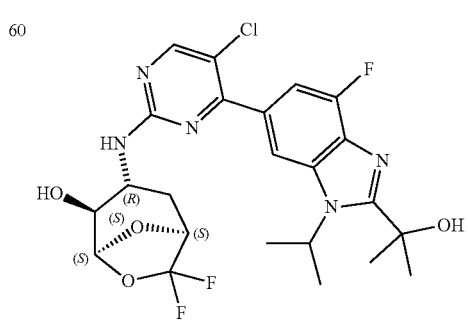 | 65 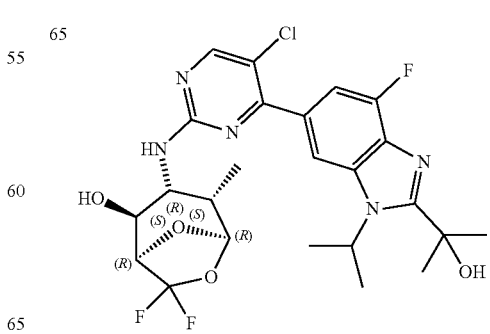 |

| 72 | 77 |
|---|---|
| 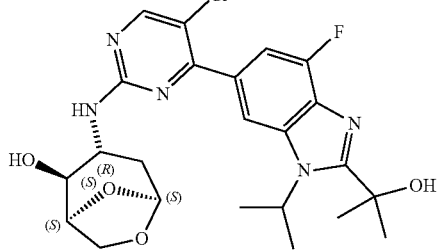 | 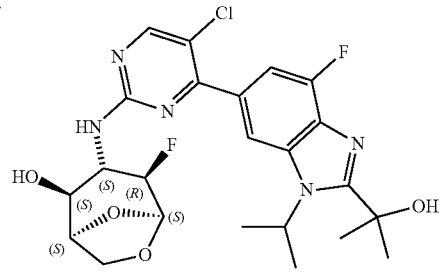 |
| 73 | 78 |
| 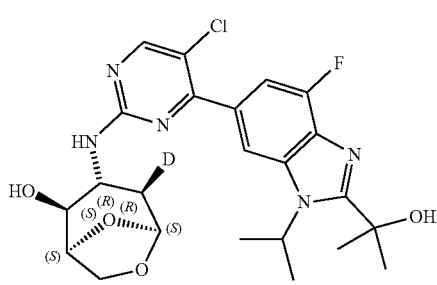 | 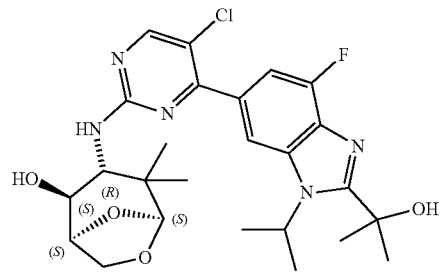 |
| 74 | 79 |
| 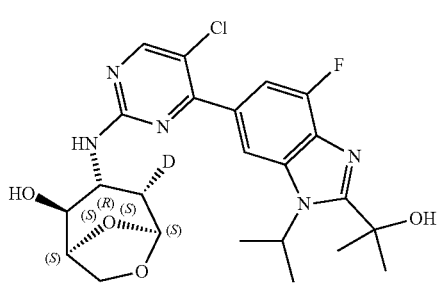 | 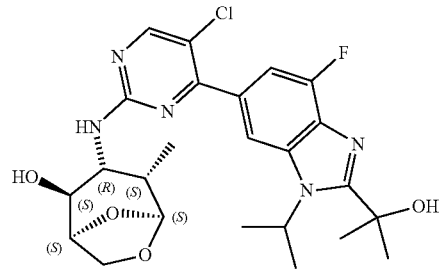 |
| 75 | 80 |
| 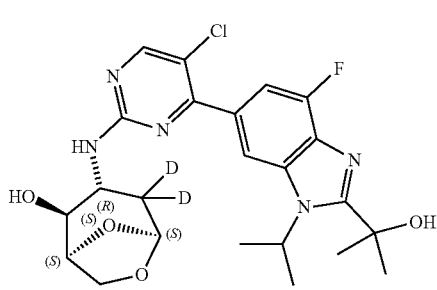 | 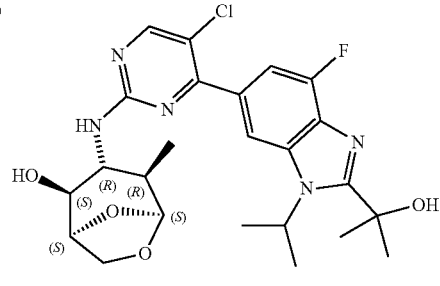 |
| 76 | 81 |
| 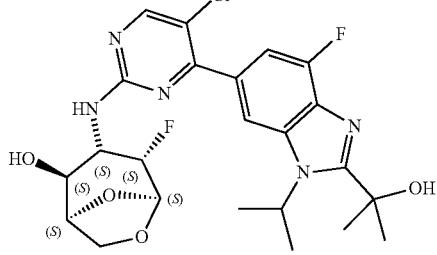 | 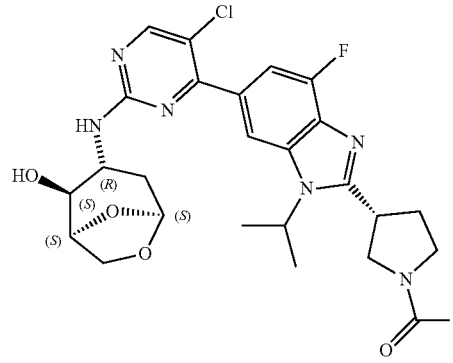 |

427
-continued
82
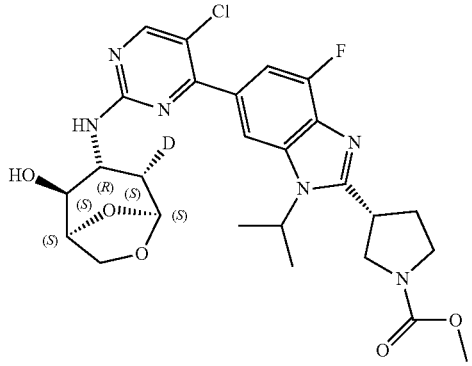
83
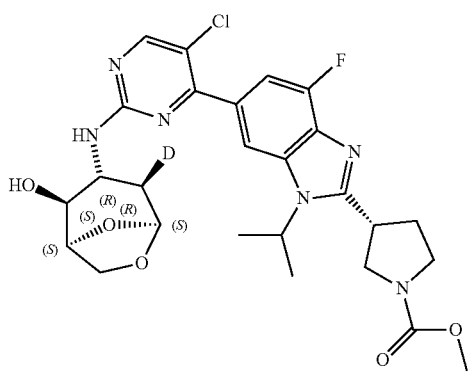
84
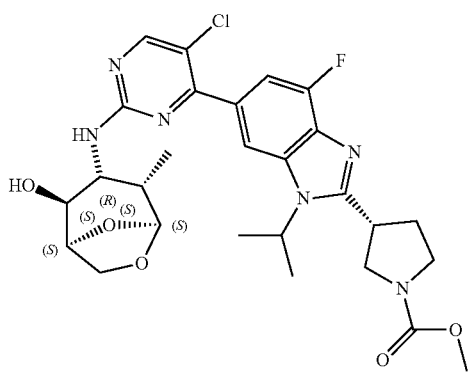
85
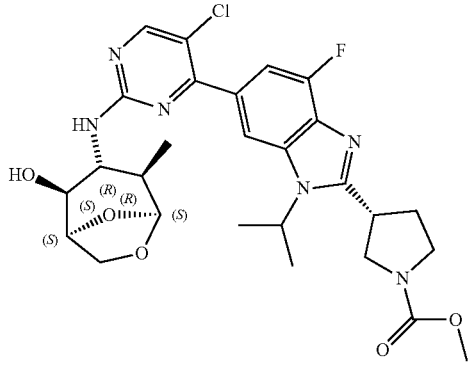
428
-continued
86
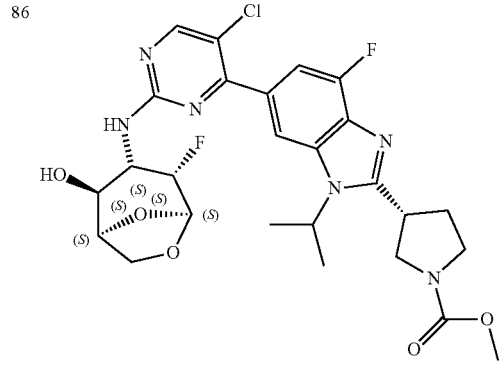
87
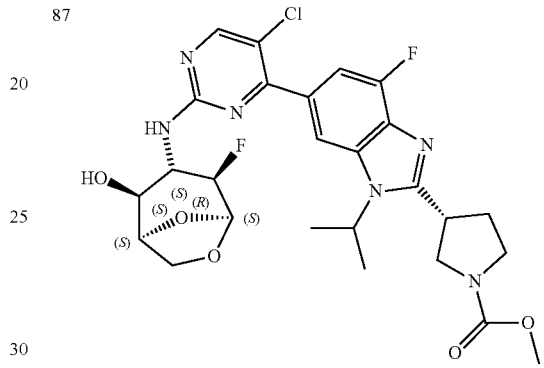
88
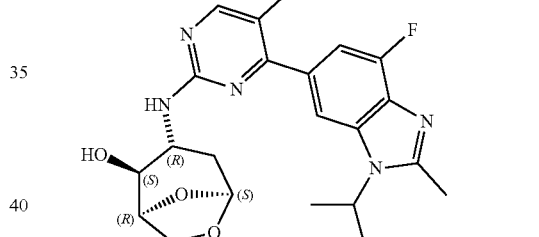
89
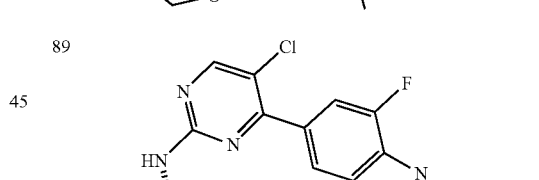
90
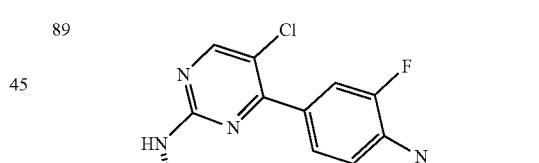

| 91 | 96 |
|---|---|
| 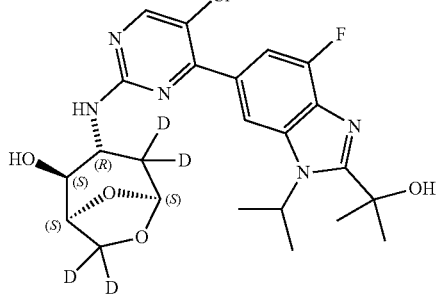 | 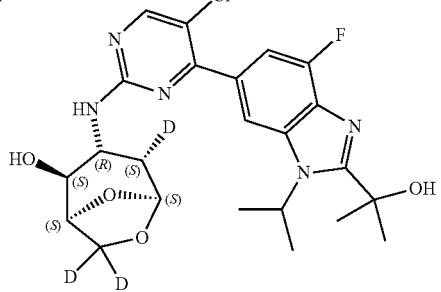 |
| 92 | 97 |
| 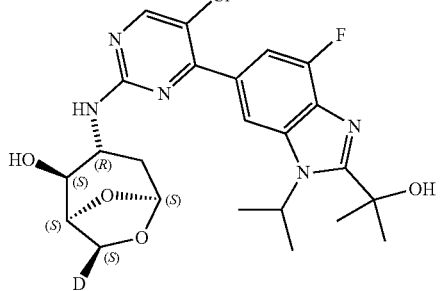 | 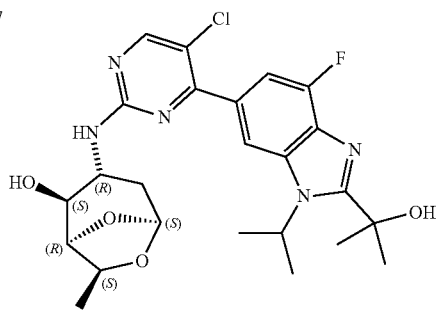 |
| 93 | 98 |
| 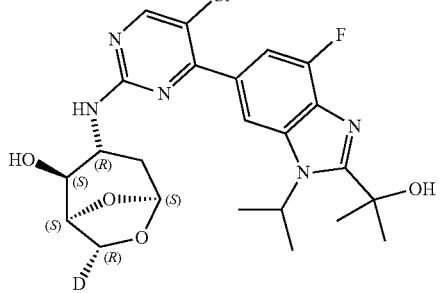 | 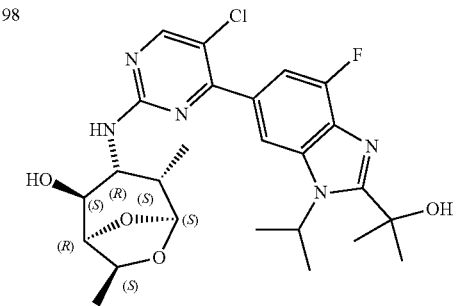 |
| 94 | 99 |
| 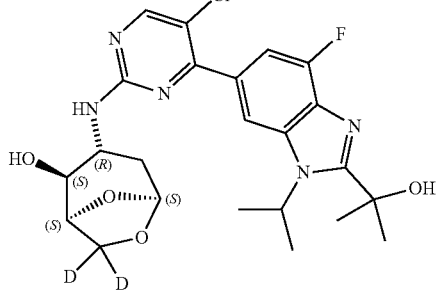 | 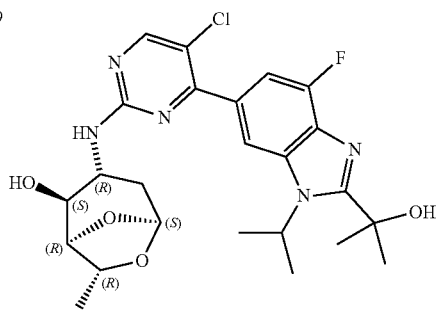 |
| 95 | 100 |
| 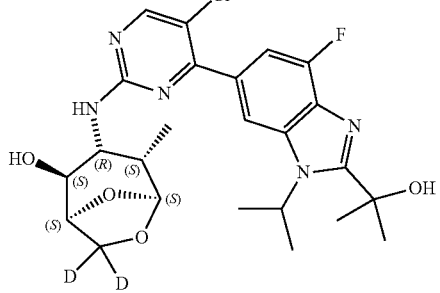 | 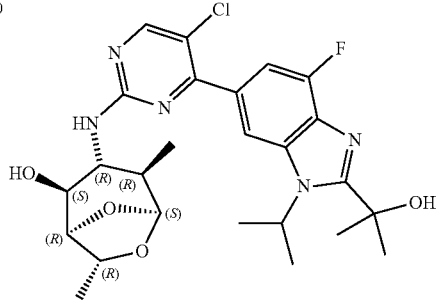 |

| | |
|---|---|
| 101 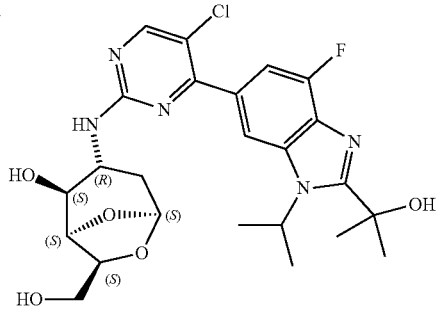 | 106 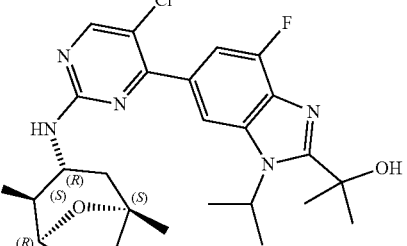 |
| 102 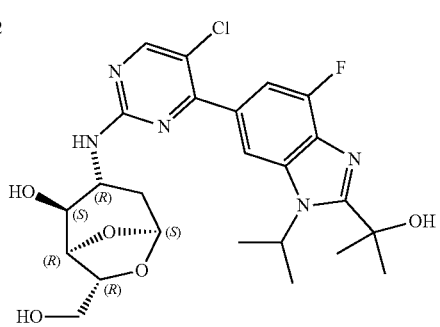 | 107 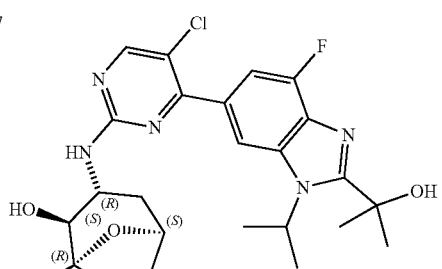 |
| 103 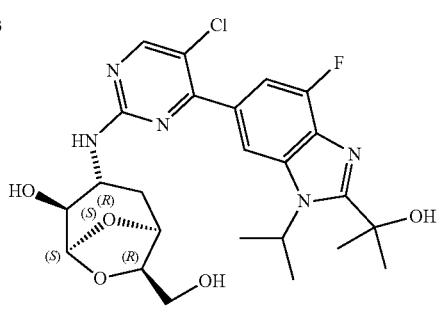 | 108 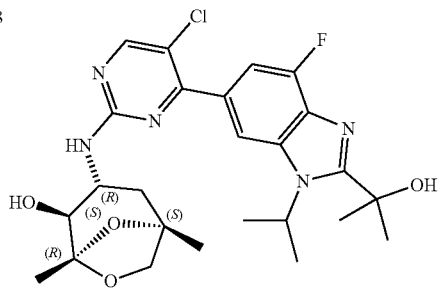 |
| 104 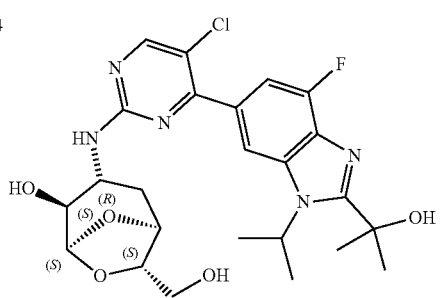 | 109 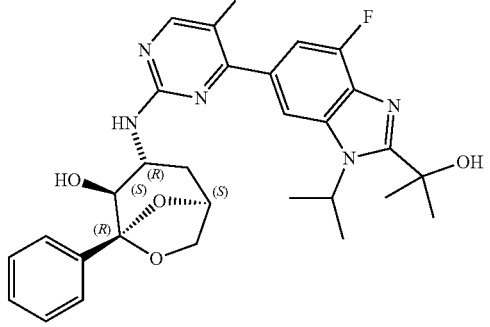 |
| 105 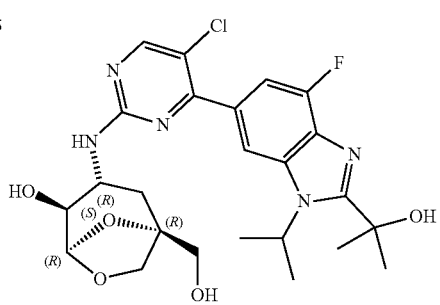 | 110 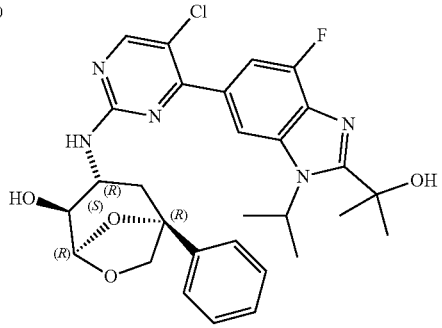 |

| 111 | 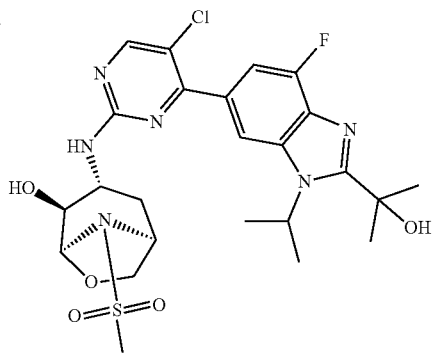 [SMILES: CC(C)n1c(C(C)(C)O)nc2c(F)cc(-c3nc(N[C@@H]4C[C@H]5CO[C@@H]([C@H]4O)N5S(C)(=O)=O)ncc3Cl)cc21] | 115 | 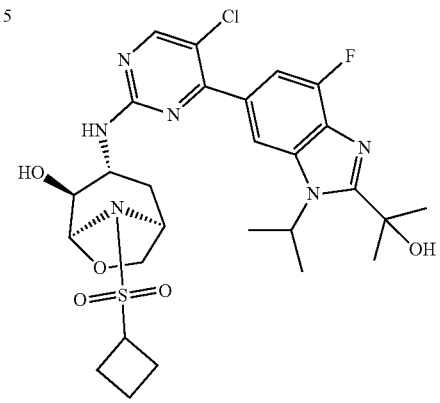 |
| 112 | 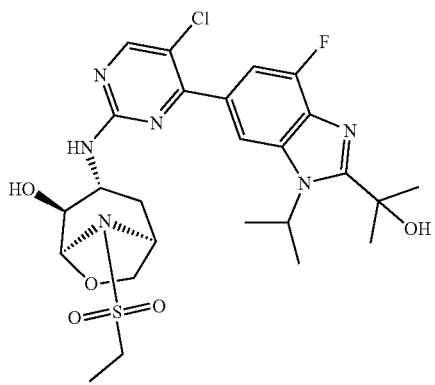 [SMILES: CCS(=O)(=O)N1[C@@H]2CO[C@H]1[C@@H](O)[C@H](Nc1ncc(Cl)c(-c3cc(F)c4nc(C(C)(C)O)n(C(C)C)c4c3)n1)C2] | 116 | 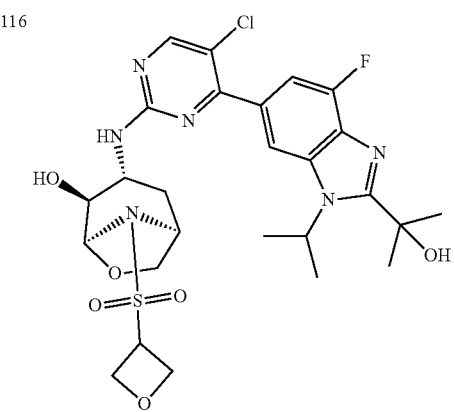 |
| 113 | 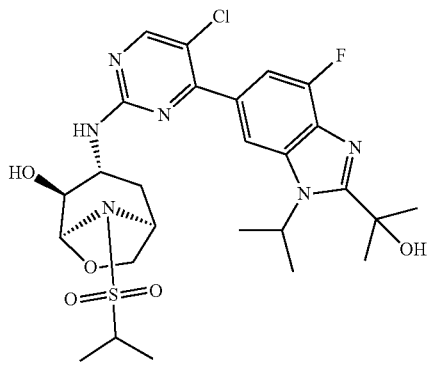 [SMILES: CC(C)n1c(C(C)(C)O)nc2c(F)cc(-c3nc(N[C@@H]4C[C@H]5CO[C@@H]([C@H]4O)N5S(=O)(=O)C(C)C)ncc3Cl)cc21] | 117 | 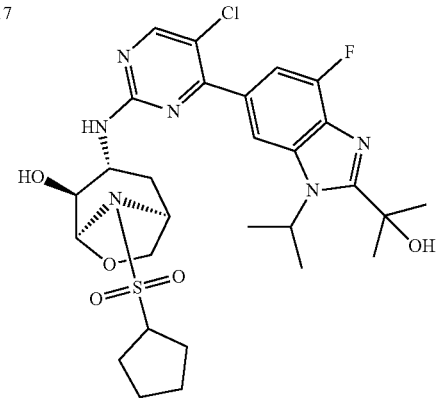 |
| 114 | 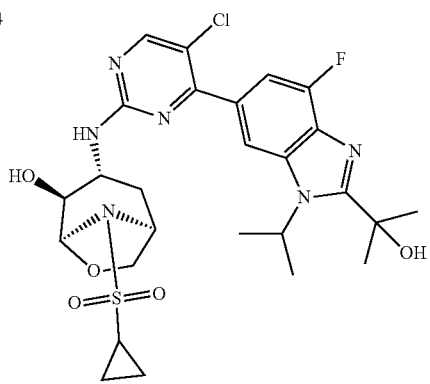 | 118 | 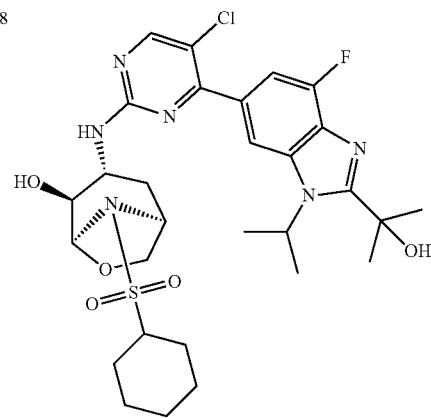 |

119
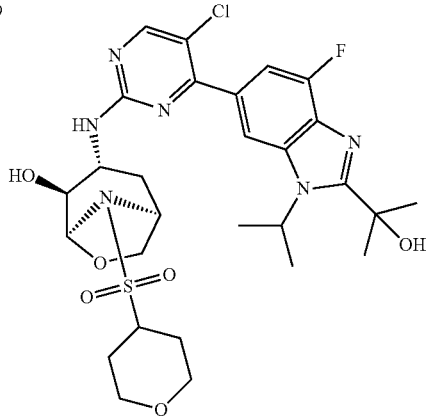
120
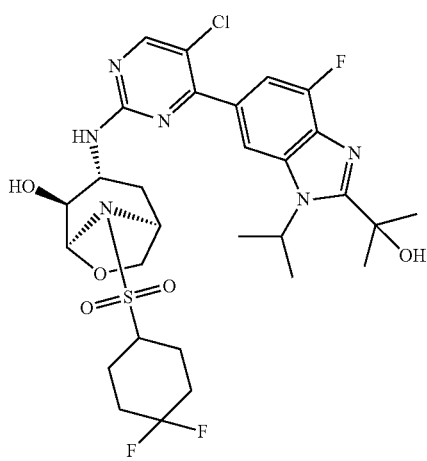 [SMILES: CC(C)n1c(C(C)(C)O)nc2c(F)cc(-c3nc(N[C@@H]4C[C@H]5CO[C@@H]([C@H]4O)N5S(=O)(=O)C4CCC(F)(F)CC4)ncc3Cl)cc21]
121
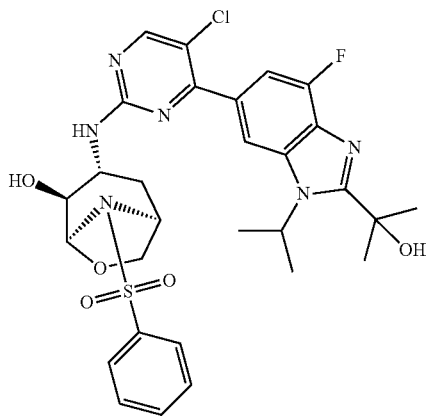 [SMILES: CC(C)n1c(C(C)(C)O)nc2c(F)cc(-c3nc(N[C@@H]4C[C@H]5CO[C@@H]([C@H]4O)N5S(=O)(=O)c4ccccc4)ncc3Cl)cc21]
122
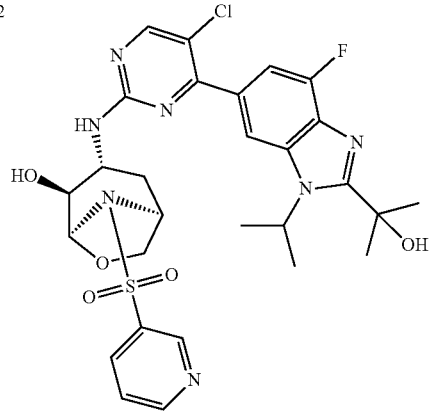
123
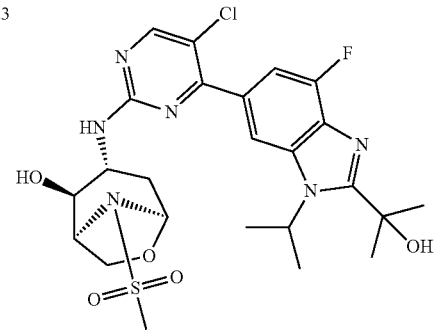
124
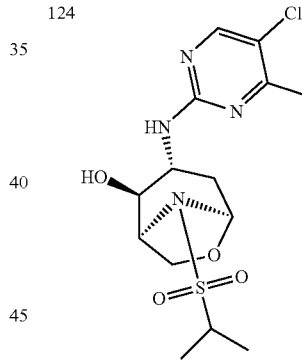
125
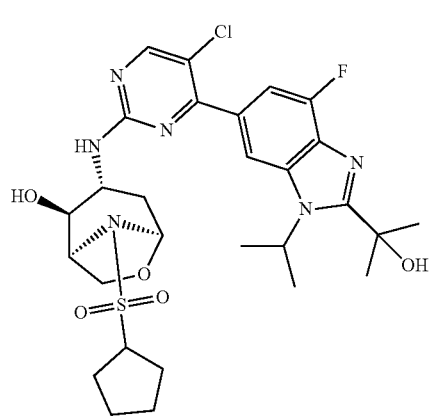 [SMILES: CC(C)n1c(C(C)(C)O)nc2c(F)cc(-c3nc(N[C@@H]4C[C@H]5OC[C@@H]([C@H]4O)N5S(=O)(=O)C4CCCC4)ncc3Cl)cc21]

| 126 | 130 |
|---|---|
| 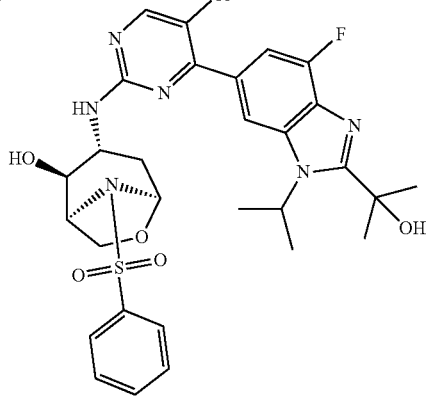 | 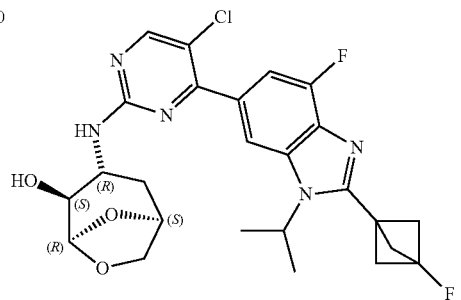 |
| 127 | 131 |
| 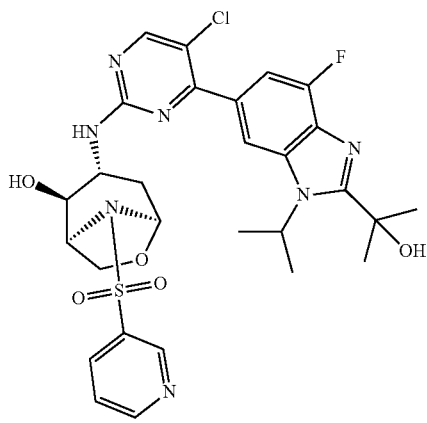 [SMILES: CC(C)n1c(C(C)(C)O)nc2c(F)cc(-c3nc(N[C@@H]4C[C@H]5OC[C@@H]([C@H]4O)N5S(=O)(=O)c4cccnc4)ncc3Cl)cc21] | 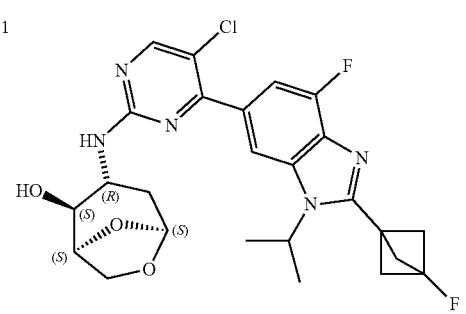 |
| 128 | 132 |
| 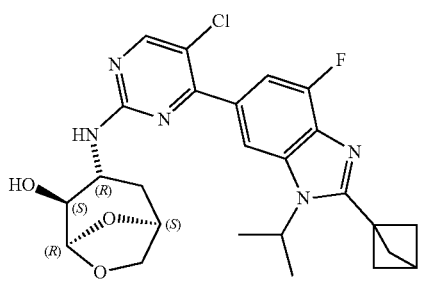 | 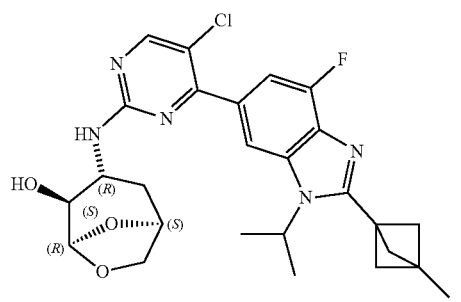 |
| 129 | 133 |
| 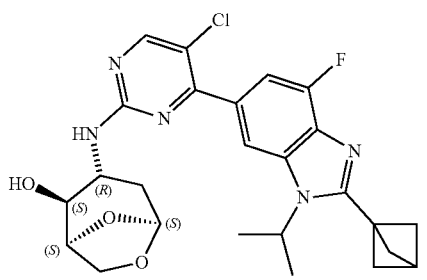 | 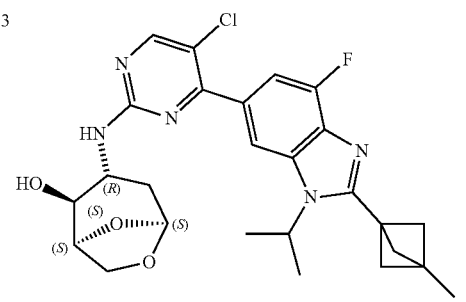 |
|  | 134 |
|  | 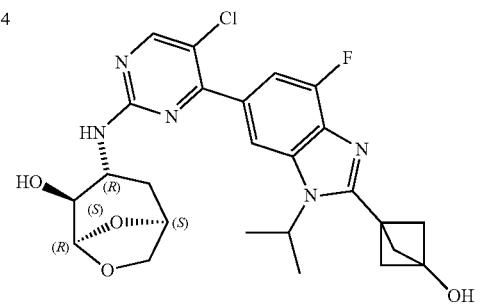 |

| 135 | 140 |
|---|---|
| 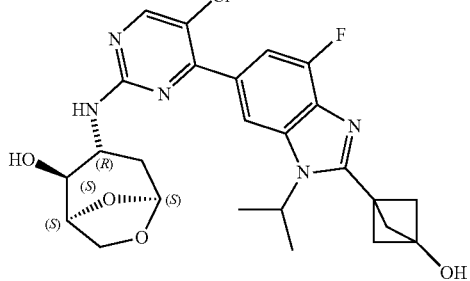 | 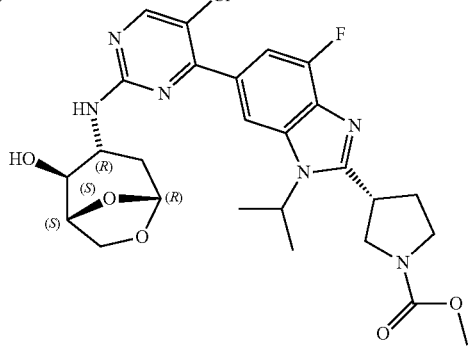 |
| 136 | 141 |
| 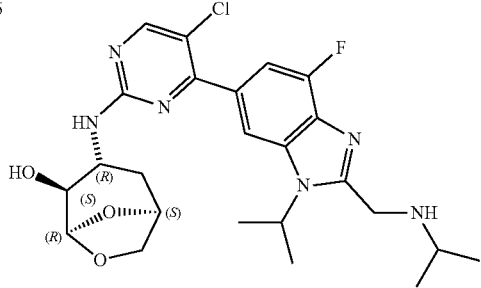 | 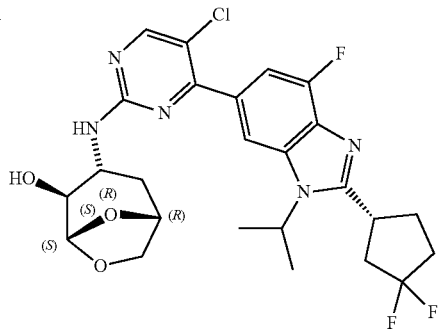 |
| 137 | 142 |
| 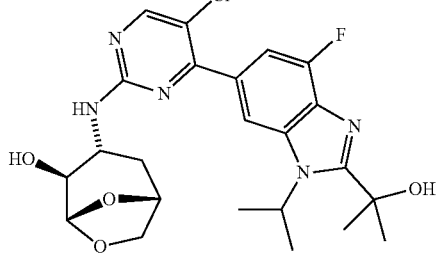 | 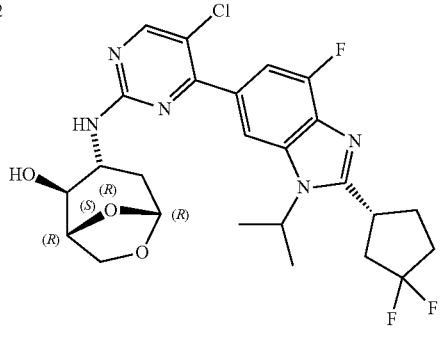 |
| 138 | 145 |
| 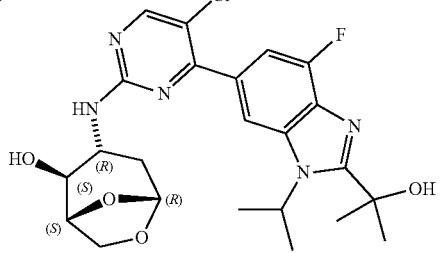 | 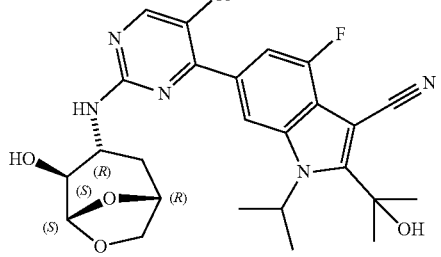 |
| 139 | 146 |
| 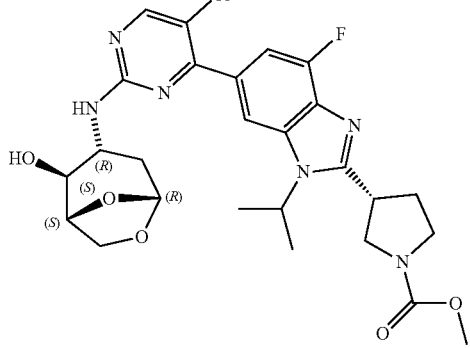 | 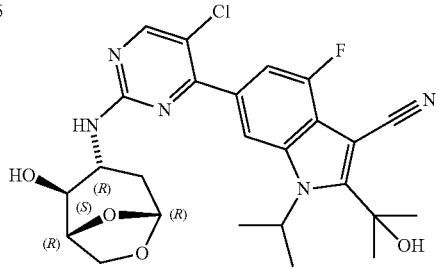 |

147 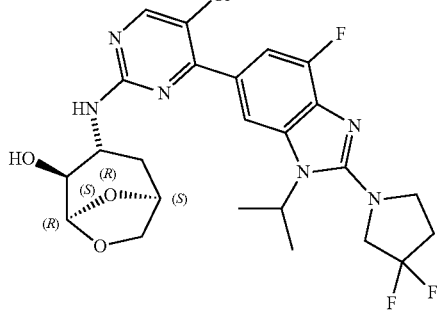
148 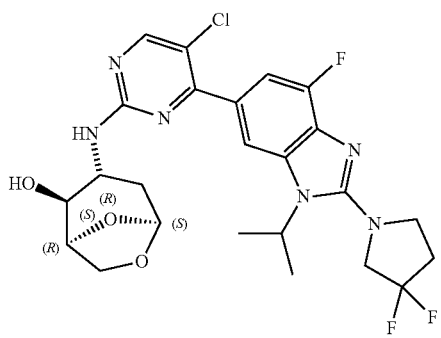
149 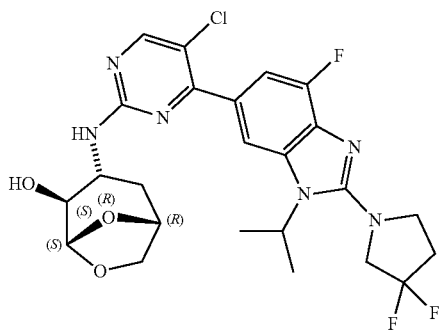
150 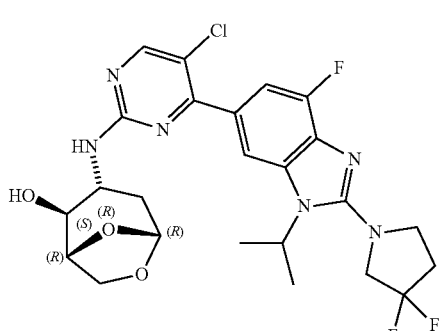
151 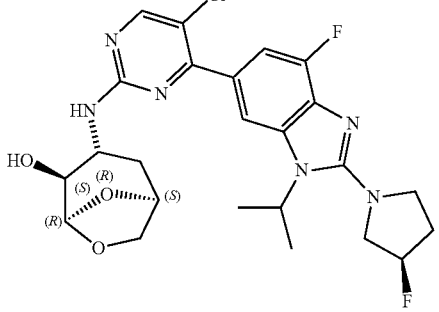
152 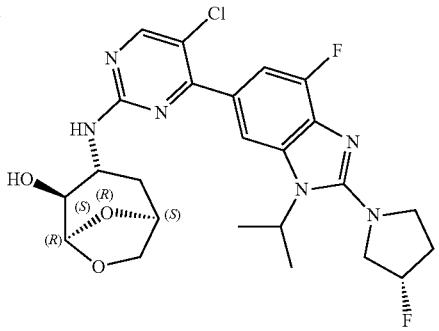
153 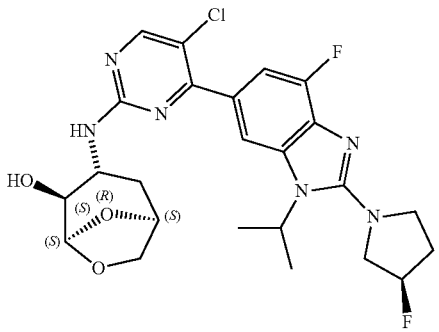
154 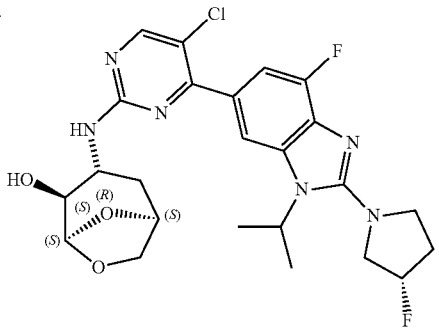
155 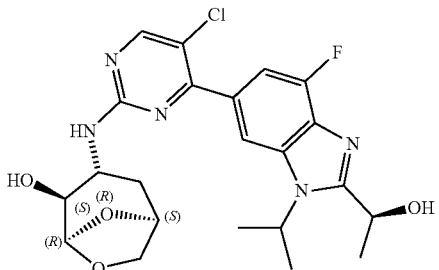

156 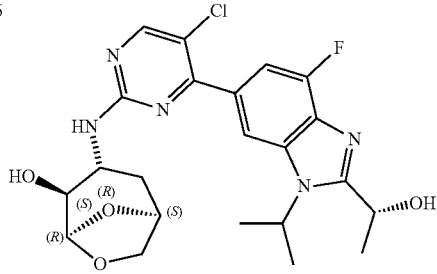
157 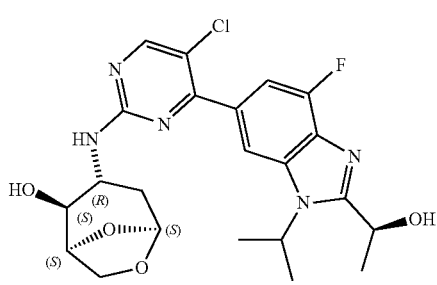
158 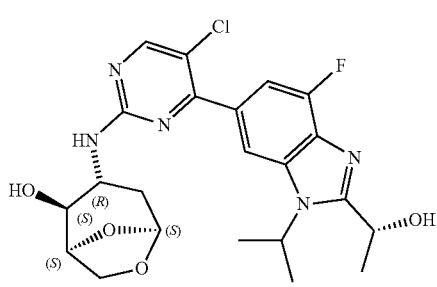
159 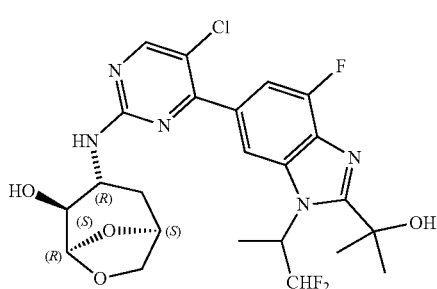
160 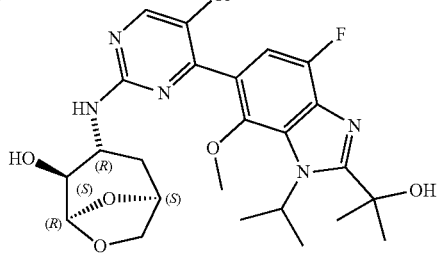
161 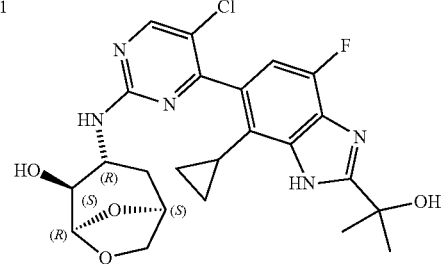
162 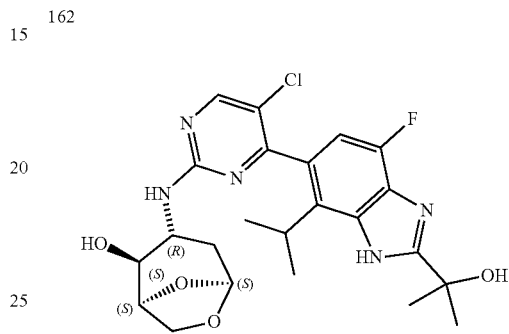
163 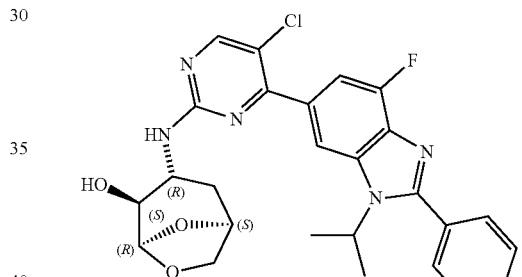
164 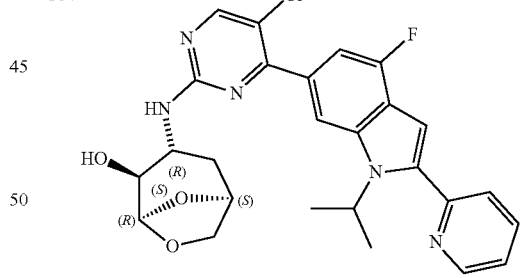
165 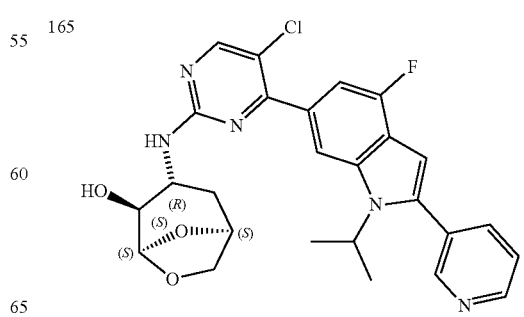

| 166 | 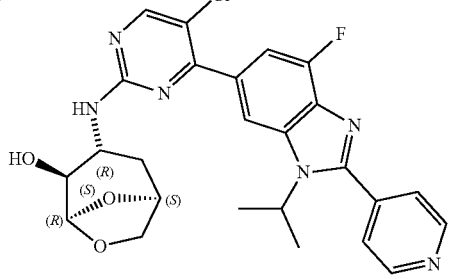 | 171 | 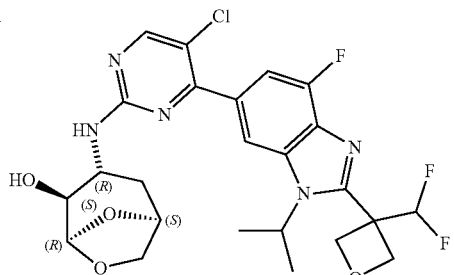 |
| 167 | 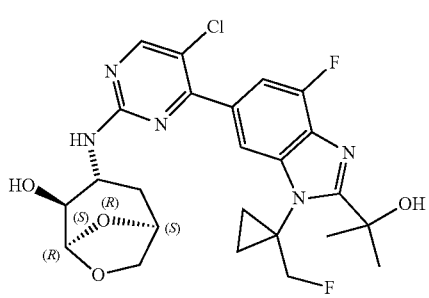 | 172 | 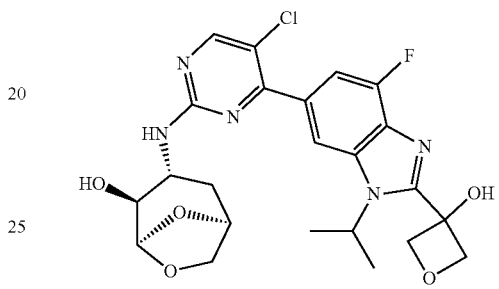 |
| 168 | 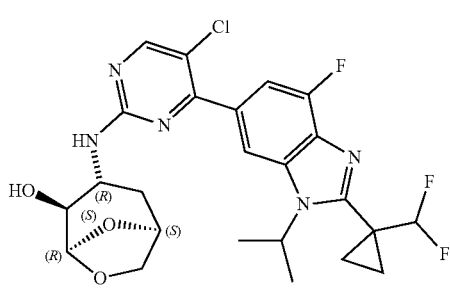 | 174 | 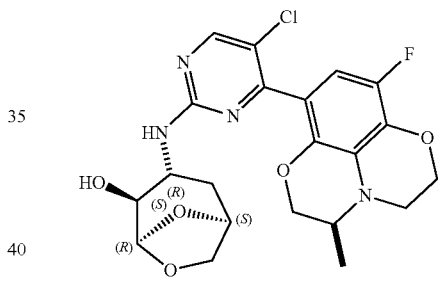 |
| 169 | 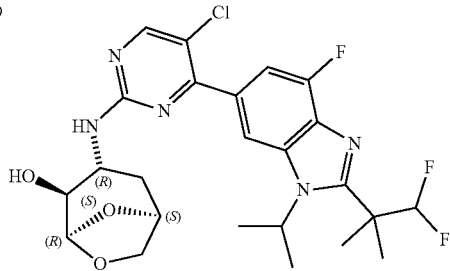 | 175 | 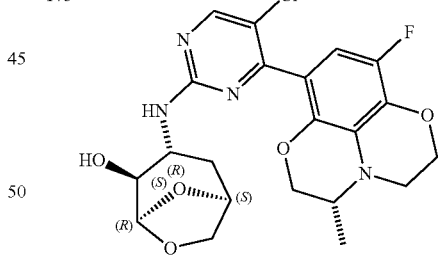 |
| 170 | 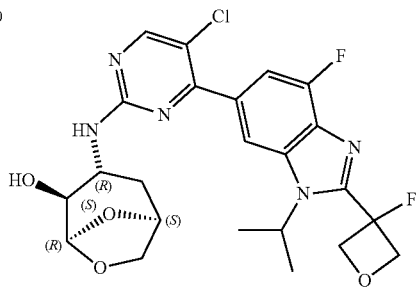 | 176 | 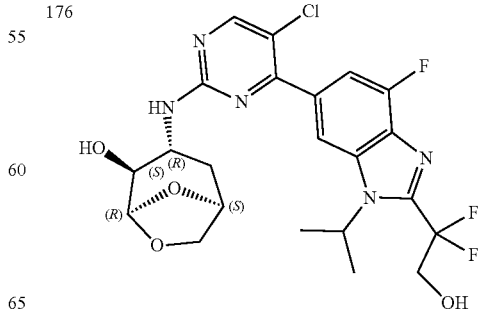 |

| 447 -continued | 448 -continued |
|---|---|
| 177 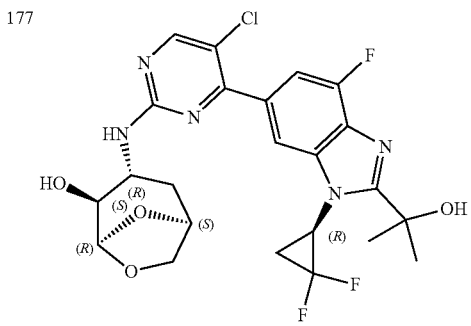 | 182 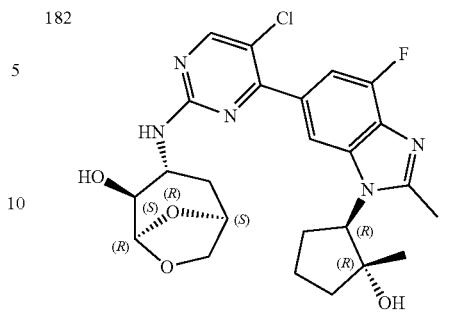 |
| 178 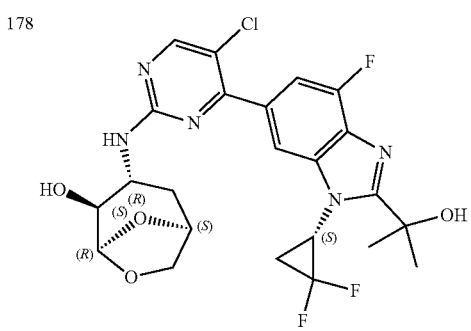 | 183 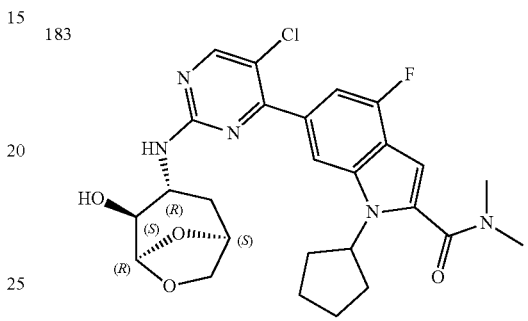 |
| 179 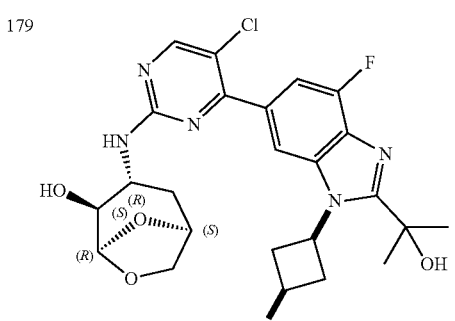 | 184 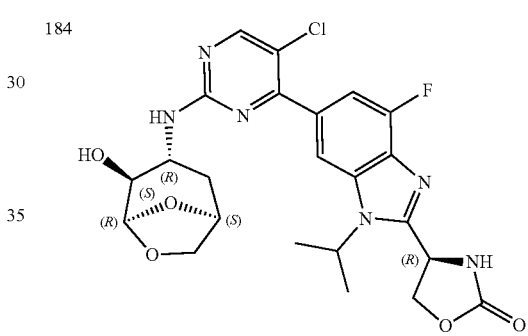 |
| 180 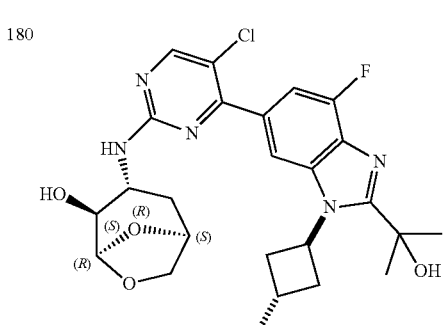 | 185 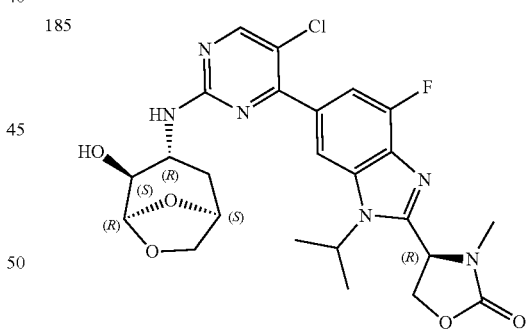 |
| 181 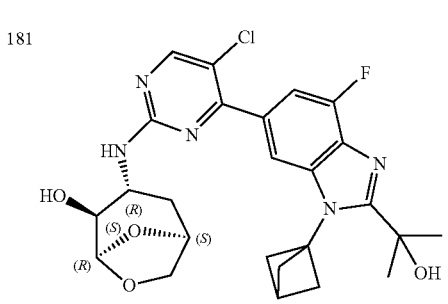 | 186 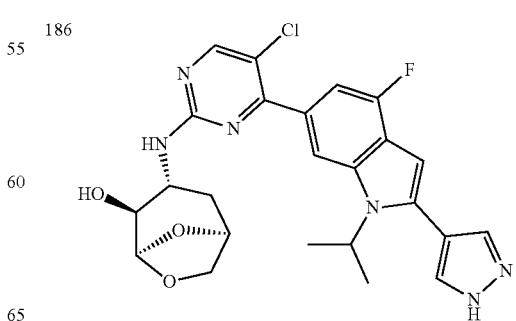 |

| | |
|---|---|
| 187 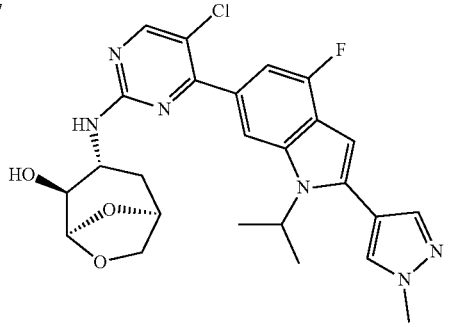 | 220 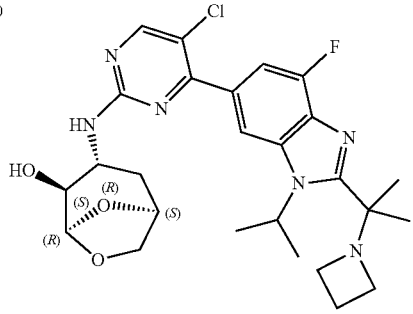 |
| 216 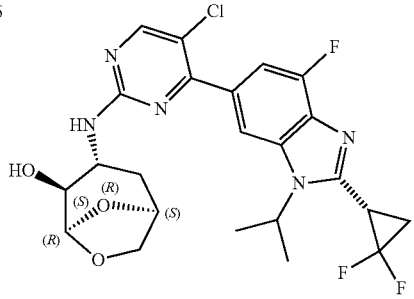 | 221 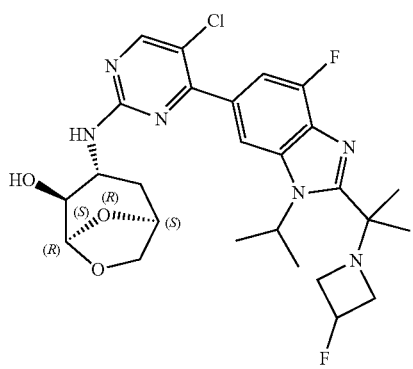 |
| 217 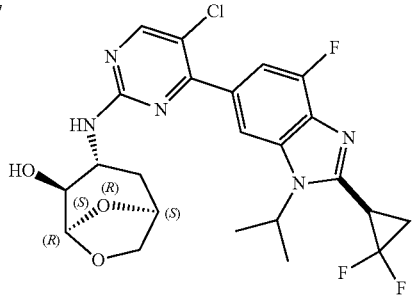 | 222 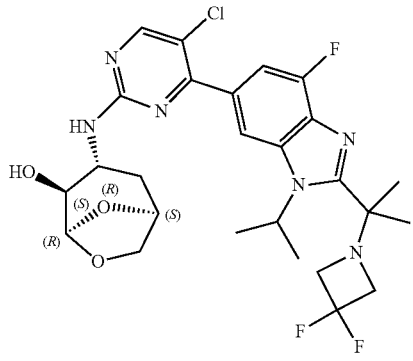 |
| 218 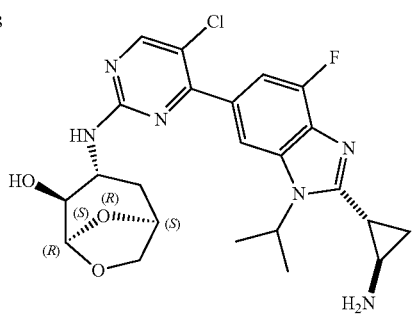 | |
| 219 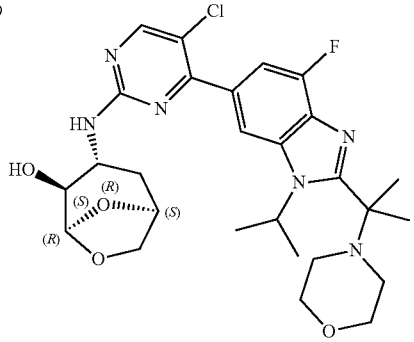 | 225 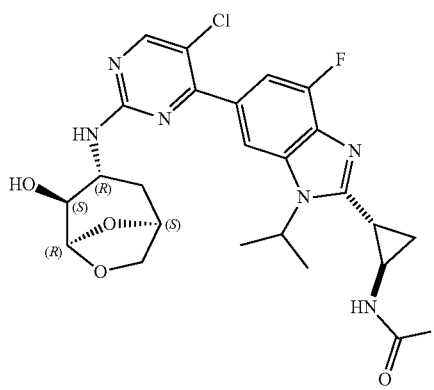 |

| 451 -continued | 452 -continued |
|---|---|
| 226 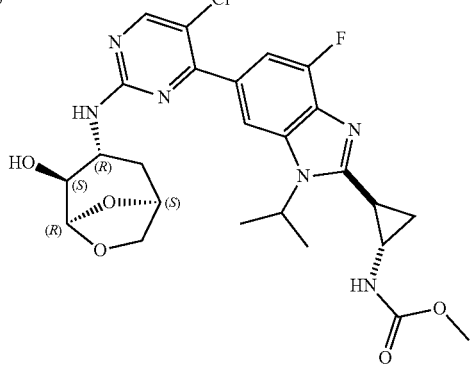 | 242 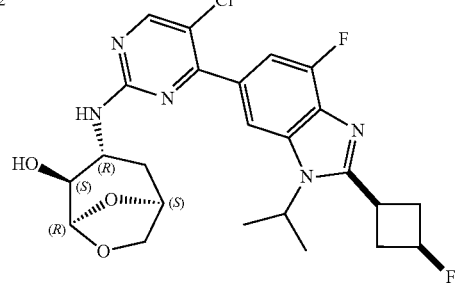 |
| 238 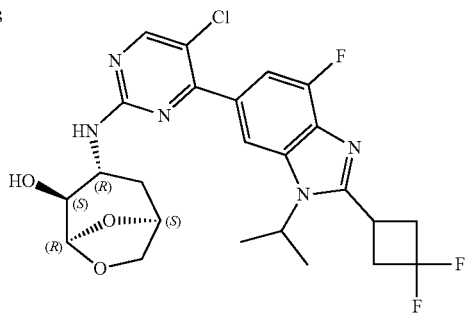 | 243 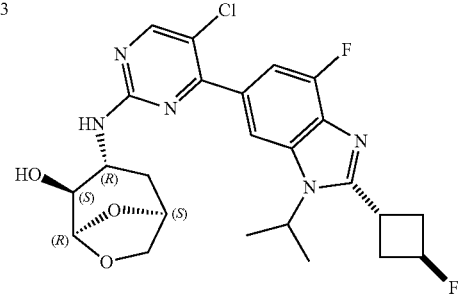 |
| 239 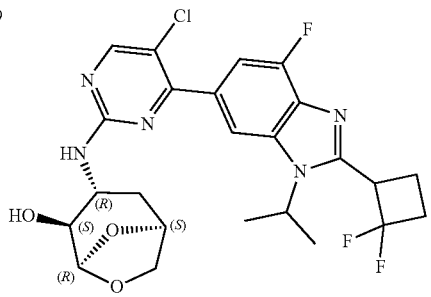 | 244 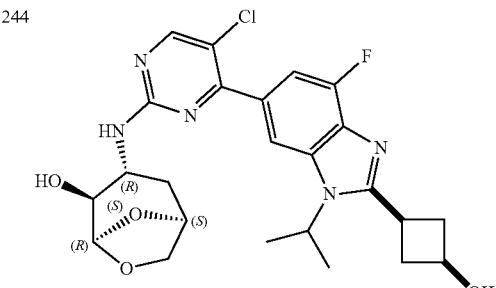 |
| 240 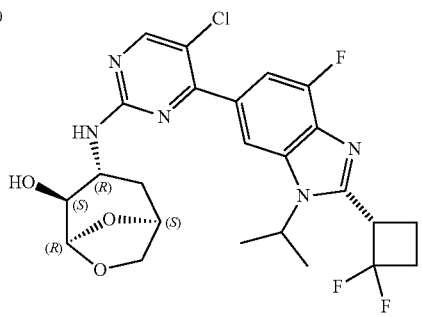 | 245 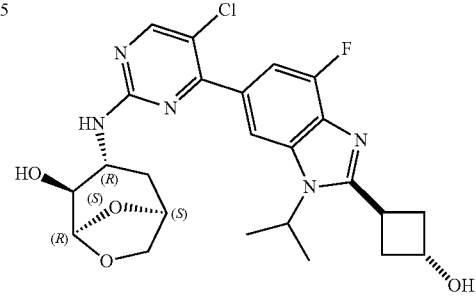 |
| 241 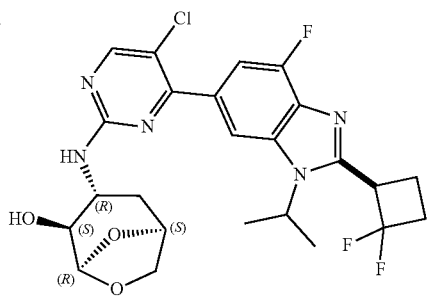 | 246 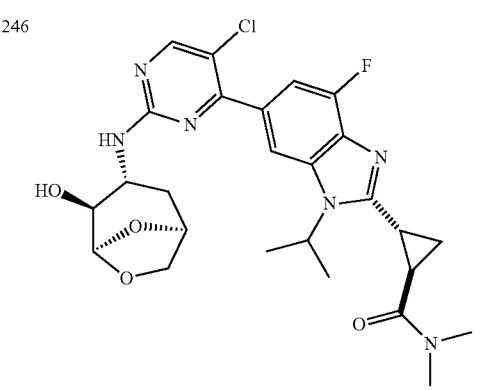 |

453
-continued
247
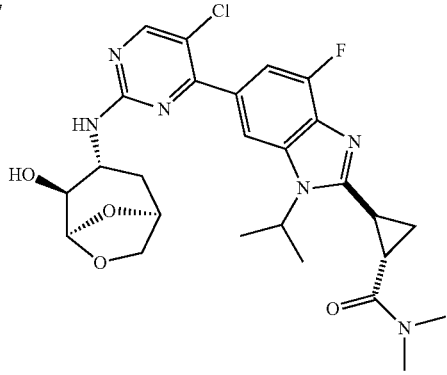
248
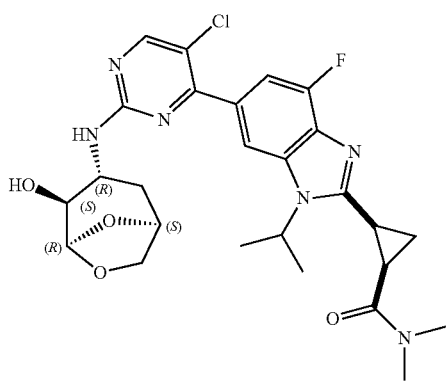
249
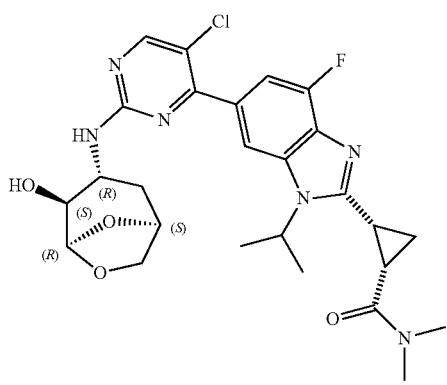
265
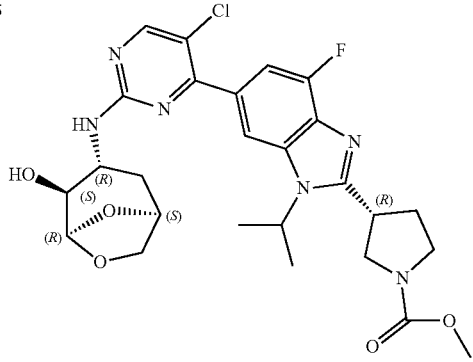
454
-continued
267
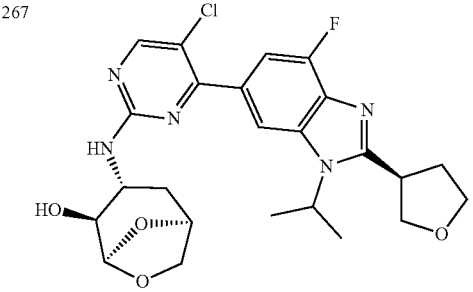
268
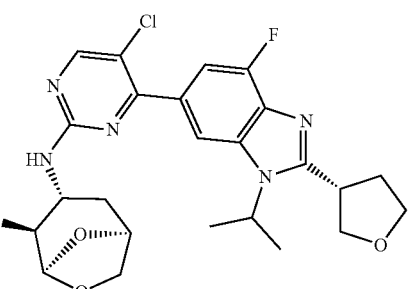
269
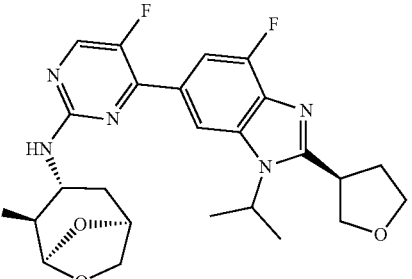
270
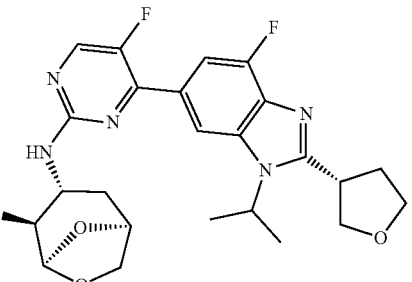
272
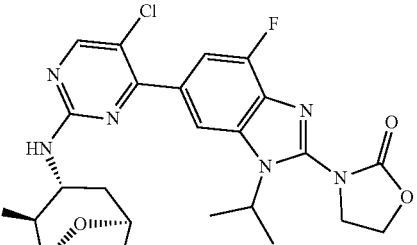

296 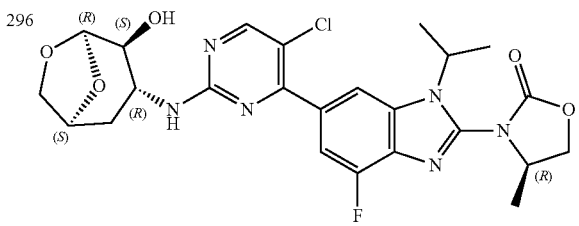
297 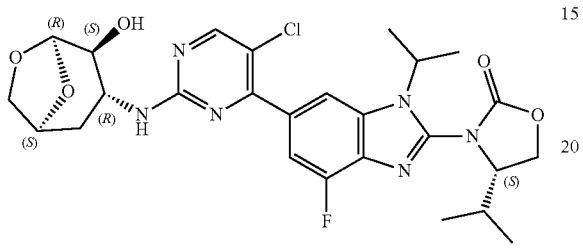
298 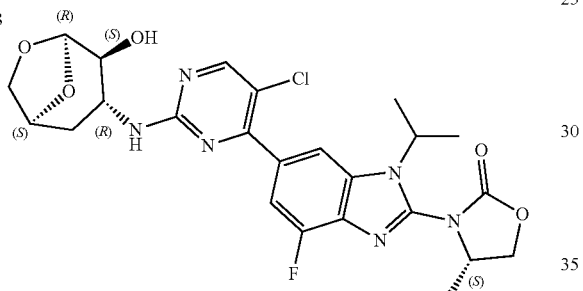
or a pharmaceutically acceptable salt of any of the above.
17. The compound according to claim 16, wherein the compound is selected from:
1 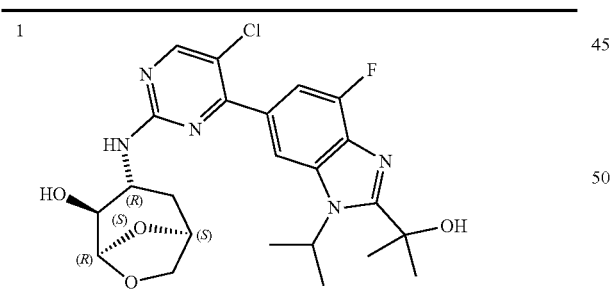
2 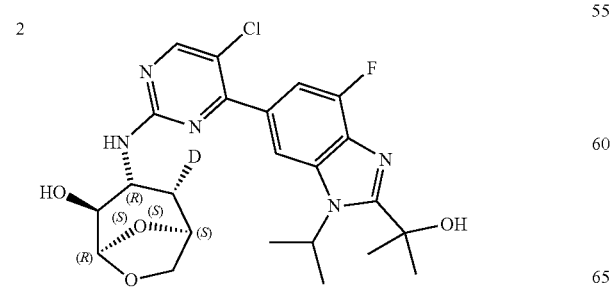
13 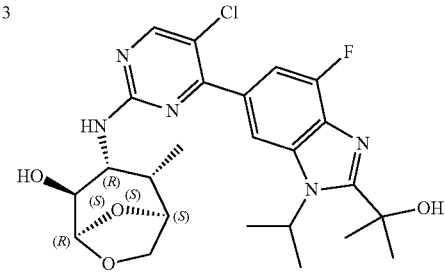
25 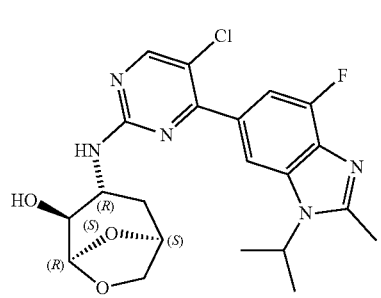
26 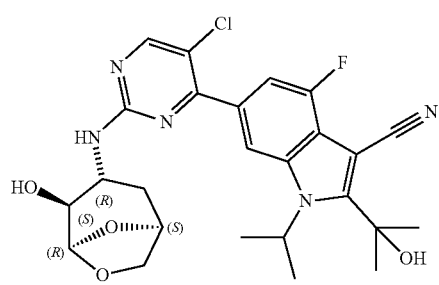
72 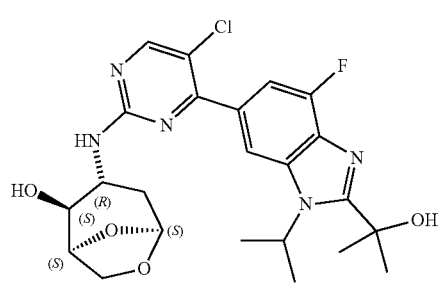
136 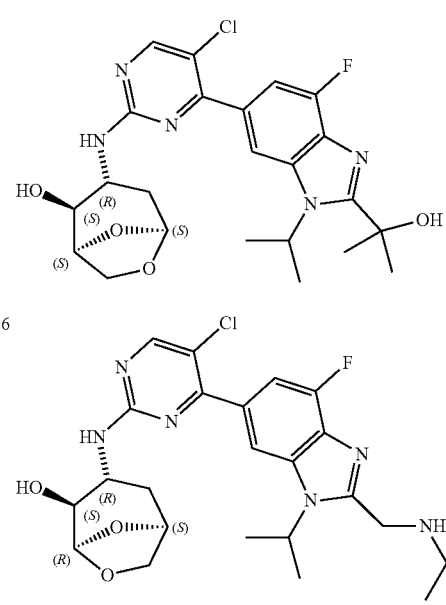

167 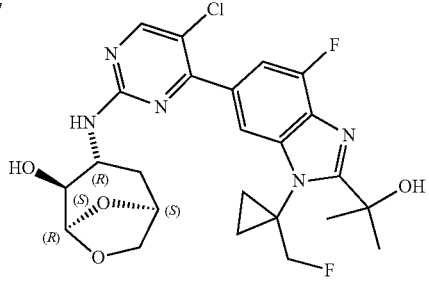
168 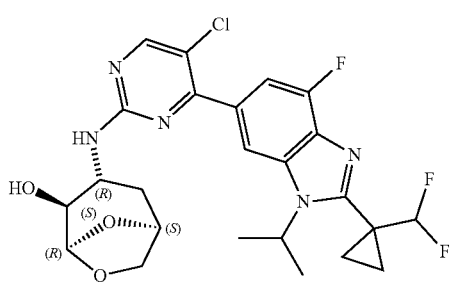
169 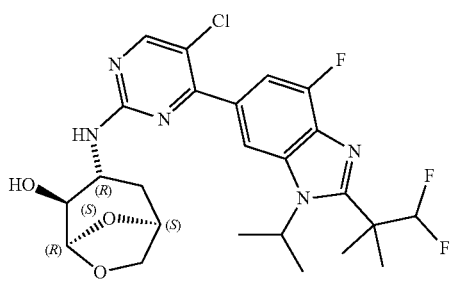
172 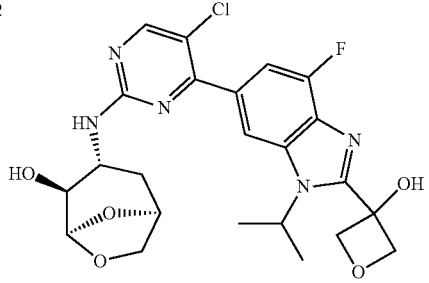
216 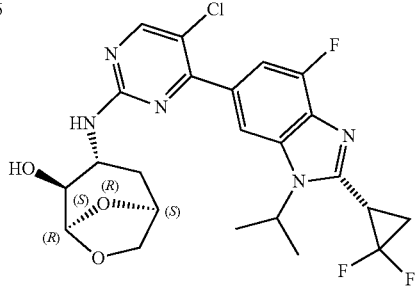
217 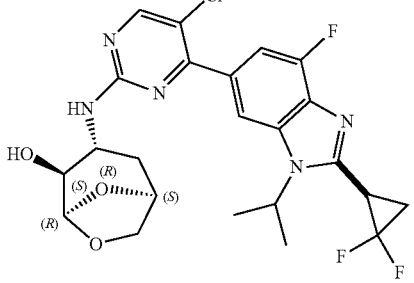
238 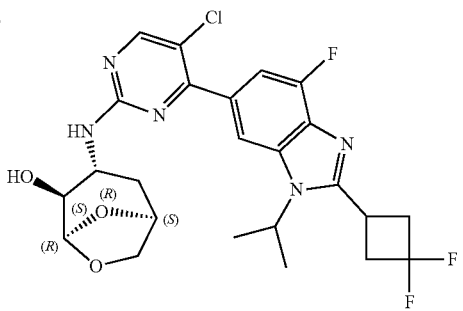
239 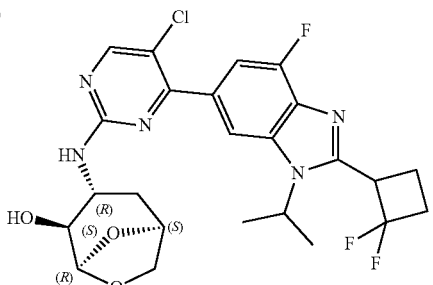
240 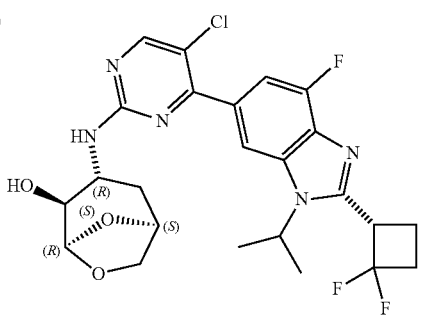
242 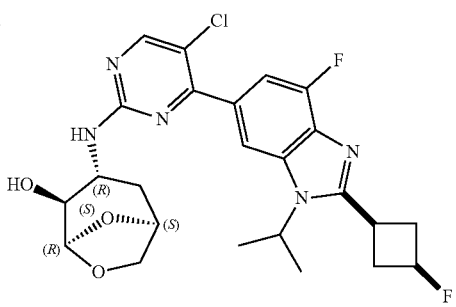

| 459 | 460 |
|---|---|
| 243 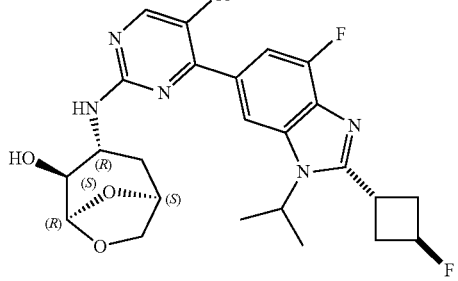 | 248 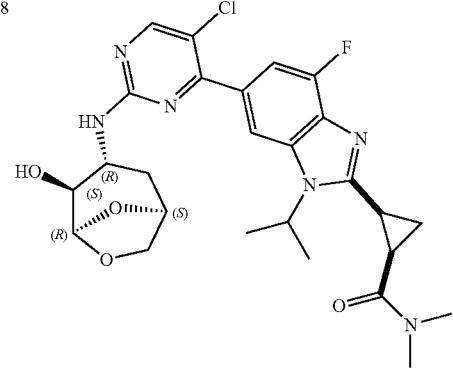 |
| 244 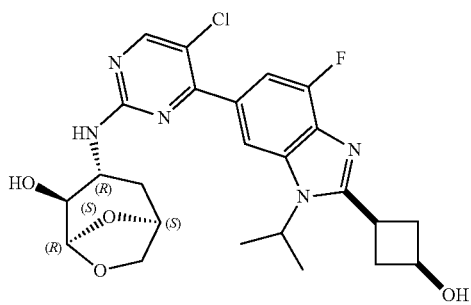 | 265 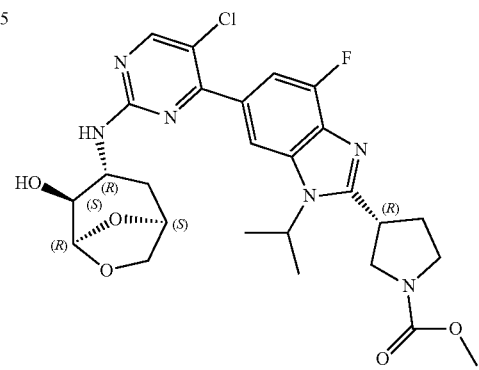 |
| 245 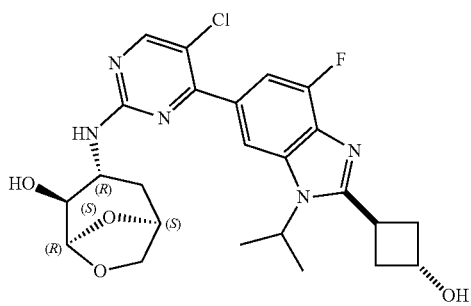 | 268 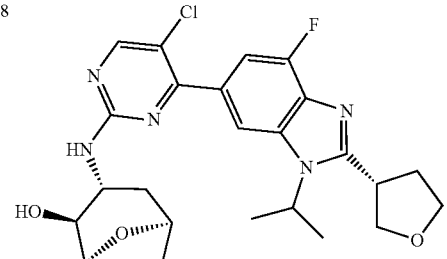 |
| | 269 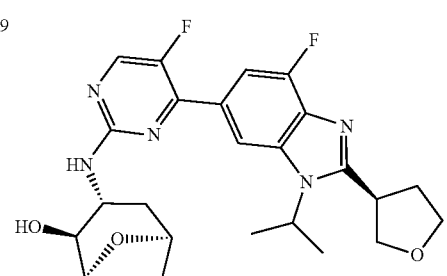 |
| 246 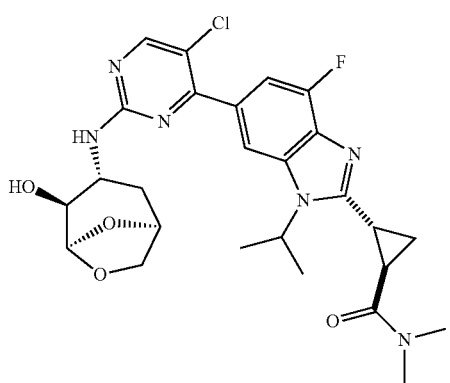 | 270 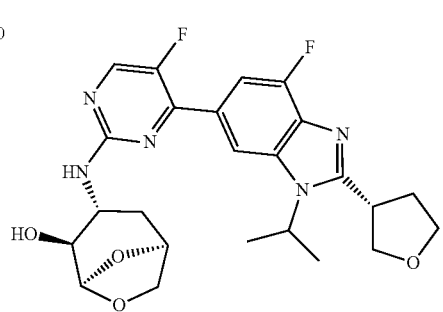 |

296 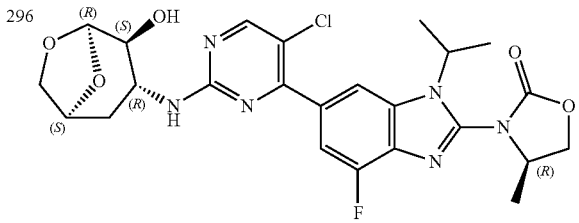

298 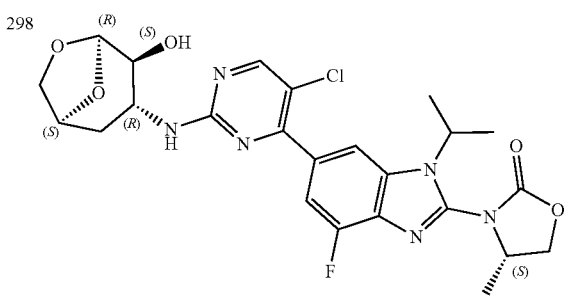

or a pharmaceutically acceptable salt of any of the above.

18. A pharmaceutical composition comprising a therapeutically effective amount of a compound according to claim 16 and one or more pharmaceutically acceptable carriers, pharmaceutically acceptable vehicles, pharmaceutically acceptable excipients, or combinations thereof.

19. A method of treating a disease or condition modulated at least in part by a cyclin-dependent kinase (CDK) in a subject in need thereof, comprising administering to the subject an effective amount of at least one compound according to claim 16.

20. A method for inhibiting a CDK in a subject, comprising administering to the subject an effective amount of at least one compound according to claim 16.

21. A method for treating cancer in a subject in need thereof, comprising administering to the subject an effective amount of at least one compound according to claim 16.

22. A compound, wherein the compound is represented by Formula (IB) or is a pharmaceutically acceptable salt thereof:

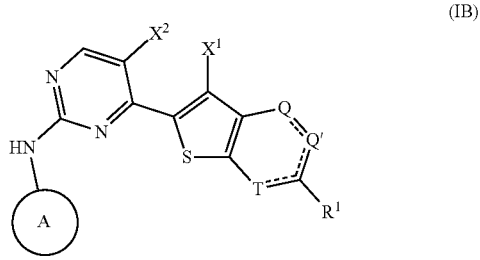

(IB)

wherein:
 is a single bond or a double bond;
$R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)OR$^{1B}$, —C(=O)N(R$^{1B}$)$_2$, —NHC(=O)OR$^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Q is CR$^Q$, N, or NR$^Q$, wherein R$^Q$ is selected from hydrogen, halogen, $C_1$-$C_4$ alkyl, and an oxo group;

Q' is CR$^{Q'}$, N, NR$^{Q'}$, wherein R$^{Q'}$ is selected from hydrogen, $C_1$-$C_4$ alkyl, and $C_1$-$C_4$ haloalkyl;

T is CR$^{T1}$ or NR$^{T2}$, wherein R$^{T1}$ is halogen or R$^{T2}$, and R$^{T2}$ is hydrogen or $C_1$-$C_6$ alkyl, wherein the $C_1$-$C_6$ alkyl is optionally substituted with 1, 2, or 3 groups independently selected from halogen, $C_1$-$C_6$ alkyl, and hydroxyl;

Ring A is

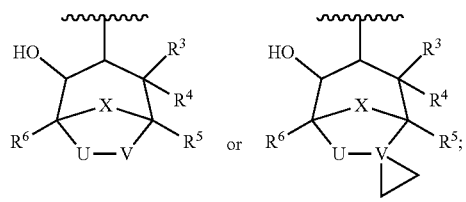

wherein:
$R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;

$R^5$ and $R^6$ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;

X is O or N—S(O)$_2$—R$^X$, wherein R$^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;

U is O or C(R$^U$)$_2$, wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and V is O, C, or C(R$^V$)$_2$, wherein R$^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

23. The compound according to claim 22, wherein the compound is selected from:
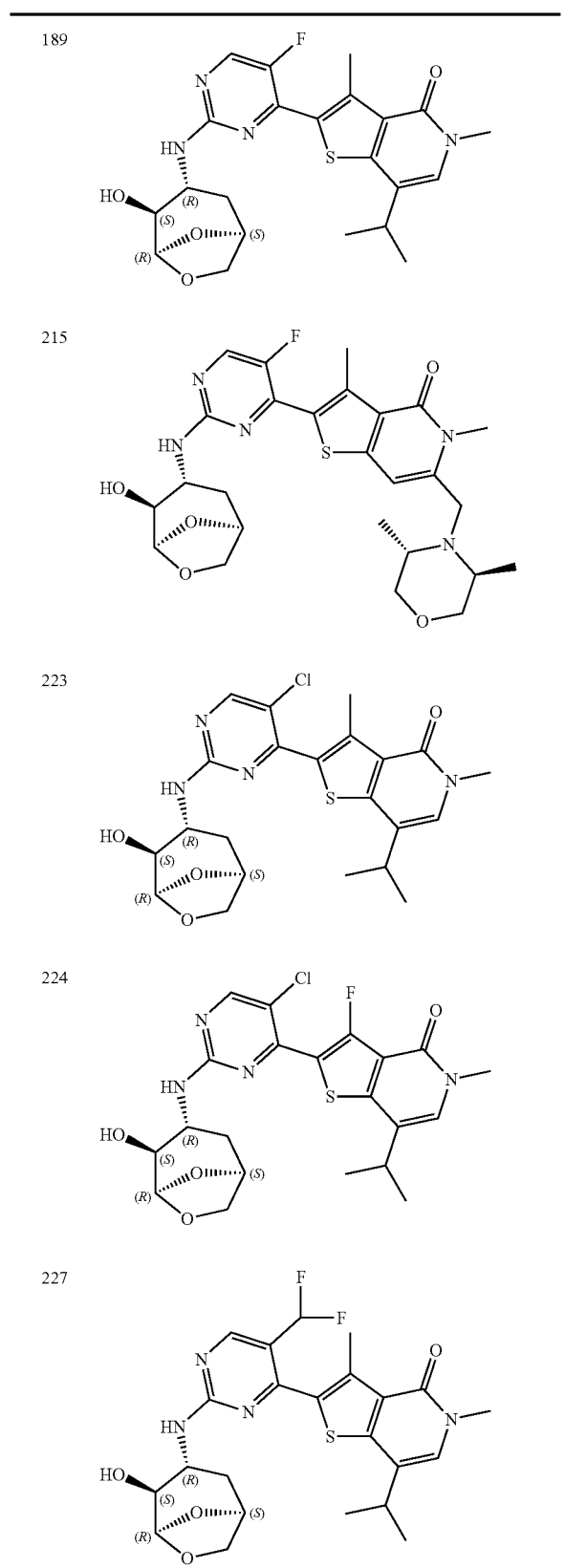
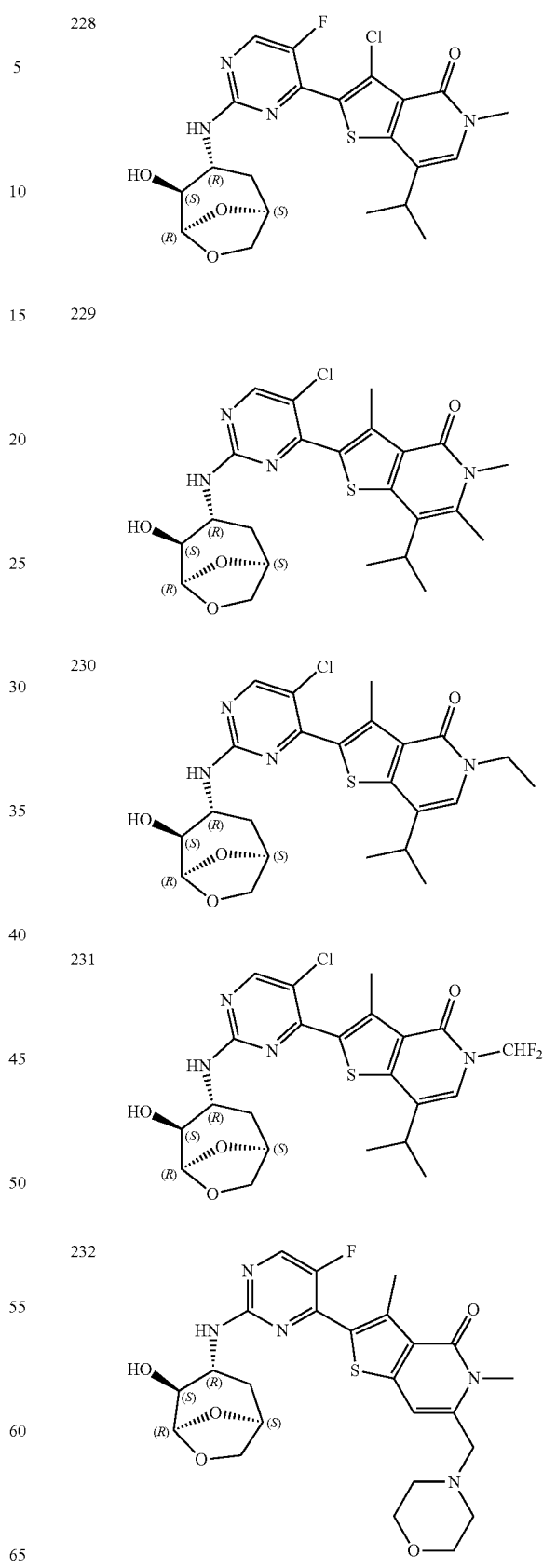

| 233 | 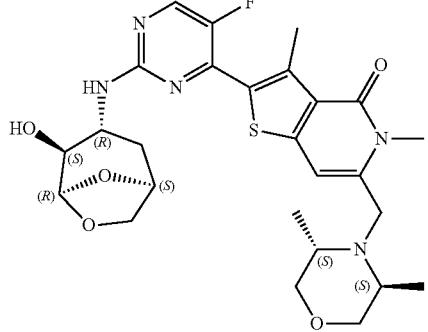 | 274 | 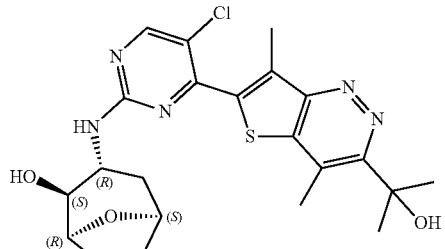 |
| 259 | 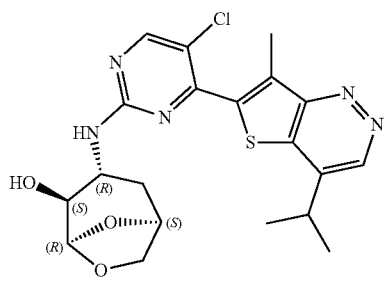 | 275 | 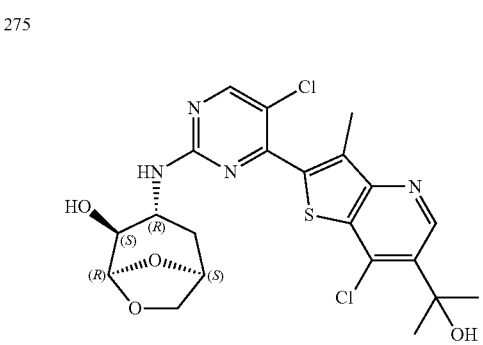 |
| 260 | 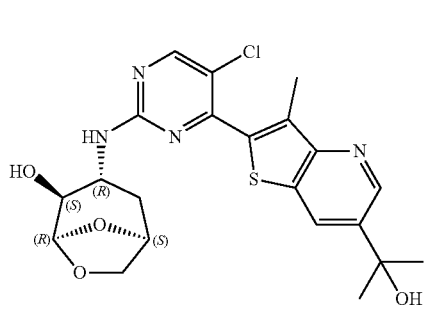 | 276 | 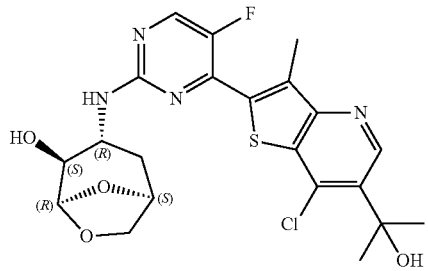 |
| 266 | 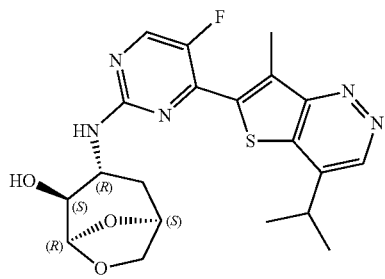 | 277 | 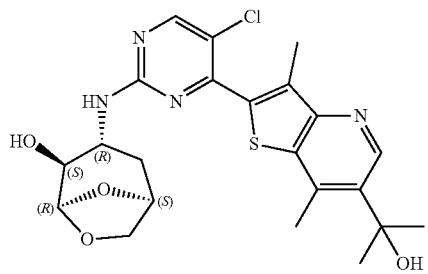 |
| 273 | 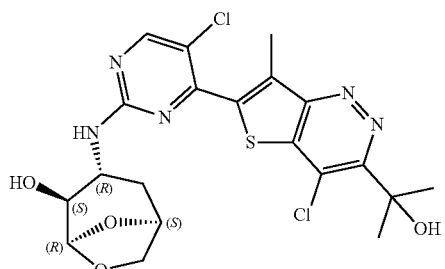 | 278 | 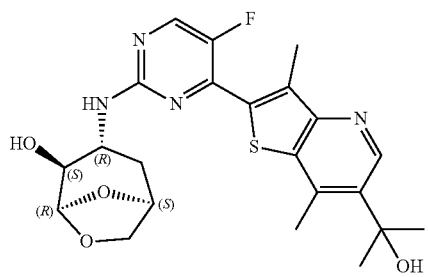 |

467

-continued

287

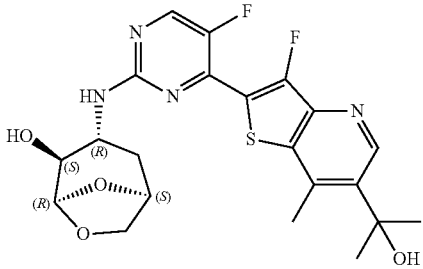

288

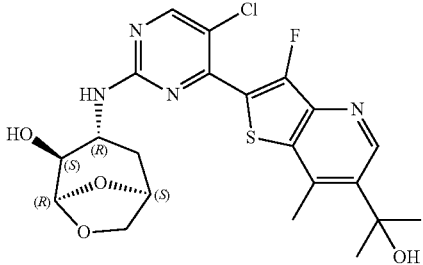

289

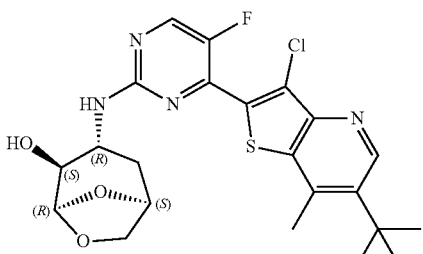

290

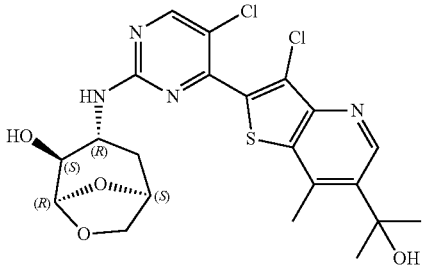

or a pharmaceutically acceptable salt of any of the above.

24. A method for treating cancer in a subject in need thereof, comprising administering to the subject an effective amount of at least one compound according to claim 23.

25. A compound, wherein the compound is represented by Formula (IC) or is a pharmaceutically acceptable salt thereof:

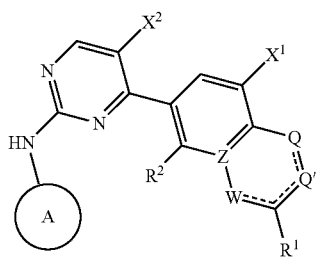

(IC)

468 wherein:

⩳ is a single bond or a double bond;

$R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;

each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)O$R^{1B}$, —C(=O)N($R^{1B}$)$_2$, —NHC(=O)O$R^{1B}$, and a 4-6 membered heterocyclic group, wherein the 4-6 membered heterocyclic group is optionally substituted with 1, 2, or 3 $R^{1C}$;

each $R^{1B}$ is independently selected from hydrogen, $C_1$-$C_6$ alkyl, and $C_3$-$C_6$ cycloalkyl;

each $R^{1C}$ is independently selected from hydrogen, hydroxyl, halogen, an oxo group, $C_1$-$C_6$ alkyl, and $C_3$-$C_6$ cycloalkyl;

$R^2$ is selected from hydrogen, $C_1$-$C_6$ alkyl, $C_1$-$C_6$ haloalkyl, $C_3$-$C_6$ cycloalkyl, $C_3$-$C_6$ cyclic haloalkyl, $C_1$-$C_6$ alkoxy, $C_3$-$C_6$ cyclic alkoxy, $C_1$-$C_6$ haloalkoxy, and a 3-7 membered heterocyclic group;

$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;

Q is N, O, or $CR^Q$, wherein $R^Q$ is selected from hydrogen, halogen, and an oxo group;

Q' is CH, CH$_2$, $CR^{Q'}$, N, or NR", wherein $R^Q$ is halogen or R", and R" is selected from $C_1$-$C_6$ alkyl, $C_3$-$C_6$ cycloalkyl, $C_1$-$C_4$ haloalkyl, and a 3-8 membered heterocyclic group, wherein each of the $C_1$-$C_6$ alkyl and $C_3$-$C_6$ cycloalkyl are each optionally substituted with 0, 1, 2, or 3 groups independently selected from halogen, $C_1$-$C_6$ alkyl, and hydroxyl;

Z is C;

W is $CR^{W1}$, N, or $NR^{W2}$; wherein $R^{W1}$ is selected from hydrogen, halogen, $C_1$-$C_6$ alkyl, $C_3$-$C_6$ cycloalkyl, and a 3-8 membered heterocyclic group, wherein each of the $C_1$-$C_6$ alkyl and $C_3$-$C_6$ cycloalkyl is optionally substituted with 1, 2, or 3 $R^{1D}$, $R^{W2}$ is selected from hydrogen, $C_1$-$C_6$ alkyl, $C_3$-$C_6$ cycloalkyl, and a 3-8 membered heterocyclic group, wherein each of the $C_1$-$C_6$ alkyl and $C_3$-$C_6$ cycloalkyl is optionally substituted with 1, 2, or 3 $R^{1D}$, and each $R^{1D}$ is independently selected from halogen, $C_1$-$C_6$ alkyl, and hydroxyl; or W, Z, $R^2$, and the C atom to which $R^2$ is attached may be taken together to form a carbocyclic ring of 5-8 atoms or a heterocyclic ring of 5-8 atoms, wherein each of the carbocyclic ring and heterocyclic ring is optionally substituted with 1, 2, 3, or 4 $R^{1E}$, and wherein each $R^{1E}$ is independently selected from $C_1$-$C_6$ alkyl, hydroxyl, and an oxo group;

Ring A is

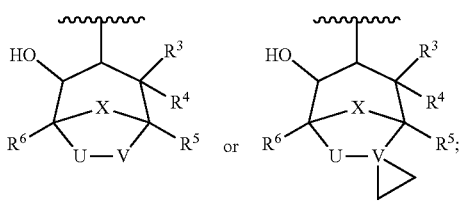

wherein:
- R³ and R⁴ are independently selected from hydrogen, deuterium, halogen, hydroxyl, $C_1$-$C_6$ alkyl, and $C_3$-$C_6$ cycloalkyl; or R³ and R⁴ may be taken together with the carbon atom to which both are attached to form a 3-7 membered cycloalkyl;
- R⁵ and R⁶ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;
- X is O or N—S(O)₂—$R^X$, wherein $R^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$ cycloalkyl, 3-7 membered heterocyclic group, aryl, and heteroaryl is optionally substituted with 1, 2, or 3 groups selected from halogen, hydroxyl, and cyano;
- U is O or $C(R^U)_2$, wherein $R^u$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and
- V is O, C, or $C(R^Y)_2$, wherein $R^Y$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;

with the proviso that one but not both of U and V is O.

26. The compound according to claim 25, wherein the compound is selected from:

173

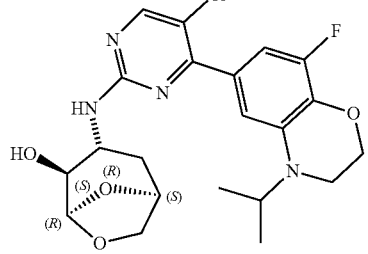

188

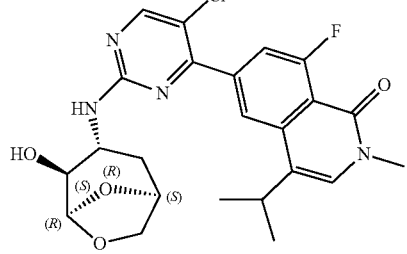

-continued

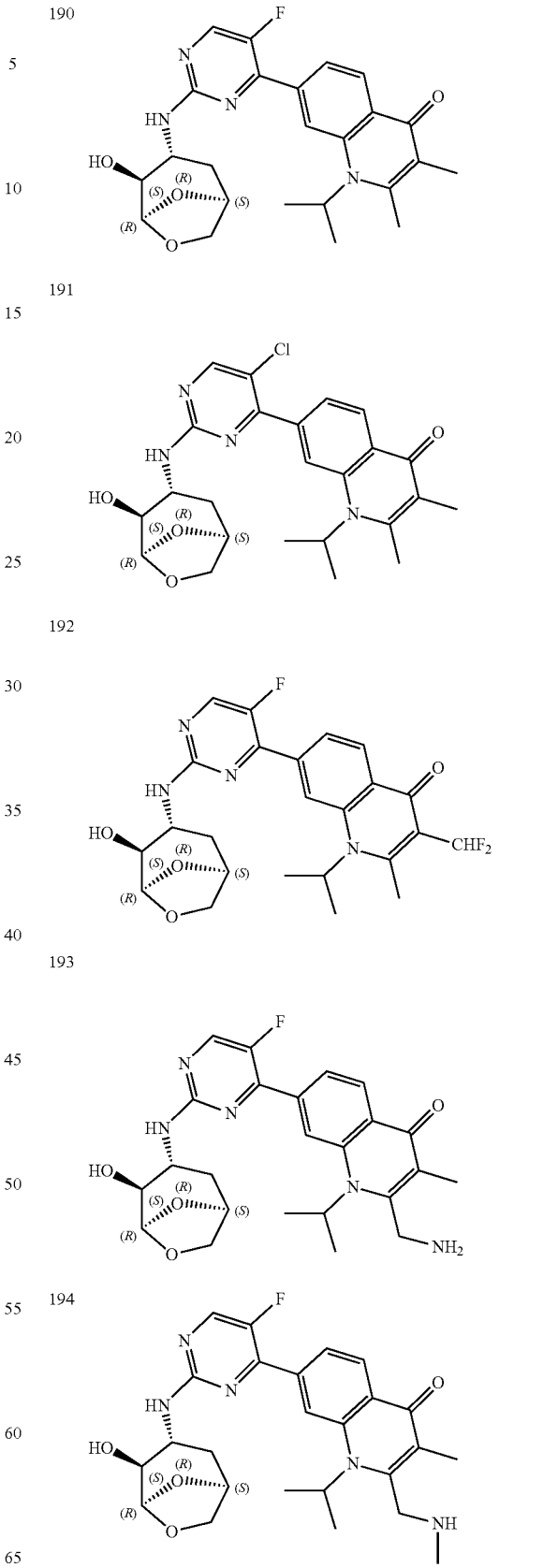

| 471 -continued | 472 -continued |
|---|---|
| 195 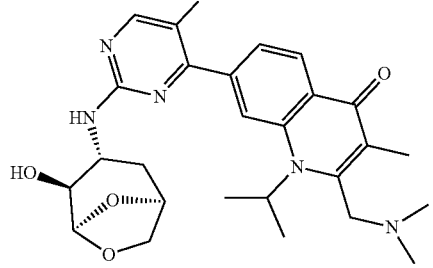 | 200 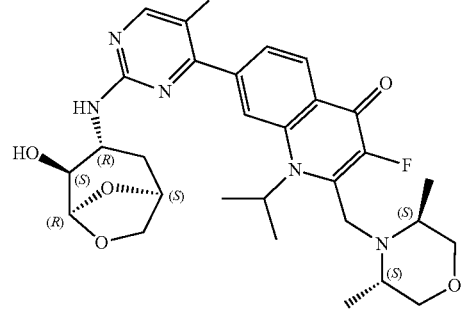 |
| 196 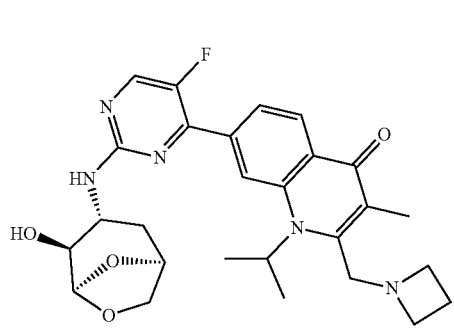 [SMILES: Cc1c(CN2CCC2)n(C(C)C)c2cc(-c3nc(N[C@@H]4C[C@H]5CO[C@H](O5)[C@H]4O)ncc3F)ccc2c1=O] | 201 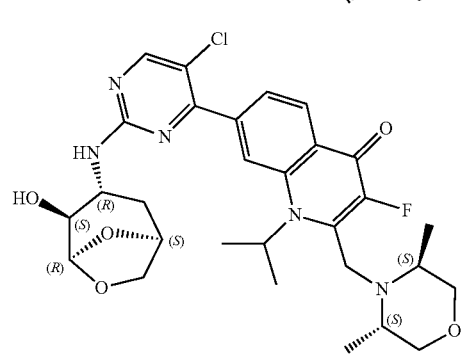 |
| 197 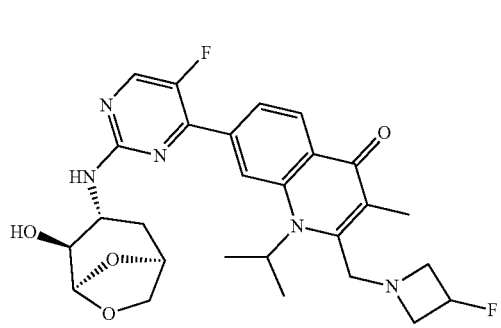 [SMILES: Cc1c(CN2CC(F)C2)n(C(C)C)c2cc(-c3nc(N[C@@H]4C[C@H]5CO[C@H](O5)[C@H]4O)ncc3F)ccc2c1=O] | 202 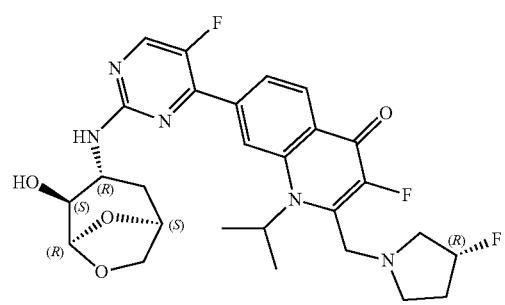 |
| 198 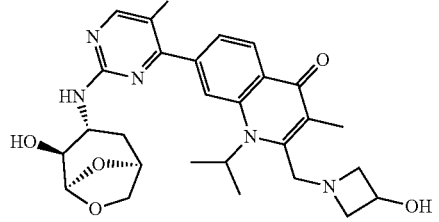 | 203 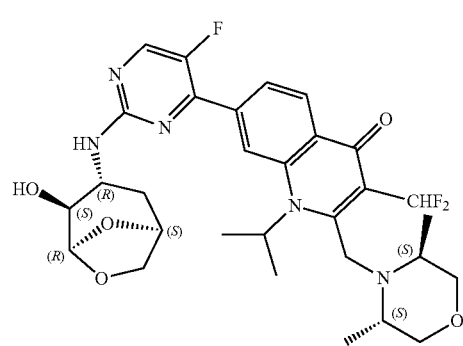 |
| 199 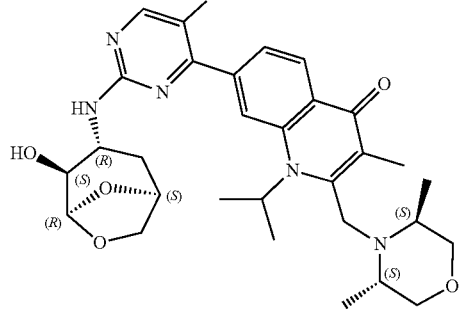 | 204 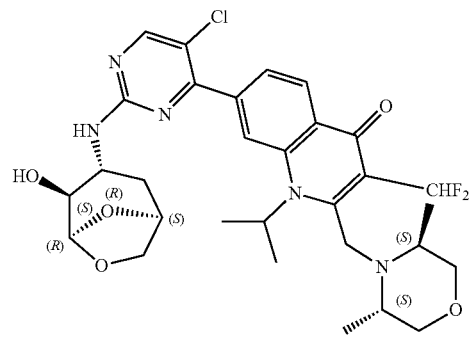 |

473
-continued
205
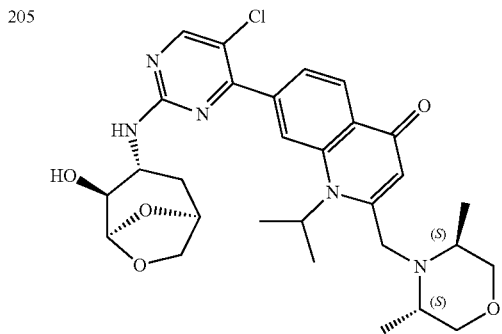
206
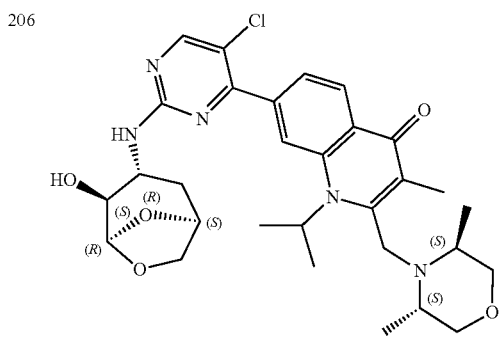
207
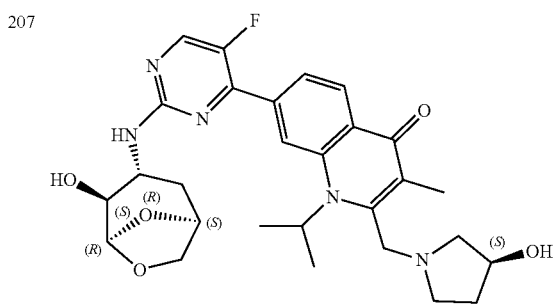
208
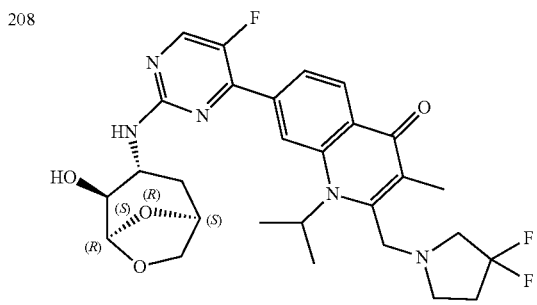
209
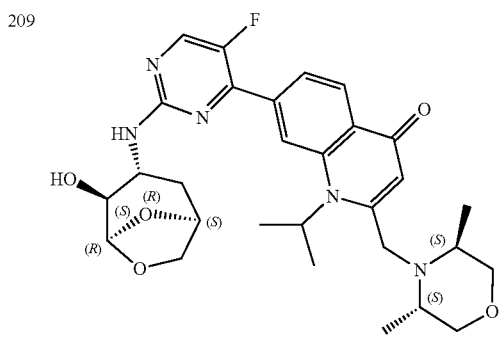
474
-continued
210
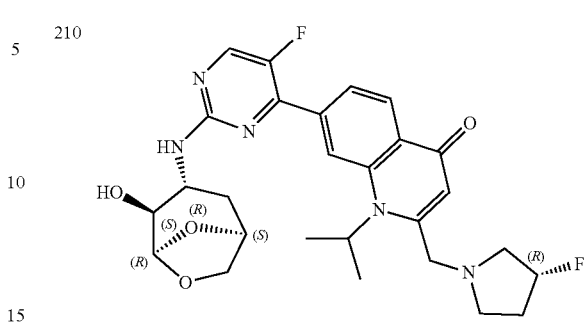
211
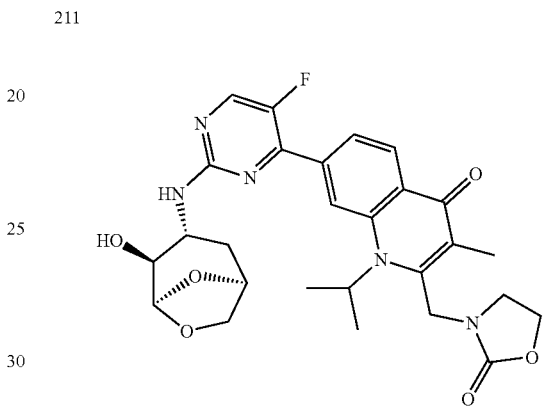
212
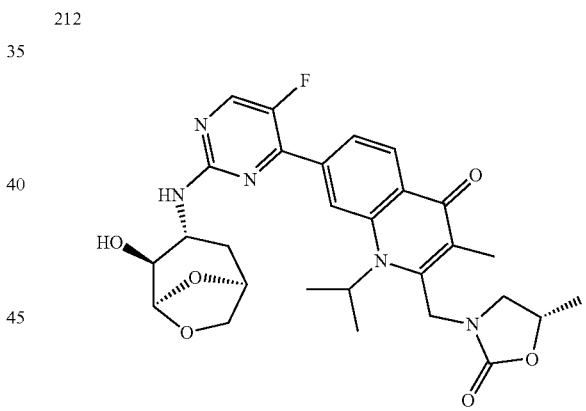
213
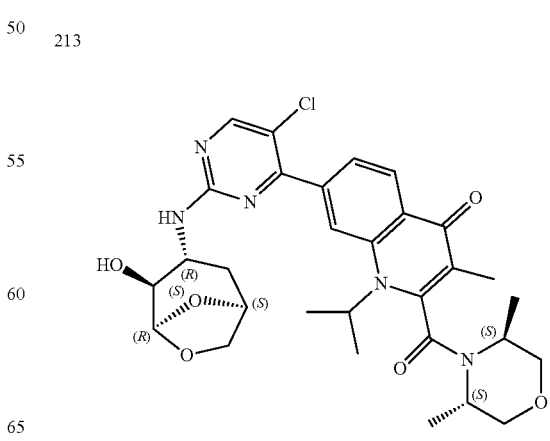

| 475 -continued | 476 -continued |
|---|---|
| 214 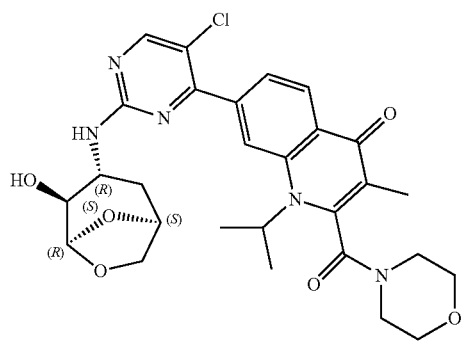 | 250 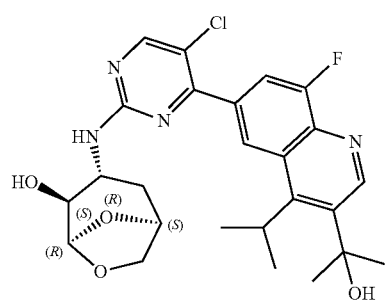 |
| 234 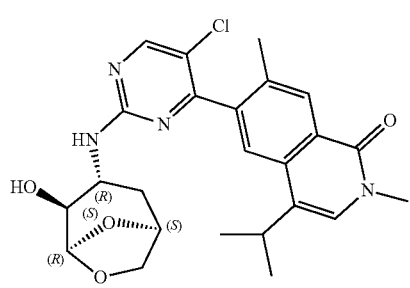 | 251 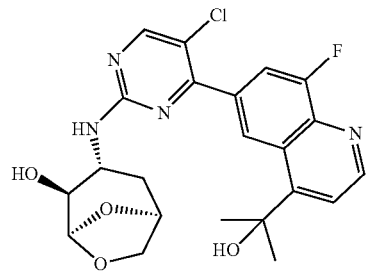 |
| 235 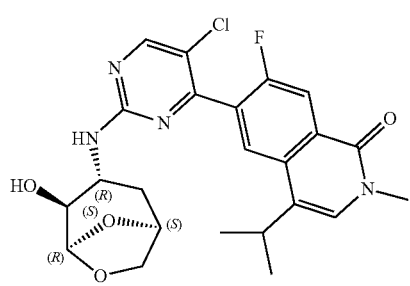 | 252 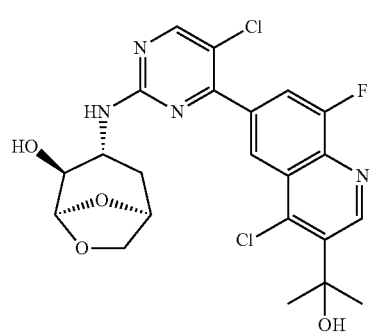 |
| 236 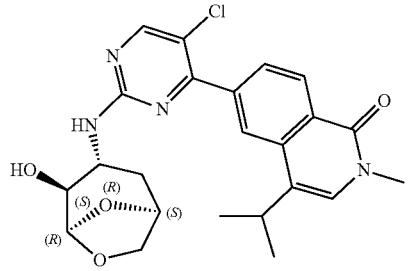 | 253 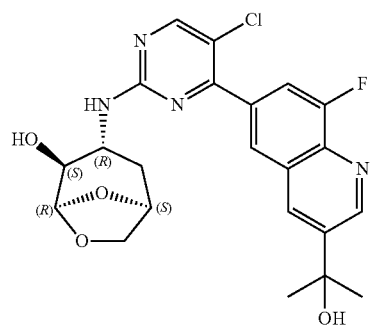 |
| 237 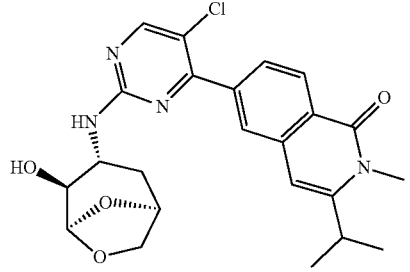 [SMILES: CC(C)c1cc2cc(-c3nc(N[C@@H]4C[C@H]5CO[C@H](O5)[C@H]4O)ncc3Cl)ccc2c(=O)n1C] | 254 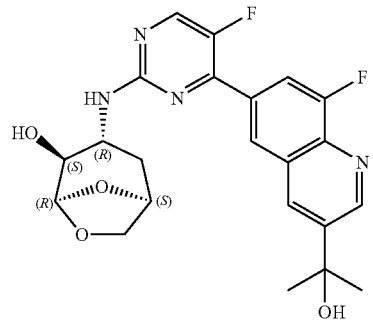 |

255 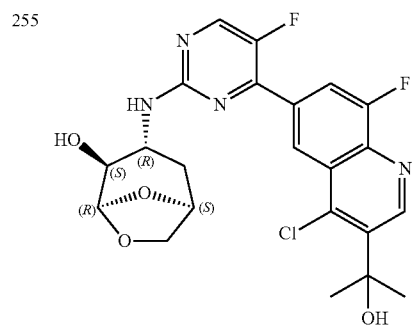
256 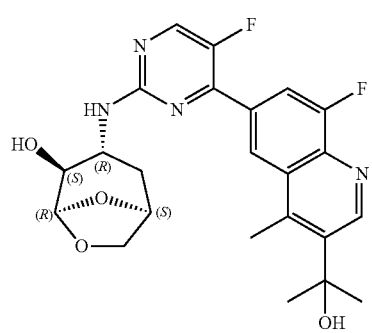
257 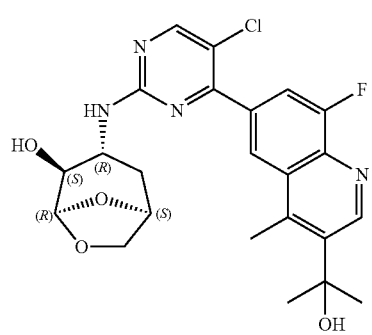
258 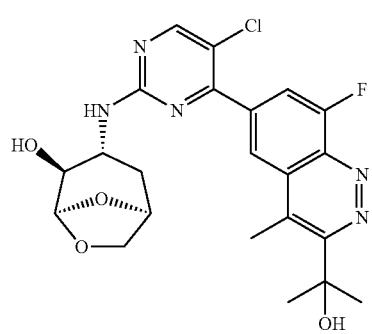
261 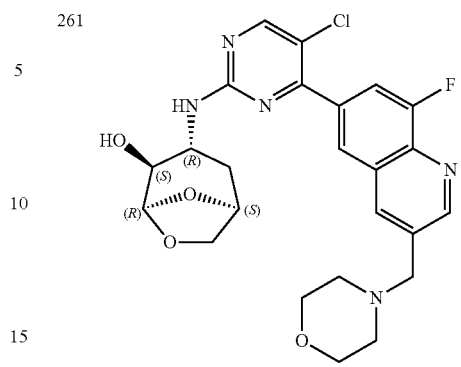
262 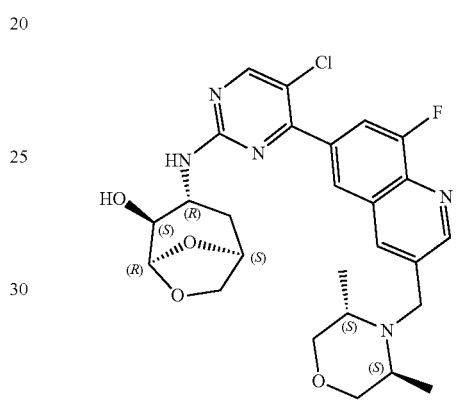
264 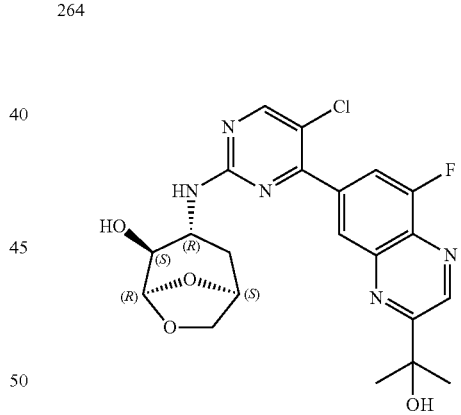
271 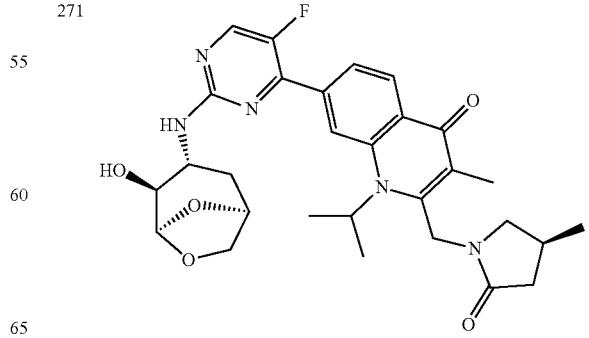

| 279 | 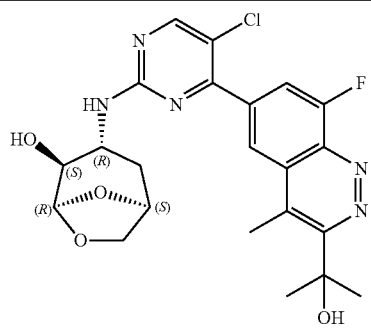 | 284 | 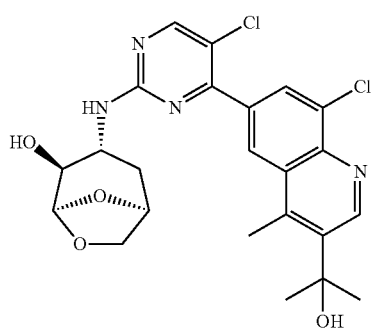 [SMILES: Cc1c(C(C)(C)O)cnc2c(Cl)cc(-c3nc(N[C@@H]4C[C@H]5CO[C@H](O5)[C@H]4O)ncc3F)cc12] |
| --- | --- | --- | --- |
| 280 | 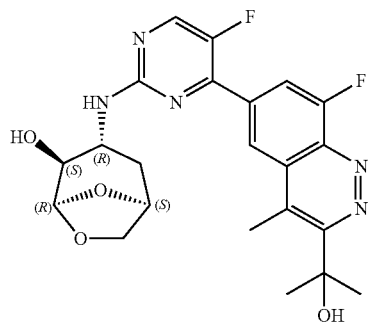 | 285 | 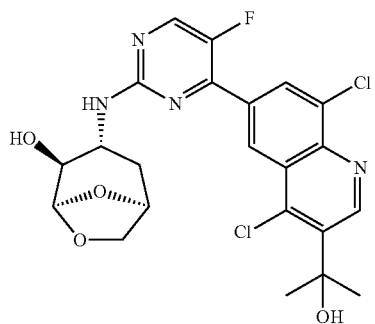 |
| 281 | 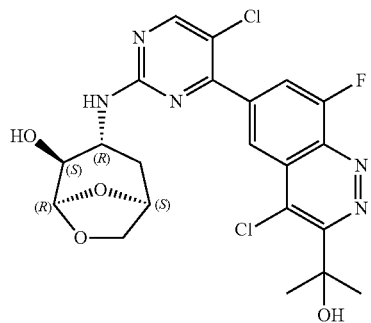 | 286 | 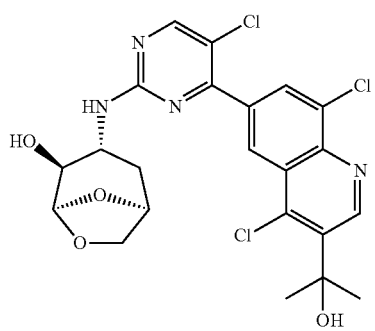 |
| 282 | 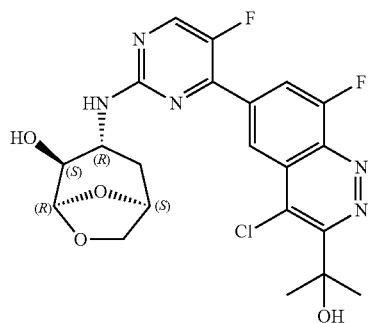 | 291 | 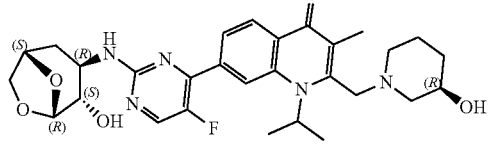 |
| 283 | 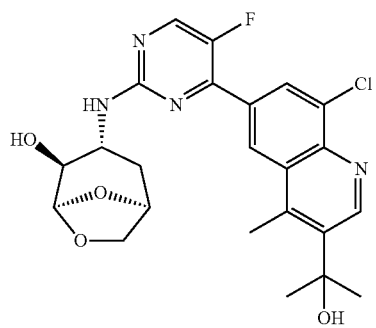 [SMILES: Cc1c(C(C)(C)O)cnc2c(Cl)cc(-c3nc(N[C@@H]4C[C@H]5CO[C@H](O5)[C@H]4O)ncc3Cl)cc12] | 292 | 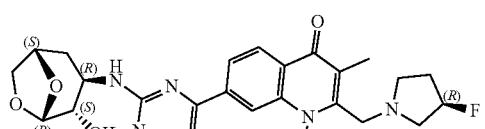 |
| | | 293 | 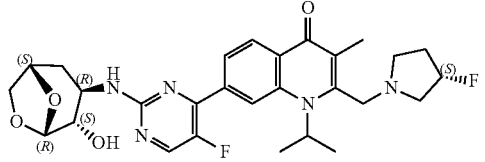 |

-continued

294

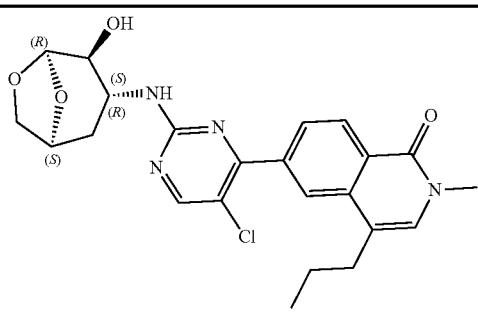

295

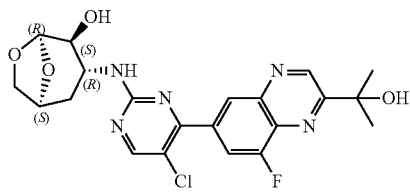

or a pharmaceutically acceptable salt of any of the above.

27. A method for treating cancer in a subject in need thereof, comprising administering to the subject an effective amount of at least one compound according to claim 26.

28. A compound, wherein the compound is represented by Formula (ID) or is a pharmaceutically acceptable salt thereof:

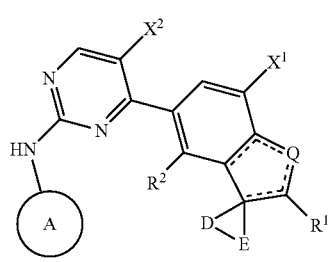

(ID)

wherein:
≈≈≈ is a single bond or a double bond;
$R^1$ is selected from hydrogen, $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, an oxo group, cyano, a 3-7 membered heterocyclic group, 6-10 membered aryl, and a 5-10 membered heteroaryl, wherein each of the $C_1$-$C_6$ alkyl, $C_3$-$C_6$ cycloalkyl, $C_1$-$C_6$ haloalkyl, $C_3$-$C_6$ cyclic haloalkyl, $C_5$-$C_8$ bicyclic alkyl, $C_1$-$C_6$ aminoalkyl, $C_1$-$C_6$ alkoxy, 3-7 membered heterocyclic group, 6-10 membered aryl, and 5-10 membered heteroaryl is independently substituted with 0, 1, 2, or 3 $R^{1A}$;
each $R^{1A}$ is independently selected from halogen, hydroxyl, an oxo group, amino, $C_1$-$C_6$ alkyl, $C_3$-$C_6$ cycloalkyl, $C_1$-$C_6$ alkoxy, $C_3$-$C_6$ cyclic alkoxy, —C(=O)O$R^{1B}$, —C(=O)N($R^{1B}$)$_2$, —NHC(=O)O$R^{1B}$, and a 4-6 membered heterocyclic group, wherein the 4-6 membered heterocyclic group is optionally substituted with 1, 2, or 3 $R^{1C}$;
each $R^{1B}$ is independently selected from hydrogen, $C_1$-$C_6$ alkyl, and $C_3$-$C_6$ cycloalkyl;
each $R^{1C}$ is independently selected from hydrogen, hydroxyl, halogen, an oxo group, $C_1$-$C_6$ alkyl, and $C_3$-$C_6$ cycloalkyl;

$R^2$ is selected from hydrogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_3$-$C_6$ cyclic alkoxy, $C_1$-$C_6$ haloalkoxy, and a 3-7 membered heterocyclic group;
$X^1$ and $X^2$ are independently selected from hydrogen, halogen, $C_1$-$C_6$ alkyl, $C_3$-$C_6$ cycloalkyl, $C_1$-$C_6$ haloalkyl, and $C_3$-$C_6$ cyclic haloalkyl;
Q is N or CR$^Q$, wherein R$^Q$ is independently selected from hydrogen, halogen, and cyano;
D and E together with the carbon atom to which they are both attached form a carbocyclic ring of 5-8 atoms or a heterocyclic ring of 5-8 atoms containing 1 to 2 heteroatoms selected from O, S, and N, wherein any carbon ring may be optionally substituted with halogen, $C_1$-$C_4$ alkyl, or hydroxyl;
Ring A is

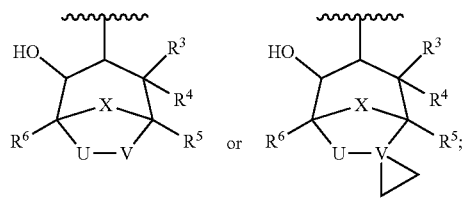

wherein:
$R^3$ and $R^4$ are independently selected from hydrogen, deuterium, halogen, hydroxyl, $C_1$-$C_6$ alkyl, and $C_3$-$C_6$ cycloalkyl; or $R^3$ and $R^4$ may be taken together with the carbon atom to which both are attached to form a 3-7 membered cycloalkyl;
$R^5$ and $R^6$ are independently selected from hydrogen, $C_1$-$C_6$ alkyl, $C_3$-$C_6$ cycloalkyl, and aryl, wherein the $C_1$-$C_6$ alkyl is optionally substituted with hydroxyl;
X is O or N—S(O)$_2$—R$^X$, wherein R$^X$ is selected from $C_1$-$C_6$ alkyl, $C_3$-$C_6$ cycloalkyl, a 3-7 membered heterocyclic group, aryl, and heteroaryl, and wherein each of the $C_3$-$C_6$cycloalkyl, 3-7 membered heterocyclic group, aryl, and heteroaryl is optionally substituted with 1, 2, or 3 groups selected from halogen, hydroxyl, and cyano;
U is O or C(R$^U$)$_2$, wherein R$^U$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl; and
V is O, C, or C(R$^V$)$_2$, wherein R$^V$ is independently selected from hydrogen, deuterium, halogen, hydroxyl, $C_1$-$C_6$ alkyl, and $C_3$-$C_6$ cycloalkyl, wherein each of the $C_1$-$C_6$ alkyl and $C_3$-$C_6$ cycloalkyl is optionally substituted with hydroxyl;
with the proviso that one but not both of U and V is O.

29. The compound according to claim 28, wherein the compound is selected from:

42

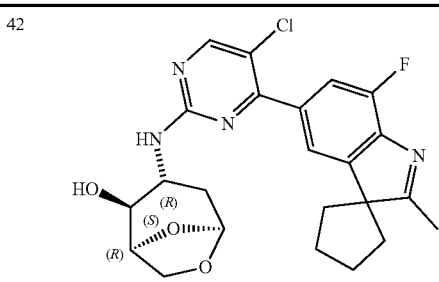

-continued

143
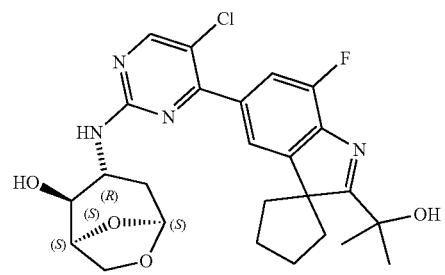

43
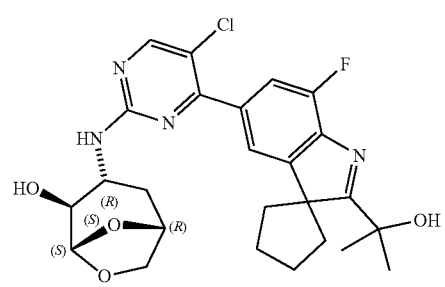

144
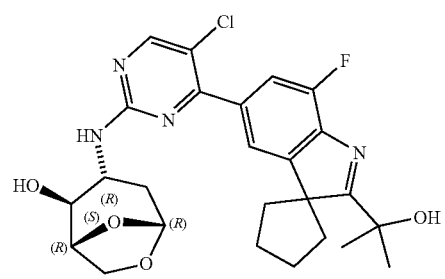

32
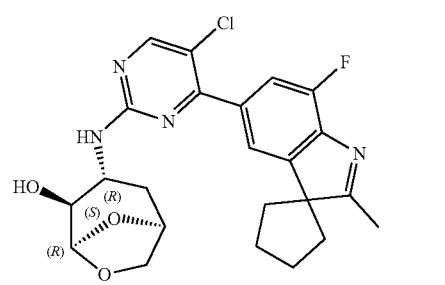

33
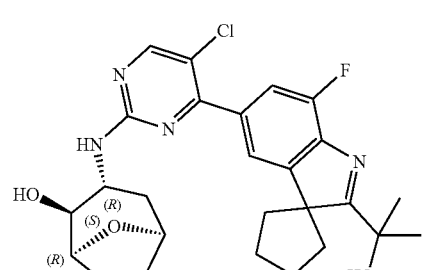

or a pharmaceutically acceptable salt of any of the above.

30. A method for treating cancer in a subject in need thereof, comprising administering to the subject an effective amount of at least one compound according to claim 29.

31. A compound, wherein the compound is selected from:

1
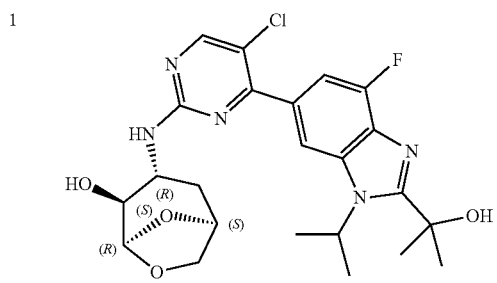

2
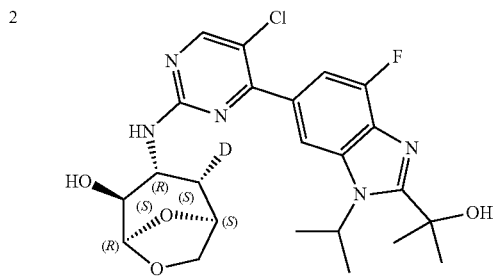

13
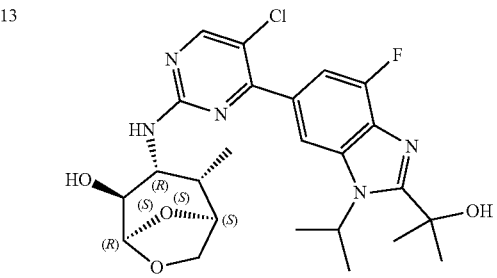

26
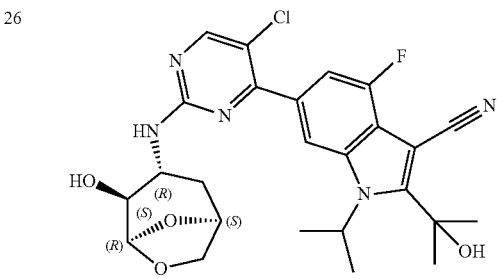

or is a pharmaceutically acceptable salt thereof.

32. The compound of claim 31, wherein the compound is:

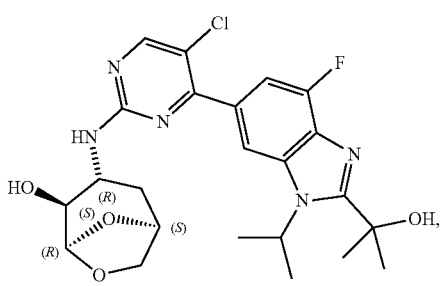

or a pharmaceutically acceptable salt thereof.

33. The compound of claim 31, wherein the compound is:

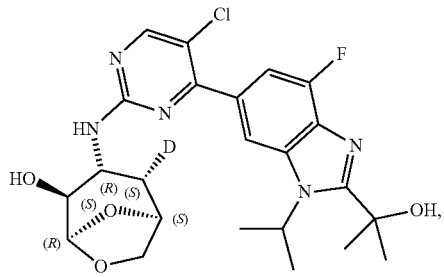

or a pharmaceutically acceptable salt thereof.

34. The compound of claim 31, wherein the compound is:

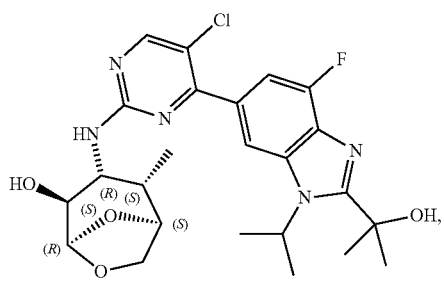

or a pharmaceutically acceptable salt thereof.

35. The compound of claim 31, wherein the compound is:

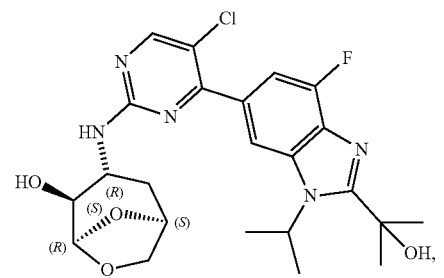

or a pharmaceutically acceptable salt thereof.

36. A compound, wherein the compound is selected from:

252

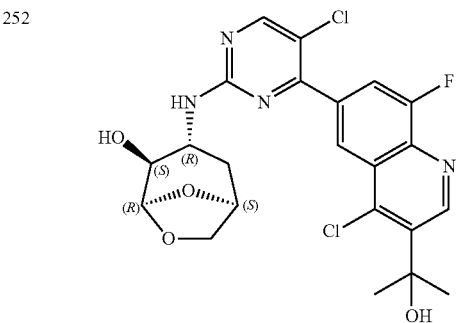

255

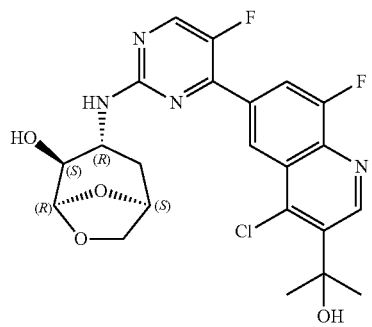

256

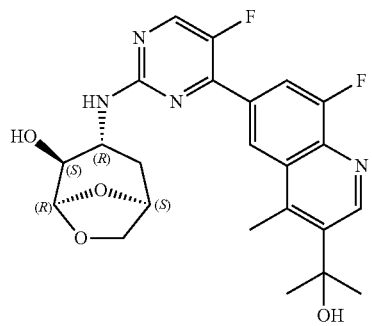

257

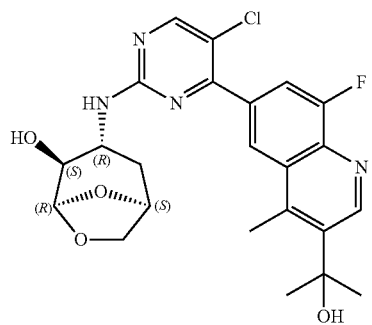

or is a pharmaceutically acceptable salt thereof.

37. The compound of claim 36, wherein the compound is:

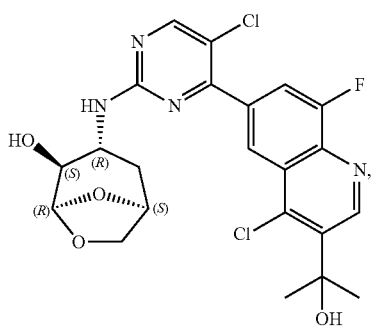

or a pharmaceutically acceptable salt thereof.

38. The compound of claim 36, wherein the compound is:

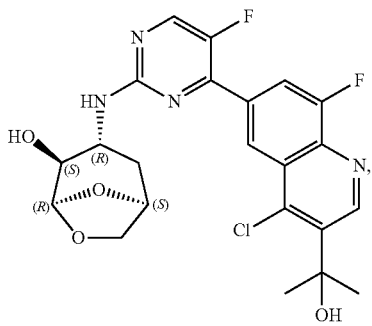

or a pharmaceutically acceptable salt thereof.

39. The compound of claim 36, wherein the compound is:

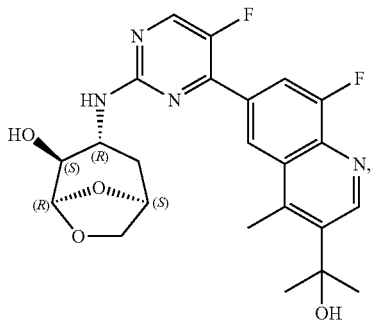

or a pharmaceutically acceptable salt thereof.

40. The compound of claim 36, wherein the compound is:

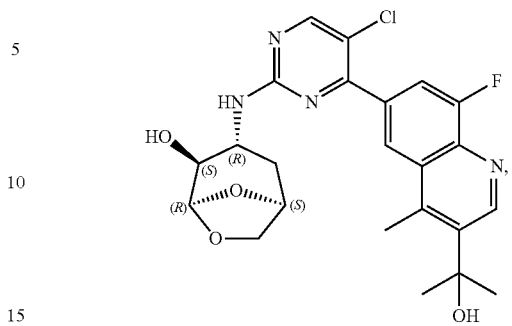

or a pharmaceutically acceptable salt thereof.

41. A pharmaceutical composition comprising a therapeutically effective amount of a compound according to claim 31 and one or more pharmaceutically acceptable carriers, pharmaceutically acceptable vehicles, pharmaceutically acceptable excipients, or combinations thereof.

42. A pharmaceutical composition comprising a therapeutically effective amount of a compound according to claim 36 and one or more pharmaceutically acceptable carriers, pharmaceutically acceptable vehicles, pharmaceutically acceptable excipients, or combinations thereof.

43. A method of treating a disease or condition modulated at least in part by a cyclin- dependent kinase (CDK) in a subject in need thereof, comprising administering to the subject an effective amount of at least one compound according to claim 31.

44. A method of treating a disease or condition modulated at least in part by a cyclin- dependent kinase (CDK) in a subject in need thereof, comprising administering to the subject an effective amount of at least one compound according to claim 36.

45. A method for inhibiting a CDK in a subject, comprising administering to the subject an effective amount of at least one compound according to claim 31.

46. A method for inhibiting a CDK in a subject, comprising administering to the subject an effective amount of at least one compound according to claim 36.

47. A method for treating cancer in a subject in need thereof, comprising administering to the subject an effective amount of a compound of claim 31 or a pharmaceutically acceptable salt thereof.

48. A method for treating cancer in a subject in need thereof, comprising administering to the subject an effective amount of a compound of claim 36 or a pharmaceutically acceptable salt thereof.

* * * * *